(12) United States Patent
Van Almsick et al.

(10) Patent No.: US 8,658,798 B2
(45) Date of Patent: Feb. 25, 2014

(54) HERBICIDE TRIAZOLYLPYRIDINE KETONES

(75) Inventors: Andreas Van Almsick, Karben (DE); Shinichi Narabu, Ibaraki (JP); Yoshitaka Sato, Ibaraki-pref. (JP); Kei Domon, Tochigi (JP); Koichi Araki, Ibaraki (JP); Shinichi Shirakura, Tochigi (JP); Seiji Ukawa, Tochigi (JP); Teruyuki Ichihara, Tochigi (JP); Chieko Ueno, Frankfurt (DE)

(73) Assignee: Bayer Cropscience AG, Monheim (DE)

( * ) Notice: Subject to any disclaimer, the term of this patent is extended or adjusted under 35 U.S.C. 154(b) by 7 days.

(21) Appl. No.: 12/671,728

(22) PCT Filed: Jul. 24, 2008

(86) PCT No.: PCT/EP2008/006063
§ 371 (c)(1),
(2), (4) Date: May 27, 2010

(87) PCT Pub. No.: WO2009/018925
PCT Pub. Date: Feb. 12, 2009

(65) Prior Publication Data
US 2011/0237800 A1   Sep. 29, 2011

(30) Foreign Application Priority Data

Aug. 3, 2007 (JP) ................................. 2007-202808

(51) Int. Cl.
*C07D 401/04* (2006.01)
*C07D 413/14* (2006.01)

(52) U.S. Cl.
USPC .................................... 546/272.1; 546/272.4

(58) Field of Classification Search
USPC ......... 514/383, 210.2, 362; 548/262.2, 300.1, 548/465, 950; 546/208, 210
See application file for complete search history.

(56) References Cited

FOREIGN PATENT DOCUMENTS

| JP | 52-003968 | 8/1978 | |
|---|---|---|---|
| JP | 03-038586 | 2/1991 | |
| JP | 2005-060299 | 3/2005 | |
| WO | 97/46530 | 12/1997 | |
| WO | WO 97/46530 | * 12/1997 | ........... C07D 213/50 |
| WO | 99/03845 | 1/1999 | |
| WO | 99/03856 | 1/1999 | |
| WO | W00015615 | 3/2000 | |
| WO | 03/106448 | 12/2003 | |
| WO | 2004029027 | 4/2004 | |
| WO | 2004/058712 | 7/2004 | |

OTHER PUBLICATIONS

International Search Report of PCT/EP2008/006063, completed Nov. 28, 2008.
International Preliminary Report on Patentability of PCT/EP2008/006063,completed Jul. 27, 2009.

* cited by examiner

*Primary Examiner* — Kamal Saeed
(74) *Attorney, Agent, or Firm* — Miles & Stockbridge, P.C.

(57) ABSTRACT

Triazolylpyridine ketones expressed by the following formula (I) and use thereof as herbicides.

8 Claims, No Drawings

HERBICIDE TRIAZOLYLPYRIDINE KETONES

CROSS REFERENCE TO RELATED APPLICATIONS

This application is a §371 National Stage Application of PCT/EP2008/006063 filed Jul. 24, 2008, which claims priority to Japanese Application 2007-202808 filed Aug. 3, 2007.

BACKGROUND OF THE INVENTION

1. Technical Field

This invention relates to novel triazolylpyridine ketones, use thereof as herbicides, manufacturing methods thereof, and novel intermediates thereof.

2. Background Art

It is already known that some kinds of aryl ketones show action as herbicides (For example, WO 97/46530-A, WO 99/03845-A, WO 00/15615-A, and Japanese Patent Application Laid-Open (JP-A) No.2005-60299).

DISCLOSURE OF INVENTION

However, compounds disclosed in the above publications are not sufficiently satisfactory in the effect and/or safety as herbicides.

The present inventors zealously studied in order to create novel compounds having higher effects and higher safety as herbicides. As a result, novel triazolylpyridine ketones of the following formula (I), which have excellent herbicide activity and show safety to crops, and which are represented by the following formula (I), have been founded out.

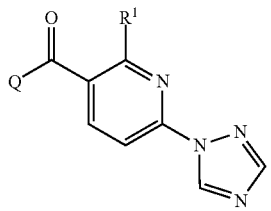

Formula (I)

In the formula, $R^1$ represents alkyl, cycloalkyl, cycloalkylalkyl, haloalkyl, alkenyl, alkynyl, aryl, aralkyl, alkoxyalkyl, cycloalkyl-alkoxyalkyl, haloalkoxyalkyl, alkenyloxyalkyl, alkynyloxyalkyl, alkylthioalkyl, alkylsulfinylalkyl, alkylsulfonylalkyl, cycloalkyl-alkylthioalkyl, cycloalkyl-alkylsulfinylalkyl, cycloalkyl-alkylsulfonylalkyl, haloalkylthioalkyl, haloalkylsulfinylalkyl, haloalkylsulfonylalkyl, alkenylthioalkyl, alkenylsulfinylalkyl, alkenylsulfonylalkyl, alkynylthioalkyl, alkynylsulfinylalkyl, alkynylsulfonylalkyl, alkoxyalkoxyalkyl, cycloalkyl-alkoxyalkoxyalkyl, haloalkoxyalkoxyalkyl, alkenyloxyalkoxyalkyl, alkynyloxyalkoxyalkyl, alkylthioalkoxyalkyl, alkylsulfinylalkoxyalkyl, alkylsulfonylalkoxyalkyl, cycloalkyl-alkylthioalkoxyalkyl, cycloalkyl-alkylsulfinylalkoxyalkyl, cycloalkyl-alkylsulfonylalkoxyalkyl, haloalkylthioalkoxyalkyl, haloalkylsulfinylalkoxyalkyl, haloalkylsulfonylalkoxyalkyl, alkenylthioalkoxyalkyl, alkenylsulfinylalkoxyalkyl, alkenylsulfonylalkoxyalkyl, alkynylthioalkoxyalkyl, alkynylsulfinylalkoxyalkyl, alkynylsulfonylalkoxyalkyl, cyclic ether-O-alkyl, cyclic ether-alkoxyalkyl, alkylsulfonylaminoalkoxyalkyl, cycloalkyl-alkylsulfonylaminoalkoxyalkyl, haloalkylsulfonylaminoalkoxyalkyl, alkylthio, alkylsulfinyl, alkylsulfonyl, alkoxy, haloalkoxy, alkoxyalkoxy, or $NR^2R^3$, $R^2$ and $R^3$ respectively represent hydrogen or alkyl, Q represents

Q1

Q2

Q3 or

Q4

$R^4$ represents hydroxy, halogen, alkylthio, substituted phenylthio, substituted benzylthio, substituted-1-pyrazolyl, substituted-l-imidazolyl, 1,2,4-triazolyl-1-yl, 1H-tetrazol-1-yl or 2H-tetrazol-2-yl, $R^5$, $R^6$, R', $R^8$, $R^9$, and $R^{10}$ respectively represent hydrogen or alkyl, $R^5$ and $R^{10}$ together represent ethylene or —CH=CH—, $R^7$ and $R^8$ together represent carbonyl, $R^{11}$ represents alkyl, $R^{12}$ represents hydrogen, alkyl, or cycloalkyl, $R^{13}$ represents hydrogen, alkyl, alkenyl, alkynyl, aralkyl, alkylsulfonyl, substituted phenylsulfonyl, acyl, or acylalkyl, $R^{14}$ represents alkyl or cycloalkyl, and $R^{15}$ represents hydrogen, alkoxycarbonyl, or alkylthio.

DETAILED DESCRIPTION OF A PREFERRED EMBODIMENT

Compounds of the above formula (I) of the present invention can be synthesized, for example, by means of either of the following manufacturing method (a), (b), (c), (d), (e), (f), (g), (h), (i), or (j)

Manufacturing Method (a)

In the case that compounds in which Q represents Q1 and $R^4$ represents hydroxyl, or Q represents Q2 and $R^{13}$ represents hydrogen are manufactured: a method of rearranging the compounds represented by the following formulae in the presence of a base and a cyanogen compound Formula (II)

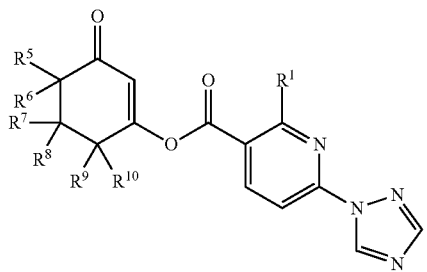

or

Formula (III)

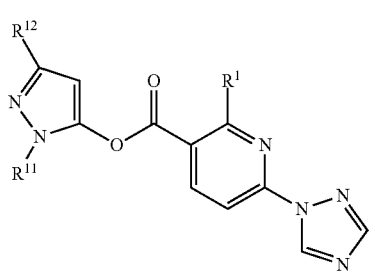

or

Formula (IV)

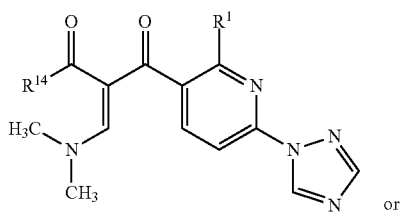

In the respective formulae, $R^1$, $R^5$, $R^6$, $R^7$, $R^8$, $R^9$, $R^{10}$, $R^{11}$, and $R^{12}$ have the same meanings as the aforementioned.

Manufacturing Method (b)

In the case that compounds in which Q represents Q3 and $R^{15}$ represents hydrogen are manufactured: a method for reacting the compounds represented by the following formulae with hydroxylamine hydrochloride Formula (V)

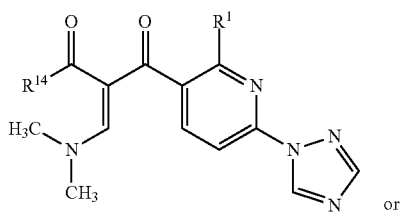

or

Formula (VI)

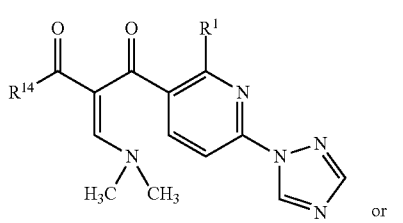

or

Formula (VII)

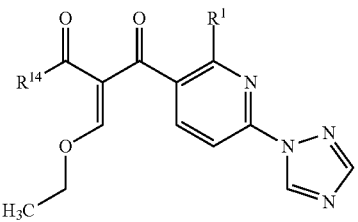

or

Formula (VIII)

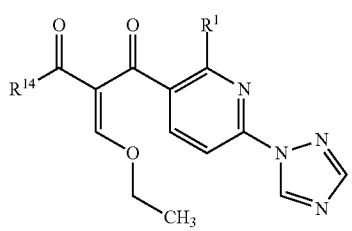

In the respective formulae, $R^1$ and $R^{14}$ have the same meanings as the aforementioned.

Manufacturing Method (c)

In the case that compounds in which Q represents Q3 and $R^{15}$ represents alkoxycarbonyl are manufactured: a method for reacting the compounds represented by the following formula (IX) with imidoyl chloride represented by the following formula (X)

Formula (IX)

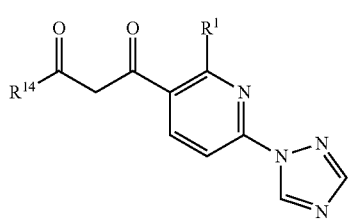

In the formula, $R^1$ and $R^{14}$ have the same meanings as the aforementioned.

Formula (X)

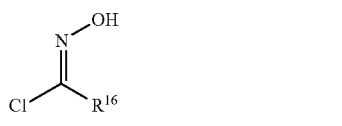

In the formula, $R^{16}$ represents alkoxycarbonyl. Manufacturing method (d)

In the case that compounds in which Q represents Q3 and $R^{15}$ represents alkoxycarbonyl are manufactured: a method for reacting the compounds represented by the following formula with 1H-1,2,4-triazole in the presence of a base

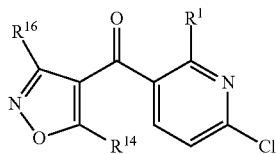

Formula (XI)

In the formula, $R^1$, $R^{14}$, and $R^{16}$ have the same meanings as the aforementioned.

Manufacturing Method (e)

In the case that compounds in which Q represents Q3 and $R^{15}$ represents alkylthio are manufactured: a method for reacting the compound represented by the following formula with hydroxylamine hydrochloride

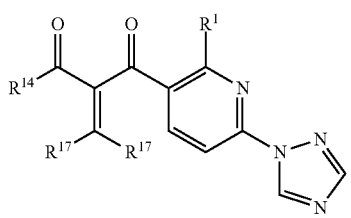

Formula (XII)

In the formula, $R^1$ and $R^{14}$ have the same meanings as the aforementioned and $R^{17}$ represents alkylthio.

Manufacturing Method (f)

In the case that compounds in which Q represents Q4 are manufactured: a method for reacting the compounds represented by the following formula (XIII) with the compounds represented by the following formula (XIV) in the presence of a base

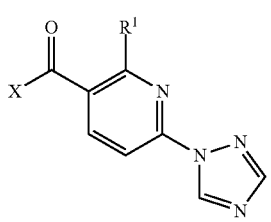

Formula (XIII)

In the formula, $R^1$ hasthe same meanings as the aforementioned and X represents halogen.

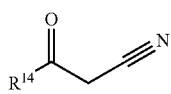

Formula (XIV)

In the formula, $R^{14}$ has the same meanings as the aforementioned.

Manufacturing Method (g)

In the case that compounds in which Q represents Q4 are manufactured: a method for causing the ring-opening reaction of the compounds represented by the following formula in the presence of a base

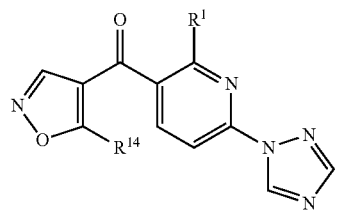

Formula (XV)

In the formula, $R^1$ and $R^{14}$ have the same meanings as the aforementioned.

Manufacturing Method (h)

In the case that compounds in which Q represents Q1 and $R^4$ represents halogen are manufactured: a method for reacting the compounds represented by the following formula with a halogenating agent

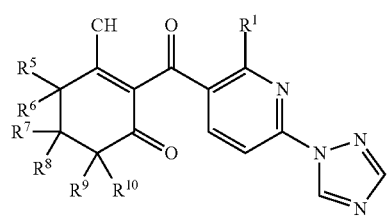

Formula (XVI)

In the formula, $R^1$, $R^5$, $R^6$, $R^7$, $R^8$, $R^9$, and $R^{10}$ have the same meanings as the aforementioned.

Manufacturing Method (i)

In the case that compounds in which Q represents Q1 and R4 represents alkylthio, substituted phenylthio, substituted benzylthio, substituted pyrazol-1-yl, substituted imidazol-1-yl, 1,2,4-triazol-1-yl, 1H-tetrazol-1-yl, or 2H-tetrazol-2-yl are manufactured: a method for reacting the compounds represented by the following formula (XVII) with the compounds represented by the following formula (XVIII)

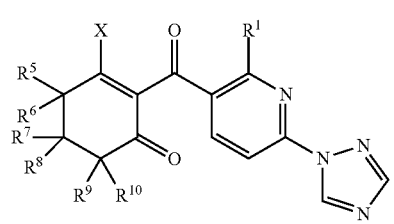

Formula (XVII)

In the formula, $R^1$, $R^5$, $R^6$, $R^7$, $R^8$, $R^9$, $R^{10}$ and X have the same meanings as the aforementioned.

  $R^{18}$—H  Formula (XVIII)

In the formula, $R^{18}$ represents alkylthio, substituted phenylthio, substituted benzylthio, substituted pyrazol-1-yl, substituted imidazol-1-yl, 1,2,4-triazol-1-yl, 1H-tetrazol-1-yl, or 2H-tetrazol-2-yl.

Manufacturing Method (j)

In the case that compounds in which Q represents Q2 and represents alkyl, alkenyl, alkynyl, aralkyl, alkylsulfonyl, substituted phenylsulfonyl, acyl, or acylalkyl are manufactured: a method for reacting the compounds represented by the following formula (XIX) with the compounds represented by the following formula (XX)

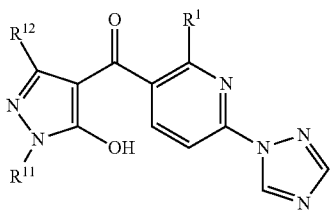

Formula (XIX)

In the formula, $R^1$, $R^{11}$, and $R^{12}$ have the same meanings as the aforementioned.

$$R^{19}-X \qquad \text{Formula (XX)}$$

In the formula, X has the same meanings as the aforementioned, and $R^{19}$ represents alkyl, alkenyl, alkynyl, aralkyl, alkylsulfonyl, substituted phenylsulfonyl, acyl, or acylalkyl.

The triazolylpyridine ketones of formula (I) provided by the present invention show stronger herbicide action than any of compounds described in the above prior art documents and have extremely superior effects as selective herbicides that do not substantially cause phytotoxicity to crops, especially effective to the general of broad-leaved weeds such as morning glories, knotweed, nightshade, fat hen, velvetleaf, amaranthus or the like, and effective to warm-season gramineous weeds such as livid amaranthus, green bristle grass, southern crabgrass, wire grass or the like, and show extremely excellent effects as herbicides for dry field crops such as wheat, corn or the like.

In the present specification, "Alkyl", for example, shows normal chain or branched chain $C_{1-12}$ alkyl such as methyl, ethyl, n- or iso-propyl, n-, iso-, sec-, or tert-butyl, n-pentyl, n-hexyl, n-heptyl, n-octyl, n-nonyl, n-decyl, n-undecyl, n-dodecyl or the like, and is preferably $C_{1-6}$ alkyl.

Moreover, for respective alkyl parts in respective groups having alkyls as a part of configuration, ones similar to those explained in the above "alkyl" can be exemplified.

"Acylamino", for example, shows alkylcarbonylamino, cyclopropylcarbonylamino, and benzoylamino, and here, as for alkyl part, alkyl having the same meanings as those explained in the above "alkyl" can be exemplified.

"Halogen" and respective halogen parts in respective halogen substituted groups show fluorine, chlorine, bromine, and iodine, and preferably show fluorine, chlorine, and bromine.

"Cycloalkyl" and the cycloalkyl part in a group having cycloalkyl as a part of configuration show $C_{3-8}$ cycloalkyl such as cyclopropyl, cyclobutyl, cyclopentyl, cyclohexyl, cycloheptyl, cyclooctyl or the like, and preferably show $C_{3-7}$ cycloalkyl.

"Alkenyl" and the alkenyl part in a group having alkenyl as a part of configuration show $C_{2-5}$ alkenyl such as vinyl, allyl, 1-propenyl, 1-(or 2-, or 3-)butenyl, 1-pentenyl or the like, and preferably show $C_{2-4}$ alkenyl.

"Alkynyl" and the alkynyl part in a group having alkynyl as a part of configuration show $C_{2-5}$ alkynyl such as ethynyl, propargyl, 1-propynyl, butan-3-ynyl, pentan-4-ynyl or the like, and preferably show $C_{2-4}$ alkynyl.

"Aryl" and the aryl part of "aralkyl" show $C_{6-12}$ aryl such as phenyl, tolyl, xylyl, naphthyl, biphenylyl or the like, and preferably show $C_{6-8}$ aryl. Preferred examples of "aralkyl" include benzyl, a-methylbenzyl, and phenethyl.

In the compounds of formula (I) of the present invention, the following compounds are preferred in which $R^1$ represents $C_{1-6}$ alkyl, $C_{3-8}$ cycloalkyl, $C_{3-8}$ cycloalkyl-$C_{1-2}$ alkyl, $C_{1-6}$ haloalkyl, $C_{2-6}$ alkenyl, $C_{2-6}$ alkynyl, $C_{6-12}$ aryl, $C_{6-12}$ aryl-$C_{1-2}$ alkyl, $C_{1-6}$-alkoxy-$C_{1-4}$ alkyl, $C_{3-8}$ cycloalkyl-$C_{1-4}$ alkoxy-$C_{1-4}$ alkyl, $C_{1-6}$ haloalkoxy-$C_{1-4}$ alkyl, $C_{2-6}$ alkenyloxy-$C_{1-4}$ alkyl, $C_{2-6}$ alkynyloxy-$C_{1-4}$ alkyl, $C_{1-6}$ alkylthio-$C_{1-4}$ alkyl, $C_{1-6}$ alkylsulfinyl-$C_{1-4}$ alkyl, $C_{1-6}$ alkylsulfonyl-$C_{1-4}$ alkyl, $C_{3-8}$ cycloalkyl-$C_{1-4}$ alkylthio-$C_{1-4}$ alkyl, $C_{3-8}$ cycloalkyl-$C_{1-4}$ alkylsulfinyl-$C_{1-4}$ alkyl, $C_{3-8}$ cycloalkyl-$C_{1-4}$ alkylsulfonyl-$C_{1-4}$ alkyl, $C_{1-6}$ haloalkylthio-$C_{1-4}$ alkyl, $C_{1-6}$ haloalkylsulfinlyl-$C_{1-4}$ alkyl, $C_{1-6}$ haloalkylsulfonyl-$C_{1-4}$ alkyl, $C_{2-6}$ alkenylthio-$C_{1-4}$ alkyl, $C_{2-6}$ alkenylsulfenyl-$C_{1-4}$ alkyl, $C_{2-6}$ alkenylsulfonyl-$C_{1-4}$ alkyl, $C_{2-6}$ alkynylthio-$C_{1-4}$ alkyl, $C_{2-6}$ alkynylsulfinyl-$C_{1-4}$ alkyl, $C_{2-6}$ alkynylsulfonyl-$C_{1-4}$ alkyl, $C_{1-6}$ al koxy-$C_{1-4}$ alkoxy-$C_{1-4}$ alkyl, $C_{3-8}$ cycloalkyl-$C_{1-4}$ al koxy-$C_{1-4}$ alkoxy-$C_{1-4}$ alkyl, $C_{1-6}$ haloalkoxy-$C_{1-4}$ alkoxy-$C_{1-4}$ alkyl, $C_{2-6}$ alkenyloxy-$C_{1-4}$ alkoxy-$C_{1-4}$ alkyl, $C_{2-6}$ alkynyloxy-$C_{1-4}$ alkoxy-$C_{1-4}$ alkyl, $C_{1-6}$ alkylthio-$C_{1-4}$ alkoxy-$C_{1-4}$ alkyl, $C_{1-6}$ alkylsulfinyl-$C_{1-4}$ alkoxy-$C_{1-4}$ alkyl, $C_{1-6}$ alkylsulfonyl-$C_{1-4}$ alkoxy-$C_{1-4}$ alkyl, $C_{3-8}$ cycloalkyl-$C_{1-4}$ alkylthio-$C_{1-4}$ alkoxy-$C_{1-4}$ alkyl, $C_{3-8}$ cycloalkyl-$C_{1-4}$ alkylsulfinyl-$C_{1-4}$ alkoxy-$C_{1-4}$ alkyl, $C_{3-8}$ cycloalkyl-$C_{1-4}$ alkylsulfonyl-$C_{1-4}$ alkoxy-$C_{1-4}$ alkyl, $C_{1-6}$ haloalkylthio-$C_{1-4}$ alkoxy-$C_{1-4}$ alkyl, $C_{1-6}$ haloalkylsulfinyl-$C_{1-4}$ alkoxy-$C_{1-4}$ alkyl, $C_{1-6}$ haloalkylsulfonyl-$C_{1-4}$ alkoxy-$C_{1-4}$ alkyl, $C_{2-6}$ alkenylthio-$C_{1-4}$ alkoxy-$C_{1-4}$ alkyl, $C_{2-6}$ alkenylsulfinyl-$C_{1-4}$ al koxy-$C_{1-4}$ alkyl, $C_{2-6}$ al kenylsulfonyl-$C_{1-4}$ alkoxy-$C_{1-4}$ alkyl, $C_{2-6}$ alkynylthio-$C_{1-4}$ alkoxy-$C_{1-4}$ alkyl, $C_{2-6}$ alkynylsulfinyl-$C_{1-4}$ alkoxy-$C_{1-4}$ alkyl, $C_{2-6}$ alkynylsulfonyl-$C_{1-4}$ alkoxy-$C_{1-4}$ alkyl, $C_{2-5}$ cyclic ether-O-$C_{1-4}$ alkyl, $C_{2-5}$ cyclic ether-$C_{1-4}$ alkoxy-$C_{1-4}$ alkyl, $C_{1-6}$ alkylsulfonylamino-$C_{1-4}$ alkoxy-$C_{1-4}$ alkyl, $C_{3-8}$ cycloalkyl-$C_{1-4}$ alkylsulfonylamino-$C_{1-4}$ alkoxy-$C_{1-4}$ alkyl, $C_{1-6}$ haloalkylsulfonylamino-$C_{1-4}$ alkoxy-$C_{1-4}$ alkyl, $C_{1-4}$ alkylthio, $C_{1-6}$ alkylsulfinyl, $C_{1-6}$ alkylsulfonyl, $C_{1-6}$ alkoxy, $C_{1-6}$ haloalkoxy, $C_{1-6}$ alkoxy-$C_{1-4}$ alkoxy, or $NR^2R^3$, $R^2$ and $R^3$ respectively represent hydrogen or $C_{1-6}$ alkyl, Q represents

Q1

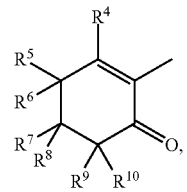

Q2

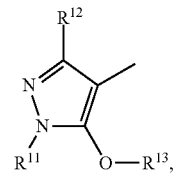

Q3

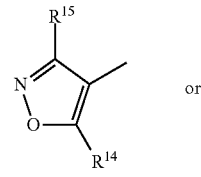

or

Q4

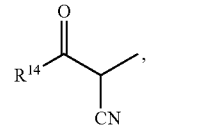

$R^4$ represents hydroxy, halogen, $C_{1-6}$ alkylthio, substituted phenylthio, substituted benzylthio, substituted-1-pyrazolyl, substituted-1-imidazolyl, 1,2,4-triazol-1-yl, 1H-tetrazol-1-yl, or 2H-tetrazol-2-yl, $R^5, R^6, R^7, R^8, R^9$, and $R^{10}$ respectively represent hydrogen or $C_{1-6}$ alkyl, $R^5$ and $R^{10}$ together represent ethylene or —CH═CH—, $R^7$ and $R^8$ together represent carbonyl, $R^{11}$ represents $C_{1-6}$ alkyl, $R^{12}$ represents hydrogen, $C_{1-6}$ alkyl, or $C_{3-8}$ cycloalkyl, $R^{13}$ represents hydrggen, $C_{1-6}$ alkyl, $C_{2-6}$ alkenyl, $C_{2-6}$ alkynyl, $C_{6-10}$ aryl-$C_{1-2}$ alkyl, $C_{1-6}$ alkylsulfonyl, substituted phenylsulfonyl, $C_{1-6}$ alkylcarbonyl, benzoyl, heteroarylcarbonyl, $C_{1-6}$ alkyl-carbonyl-$C_{1-4}$ alkyl, benzoyl-$C_{1-4}$ alkyl, or heteroarylcarbonyl-$C_{1-4}$ alkyl, $R^{14}$ represents $C_{1-6}$ alkyl or $C_{3-8}$ cycloalkyl, and $R^{15}$ represents hydrogen, $C_{1-6}$ alkoxy-carbonyl or $C_{1-6}$ alkylthio.

Among the compounds of formula (I), the following compounds are especially preferred in which $R^1$ represents $C_{1-4}$ alkyl, $C_{3-7}$ cycloalkyl, $C_{3-7}$ cycloalkyl-$C_{1-2}$ alkyl, $C_{1-4}$ haloalkyl, $C_{2-4}$ alkenyl, $C_{2-4}$ alkynyl, $C_{6-8}$ aryl, $C_{6-8}$ aryl-$C_{1-2}$ alkyl, $C_{1-4}$ alkoxy-$C_{1-4}$ alkyl, $C_{3-7}$ cycloalkyl-$C_{1-4}$ alkoxy-$C_{1-4}$ alkyl, $C_{1-4}$ haloalkoxy-$C_{1-4}$ alkyl, $C_{2-9}$ alkenyloxy-$C_{1-4}$ alkyl, $C_{2-4}$ alkynyloxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, $C_{3-7}$ cycloalkyl-$C_{1-4}$ alkylthio-$C_{1-4}$ alkyl, $C_{3-7}$ cycloalkyl-$C_{1-4}$ alkylsulfinyl-$C_{1-4}$ alkyl, $C_{3-7}$ cycloalkyl-$C_{1-4}$ alkylsulfonyl-$C_{1-4}$ alkyl, $C_{1-4}$ haloalkylthio-$C_{1-4}$ alkyl, $C_{1-4}$ haloalkylsulfinyl-$C_{1-4}$ alkyl, $C_{1-9}$ haloalkylsulfonyl-$C_{1-4}$ alkyl, $C_{2-4}$ alkenylthio-$C_{1-4}$ alkyl, $C_{2-4}$ alkenylsulfinyl-$C_{1-4}$ alkyl, $C_{2-4}$ alkenylsulfonyl-$C_{1-4}$ alkyl, $C_{2-4}$ alkynylthio-$C_{1-4}$ alkyl, $C_{2-4}$ alkynylsulfinyl-$C_{1-4}$ alkyl, $C_{2-9}$ alkynylsulfonyl-$C_{1-4}$ alkyl, $C_{1-4}$ alkoxy-$C_{1-4}$ alkoxy-$C_{1-4}$ alkyl, $C_{3-7}$ Cycloalkyl-$C_{1-4}$ alkoxy-$C_{1-4}$ alkoxy-$C_{1-4}$ alkyl, $C_{1-4}$ haloalkoxy-$C_{1-4}$ alkoxy-$C_{1-4}$ alkyl, $C_{2-4}$ alkenyloxy-$C_{1-4}$ alkoxy-$C_{1-4}$ alkyl, $C_{2-9}$ alkynyloxy-$C_{1-4}$ alkoxy-$C_{1-4}$ alkyl, $C_{1-4}$ alkylthio-$C_{1-4}$ alkoxy-$C_{1-4}$ alkyl, $C_{1-4}$ alkylsulfinyl-$C_{1-4}$ alkoxy-$C_{1-4}$ alkyl, $C_{1-4}$ alkylsulfonyl-$C_{1-4}$ alkoxy-$C_{1-4}$ alkyl, $C_{3-7}$ cycloalkyl-$C_{1-4}$ alkylthio-$C_{1-4}$ alkoxy-$C_{1-4}$ alkyl, $C_{3-7}$ cycloalkyl-$C_{1-4}$ alkylsulfinyl-$C_{1-4}$ alkoxy-$C_{1-4}$ alkyl, $C_{3-7}$ cycloalkyl-$C_{1-4}$ alkylsulfonyl-$C_{1-4}$ alkoxy-$C_{1-4}$ alkyl, $C_{1-4}$ haloalkylthio-$C_{1-4}$ alkoxy-$C_{1-4}$ alkyl, $C_{1-4}$ haloalkylsulfinyl-$C_{1-4}$ alkoxy-$C_{1-4}$ alkyl, $C_{1-4}$ haloalkylsulfonyl-$C_{1-4}$ alkoxy-$C_{1-4}$ alkyl, $C_{2-4}$ alkenylthio-$C_{1-4}$ alkoxy-$C_{1-4}$ alkyl, $C_{2-4}$ alkenylsulfinyl-$C_{1-4}$ alkoxy-$C_{1-4}$ alkyl, $C_{2-4}$ alkenylsulfonyl-$C_{1-4}$ alkoxy-$C_{1-4}$ alkyl, $C_{2-4}$ alkynylthio-$C_{1-4}$ alkoxy-$C_{1-4}$ alkyl, $C_{2-4}$ alkynylsulfinyl-$C_{1-4}$ alkoxy-$C_{1-4}$ alkyl, $C_{2-4}$ alkynylsulfonyl-$C_{1-4}$ alkoxy-$C_{1-4}$ alkyl, $C_{2-4}$ cyclic ether-O-$C_{1-4}$ alkyl, $C_{2-4}$ cyclic ether-$C_{1-4}$ alkoxy-$C_{1-4}$ alkyl, $C_{1-4}$ alkylsulfonylamino-$C_{1-4}$ alkoxy-$C_{1-4}$ alkyl, $C_{3-7}$ cycloalkyl-$C_{1-4}$ alkylsulfonylamino-$C_{1-4}$ alkoxy-$C_{1-4}$ alkyl, $C_{1-4}$ haloalkylsulfonylamino-$C_{1-4}$ alkoxy-$C_{1-4}$ alkyl, $C_{1-4}$ alkylthio, $C_{1-4}$ alkylsulfinyl, $C_{1-4}$ alkylsulfonyl, $C_{1-4}$ alkoxy, $C_{1-4}$ haloalkoxy, $C_{1-4}$ alkoxy-$C_{1-4}$ alkoxy or $NR^2R^3$, $R^2$ and $R^3$ respectively represent hydrogen or $C_{1-4}$ alkyl, Q represents

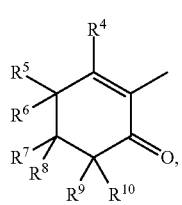

Q1

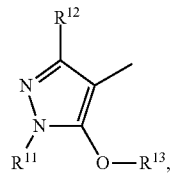

Q2

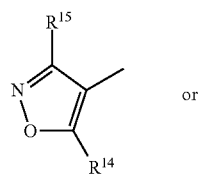

Q3 or

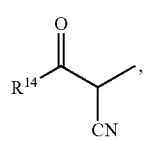

Q4

$R^4$ represents hydroxy, halogen, $C_{1-4}$ alkylthio, substituted phenylthio, substituted benzylthio, substituted-1-pyrazolyl, substituted-1-imidazolyl, 1,2,4-triazol-1-yl, 1H-tetrazol-1-yl, or 2H-tetrazol-2-yl, $R^5, R^6, R^7, R^9, R^9$, and $R^{10}$ respectively represent hydrogen or $C_{1-4}$ alkyl, $R^5$ and $R^{10}$ together represent ethylene or —CH═CH—, $R^7$ and $R^8$ together represent carbonyl, $R^{11}$ represents $C_{1-4}$ alkyl, $R^{12}$ represents hydrogen, $C_{1-4}$ alkyl, or $C_{3-7}$ cycloalkyl, $R^{13}$ represents hydrogen, $C_{1-4}$ alkyl, $C_{2-4}$ alkenyl, $C_{2-9}$ alkynyl, $C_{6-8}$ aryl-$C_{1-2}$ alkyl, $C_{1-4}$ alkylsulfonyl, substituted phenylsulfonyl, $C_{1-4}$ alkylcarbonyl, benzoyl, heteroarylcarbonyl, $C_{1-4}$ alkyl-carbonyl-$C_{1-4}$ alkyl, benzoyl-$C_{1-4}$ alkyl, or heteroarylcarbonyl-$C_{1-4}$ alkyl, $R^{14}$ represents $C_{1-4}$ alkyl or $C_{3-7}$ cycloalkyl, and $R^{15}$ represents hydrogen, $C_{1-4}$ alkoxy-carbonyl or $C_{1-4}$ alkylthio.

The case in which, for example, 3-oxo-1-cyclohexen-1-yl 2-methyl-6-(1H-1,2,4-triazole-1-yl)nicotinate is used as a raw material and acetocyanhydrin is used as a cyanogen compound in the manufacturing method (a) can be represented by the following reaction formula.

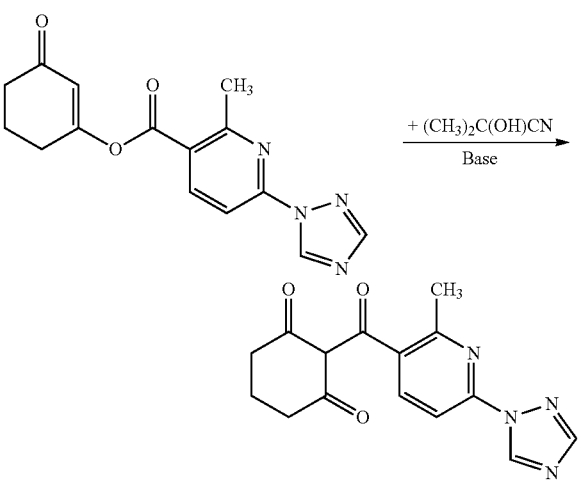

The case in which, for example, 1-cyclopropyl-2-[(dimethylamino)methylene]-3-[2-methyl-6-(1H-triazol-1-yl)pyridin-3-yl]propan-1,3-dione and hydroxylamine hydrochloride are used as raw materials in the manufacturing method (b) can be represented by the following reaction formula.

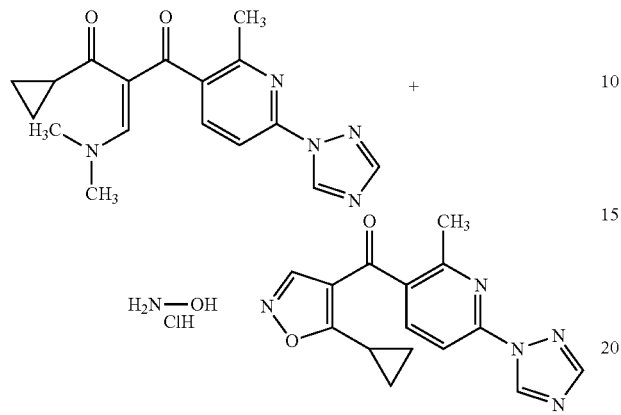

The case in which, for example, 1-cyclopropyl-3-[2-methyl-6-(1H-1,2,4-triazol-1-yl)pyridin-3-yl]propan-1,3-dione and ethyl chlorooxyimidoacetate are used as raw materials in the manufacturing method (c) can be represented by the following reaction formula.

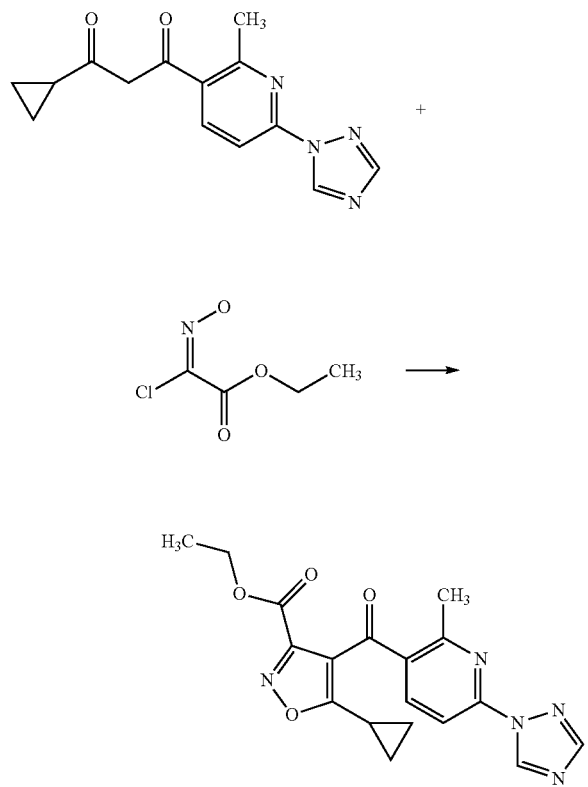

The case in which, for example, ethyl 4-[(6-chloro-2-methylpyridin-3-yl)carbonyl]-5-cyclopropylisooxazole-3-carboxylic acid ester and triazole are used as raw materials and, for example, potassium carbonate is used as a base in the manufacturing method (d) can be represented by the following reaction formula.

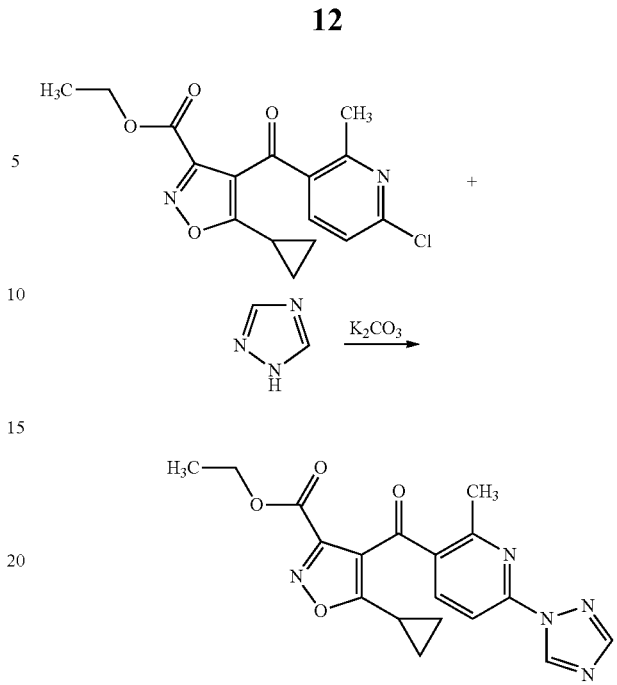

The case in which, for example, 2-[bis(methylthio)methylene]-1-cyclopropyl-3-[2-methyl-6-(1H-1,2,4-triazol-1-yl)pyridin-3-yl]-1-propan-1,3-dione and hydroxylamine hydrochloride are used as raw materials in the manufacturing method (e) can be represented by the following reaction formula.

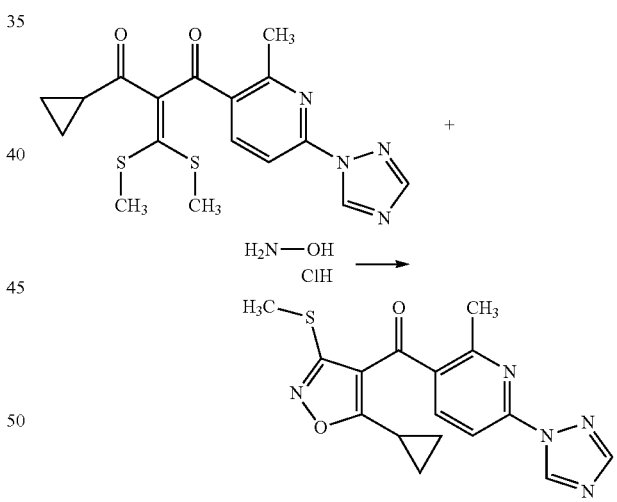

The case in which, for example, 2-methyl-6-(1H-1,2,4-triazol-1-yl) nicotinic acid chloride is used as a raw material and, for example, sodium hydride is used as a base in the manufacturing method (f) can be represented by the following reaction formula.

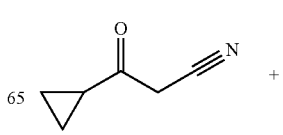

-continued

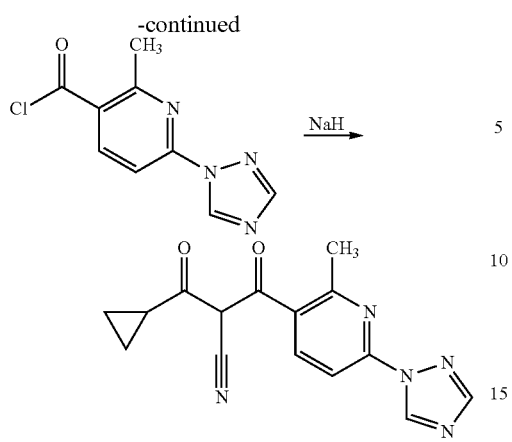

The case in which, for example, (5-cyclopropylisooxazol-4-yl)[2-methyl-6-(1H-1,2,4-triazol-1-yl)pyridin-3-yl]methanone is used as a raw material, and, for example, triethylamine is used as a base in the manufacturing method (g) can be represented by the following reaction formula.

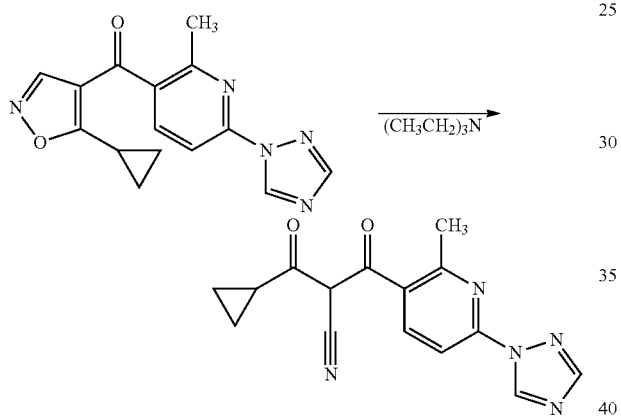

The case in which, for example, 2-{[2-methyl-6-(1H-1,2,4-triazol-1-yl)pyridin-3-yl]}cyclohexan-1,3-dione is used as a raw material and, for example, oxalyl dichloride is used as a chlorinating agent in the manufacturing method (h) can be represented by the following reaction formula.

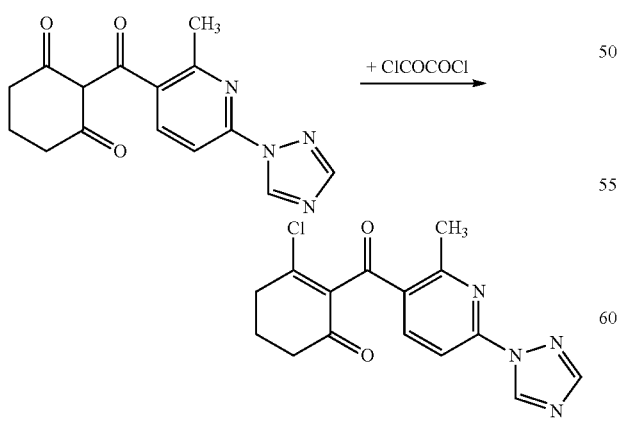

The case in which, for example, 3-chloro-2-{[2-methyl-6-(1H-1,2,4-triazol-1-yl)pyridin-3-ylcarbonyl]}-2-cyclo-hexen-1-one and thiophenol are used as raw materials in the manufacturing method (i) can be represented by the following reaction formula.

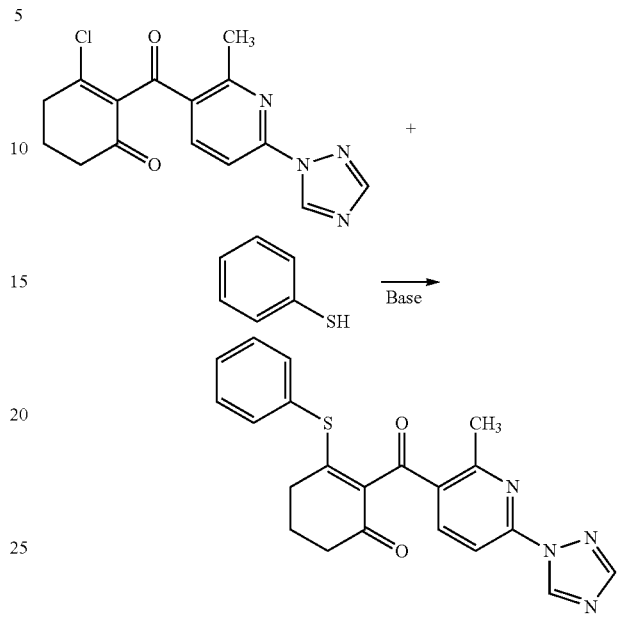

The case in which, for example, (5-hydroxy-1-methyl-1H-pyrazol-4-yl)[2-methyl-6-(1H-1,2,4-triazol-1-yl)pyridin-3-yl]methanone and phenacyl bromide are used as raw materials, and, for example, potassium carbonate is used as a base in the manufacturing method (j) can be represented by the following reaction formula.

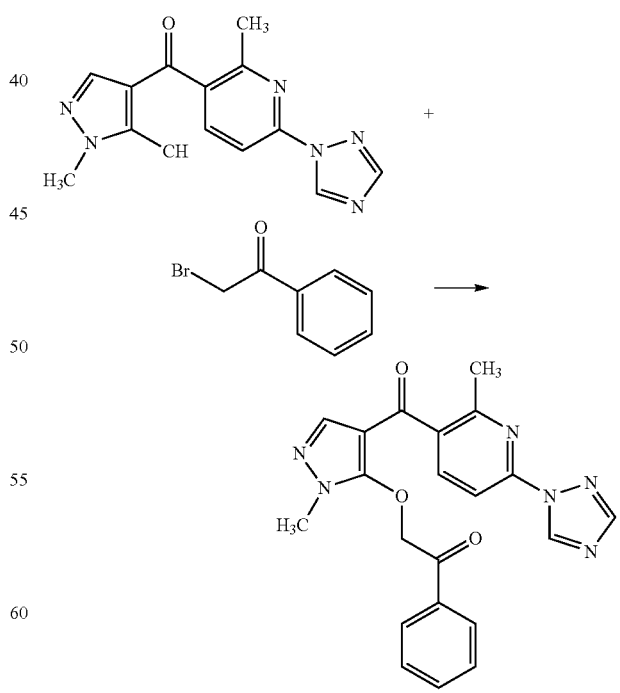

The compounds of formulae (II), (III), and (IV) serving as the raw materials in the manufacturing method (a) are novel ones, and can be obtained by reacting the compounds represented by the following formula (XXI) with the compounds represented by the following formula (XXII) or (XXIII).

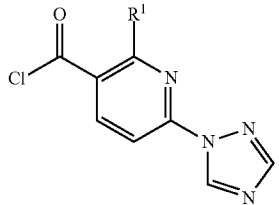

Formula (XXI)

In the formula, $R^1$ has the same meanings as the aforementioned.

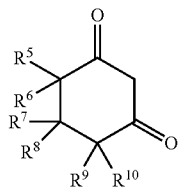

Formula (XXII)

In the formula, $R^5$, $R^6$, $R^7$, $R^8$, $R^9$ and $R^{10}$ have the same meanings as the aforementioned.

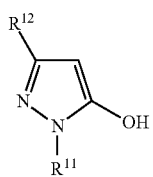

Formula (XXIII)

In the formula, $R^{11}$ and $R^{12}$ have the same meanings as the aforementioned.

The compounds of formula (XXI) are novel ones, and can be obtained by reacting the compounds represented by the following formula with thionyl chloride.

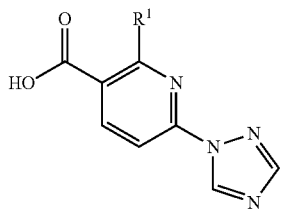

Formula (XXIV)

In the formula, $R^1$ has the same meanings as the aforementioned.

The compounds of formula (XXIV) are novel ones, and can be obtained by hydrolyzing the compounds represented by the following formula.

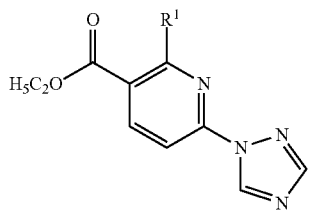

Formula (XXV)

In the formula, $R^1$ has the same meanings as the aforementioned.

The compounds of formula (XXV) are obtained by reacting the compounds represented by the following formula with 1H-1,2,4-triazole.

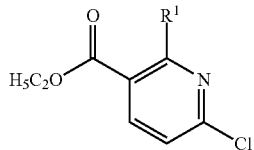

Formula (XXVI)

In the formula, $R^1$ has the same meanings as the aforementioned.

The compounds of formula (XXVI) are obtained, for example, by reacting the compounds represented by the following formula with phosphorus oxychloride. (Refer to J. Org. Chem., 1954, vol. 19, No. 2, pages 183-193).

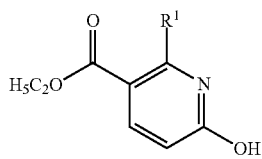

Formula (XXVII)

In the formula, $R^1$ has the same meanings as the aforementioned.

Among compounds of formula (XXVII), for example, 6-oxo compound that is the tautomer of a compound of formula (XXVII) in which $R^1$ is methyl is a publicly known compound described in J. Org. Chem., 1954, vol. 19, No. 2, pages 183-193.

Moreover, the tautomer of a compound of formula (XXVII) in which $R^1$ is trifluoromethyl is a publicly known compound described in WO2004/029027 or the like.

Among compounds of formula (XXIV), for example, a compound of formula (XXIV) in which $R^1$ is methoxymethyl, trifluoroethoxymethyl, or 2-(methoxy)ethoxymethyl can be obtained by reacting the compound of formula (XXV) in which $R^1$ is bromomethyl with corresponding metal alkoxide, and subsequently by hydrolyzing the resultant product without isolating the product.

Moreover, the compound of formula (XXIV) in which $R^1$ is 2-(methoxy)ethoxymethyl can be synthesized by continuously subjecting ethyl 2-(bromomethyl)-6-chloronicotinate corresponding to formula (XXVI) in which $R^1$ is bromomethyl to a three-step reaction of alkoxyalkylation, triazolylation, and hydrolysis without isolating the intermediate products.

Among compounds of formula (XXV), for example, the compound of formula (XXV) in which $R^1$ is methylthiomethyl can be obtained by reacting the compound of formula (XXV) in which $R^1$ is bromomethyl with corresponding metal thioalkoxide. Moreover, by oxidizing this methylthiomethyl compound, the compound of formula (XXV) in which $R^1$ is methylsulfonylmethyl can also be obtained.

Compounds of formulae (XXII) and (XXIII) are publicly known compounds.

Typical examples of the compounds of formula (XXII) include the following.

Cyclohexan-1,3-dione, 4-methylcyclohexan-1,3-dione, 4,4-dimethylcyclohexan-1,3-dione,
2,2,4,4-tetramethylcyclohexan-1,3,5-trione, bicyclo[3.2.1]octan-2,4-dione,
bicyclo[3.2.1]-6-octen-2,4-dione.

Moreover, typical examples of the compounds of formula (XXIII) include the following.

1-Methyl-1H-pyrazol-5-ol, 1-ethyl-1H-pyrazol-5-ol, 1,3-dimethyl-1H-pyrazol-5-ol,
3-cyclopropyl-1-methyl-1H-pyrazol-5-ol.

Typical examples of the compounds of formulae (II), (III), and (IV) as the raw materials in the manufacturing method (a) include the following.

3-Oxo-1-cyclohexen-1-yl 2-(methoxymethyl)-6-(1H-1,2,4-triazol-1-yl)nicotinate,
3-oxo-1-cyclohexen-1-yl 2-[(methylthio)methyl]-6-(1H-1,2,4-triazol-1-yl)nicotinate,
4,4-dimethyl-3-oxo-1-cyclohexen-1-yl 2-methyl-6-(1H-1,2,4-triazol-1-yl)nicotinate,
4-oxobicyclo[3.2.1]-2-octen-2-yl 2-methyl-6-(1H-1,2,4-triazol-1-yl)nicotinate,
1-ethyl-1H-pyrazol-5-yl 2-methyl-6-(1H-1,2,4,-triazol-1-yl)nicotinate,
1,3-dimethyl-1H-pyrazol-5-yl 2-(methoxymethyl)-6-(1H-1,2,4-triazol-1-yl)nicotinate,
3-cyclopropyl-1-methyl-1H-pyrazol-5-yl 2-methyl-6-(1H-1,2,4-triazol-1-yl)nicotinate,
1-methyl-1H-pyrazole-5-yl 2-[(methylthio)methyl]-6-(1H-1,2,4-triazol-1-yl)nicotinate.

The compounds of formulae (V) and (VI) as the raw materials in the manufacturing method (b) are novel ones, and, for example, can be obtained as a mixture of formulae (V) and (VI) by reacting the compounds of formula (IX) with dimethylformamide dimethylacetal.

Moreover, the compounds of formulae (VII) and (VIII) are also novel ones, and can be obtained as a mixture of formulae (VII) and (VIII) by reacting the compounds of formula (IX) with ethyl orthoformate.

The compounds of formula (V) and the compounds of formula (VI), and the compounds of formula (VII) and the compounds of formula (VIII) are geometrical isomers.

Typical examples of compounds of formulae (V), (VI), (VII), and (VIII) as the raw materials in the manufacturing method (b) include the following.

(2E)-1-cyclopropyl-2-[(dimethylamino)methylene]-3-[2-methyl-6-(1H-1,2,4-triazol-1-yl)pyridin-3-yl]propan-1,3-dione,
(2E)-1-cyclopropyl-2-[(dimethylamino)methylene]-3-[2-methyl-6-(1H-1,2,4-triazole-1-yl)pyridin-3-yl]propan-1, 3-dione,
(2E)-1-cyclopropyl-2-[(dimethylamino)methylene]-3-[2-(methoxymethyl)-6-(1H-1,2,4,-triazol-1-yl)pyridin-3-yl]propan-1,3-dione,
(2E)-2-[(dimethylamino)methylene]-4,4-dimethyl-1-[2-methyl-6-(1H-1,2,4,-triazol-1-yl)pyridin-3-yl]pentan-1,3-dione,
(2E)-1-cyclopropyl-2-[(dimethylamino)methylene]-3-[2-(methylthio)methyl]-6-(1H-1,2,4-triazol-1-yl)pyridin-3-yl]propane-1,3-dione,
(2E)-1-cyclopropyl-2-[(dimethylamino)methylene]-3-[6-(1H-1,2,4-triazole-1-yl)-2-(trifluoromethyl)pyridin-3-yl]propan-1,3-dione.
(2Z)-1-cyclopropyl-2-[(dimethylamino)methylene]-3-[2-(methoxymethyl)-6-(1H-1,2,4,-triazol-1-yl)pyridin-3-yl]propane-1,3-dione,
(2Z)-1-cyclopropyl-2-[(dimethylamino)methylene]-3-[2-methyl-6-(1H-1,2,4-triazol-1-yl)pyridin-3-yl]propan-1,3-dione,
(2Z)-2-[(dimethylamino)methylene]-4,4-dimethyl-1-[2-methyl-6-(1H-1,2,4-triazol-1-yl)pyridin-3-yl]pentan-1,3-dione,
(2Z)-1-cyclopropyl-2-[(dimethylamino)methylene]-3-{2-[(methylthio)methyl]-6-(1H-1,2,4,-triazol-1-yl)pyridin-3-yl}propane-1,3-dione],
(2Z)-1-cyclopropyl-2-[(dimethylamino)methylene]-3-[6-(1H-1,2,4-triazol-1-yl)-2-(trifluoromethyl)pyridin-3-yl]propan-1, 3-dione,
(2E)-1-cyclopropyl-2-(ethoxymethylene)-3-[2-(methoxymethyl)-6-(1H-1,2,4-triazole-1-yl)pyridin-3-yl]propan-1,3-dione,
(2E)-1-cyclopropyl-2-(ethoxymethylene)-3-[2-methyl-6-(1H-1,2,4,-triazol-1-yl)pyridin-3-yl]propan-1, 3-dione,
(2E)-2-(ethoxymethylene)-4,4-dimethyl-1-[2-methyl-6-(1H-1,2,4-triazol-1-yl)pyridin-3-yl]pentan-1,3-dione,
(2E)-1-cyclopropyl-2-(ethoxymethylene)-3-{2-[(methylthio)methyl]-6-(1H-1,2,4-triazol-1-yl)pyridin-3-yl}propan-1,3-dione,
(2E)-1-cyclopropyl-2-(ethoxymethylene)-3-[6-(1H-1,2,4-triazol-1-yl)-2-(trifluoromethyl)pyridin-3-yl]propan-1,3-dione,
(2Z)-1-cyclopropyl-2-(ethoxymethylene)-3-[2-(methoxymethyl)-6-(1H-1,2,4-triazol-1-yl)pyridin-3-yl]propane-1,3-dione,
(2Z)-1-cyclopropyl-2-(ethoxymethylene)-3-[2-methyl-6-(1H-1,2,4,-triazol-1-yl)pyridin-3-yl]propane-1,3-dione,
(2Z)-2-(ethoxymethylene)-4,4-dimethyl-1-[2-methyl-6-(1H-1,2,4,-triazol-1-yl)pyridin-3-yl]pentan-1,3-dione,
(2Z)-1-cyclopropyl-2-(ethoxymethylene)-3-{2-[(methylthio)methyl]-6-(1H-1,2,4,-triazol-1-yl)pyridin-3-yl}propan-1,3-dione,
(2Z)-1-cyclopropyl-2-(ethoxymethylene)-3-[6-(1H-1,2,4,-triazol-1-yl)-2-(trifluoromethyl)pyridin-3-yl]propan-1,3-dione.

The compounds of formula (IX) as the raw material in the manufacturing method (c) are novel ones, and can be obtained, for example, by reacting the compounds represented by the following formula with acid.

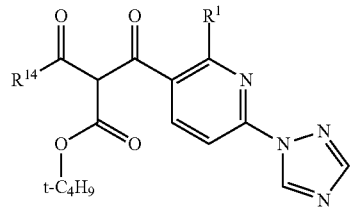

Formula (XXVIII)

In the formula, $R^1$ and $R^{14}$ have the same meanings as the aforementioned.

The compounds of formula (XXVIII) can be obtained by reacting the compounds of the formula (XXI) with the compounds represented by the following formula.

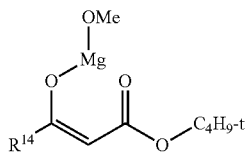

Formula (XXIX)

In the formula, $R^{14}$ has the same meanings as the aforementioned.

The compounds of formula (XXIX) are publicly known compounds described in WO99/03856.

The acid reacted with the compounds of formula (XXVIII) is, for example, hydrochloric acid, sulfuric acid, or trifluoro acetic acid.

Typical examples of the compounds of formula (IX) as the raw material in the manufacturing method (c) include the following.
1-Cyclopropyl-3-[(6-(1H-1,2,4-triazol-1-yl)-2-(trifluoromethyl)pyridin-3-yl]propane-1,3-dione,
1-cyclopropyl-3-[2-(methoxymethyl)-6-(1H-1,2,4-triazol-1-yl)pyridin-3-yl]propan-1,3-dione,
4, 4-dimethyl-1-[2-methyl-6-(1H-1,2,4-triazol-1-yl)pyridin-3-yl]pentan-1,3-dione,
1-cyclopropyl-3-{2-[(methylthio)methyl]-6-(1H-1,2,4-triazol-1-yl)pyridin-3-yl}propan-1,3-dione.

The compounds of formula (X) as the raw material in the manufacturing method (c) are imidoyl chlorides well known in organic chemistry, and a typical example thereof is ethyl 2-chloro-2-(hydroxyimino) acetate.

The compounds of formula (XI) as the raw material in the manufacturing method (d) are novel ones, and can be obtained, for example, by reacting the compounds represented by the following formula with the compounds of formula (X).

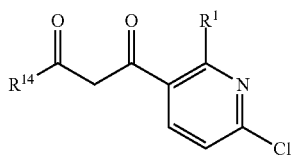

Formula (XXX)

In the formula, $R^1$ and $R^{14}$ have the same meanings as the aforementioned.

The compounds of formula (XXX) are novel ones, and can be obtained, for example, by reacting the compounds represented by the following formula with acid.

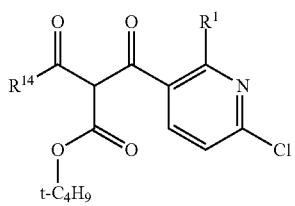

Formula (XXXI)

In the formula, $R^1$ and $R^{14}$ have the same meanings as the aforementioned.

The compounds of formula (XXXI) are novel ones, and can be obtained, for example, by reacting the compounds represented by the following formula with the compounds represented by formula (XXIX).

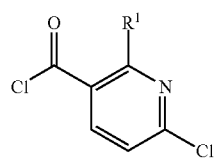

Formula (XXXII)

In the formula, $R^1$ has the same meanings as the aforementioned.

The compounds of formula (XXXII) can be obtained easily by hydrolyzing the compounds of the formula (XXVI), and subsequently reacting the obtained compounds with thionyl chloride.

Among compounds of formula (XXXII), the compound in which $R^1$ is methyl is publicly known one described in Japanese Patent Laid-Open No. 3-38586, and the compound in which $R^1$ is methoxy is publicly known one described in Japanese Patent Laid-Open No. 52-3968.

As the acid to be reacted with the compounds of formula (XXXI), compounds the same as those explained in the manufacturing method (c) can be used.

Typical examples of the compounds of formula (XI) as the raw material in the manufacturing method (d) include the following.
Ethyl 4-{[6-chloro-2-(trifluoromethyl)pyridin-3-yl]carbonyl-5-cyclopropylisooxazole-3-carboxylic acid ester, ethyl 5-tert-butyl-4-[(6-chloro-2-methylpyridin-3-yl)carbonyl]isooxazole-3-carboxylic acid ester.

The compounds of formula (XII) as the raw material in the manufacturing method (e) are novel ones, and can be obtained, for example, by reacting the compounds represented by formula (IX) with carbon disulfide and methyl iodide in the presence of potassium fluoride carried by alumina.

Typical examples of the compounds of formula (XII) include the following.
2-[Bis(methylthio)methylene]-1-cyclopropyl-3-[6-(1H-1,2,4-triazol-1-yl)-2-(trifluoromethyl)pyridin-3-yl]propan-1,3-dione,
2-[bis(methylthio)methylene]-1-[2-(methoxymethyl)-6-(1H-1,2,4-triazol-1-yl)pyridin-3-yl]-4,4-dimethylpentan-1,3-dione,
2-[bis(methylthio)methylene]-1-cyclopropyl-3-[2-(methoxymethyl)-6-(1H-1,2,4-triazol-3-yl)pyridin-3-yl]propan-1, 3-dione,
2-[bis(methylthio)methylene]-1-cyclopropyl-3-{2-[(methylthio)methyl]-6-(1H-1,2,4,-triazol-3-yl)pyridin-3-yl}propan-1,3-dione.

The compounds of formula (XIII) as the raw material in the manufacturing method (f) include the compounds of formula (XXI) and are novel ones, and their representative ones are compounds corresponding to the compounds of formula (XXI).

Typical examples of the compounds of formula (XIII) include the following.
2-(Methoxymethyl)-6-(1H-1,2,4-triazol-1-yl)nicotinic acid chloride, 6-(1H-1,2,4-triazol-1-yl)-2-(trifluoromethyl)nicotinic acid chloride,
2-[(methylthio)methyl]-6-(1H-1,2,4-triazol-1-yl)nicotinic acid chloride,
6-(1H-1,2,4-triazol-1-yl)-2-[(2,2,2-trifluoroethoxy)methyl] nicotinic acid chloride,
2-[(2-methoxyethoxy)methyl]-6-(1H-1,2,4-triazol-1-yl) nicotinic acid chloride.

Similarly, the compounds of formula (XIV) as the raw material in the manufacturing method (f) are publicly known ones, and examples thereof include the following compounds.
3-Oxobutanenitrile, 3-oxopentanenitrile,
3-cyclopropyl-3-oxopropanenitrile,
4,4-dimethyl-3-oxopentanenitrile.

The compounds of formula (XV) as the raw material in the manufacturing method (g) corresponds to the compounds in which Q is Q3 and $R^{15}$ is hydrogen in the formula (I) of the present invention.

The compounds of formula (XV) can be obtained by the manufacturing method (b).

Typical examples of the compounds of formula (XV) include the following.
(5-Cyclopropylisooxazol-4-yl)[2-(methoxymethyl)-6-(1H-1,2,4-triazol-1-yl]pyridin-3-yl)methanone,
(5-cyclopropylisooxazol-4-yl){2-[(methylthio)methyl]-6-(1H-1,2,4-triazol-1-yl)pyridin-3-yl}methanone,
(5-cyclopropylisooxazol-4-yl)[6-(1H-1,2,4-triazol-1-yl)-2-(trifluoromethyl)pyridin-3-yl]methanone,
(5-tert-butylisooxazol-4-yl)[2-methyl-6-(1H-1,2,4,-triazol-1-yl)pyridin-3-yl]methanone.

The compounds of respective formulae (XVI), (XVII), and (XIX) as the raw materials in the manufacturing methods of (h), (i), and (j) are also included in the formula (I) of the present invention, and can be obtained by the manufacturing method (a).

Typical examples of the compounds of formula (XVI) include the following.
2-{[6-(1H-1,2,4-triazol-1-yl)-2-(trifluoromethyl)pyridin-3-yl]carbonyl}cyclohexan-1,3-dione,
2-{[2-(methoxymethyl)-6-(1H-1,2,4-triazol-1-yl)pyridin-3-yl]carbonyl}cyclohexan-1,3-dione,
2-({2-[(methylthio)methyl]-6-(1H-1,2,4-triazol-1-yl)pyridin-3-yl}carbonyl)cyclohexan-1,3-dione,
4,4-dimethyl-2-{[2-methyl-6-(1H-1,2,4,-triazol-1-yl)pyridin-3-yl]carbonyl}cyclohexan-1,3-dione,
3-{[2-methyl-6-(1H-1,2,4,-triazol-1-yl)pyridin-3-yl]carbonyl)bicyclo[3.2.1]octan-2,4-dione.

Typical examples of the compounds of formula (XVII) include the following.
3-Chloro-2-{[6-(1H-1,2,4-triazol-1-yl)-2-(trifluoromethyl)pyridin-3-yl]carbonyl-2-cyclohexen-1-one,
3-chloro-2-{[2-(methoxymethyl)-6-(1H-1,2,4-triazol-1-yl)pyridin-3-yl]carbonyl}-2-cyclohexen-1-one,
3-chloro-2-({2-[(methylthio)methyl]-6-(1H-1,2,4-triazol-1-yl)pyridine-3-yl}carbonyl)-2-cyclohexen-1-one,
4-chloro-3-{[2-methyl-6-(1H-1,2,4,-triazol-1-yl)pyridin-3-yl]carbonyl}bicyclo[3.2.1]-3-octen-2-one.

Typical examples of the compounds of formula (XIX) include the following.
(1-Ethyl-hydroxy-1H-pyrazol-4-yl)[2-methyl-6-(1H-1,2,4-triazol-1-yl)pyridin-3-yl]methanone,
(5-hydroxy-1,3-dimethyl-1H-pyrazol-4-yl)[2-methyl-6-(1H-1,2,4-triazol-1-yl)pyridin-3-yl]methanone,
(3-cyclopropane-5-hydroxy-1-methyl-1H-pyrazol-4-yl)[2-methyl-6-(1H-1,2,4-triazol-1-yl)pyridin-3-yl]methanone,
(5-hydroxy-1-methyl-1H-pyrazol-4-yl)[(methoxymethyl)-6-(1H-1,2,4-triazol-1-yl)pyridin-3-yl]methanone.

The halogenating agent in the manufacturing method (h), the compounds of formula (XVIII) as the raw material in the manufacturing method (i), and the compounds of formula (XX) as the raw material in the manufacturing method (j) are well known.

As the halogenating agent, the following ones can be used. Phosphorus oxychloride, phosporus oxybromide, phosporus trichloride, phosporus tribromide, oxalyl dichloride, oxalyl dibromide, thionyl chloride, and thionyl bromide.

Examples of the compounds of formula (XVIII) include the following.
Methanethiol, thiophenol, benzylthiol, imidazole, pyrazole, 1,2,4-triazole, and tetrazole.

Examples of the compounds of formula (XX) include the following.
Iodomethane, allyl bromide, propargyl bromide, benzyl bromide, methanesulfonyl chloride, ethanesulfonyl chloride, propanesulfonyl chloride, benzenesulfonyl chloride, p-toluenesulfonyl chloride, and phenacyl chloride.

The reaction of the manufacturing method (a) can be carried out in a suitable diluent, and examples of the diluent include aliphatic, cycloaliphatic, and aromatic hydrocarbons (that are chlorinated in some cases), for example, toluene, dichloromethane, chloroform, and 1,2-dichloroethane; ethers, for example, ethyl ether, dimethoxyethane (DME), and tetrahydrofuran (THF); ketones, for example, methyl isobutyl ketone (MIBK); nitriles, for example, acetonitrile; esters, for example, ethyl acetate; acid amides, for example, dimethylformamide (DMF).

The manufacturing method (a) can be carried out in the presence of a cyanogen compound and a base, and examples of the cyanide compound include sodium cyanide, potassium cyanide, acetone cyanohydrin, and hydrogen cyanide. Examples of the base include inorganic bases such as hydroxides and carbonates of alkaline metals and alkaline earth metals, for example, sodium carbonate, potassium carbonate, lithium hydroxide, sodium hydroxide, potassium hydroxide, and calcium hydroxide; and organic bases such as tertiary amines, dialkylaminoanilines, and pyridines, for example, triethylamine, pyridine, 4-dimethylaminopyridine (DMAP), 1,4-diazabicyclo[2,2,2]octane (DABCO), and 1,8-diazabicyclo[5.4.0]undec-7-ene (DBU).

The manufacturing method .(a) can be carried out by adding a phase transfer catalyst, and examples of the phase transfer catalysts include crown ethers, for example, dibenzo-18-crown-6, 18-crown-6, and 15-crown-5.

The manufacturing method (a) can be carried out in a substantially wide temperature range. The temperature is generally from about −10 to about 80° C., and preferably from about 5 to about 40° C. Moreover, it is desirable that the reaction is carried out under normal pressure, but the operation can also be carried out under pressure or under reduced pressure in some cases.

In the manufacturing method (a), a target compound of formula (I) can be obtained, for example, by reacting 1 to 4 mol of triethylamine with 1 mol of a compound of formula (II) in a diluent, for example, acetonitrile, in the presence of 0.01 to 0.5 mol of acetone cyanohydrin.

When rearrangement reaction of the compounds of formula (IV) are carried out in the manufacturing method (a), the rearrangement of the compound of formula (IV) can be conducted in the presence of a base.

Such a reaction can be carried out in an appropriate diluent, and examples of the diluent include ethers, for example, dioxane, and tetrahydrofuran (THF); and alcohols, for example, tert-amylalcohol, and tert-butylalcohol.

Moreover, examples of the base include inorganic bases such as carbonates of alkaline metals, for example, sodium carbonate, and potassium carbonate; and organic bases, such as tertiary amines, for example, triethylamine, pyridine, and 4-dimethylaminopyridine (DMAP).

The reaction can be carried out in a substantially wide temperature range, and the temperature is generally from about 5 to about 200° C., and preferably from about 25 to about 130° C. Moreover, it is desirable that the reaction is carried out under normal pressure, but the operation can be carried out under pressure or under reduced pressure in some cases.

In the reaction, a target compound of formula (I) can be obtained, for example, by reacting 0.5 to 2 mol of potassium carbonate with 1 mol of the compound of formula (IV) in a diluent, for example, dioxane.

The reaction of the manufacturing method (b) can be carried out in an appropriate diluent, and examples of the diluent include aliphatic, cycloaliphatic, and aromatic hydrocarbons (that may be chlorinated in some cases), for example, toluene, dichloromethane, chloroform, and 1,2-dichloroethane; ethers, for example, tetrahydrofuran (THF); nitriles, for example, acetonitrile; and alcohols, for example, methanol, ethanol, and isopropanol.

The manufacturing method (b) can be carried out in a substantially wide temperature range. The temperature is generally from about −10 to about 100° C., and preferably from about 0 to about 50° C. Moreover, it is desirable that the reaction is carried out under normal pressure, but the operation can be carried out under pressure or under reduced pressure in some cases.

In the manufacturing method (b), a target compound of the formula (I) can be obtained, for example, by reacting 1 to 1.5 mol of hydroxylamine hydrochloride with 1 mol of the compound of formula (V) in a diluent, for example ethanol, in the presence of 1 to 1.5 mol of sodium acetate.

The manufacturing method (b) can be successively carried out without isolating the compounds of formulae (V), (VI), (VII) and (VIII), and a target compound of formula (I) can be obtained.

The reaction of the manufacturing method (c) can be carried out in an appropriate diluent, and examples of the diluent include aliphatic, cycloaliphatic, and aromatic hydrocarbons (that may be chlorinated in some cases), for example, toluene, dichloromethane, chloroform, and 1,2-dichloroethane; ethers, for example, tetrahydrofuran (THF); nitriles, for example, acetonitrile; and alcohols, for example, methanol, ethanol, and isopropanol.

The manufacturing method (c) can be carried out in the presence of a base, and examples of the bases include inorganic bases such as acetates, carbonates, and bicarbonates of alkaline metals and alkaline earth metals, for example, sodium acetate, sodium hydrogen carbonate, potassium hydrogen carbonate, sodium carbonate, and potassium carbonate; and organic bases such as tertiary amines, dialkylaminoanilines, and pyridines, for example, triethylamine, pyridine, and 4-dimethylaminopyridine (DMAP).

The manufacturing method (c) can be carried out in a substantially wide temperature range. The temperature is generally from about −10 to about 100° C., and preferably from about 0 to about 50° C.: Moreover, it is desirable that the reaction is carried out under normal pressure, but the operation can be carried out under pressure or under reduced pressure in some cases.

In the manufacturing method (c), a target compound of the formula (I) can be obtained, for example, by reacting 1 to 1.5 mol of the compound of formula (X) with 1 mol of the compound of formula (IX) in a diluent, for example, toluene.

The reaction of the manufacturing method (d) can be carried out in an appropriate diluent, and examples of the diluent include aliphatic, cycloaliphatic, and aromatic hydrocarbons (that may be chlorinated in some cases), for example, pentane, hexane, cyclohexane, petroleum ether, ligroin, benzene, toluene, xylene, dichloromethane, chloroform, carbon tetrachloride, 1,2-dichloroethane, chlorobenzene, and dichlorobenzene; ethers, for example, ethyl ether, methyl ethyl ether, isopropyl ether, butyl ether, dioxane, dimethoxyethane (DME), tetrahydrofuran (THF), and diethylene glycol dimethyl ether (DGM); ketones, for example, acetone, methyl ethyl ketone (MEK), methyl isopropyl ketone, and methyl isobutyl ketone (MIBK); nitriles, for example, acetonitrile, propionitrile, and acrylonitrile; esters, for example, ethyl acetate, and amyl acetate; acid amides, for example, dimethylformamide (DMF), dimethylacetamide (DMA), N-methylpyrolidone, 1,3-dimethyl-2-imidazolidinone, and hexamethylphosphoric triamide (HMPA); sulfones and sulfoxides, for example, dimethyl sulfoxide (DMSO), and sulfolane; and bases, for example, pyridine.

The manufacturing method (d) can be carried out in the presence of an acid binding agent, and examples of such an acid binding agent include inorganic bases, such as hydrides, hydroxides, carbonates and bicarbonates of alkaline metals and alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, and calcium hydroxide; inorganic alkaline metal amides, for example, lithium amide, sodium amide, and potassium amide; organic bases such as alcoholate, tertiary amines, dialkylaminoanilines and pyridines, for example, triethylamine, 1,1,4,4-tetramethylethylenediamine (TMEDA), N,N-diethylaniline, pyridine, 4-dimethylaminopyridine (DMAP), 1,4 diazabicyclo[2,2,2]octane (DABCO), and 1,8-diazabicyclo[5,4,0] undec-7-ene (DBU); and organic lithium compounds, for example, methyl lithium, n-butyl lithium, sec-butyl lithium, tert-butyl lithium, phenyl lithium, dimethyl copper lithium, lithium diisopropylamide, lithium cyclohexylisopropylamide, lithium dicyclohexylamide, n-butyl lithium/DABCO, n-butyl lithium/DBU, and n-butyl lithium/TMEDA.

The manufacturing method. (d) can be carried out in a substantially wide temperature range. It is generally carried out between about 25 and about 180° C., preferably between about 50 and about 180° C. Moreover, it is desirable that the reaction is carried out under normal pressure, but the operation can also be carried out under pressure or under reduced. pressure.

In the manufacturing method (d), a target compound can be obtained, for example, by reacting 1 mol to .5 mol of 1H-1, 2,4-triazole with 1 mol of the compound of formula (XI) in a diluent, for example, dimethylformamide in the presence of a base, for example, potassium carbonate.

The reaction of the manufacturing method (e) can be carried out under conditions similar to those of the manufacturing method (b).

The manufacturing method (f) can be carried out in an appropriate diluent, and examples of the diluent include aliphatic, cycloaliphatic, and aromatic hydrocarbons (that may be chlorinated in some cases), for example, pentane, hexane, cyclohexane, petroleum ether, ligroin, benzene, toluene, xylene, dichloromethane, chloroform, carbon tetrachloride, 1,2-dichloroethane, chlorobenzene, and dichlorobenzene; ethers, for example, ethyl ether, methyl ethyl ether, isopropyl ether, butyl ether, dioxane, dimethoxyethane (DME), tetrahydrofuran (THF), and diethylene glycol dimethyl ether (DGM); acid amides, for example, dimethylformamide (DMF), dimethylacetamide (DMA), N-methylpyrolidone, 1,3-dimethyl-2-imidazolidinone, and hexamethylphosphoric triamide (HMPA); sulfones and sulfoxides, for example, dimethylsulfoxide (DMSO), and sulfolane; and bases, for example, pyridine.

The manufacturing method (f) can be carried out in the presence of an acid binding agent, and examples of the acid binding agent include inorganic bases such as hydrides, hydroxides, carbonates, and bicarbonates of alkaline metals and alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, and calcium hydroxide; inorganic alkaline metal amides, for example, lithium amide, sodium amide, and potassium amide; organic bases such as alcoholate, tertiary amines, dialkylaminoanilins, and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU); and organic lithium compounds, for example, methyl lithium, n-butyl lithium, sec-butyl lithium, tert-butyl lithium, phenyl lithium, dimethyl copper lithium, lithium diisopropyl amide, lithium cyclohexylisopropylamide, lithium dicyclohexylamide, n-butyl lithium/DABCO, n-butyl lithium/DBU, and n-butyl lithium/TMEDA.

The manufacturing method (f) can be carried out in a substantially wide temperature range. It is generally carried out between about −70 and about 200° C., and preferably between about −50 and about 100° C. Moreover, it is desirable that the reaction is carried out under normal pressure, but the operation can be carried out under pressure or under reduced pressure.

In manufacturing method (f), a target compound can be obtained, for example, by reacting 1 mol to 2 mol of the compound of formula (XIV) with 1 mol of the compound of formula (XIII) in a diluent, for example THF in the presence of 1.0 mol to 3 mol of sodium hydride.

The reaction of the manufacturing method (g) can be carried out in an appropriate diluent, and examples of the diluent include water; aliphatic, cycloaliphatic, and aromatic hydrocarbons (that may be chlorinated in some cases), for example, pentane, hexane, cyclohexane, petroleum ether, ligroin, benzene, toluene, xylene, dichloromethane, chloroform, carbon tetrachloride, 1,2-dichloroethane, chlorobenzene, and dichlorobenzene; ethers, for example, ethyl ether, methyl ethyl ether, isopropyl ether, butyl ether, dioxane, dimethoxyethane (DME), tetrahydrofuran (THF), and diethylene glycol dimethyl ether (DGM); alcohols, for example, methanol, ethanol, isopropanol, butanol, and ethylene glycol; esters, for example, ethyl acetate, and amyl acetate; acid amides, for example, dimethylformamide (DMF), dimethylacetamide (DMA), N-methylpyrolidone, 1,3-dimethyl2-imidazolidinone, and hexamethylphosphoric triamide (HMPA); sulfones and sulfoxides, for example, dimethyl sulfoxide (DMSO), and sulfolane; and bases, for example, pyridine.

The manufacturing method (g) can be carried out in a substantially wide temperature range. It is generally carried out between about −70 and about 200° C., and preferably between about −30 and about 100° C. Moreover, it is desirable that the reaction is carried out under normal pressure, but the operation can also be carried out under pressure or under reduced pressure.

In the manufacturing method (g), a target compound can be obtained, for example, by reacting 1 mol of the compound of formula (XV) in a diluent, for example, dichloromethane in the presence of 1 mol to 3 mol of triethylamine.

The reaction of the manufacturing method (h) can be carried out in an appropriate diluent, and examples of the diluent include aliphatic, cycloaliphatic, and aromatic hydrocarbons (that may be chlorinated in some cases), for example, pentane, hexane, cyclohexane, petroleum ether, ligroin, benzene, toluene, xylene, dichloromethane, chloroform, carbon tetrachloride, 1,2-dichloroethane, and chlorobenzene; ethers, for example, ethyl ether, methyl ethyl ether, isopropyl ether, butyl ether, dioxane, dimethoxyethane (DME), tetrahydrofuran (THF), and diethylene glycol dimethyl ether (DGM); ketones, for example, acetone, methyl ethyl ketone (MEK), methyl isopropyl ketone, and methyl isobutyl ketone (MIBK); nitriles, for example acetonitrile, and propionitrile; esters, for example, ethyl acetate, and amyl acetate; and acid amides, for example, dimethylformamide (DMF), dimethyl acetamide (DMA), N-methylpyrolidone, 1,3-dimethyl-2-imidazolidinone, and hexamethylphosphoric triamide (RMPA).

The reaction of the manufacturing method (h) can be carried out in a substantially wide temperature range. The temperature is generally from about −20 to about 100° C., and preferably about 0 to about 50° C. Moreover, it is desirable that the reaction is carried out under normal pressure, but the operation can also be carried out under pressure or under reduced pressure in some cases.

In the manufacturing method (h), a target compound of formula (I) can be obtained, for example, by reacting 1 to 5 mol of oxalyl dichloride with 1 mol of the compound of formula (XVI) in a diluent, for example, dichloromethane.

The reaction of the manufacturing method (i) can be carried out in an appropriate diluent, and examples of the diluent include aliphatic, cycloaliphatic, and aromatic hydrocarbons (that may be chlorinated in some cases), for example, pentane, hexane, cyclohexane, petroleum ether, ligroin, benzene, toluene, xylene, dichloromethane, chloroform, carbon tetrachloride, 1,2-dichloroethane, chlorobenzene, and dichlorobenzene; ethers, for example, ethyl ether, methyl ethyl ether, isopropyl ether, butyl ether, dioxane, dimethoxyethane (DME), tetrahydrofuran (THF), and diethylene glycol dimethyl ether (DGM); ketones, for example, acetone, methyl ethyl ketone (MEK), methyl isopropyl ketone, and methyl isobutyl ketone (MIBK); nitriles, for example, acetonitrile, propionitrile, and acrylonitrile; esters, for example, ethyl acetate, and amyl acetate; acid amides, for example, dimethylformamide (DMF), dimethylacetamide (DMA), and N-methylpyrolidone; sulfones and sulfoxides, for example, dimethlsulfoxide (DMSO), and sulfolane; and bases, for example, pyridine.

The manufacturing method (i) can be carried out in the presence of an acid binding agent, and examples of the acid binding agent include inorganic bases such as hydrides and carbonates of alkaline metals, for example, sodium hydride, lithium hydride, sodium carbonate, and potassium carbonate; and organic bases such as tertiary amines, dialkylaminoanilines and pyridines, for example, triethylamine, 1,1,4,4-tetramethylethylenediamine (TMEDA), pyridine, 4-dimethyaminopyridine (DMAP), 1,4-diazabicyclo[2,2,2]octane (DABCO), and 1,8-diazabicyclo[5,4,0]undec-7-ene (DBU).

The reaction of the manufacturing method (i) can be carried out in a substantially wide temperature range. The temperature is generally from about −20 to about 140° C., and preferably from about 0 to about 100° C. Moreover, it is desirable that the reaction is carried out under normal pressure, but the operation can also be carried out under pressure or under reduced pressure in some cases.

In the manufacturing method (i), a target compound of formula (I) can be obtained, for example, by reacting 1 to 5 mol of the compound of formula (XVIII) with 1 mol of the compound of formula (XVII) in a diluent, for example, tetrahydrofuran in the presence of 1 to 5 mol of triethylamine.

The reaction of the manufacturing method (j) can be carried out under conditions similar to those of the manufacturing method (h).

The active compound of formula (I) of the present invention shows excellent herbicide activity for various weeds as shown in biological test examples described later, and can be used as a herbicide. In the present specification, the weeds mean, in a broad sense, all plants growing in locations where they are undesired. The compound of the present invention acts as a selective herbicide depending on the application concentration. The active compound can be used, for example, between the following weeds and cultivated plants.

The genus of dicotyledonous weeds: *Sinapis, Capsella, Leipidium, Galium, Stellaria, Chenopodium, Kochia, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia, SeSbania, Trifolium, Abutilon, Lamium, Matricaria, Artemisia, Sesbania, Pharbitis, Amaranthus* and the like.

The genus of dicotyledonous cultivated plants: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita* and the like.

The genus of monocotyledonous weeds: *Echinochlona, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon, Commelina, Brachiaria, Leptochloa, Echinochloa* and the like.

The genus of monocotyledonous cultivated plants: *Oryza, Zea, Triticum, Hordeum, Avena, Secale, Sorghum, Panicum, Saccharum, Ananas, Asparagus, Allium* and the like.

However, use of the active compound of formula (I) of the present invention is not limited only for weeds of these kinds of grasses, and can be applied similarly to weeds of other kinds of grasses.

Use of the compound of the present invention is not limited to the above plants and similarly applicable to other plants. Moreover, the active compounds of the present invention can non-selectively control weeds according to the application concentration, and can be used at, for example, an industrial site such as a factory, a railroad track, a road, a forested site, a non-forested site or the like. Furthermore, the active compounds of the present invention can be used to control weeds in perennial plant cultivation, and can be applied to, for example, planting, ornamental planting, orchard, grape vineyard, citrus orchard, nut orchard, banana plantation, coffee plantation, tea plantation, rubber plant plantation, guinea oil palm plantation, cocoa plantation, small orchard, hop plantation or the like, and, in annual plant cultivation, can also be applied to selectively control weeds.

The active compounds of the present invention, for actual use, can be prepared in customary formulations. Examples of the formulations include solution, wettable powder, emulsion, suspension, dust, water-dispersible granule, tablet, granule, suspended emulsifiable concentrate, and microcapsules in a polymer substance.

These formulations can be manufactured by known methods per se. For example, they can be prepared by mixing the active compounds with extenders, namely, liquid or solid diluents or carriers, and, optionally, with surfactants, namely emulsifiers and/or dispersants and/or foam-forming agents.

Examples of the liquid diluents or carriers include aromatic hydrocarbons (for example, xylene, toluene, and alkyl naphthalene), chlorinated aromatic or chlorinated aliphatic hydrocarbons (for example, chlorobenzenes, ethylene chlorides, and methylene chloride), aliphatic hydrocarbons [for example, cyclohexane, and paraffins (for example, mineral oil fraction)], alcohols (for example, butanol, and glycol) and ethers and esters thereof, ketones (for example, acetone, methyl ethyl ketone, methyl isobutyl ketone, and cyclohexanone), strongly polar solvents (for example, dimethylformamide, and dimethylsulfoxide), and water. In the case where water is used as an extender, for example, an organic solvent can be used as an auxiliary solvent.

Examples of the solid diluent or carrier include crushed natural mineral (for example, kaolin, clay, talc, chalk, quartz, attapulgite, montmorillonite, and diatomaceous earth), and crushed synthetic mineral (for example, high-dispersed silicic acid, alumina, and silicate). Examples of the solid carrier for use in granule include crushed and sorted rock (for example, calcite, marble, pumice, meerschaum, and dolomite), synthesized grain of inorganic and organic powder, fine granular body of organic material (for example, sawdust, shell of coco, corncob, and stem of cigarette).

Examples of the emulsifier and/or the foam-forming agent include nonionic and anionic emulsifiers [for example, polyoxyethylene fatty acid ester, polyoxyethylene fatty acid alcohol ether (for example, alkylaryl polyglycol ether, alkylsulfonate, alkylsulfate, and arylsulfonate)], and albumin hydrolysate.

As the decomposing agent, for example, lignin sulfite waste fluid and methyl cellulose are included.

A fixing agent can also be used in formulations (powder material, granule, and emulsion), and examples of the fixing agent include carboxymethylcellulose, and natural and synthetic polymer (for example, gum arabic, polyvinyl alcohol, and polyvinyl acetate).

A coloring agent can also be used and examples of the coloring agent include inorganic pigments (for example, iron oxide, titanium oxide, and Prussian blue), organic dyes such as alizarin dyes, azo dyes, and metal phthalocyanine dyes, and trace elements such as salts of metals including iron, manganese, boron, copper, cobalt, molybdenum, and zinc.

The formulations can generally contain the active compound(s) of formula (I) within a range of 0.1 to 95 wt %, and preferably contains the compound(s) within a range of 0.5 to 90 wt %.

The active compound of formula (I) of the present invention can be used for controlling weeds as such or in their formulation foams. Moreover, the active compound of formula (I) of the present invention can also be used in combination with a known herbicide. A mixed herbicide composition with a known herbicide may be previously prepared as a final formulation form, or can be prepared by tank-mixing on occasion of application.

For example, the following herbicides shown in common names can be exemplified as specific examples of herbicides that can be used in combination with the active compounds of formula (I) of the present invention.

Sulfonylurea herbicides: for example, chlorsulfuron, sulfometuron methyl, chlorimuron ethyl, triasulfuron, amidosulfuron, oxasulfuron, tribenuron ethyl, prosulfuron, ethametsulfuron methyl, triflusulfuron methyl, thifensuluron methyl, flazasulfuron, rimsulfuron, nicosulfuron, flupyrsulfuron, bensulfuron methyl, pyrazosulfuron ethyl, foramsulfuron, sulfosulfuron, cinosulfuron, azimsulfuron, metsulfuron-methyl, halosulfuron methyl, ethoxysulfuron, cyclosulfamuron, and iodosulfuron;

carbamate herbicides: for example, phenmedipham, chloropropham, asulam, benthiocarb, molinate, esprocarb, pyributicarb, dimepiperate, and swep;

chloroacetanilide herbicides: for example, propachlor, metazachlor, alachlor, acetochlor, metolachlor, butachlor, pretilachlor, and thenylchlor;

diphenylether herbicides: for example, acifluorfen, oxifluorfen, lactofen, fomesafen, aclonifen, chlomethoxynyl, bifenox, and CNP; triazine herbicides: for example, simazine, atrazine, propazine, cyanazine, ametryn, simetryn, dimethametryn, and prometryn;

phenoxy acid or benzoic acid herbicides: for example, 2,3,6-TBA, dicamba, quinclorac, quinmerac, clopyralid, picloram, triclopyr, fluroxypyr, fenoxaprop, diclofop methyl, fluazifop buthyl, haloxyfop methyl, quizalofop ethyl, cyhalofop butyl, 2,4-PA, MCP, MCPB, and phenothiol;

acid amide or urea herbicides: for example, izoxaben, diflufenican, diuron, linuron, fluometuron, difenoxuron, methyldymron, isoproturon, isouron, tebuthiuron, methabenzthiazuron, propanil, mefenacet, chlomeprop, naproanilide, bromobutide, dymron, cumyluron, etobenzanide, and oxaziclomefone;

organic phosphorus herbicides: for example, glyphosate, bialaphos, glufosinate, L-glufosinate, amiprofos methyl, anilofos, bensulide, piperophos, and butamifos;

dinitroaniline herbicides: for example, trifluralin, and prodiamine;

phenol herbicides: for example, bromoxynil, ioxynil, and dinoseb;

cyclohexanedione herbicides: for example, alloxydim, sethoxydim, cloproxydim, clethodim, cycloxydim, and tralkoxydim;

imidazolinone herbicides: for example, imazamethabenz, imazapyr, imazamethapyr, imazethapyr, imazamox, and imazaquin;

bipyridium herbicides: for example, paraquat, and diquat;

carbamoyltetrazolinone herbicides: for example, fentrazamide;

nitrile herbicides: cichlobenil; and other herbicides: for example, bentazone, tridiphane, indanofan, amitrol, carfentrazone ethyl, sulfentrazone, fenchlorazol ethyl, isoxaflutole, clomazone, maleic acid hydrazide, pyridate, chloridazon, norflurazon, pyrithiobac, bromacil, terbacil, metribuzin, oxaziclomefone, cinmethylin, flumiclorac pentyl, flumioxazin, fluthiacet methyl, azafenidin, benfuresate, oxadiazon, oxadiargyl, pentoxazone, cafenstrole, pyriminobac, bispyribac sodium, pyribenzoxim, pyriftalid, pyraflufen ethyl, benzobicyclon, dithiopyr, dalapon, and chiorthiamid.

The above active compounds are known herbicides described in "Pesticide Manual", published by British Crop Protect Council in 2000.

Moreover, when the active compounds of formula (I) of the present invention are blended with a phytotoxicity-reducing agent, phytotoxicity is reduced by this blending, and wider spectrum of weed controlling is provided, and thereby wider application as selective herbicide can be provided.

Examples of the phytotoxicity-reducing agent include the following compounds represented by general names or development codes.

AD-67, BAS-145138, benoxacor, cloquintocet-mexyl, cyometrinil, 2,4-D, DKA-24, dichlormid, dymron, fenchlorim, fenclorazole ethyl, flurazole, fluxofenim, furilazole, isoxadifen-ethyl, mefenpyr-diethyl, MG-191, naphthalic anhydride, oxabetrinil, PPG-1292, and R-29148.

The above phytotoxicity-reducing agent is also described in "Pesticide Manual" published by British Crop Protect Council in 2000.

Furthermore, the above phytotoxicity-reducing agent can be blended with a mixed herbicide composition containing the compound of formula (I) of the present invention and the above herbicide. By this blending, phytotoxicity is reduced and a wider spectrum of weed controlling is provided, and application as a selective herbicide can be made wider.

Surprisingly, a synergy effect can be demonstrated in several blending herbicide composition composed of the compounds of the present invention and known herbicides and/or phytotoxicity-reducing agents.

In the case that the active compounds of formula (I) of the present invention are used, these can be used directly as they are, or used in formulations such as prepared liquid for spraying, emulsion, tablet, suspension, powder, or granule, or application forms prepared by diluting. The active compounds of formula (I) of the present invention can be applied, for example, by the method of liquid agent scattering (watering), spraying, atomizing, or spreading granules.

The active compounds of formula (I) of the present invention can be used at every stage before germination or after germination of plant. Moreover, they can be taken into the soil prior to seeding.

The application amount of the active compounds of the present invention can be changed in a substantial range, and basically varies, depending on nature of desired effect. When the active compound is used as a herbicide, the application amount of the active compound per 1 hectare can be, for example, is about 0.005 to about 4 kg, and is preferably about 0.01 to about 2 kg.

Next, manufacturing and use of the compounds of the present invention are shown more concretely by the following examples, but the present invention should not be limited to only them.

EXAMPLES

Compound Example

Synthesis Example 1

Synthesis of 2-{[2-methyl-6-(1H-1,2,4-triazol-1-yl)pyridin-3-yl]carbonyl}cyclohexan-1,3-dione

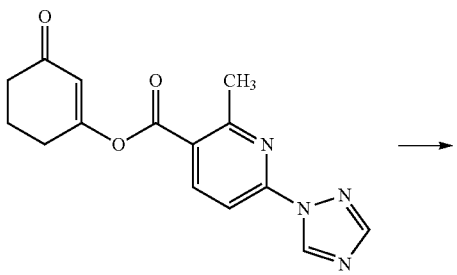

-continued

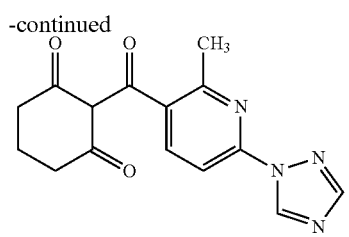

To acetonitrile (5 ml) solution of 3-oxo-1-cyclohexen-1-yl 2-methyl-6-(1H-1,2,4-triazol-1-yl)nicotinate (0.13 g, 0.44 mmol) and triethylamine (0.09 g, 0.87 mmol), a catalytic amount of acetone cyanohydrine was added. The obtained solution was stirred at room temperature around the clock. Volatile materials were evaporated under reduced pressure from the obtained reaction solution, and the obtained residue was made acidic with citric acid aqueous solution, and was extracted with ethyl acetate. After washing the obtained organic layer with water, the organic layer was dried with magnesium sulfate and concentrated to obtain the desired product (0.1 g, yield 77%).

$^1$H NMR (CDCl$_3$, 300 MHz)

δ 2.02-2.16 (2H, m), 2.49 (3H, s), 2.45-2.59 (2H, m), 2.70-2.91 (2H, m), 7.59 (1H, d), 7.74(1H, d), 8.09 (1H, s), 9.21 (1H, s)

Synthesis example 2

Synthesis of (5-hydroxy-1-methyl-1H-pyrazol-4-yl)[2-methyl-6-(1H-1,2,4-triazol-1-yl)pyridin-3-yl]methanone

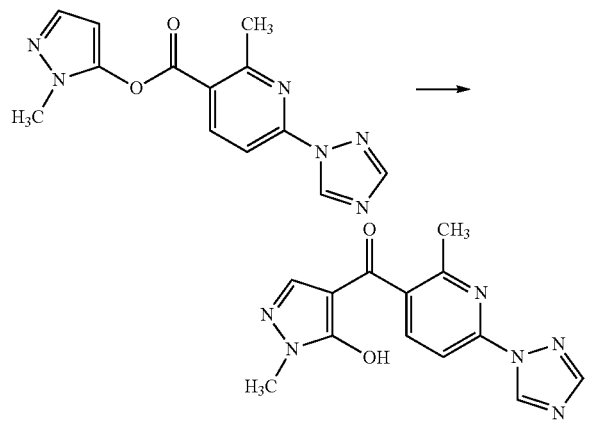

To acetonitrile (5 ml) solution of 1-methyl-1H-pyrazole-5-yl 2-methyl-6-(1H-1,2,4-triazol-1-yl)nicotinate (0.19 g, 0.65 mmol) and triethylamine (0.13 g, 1.29 mmol) , a catalytic amount of acetone cyanohydrin was added. The obtained solution was stirred at room temperature around the clock. Volatile materials were evaporated under reduced pressure from the obtained reaction solution, and the obtained residue was made acidic with citric acid aqueous solution, and was extracted with ethyl acetate. After washing the obtained organic layer with water, the organic layer was dried with magnesium sulfate and concentrated to obtain the desired product (0.18 g, yield 93%).

$^1$H NMR (CDCl$_3$, 300 MHz)

δ 2.71 (3H, s), 3.73 (3H, s), 7.43 (1H, s), 7.84 (1H, d), 8.00 (1H, d), 8.13 (1H, s), 9.25 (1H, s)

Synthesis Example 3

Synthesis of ethyl 5-cyclopropyl-4-{[2-methyl-6-(1H-1,2,4-triazol-1-yl)pyridin-3-yl]carbonyl}isooxazole-3-carboxylic acid ester

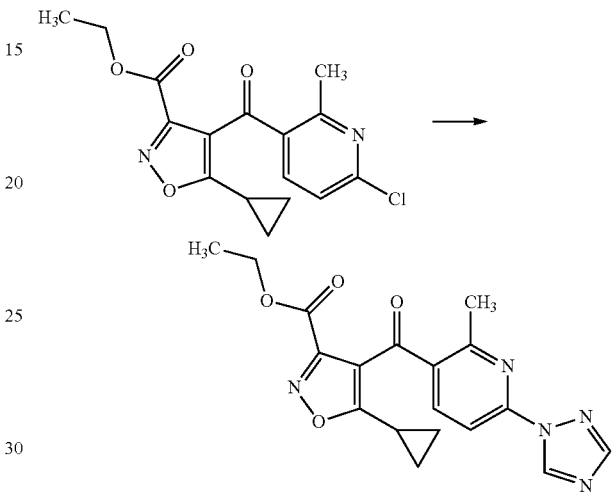

4-[(6-Chloro-2-methylpyridin-3-yl)carbonyl]-5-cyclopropylisooxazole-3-carboxylic acid ester (0.2 g, 0.6 mmol), triazole (0.08 g, 1.19 mmol) and potassium carbonate (0.17 g, 1.19 mmol) were stirred in DMF (5 ml) at 100° C. for four hours. To the obtained reaction solution, water and ethyl acetate were added. The organic layer was separated. Furthermore, water layer was extracted with ethyl acetate. After washing all the obtained organic layer with water, the organic layer was dried with magnesium sulfate and concentrated. The obtained residue was separated and purified by column chromatography to obtain the desired product (0.15 g, yield 68%).

$^1$H NMR (CDCl$_3$, 300 MHz)

δ 1.16-1.38 (7H, m) , 2.30-2.39 (1H, m) , 2.77 (3H, s), 4.10-4.17 (2H, q), 7.75 (1H, d), 7.85 (1H, d), 8.11 (1H, s), 9.24 (1H, s)

Synthesis Example 4

Synthesis of (5-cyclopropylisooxazol-4-yl)[2-methyl-6-(1H-1,2,4-triazol-1-yl)pyridin-3-yl]methanone

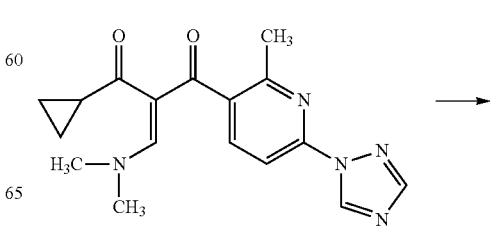

-continued

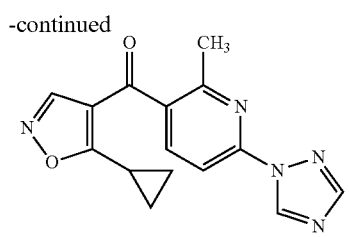

To ethanol (5 ml) solution of 1-cyclopropyl-2-[(dimethylamino)methylene]-3-[2-methyl6-(1H-triazol-1-yl)pyridin-3-yl]propan-1,3-dione (0.29 g, 0.89 mmol), hydroxylamine hydrochloride (0.07 g, 0.98 mmol) was added. The obtained solution was stirred at room temperature around the clock. To obtained reaction solution, water and ethyl acetate were added. The organic layer was separated. Furthermore, the water layer was extracted with ethyl acetate. All the obtained organic layer was washed with water, dried with magnesium sulfate and concentrated. The obtained residue was separated and purified by column chromatography to obtain the desired product (0.19 g, yield 72%).

$^1$H NMR (CDCl$_3$, 300 MHz)
δ 1.21-1.40 (4H, m), 2.60-2.73 (1H, m), 2.66 (3H, s), 7.82 (1H, d), 7.90 (1H, d), 8.11(1H, s), 8.22 (1H, s), 9.22 (1H, s)

Synthesis Example 5

Synthesis of 3-cyclopropyl-2-{[2-methyl-6-(1H-1,2,4-triazol-1-yl)-pyridin-3-yl]carbonyl}-3-oxopropanenitrile

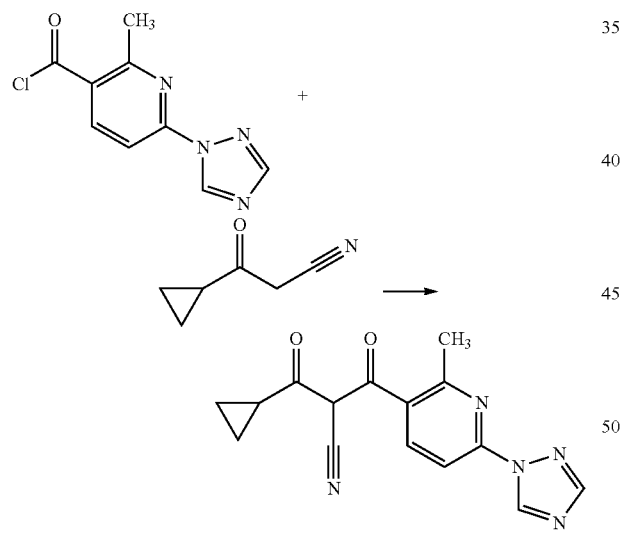

A THF (2 ml) suspension of sodium hydride (0.06 g, 60% oil suspension, 18.78 mmol) was cooled in an ice bath, and a THF (2 ml) solution of 3-cyclopropyl-3-oxopropanenitrile was dripped thereto. To the obtained reaction solution, a THF (3 ml) solution of 2-methyl-6-(1H-1,2,4-triazol-1-yl) nicotinic acid chloride (0.16 g, 0.73 mmol) was dripped. The resultant was stirred at room temperature for 3 hours. The obtained reaction solution was made acidic with a citric acid aqueous solution, and the product was extracted with ethyl acetate. The obtained organic layer was washed with water, dried with magnesium sulfate and concentrated to obtain the desired product (0.14 g, yield 64%).

$^1$H NMR (CDCl$_3$, 300 MHz)
δ 1.26-1.49 (4H, m), 2.38-2.46 (1H, m), 2.70 (3H, s), 7.85 (1H, d), 8.05 (1H, d), 8.12 (1H, s), 9.23 (1H, s)

Compounds obtained by operating on the basis of the manufacturing method of the compounds of the present invention explained in the synthesis example 1 to 5 are shown in the following table 1 to table 175 together with the compounds synthesized by the synthesis example 1 to 5.

Moreover, the NMR data of physical property values of some compounds are shown in table 176.

TABLE 1

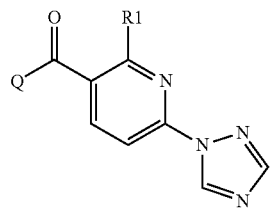

| | |
|---|---|
| 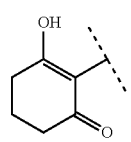 | Q1a |
| 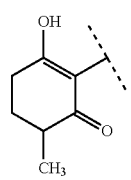 | Q1b |
| 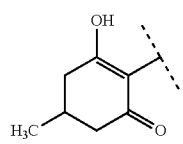 | Q1c |
| 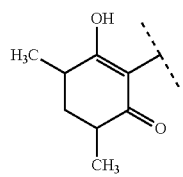 | Q1d |
| 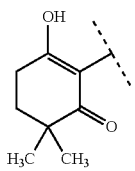 | Q1e |
| 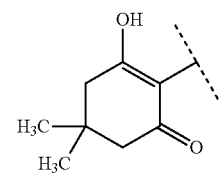 | Q1f |

TABLE 1-continued

| | | | |
|---|---|---|---|
| Q1g |  | | |
| Q1h | 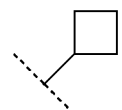 | | |
| Q1i | 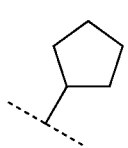 | | |

| compound number | Q | R1 | physical property (melting point-ND) |
|---|---|---|---|
| 1-1 | Q1a | CH$_3$ | NMR |
| 1-2 | Q1a | CH$_2$CH$_3$ | |
| 1-3 | Q1a | (CH$_2$)$_2$CH$_3$ | |
| 1-4 | Q1a | 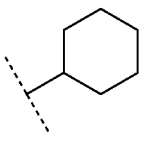 | |
| 1-5 | Q1a |  | |
| 1-6 | Q1a | 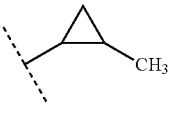 | |
| 1-7 | Q1a |  | |
| 1-8 | Q1a | 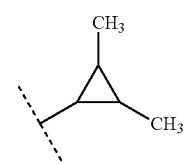 | |
| 1-9 | Q1a | 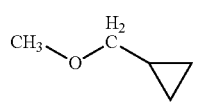 | |
| 1-10 | Q1a | 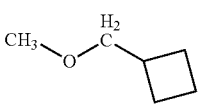 | |
| 1-11 | Q1a | 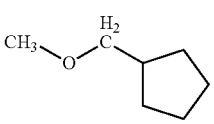 | |
| 1-12 | Q1a | CF$_3$ | 138-145° C. |
| 1-13 | Q1a | CH$_2$CF$_3$ | |
| 1-14 | Q1a | CF$_2$CF$_3$ | |
| 1-15 | Q1a | CH$_2$CH=CH$_2$ | |
| 1-16 | Q1a | CH2C≡CH | |
| 1-17 | Q1a | C$_6$H$_5$ | |
| 1-18 | Q1a | CH$_2$C$_6$H$_5$ | |
| 1-19 | Q1a | CH$_2$OCH$_3$ | NMR |
| 1-20 | Q1a | CH$_2$OCH$_2$CH$_3$ | |
| 1-21 | Q1a | CH$_2$O(CH2)$_2$CH$_3$ | |
| 1-22 | Q1a | (CH$_2$)$_2$OCH$_3$ | |
| 1-23 | Q1a | (CH$_2$)$_3$OCH$_3$ | |
| 1-24 | Q1a | 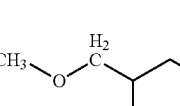 | |
| 1-25 | Q1a | 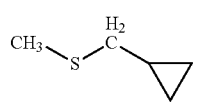 | |
| 1-26 | Q1a | 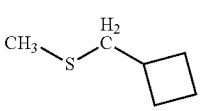 | |
| 1-27 | Q1a | CH$_3$-O-CH$_2$-cyclohexyl | |
| 1-28 | Q1a | CH$_2$OCH$_2$CF$_3$ | NMR |
| 1-29 | Q1a | CH$_2$OCF$_2$CHF$_2$ | |
| 1-30 | Q1a | CH$_2$OCH2CF2CF3 | |
| 1-31 | Q1a | CH$_2$OCH$_2$CH=CH$_2$ | |
| 1-32 | Q1a | CH$_2$OCH$_2$CH=CCl$_2$ | |
| 1-33 | Q1a | CH$_2$OCH$_2$CF=CF$_2$ | |
| 1-34 | Q1a | CH$_2$OC$_2$C≡CH | |
| 1-35 | Q1a | CH$_2$OCH$_2$C≡CCH$_3$ | |
| 1-36 | Q1a | CH$_2$SCH$_3$ | 1.5755(24) |
| 1-37 | Q1a | CH$_2$SCH$_2$CH$_3$ | |
| 1-38 | Q1a | CH$_2$S(CH$_2$)$_2$CH$_3$ | |
| 1-39 | Q1a | CH$_3$-S-CH$_2$-cyclopropyl | |
| 1-40 | Q1a | CH$_3$-S-CH$_2$-cyclobutyl | |

TABLE 2

| compound number | Q | R1 | physical property (melting point-ND) |
|---|---|---|---|
| 1-41 | Q1a | 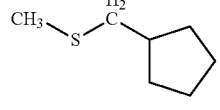 CH$_3$-S-CH$_2$-cyclopentyl | |
| 1-42 | Q1a | 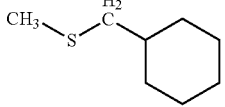 CH$_3$-S-CH$_2$-cyclohexyl | |
| 1-43 | Q1a | CH$_2$SCH$_2$CF$_3$ | |
| 1-44 | Q1a | CH$_2$SCH$_2$CH=CH$_2$ | |
| 1-45 | Q1a | CH$_2$SCH$_2$C≡CH | |
| 1-46 | Q1a | CH$_2$SOCH$_3$ | |
| 1-47 | Q1a | CH$_2$SOCH$_2$CH$_3$ | |
| 1-48 | Q1a | CH$_2$SO(CH$_2$)$_2$CH$_3$ | |
| 1-49 | Q1a | 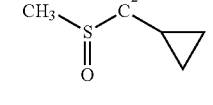 CH$_3$-S(O)-CH$_2$-cyclopropyl | |
| 1-50 | Q1a | 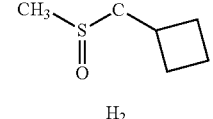 CH$_3$-S(O)-CH$_2$-cyclobutyl | |
| 1-51 | Q1a | 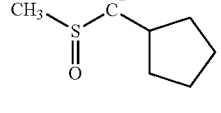 CH$_3$-S(O)-CH$_2$-cyclopentyl | |
| 1-52 | Q1a | 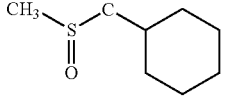 CH$_3$-S(O)-CH$_2$-cyclohexyl | |
| 1-53 | Q1a | CH$_2$SOCH$_2$CF$_3$ | |
| 1-54 | Q1a | CH$_2$SOCH$_2$CH=CH$_2$ | |
| 1-55 | Q1a | CH$_2$SOCH$_2$C≡CH | |
| 1-56 | Q1a | CH$_2$SO$_2$CH$_3$ | 173-174° C. |
| 1-57 | Q1a | CH$_2$SO$_2$CH$_2$CH$_3$ | |
| 1-58 | Q1a | CH$_2$SO$_2$(CH$_2$)$_2$CH$_3$ | |
| 1-59 | Q1a | 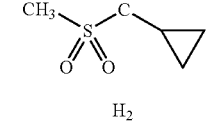 CH$_3$-S(O)$_2$-CH$_2$-cyclopropyl | |
| 1-60 | Q1a | 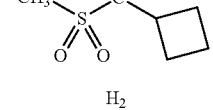 CH$_3$-S(O)$_2$-CH$_2$-cyclobutyl | |
| 1-61 | Q1a | 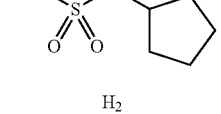 CH$_3$-S(O)$_2$-CH$_2$-cyclopentyl | |
| 1-62 | Q1a | 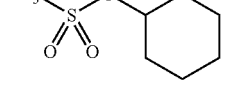 CH$_3$-S(O)$_2$-CH$_2$-cyclohexyl | |

TABLE 2-continued

| compound number | Q | R1 | physical property (melting point-ND) |
|---|---|---|---|
| 1-63 | Q1a | CH$_2$SO$_2$CH$_2$CF$_3$ | |
| 1-64 | Q1a | CH$_2$SO$_2$CH$_2$CH=CH$_2$ | |
| 1-65 | Q1a | CH$_2$SO$_2$CH$_2$C≡CH | |
| 1-66 | Q1a | CH$_2$O(CH$_2$)$_2$OCH$_3$ | NMR |
| 1-67 | Q1a | CH$_2$O(CH$_2$)$_2$OCH$_2$CH$_3$ | |
| 1-68 | Q1a |  CH$_2$O(CH$_2$)$_2$OCH$_2$-cyclopropyl | |
| 1-69 | Q1a | CH$_2$O(CH$_2$)$_2$OCH$_2$CF$_3$ | |
| 1-70 | Q1a | CH$_2$O(CH$_2$)$_2$OCH$_2$CH=CH$_2$ | |
| 1-71 | Q1a | CH$_2$O(CH$_2$)$_2$OCH$_2$C≡CH | |
| 1-72 | Q1a | CH$_2$O(CH$_2$)$_2$SCH$_3$ | |
| 1-73 | Q1a |  CH$_2$O(CH$_2$)$_2$SCH$_2$-cyclopropyl | |
| 1-74 | Q1a | CH$_2$O(CH$_2$)$_2$SCH$_2$CF$_3$ | |
| 1-75 | Q1a | CH$_2$O(CH$_2$)$_2$SCH$_2$CH=CH$_2$ | |
| 1-76 | Q1a | CH$_2$O(CH$_2$)$_2$SCH$_2$C≡CH | |
| 1-77 | Q1a | CH$_2$O(CH$_2$)$_2$SOCH$_3$ | |
| 1-78 | Q1a |  CH$_2$O(CH$_2$)$_2$SOCH$_2$-cyclopropyl | |
| 1-79 | Q1a | CH$_2$O(CH$_2$)$_2$SOCH$_2$CF$_3$ | |
| 1-80 | Q1a | CH$_2$O(CH$_2$)$_2$SOCH$_2$CH=CH$_2$ | |

TABLE 3

| compound number | Q | R1 | physical property (melting point-ND) |
|---|---|---|---|
| 1-81 | Q1a | CH$_2$O(CH$_2$)$_2$SOCH$_2$C≡CH | |
| 1-82 | Q1a | CH$_2$O(CH$_2$)$_2$SO$_2$CH$_3$ | |
| 1-83 | Q1a |  CH$_2$O(CH$_2$)$_2$SO$_2$CH$_2$-cyclopropyl | |
| 1-84 | Q1a | CH$_2$O(CH$_2$)$_2$SO$_2$CH$_2$CF$_3$ | |
| 1-85 | Q1a | CH$_2$O(CH$_2$)$_2$SO$_2$CH$_2$CH=CH$_2$ | |
| 1-86 | Q1a | CH$_2$O(CH$_2$)$_2$SO$_2$CH$_2$C≡CH | |
| 1-87 | Q1a | 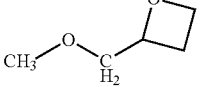 CH$_3$-O-CH$_2$-oxetanyl | |
| 1-88 | Q1a | 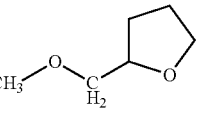 CH$_3$-O-CH$_2$-tetrahydrofuranyl | |
| 1-89 | Q1a | 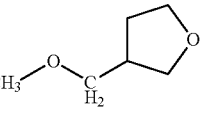 CH$_3$-O-CH$_2$-tetrahydrofuranyl | |
| 1-90 | Q1a | 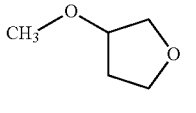 CH$_3$-O-tetrahydrofuranyl | |

TABLE 3-continued

| compound number | Q | R1 | physical property (melting point-ND) |
|---|---|---|---|
| 1-91 | Q1a | $CH_3-O-CH_2-CH_2-O-CH_2-$(oxetan-2-yl) | |
| 1-92 | Q1a | $CH_3-O-CH_2-CH_2-O-CH_2-$(tetrahydrofuran-2-yl) | |
| 1-93 | Q1a | $CH_3-O-CH_2-CH_2-O-CH_2-$(tetrahydrofuran-3-yl) | |
| 1-94 | Q1a | $CH_3-O-CH_2-CH_2-O-$(tetrahydrofuran-3-yl) | |
| 1-95 | Q1a | $CH_2O(CH_2)_2NHSO_2CH_3$ | |
| 1-96 | Q1a | $CH_2O(CH_2)_2N(CH_3)(SO_2CH_3)$ | |
| 1-97 | Q1a | $CH_2O(CH_2)_2NH(SO_2CH_2$—cyclopropyl$)$ | |
| 1-98 | Q1a | $CH_2O(CH_2)_2NHSO_2CF_3$ | |
| 1-99 | Q1a | $CH_2O(CH_2)_2NHSO_2CHF_2$ | |
| 1-100 | Q1a | $CH_2O(CH_2)_2NHSO_2CH_2CF_3$ | |
| 1-101 | Q1a | $SCH_3$ | |
| 1-102 | Q1a | $SOCH_3$ | |
| 1-103 | Q1a | $SO_2CH_3$ | |
| 1-104 | Q1a | $OCH_3$ | |
| 1-105 | Q1a | $OCH_2CH_3$ | |
| 1-106 | Q1a | $O(CH_2)_2CH_3$ | |
| 1-107 | Q1a | $OCH_2CF_3$ | |
| 1-108 | Q1a | $OCF_2CF_3$ | |
| 1-109 | Q1a | $O(CH_2)_2OCH_3$ | |
| 1-110 | Q1a | $NHCH_3$ | |
| 1-111 | Q1a | $NHCH_2CH_3$ | |
| 1-112 | Q1a | $N(CH_3)_2$ | |
| 1-113 | Q1a | $N(CH_2CH_3)_2$ | |
| 1-114 | Q1a | $N(CH_3)(CH_2CH_3)$ | |
| 1-115 | Q1b | $CH_3$ | NMR |
| 1-116 | Q1b | $CH_2CH_3$ | |
| 1-117 | Q1b | $(CH_2)_2CH_3$ | |
| 1-118 | Q1b | cyclopropyl | |
| 1-119 | Q1b | cyclobutyl | |
| 1-120 | Q1b | cyclopentyl | |

TABLE 4

| compound number | Q | R1 | physical property (melting point-ND) |
|---|---|---|---|
| 1-121 | Q1b | cyclohexyl | |
| 1-122 | Q1b | 1-methylcyclopropyl | |
| 1-123 | Q1b | 2-methylcyclopropyl | |
| 1-124 | Q1b | 2,2-dimethylcyclopropyl | |
| 1-125 | Q1b | 2,3-dimethylcyclopropyl | |
| 1-126 | Q1b | $CF_3$ | 1.5395(25) |
| 1-127 | Q1b | $CH_2CF_3$ | |
| 1-128 | Q1b | $CF_2CF_3$ | |
| 1-129 | Q1b | $CH_2CH=CH_2$ | |
| 1-130 | Q1b | $CH_2C\equiv CH$ | |
| 1-131 | Q1b | $C_6C_5$ | |
| 1-132 | Q1b | $CH_2C_6H_5$ | |
| 1-133 | Q1b | $CH_2OCH_3$ | 1.5685(25) |
| 1-134 | Q1b | $CH_2OCH_2CH_3$ | |
| 1-135 | Q1b | $CH_2O(CH2)_2CH_3$ | |
| 1-136 | Q1b | $(CH_2)_2OCH_3$ | |
| 1-137 | Q1b | $(CH_2)_3OCH_3$ | |
| 1-138 | Q1b | $CH_3-O-CH_2-$cyclopropyl | |
| 1-139 | Q1b | $CH_3-O-CH_2-$cyclobutyl | |
| 1-140 | Q1b | $CH_3-O-CH_2-$cyclopentyl | |
| 1-141 | Q1b | $CH_3-O-CH_2-$cyclohexyl | |
| 1-142 | Q1b | $CH_2OCH_2CF_3$ | NMR |
| 1-143 | Q1b | $CH_2OCF_2CHF_2$ | |
| 1-144 | Q1b | $CH_2OCH2CF2CF3$ | |
| 1-145 | Q1b | $CH_2OCH_2CH=CH_2$ | |
| 1-146 | Q1b | $CH_2OCH_2CH=CCl_2$ | |

TABLE 4-continued

| compound number | Q | R1 | physical property (melting point-ND) |
|---|---|---|---|
| 1-147 | Q1b | CH$_2$OCH$_2$CF=CF$_2$ | |
| 1-148 | Q1b | CH$_2$OC$_2$C≡CH | |
| 1-149 | Q1b | CH$_2$OCH$_2$C≡CCH$_3$ | |
| 1-150 | Q1b | CH$_2$SCH$_3$ | |
| 1-151 | Q1b | CH$_2$SCH$_2$CH$_3$ | |
| 1-152 | Q1b | CH$_2$S(CH$_2$)$_2$CH$_3$ | |
| 1-153 | Q1b | CH$_3$-S-CH$_2$-cyclopropyl | |
| 1-154 | Q1b | CH$_3$-S-CH$_2$-cyclobutyl | |
| 1-155 | Q1b | CH$_3$-S-CH$_2$-cyclopentyl | |
| 1-156 | Q1b | CH$_3$-S-CH$_2$-cyclohexyl | |
| 1-157 | Q1b | CH$_2$SCH$_2$CF$_3$ | |
| 1-158 | Q1b | CH$_2$SCH$_2$CH=CH$_2$ | |
| 1-159 | Q1b | CH$_2$SCH$_2$C≡CH | |
| 1-160 | Q1b | CH$_2$SOCH$_3$ | |

TABLE 5

| compound number | Q | R1 | physical property (melting point-ND) |
|---|---|---|---|
| 1-161 | Q1b | CH$_2$SOCH$_2$CH$_3$ | |
| 1-162 | Q1b | CH$_2$SO(CH$_2$)$_2$CH$_3$ | |
| 1-163 | Q1b | CH$_3$-S(O)-CH$_2$-cyclopropyl | |
| 1-164 | Q1b | CH$_3$-S(O)-CH$_2$-cyclobutyl | |
| 1-165 | Q1b | CH$_3$-S(O)-CH$_2$-cyclopentyl | |
| 1-166 | Q1b | CH$_3$-S(O)-CH$_2$-cyclohexyl | |
| 1-167 | Q1b | CH$_2$SOCH$_2$CF$_3$ | |
| 1-168 | Q1b | CH$_2$SOCH$_2$CH=CH$_2$ | |
| 1-169 | Q1b | CH$_2$SOCH$_2$C≡CH | |
| 1-170 | Q1b | CH$_2$SO$_2$CH$_3$ | |
| 1-171 | Q1b | CH$_2$SO$_2$CH$_2$CH$_3$ | |
| 1-172 | Q1b | CH$_2$SO$_2$(CH$_2$)$_2$CH$_3$ | |
| 1-173 | Q1b | CH$_3$-SO$_2$-CH$_2$-cyclopropyl | |
| 1-174 | Q1b | CH$_3$-SO$_2$-CH$_2$-cyclobutyl | |
| 1-175 | Q1b | CH$_3$-SO$_2$-CH$_2$-cyclopentyl | |
| 1-176 | Q1b | CH$_3$-SO$_2$-CH$_2$-cyclohexyl | |
| 1-177 | Q1b | CH$_2$SO$_2$CH$_2$CF$_3$ | |
| 1-178 | Q1b | CH$_2$SO$_2$CH$_2$CH=CH$_2$ | |
| 1-179 | Q1b | CH$_2$SO$_2$CH$_2$C≡CH | |
| 1-180 | Q1b | CH$_2$O(CH$_2$)$_2$OCH$_3$ | |
| 1-181 | Q1b | CH$_2$O(CH$_2$)$_2$OCH$_2$CH$_3$ | |
| 1-182 | Q1b | CH$_2$O(CH$_2$)$_2$OCH$_2$-cyclopropyl | |
| 1-183 | Q1b | CH$_2$O(CH$_2$)$_2$OCH$_2$CF$_3$ | |
| 1-184 | Q1b | CH$_2$O(CH$_2$)$_2$OCH$_2$CH=CH$_2$ | |
| 1-185 | Q1b | CH$_2$O(CH$_2$)$_2$OCH$_2$C≡CH | |
| 1-186 | Q1b | CH$_2$O(CH$_2$)$_2$SCH$_3$ | |
| 1-187 | Q1b | CH$_2$O(CH$_2$)$_2$SCH$_2$-cyclopropyl | |
| 1-188 | Q1b | CH$_2$O(CH$_2$)$_2$SCH$_2$CF$_3$ | |
| 1-189 | Q1b | CH$_2$O(CH$_2$)$_2$SCH$_2$CH=CH$_2$ | |
| 1-190 | Q1b | CH$_2$O(CH$_2$)$_2$SCH$_2$C≡CH | |
| 1-191 | Q1b | CH$_2$O(CH$_2$)$_2$SOCH$_3$ | |
| 1-192 | Q1b | CH$_2$O(CH$_2$)$_2$SOCH$_2$-cyclopropyl | |
| 1-193 | Q1b | CH$_2$O(CH$_2$)$_2$SOCH$_2$CF$_3$ | |
| 1-194 | Q1b | CH$_2$O(CH$_2$)$_2$SOCH$_2$CH=CH$_2$ | |
| 1-195 | Q1b | CH$_2$O(CH$_2$)$_2$SOCH$_2$C≡CH | |
| 1-196 | Q1b | CH$_2$O(CH$_2$)$_2$SO$_2$CH$_3$ | |
| 1-197 | Q1b | CH$_2$O(CH$_2$)$_2$SO$_2$CH$_2$-cyclopropyl | |
| 1-198 | Q1b | CH$_2$O(CH$_2$)$_2$SO$_2$CH$_2$CF$_3$ | |
| 1-199 | Q1b | CH$_2$O(CH$_2$)$_2$SO$_2$CH$_2$CH=CH$_2$ | |
| 1-200 | Q1b | CH$_2$O(CH$_2$)$_2$SO$_2$CH$_2$C≡CH | |

TABLE 6

| compound number | Q | R1 | physical property (melting point-ND) |
|---|---|---|---|
| 1-201 | Q1b | 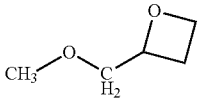 | |
| 1-202 | Q1b | 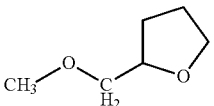 | |
| 1-203 | Q1b | 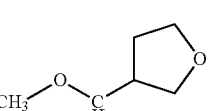 | |
| 1-204 | Q1b | 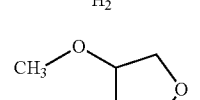 | |
| 1-205 | Q1b | 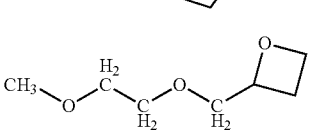 | |
| 1-206 | Q1b | 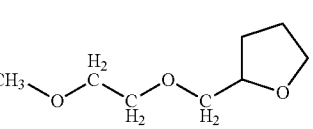 | |
| 1-207 | Q1b | 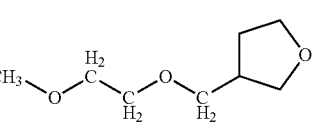 | |
| 1-208 | Q1b | 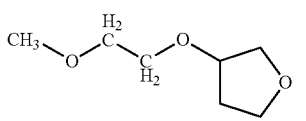 | |
| 1-209 | Q1b | $CH_2O(CH_2)_2NHSO_2CH_3$ | |
| 1-210 | Q1b | $CH_2O(CH_2)_2N(CH_3)(SO_2CH_3)$ | |
| 1-211 | Q1b | $CH_2O(CH_2)_2NH(SO_2CH_2$—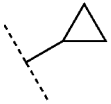$)$ | |
| 1-212 | Q1b | $CH_2O(CH_2)_2NHSO_2CF_3$ | |
| 1-213 | Q1b | $CH_2O(CH_2)_2NHSO_2CHF_2$ | |
| 1-214 | Q1b | $CH_2O(CH_2)_2NHSO_2CH_2CF_3$ | |
| 1-215 | Q1b | $SCH_3$ | |
| 1-216 | Q1b | $SOCH_3$ | |
| 1-217 | Q1b | $SO_2CH_3$ | |
| 1-218 | Q1b | $OCH_3$ | |
| 1-219 | Q1b | $OCH_2CH_3$ | |
| 1-220 | Q1b | $O(CH_2)_2CH_3$ | |
| 1-221 | Q1b | $OCH_2CF_3$ | |
| 1-222 | Q1b | $OCF_2CF_3$ | |
| 1-223 | Q1b | $O(CH_2)_2OCH_3$ | |
| 1-224 | Q1b | $NHCH_3$ | |
| 1-225 | Q1b | $NHCH_2CH_3$ | |
| 1-226 | Q1b | $N(CH_3)_2$ | |
| 1-227 | Q1b | $N(CH_2CH_3)_2$ | |
| 1-228 | Q1b | $N(CH_3)(CH_2CH_3)$ | |
| 1-229 | Q1c | $CH_3$ | |
| 1-230 | Q1c | $CH_2CH_3$ | |
| 1-231 | Q1c | $(CH_2)_2CH_3$ | |

TABLE 6-continued

| compound number | Q | R1 | physical property (melting point-ND) |
|---|---|---|---|
| 1-232 | Q1c | 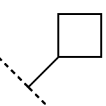 | |
| 1-233 | Q1c | 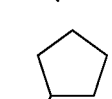 | |
| 1-234 | Q1c | 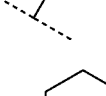 | |
| 1-235 | Q1c | 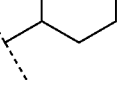 | |
| 1-236 | Q1c |  | |
| 1-237 | Q1c | 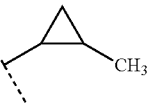 | |
| 1-238 | Q1c | 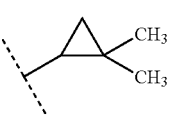 | |
| 1-239 | Q1c | | |
| 1-240 | Q1c | $CF_3$ | |

TABLE 7

| compound number | Q | R1 | physical property (melting point-ND) |
|---|---|---|---|
| 1-241 | Q1c | $CH_2CF_3$ | |
| 1-242 | Q1c | $CF_2CF_3$ | |
| 1-243 | Q1c | $CH_2CH\!=\!CH_2$ | |
| 1-244 | Q1c | $CH2C\!\equiv\!CH$ | |
| 1-245 | Q1c | $C_6C_5$ | |
| 1-246 | Q1c | $CH_2C_6H_5$ | |
| 1-247 | Q1c | $CH_2OCH_3$ | |
| 1-248 | Q1c | $CH_2OCH_2CH_3$ | |
| 1-249 | Q1c | $CH_2O(CH2)_2CH_3$ | |
| 1-250 | Q1c | $(CH_2)_2OCH_3$ | |

TABLE 7-continued

| compound number | Q | R1 | physical property (melting point-ND) |
|---|---|---|---|
| 1-251 | Q1c | (CH₂)₃OCH₃ | |
| 1-252 | Q1c | 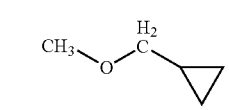 | |
| 1-253 | Q1c | 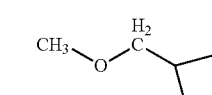 | |
| 1-254 | Q1c | 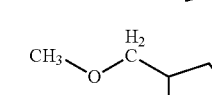 | |
| 1-255 | Q1c | 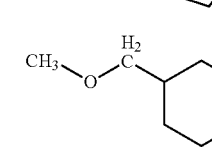 | |
| 1-256 | Q1c | CH₂OCH₂CF₃ | |
| 1-257 | Q1c | CH₂OCF₂CHF₂ | |
| 1-258 | Q1c | CH₂OCH2CF2CF3 | |
| 1-259 | Q1c | CH₂OCH₂CH=CH₂ | |
| 1-260 | Q1c | CH₂OCH₂CH=CCl₂ | |
| 1-261 | Q1c | CH₂OCH₂CF=CF₂ | |
| 1-262 | Q1c | CH₂OC₂C≡CH | |
| 1-263 | Q1c | CH₂OCH₂C≡CCH₃ | |
| 1-264 | Q1c | CH₂SCH₃ | |
| 1-265 | Q1c | CH₂SCH₂CH₃ | |
| 1-266 | Q1c | CH₂S(CH₂)₂CH₃ | |
| 1-267 | Q1c | 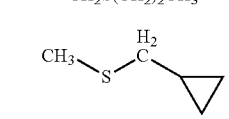 | |
| 1-268 | Q1c | 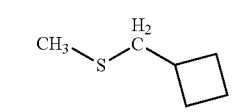 | |
| 1-269 | Q1c | 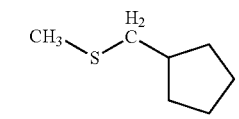 | |
| 1-270 | Q1c | 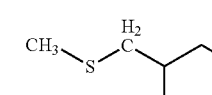 | |
| 1-271 | Q1c | CH₂SCH₂CF₃ | |
| 1-272 | Q1c | CH₂SCH₂CH=CH₂ | |
| 1-273 | Q1c | CH₂SCH₂C≡CH | |
| 1-274 | Q1c | CH₂SOCH₃ | |
| 1-275 | Q1c | CH₂SOCH₂CH₃ | |
| 1-276 | Q1c | CH₂SO(CH₂)₂CH₃ | |
| 1-277 | Q1c | 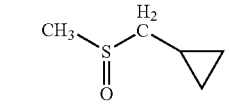 | |
| 1-278 | Q1c | 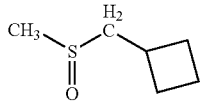 | |
| 1-279 | Q1c | 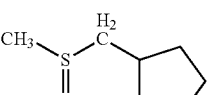 | |
| 1-280 | Q1c | 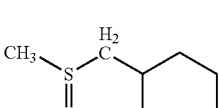 | |

TABLE 8

| compound number | Q | R1 | physical property (melting point-ND) |
|---|---|---|---|
| 1-281 | Q1c | CH₂SOCH₂CF₃ | |
| 1-282 | Q1c | CH₂SOCH₂CH=CH₂ | |
| 1-283 | Q1c | CH₂SOCH₂C≡CH | |
| 1-284 | Q1c | CH₂SO₂CH₃ | |
| 1-285 | Q1c | CH₂SO₂CH₂CH₃ | |
| 1-286 | Q1c | CH₂SO₂(CH₂)₂CH₃ | |
| 1-287 | Q1c | 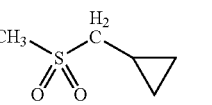 | |
| 1-288 | Q1c | 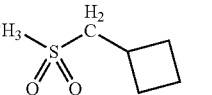 | |
| 1-289 | Q1c | 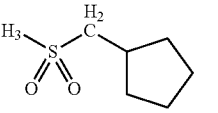 | |
| 1-290 | Q1c | 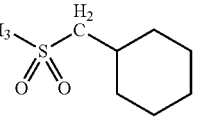 | |
| 1-291 | Q1c | CH₂SO₂CH₂CF₃ | |
| 1-292 | Q1c | CH₂SO₂CH₂CH=CH₂ | |
| 1-293 | Q1c | CH₂SO₂CH₂C≡CH | |
| 1-294 | Q1c | CH₂O(CH₂)₂OCH₃ | |
| 1-295 | Q1c | CH₂O(CH₂)₂OCH₂CH₃ | |
| 1-296 | Q1c | CH₂O(CH₂)₂OCH₂— | |
| 1-297 | Q1c | CH₂O(CH₂)₂OCH₂CF₃ | |
| 1-298 | Q1c | CH₂O(CH₂)₂OCH₂CH=CH₂ | |
| 1-299 | Q1c | CH₂O(CH₂)₂OCH₂C≡CH | |
| 1-300 | Q1c | CH₂O(CH₂)₂SCH₃ | |

TABLE 8-continued

| compound number | Q | R1 | physical property (melting point-ND) |
|---|---|---|---|
| 1-301 | Q1c | CH$_2$O(CH$_2$)$_2$SCH$_2$-△ | |
| 1-302 | Q1c | CH$_2$O(CH$_2$)$_2$SCH$_2$CF$_3$ | |
| 1-303 | Q1c | CH$_2$O(CH$_2$)$_2$SCH$_2$CH=CH$_2$ | |
| 1-304 | Q1c | CH$_2$O(CH$_2$)$_2$SCH$_2$C≡CH | |
| 1-305 | Q1c | CH$_2$O(CH$_2$)$_2$SOCH$_3$ | |
| 1-306 | Q1c | CH$_2$O(CH$_2$)$_2$SOCH$_2$-△ | |
| 1-307 | Q1c | CH$_2$O(CH$_2$)$_2$SOCH$_2$CF$_3$ | |
| 1-308 | Q1c | CH$_2$O(CH$_2$)$_2$SOCH$_2$CH=CH$_2$ | |
| 1-309 | Q1c | CH$_2$O(CH$_2$)$_2$SOCH$_2$C≡CH | |
| 1-310 | Q1c | CH$_2$O(CH$_2$)$_2$SO$_2$CH$_3$ | |
| 1-311 | Q1c | CH$_2$O(CH$_2$)$_2$SO$_2$CH$_2$-△ | |
| 1-312 | Q1c | CH$_2$O(CH$_2$)$_2$SO$_2$CH$_2$CF$_3$ | |
| 1-313 | Q1c | CH$_2$O(CH$_2$)$_2$SOCH$_2$CH=CH$_2$ | |
| 1-314 | Q1c | CH$_2$O(CH$_2$)$_2$SO$_2$CH$_2$C≡CH | |
| 1-315 | Q1c | CH$_3$O-CH$_2$-(oxetanyl) | |
| 1-316 | Q1c | CH$_3$O-CH$_2$-(tetrahydrofuran-2-yl) | |
| 1-317 | Q1c | CH$_3$O-CH$_2$-(tetrahydrofuran-3-yl) | |
| 1-318 | Q1c | CH$_3$O-(tetrahydrofuran-3-yl) | |
| 1-319 | Q1c | CH$_3$O-CH$_2$-O-CH$_2$-(oxetanyl) | |
| 1-320 | Q1c | CH$_3$O-CH$_2$-O-CH$_2$-(tetrahydrofuran-2-yl) | |

TABLE 9

| compound number | Q | R1 | physical property (melting point-ND) |
|---|---|---|---|
| 1-321 | Q1c | CH$_3$O-CH$_2$-O-CH$_2$-(tetrahydrofuran-3-yl) | |
| 1-322 | Q1c | CH$_3$O-CH$_2$-O-(tetrahydrofuran-3-yl) | |
| 1-323 | Q1c | CH$_2$O(CH$_2$)$_2$NHSO$_2$CH$_3$ | |
| 1-324 | Q1c | CH$_2$O(CH$_2$)$_2$N(CH$_3$)(SO$_2$CH$_3$) | |
| 1-325 | Q1c | CH$_2$O(CH$_2$)$_2$NH(SO$_2$CH$_2$-△) | |
| 1-326 | Q1c | CH$_2$O(CH$_2$)$_2$NHSO$_2$CF$_3$ | |
| 1-327 | Q1c | CH$_2$O(CH$_2$)$_2$NHSO$_2$CHF$_2$ | |
| 1-328 | Q1c | CH$_2$O(CH$_2$)$_2$NHSO$_2$CH$_2$CF$_3$ | |
| 1-329 | Q1c | SCH$_3$ | |
| 1-330 | Q1c | SOCH$_3$ | |
| 1-331 | Q1c | SO$_2$CH$_3$ | |
| 1-332 | Q1c | OCH$_3$ | |
| 1-333 | Q1c | OCH$_2$CH$_3$ | |
| 1-334 | Q1c | O(CH$_2$)$_2$CH$_3$ | |
| 1-335 | Q1c | OCH$_2$CF$_3$ | |
| 1-336 | Q1c | OCF$_2$CF$_3$ | |
| 1-337 | Q1c | O(CH$_2$)$_2$OCH$_3$ | |
| 1-338 | Q1c | NHCH$_3$ | |
| 1-339 | Q1c | NHCH$_2$CH$_3$ | |
| 1-340 | Q1c | N(CH$_3$)$_2$ | |
| 1-341 | Q1c | N(CH$_2$CH$_3$)$_2$ | |
| 1-342 | Q1c | N(CH$_3$)(CH$_2$CH$_3$) | |
| 1-343 | Q1d | CH$_3$ | |
| 1-344 | Q1d | CH$_2$CH$_3$ | |
| 1-345 | Q1d | (CH$_2$)$_2$CH$_3$ | |
| 1-346 | Q1d | cyclopropyl | |
| 1-347 | Q1d | cyclobutyl | |
| 1-348 | Q1d | cyclopentyl | |
| 1-349 | Q1d | cyclohexyl | |
| 1-350 | Q1d | 1-methylcyclopropyl | |
| 1-351 | Q1d | 2-methylcyclopropyl | |

TABLE 9-continued

| compound number | Q | R1 | physical property (melting point-ND) |
|---|---|---|---|
| 1-352 | Q1d | 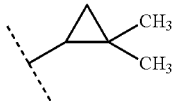 | |
| 1-353 | Q1d | 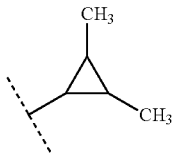 | |
| 1-354 | Q1d | CF$_3$ | |
| 1-355 | Q1d | CH$_2$CF$_3$ | |
| 1-356 | Q1d | CF$_2$CF$_3$ | |
| 1-357 | Q1d | CH$_2$CH=CH$_2$ | |
| 1-358 | Q1d | CH$_2$C≡CH | |
| 1-359 | Q1d | C$_6$H$_5$ | |
| 1-360 | Q1d | CH$_2$C$_6$H$_5$ | |

TABLE 10

| compound number | Q | R1 | physical property (melting point-ND) |
|---|---|---|---|
| 1-361 | Q1d | CH$_2$OCH$_3$ | |
| 1-362 | Q1d | CH$_2$OCH$_2$CH$_3$ | |
| 1-363 | Q1d | CH$_2$O(CH2)$_2$CH$_3$ | |
| 1-364 | Q1d | (CH$_2$)$_2$OCH$_3$ | |
| 1-365 | Q1d | (CH$_2$)$_3$OCH$_3$ | |
| 1-366 | Q1d | 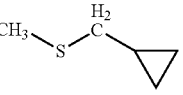 | |
| 1-367 | Q1d | 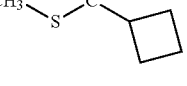 | |
| 1-368 | Q1d | 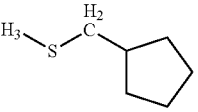 | |
| 1-369 | Q1d | 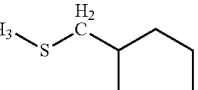 | |
| 1-370 | Q1d | CH$_2$OCH$_2$CF$_3$ | |
| 1-371 | Q1d | CH$_2$OCF$_2$CHF$_2$ | |
| 1-372 | Q1d | CH$_2$OCH2CF2CF3 | |
| 1-373 | Q1d | CH$_2$OCH$_2$CH=CH$_2$ | |
| 1-374 | Q1d | CH$_2$OCH$_2$CH=CCl$_2$ | |
| 1-375 | Q1d | CH$_2$OCH$_2$CF=CF$_2$ | |
| 1-376 | Q1d | CH$_2$OC$_2$C≡CH | |
| 1-377 | Q1d | CH$_2$OCH$_2$C≡CCH$_3$ | |
| 1-378 | Q1d | CH$_2$SCH$_3$ | |
| 1-379 | Q1d | CH$_2$SCH$_2$CH$_3$ | |
| 1-380 | Q1d | CH$_2$S(CH$_2$)$_2$CH$_3$ | |

TABLE 10-continued

| compound number | Q | R1 | physical property (melting point-ND) |
|---|---|---|---|
| 1-381 | Q1d | 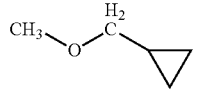 | |
| 1-382 | Q1d | 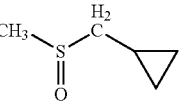 | |
| 1-383 | Q1d | 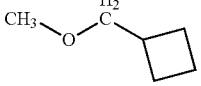 | |
| 1-384 | Q1d | 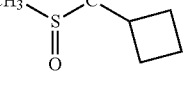 | |
| 1-385 | Q1d | CH$_2$SCH$_2$CF$_3$ | |
| 1-386 | Q1d | CH$_2$SCH$_2$CH=CH$_2$ | |
| 1-387 | Q1d | CH$_2$SCH$_2$C≡CH | |
| 1-388 | Q1d | CH$_2$SOCH$_3$ | |
| 1-389 | Q1d | CH$_2$SOCH$_2$CH$_3$ | |
| 1-390 | Q1d | CH$_2$SO(CH$_2$)$_2$CH$_3$ | |
| 1-391 | Q1d | 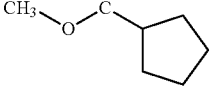 | |
| 1-392 | Q1d | 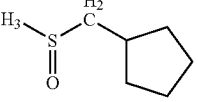 | |
| 1-393 | Q1d | 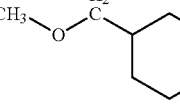 | |
| 1-394 | Q1d | 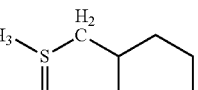 | |
| 1-395 | Q1d | CH$_2$SOCH$_2$CF$_3$ | |
| 1-396 | Q1d | CH$_2$SOCH$_2$CH=CH$_2$ | |
| 1-397 | Q1d | CH$_2$SOCH$_2$C≡CH | |
| 1-398 | Q1d | CH$_2$SO$_2$CH$_3$ | |
| 1-399 | Q1d | CH$_2$SO$_2$CH$_2$CH$_3$ | |
| 1-400 | Q1d | CH$_2$SO$_2$(CH$_2$)$_2$CH$_3$ | |

TABLE 11

| compound number | Q | R1 | physical property (melting point-ND) |
|---|---|---|---|
| 1-401 | Q1d | CH₃-SO₂-CH₂-cyclopropyl | |
| 1-402 | Q1d | CH₃-SO₂-CH₂-cyclobutyl | |
| 1-403 | Q1d | CH₃-SO₂-CH₂-cyclopentyl | |
| 1-404 | Q1d | CH₃-SO₂-CH₂-cyclohexyl | |
| 1-405 | Q1d | CH$_2$SO$_2$CH$_2$CF$_3$ | |
| 1-406 | Q1d | CH$_2$SO$_2$CH$_2$CH=CH$_2$ | |
| 1-407 | Q1d | CH$_2$SO$_2$CH$_2$C≡CH | |
| 1-408 | Q1d | CH$_2$O(CH$_2$)$_2$OCH$_3$ | |
| 1-409 | Q1d | CH$_2$O(CH$_2$)$_2$OCH$_2$CH$_3$ | |
| 1-410 | Q1d | CH$_2$O(CH$_2$)$_2$OCH$_2$-cyclopropyl | |
| 1-411 | Q1d | CH$_2$O(CH$_2$)$_2$OCH$_2$CF$_3$ | |
| 1-412 | Q1d | CH$_2$O(CH$_2$)$_2$OCH$_2$CH=CH$_2$ | |
| 1-413 | Q1d | CH$_2$O(CH$_2$)$_2$OCH$_2$C≡CH | |
| 1-414 | Q1d | CH$_2$O(CH$_2$)$_2$SCH$_3$ | |
| 1-415 | Q1d | CH$_2$O(CH$_2$)$_2$SCH$_2$-cyclopropyl | |
| 1-416 | Q1d | CH$_2$O(CH$_2$)$_2$SCH$_2$CF$_3$ | |
| 1-417 | Q1d | CH$_2$O(CH$_2$)$_2$SCH=CH$_2$ | |
| 1-418 | Q1d | CH$_2$O(CH$_2$)$_2$SCH$_2$C≡CH | |
| 1-419 | Q1d | CH$_2$O(CH$_2$)$_2$SOCH$_3$ | |
| 1-420 | Q1d | CH$_2$O(CH$_2$)$_2$SOCH$_2$-cyclopropyl | |
| 1-421 | Q1d | CH$_2$O(CH$_2$)$_2$SOCH$_2$CF$_3$ | |
| 1-422 | Q1d | CH$_2$O(CH$_2$)$_2$SOCH$_2$CH=CH$_2$ | |
| 1-423 | Q1d | CH$_2$O(CH$_2$)$_2$SOCH$_2$C≡CH | |
| 1-424 | Q1d | CH$_2$O(CH$_2$)$_2$SO$_2$CH$_3$ | |
| 1-425 | Q1d | CH$_2$O(CH$_2$)$_2$SO$_2$CH$_3$-cyclopropyl | |
| 1-426 | Q1d | CH$_2$O(CH$_2$)$_2$SO$_2$CH$_2$CF$_3$ | |
| 1-427 | Q1d | CH$_2$O(CH$_2$)$_2$SO$_2$CH$_2$CH=CH$_2$ | |
| 1-428 | Q1d | CH$_2$O(CH$_2$)$_2$SO$_2$CH$_2$C≡CH | |
| 1-429 | Q1d | CH₃-O-CH₂-oxetanyl | |
| 1-430 | Q1d | CH₃-O-CH₂-tetrahydrofuranyl | |
| 1-431 | Q1d | CH₃-O-CH₂-tetrahydrofuranyl | |
| 1-432 | Q1d | CH₃-O-tetrahydrofuranyl | |
| 1-433 | Q1d | CH₃-O-CH₂-O-CH₂-oxetanyl | |
| 1-434 | Q1d | CH₃-O-CH₂-O-CH₂-tetrahydrofuranyl | |
| 1-435 | Q1d | CH₃-O-CH₂-O-CH₂-tetrahydrofuranyl | |
| 1-436 | Q1d | CH₃-O-CH₂-O-tetrahydrofuranyl | |
| 1-437 | Q1d | CH$_2$O(CH$_2$)$_2$NHSO$_2$CH$_3$ | |
| 1-438 | Q1d | CH$_2$O(CH$_2$)$_2$N(CH$_3$)(SO$_2$CH$_3$) | |
| 1-439 | Q1d | CH$_2$O(CH$_2$)$_2$NH(SO$_2$CH$_2$-cyclopropyl) | |
| 1-440 | Q1d | CH$_2$O(CH$_2$)$_2$NHSO$_2$CF$_3$ | |

TABLE 12

| compound number | Q | R1 | physical property (melting point-ND) |
|---|---|---|---|
| 1-441 | Q1d | CH$_2$O(CH$_2$)$_2$NHSO$_2$CHF$_2$ | |
| 1-442 | Q1d | CH$_2$O(CH$_2$)$_2$NHSO$_2$CH$_2$CF$_3$ | |
| 1-443 | Q1d | SCH$_3$ | |
| 1-444 | Q1d | SOCH$_3$ | |
| 1-445 | Q1d | SO$_2$CH$_3$ | |
| 1-446 | Q1d | OCH$_3$ | |
| 1-447 | Q1d | OCH$_2$CH$_3$ | |
| 1-448 | Q1d | O(CH$_2$)$_2$CH$_3$ | |
| 1-449 | Q1d | OCH$_2$CF$_3$ | |
| 1-450 | Q1d | OCF$_2$CF$_3$ | |
| 1-451 | Q1d | O(CH$_2$)$_2$OCH$_3$ | |
| 1-452 | Q1d | NHCH$_3$ | |
| 1-453 | Q1d | NHCH$_2$CH$_3$ | |
| 1-454 | Q1d | N(CH$_3$)$_2$ | |
| 1-455 | Q1d | N(CH$_2$CH$_3$)$_2$ | |
| 1-456 | Q1d | N(CH$_3$)(CH$_2$CH$_3$) | |
| 1-457 | Q1e | CH$_3$ | NMR |
| 1-458 | Q1e | CH$_2$CH$_3$ | |
| 1-459 | Q1e | (CH$_2$)$_2$CH$_3$ | |

TABLE 12-continued

| compound number | Q | R1 | physical property (melting point-ND) |
|---|---|---|---|
| 1-460 | Q1e | cyclopropyl | |
| 1-461 | Q1e | cyclobutyl | |
| 1-462 | Q1e | cyclopentyl | |
| 1-463 | Q1e | cyclohexyl | |
| 1-464 | Q1e | 1-methylcyclopropyl | |
| 1-465 | Q1e | 2-methylcyclopropyl | |
| 1-466 | Q1e | 2,2-dimethylcyclopropyl | |
| 1-467 | Q1e | 2,3-dimethyl (or 1,2-dimethyl) cyclopropyl | |
| 1-468 | Q1e | $CF_3$ | |
| 1-469 | Q1e | $CH_2CF_3$ | |
| 1-470 | Q1e | $CF_2CF_3$ | |
| 1-471 | Q1e | $CH_2CH\!=\!CH_2$ | |
| 1-472 | Q1e | $CH_2C\!\equiv\!CH$ | |
| 1-473 | Q1e | $C_6H_5$ | |
| 1-474 | Q1e | $CH_2C_6H_5$ | |
| 1-475 | Q1e | $CH_2OCH_3$ | |
| 1-476 | Q1e | $CH_2OCH_2CH_3$ | |
| 1-477 | Q1e | $CH_2O(CH2)_2CH_3$ | |
| 1-478 | Q1e | $(CH_2)_2OCH_3$ | |
| 1-479 | Q1e | $(CH_2)_3OCH_3$ | |
| 1-480 | Q1e | $CH_3OCH_2$-cyclopropyl | |

TABLE 13

| compound number | Q | R1 | physical property (melting point-ND) |
|---|---|---|---|
| 1-481 | Q1e | $CH_3OCH_2$-cyclobutyl | |
| 1-482 | Q1e | $CH_3OCH_2$-cyclopentyl | |
| 1-483 | Q1e | $CH_3OCH_2$-cyclohexyl | |
| 1-484 | Q1e | $CH_2OCH_2CF_3$ | |
| 1-485 | Q1e | | |
| 1-486 | Q1e | $CH_2OCH2CF2CF3$ | |
| 1-487 | Q1e | $CH_2OCH_2CH\!=\!CH_2$ | |
| 1-488 | Q1e | $CH_2OCH_2CH\!=\!CCl_2$ | |
| 1-489 | Q1e | $CH_2OCH_2CF\!=\!CF_2$ | |
| 1-490 | Q1e | $CH_2OC_2C\!\equiv\!CH$ | |
| 1-491 | Q1e | $CH_2OCH_2C\!\equiv\!CCH_3$ | |
| 1-492 | Q1e | $CH_2SCH_3$ | |
| 1-493 | Q1e | $CH_2SCH_2CH_3$ | |
| 1-494 | Q1e | $CH_2S(CH_2)_2CH_3$ | |
| 1-495 | Q1e | $CH_3SCH_2$-cyclopropyl | |
| 1-496 | Q1e | $CH_3SCH_2$-cyclobutyl | |
| 1-497 | Q1e | $CH_3SCH_2$-cyclopentyl | |
| 1-498 | Q1e | $CH_3SCH_2$-cyclohexyl | |
| 1-499 | Q1e | $CH_2SCH_2CF_3$ | |
| 1-500 | Q1e | $CH_2SCH_2CH\!=\!CH_2$ | |
| 1-501 | Q1e | $CH_2SCH_2C\!\equiv\!CH$ | |
| 1-502 | Q1e | $CH_2SOCH_3$ | |
| 1-503 | Q1e | $CH_2SOCH_2CH_3$ | |
| 1-504 | Q1e | $CH_2SO(CH_2)_2CH_3$ | |
| 1-505 | Q1e | $CH_3S(O)CH_2$-cyclopropyl | |
| 1-506 | Q1e | $CH_3S(O)CH_2$-cyclobutyl | |

TABLE 13-continued

| compound number | Q | R1 | physical property (melting point-ND) |
|---|---|---|---|
| 1-507 | Q1e | CH$_3$-S(=O)-CH$_2$-cyclopentyl | |
| 1-508 | Q1e | CH$_3$-S(=O)-CH$_2$-cyclohexyl | |
| 1-509 | Q1e | CH$_2$SOCH$_2$CF$_3$ | |
| 1-510 | Q1e | CH$_2$SOCH$_2$CH=CH$_2$ | |
| 1-511 | Q1e | CH$_2$SOCH$_2$C≡CH | |
| 1-512 | Q1e | CH$_2$SO$_2$CH$_3$ | |
| 1-513 | Q1e | CH$_2$SO$_2$CH$_2$CH$_3$ | |
| 1-514 | Q1e | CH$_2$SO$_2$(CH$_2$)$_2$CH$_4$ | |
| 1-515 | Q1e | CH$_3$-S(O)$_2$-CH$_2$-cyclopropyl | |
| 1-516 | Q1e | CH$_3$-S(O)$_2$-CH$_2$-cyclobutyl | |
| 1-517 | Q1e | CH$_3$-S(O)$_2$-CH$_2$-cyclopentyl | |
| 1-518 | Q1e | CH$_3$-S(O)$_2$-CH$_2$-cyclohexyl | |
| 1-519 | Q1e | CH$_2$SO$_2$CH$_2$CF$_3$ | |
| 1-520 | Q1e | CH$_2$SO$_2$CH$_2$CH=CH$_2$ | |

TABLE 14

| compound number | Q | R1 | physical property (melting point-ND) |
|---|---|---|---|
| 1-521 | Q1e | CH$_2$SO$_2$CH$_2$C≡CH | |
| 1-522 | Q1e | CH$_2$O(CH$_2$)$_2$OCH$_3$ | |
| 1-523 | Q1e | CH$_2$O(CH$_2$)$_2$OCH$_2$CH$_3$ | |
| 1-524 | Q1e | CH$_2$O(CH$_2$)$_2$OCH$_2$-cyclopropyl | |
| 1-525 | Q1e | CH$_2$O(CH$_2$)$_2$OCH$_2$CF$_3$ | |
| 1-526 | Q1e | CH$_2$O(CH$_2$)$_2$OCH$_2$CH=CH$_2$ | |
| 1-527 | Q1e | CH$_2$O(CH$_2$)$_2$OCH$_2$C≡CH | |
| 1-528 | Q1e | CH$_2$O(CH$_2$)$_2$SCH$_3$ | |
| 1-529 | Q1e | CH$_2$O(CH$_2$)$_2$SCH$_2$-cyclopropyl | |
| 1-530 | Q1e | CH$_2$O(CH$_2$)$_2$SCH$_2$CF$_3$ | |
| 1-531 | Q1e | CH$_2$O(CH$_2$)$_2$SCH=CH$_2$ | |
| 1-532 | Q1e | CH$_2$O(CH$_2$)$_2$SCH$_2$C≡CH | |
| 1-533 | Q1e | CH$_2$O(CH$_2$)$_2$SOCH$_3$ | |
| 1-534 | Q1e | CH$_2$O(CH$_2$)$_2$SOCH$_2$-cyclopropyl | |
| 1-535 | Q1e | CH$_2$O(CH$_2$)$_2$SOCH$_2$CF$_3$ | |
| 1-536 | Q1e | CH$_2$O(CH$_2$)$_2$SOCH$_2$CH=CH$_2$ | |
| 1-537 | Q1e | CH$_2$O(CH$_2$)$_2$SOCH$_2$C≡CH | |
| 1-538 | Q1e | CH$_2$O(CH$_2$)$_2$SO$_2$CH$_3$ | |
| 1-539 | Q1e | CH$_2$O(CH$_2$)$_2$SO$_2$CH$_2$-cyclopropyl | |
| 1-540 | Q1e | CH$_2$O(CH$_2$)$_2$SO$_2$CH$_2$CF$_3$ | |
| 1-541 | Q1e | CH$_2$O(CH$_2$)$_2$SO$_2$CH$_2$CH=CH$_2$ | |
| 1-542 | Q1e | CH$_2$O(CH$_2$)$_2$SO$_2$CH$_2$C≡CH | |
| 1-543 | Q1e | CH$_3$-O-CH$_2$-(oxetan-2-yl) | |
| 1-544 | Q1e | CH$_3$-O-CH$_2$-(tetrahydrofuran-2-yl) | |
| 1-545 | Q1e | CH$_3$-O-CH$_2$-(tetrahydrofuran-3-yl) | |
| 1-546 | Q1e | CH$_3$-O-(tetrahydrofuran-3-yl) | |
| 1-547 | Q1e | CH$_3$-O-CH$_2$-CH$_2$-O-CH$_2$-(oxetan-2-yl) | |
| 1-548 | Q1e | CH$_3$-O-CH$_2$-CH$_2$-O-CH$_2$-(tetrahydrofuran-2-yl) | |
| 1-549 | Q1e | CH$_3$-O-CH$_2$-CH$_2$-O-CH$_2$-(tetrahydrofuran-3-yl) | |
| 1-550 | Q1e | CH$_3$-O-CH$_2$-CH$_2$-O-(tetrahydrofuran-3-yl) | |
| 1-551 | Q1e | CH$_2$O(CH$_2$)$_2$NHSO$_2$CH$_3$ | |
| 1-552 | Q1e | CH$_2$O(CH$_2$)$_2$N(CH$_3$)(SO$_2$CH$_3$) | |
| 1-553 | Q1e | CH$_2$O(CH$_2$)$_2$NH(SO$_2$CH$_2$-cyclopropyl) | |
| 1-554 | Q1e | CH$_2$O(CH$_2$)$_2$NHSO$_2$CF$_3$ | |
| 1-555 | Q1e | CH$_2$O(CH$_2$)$_2$NHSO$_2$CHF$_3$ | |

TABLE 14-continued

| compound number | Q | R1 | physical property (melting point-ND) |
|---|---|---|---|
| 1-556 | Q1e | CH₂O(CH₂)₂NHSO₂CH₂CF₃ | |
| 1-557 | Q1e | SCH₃ | |
| 1-558 | Q1e | SOCH₃ | |
| 1-559 | Q1e | SO₂CH₃ | |
| 1-560 | Q1e | OCH₃ | |

TABLE 15

| compound number | Q | R1 | physical property (melting point-ND) |
|---|---|---|---|
| 1-561 | Q1e | OCH₂CH₃ | |
| 1-562 | Q1e | O(CH₂)₂CH₃ | |
| 1-563 | Q1e | OCH₂CF₃ | |
| 1-564 | Q1e | OCF₂CF₃ | |
| 1-565 | Q1e | O(CH₂)₂OCH₃ | |
| 1-566 | Q1e | NHCH₃ | |
| 1-567 | Q1e | NHCH₂CH₃ | |
| 1-568 | Q1e | N(CH₃)₂ | |
| 1-569 | Q1e | N(CH₂CH₃)₂ | |
| 1-570 | Q1e | N(CH₃)(CH₂CH₃) | |
| 1-571 | Q1f | CH₃ | |
| 1-572 | Q1f | CH₂CH₃ | |
| 1-573 | Q1f | (CH₂)₂CH₃ | |
| 1-574 | Q1f | 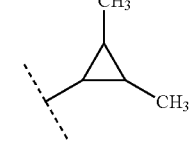 | |
| 1-575 | Q1f | 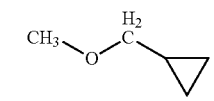 | |
| 1-576 | Q1f | 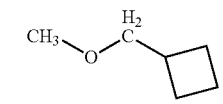 | |
| 1-577 | Q1f | 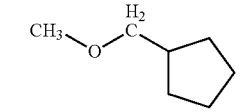 | |
| 1-578 | Q1f | 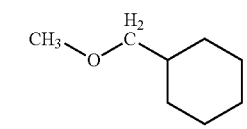 | |
| 1-579 | Q1f | 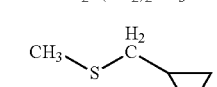 | |
| 1-580 | Q1f | (structure with cyclopropane and two CH₃) | |

TABLE 15-continued

| compound number | Q | R1 | physical property (melting point-ND) |
|---|---|---|---|
| 1-581 | Q1f | (cyclopropane with two CH₃ groups) | |
| 1-582 | Q1f | CF₃ | |
| 1-583 | Q1f | CH₂CF₃ | |
| 1-584 | Q1f | CF₂CF₃ | |
| 1-585 | Q1f | CH₂CH=CH₂ | |
| 1-586 | Q1f | CH₂C≡CH | |
| 1-587 | Q1f | C₆H₅ | |
| 1-588 | Q1f | CH₂C₆H₅ | |
| 1-589 | Q1f | CH₂OCH₃ | |
| 1-590 | Q1f | CH₂OCH₂CH₃ | |
| 1-591 | Q1f | CH₂O(CH2)₂CH₃ | |
| 1-592 | Q1f | (CH₂)₂OCH₃ | |
| 1-593 | Q1f | (CH₂)₃OCH₃ | |
| 1-594 | Q1f | CH₃—O—CH₂—cyclopropyl | |
| 1-595 | Q1f | CH₃—O—CH₂—cyclobutyl | |
| 1-596 | Q1f | CH₃—O—CH₂—cyclopentyl | |
| 1-597 | Q1f | CH₃—O—CH₂—cyclohexyl | |
| 1-598 | Q1f | CH₂OCH₂CF₃ | |
| 1-599 | Q1f | CH₂OCF₂CHF₂ | |
| 1-600 | Q1f | CH₂OCH2CF2CF3 | |

TABLE 16

| compound number | Q | R1 | physical property (melting point-ND) |
|---|---|---|---|
| 1-601 | Q1f | CH₂OCH₂CH=CH₂ | |
| 1-602 | Q1f | CH₂OCH₂CH=CCl₂ | |
| 1-603 | Q1f | CH₂OCH₂CF=CF₂ | |
| 1-604 | Q1f | CH₂OC₂C≡CH | |
| 1-605 | Q1f | CH₂OCH₂C≡CCH₃ | |
| 1-606 | Q1f | CH₂SCH₃ | |
| 1-607 | Q1f | CH₂SCH₂CH₃ | |
| 1-608 | Q1f | CH₂S(CH₂)₂CH₃ | |
| 1-609 | Q1f | CH₃—S—CH₂—cyclopropyl | |

TABLE 16-continued

| compound number | Q | R1 | physical property (melting point-ND) |
|---|---|---|---|
| 1-610 | Q1f | CH$_3$-S-CH$_2$-cyclobutyl | |
| 1-611 | Q1f | CH$_3$-S-CH$_2$-cyclopentyl | |
| 1-612 | Q1f | CH$_3$-S-CH$_2$-cyclohexyl | |
| 1-613 | Q1f | CH$_2$SCH$_2$CF$_3$ | |
| 1-614 | Q1f | CH$_2$SCH$_2$CH=CH$_2$ | |
| 1-615 | Q1f | CH$_2$SCH$_2$C≡CH | |
| 1-616 | Q1f | CH$_2$SOCH$_3$ | |
| 1-617 | Q1f | CH$_2$SOCH$_2$CH$_3$ | |
| 1-618 | Q1f | CH$_2$SO(CH$_2$)$_2$CH$_3$ | |
| 1-619 | Q1f | CH$_3$-S(O)-CH$_2$-cyclopropyl | |
| 1-620 | Q1f | CH$_3$-S(O)-CH$_2$-cyclobutyl | |
| 1-621 | Q1f | CH$_3$-S(O)-CH$_2$-cyclopentyl | |
| 1-622 | Q1f | CH$_3$-S(O)-CH$_2$-cyclohexyl | |
| 1-623 | Q1f | CH$_2$SOCH$_2$CF$_3$ | |
| 1-624 | Q1f | CH$_2$SOCH$_2$CH=CH$_2$ | |
| 1-625 | Q1f | CH$_2$SOCH$_2$C≡CH | |
| 1-626 | Q1f | CH$_2$SO$_2$CH$_3$ | |
| 1-627 | Q1f | CH$_2$SO$_2$CH$_2$CH$_3$ | |
| 1-628 | Q1f | CH$_2$SO$_2$(CH$_2$)$_2$CH$_4$ | |
| 1-629 | Q1f | CH$_3$-SO$_2$-CH$_2$-cyclopropyl | |
| 1-630 | Q1f | CH$_3$-SO$_2$-CH$_2$-cyclobutyl | |
| 1-631 | Q1f | CH$_3$-SO$_2$-CH$_2$-cyclopentyl | |

TABLE 16-continued

| compound number | Q | R1 | physical property (melting point-ND) |
|---|---|---|---|
| 1-632 | Q1f | CH$_3$-SO$_2$-CH$_2$-cyclohexyl | |
| 1-633 | Q1f | CH$_2$SO$_2$CH$_2$CF$_3$ | |
| 1-634 | Q1f | CH$_2$SO$_2$CH$_2$CH=CH$_2$ | |
| 1-635 | Q1f | CH$_2$SO$_2$CH$_2$C≡CH | |
| 1-636 | Q1f | CH$_2$O(CH$_2$)$_2$OCH$_3$ | |
| 1-637 | Q1f | CH$_2$O(CH$_2$)$_2$OCH$_2$CH$_3$ | |
| 1-638 | Q1f | CH$_2$O(CH$_2$)$_2$OCH$_2$-cyclopropyl | |
| 1-639 | Q1f | CH$_2$O(CH$_2$)$_2$OCH$_2$CF$_3$ | |
| 1-640 | Q1f | CH$_2$O(CH$_2$)$_2$OCH$_2$CH=CH$_2$ | |

TABLE 17

| compound number | Q | R1 | physical property (melting point-ND) |
|---|---|---|---|
| 1-641 | Q1f | CH$_2$O(CH$_2$)$_2$OCH$_2$C≡CH | |
| 1-642 | Q1f | CH$_2$O(CH$_2$)$_2$SCH$_3$ | |
| 1-643 | Q1f | CH$_2$O(CH$_2$)$_2$SCH$_2$-cyclopropyl | |
| 1-644 | Q1f | CH$_2$O(CH$_2$)$_2$SCH$_2$CF$_3$ | |
| 1-645 | Q1f | CH$_2$O(CH$_2$)$_2$SCH=CH$_2$ | |
| 1-646 | Q1f | CH$_2$O(CH$_2$)$_2$SCH$_2$C≡CH | |
| 1-647 | Q1f | CH$_2$O(CH$_2$)$_2$SOCH$_3$ | |
| 1-648 | Q1f | CH$_2$O(CH$_2$)$_2$SOCH$_2$-cyclopropyl | |
| 1-649 | Q1f | CH$_2$O(CH$_2$)$_2$SOCH$_2$CF$_3$ | |
| 1-650 | Q1f | CH$_2$O(CH$_2$)$_2$SOCH$_2$CH=CH$_2$ | |
| 1-651 | Q1f | CH$_2$O(CH$_2$)$_2$SOCH$_2$C≡CH | |
| 1-652 | Q1f | CH$_2$O(CH$_2$)$_2$SO$_2$CH$_3$ | |
| 1-653 | Q1f | CH$_2$O(CH$_2$)$_2$SO$_2$CH$_2$-cyclopropyl | |
| 1-654 | Q1f | CH$_2$O(CH$_2$)$_2$SO$_2$CH$_2$CF$_3$ | |
| 1-655 | Q1f | CH$_2$O(CH$_2$)$_2$SO$_2$CH$_2$CH=CH$_2$ | |
| 1-656 | Q1f | CH$_2$O(CH$_2$)$_2$SO$_2$CH$_2$C≡CH | |
| 1-657 | Q1f | CH$_3$-O-CH$_2$-oxetanyl | |
| 1-658 | Q1f | CH$_3$-O-CH$_2$-tetrahydrofuran-2-yl | |
| 1-659 | Q1f | CH$_3$-O-CH$_2$-tetrahydrofuran-3-yl | |

TABLE 17-continued

| compound number | Q | R1 | physical property (melting point-ND) |
|---|---|---|---|
| 1-660 | Q1f | 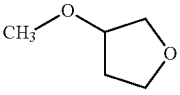 | |
| 1-661 | Q1f | 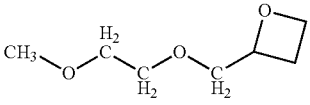 | |
| 1-662 | Q1f | 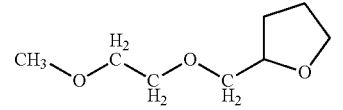 | |
| 1-663 | Q1f | 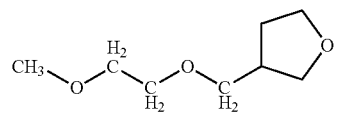 | |
| 1-664 | Q1f | 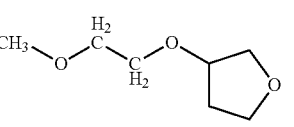 | |
| 1-665 | Q1f | $CH_2O(CH_2)_2NHSO_2CH_3$ | |
| 1-666 | Q1f | $CH_2O(CH_2)_2N(CH_3)(SO_2CH_3)$ | |
| 1-667 | Q1f | $CH_2O(CH_2)_2NH(SO_2CH_2$—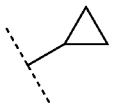) | |
| 1-668 | Q1f | $CH_2O(CH_2)_2NHSO_2CF_3$ | |
| 1-669 | Q1f | $CH_2O(CH_2)_2NHSO_2CHF_3$ | |
| 1-670 | Q1f | $CH_2O(CH_2)_2NHSO_2CH_2CF_3$ | |
| 1-671 | Q1f | $SCH_3$ | |
| 1-672 | Q1f | $SOCH_3$ | |
| 1-673 | Q1f | $SO_2CH_3$ | |
| 1-674 | Q1f | $OCH_3$ | |
| 1-675 | Q1f | $OCH_2CH_3$ | |
| 1-676 | Q1f | $O(CH_2)_2CH_3$ | |
| 1-677 | Q1f | $OCH_2CF_3$ | |
| 1-678 | Q1f | $OCF_2CF_3$ | |
| 1-679 | Q1f | $O(CH_2)_2OCH_3$ | |
| 1-680 | Q1f | $NHCH_3$ | |

TABLE 18

| compound number | Q | R1 | physical property (melting point-ND) |
|---|---|---|---|
| 1-681 | Q1f | $NHCH_2CH_3$ | |
| 1-682 | Q1f | $N(CH_3)_2$ | |
| 1-683 | Q1f | $N(CH_2CH_3)_2$ | |
| 1-684 | Q1f | $N(CH_3)(CH_2CH_3)$ | |
| 1-685 | Q1g | $CH_3$ | NMR |
| 1-686 | Q1g | $CH_2CH_3$ | |
| 1-687 | Q1g | $(CH_2)_2CH_3$ | |
| 1-688 | Q1g | 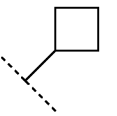 | |

TABLE 18-continued

| compound number | Q | R1 | physical property (melting point-ND) |
|---|---|---|---|
| 1-689 | Q1g | 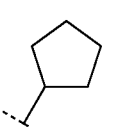 | |
| 1-690 | Q1g | 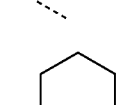 | |
| 1-691 | Q1g | 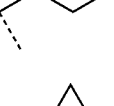 | |
| 1-692 | Q1g | 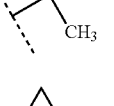 | |
| 1-693 | Q1g | 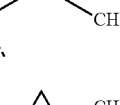 | |
| 1-694 | Q1g | 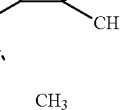 | |
| 1-695 | Q1g | 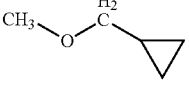 | |
| 1-696 | Q1g | $CF_3$ | |
| 1-697 | Q1g | $CH_2CF_3$ | |
| 1-698 | Q1g | $CF_2CF_3$ | |
| 1-699 | Q1g | $CH_2CH{=}CH_2$ | |
| 1-700 | Q1g | $CH_2C{\equiv}CH$ | |
| 1-701 | Q1g | $C_6H_5$ | |
| 1-702 | Q1g | $CH_2C_6H_5$ | |
| 1-703 | Q1g | $CH_2OCH_3$ | 114-120° C. |
| 1-704 | Q1g | $CH_2OCH_2CH_3$ | |
| 1-705 | Q1g | $CH_2O(CH2)_2CH_3$ | |
| 1-706 | Q1g | $(CH_2)_2OCH_3$ | |
| 1-707 | Q1g | $(CH_2)_3OCH_3$ | |
| 1-708 | Q1g | 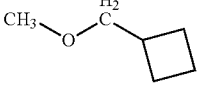 | |
| 1-709 | Q1g |  | |

TABLE 18-continued

| compound number | Q | R1 | physical property (melting point-ND) |
|---|---|---|---|
| 1-710 | Q1g | CH₃-O-CH₂-cyclopentyl | |
| 1-711 | Q1g | CH₃-O-CH₂-cyclohexyl | |
| 1-712 | Q1g | CH$_2$OCH$_2$CF$_3$ | NMR |
| 1-713 | Q1g | CH$_2$OCF$_2$CHF$_2$ | |
| 1-714 | Q1g | CH$_2$OCH2CF2CF3 | |
| 1-715 | Q1g | CH$_2$OCH$_2$CH=CH$_2$ | |
| 1-716 | Q1g | CH$_2$OCH$_2$CH=CCl$_2$ | |
| 1-717 | Q1g | CH$_2$OCH$_2$CF=CF$_2$ | |
| 1-718 | Q1g | CH$_2$OC$_2$C≡CH | |
| 1-719 | Q1g | CH$_2$OCH$_2$C≡CCH$_3$ | |
| 1-720 | Q1g | CH$_2$SCH$_3$ | |

TABLE 19

| compound number | Q | R1 | physical property (melting point-ND) |
|---|---|---|---|
| 1-721 | Q1g | CH$_2$SCH$_2$CH$_3$ | |
| 1-722 | Q1g | CH$_2$S(CH$_2$)$_2$CH$_3$ | |
| 1-723 | Q1g | CH₃-S-CH₂-cyclopropyl | |
| 1-724 | Q1g | CH₃-S-CH₂-cyclobutyl | |
| 1-725 | Q1g | CH₃-S-CH₂-cyclopentyl | |
| 1-726 | Q1g | CH₃-S-CH₂-cyclohexyl | |
| 1-727 | Q1g | CH$_2$SCH$_2$CF$_3$ | |
| 1-728 | Q1g | CH$_2$SCH$_2$CH=CH$_2$ | |
| 1-729 | Q1g | CH$_2$SCH$_2$C≡CH | |
| 1-730 | Q1g | CH$_2$SOCH$_3$ | |
| 1-731 | Q1g | CH$_2$SOCH$_2$CH$_3$ | |
| 1-732 | Q1g | CH$_2$SO(CH$_2$)$_2$CH$_3$ | |
| 1-733 | Q1g | CH₃-S(O)-CH₂-cyclopropyl | |

TABLE 19-continued

| compound number | Q | R1 | physical property (melting point-ND) |
|---|---|---|---|
| 1-734 | Q1g | CH₃-S(O)-CH₂-cyclobutyl | |
| 1-735 | Q1g | CH₃-S(O)-CH₂-cyclopentyl | |
| 1-736 | Q1g | CH₃-S(O)-CH₂-cyclohexyl | |
| 1-737 | Q1g | CH$_2$SOCH$_2$CF$_3$ | |
| 1-738 | Q1g | CH$_2$SOCH$_2$CH=CH$_2$ | |
| 1-739 | Q1g | CH$_2$SOCH$_2$C≡CH | |
| 1-740 | Q1g | CH$_2$SO$_2$CH$_3$ | |
| 1-741 | Q1g | CH$_2$SO$_2$CH$_2$CH$_3$ | |
| 1-742 | Q1g | CH$_2$SO$_2$(CH$_2$)$_2$CH$_3$ | |
| 1-743 | Q1g | CH₃-SO₂-CH₂-cyclopropyl | |
| 1-744 | Q1g | CH₃-SO₂-CH₂-cyclobutyl | |
| 1-745 | Q1g | CH₃-SO₂-CH₂-cyclopentyl | |
| 1-746 | Q1g | CH₃-SO₂-CH₂-cyclohexyl | |
| 1-747 | Q1g | CH$_2$SO$_2$CH$_2$CF$_3$ | |
| 1-748 | Q1g | CH$_2$SO$_2$CH$_2$CH=CH$_2$ | |
| 1-749 | Q1g | CH$_2$SO$_2$CH$_2$C≡CH | |
| 1-750 | Q1g | CH$_2$O(CH$_2$)$_2$OCH$_3$ | |
| 1-751 | Q1g | CH$_2$O(CH$_2$)$_2$OCH$_2$CH$_3$ | |
| 1-752 | Q1g | CH$_2$O(CH$_2$)$_2$OCH$_2$-cyclopropyl | |
| 1-753 | Q1g | CH$_2$O(CH$_2$)$_2$OCH$_2$CF$_3$ | |
| 1-754 | Q1g | CH$_2$O(CH$_2$)$_2$OCH$_2$CH=CH$_2$ | |
| 1-755 | Q1g | CH$_2$O(CH$_2$)$_2$OCH$_2$C≡CH | |
| 1-756 | Q1g | CH$_2$O(CH$_2$)$_2$SCH$_3$ | |
| 1-757 | Q1g | CH$_2$O(CH$_2$)$_2$SCH$_2$-cyclopropyl | |
| 1-758 | Q1g | CH$_2$O(CH$_2$)$_2$SCH$_2$CF$_3$ | |
| 1-759 | Q1g | CH$_2$O(CH$_2$)$_2$SCH=CH$_2$ | |
| 1-760 | Q1g | CH$_2$O(CH$_2$)$_2$SCH$_2$C≡CH | |

TABLE 20

| compound number | Q | R1 | physical property (melting point-ND) |
|---|---|---|---|
| 1-761 | Q1g | CH$_2$O(CH$_2$)$_2$SOCH$_3$ | |
| 1-762 | Q1g |  | |
| 1-763 | Q1g | CH$_2$O(CH$_2$)$_2$SOCH$_2$CF$_3$ | |
| 1-764 | Q1g | CH$_2$O(CH$_2$)$_2$SOCH$_2$CH=CH$_2$ | |
| 1-765 | Q1g | CH$_2$O(CH$_2$)$_2$SOCH$_2$C≡CH | |
| 1-766 | Q1g | CH$_2$O(CH$_2$)$_2$SO$_2$CH$_3$ | |
| 1-767 | Q1g |  | |
| 1-768 | Q1g | CH$_2$O(CH$_2$)$_2$SO$_2$CH$_2$CF$_3$ | |
| 1-769 | Q1g | CH$_2$O(CH$_2$)$_2$SO$_2$CH$_2$CH=CH$_2$ | |
| 1-770 | Q1g | CH$_2$O(CH$_2$)$_2$SO$_2$CH$_2$C≡CH | |
| 1-771 | Q1g | 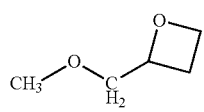 | |
| 1-772 | Q1g | 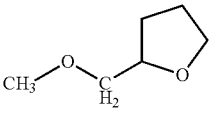 | |
| 1-773 | Q1g | 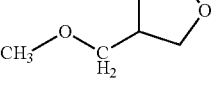 | |
| 1-774 | Q1g | 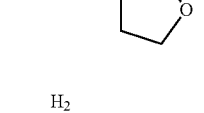 | |
| 1-775 | Q1g | 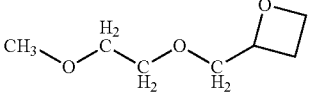 | |
| 1-776 | Q1g | 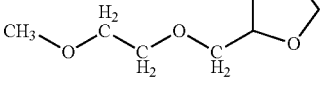 | |
| 1-777 | Q1g | 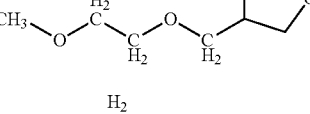 | |
| 1-778 | Q1g | 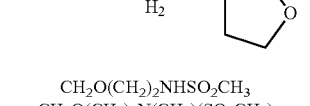 | |
| 1-779 | Q1g | CH$_2$O(CH$_2$)$_2$NHSO$_2$CH$_3$ | |
| 1-780 | Q1g | CH$_2$O(CH$_2$)$_2$N(CH$_3$)(SO$_2$CH$_3$) | |
| 1-781 | Q1g | CH$_2$O(CH$_2$)$_2$NH(SO$_2$CH$_2$—) | |
| 1-782 | Q1g | CH$_2$O(CH$_2$)$_2$NHSO$_2$CF$_3$ | |
| 1-783 | Q1g | CH$_2$O(CH$_2$)$_2$NHSO$_2$CHF$_3$ | |
| 1-784 | Q1g | CH$_2$O(CH$_2$)$_2$NHSO$_2$CH$_2$CF$_3$ | |
| 1-785 | Q1g | SCH$_3$ | |
| 1-786 | Q1g | SOCH$_3$ | |
| 1-787 | Q1g | SO$_2$CH$_3$ | |
| 1-788 | Q1g | OCH$_3$ | |
| 1-789 | Q1g | OCH$_2$CH$_3$ | |
| 1-790 | Q1g | O(CH$_2$)$_2$CH$_3$ | |
| 1-791 | Q1g | OCH$_2$CF$_3$ | |
| 1-792 | Q1g | OCF$_2$CF$_3$ | |
| 1-793 | Q1g | O(CH$_2$)$_2$OCH$_3$ | |
| 1-794 | Q1g | NHCH$_3$ | |
| 1-795 | Q1g | NHCH$_2$CH$_3$ | |
| 1-796 | Q1g | N(CH$_3$)$_2$ | |
| 1-797 | Q1g | N(CH$_2$CH$_3$)$_2$ | |
| 1-798 | Q1g | N(CH$_3$)(CH$_2$CH$_3$) | |
| 1-799 | Q1h | CH$_3$ | NMR |
| 1-800 | Q1h | CH$_2$CH$_3$ | |

TABLE 21

| compound number | Q | R1 | physical property (melting point-ND) |
|---|---|---|---|
| 1-801 | Q1h | (CH$_2$)$_2$CH$_3$ | |
| 1-802 | Q1h | | |
| 1-803 | Q1h | | |
| 1-804 | Q1h | | |
| 1-805 | Q1h | | |
| 1-806 | Q1h | | |
| 1-807 | Q1h | | |
| 1-808 | Q1h | | |

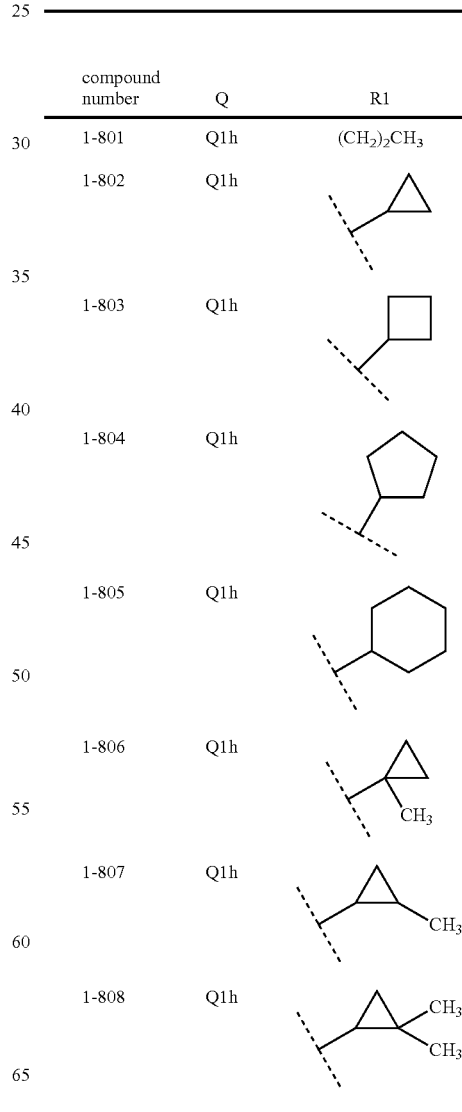

TABLE 21-continued

| compound number | Q | R1 | physical property (melting point-ND) |
|---|---|---|---|
| 1-809 | Q1h | 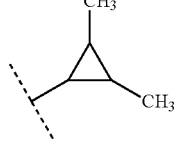 | |
| 1-810 | Q1h | CF$_3$ | 1.5495(25) |
| 1-811 | Q1h | CH$_2$CF$_3$ | |
| 1-812 | Q1h | CF$_2$CF$_3$ | |
| 1-813 | Q1h | CH$_2$CH=CH$_2$ | |
| 1-814 | Q1h | CH$_2$C≡CH | |
| 1-815 | Q1h | C$_6$H$_5$ | |
| 1-816 | Q1h | CH$_2$C$_6$H$_5$ | |
| 1-817 | Q1h | CH$_2$OCH$_3$ | 1.5773(25) |
| 1-818 | Q1h | CH$_2$OCH$_2$CH$_3$ | |
| 1-819 | Q1h | CH$_2$O(CH$_2$)$_2$CH$_3$ | |
| 1-820 | Q1h | (CH$_2$)$_2$OCH$_3$ | |
| 1-821 | Q1h | (CH$_2$)$_3$OCH$_3$ | |
| 1-822 | Q1h | 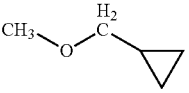 | |
| 1-823 | Q1h | 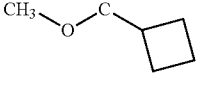 | |
| 1-824 | Q1h | 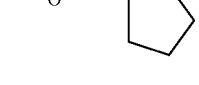 | |
| 1-825 | Q1h | 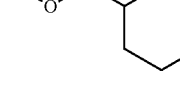 | |
| 1-826 | Q1h | CH$_2$OCH$_2$CF$_3$ | NMR |
| 1-827 | Q1h | CH$_2$OCF$_2$CHF$_2$ | |
| 1-828 | Q1h | CH$_2$OCH2CF2CF3 | |
| 1-829 | Q1h | CH$_2$OCH$_2$CH=CH$_2$ | |
| 1-830 | Q1h | CH$_2$OCH$_2$CH=CCl$_2$ | |
| 1-831 | Q1h | CH$_2$OCH$_2$CF=CF$_2$ | |
| 1-832 | Q1h | CH$_2$OC$_2$C≡CH | |
| 1-833 | Q1h | CH$_2$OCH$_2$C≡CCH$_3$ | |
| 1-834 | Q1h | CH$_2$SCH$_3$ | |
| 1-835 | Q1h | CH$_2$SCH$_2$CH$_3$ | |
| 1-836 | Q1h | CH$_2$S(CH$_2$)$_2$CH$_3$ | |
| 1-837 | Q1h | 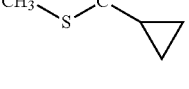 | |
| 1-838 | Q1h | 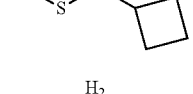 | |
| 1-839 | Q1h | 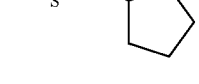 | |

TABLE 21-continued

| compound number | Q | R1 | physical property (melting point-ND) |
|---|---|---|---|
| 1-840 | Q1h | 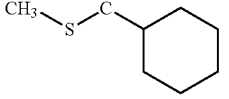 | |

TABLE 22

| compound number | Q | R1 | physical property (melting point-ND) |
|---|---|---|---|
| 1-841 | Q1h | CH$_2$SCH$_2$CF$_3$ | |
| 1-842 | Q1h | CH$_2$SCH$_2$CH=CH$_2$ | |
| 1-843 | Q1h | CH$_2$SCH$_2$C≡CH | |
| 1-844 | Q1h | CH$_2$SOCH$_3$ | |
| 1-845 | Q1h | CH$_2$SOCH$_2$CH$_3$ | |
| 1-846 | Q1h | CH$_2$SO(CH$_2$)$_2$CH$_3$ | |
| 1-847 | Q1h | 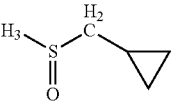 | |
| 1-848 | Q1h | 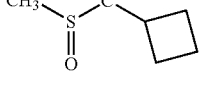 | |
| 1-849 | Q1h | 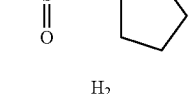 | |
| 1-850 | Q1h | 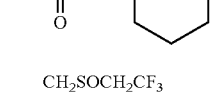 | |
| 1-851 | Q1h | CH$_2$SOCH$_2$CF$_3$ | |
| 1-852 | Q1h | CH$_2$SOCH$_2$CH=CH$_2$ | |
| 1-853 | Q1h | CH$_2$SOCH$_2$C≡CH | |
| 1-854 | Q1h | CH$_2$SO$_2$CH$_3$ | |
| 1-855 | Q1h | CH$_2$SO$_2$CH$_2$CH$_3$ | |
| 1-856 | Q1h | CH$_2$SO$_2$(CH$_2$)$_2$CH$_3$ | |
| 1-857 | Q1h | 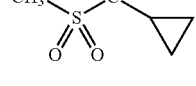 | |
| 1-858 | Q1h | 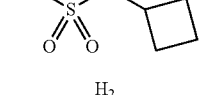 | |
| 1-859 | Q1h | 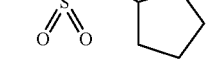 | |

TABLE 22-continued

| compound number | Q | R1 | physical property (melting point-ND) |
|---|---|---|---|
| 1-860 | Q1h | CH₃-S(O₂)-CH₂-cyclohexyl | |
| 1-861 | Q1h | CH$_2$SO$_2$CH$_2$CF$_3$ | |
| 1-862 | Q1h | CH$_2$SO$_2$CH$_2$CH=CH$_2$ | |
| 1-863 | Q1h | CH$_2$SO$_2$CH$_2$C≡CH | |
| 1-864 | Q1h | CH$_2$O(CH$_2$)$_2$OCH$_3$ | |
| 1-865 | Q1h | CH$_2$O(CH$_2$)$_2$OCH$_2$CH$_3$ | |
| 1-866 | Q1h | CH$_2$O(CH$_2$)$_2$OCH$_2$-cyclopropyl | |
| 1-867 | Q1h | CH$_2$O(CH$_2$)$_2$OCH$_2$CF$_3$ | |
| 1-868 | Q1h | CH$_2$O(CH$_2$)$_2$OCH$_2$CH=CH$_2$ | |
| 1-869 | Q1h | CH$_2$O(CH$_2$)$_2$OCH$_2$C≡CH | |
| 1-870 | Q1h | CH$_2$O(CH$_2$)$_2$SCH$_3$ | |
| 1-871 | Q1h | CH$_2$O(CH$_2$)$_2$SCH$_2$-isopropyl | |
| 1-872 | Q1h | CH$_2$O(CH$_2$)$_2$SCH$_2$CF$_3$ | |
| 1-873 | Q1h | CH$_2$O(CH$_2$)$_2$SCH=CH$_2$ | |
| 1-874 | Q1h | CH$_2$O(CH$_2$)$_2$SCH$_2$C≡CH | |
| 1-875 | Q1h | CH$_2$O(CH$_2$)$_2$SOCH$_3$ | |
| 1-876 | Q1h | CH$_2$O(CH$_2$)$_2$SOCH$_2$-cyclopropyl | |
| 1-877 | Q1h | CH$_2$O(CH$_2$)$_2$SOCH$_2$CF$_3$ | |
| 1-878 | Q1h | CH$_2$O(CH$_2$)$_2$SOCH$_2$CH=CH$_2$ | |
| 1-879 | Q1h | CH$_2$O(CH$_2$)$_2$SOCH$_2$C≡CH | |
| 1-880 | Q1h | CH$_2$O(CH$_2$)$_2$SO$_2$CH$_3$ | |

TABLE 23

| compound number | Q | R1 | physical property (melting point-ND) |
|---|---|---|---|
| 1-881 | Q1h | CH$_2$O(CH$_2$)$_2$SO$_2$CH$_2$-cyclopropyl | |
| 1-882 | Q1h | CH$_2$O(CH$_2$)$_2$SO$_2$CH$_2$CF$_3$ | |
| 1-883 | Q1h | CH$_2$O(CH$_2$)$_2$SO$_2$CH$_2$CH=CH$_2$ | |
| 1-884 | Q1h | CH$_2$O(CH$_2$)$_2$SO$_2$CH$_2$C≡CH | |
| 1-885 | Q1h | CH$_3$-O-CH$_2$-(oxetanyl) | |
| 1-886 | Q1h | CH$_3$-O-CH$_2$-(tetrahydrofuran-2-yl) | |
| 1-887 | Q1h | CH$_3$-O-CH$_2$-(tetrahydrofuran-3-yl) | |

TABLE 23-continued

| compound number | Q | R1 | physical property (melting point-ND) |
|---|---|---|---|
| 1-888 | Q1h | CH$_3$-O-(tetrahydrofuran-3-yl) | |
| 1-889 | Q1h | CH$_3$-O-CH$_2$-O-CH$_2$-(oxetanyl) | |
| 1-890 | Q1h | CH$_3$-O-CH$_2$-O-CH$_2$-(tetrahydrofuran-2-yl) | |
| 1-891 | Q1h | CH$_3$-O-CH$_2$-O-CH$_2$-(tetrahydrofuran-3-yl) | |
| 1-892 | Q1h | CH$_3$-O-CH$_2$-O-(tetrahydrofuran-3-yl) | |
| 1-893 | Q1h | CH$_2$O(CH$_2$)$_2$NHSO$_2$CH$_3$ | |
| 1-894 | Q1h | CH$_2$O(CH$_2$)$_2$N(CH$_3$)(SO$_2$CH$_3$) | |
| 1-895 | Q1h | CH$_2$O(CH$_2$)$_2$NH(SO$_2$CH$_2$-cyclopropyl) | |
| 1-896 | Q1h | CH$_2$O(CH$_2$)$_2$NHSO$_2$CF$_3$ | |
| 1-897 | Q1h | CH$_2$O(CH$_2$)$_2$NHSO$_2$CHF$_3$ | |
| 1-898 | Q1h | CH$_2$O(CH$_2$)$_2$NHSO$_2$CH$_2$CF$_3$ | |
| 1-899 | Q1h | SCH$_3$ | |
| 1-900 | Q1h | SOCH$_3$ | |
| 1-901 | Q1h | SO$_2$CH$_3$ | |
| 1-902 | Q1h | OCH$_3$ | |
| 1-903 | Q1h | OCH$_2$CH$_3$ | |
| 1-904 | Q1h | O(CH$_2$)$_2$CH$_3$ | |
| 1-905 | Q1h | OCH$_2$CF$_3$ | |
| 1-906 | Q1h | OCF$_2$CF$_3$ | |
| 1-907 | Q1h | O(CH$_2$)$_2$OCH$_3$ | |
| 1-908 | Q1h | NHCH$_3$ | |
| 1-909 | Q1h | NHCH$_2$CH$_3$ | |
| 1-910 | Q1h | N(CH$_3$)$_2$ | |
| 1-911 | Q1h | N(CH$_2$CH$_3$)$_2$ | |
| 1-912 | Q1h | N(CH$_3$)(CH$_2$CH$_3$) | |
| 1-913 | Q1i | CH$_3$ | NMR |
| 1-914 | Q1i | CH$_2$CH$_3$ | |
| 1-915 | Q1i | (CH$_2$)$_2$CH$_3$ | |
| 1-916 | Q1i | cyclopropyl | |
| 1-917 | Q1i | cyclobutyl | |

TABLE 23-continued

| compound number | Q | R1 | physical property (melting point-ND) |
|---|---|---|---|
| 1-918 | Q1i | 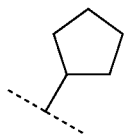 | |
| 1-919 | Q1i | 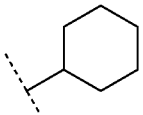 | |
| 1-920 | Q1i | 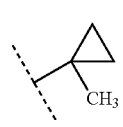 | |

TABLE 24

| compound number | Q | R1 | physical property (melting point-ND) |
|---|---|---|---|
| 1-921 | Q1i | 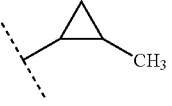 | |
| 1-922 | Q1i | 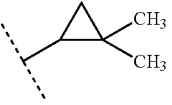 | |
| 1-923 | Q1i | 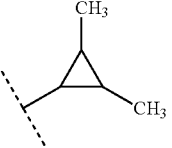 | |
| 1-924 | Q1i | CF$_3$ | |
| 1-925 | Q1i | CH$_2$CF$_3$ | |
| 1-926 | Q1i | CF$_2$CF$_3$ | |
| 1-927 | Q1i | CH$_2$CH=CH$_2$ | |
| 1-928 | Q1i | CH$_2$C≡CH | |
| 1-929 | Q1i | C$_6$H$_5$ | |
| 1-930 | Q1i | CH$_2$C$_6$H$_5$ | |
| 1-931 | Q1i | CH$_2$OCH$_3$ | |
| 1-932 | Q1i | CH$_2$OCH$_2$CH$_3$ | |
| 1-933 | Q1i | CH$_2$O(CH2)$_2$CH$_3$ | |
| 1-934 | Q1i | (CH$_2$)$_2$OCH$_3$ | |
| 1-935 | Q1i | (CH$_2$)$_3$OCH$_3$ | |
| 1-936 | Q1i | 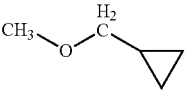 | |
| 1-937 | Q1i | 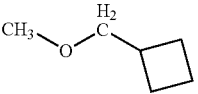 | |

TABLE 24-continued

| compound number | Q | R1 | physical property (melting point-ND) |
|---|---|---|---|
| 1-938 | Q1i | 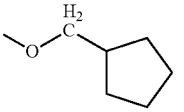 | |
| 1-939 | Q1i | 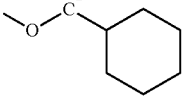 | |
| 1-940 | Q1i | CH$_2$OCH$_2$CF$_3$ | |
| 1-941 | Q1i | CH$_2$OCF$_2$CHF$_2$ | |
| 1-942 | Q1i | CH$_2$OCH2CF2CF3 | |
| 1-943 | Q1i | CH$_2$OCH$_2$CH=CH$_2$ | |
| 1-944 | Q1i | CH$_2$OCH$_2$CH=CCl$_2$ | |
| 1-945 | Q1i | CH$_2$OCH$_2$CF=CF$_2$ | |
| 1-946 | Q1i | CH$_2$OC$_2$C≡CH | |
| 1-947 | Q1i | CH$_2$OCH$_2$C≡CCH$_3$ | |
| 1-948 | Q1i | CH$_2$SCH$_3$ | |
| 1-949 | Q1i | CH$_2$SCH$_2$CH$_3$ | |
| 1-950 | Q1i | CH$_2$S(CH$_2$)$_2$CH$_3$ | |
| 1-951 | Q1i | 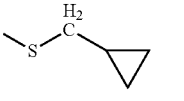 | |
| 1-952 | Q1i | 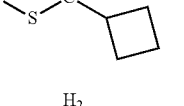 | |
| 1-953 | Q1i | 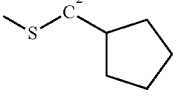 | |
| 1-954 | Q1i | 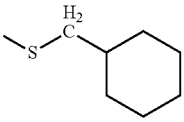 | |
| 1-955 | Q1i | CH$_2$SCH$_2$CF$_3$ | |
| 1-956 | Q1i | CH$_2$SCH$_2$CH=CH$_2$ | |
| 1-957 | Q1i | CH$_2$SCH$_2$C≡CH | |
| 1-958 | Q1i | CH$_2$SOCH$_3$ | |
| 1-959 | Q1i | CH$_2$SOCH$_2$CH$_3$ | |
| 1-960 | Q1i | CH$_2$SO(CH$_2$)$_2$CH$_3$ | |

TABLE 25

| compound number | Q | R1 | physical property (melting point-ND) |
|---|---|---|---|
| 1-961 | Q1i | 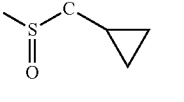 | |

TABLE 25-continued

| compound number | Q | R1 | physical property (melting point-ND) |
|---|---|---|---|
| 1-962 | Q1i | CH₃-S(=O)-CH₂-cyclobutyl | |
| 1-963 | Q1i | CH₃-S(=O)-CH₂-cyclopentyl | |
| 1-964 | Q1i | CH₃-S(=O)-CH₂-cyclohexyl | |
| 1-965 | Q1i | CH$_2$SOCH$_2$CF$_3$ | |
| 1-966 | Q1i | CH$_2$SOCH$_2$CH=CH$_2$ | |
| 1-967 | Q1i | CH$_2$SOCH$_2$C≡CH | |
| 1-968 | Q1i | CH$_2$SO$_2$CH$_3$ | |
| 1-969 | Q1i | CH$_2$SO$_2$CH$_2$CH$_3$ | |
| 1-970 | Q1i | CH$_2$SO$_2$(CH$_2$)$_2$CH$_3$ | |
| 1-971 | Q1i | CH₃-S(=O)₂-CH₂-cyclopropyl | |
| 1-972 | Q1i | CH₃-S(=O)₂-CH₂-cyclobutyl | |
| 1-973 | Q1i | CH₃-S(=O)₂-CH₂-cyclopentyl | |
| 1-974 | Q1i | CH₃-S(=O)₂-CH₂-cyclohexyl | |
| 1-975 | Q1i | CH$_2$SO$_2$CH$_2$CF$_3$ | |
| 1-976 | Q1i | CH$_2$SO$_2$CH$_2$CH=CH$_2$ | |
| 1-977 | Q1i | CH$_2$SO$_2$CH$_2$C≡CH | |
| 1-978 | Q1i | CH$_2$O(CH$_2$)$_2$OCH$_3$ | |
| 1-979 | Q1i | CH$_2$O(CH$_2$)$_2$OCH$_2$CH$_3$ | |
| 1-980 | Q1i | CH$_2$O(CH$_2$)$_2$OCH$_2$-cyclopropyl | |
| 1-981 | Q1i | CH$_2$O(CH$_2$)$_2$OCH$_2$CF$_3$ | |
| 1-982 | Q1i | CH$_2$O(CH$_2$)$_2$OCH$_2$CH=CH$_2$ | |
| 1-983 | Q1i | CH$_2$O(CH$_2$)$_2$OCH$_2$C≡CH | |
| 1-984 | Q1i | CH$_2$O(CH$_2$)$_2$SCH$_3$ | |
| 1-985 | Q1i | CH$_2$O(CH$_2$)$_2$SCH$_2$-cyclopropyl | |
| 1-986 | Q1i | CH$_2$O(CH$_2$)$_2$SCH$_2$CF$_3$ | |
| 1-987 | Q1i | CH$_2$O(CH$_2$)$_2$SCH$_2$CH=CH$_2$ | |
| 1-988 | Q1i | CH$_2$O(CH$_2$)$_2$SCH$_2$C≡CH | |
| 1-989 | Q1i | CH$_2$O(CH$_2$)$_2$SOCH$_3$ | |
| 1-990 | Q1i | CH$_2$O(CH$_2$)$_2$SOCH$_2$-cyclopropyl | |
| 1-991 | Q1i | CH$_2$O(CH$_2$)$_2$SOCH$_2$CF$_3$ | |
| 1-992 | Q1i | CH$_2$O(CH$_2$)$_2$SOCH$_2$CH=CH$_2$ | |
| 1-993 | Q1i | CH$_2$O(CH$_2$)$_2$SOCH$_2$C≡CH | |
| 1-994 | Q1i | CH$_2$O(CH$_2$)$_2$SO$_2$CH$_3$ | |
| 1-995 | Q1i | CH$_2$O(CH$_2$)$_2$SO$_2$CH$_2$-cyclopropyl | |
| 1-996 | Q1i | CH$_2$O(CH$_2$)$_2$SO$_2$CH$_2$CF$_3$ | |
| 1-997 | Q1i | CH$_2$O(CH$_2$)$_2$SO$_2$CH$_2$CH=CH$_2$ | |
| 1-998 | Q1i | CH$_2$O(CH$_2$)$_2$SO$_2$CH$_2$C≡CH | |
| 1-999 | Q1i | CH₃-O-CH₂-(oxetan-2-yl) | |
| 1-1000 | Q1i | CH₃-O-CH₂-(tetrahydrofuran-2-yl) | |

TABLE 26

| compound number | Q | R1 | physical property (melting point-ND) |
|---|---|---|---|
| 1-1001 | Q1i | CH₃-O-CH₂-(tetrahydrofuran-3-yl) | |
| 1-1002 | Q1i | CH₃-O-(tetrahydrofuran-3-yl) | |
| 1-1003 | Q1i | CH₃-O-CH₂-O-CH₂-(oxetan-2-yl) | |

TABLE 26-continued

| compound number | Q | R1 | physical property (melting point-ND) |
|---|---|---|---|
| 1-1004 | Q1i | 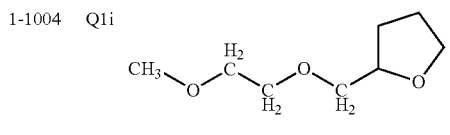 | |
| 1-1005 | Q1i | 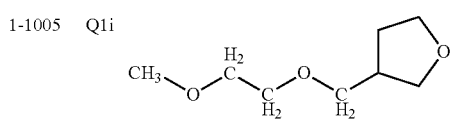 | |
| 1-1006 | Q1i | 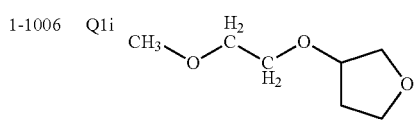 | |
| 1-1007 | Q1i | CH$_2$O(CH$_2$)$_2$NHSO$_2$CH$_3$ | |
| 1-1008 | Q1i | CH$_2$O(CH$_2$)$_2$N(CH$_3$)(SO$_2$CH$_3$) | |
| 1-1009 | Q1i | CH$_2$O(CH$_2$)$_2$NH(SO$_2$CH$_2$—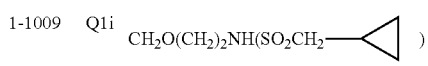) | |
| 1-1010 | Q1i | CH$_2$O(CH$_2$)$_2$NHSO$_2$CF$_3$ | |
| 1-1011 | Q1i | CH$_2$O(CH$_2$)$_2$NHSO$_2$CHF$_2$ | |
| 1-1012 | Q1i | CH$_2$O(CH$_2$)$_2$NHSO$_2$CH$_2$CF$_3$ | |
| 1-1013 | Q1i | SCH$_3$ | |
| 1-1014 | Q1i | SOCH$_3$ | |
| 1-1015 | Q1i | SO$_2$CH$_3$ | |
| 1-1016 | Q1i | OCH$_3$ | |
| 1-1017 | Q1i | OCH$_2$CH$_3$ | |
| 1-1018 | Q1i | O(CH$_2$)$_2$CH$_3$ | |
| 1-1019 | Q1i | OCH$_2$CF$_3$ | |
| 1-1020 | Q1i | OCF$_2$CF$_3$ | |
| 1-1021 | Q1i | O(CH$_2$)$_2$OCH$_3$ | |
| 1-1022 | Q1i | NHCH$_3$ | |
| 1-1023 | Q1i | NHCH$_2$CH$_3$ | |
| 1-1024 | Q1i | N(CH$_3$)$_2$ | |
| 1-1025 | Q1i | N(CH$_2$CH$_3$)$_2$ | |
| 1-1026 | Q1i | N(CH$_3$)(CH$_2$CH$_3$) | |

TABLE 27

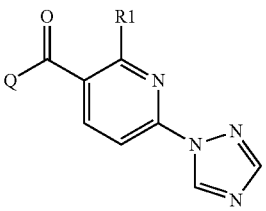

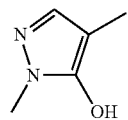 Q2a

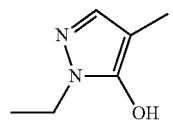 Q2b

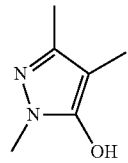 Q2c

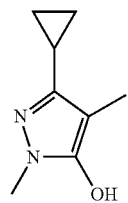 Q2d

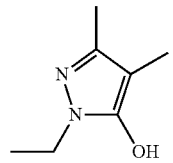 Q2e

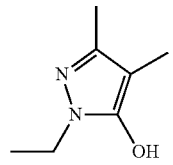 Q2f

| compound number | Q | R1 | physical property (melting point-ND) |
|---|---|---|---|
| 2-1 | Q2a | CH$_3$ | NMR |
| 2-2 | Q2a | CH$_2$CH$_3$ | |
| 2-3 | Q2a | (CH$_2$)$_2$CH$_3$ | |
| 2-4 | Q2a |  | |

TABLE 27-continued
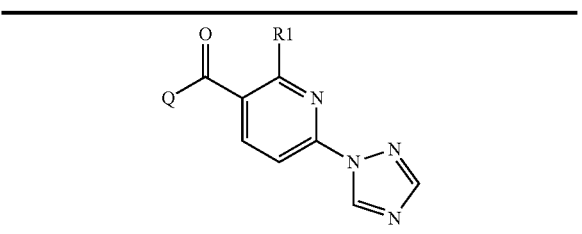
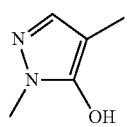 Q2a
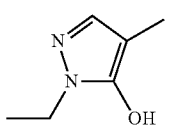 Q2b
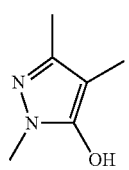 Q2c
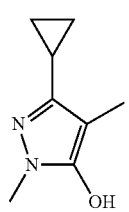 Q2d
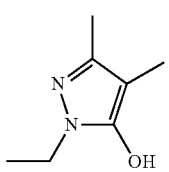 Q2e
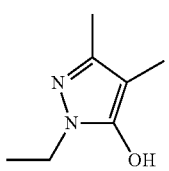 Q2f
| compound number | Q | R1 | physical property (melting point-ND) |
|---|---|---|---|
| 2-5 | Q2a | 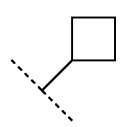 | |
TABLE 27-continued
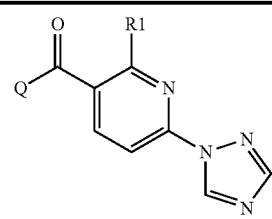
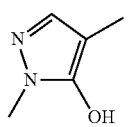 Q2a
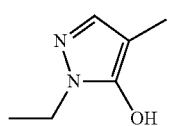 Q2b
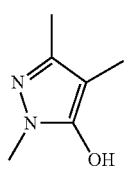 Q2c
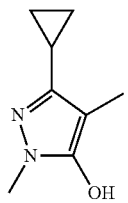 Q2d
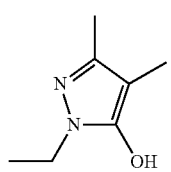 Q2e
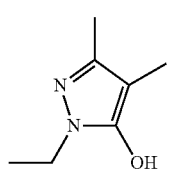 Q2f
| compound number | Q | R1 | physical property (melting point-ND) |
|---|---|---|---|
| 2-6 | Q2a | 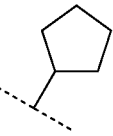 | |

TABLE 27-continued

| compound number | Q | R1 | physical property (melting point-ND) |
|---|---|---|---|
| 2-7 | Q2a | cyclohexyl | |
| 2-8 | Q2a | 1-methylcyclopropyl | |

TABLE 27-continued
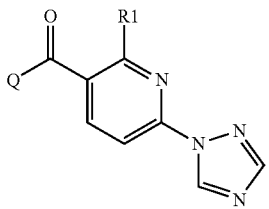
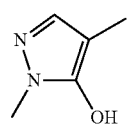
Q2a
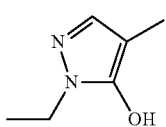
Q2b
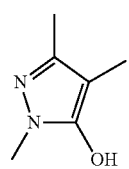
Q2c
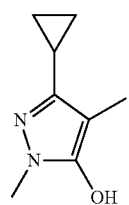
Q2d
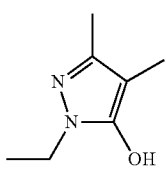
Q2e
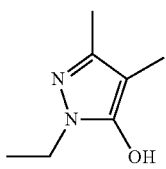
Q2f
| compound number | Q | R1 | physical property (melting point-ND) |
|---|---|---|---|
| 2-9 | Q2a | 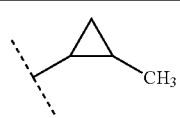 | |
TABLE 27-continued
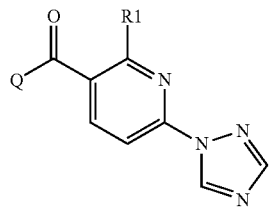
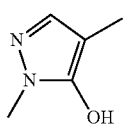
Q2a
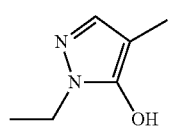
Q2b
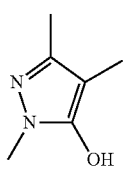
Q2c
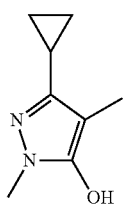
Q2d
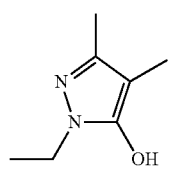
Q2e
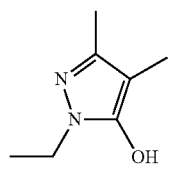
Q2f
| compound number | Q | R1 | physical property (melting point-ND) |
|---|---|---|---|
| 2-10 | Q2a | 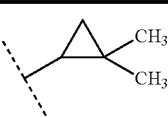 | |

TABLE 27-continued

| compound number | Q | R1 | physical property (melting point-ND) |
|---|---|---|---|
| 2-11 | Q2a | (1,2-dimethylcyclopropyl) | |
| 2-12 | Q2a | CF$_3$ | 174-178° C. |
| 2-13 | Q2a | CH$_2$CF$_3$ | |
| 2-14 | Q2a | CF$_2$CF$_3$ | |
| 2-15 | Q2a | CH$_2$CH=CH$_2$ | |
| 2-16 | Q2a | CH$_2$C≡CH | |
| 2-17 | Q2a | C$_6$H$_5$ | |
| 2-18 | Q2a | CH$_2$C$_6$H$_5$ | |
| 2-19 | Q2a | CH$_2$OCH$_3$ | |

TABLE 27-continued
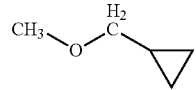
| compound number | Q | R1 | physical property (melting point-ND) |
|---|---|---|---|
| 2-20 | Q2a | CH$_2$OCH$_2$CH$_3$ | |
| 2-21 | Q2a | CH$_2$O(CH$_2$)$_2$CH$_3$ | |
| 2-22 | Q2a | (CH$_2$)$_2$OCH$_3$ | |
| 2-23 | Q2a | (CH$_2$)$_3$OCH$_3$ | |
| 2-24 | Q2a | CH$_3$–O–CH$_2$–cyclopropyl | |
| 2-25 | Q2a | CH$_3$–O–CH$_2$–cyclobutyl | |

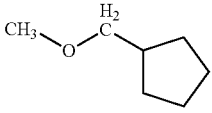
| compound number | Q | R1 | physical property (melting point-ND) |
|---|---|---|---|
| 2-26 | Q2a | CH₃-O-CH(H₂)-cyclopentyl | |
| 2-27 | Q2a | CH₃-O-CH(H₂)-cyclohexyl | |
| 2-28 | Q2a | CH₂OCH₂CF₃ | NMR |
| 2-29 | Q2a | CH₂OCF₂CHF₂ | |
| 2-30 | Q2a | CH₂OCH2CF2CF3 | |

TABLE 27-continued
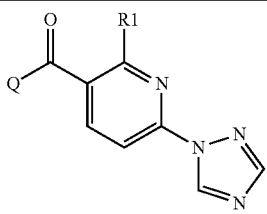
Q2a
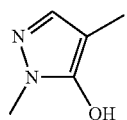
Q2b
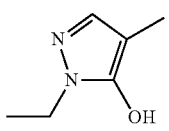
Q2c
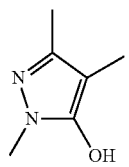
Q2d
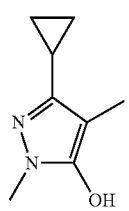
Q2e
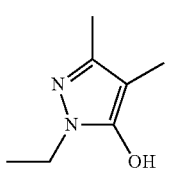
Q2f
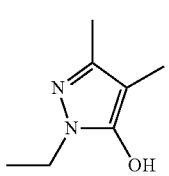
| compound number | Q | R1 | physical property (melting point-ND) |
|---|---|---|---|
| 2-31 | Q2a | CH$_2$OCH$_2$CH=CH$_2$ | |
| 2-32 | Q2a | CH$_2$OCH$_2$CH=CCl$_2$ | |
| 2-33 | Q2a | CH$_2$OCH$_2$CF=CF$_2$ | |
| 2-34 | Q2a | CH$_2$OC$_2$C≡CH | |
| 2-35 | Q2a | CH$_2$OCH$_2$C≡CCH$_3$ | |
| 2-36 | Q2a | CH$_2$SCH$_3$ | |
| 2-37 | Q2a | CH$_2$SCH$_2$CH$_3$ | |
| 2-38 | Q2a | CH$_2$S(CH$_2$)$_2$CH$_3$ | |
TABLE 27-continued
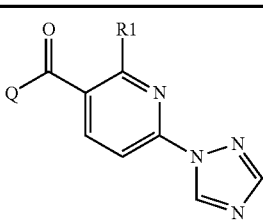
Q2a
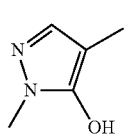
Q2b
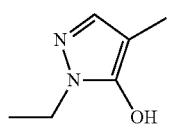
Q2c
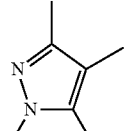
Q2d
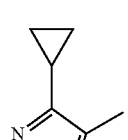
Q2e
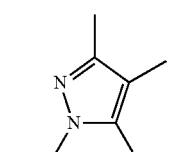
Q2f
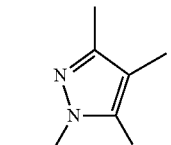
| compound number | Q | R1 | physical property (melting point-ND) |
|---|---|---|---|
| 2-39 | Q2a | CH$_3$-S-CH(H$_2$)-cyclopropyl | |

TABLE 27-continued

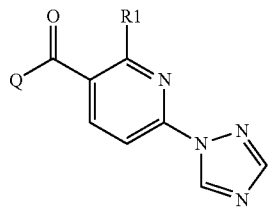

| | |
|---|---|
| Q2a | 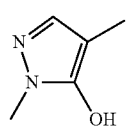 |
| Q2b | 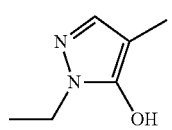 |
| Q2c | 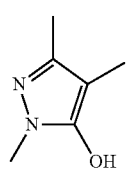 |
| Q2d | 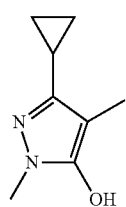 |
| Q2e | 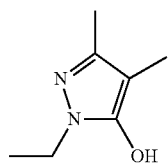 |
| Q2f | 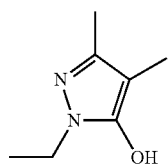 |

| compound number | Q | R1 | physical property (melting point-ND) |
|---|---|---|---|
| 2-40 | Q2a |  | |

TABLE 28

| compound number | Q | R1 | physical property (melting point-ND) |
|---|---|---|---|
| 2-41 | Q2a |  | |
| 2-42 | Q2a | (CH$_3$-S-CH$_2$-cyclohexyl) | |
| 2-43 | Q2a | CH$_2$SCH$_2$CF$_3$ | |
| 2-44 | Q2a | CH$_2$SCH$_2$CH=CH$_2$ | |
| 2-45 | Q2a | CH$_2$SCH$_2$C≡CH | |
| 2-46 | Q2a | CH$_2$SOCH$_3$ | |
| 2-47 | Q2a | CH$_2$SOCH$_2$CH$_3$ | |
| 2-48 | Q2a | CH$_2$SO(CH$_2$)$_2$CH$_3$ | |
| 2-49 | Q2a | (CH$_3$-S(O)-CH$_2$-cyclopropyl) | |
| 2-50 | Q2a | (CH$_3$-S(O)-CH$_2$-cyclobutyl) | |
| 2-51 | Q2a | (CH$_3$-S(O)-CH$_2$-cyclopentyl) | |
| 2-52 | Q2a | (CH$_3$-S(O)-CH$_2$-cyclopropyl) | |
| 2-53 | Q2a | CH$_2$SOCH$_2$CF$_3$ | |
| 2-54 | Q2a | CH$_2$SOCH$_2$CH=CH$_2$ | |
| 2-55 | Q2a | CH$_2$SOCH$_2$C≡CH | |
| 2-56 | Q2a | CH$_2$SO$_2$CH$_3$ | |
| 2-57 | Q2a | CH$_2$SO$_2$CH$_2$CH$_3$ | |
| 2-58 | Q2a | CH$_2$SO$_2$(CH$_2$)$_2$CH$_3$ | |
| 2-59 | Q2a | (CH$_3$-SO$_2$-CH$_2$-cyclopropyl) | |
| 2-60 | Q2a | (CH$_3$-SO$_2$-CH$_2$-cyclobutyl) | |
| 2-61 | Q2a | (CH$_3$-SO$_2$-CH$_2$-cyclopentyl) | |
| 2-62 | Q2a | (CH$_3$-SO$_2$-CH$_2$-cyclohexyl) | |
| 2-63 | Q2a | CH$_2$SO$_2$CH$_2$CF$_3$ | |

TABLE 28-continued

| compound number | Q | R1 | physical property (melting point-ND) |
|---|---|---|---|
| 2-64 | Q2a | CH$_2$SO$_2$CH$_2$CH=CH$_2$ | |
| 2-65 | Q2a | CH$_2$SO$_2$CH$_2$C≡CH | |
| 2-66 | Q2a | CH$_2$O(CH$_2$)$_2$OCH$_3$ | |
| 2-67 | Q2a | CH$_2$O(CH$_2$)$_2$OCH$_2$CH$_3$ | |
| 2-68 | Q2a | CH$_2$O(CH$_2$)$_2$OCH$_2$- | |
| 2-69 | Q2a | CH$_2$O(CH$_2$)$_2$OCH$_2$CF$_3$ | |
| 2-70 | Q2a | CH$_2$O(CH$_2$)$_2$OCH$_2$CH=CH$_2$ | |
| 2-71 | Q2a | CH$_2$O(CH$_2$)$_2$OCH$_2$C≡CH | |
| 2-72 | Q2a | CH$_2$O(CH$_2$)$_2$SCH$_3$ | |
| 2-73 | Q2a | CH$_2$O(CH$_2$)$_2$SCH$_2$- | |
| 2-74 | Q2a | CH$_2$O(CH$_2$)$_2$SCH$_2$CF$_3$ | |
| 2-75 | Q2a | CH$_2$O(CH$_2$)$_2$SCH$_2$CH=CH$_2$ | |
| 2-76 | Q2a | CH$_2$O(CH$_2$)$_2$SCH$_2$C≡CH | |
| 2-77 | Q2a | CH$_2$O(CH$_2$)$_2$SOCH$_3$ | |
| 2-78 | Q2a | CH$_2$O(CH$_2$)$_2$SOCH$_2$- | |
| 2-79 | Q2a | CH$_2$O(CH$_2$)$_2$SOCH$_2$CF$_3$ | |
| 2-80 | Q2a | CH$_2$O(CH$_2$)$_2$SOCH$_2$CH=CH$_2$ | |

TABLE 29

| compound number | Q | R1 | physical property (melting point-ND) |
|---|---|---|---|
| 2-81 | Q2a | CH$_2$O(CH$_2$)$_2$SOCH$_2$C≡CH | |
| 2-82 | Q2a | CH$_2$O(CH$_2$)$_2$SO$_2$CH$_3$ | |
| 2-83 | Q2a | CH$_2$O(CH$_2$)$_2$SO$_2$CH$_2$-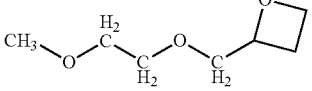 | |
| 2-84 | Q2a | CH$_2$O(CH$_2$)$_2$SO$_2$CH$_2$CF$_3$ | |
| 2-85 | Q2a | CH$_2$O(CH$_2$)$_2$SO$_2$CH$_2$CH=CH$_2$ | |
| 2-86 | Q2a | CH$_2$O(CH$_2$)$_2$SO$_2$CH$_2$C≡CH | |
| 2-87 | Q2a | 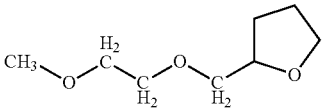 | |
| 2-88 | Q2a | 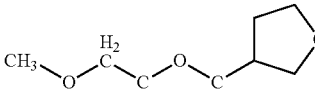 | |
| 2-89 | Q2a | 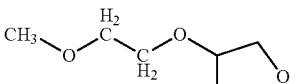 | |
| 2-90 | Q2a |  | |
| 2-91 | Q2a |  | |
| 2-92 | Q2a | 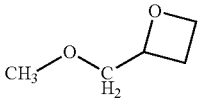 | |
| 2-93 | Q2a | 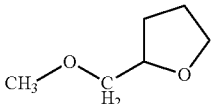 | |
| 2-94 | Q2a | 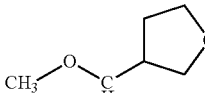 | |
| 2-95 | Q2a | CH$_2$O(CH$_2$)$_2$NHSO$_2$CH$_3$ | |
| 2-96 | Q2a | CH$_2$O(CH$_2$)$_2$N(CH$_3$)(SO$_2$CH$_3$) | |
| 2-97 | Q2a | CH$_2$O(CH$_2$)$_2$NH(SO$_2$CH$_2$-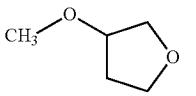) | |
| 2-98 | Q2a | CH$_2$O(CH$_2$)$_2$NHSO$_2$CF$_3$ | |
| 2-99 | Q2a | CH$_2$O(CH$_2$)$_2$NHSO$_2$CHF$_2$ | |
| 2-100 | Q2a | CH$_2$O(CH$_2$)$_2$NHSO$_2$CH$_2$CF$_3$ | |
| 2-101 | Q2a | SCH$_3$ | |
| 2-102 | Q2a | SOCH$_3$ | |
| 2-103 | Q2a | SO$_2$CH$_3$ | |
| 2-104 | Q2a | OCH$_3$ | |
| 2-105 | Q2a | OCH$_2$CH$_3$ | |
| 2-106 | Q2a | O(CH$_2$)$_2$CH$_3$ | |
| 2-107 | Q2a | OCH$_2$CF$_3$ | |
| 2-108 | Q2a | OCF$_2$CF$_3$ | |
| 2-109 | Q2a | O(CH$_2$)$_2$OCH$_3$ | |
| 2-110 | Q2a | NHCH$_3$ | |
| 2-111 | Q2a | NHCH$_2$CH$_3$ | |
| 2-112 | Q2a | N(CH$_3$)$_2$ | |
| 2-113 | Q2a | N(CH$_2$CH$_3$)$_2$ | |
| 2-114 | Q2a | N(CH$_3$)(CH$_2$CH$_3$) | |
| 2-115 | Q2b | CH$_3$ | |
| 2-116 | Q2b | CH$_2$CH$_3$ | |
| 2-117 | Q2b | (CH$_2$)$_2$CH$_3$ | |
| 2-118 | Q2b |  | |
| 2-119 | Q2b |  | |
| 2-120 | Q2b |  | |

TABLE 30

| compound number | Q | R1 | physical property (melting point-ND) |
|---|---|---|---|
| 2-121 | Q2b | cyclohexyl-CH2- | |
| 2-122 | Q2b | 1-methylcyclopropyl | |
| 2-123 | Q2b | (2-methylcyclopropyl) | |
| 2-124 | Q2b | (2,2-dimethylcyclopropyl) | |
| 2-125 | Q2b | (2,3-dimethylcyclopropyl) | |
| 2-126 | Q2b | $CF_3$ | |
| 2-127 | Q2b | $CH_2CF_3$ | |
| 2-128 | Q2b | $CF_2CF_3$ | |
| 2-129 | Q2b | $CH_2CH=CH_2$ | |
| 2-130 | Q2b | $CH_2C\equiv CH$ | |
| 2-131 | Q2b | $C_6H_5$ | |
| 2-132 | Q2b | $CH_2C_6H_5$ | |
| 2-133 | Q2b | $CH_2OCH_3$ | |
| 2-134 | Q2b | $CH_2OCH_2CH_3$ | |
| 2-135 | Q2b | $CH_2O(CH2)_2CH_3$ | |
| 2-136 | Q2b | $(CH_2)_2OCH_3$ | |
| 2-137 | Q2b | $(CH_2)_3OCH_3$ | |
| 2-138 | Q2b | $CH_3O$-$CH_2$-cyclopropyl | |
| 2-139 | Q2b | $CH_3O$-$CH_2$-cyclobutyl | |
| 2-140 | Q2b | $CH_3O$-$CH_2$-cyclopentyl | |
| 2-141 | Q2b | $CH_3O$-$CH_2$-cyclohexyl | |
| 2-142 | Q2b | $CH_2OCH_2CF_3$ | |
| 2-143 | Q2b | $CH_2OCF_2CHF_2$ | |
| 2-144 | Q2b | $CH_2OCH2CF2CF3$ | |
| 2-145 | Q2b | $CH_2OCH_2CH=CH_2$ | |
| 2-146 | Q2b | $CH_2OCH_2CH=CCl_2$ | |
| 2-147 | Q2b | $CH_2OCH_2CF=CF_2$ | |
| 2-148 | Q2b | $CH_2OC_2C\equiv CH$ | |
| 2-149 | Q2b | $CH_2OCH_2C\equiv CCH_3$ | |
| 2-150 | Q2b | $CH_2SCH_3$ | |
| 2-151 | Q2b | $CH_2SCH_2CH_3$ | |
| 2-152 | Q2b | $CH_2S(CH_2)_2CH_3$ | |
| 2-153 | Q2b | $CH_3S$-$CH_2$-cyclopropyl | |
| 2-154 | Q2b | $CH_3S$-$CH_2$-cyclobutyl | |
| 2-155 | Q2b | $CH_3S$-$CH_2$-cyclopentyl | |
| 2-156 | Q2b | $CH_3S$-$CH_2$-cyclohexyl | |
| 2-157 | Q2b | $CH_2SCH_2CF_3$ | |
| 2-158 | Q2b | $CH_2SCH_2CH=CH_2$ | |
| 2-159 | Q2b | $CH_2SCH_2C\equiv CH$ | |
| 2-160 | Q2b | $CH_2SOCH_3$ | |

TABLE 31

| compound number | Q | R1 | physical property (melting point-ND) |
|---|---|---|---|
| 2-161 | Q2b | $CH_2SOCH_2CH_3$ | |
| 2-162 | Q2b | $CH_2SO(CH_2)_2CH_3$ | |
| 2-163 | Q2b | $CH_3S(O)$-$CH_2$-cyclopropyl | |
| 2-164 | Q2b | $CH_3S(O)$-$CH_2$-cyclobutyl | |
| 2-165 | Q2b | $CH_3S(O)$-$CH_2$-cyclopentyl | |
| 2-166 | Q2b | $CH_3S(O)$-$CH_2$-cyclohexyl | |
| 2-167 | Q2b | $CH_2SOCH_2CF_3$ | |
| 2-168 | Q2b | $CH_2SOCH_2CH=CH_2$ | |

TABLE 31-continued

| compound number | Q | R1 | physical property (melting point-ND) |
|---|---|---|---|
| 2-169 | Q2b | CH$_2$SOCH$_2$C≡CH | |
| 2-170 | Q2b | CH$_2$SO$_2$CH$_3$ | |
| 2-171 | Q2b | CH$_2$SO$_2$CH$_2$CH$_3$ | |
| 2-172 | Q2b | CH$_2$SO$_2$(CH$_2$)$_2$CH$_3$ | |
| 2-173 | Q2b | CH$_3$-S(O)$_2$-CH$_2$-cyclopropyl | |
| 2-174 | Q2b | CH$_3$-S(O)$_2$-CH$_2$-cyclobutyl | |
| 2-175 | Q2b | CH$_3$-S(O)$_2$-CH$_2$-cyclopentyl | |
| 2-176 | Q2b | CH$_3$-S(O)$_2$-CH$_2$-cyclohexyl | |
| 2-177 | Q2b | CH$_2$SO$_2$CH$_2$CF$_3$ | |
| 2-178 | Q2b | CH$_2$SO$_2$CH$_2$CH=CH$_2$ | |
| 2-179 | Q2b | CH$_2$SO$_2$CH$_2$C≡CH | |
| 2-180 | Q2b | CH$_2$O(CH$_2$)$_2$OCH$_3$ | |
| 2-181 | Q2b | CH$_2$O(CH$_2$)$_2$OCH$_2$CH$_3$ | |
| 2-182 | Q2b | CH$_2$O(CH$_2$)$_2$OCH$_2$-cyclopropyl | |
| 2-183 | Q2b | CH$_2$O(CH$_2$)$_2$OCH$_2$CF$_3$ | |
| 2-184 | Q2b | CH$_2$O(CH$_2$)$_2$OCH$_2$CH=CH$_2$ | |
| 2-185 | Q2b | CH$_2$O(CH$_2$)$_2$OCH$_2$C≡CH | |
| 2-186 | Q2b | CH$_2$O(CH$_2$)$_2$SCH$_3$ | |
| 2-187 | Q2b | CH$_2$O(CH$_2$)$_2$SCH$_2$-cyclopropyl | |
| 2-188 | Q2b | CH$_2$O(CH$_2$)$_2$SCH$_2$CF$_3$ | |
| 2-189 | Q2b | CH$_2$O(CH$_2$)$_2$SCH$_2$CH=CH$_2$ | |
| 2-190 | Q2b | CH$_2$O(CH$_2$)$_2$SCH$_2$C≡CH | |
| 2-191 | Q2b | CH$_2$O(CH$_2$)$_2$SOCH$_3$ | |
| 2-192 | Q2b | CH$_2$O(CH$_2$)$_2$SOCH$_2$-cyclopropyl | |
| 2-193 | Q2b | CH$_2$O(CH$_2$)$_2$SOCH$_2$CF$_3$ | |
| 2-194 | Q2b | CH$_2$O(CH$_2$)$_2$SOCH$_2$CH=CH$_2$ | |
| 2-195 | Q2b | CH$_2$O(CH$_2$)$_2$SOCH$_2$C≡CH | |
| 2-196 | Q2b | CH$_2$O(CH$_2$)$_2$SO$_2$CH$_3$ | |
| 2-197 | Q2b | CH$_2$O(CH$_2$)$_2$SO$_2$CH$_2$-cyclopropyl | |
| 2-198 | Q2b | CH$_2$O(CH$_2$)$_2$SO$_2$CH$_2$CF$_3$ | |
| 2-199 | Q2b | CH$_2$O(CH$_2$)$_2$SO$_2$CH$_2$CH=CH$_2$ | |
| 2-200 | Q2b | CH$_2$O(CH$_2$)$_2$SO$_2$CH$_2$C≡CH | |

TABLE 32

| compound number | Q | R1 | physical property (melting point-ND) |
|---|---|---|---|
| 2-201 | Q2b | CH$_3$-O-CH$_2$-oxetanyl | |
| 2-202 | Q2b | CH$_3$-O-CH$_2$-tetrahydrofuranyl | |
| 2-203 | Q2b | CH$_3$-O-CH$_2$-tetrahydrofuranyl | |
| 2-204 | Q2b | CH$_3$-O-tetrahydrofuranyl | |
| 2-205 | Q2b | CH$_3$-O-CH$_2$-O-CH$_2$-oxetanyl | |
| 2-206 | Q2b | CH$_3$-O-CH$_2$-O-CH$_2$-tetrahydrofuranyl | |
| 2-207 | Q2b | CH$_3$-O-CH$_2$-O-CH$_2$-tetrahydrofuranyl | |
| 2-208 | Q2b | CH$_3$-O-CH$_2$-O-tetrahydrofuranyl | |
| 2-209 | Q2b | CH$_2$O(CH$_2$)$_2$NHSO$_2$CH$_3$ | |
| 2-210 | Q2b | CH$_2$O(CH$_2$)$_2$N(CH$_3$)(SO$_2$CH$_3$) | |
| 2-211 | Q2b | CH$_2$O(CH$_2$)$_2$NH(SO$_2$CH$_2$-cyclopropyl) | |
| 2-212 | Q2b | CH$_2$O(CH$_2$)$_2$NHSO$_2$CF$_3$ | |
| 2-213 | Q2b | CH$_2$O(CH$_2$)$_2$NHSO$_2$CHF$_2$ | |
| 2-214 | Q2b | CH$_2$O(CH$_2$)$_2$NHSO$_2$CH$_2$CF$_3$ | |
| 2-215 | Q2b | SCH$_3$ | |
| 2-216 | Q2b | SOCH$_3$ | |
| 2-217 | Q2b | SO$_2$CH$_3$ | |
| 2-218 | Q2b | OCH$_3$ | |
| 2-219 | Q2b | OCH$_2$CH$_3$ | |
| 2-220 | Q2b | O(CH$_2$)$_2$CH$_3$ | |
| 2-221 | Q2b | OCH$_2$CF$_3$ | |
| 2-222 | Q2b | OCF$_2$CF$_3$ | |
| 2-223 | Q2b | O(CH$_2$)$_2$OCH$_3$ | |
| 2-224 | Q2b | NHCH$_3$ | |
| 2-225 | Q2b | NHCH$_2$CH$_3$ | |
| 2-226 | Q2b | N(CH$_3$)$_2$ | |
| 2-227 | Q2b | N(CH$_2$CH$_3$)$_2$ | |
| 2-228 | Q2b | N(CH$_3$)(CH$_2$CH$_3$) | |
| 2-229 | Q2c | CH$_3$ | NMR |
| 2-230 | Q2c | CH$_2$CH$_3$ | |

TABLE 32-continued

| compound number | Q | R1 | physical property (melting point-ND) |
|---|---|---|---|
| 2-231 | Q2c | (CH$_2$)$_2$CH$_3$ | |
| 2-232 | Q2c | 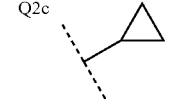 | |
| 2-233 | Q2c | 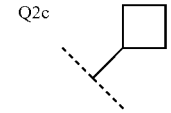 | |
| 2-234 | Q2c | 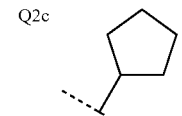 | |
| 2-235 | Q2c | 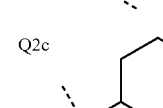 | |
| 2-236 | Q2c |  | |
| 2-237 | Q2c | 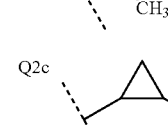 | |
| 2-238 | Q2c |  | |
| 2-239 | Q2c | 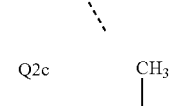 | |
| 2-240 | Q2c | CF$_3$ | |

TABLE 33

| compound number | Q | R1 | physical property (melting point-ND) |
|---|---|---|---|
| 2-241 | Q2c | CH$_2$CF$_3$ | |
| 2-242 | Q2c | CF$_2$CF$_3$ | |
| 2-243 | Q2c | CH$_2$CH=CH$_2$ | |
| 2-244 | Q2c | CH$_2$C≡CH | |
| 2-245 | Q2c | C$_6$H$_5$ | |
| 2-246 | Q2c | CH$_2$C$_6$H$_5$ | |
| 2-247 | Q2c | CH$_2$OCH$_3$ | |
| 2-248 | Q2c | CH$_2$OCH$_2$CH$_3$ | |

TABLE 33-continued

| compound number | Q | R1 | physical property (melting point-ND) |
|---|---|---|---|
| 2-249 | Q2c | CH$_2$O(CH$_2$)$_2$CH$_3$ | |
| 2-250 | Q2c | (CH$_2$)$_2$OCH$_3$ | |
| 2-251 | Q2c | (CH$_2$)$_3$OCH$_3$ | |
| 2-252 | Q2c | 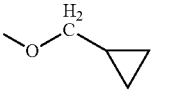 | |
| 2-253 | Q2c | 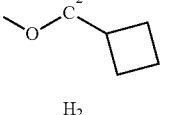 | |
| 2-254 | Q2c | 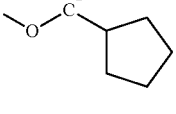 | |
| 2-255 | Q2c | 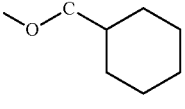 | |
| 2-256 | Q2c | CH$_2$OCH$_2$CF$_3$ | |
| 2-257 | Q2c | CH$_2$OCF$_2$CHF$_2$ | |
| 2-258 | Q2c | CH$_2$OCH2CF2CF3 | |
| 2-259 | Q2c | CH$_2$OCH$_2$CH=CH$_2$ | |
| 2-260 | Q2c | CH$_2$OCH$_2$CH=CCl$_2$ | |
| 2-261 | Q2c | CH$_2$OCH$_2$CF=CF$_2$ | |
| 2-262 | Q2c | CH$_2$OC$_2$C≡CH | |
| 2-263 | Q2c | CH$_2$OCH$_2$C≡CCH$_3$ | |
| 2-264 | Q2c | CH$_2$SCH$_3$ | |
| 2-265 | Q2c | CH$_2$SCH$_2$CH$_3$ | |
| 2-266 | Q2c | CH$_2$S(CH$_2$)$_2$CH$_3$ | |
| 2-267 | Q2c | 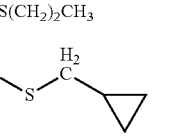 | |
| 2-268 | Q2c | 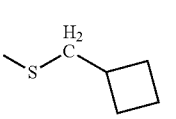 | |
| 2-269 | Q2c | 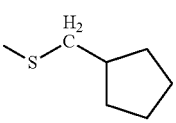 | |
| 2-270 | Q2c | 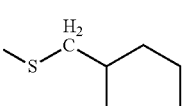 | |
| 2-271 | Q2c | CH$_2$SCH$_2$CF$_3$ | |
| 2-272 | Q2c | CH$_2$SCH$_2$CH=CH$_2$ | |
| 2-273 | Q2c | CH$_2$SCH$_2$C≡CH | |
| 2-274 | Q2c | CH$_2$SOCH$_3$ | |
| 2-275 | Q2c | CH$_2$SOCH$_2$CH$_3$ | |
| 2-276 | Q2c | CH$_2$SO(CH$_2$)$_2$CH$_3$ | |
| 2-277 | Q2c | 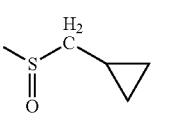 | |

TABLE 33-continued

| compound number | Q | R1 | physical property (melting point-ND) |
|---|---|---|---|
| 2-278 | Q2c | CH₃-S(=O)-CH₂-cyclobutyl | |
| 2-279 | Q2c | CH₃-S(=O)-CH₂-cyclopentyl | |
| 2-280 | Q2c | CH₃-S(=O)-CH₂-cyclohexyl | |

TABLE 34

| compound number | Q | R1 | physical property (melting point-ND) |
|---|---|---|---|
| 2-281 | Q2c | CH₂SOCH₂CF₃ | |
| 2-282 | Q2c | CH₂SOCH₂CH=CH₂ | |
| 2-283 | Q2c | CH₂SOCH₂C≡CH | |
| 2-284 | Q2c | CH₂SO₂CH₃ | |
| 2-285 | Q2c | CH₂SO₂CH₂CH₃ | |
| 2-286 | Q2c | CH₂SO₂(CH₂)₂CH₃ | |
| 2-287 | Q2c | CH₃-S(=O)₂-CH₂-cyclopropyl | |
| 2-288 | Q2c | CH₃-S(=O)₂-CH₂-cyclobutyl | |
| 2-289 | Q2c | CH₃-S(=O)₂-CH₂-cyclopentyl | |
| 2-290 | Q2c | CH₃-S(=O)₂-CH₂-cyclohexyl | |
| 2-291 | Q2c | CH₂SO₂CH₂CF₃ | |
| 2-292 | Q2c | CH₂SO₂CH₂CH=CH₂ | |
| 2-293 | Q2c | CH₂SO₂CH₂C≡CH | |
| 2-294 | Q2c | CH₂O(CH₂)₂OCH₃ | |
| 2-295 | Q2c | CH₂O(CH₂)₂OCH₂CH₃ | |
| 2-296 | Q2c | CH₂O(CH₂)₂OCH₂-cyclopropyl | |
| 2-297 | Q2c | CH₂O(CH₂)₂OCH₂CF₃ | |
| 2-298 | Q2c | CH₂O(CH₂)₂OCH₂CH=CH₂ | |
| 2-299 | Q2c | CH₂O(CH₂)₂OCH₂C≡CH | |
| 2-300 | Q2c | CH₂O(CH₂)₂SCH₃ | |

TABLE 34-continued

| compound number | Q | R1 | physical property (melting point-ND) |
|---|---|---|---|
| 2-301 | Q2c | CH₂O(CH₂)₂SCH₂-cyclopropyl | |
| 2-302 | Q2c | CH₂O(CH₂)₂SCH₂CF₃ | |
| 2-303 | Q2c | CH₂O(CH₂)₂SCH₂CH=CH₂ | |
| 2-304 | Q2c | CH₂O(CH₂)₂SCH₂C≡CH | |
| 2-305 | Q2c | CH₂O(CH₂)₂SOCH₃ | |
| 2-306 | Q2c | CH₂O(CH₂)₂SOCH₂-cyclopropyl | |
| 2-307 | Q2c | CH₂O(CH₂)₂SOCH₂CF₃ | |
| 2-308 | Q2c | CH₂O(CH₂)₂SOCH₂CH=CH₂ | |
| 2-309 | Q2c | CH₂O(CH₂)₂SOCH₂C≡CH | |
| 2-310 | Q2c | CH₂O(CH₂)₂SO₂CH₃ | |
| 2-311 | Q2c | CH₂O(CH₂)₂SO₂CH₂-cyclopropyl | |
| 2-312 | Q2c | CH₂O(CH₂)₂SO₂CH₂CF₃ | |
| 2-313 | Q2c | CH₂O(CH₂)₂SO₂CH₂CH=CH₂ | |
| 2-314 | Q2c | CH₂O(CH₂)₂SO₂CH₂C≡CH | |
| 2-315 | Q2c | CH₃-O-CH₂-(oxetan-2-yl) | |
| 2-316 | Q2c | CH₃-O-CH₂-(tetrahydrofuran-2-yl) | |
| 2-317 | Q2c | CH₃-O-CH₂-(tetrahydrofuran-3-yl) | |
| 2-318 | Q2c | CH₃-O-(tetrahydrofuran-3-yl) | |
| 2-319 | Q2c | CH₃-O-CH₂-O-CH₂-(oxetan-2-yl) | |
| 2-320 | Q2c | CH₃-O-CH₂-O-CH₂-(tetrahydrofuran-2-yl) | |

TABLE 35

| compound number | Q | R1 | physical property (melting point-ND) |
|---|---|---|---|
| 2-321 | Q2c | CH$_3$-O-CH$_2$-CH$_2$-O-CH$_2$-(tetrahydrofuran-3-yl) | |
| 2-322 | Q2c | CH$_3$-O-CH$_2$-CH$_2$-O-(tetrahydrofuran-3-yl) | |
| 2-323 | Q2c | CH$_2$O(CH$_2$)$_2$NHSO$_2$CH$_3$ | |
| 2-324 | Q2c | CH$_2$O(CH$_2$)$_2$N(CH$_3$)(SO$_2$CH$_3$) | |
| 2-325 | Q2c | CH$_2$O(CH$_2$)$_2$NH(SO$_2$CH$_2$-cyclopropyl) | |
| 2-326 | Q2c | CH$_2$O(CH$_2$)$_2$NHSO$_2$CF$_3$ | |
| 2-327 | Q2c | CH$_2$O(CH$_2$)$_2$NHSO$_2$CHF$_2$ | |
| 2-328 | Q2c | CH$_2$O(CH$_2$)$_2$NHSO$_2$CH$_2$CF$_3$ | |
| 2-329 | Q2c | SCH$_3$ | |
| 2-330 | Q2c | SOCH$_3$ | |
| 2-331 | Q2c | SO$_2$CH$_3$ | |
| 2-332 | Q2c | OCH$_3$ | |
| 2-333 | Q2c | OCH$_2$CH$_3$ | |
| 2-334 | Q2c | O(CH$_2$)$_2$CH$_3$ | |
| 2-335 | Q2c | OCH$_2$CF$_3$ | |
| 2-336 | Q2c | OCF$_2$CF$_3$ | |
| 2-337 | Q2c | O(CH$_2$)$_2$OCH$_3$ | |
| 2-338 | Q2c | NHCH$_3$ | |
| 2-339 | Q2c | NHCH$_2$CH$_3$ | |
| 2-340 | Q2c | N(CH$_3$)$_2$ | |
| 2-341 | Q2c | N(CH$_2$CH$_3$)$_2$ | |
| 2-342 | Q2c | N(CH$_3$)(CH$_2$CH$_3$) | |
| 2-343 | Q2d | CH$_3$ | |
| 2-344 | Q2d | CH$_2$CH$_3$ | |
| 2-345 | Q2d | (CH$_2$)$_2$CH$_3$ | |
| 2-346 | Q2d | CH$_2$-cyclopropyl | |
| 2-347 | Q2d | CH$_2$-cyclobutyl | |
| 2-348 | Q2d | CH$_2$-cyclopentyl | |
| 2-349 | Q2d | CH$_2$-cyclohexyl | |
| 2-350 | Q2d | CH(CH$_3$)-cyclopropyl | |
| 2-351 | Q2d | CH$_2$-(2-methylcyclopropyl) | |
| 2-352 | Q2d | CH$_2$-(2,2-dimethylcyclopropyl) | |
| 2-353 | Q2d | CH$_2$-(2,3-dimethylcyclopropyl) | |
| 2-354 | Q2d | CF$_3$ | |
| 2-355 | Q2d | CH$_2$CF$_3$ | |
| 2-356 | Q2d | CF$_2$CF$_3$ | |
| 2-357 | Q2d | CH$_2$CH=CH$_2$ | |
| 2-358 | Q2d | CH2C≡CH | |
| 2-359 | Q2d | C$_6$H$_5$ | |
| 2-360 | Q2d | CH$_2$C$_6$H$_5$ | |

TABLE 36

| compound number | Q | R1 | physical property (melting point-ND) |
|---|---|---|---|
| 2-361 | Q2d | CH$_2$OCH$_3$ | |
| 2-362 | Q2d | CH$_2$OCH$_2$CH$_3$ | |
| 2-363 | Q2d | CH$_2$O(CH2)$_2$CH$_3$ | |
| 2-364 | Q2d | (CH$_2$)$_2$OCH$_3$ | |
| 2-365 | Q2d | (CH$_2$)$_3$OCH$_3$ | |
| 2-366 | Q2d | CH$_3$-O-CH$_2$-cyclopropyl | |
| 2-367 | Q2d | CH$_3$-O-CH$_2$-cyclobutyl | |
| 2-368 | Q2d | CH$_3$-O-CH$_2$-cyclopentyl | |
| 2-369 | Q2d | CH$_3$-O-CH$_2$-cyclohexyl | |
| 2-370 | Q2d | CH$_2$OCH$_2$CF$_3$ | |
| 2-371 | Q2d | CH$_2$OCF$_2$CHF$_2$ | |
| 2-372 | Q2d | CH$_2$OCH2CF2CF3 | |
| 2-373 | Q2d | CH$_2$OCH$_2$CH=CH$_2$ | |
| 2-374 | Q2d | CH$_2$OCH$_2$CH=CCl$_2$ | |
| 2-375 | Q2d | CH$_2$OCH$_2$CF=CF$_2$ | |
| 2-376 | Q2d | CH$_2$OC$_2$C≡CH | |

TABLE 36-continued

| compound number | Q | R1 | physical property (melting point-ND) |
|---|---|---|---|
| 2-377 | Q2d | $CH_2OCH_2C\equiv CCH_3$ | |
| 2-378 | Q2d | $CH_2SCH_3$ | |
| 2-379 | Q2d | $CH_2SCH_2CH_3$ | |
| 2-380 | Q2d | $CH_2S(CH_2)_2CH_3$ | |
| 2-381 | Q2d | $CH_3$-S-$CH_2$-cyclopropyl | |
| 2-382 | Q2d | $CH_3$-S-$CH_2$-cyclobutyl | |
| 2-383 | Q2d | $CH_3$-S-$CH_2$-cyclopentyl | |
| 2-384 | Q2d | $CH_3$-S-$CH_2$-cyclohexyl | |
| 2-385 | Q2d | $CH_2SCH_2CF_3$ | |
| 2-386 | Q2d | $CH_2SCH_2CH=CH_2$ | |
| 2-387 | Q2d | $CH_2SCH_2C\equiv CH$ | |
| 2-388 | Q2d | $CH_2SOCH_3$ | |
| 2-389 | Q2d | $CH_2SOCH_2CH_3$ | |
| 2-390 | Q2d | $CH_2SO(CH_2)_2CH_3$ | |
| 2-391 | Q2d | $CH_3$-S(O)-$CH_2$-cyclopropyl | |
| 2-392 | Q2d | $CH_3$-S(O)-$CH_2$-cyclobutyl | |
| 2-393 | Q2d | $CH_3$-S(O)-$CH_2$-cyclopentyl | |
| 2-394 | Q2d | $CH_3$-S(O)-$CH_2$-cyclohexyl | |
| 2-395 | Q2d | $CH_2SOCH_2CF_3$ | |
| 2-396 | Q2d | $CH_2SOCH_2CH=CH_2$ | |
| 2-397 | Q2d | $CH_2SOCH_2C\equiv CH$ | |
| 2-398 | Q2d | $CH_2SO_2CH_3$ | |
| 2-399 | Q2d | $CH_2SO_2CH_2CH_3$ | |
| 2-400 | Q2d | $CH_2SO_2(CH_2)_2CH_3$ | |

TABLE 37

| compound number | Q | R1 | physical property (melting point-ND) |
|---|---|---|---|
| 2-401 | Q2d | $CH_3$-S(O)$_2$-$CH_2$-cyclopropyl | |
| 2-402 | Q2d | $CH_3$-S(O)$_2$-$CH_2$-cyclobutyl | |
| 2-403 | Q2d | $CH_3$-S(O)$_2$-$CH_2$-cyclopentyl | |
| 2-404 | Q2d | $CH_3$-S(O)$_2$-$CH_2$-cyclohexyl | |
| 2-405 | Q2d | $CH_2SO_2CH_2CF_3$ | |
| 2-406 | Q2d | $CH_2SO_2CH_2CH=CH_2$ | |
| 2-407 | Q2d | $CH_2SO_2CH_2C\equiv CH$ | |
| 2-408 | Q2d | $CH_2O(CH_2)_2OCH_3$ | |
| 2-409 | Q2d | $CH_2O(CH_2)_2OCH_2CH_3$ | |
| 2-410 | Q2d | $CH_2O(CH_2)_2OCH_2$-cyclopropyl | |
| 2-411 | Q2d | $CH_2O(CH_2)_2OCH_2CF_3$ | |
| 2-412 | Q2d | $CH_2O(CH_2)_2OCH_2CH=CH_2$ | |
| 2-413 | Q2d | $CH_2O(CH_2)_2OCH_2C\equiv CH$ | |
| 2-414 | Q2d | $CH_2O(CH_2)_2SCH_3$ | |
| 2-415 | Q2d | $CH_2O(CH_2)_2SCH_2$-cyclopropyl | |
| 2-416 | Q2d | $CH_2O(CH_2)_2SCH_2CF_3$ | |
| 2-417 | Q2d | $CH_2O(CH_2)_2SCH_2CH=CH_2$ | |
| 2-418 | Q2d | $CH_2O(CH_2)_2SCH_2C\equiv CH$ | |
| 2-419 | Q2d | $CH_2O(CH_2)_2SOCH_3$ | |
| 2-420 | Q2d | $CH_2O(CH_2)_2SOCH_2$-cyclopropyl | |
| 2-421 | Q2d | $CH_2O(CH_2)_2SOCH_2CF_3$ | |
| 2-422 | Q2d | $CH_2O(CH_2)_2SOCH_2CH=CH_2$ | |
| 2-423 | Q2d | $CH_2O(CH_2)_2SOCH_2C\equiv CH$ | |
| 2-424 | Q2d | $CH_2O(CH_2)_2SO_2CH_3$ | |
| 2-425 | Q2d | $CH_2O(CH_2)_2SO_2CH_2$-cyclopropyl | |
| 2-426 | Q2d | $CH_2O(CH_2)_2SO_2CH_2CF_3$ | |
| 2-427 | Q2d | $CH_2O(CH_2)_2SO_2CH_2CH=CH_2$ | |
| 2-428 | Q2d | $CH_2O(CH_2)_2SO_2CH_2C\equiv CH$ | |
| 2-429 | Q2d | $CH_3$-O-$CH_2$-oxetanyl | |
| 2-430 | Q2d | $CH_3$-O-$CH_2$-tetrahydrofuranyl | |

TABLE 37-continued

| compound number | Q | R1 | physical property (melting point-ND) |
|---|---|---|---|
| 2-431 | Q2d | CH₃-O-CH₂-(tetrahydrofuran-3-yl) | |
| 2-432 | Q2d | CH₃-O-(tetrahydrofuran-3-yl) | |
| 2-433 | Q2d | CH₃-O-CH₂-O-CH₂-(oxetan-2-yl) | |
| 2-434 | Q2d | CH₃-O-CH₂-O-CH₂-(tetrahydrofuran-2-yl) | |
| 2-435 | Q2d | CH₃-O-CH₂-O-CH₂-(tetrahydrofuran-3-yl) | |
| 2-436 | Q2d | CH₃-O-CH₂-O-(tetrahydrofuran-3-yl) | |
| 2-437 | Q2d | CH₂O(CH₂)₂NHSO₂CH₃ | |
| 2-438 | Q2d | CH₂O(CH₂)₂N(CH₃)(SO₂CH₃) | |
| 2-439 | Q2d | CH₂O(CH₂)₂NH(SO₂CH₂-cyclopropyl) | |
| 2-440 | Q2d | CH₂O(CH₂)₂NHSO₂CF₃ | |

TABLE 38

| compound number | Q | R1 | physical property (melting point-ND) |
|---|---|---|---|
| 2-441 | Q2d | CH₂O(CH₂)₂NHSO₂CHF₂ | |
| 2-442 | Q2d | CH₂O(CH₂)₂NHSO₂CH₂CF₃ | |
| 2-443 | Q2d | SCH₃ | |
| 2-444 | Q2d | SOCH₃ | |
| 2-445 | Q2d | SO₂CH₃ | |
| 2-446 | Q2d | OCH₃ | |
| 2-447 | Q2d | OCH₂CH₃ | |
| 2-448 | Q2d | O(CH₂)₂CH₃ | |
| 2-449 | Q2d | OCH₂CF₃ | |
| 2-450 | Q2d | OCF₂CF₃ | |
| 2-451 | Q2d | O(CH₂)₂OCH₃ | |
| 2-452 | Q2d | NHCH₃ | |
| 2-453 | Q2d | NHCH₂CH₃ | |
| 2-454 | Q2d | N(CH₃)₂ | |
| 2-455 | Q2d | N(CH₂CH₃)₂ | |
| 2-456 | Q2d | N(CH₃)(CH₂CH₃) | |
| 2-457 | Q2e | CH₃ | |
| 2-458 | Q2e | CH₂CH₃ | |
| 2-459 | Q2e | (CH₂)₂CH₃ | |

TABLE 38-continued

| compound number | Q | R1 | physical property (melting point-ND) |
|---|---|---|---|
| 2-460 | Q2e | cyclopropyl | |
| 2-461 | Q2e | cyclobutyl | |
| 2-462 | Q2e | cyclopentyl | |
| 2-463 | Q2e | cyclohexyl | |
| 2-464 | Q2e | 1-methylcyclopropyl | |
| 2-465 | Q2e | 2-methylcyclopropyl | |
| 2-466 | Q2e | 1,1-dimethylcyclopropyl | |
| 2-467 | Q2e | 2,3-dimethylcyclopropyl | |
| 2-468 | Q2e | CF₃ | |
| 2-469 | Q2e | CH₂CF₃ | |
| 2-470 | Q2e | CF₂CF₃ | |
| 2-471 | Q2e | CH₂CH=CH₂ | |
| 2-472 | Q2e | CH2C≡CH | |
| 2-473 | Q2e | C₆H₅ | |
| 2-474 | Q2e | CH₂C₆H₅ | |
| 2-475 | Q2e | CH₂OCH₃ | |
| 2-476 | Q2e | CH₂OCH₂CH₃ | |
| 2-477 | Q2e | CH₂O(CH2)₂CH₃ | |
| 2-478 | Q2e | (CH₂)₂OCH₃ | |
| 2-479 | Q2e | (CH₂)₃OCH₃ | |
| 2-480 | Q2e | CH₃-O-CH₂-cyclopropyl | |

TABLE 39

| compound number | Q | R1 | physical property (melting point-ND) |
|---|---|---|---|
| 2-481 | Q2e | CH$_3$-O-CH$_2$-cyclobutyl | |
| 2-482 | Q2e | CH$_3$-O-CH$_2$-cyclopentyl | |
| 2-483 | Q2e | CH$_3$-O-CH$_2$-cyclohexyl | |
| 2-484 | Q2e | CH$_2$OCH$_2$CF$_3$ | |
| 2-485 | Q2e | | |
| 2-486 | Q2e | CH$_2$OCH2CF2CF3 | |
| 2-487 | Q2e | CH$_2$OCH$_2$CH=CH$_2$ | |
| 2-488 | Q2e | CH$_2$OCH$_2$CH=CCl$_2$ | |
| 2-489 | Q2e | CH$_2$OCH$_2$CF=CF$_2$ | |
| 2-490 | Q2e | CH$_2$OC$_2$C≡CH | |
| 2-491 | Q2e | CH$_2$OCH$_2$C≡CCH$_3$ | |
| 2-492 | Q2e | CH$_2$SCH$_3$ | |
| 2-493 | Q2e | CH$_2$SCH$_2$CH$_3$ | |
| 2-494 | Q2e | CH$_2$S(CH$_2$)$_2$CH$_3$ | |
| 2-495 | Q2e | CH$_3$-S-CH$_2$-cyclopropyl | |
| 2-496 | Q2e | CH$_3$-S-CH$_2$-cyclobutyl | |
| 2-497 | Q2e | CH$_3$-S-CH$_2$-cyclopentyl | |
| 2-498 | Q2e | CH$_3$-S-CH$_2$-cyclohexyl | |
| 2-499 | Q2e | CH$_2$SCH$_2$CF$_3$ | |
| 2-500 | Q2e | CH$_2$SCH$_2$CH=CH$_2$ | |
| 2-501 | Q2e | CH$_2$SCH$_2$C≡CH | |
| 2-502 | Q2e | CH$_2$SOCH$_3$ | |
| 2-503 | Q2e | CH$_2$SOCH$_2$CH$_3$ | |
| 2-504 | Q2e | CH$_2$SO(CH$_2$)$_2$CH$_3$ | |
| 2-505 | Q2e | CH$_3$-S(=O)-CH$_2$-cyclopropyl | |
| 2-506 | Q2e | CH$_3$-S(=O)-CH$_2$-cyclobutyl | |

TABLE 39-continued

| compound number | Q | R1 | physical property (melting point-ND) |
|---|---|---|---|
| 2-507 | Q2e | CH$_3$-S(=O)-CH$_2$-cyclopentyl | |
| 2-508 | Q2e | CH$_3$-S(=O)-CH$_2$-cyclohexyl | |
| 2-509 | Q2e | CH$_2$SOCH$_2$CF$_3$ | |
| 2-510 | Q2e | CH$_2$SOCH$_2$CH=CH$_2$ | |
| 2-511 | Q2e | CH$_2$SOCH$_2$C≡CH | |
| 2-512 | Q2e | CH$_2$SO$_2$CH$_3$ | |
| 2-513 | Q2e | CH$_2$SO$_2$CH$_2$CH$_3$ | |
| 2-514 | Q2e | CH$_2$SO$_2$(CH$_2$)$_2$CH$_3$ | |
| 2-515 | Q2e | CH$_3$-S(=O)$_2$-CH$_2$-cyclopropyl | |
| 2-516 | Q2e | CH$_3$-S(=O)$_2$-CH$_2$-cyclobutyl | |
| 2-517 | Q2e | CH$_3$-S(=O)$_2$-CH$_2$-cyclopentyl | |
| 2-518 | Q2e | CH$_3$-S(=O)$_2$-CH$_2$-cyclohexyl | |
| 2-519 | Q2e | CH$_2$SO$_2$CH$_2$CF$_3$ | |
| 2-520 | Q2e | CH$_2$SO$_2$CH$_2$CH=CH$_2$ | |

TABLE 40

| compound number | Q | R1 | physical property (melting point-ND) |
|---|---|---|---|
| 2-521 | Q2e | CH$_2$SO$_2$CH$_2$C≡CH | |
| 2-522 | Q2e | CH$_2$O(CH$_2$)$_2$OCH$_3$ | |
| 2-523 | Q2e | CH$_2$O(CH$_2$)$_2$OCH$_2$CH$_3$ | |
| 2-524 | Q2e | CH$_2$O(CH$_2$)$_2$OCH$_2$-cyclopropyl | |
| 2-525 | Q2e | CH$_2$O(CH$_2$)$_2$OCH$_2$CF$_3$ | |
| 2-526 | Q2e | CH$_2$O(CH$_2$)$_2$OCH$_2$CH=CH$_2$ | |
| 2-527 | Q2e | CH$_2$O(CH$_2$)$_2$OCH$_2$C≡CH | |
| 2-528 | Q2e | CH$_2$O(CH$_2$)$_2$SCH$_3$ | |
| 2-529 | Q2e | CH$_2$O(CH$_2$)$_2$SCH$_2$-cyclopropyl | |
| 2-530 | Q2e | CH$_2$O(CH$_2$)$_2$SCH$_2$CF$_3$ | |
| 2-531 | Q2e | CH$_2$O(CH$_2$)$_2$SCH$_2$CH=CH$_2$ | |
| 2-532 | Q2e | CH$_2$O(CH$_2$)$_2$SCH$_2$C≡CH | |

TABLE 40-continued

| compound number | Q | R1 | physical property (melting point-ND) |
|---|---|---|---|
| 2-533 | Q2e | CH$_2$O(CH$_2$)$_2$SOCH$_3$ | |
| 2-534 | Q2e | CH$_2$O(CH$_2$)$_2$SOCH$_2$— | |
| 2-535 | Q2e | CH$_2$O(CH$_2$)$_2$SOCH$_2$CF$_3$ | |
| 2-536 | Q2e | CH$_2$O(CH$_2$)$_2$SOCH$_2$CH=CH$_2$ | |
| 2-537 | Q2e | CH$_2$O(CH$_2$)$_2$SOCH$_2$C≡CH | |
| 2-538 | Q2e | CH$_2$O(CH$_2$)$_2$SO$_2$CH$_3$ | |
| 2-539 | Q2e | CH$_2$O(CH$_2$)$_2$SO$_2$CH$_2$— | |
| 2-540 | Q2e | CH$_2$O(CH$_2$)$_2$SO$_2$CH$_2$CF$_3$ | |
| 2-541 | Q2e | CH$_2$O(CH$_2$)$_2$SO$_2$CH$_2$CH=CH$_2$ | |
| 2-542 | Q2e | CH$_2$O(CH$_2$)$_2$SO$_2$CH$_2$C≡CH | |
| 2-543 | Q2e | 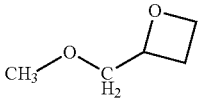 | |
| 2-544 | Q2e | 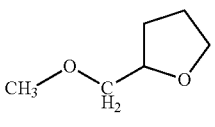 | |
| 2-545 | Q2e | 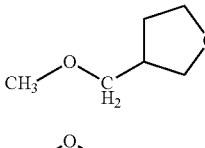 | |
| 2-546 | Q2e | 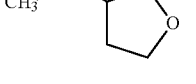 | |
| 2-547 | Q2e | 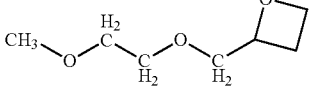 | |
| 2-548 | Q2e | 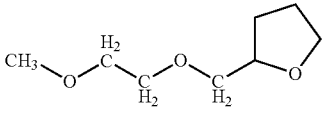 | |
| 2-549 | Q2e | 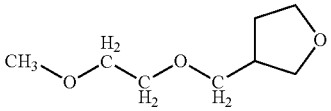 | |
| 2-550 | Q2e | 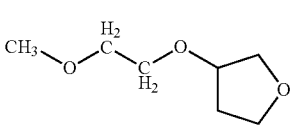 | |
| 2-551 | Q2e | CH$_2$O(CH$_2$)$_2$NHSO$_2$CH$_3$ | |
| 2-552 | Q2e | CH$_2$O(CH$_2$)$_2$N(CH$_3$)(SO$_2$CH$_3$) | |
| 2-553 | Q2e | CH$_2$O(CH$_2$)$_2$NH(SO$_2$CH$_2$—) | |
| 2-554 | Q2e | CH$_2$O(CH$_2$)$_2$NHSO$_2$CF$_3$ | |
| 2-555 | Q2e | CH$_2$O(CH$_2$)$_2$NHSO$_2$CHF$_2$ | |
| 2-556 | Q2e | CH$_2$O(CH$_2$)$_2$NHSO$_2$CH$_2$CF$_3$ | |

TABLE 40-continued

| compound number | Q | R1 | physical property (melting point-ND) |
|---|---|---|---|
| 2-557 | Q2e | SCH$_3$ | |
| 2-558 | Q2e | SOCH$_3$ | |
| 2-559 | Q2e | SO$_2$CH$_3$ | |
| 2-560 | Q2e | OCH$_3$ | |

TABLE 41

| compound number | Q | R1 | physical property (melting point-ND) |
|---|---|---|---|
| 2-561 | Q2e | OCH$_2$CH$_3$ | |
| 2-562 | Q2e | O(CH$_2$)$_2$CH$_3$ | |
| 2-563 | Q2e | OCH$_2$CF$_3$ | |
| 2-564 | Q2e | OCF$_2$CF$_3$ | |
| 2-565 | Q2e | O(CH$_2$)$_2$OCH$_3$ | |
| 2-566 | Q2e | NHCH$_3$ | |
| 2-567 | Q2e | NHCH$_2$CH$_3$ | |
| 2-568 | Q2e | N(CH$_3$)$_2$ | |
| 2-569 | Q2e | N(CH$_2$CH$_3$)$_2$ | |
| 2-570 | Q2e | N(CH$_3$)(CH$_2$CH$_3$) | |
| 2-571 | Q2f | CH$_3$ | |
| 2-572 | Q2f | CH$_2$CH$_3$ | |
| 2-573 | Q2f | (CH$_2$)$_2$CH$_3$ | |
| 2-574 | Q2f |  | |
| 2-575 | Q2f |  | |
| 2-576 | Q2f |  | |
| 2-577 | Q2f |  | |
| 2-578 | Q2f |  | |
| 2-579 | Q2f |  | |
| 2-580 | Q2f |  | |

TABLE 41-continued

| compound number | Q | R1 | physical property (melting point-ND) |
|---|---|---|---|
| 2-581 | Q2f | 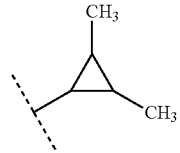 | |
| 2-582 | Q2f | CF$_3$ | |
| 2-583 | Q2f | CH$_2$CF$_3$ | |
| 2-584 | Q2f | CF$_2$CF$_3$ | |
| 2-585 | Q2f | CH$_2$CH=CH$_2$ | |
| 2-586 | Q2f | CH2C≡CH | |
| 2-587 | Q2f | C$_6$H$_5$ | |
| 2-588 | Q2f | CH$_2$C$_6$H$_5$ | |
| 2-589 | Q2f | CH$_2$OCH$_3$ | |
| 2-590 | Q2f | CH$_2$OCH$_2$CH$_3$ | |
| 2-591 | Q2f | CH$_2$O(CH2)$_2$CH$_3$ | |
| 2-592 | Q2f | (CH$_2$)$_2$OCH$_3$ | |
| 2-593 | Q2f | (CH$_2$)$_3$OCH$_3$ | |
| 2-594 | Q2f | 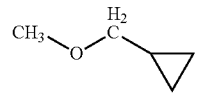 | |
| 2-595 | Q2f | 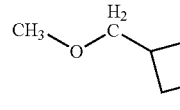 | |
| 2-596 | Q2f | 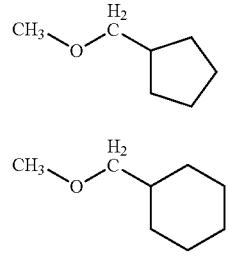 | |
| 2-597 | Q2f | 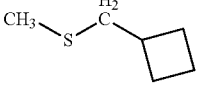 | |
| 2-598 | Q2f | CH$_2$OCH$_2$CF$_3$ | |
| 2-599 | Q2f | CH$_2$OCF$_2$CHF$_2$ | |
| 2-600 | Q2f | CH$_2$OCH2CF2CF3 | |

TABLE 42

| compound number | Q | R1 | physical property (melting point-ND) |
|---|---|---|---|
| 2-601 | Q2f | CH$_2$OCH$_2$CH=CH$_2$ | |
| 2-602 | Q2f | CH$_2$OCH$_2$CH=CCl$_2$ | |
| 2-603 | Q2f | CH$_2$OCH$_2$CF=CF$_2$ | |
| 2-604 | Q2f | CH$_2$OC$_2$C≡CH | |
| 2-605 | Q2f | CH$_2$OCH$_2$C=CCH$_3$ | |
| 2-606 | Q2f | CH$_2$SCH$_3$ | |
| 2-607 | Q2f | CH$_2$SCH$_2$CH$_3$ | |
| 2-608 | Q2f | CH$_2$S(CH$_2$)$_2$CH$_3$ | |
| 2-609 | Q2f | 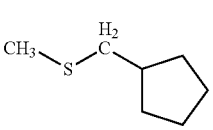 | |
| 2-610 | Q2f | 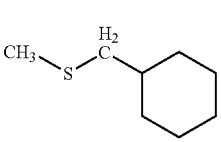 | |
| 2-611 | Q2f | 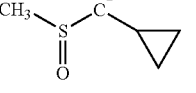 | |
| 2-612 | Q2f | 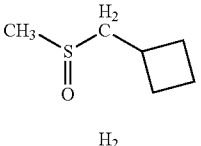 | |
| 2-613 | Q2f | CH$_2$SCH$_2$CF$_3$ | |
| 2-614 | Q2f | CH$_2$SCH$_2$CH=CH$_2$ | |
| 2-615 | Q2f | CH$_2$SCH$_2$C≡CH | |
| 2-616 | Q2f | CH$_2$SOCH$_3$ | |
| 2-617 | Q2f | CH$_2$SOCH$_2$CH$_3$ | |
| 2-618 | Q2f | CH$_2$SO(CH$_2$)$_2$CH$_3$ | |
| 2-619 | Q2f | 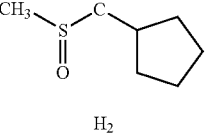 | |
| 2-620 | Q2f | 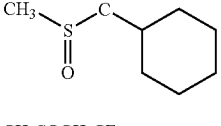 | |
| 2-621 | Q2f | 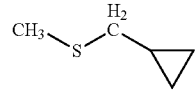 | |
| 2-622 | Q2f | 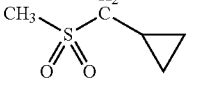 | |
| 2-623 | Q2f | CH$_2$SOCH$_2$CF$_3$ | |
| 2-624 | Q2f | CH$_2$SOCH$_2$CH=CH$_2$ | |
| 2-625 | Q2f | CH$_2$SOCH$_2$C≡CH | |
| 2-626 | Q2f | CH$_2$SO$_2$CH$_3$ | |
| 2-627 | Q2f | CH$_2$SO$_2$CH$_2$CH$_3$ | |
| 2-628 | Q2f | CH$_2$SO$_2$(CH$_2$)$_2$CH$_3$ | |
| 2-629 | Q2f | 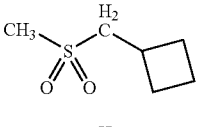 | |
| 2-630 | Q2f | 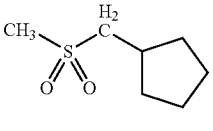 | |
| 2-631 | Q2f | | |

TABLE 42-continued

| compound number | Q | R1 | physical property (melting point-ND) |
|---|---|---|---|
| 2-632 | Q2f |  | |
| 2-633 | Q2f | CH₂SO₂CH₂CF₃ | |
| 2-634 | Q2f | CH₂SO₂CH₂CH=CH₂ | |
| 2-635 | Q2f | CH₂SO₂CH₂C≡CH | |
| 2-636 | Q2f | CH₂O(CH₂)₂OCH₃ | |
| 2-637 | Q2f | CH₂O(CH₂)₂OCH₂CH₃ | |
| 2-638 | Q2f | CH₂O(CH₂)₂OCH₂—⟨cyclopropyl⟩ | |
| 2-639 | Q2f | CH₂O(CH₂)2OCH₂CF₃ | |
| 2-640 | Q2f | CH₂O(CH₂)₂OCH₂CH=CH₂ | |

TABLE 43

| compound number | Q | R1 | physical property (melting point-ND) |
|---|---|---|---|
| 2-641 | Q2f | CH₂O(CH₂)₂OCH₂C≡CH | |
| 2-642 | Q2f | CH₂O(CH₂)₂SCH₃ | |
| 2-643 | Q2f | CH₂O(CH₂)₂SCH₂—⟨cyclopropyl⟩ | |
| 2-644 | Q2f | CH₂O(CH₂)₂SCH₂CF₃ | |
| 2-645 | Q2f | CH₂O(CH₂)2SCH₂CH=CH₂ | |
| 2-646 | Q2f | CH₂O(CH₂)₂SCH₂C≡CH | |
| 2-647 | Q2f | CH₂O(CH₂)₂SOCH₃ | |
| 2-648 | Q2f | CH₂O(CH₂)₂SOCH₂—⟨cyclopropyl⟩ | |
| 2-649 | Q2f | CH₂O(CH₂)₂SOCH₂CF₃ | |
| 2-650 | Q2f | CH₂O(CH₂)₂SOCH₂CH=CH₂ | |
| 2-651 | Q2f | CH₂O(CH₂)₂SOCH₂C≡CH | |
| 2-652 | Q2f | CH₂O(CH₂)₂SO₂CH₃ | |
| 2-653 | Q2f | CH₂O(CH₂)₂SO₂CH₂—⟨cyclopropyl⟩ | |
| 2-654 | Q2f | CH₂O(CH₂)₂SO₂CH₂CF₃ | |
| 2-655 | Q2f | CH₂O(CH₂)₂SO₂CH₂CH=CH₂ | |
| 2-656 | Q2f | CH₂O(CH₂)₂SO₂CH₂C≡CH | |
| 2-657 | Q2f | CH₃—O—CH₂—⟨oxetanyl⟩ | |
| 2-658 | Q2f | CH₃—O—CH₂—⟨tetrahydrofuran-2-yl⟩ | |
| 2-659 | Q2f | CH₃—O—CH₂—⟨tetrahydrofuran-3-yl⟩ | |
| 2-660 | Q2f | CH₃—O—⟨tetrahydrofuran-3-yl⟩ | |
| 2-661 | Q2f | CH₃—O—CH₂—CH₂—O—CH₂—⟨oxetanyl⟩ | |
| 2-662 | Q2f | CH₃—O—CH₂—CH₂—O—CH₂—⟨tetrahydrofuran-2-yl⟩ | |
| 2-663 | Q2f | CH₃—O—CH₂—CH₂—O—CH₂—⟨tetrahydrofuran-3-yl⟩ | |
| 2-664 | Q2f | CH₃—O—CH₂—CH₂—O—⟨tetrahydrofuran-3-yl⟩ | |
| 2-665 | Q2f | CH₂O(CH₂)₂NHSO₂CH₃ | |
| 2-666 | Q2f | CH₂(CH₂)₂N(CH₃)(SO₂CH₃) | |
| 2-667 | Q2f | CH₂O(CH₂)₂NH(SO₂CH₂—⟨cyclopropyl⟩) | |
| 2-668 | Q2f | CH₂O(CH₂)₂NHSO₂CF₃ | |
| 2-669 | Q2f | CH₂O(CH₂)₂NHSO₂CHF₂ | |
| 2-670 | Q2f | CH₂O(CH₂)₂NHSO₂CH₂CF₃ | |
| 2-671 | Q2f | SCH₃ | |
| 2-672 | Q2f | SOCH₃ | |
| 2-673 | Q2f | SO₂CH₃ | |
| 2-674 | Q2f | OCH₃ | |
| 2-675 | Q2f | OCH₂CH₃ | |
| 2-676 | Q2f | O(CH₂)₂CH₃ | |
| 2-677 | Q2f | OCH₂CF₃ | |
| 2-678 | Q2f | OCF₂CF₃ | |
| 2-679 | Q2f | O(CH₂)₂OCH₃ | |
| 2-680 | Q2f | NHCH₃ | |

TABLE 44

| compound number | Q | R1 | physical property (melting point-ND) |
|---|---|---|---|
| 2-681 | Q2f | NHCH₂CH₃ | |
| 2-682 | Q2f | N(CH₃)₂ | |
| 2-683 | Q2f | N(CH₂CH₃)₂ | |
| 2-684 | Q2f | N(CH₃)(CH₂CH₃) | |

TABLE 45
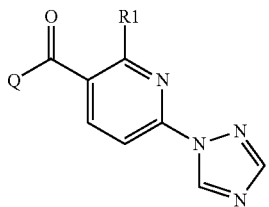
Q
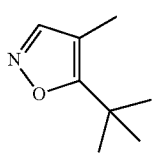 Q3a
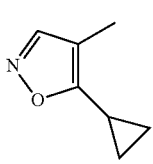 Q3b
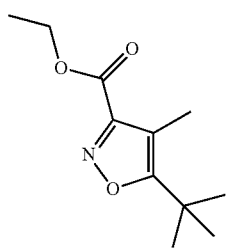 Q3c
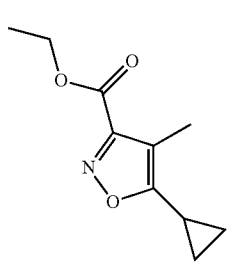 Q3d
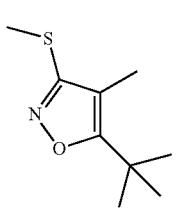 Q3e
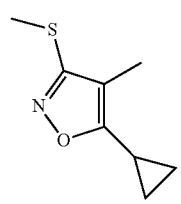 Q3f
| compound number | Q | R1 | physical property (melting point-ND) |
|---|---|---|---|
| 3-1 | Q3a | CH₃ | |
| 3-2 | Q3a | CH₂CH₃ | |
| 3-3 | Q3a | (CH₂)₂CH₃ | |
| 3-4 | Q3a | cyclopropyl | |
| 3-5 | Q3a | cyclobutyl | |
| 3-6 | Q3a | cyclopentyl | |
| 3-7 | Q3a | cyclohexyl | |
| 3-8 | Q3a | 1-methylcyclopropyl | |
| 3-9 | Q3a | 2-methylcyclopropyl | |
| 3-10 | Q3a | 2,2-dimethylcyclopropyl | |
| 3-11 | Q3a | 2,3-dimethylcyclopropyl | |
| 3-12 | Q3a | CF₃ | |
| 3-13 | Q3a | CH₂CF₃ | |
| 3-14 | Q3a | CF₂CF₃ | |
| 3-15 | Q3a | CH₂CH=CH₂ | |
| 3-16 | Q3a | CH2C≡CH | |

TABLE 45-continued

| | | |
|---|---|---|
| 3-17 | Q3a | C$_6$H$_5$ |
| 3-18 | Q3a | CH$_2$C$_6$H$_5$ |
| 3-19 | Q3a | CH$_2$OCH$_3$ |
| 3-20 | Q3a | CH$_2$OCH$_2$CH$_3$ |
| 3-21 | Q3a | CH$_2$O(CH2)$_2$CH$_3$ |
| 3-22 | Q3a | (CH$_2$)$_2$OCH$_3$ |
| 3-23 | Q3a | (CH$_2$)$_3$OCH$_3$ |
| 3-24 | Q3a | 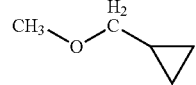 |
| 3-25 | Q3a | 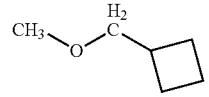 |
| 3-26 | Q3a | 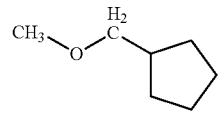 |
| 3-27 | Q3a | 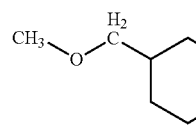 |
| 3-28 | Q3a | CH$_2$OCH$_2$CF$_3$ |
| 3-29 | Q3a | CH$_2$OCF$_2$CHF$_2$ |
| 3-30 | Q3a | CH$_2$OCH2CF2CF3 |
| 3-31 | Q3a | CH$_2$OCH$_2$CH=CH$_2$ |
| 3-32 | Q3a | CH$_2$OCH$_2$CH=CCl$_2$ |
| 3-33 | Q3a | CH$_2$OCH$_2$CF=CF$_2$ |
| 3-34 | Q3a | CH$_2$OC$_2$C≡CH |
| 3-35 | Q3a | CH$_2$OCH$_2$C≡CCH$_3$ |
| 3-36 | Q3a | CH$_2$SCH$_3$ |
| 3-37 | Q3a | CH$_2$SCH$_2$CH$_3$ |
| 3-38 | Q3a | CH$_2$S(CH$_2$)$_2$CH$_3$ |
| 3-39 | Q3a | 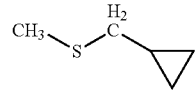 |
| 3-40 | Q3a | 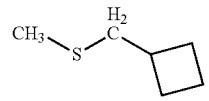 |

TABLE 46

| compound number | Q | R1 | physical property (melting point-ND) |
|---|---|---|---|
| 3-41 | Q3a | | |
| 3-42 | Q3a | 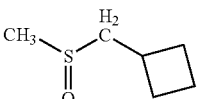 | |
| 3-43 | Q3a | CH$_2$SCH$_2$CF$_3$ | |
| 3-44 | Q3a | CH$_2$SCH$_2$CH=CH$_2$ | |
| 3-45 | Q3a | CH$_2$SCH$_2$C≡CH | |

TABLE 46-continued

| compound number | Q | R1 | physical property (melting point-ND) |
|---|---|---|---|
| 3-46 | Q3a | CH$_2$SOCH$_3$ | |
| 3-47 | Q3a | CH$_2$SOCH$_2$CH$_3$ | |
| 3-48 | Q3a | CH$_2$SO(CH$_2$)$_2$CH$_3$ | |
| 3-49 | Q3a | 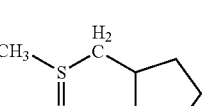 | |
| 3-50 | Q3a | 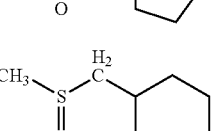 | |
| 3-51 | Q3a | 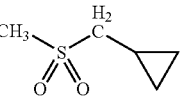 | |
| 3-52 | Q3a | 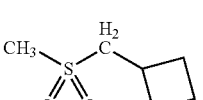 | |
| 3-53 | Q3a | CH$_2$SOCH$_2$CF$_3$ | |
| 3-54 | Q3a | CH$_2$SOCH$_2$CH=CH$_2$ | |
| 3-55 | Q3a | CH$_2$SOCH$_2$C≡CH | |
| 3-56 | Q3a | CH$_2$SO$_2$CH$_3$ | |
| 3-57 | Q3a | CH$_2$SO$_2$CH$_2$CH$_3$ | |
| 3-58 | Q3a | CH$_2$SO$_2$(CH$_2$)$_2$CH$_3$ | |
| 3-59 | Q3a | 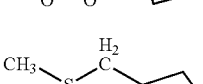 | |
| 3-60 | Q3a | 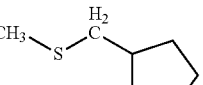 | |
| 3-61 | Q3a | 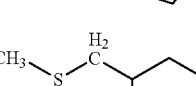 | |
| 3-62 | Q3a | | |
| 3-63 | Q3a | CH$_2$SO$_2$CH$_2$CF$_3$ | |
| 3-64 | Q3a | CH$_2$SO$_2$CH$_2$CH=CH$_2$ | |
| 3-65 | Q3a | CH$_2$SO$_2$CH$_2$C≡CH | |
| 3-66 | Q3a | CH$_2$O(CH$_2$)$_2$OCH$_3$ | |
| 3-67 | Q3a | CH$_2$O(CH$_2$)$_2$OCH$_2$CH$_3$ | |
| 3-68 | Q3a | CH$_2$O(CH$_2$)$_2$OCH$_2$-cyclopropyl | |
| 3-69 | Q3a | CH$_2$O(CH$_2$)$_2$OCH$_2$CF$_3$ | |
| 3-70 | Q3a | CH$_2$O(CH$_2$)$_2$OCH$_2$CH=CH$_2$ | |
| 3-71 | Q3a | CH$_2$O(CH$_2$)$_2$OCH$_2$C≡CH | |
| 3-72 | Q3a | CH$_2$O(CH$_2$)$_2$SCH$_3$ | |

TABLE 46-continued

| compound number | Q | R1 | physical property (melting point-ND) |
|---|---|---|---|
| 3-73 | Q3a | CH$_2$O(CH$_2$)$_2$SCH$_2$-△ | |
| 3-74 | Q3a | CH$_2$O(CH$_2$)$_2$SCH$_2$CF$_3$ | |
| 3-75 | Q3a | CH$_2$O(CH$_2$)$_2$SCH$_2$CH=CH$_2$ | |
| 3-76 | Q3a | CH$_2$O(CH$_2$)$_2$SCH$_2$C≡CH | |
| 3-77 | Q3a | CH$_2$O(CH$_2$)$_2$SOCH$_3$ | |
| 3-78 | Q3a | CH$_2$O(CH$_2$)$_2$SOCH$_2$-△ | |
| 3-79 | Q3a | CH$_2$O(CH$_2$)$_2$SOCH$_2$CF$_3$ | |
| 3-80 | Q3a | CH$_2$O(CH$_2$)$_2$SOCH$_2$CH=CH$_2$ | |

TABLE 47

| compound number | Q | R1 | physical property (melting point-ND) |
|---|---|---|---|
| 3-81 | Q3a | CH$_2$O(CH$_2$)$_2$SOCH$_2$C≡CH | |
| 3-82 | Q3a | CH$_2$O(CH$_2$)$_2$SO$_2$CH$_3$ | |
| 3-83 | Q3a | CH$_2$O(CH$_2$)$_2$SO$_2$CH$_2$-△ | |
| 3-84 | Q3a | CH$_2$O(CH$_2$)$_2$SO$_2$CH$_2$CF$_3$ | |
| 3-85 | Q3a | CH$_2$O(CH$_2$)$_2$SO$_2$CH$_2$CH=CH$_2$ | |
| 3-86 | Q3a | CH$_2$O(CH$_2$)$_2$SO$_2$CH$_2$C≡CH | |
| 3-87 | Q3a | CH$_3$-O-CH$_2$-(oxetane) | |
| 3-88 | Q3a | CH$_3$-O-CH$_2$-(tetrahydrofuran-2-yl) | |
| 3-89 | Q3a | CH$_3$-O-CH$_2$-(tetrahydrofuran-3-yl) | |
| 3-90 | Q3a | CH$_3$-O-(tetrahydrofuran-3-yl) | |
| 3-91 | Q3a | CH$_3$-O-CH$_2$-CH$_2$-O-CH$_2$-(oxetane) | |
| 3-92 | Q3a | CH$_3$-O-CH$_2$-CH$_2$-O-CH$_2$-(tetrahydrofuran-2-yl) | |

TABLE 47-continued

| compound number | Q | R1 | physical property (melting point-ND) |
|---|---|---|---|
| 3-93 | Q3a | CH$_3$-O-CH$_2$-CH$_2$-O-CH$_2$-(tetrahydrofuran-3-yl) | |
| 3-94 | Q3a | CH$_3$-O-CH$_2$-CH$_2$-O-(tetrahydrofuran-3-yl) | |
| 3-95 | Q3a | CH$_2$O(CH$_2$)$_2$NHSO$_2$CH$_3$ | |
| 3-96 | Q3a | CH$_2$O(CH$_2$)$_2$N(CH$_3$)(SO$_2$CH$_3$) | |
| 3-97 | Q3a | CH$_2$O(CH$_2$)$_2$NH(SO$_2$CH$_2$-△) | |
| 3-98 | Q3a | CH$_2$O(CH$_2$)$_2$NHSO$_2$CF$_3$ | |
| 3-99 | Q3a | CH$_2$O(CH$_2$)$_2$NHSO$_2$CHF$_2$ | |
| 3-100 | Q3a | CH$_2$O(CH$_2$)$_2$NHSO$_2$CH$_2$CF$_3$ | |
| 3-101 | Q3a | SCH$_3$ | |
| 3-102 | Q3a | SOCH$_3$ | |
| 3-103 | Q3a | SO$_2$CH$_3$ | |
| 3-104 | Q3a | OCH$_3$ | |
| 3-105 | Q3a | OCH$_2$CH$_3$ | |
| 3-106 | Q3a | O(CH$_2$)$_2$CH$_3$ | |
| 3-107 | Q3a | OCH$_2$CF$_3$ | |
| 3-108 | Q3a | OCF$_2$CF$_3$ | |
| 3-109 | Q3a | O(CH$_2$)$_2$OCH$_3$ | |
| 3-110 | Q3a | NHCH$_3$ | |
| 3-111 | Q3a | NHCH$_2$CH$_3$ | |
| 3-112 | Q3a | N(CH$_3$)$_2$ | |
| 3-113 | Q3a | N(CH$_2$CH$_3$)$_2$ | |
| 3-114 | Q3a | N(CH$_3$)(CH$_2$CH$_3$) | |
| 3-115 | Q3b | CH$_3$ | |
| 3-116 | Q3b | CH$_2$CH$_3$ | |
| 3-117 | Q3b | (CH$_2$)$_2$CH$_3$ | |
| 3-118 | Q3b | cyclopropyl | |
| 3-119 | Q3b | cyclobutyl | |
| 3-120 | Q3b | cyclopentyl | |

TABLE 48

| compound number | Q | R1 | physical property (melting point-ND) |
|---|---|---|---|
| 3-121 | Q3b | cyclohexyl | |

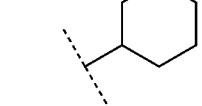

TABLE 48-continued

| compound number | Q | R1 | physical property (melting point-ND) |
|---|---|---|---|
| 3-122 | Q3b |  | |
| 3-123 | Q3b | 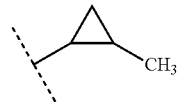 | |
| 3-124 | Q3b |  | |
| 3-125 | Q3b | 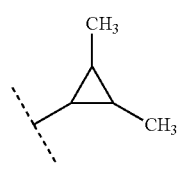 | |
| 3-126 | Q3b | CF$_3$ | |
| 3-127 | Q3b | CH$_2$CF$_3$ | |
| 3-128 | Q3b | CF$_2$CF$_3$ | |
| 3-129 | Q3b | CH$_2$CH=CH$_2$ | |
| 3-130 | Q3b | CH2C≡CH | |
| 3-131 | Q3b | C$_6$H$_5$ | |
| 3-132 | Q3b | CH$_2$C$_6$H$_5$ | |
| 3-133 | Q3b | CH$_2$OCH$_3$ | |
| 3-134 | Q3b | CH$_2$OCH$_2$CH$_3$ | |
| 3-135 | Q3b | CH$_2$O(CH2)$_2$CH$_3$ | |
| 3-136 | Q3b | (CH$_2$)$_2$OCH$_3$ | |
| 3-137 | Q3b | (CH$_2$)$_3$OCH$_3$ | |
| 3-138 | Q3b | 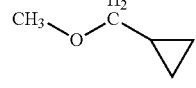 | |
| 3-139 | Q3b | 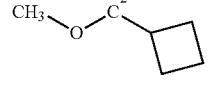 | |
| 3-140 | Q3b | 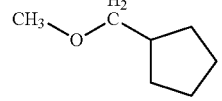 | |
| 3-141 | Q3b | 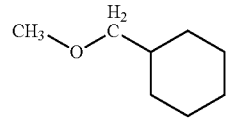 | |
| 3-142 | Q3b | CH$_2$OCH$_2$CF$_3$ | |
| 3-143 | Q3b | CH$_2$OCF$_2$CHF$_2$ | |
| 3-144 | Q3b | CH$_2$OCH2CF2CF3 | |
| 3-145 | Q3b | CH$_2$OCH$_2$CH=CH$_2$ | |
| 3-146 | Q3b | CH$_2$OCH$_2$CH=CCl$_2$ | |
| 3-147 | Q3b | CH$_2$OCH$_2$CF=CF$_2$ | |
| 3-148 | Q3b | CH$_2$OC$_2$C≡CH | |
| 3-149 | Q3b | CH$_2$OCH$_2$C≡CCH$_3$ | |
| 3-150 | Q3b | CH$_2$SCH$_3$ | |
| 3-151 | Q3b | CH$_2$SCH$_2$CH$_3$ | |
| 3-152 | Q3b | CH$_2$S(CH$_2$)$_2$CH$_3$ | |

TABLE 48-continued

| compound number | Q | R1 | physical property (melting point-ND) |
|---|---|---|---|
| 3-153 | Q3b | 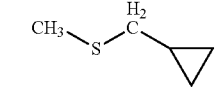 | |
| 3-154 | Q3b | 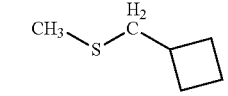 | |
| 3-155 | Q3b | 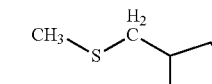 | |
| 3-156 | Q3b | 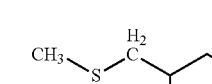 | |
| 3-157 | Q3b | CH$_2$SCH$_2$CF$_3$ | |
| 3-158 | Q3b | CH$_2$SCH$_2$CH=CH$_2$ | |
| 3-159 | Q3b | CH$_2$SCH$_2$C≡CH | |
| 3-160 | Q3b | CH$_2$SOCH$_3$ | |

TABLE 49

| compound number | Q | R1 | physical property (melting point-ND) |
|---|---|---|---|
| 3-161 | Q3b | CH$_2$SOCH$_2$CH$_3$ | |
| 3-162 | Q3b | CH$_2$SO(CH$_2$)$_2$CH$_3$ | |
| 3-163 | Q3b | 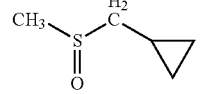 | |
| 3-164 | Q3b | 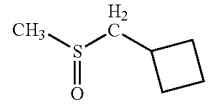 | |
| 3-165 | Q3b | 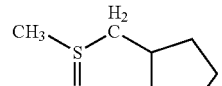 | |
| 3-166 | Q3b | 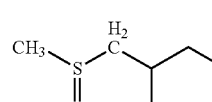 | |
| 3-167 | Q3b | CH$_2$SOCH$_2$CF$_3$ | |
| 3-168 | Q3b | CH$_2$SOCH$_2$CH=CH$_2$ | |
| 3-169 | Q3b | CH$_2$SOCH$_2$C≡CH | |
| 3-170 | Q3b | CH$_2$SO$_2$CH$_3$ | |
| 3-171 | Q3b | CH$_2$SO$_2$CH$_2$CH$_3$ | |
| 3-172 | Q3b | CH$_2$SO$_2$(CH$_2$)$_2$CH$_3$ | |

TABLE 49-continued

| compound number | Q | R1 | physical property (melting point-ND) |
|---|---|---|---|
| 3-173 | Q3b | CH₃SO₂CH₂-cyclopropyl | |
| 3-174 | Q3b | CH₃SO₂CH₂-cyclobutyl | |
| 3-175 | Q3b | CH₃SO₂CH₂-cyclopentyl | |
| 3-176 | Q3b | CH₃SO₂CH₂-cyclohexyl | |
| 3-177 | Q3b | CH₂SO₂CH₂CF₃ | |
| 3-178 | Q3b | CH₂SO₂CH₂CH=CH₂ | |
| 3-179 | Q3b | CH₂SO₂CH₂C≡CH | |
| 3-180 | Q3b | CH₂O(CH₂)₂OCH₃ | |
| 3-181 | Q3b | CH₂O(CH₂)₂OCH₂CH₃ | |
| 3-182 | Q3b | CH₂O(CH₂)₂OCH₂-cyclopropyl | |
| 3-183 | Q3b | CH₂O(CH₂)₂OCH₂CF₃ | |
| 3-184 | Q3b | CH₂O(CH₂)₂OCH₂CH=CH₂ | |
| 3-185 | Q3b | CH₂O(CH₂)₂OCH₂C≡CH | |
| 3-186 | Q3b | CH₂O(CH₂)₂SCH₃ | |
| 3-187 | Q3b | CH₂O(CH₂)₂SCH₂-cyclopropyl | |
| 3-188 | Q3b | CH₂O(CH₂)₂SCH₂CF₃ | |
| 3-189 | CQ3b | CH₂O(CH₂)₂SCH₂CH=CH₂ | |
| 3-190 | Q3b | CH₂O(CH₂)₂SCH₂C≡CH | |
| 3-191 | Q3b | CH₂O(CH₂)₂SOCH₃ | |
| 3-192 | Q3b | CH₂O(CH₂)₂SOCH₂-cyclopropyl | |
| 3-193 | Q3b | CH₂O(CH₂)₂SOCH₂CF₃ | |
| 3-194 | Q3b | CH₂O(CH₂)₂SOCH₂CH=CH₂ | |
| 3-195 | Q3b | CH₂O(CH₂)₂SOCH₂C≡CH | |
| 3-196 | Q3b | CH₂O(CH₂)₂SO₂CH₃ | |
| 3-197 | Q3b | CH₂O(CH₂)₂SO₂CH₂-cyclopropyl | |
| 3-198 | Q3b | CH₂O(CH₂)₂SO₂CH₂CF₃ | |
| 3-199 | Q3b | CH₂O(CH₂)₂SO₂CH₂CH=CH₂ | |
| 3-200 | Q3b | CH₂O(CH₂)₂SO₂CH₂C≡CH | |

TABLE 50

| compound number | Q | R1 | physical property (melting point-ND) |
|---|---|---|---|
| 3-201 | Q3b | CH₃OCH₂-oxetanyl | |
| 3-202 | Q3b | CH₃OCH₂-tetrahydrofuran-2-yl | |
| 3-203 | Q3b | CH₃OCH₂-tetrahydrofuran-3-yl | |
| 3-204 | Q3b | CH₃O-tetrahydrofuran-3-yl | |
| 3-205 | Q3b | CH₃OCH₂CH₂OCH₂-oxetanyl | |
| 3-206 | Q3b | CH₃OCH₂CH₂OCH₂-tetrahydrofuran-2-yl | |
| 3-207 | Q3b | CH₃OCH₂CH₂OCH₂-tetrahydrofuran-3-yl | |
| 3-208 | Q3b | CH₃OCH₂CH₂O-tetrahydrofuran-3-yl | |
| 3-209 | Q3b | CH₂O(CH₂)₂NHSO₂CH₃ | |
| 3-210 | Q3b | CH₂O(CH₂)₂N(CH₃)(SO₂CH₃) | |
| 3-211 | Q3b | CH₂O(CH₂)₂NH(SO₂CH₂-cyclopropyl) | |
| 3-212 | Q3b | CH₂O(CH₂)₂NHSO₂CF₃ | |
| 3-213 | Q3b | CH₂O(CH₂)₂NHSO₂CHF₂ | |
| 3-214 | Q3b | CH₂O(CH₂)₂NHSO₂CH₂CF₃ | |
| 3-215 | Q3b | SCH₃ | |
| 3-216 | Q3b | SOCH₃ | |
| 3-217 | Q3b | SO₂CH₃ | |
| 3-218 | Q3b | OCH₃ | |
| 3-219 | Q3b | OCH₂CH₃ | |
| 3-220 | Q3b | O(CH₂)₂CH₃ | |
| 3-221 | Q3b | OCH₂CF₃ | |
| 3-222 | Q3b | OCF₂CF₃ | |
| 3-223 | Q3b | O(CH₂)₂OCH₃ | |
| 3-224 | Q3b | NHCH₃ | |
| 3-225 | Q3b | NHCH₂CH₃ | |
| 3-226 | Q3b | N(CH₃)₂ | |
| 3-227 | Q3b | N(CH₂CH₃)₂ | |
| 3-228 | Q3b | N(CH₃)(CH₂CH₃) | |
| 3-229 | Q3c | CH₃ | |
| 3-230 | Q3c | CH₂CH₃ | |
| 3-231 | Q3c | (CH₂)₂CH₃ | |

TABLE 50-continued

| compound number | Q | R1 | physical property (melting point-ND) |
|---|---|---|---|
| 3-232 | Q3c | cyclopropyl-CH2- | |
| 3-233 | Q3c | cyclobutyl-CH2- | |
| 3-234 | Q3c | cyclopentyl-CH2- | |
| 3-235 | Q3c | cyclohexyl-CH2- | |
| 3-236 | Q3c | 1-methylcyclopropyl-CH2- | |
| 3-237 | Q3c | (2-methylcyclopropyl)-CH2- | |
| 3-238 | Q3c | (2,2-dimethylcyclopropyl)-CH2- | |
| 3-239 | Q3c | (2,3-dimethylcyclopropyl)-CH2- | |
| 3-240 | Q3c | $CF_3$ | |

TABLE 51

| compound number | Q | R1 | physical property (melting point-ND) |
|---|---|---|---|
| 3-241 | Q3c | $CH_2CF_3$ | |
| 3-242 | Q3c | $CF_2CH_3$ | |
| 3-243 | Q3c | $CH_2CH=CH_2$ | |
| 3-244 | Q3c | $CH2C\equiv CH$ | |
| 3-245 | Q3c | $C_6H_5$ | |
| 3-246 | Q3c | $CH_2C_6H_5$ | |
| 3-247 | Q3c | $CH_2OCH_3$ | |
| 3-248 | Q3c | $CH_2OCH_2CH_3$ | |
| 3-249 | Q3c | $CH_2O(CH2)_2CH_3$ | |
| 3-250 | Q3c | $(CH_2)_2OCH_3$ | |

TABLE 51-continued

| compound number | Q | R1 | physical property (melting point-ND) |
|---|---|---|---|
| 3-251 | Q3c | $(CH_2)_3OCH_3$ | |
| 3-252 | Q3c | $CH_3$-O-$CH_2$-cyclopropyl | |
| 3-253 | Q3c | $CH_3$-O-$CH_2$-cyclobutyl | |
| 3-254 | Q3c | $CH_3$-O-$CH_2$-cyclopentyl | |
| 3-255 | Q3c | $CH_3$-O-$CH_2$-cyclohexyl | |
| 3-256 | Q3c | $CH_2OCH_2CF_3$ | |
| 3-257 | Q3c | $CH_2OCF_2CHF_3$ | |
| 3-258 | Q3c | $CH_2OCH2CF2CF3$ | |
| 3-259 | Q3c | $CH_2OCH_2CH=CH_2$ | |
| 3-260 | Q3c | $CH_2OCH_2CH=CCl_2$ | |
| 3-261 | Q3c | $CH_2OCH_2CF=CF_2$ | |
| 3-262 | Q3c | $CH_2OC_2C\equiv CH$ | |
| 3-263 | Q3c | $CH_2OCH_2C\equiv CCH_3$ | |
| 3-264 | Q3c | $CH_2SCH_3$ | |
| 3-265 | Q3c | $CH_2SCH_2CH_3$ | |
| 3-266 | Q3c | $CH_2S(CH_2)_2CH_3$ | |
| 3-267 | Q3c | $CH_3$-S-$CH_2$-cyclopropyl | |
| 3-268 | Q3c | $CH_3$-S-$CH_2$-cyclobutyl | |
| 3-269 | Q3c | $CH_3$-S-$CH_2$-cyclopentyl | |
| 3-270 | Q3c | $CH_3$-S-$CH_2$-cyclohexyl | |
| 3-271 | Q3c | $CH_2SCH_2CF_3$ | |
| 3-272 | Q3c | $CH_2SCH_2CH=CH_2$ | |
| 3-273 | Q3c | $CH_2SCH_2C\equiv CH$ | |
| 3-274 | Q3c | $CH_2SOCH_3$ | |
| 3-275 | Q3c | $CH_2SOCH_2CH_3$ | |
| 3-276 | Q3c | $CH_2SO(CH_2)_2CH_3$ | |
| 3-277 | Q3c | $CH_3$-S(O)-$CH_2$-cyclopropyl | |

TABLE 51-continued

| compound number | Q | R1 | physical property (melting point-ND) |
|---|---|---|---|
| 3-278 | Q3c | CH₃-S(=O)-CH₂-cyclobutyl | |
| 3-279 | Q3c | CH₃-S(=O)-CH₂-cyclopentyl | |
| 3-280 | Q3c | CH₃-S(=O)-CH₂-cyclohexyl | |

TABLE 52

| compound number | Q | R1 | physical property (melting point-ND) |
|---|---|---|---|
| 3-281 | Q3c | CH₂SOCH₂CF₃ | |
| 3-282 | Q3c | CH₂SOCH₂CH=CH₂ | |
| 3-283 | Q3c | CH₂SOCH₂C≡CH | |
| 3-284 | Q3c | CH₂SO₂CH₃ | |
| 3-285 | Q3c | CH₂SO₂CH₂CH₃ | |
| 3-286 | Q3c | CH₂SO₂(CH₂)₂CH₃ | |
| 3-287 | Q3c | CH₃-S(O)₂-CH₂-cyclopropyl | |
| 3-288 | Q3c | CH₃-S(O)₂-CH₂-cyclobutyl | |
| 3-289 | Q3c | CH₃-S(O)₂-CH₂-cyclopentyl | |
| 3-290 | Q3c | CH₃-S(O)₂-CH₂-cyclohexyl | |
| 3-291 | Q3c | CH₂SO₂CH₂CF₃ | |
| 3-292 | Q3c | CH₂SO₂CH₂CH=CH₂ | |
| 3-293 | Q3c | CH₂SO₂CH₂C≡CH | |
| 3-294 | Q3c | CH₂O(CH₂)₂OCH₃ | |
| 3-295 | Q3c | CH₂O(CH₂)₂OCH₂CH₃ | |
| 3-296 | Q3c | CH₂O(CH₂)₂OCH₂-cyclopropyl | |
| 3-297 | Q3c | CH₂O(CH₂)₂OCH₂CF₃ | |
| 3-298 | Q3c | CH₂O(CH₂)₂OCH₂CH=CH₂ | |
| 3-299 | Q3c | CH₂O(CH₂)₂OCH₂C≡CH | |
| 3-300 | Q3c | CH₂O(CH₂)₂SCH₃ | |
| 3-301 | Q3c | CH₂O(CH₂)₂SCH₂-cyclopropyl | |
| 3-302 | Q3c | CH₂O(CH₂)₂SCH₂CF₃ | |
| 3-303 | Q3c | CH₂O(CH₂)₂SCH₂CH=CH₂ | |
| 3-304 | Q3c | CH₂O(CH₂)₂SCH₂C≡CH | |
| 3-305 | Q3c | CH₂O(CH₂)₂SOCH₃ | |
| 3-306 | Q3c | CH₂O(CH₂)₂SOCH₂-cyclopropyl | |
| 3-307 | Q3c | CH₂O(CH₂)₂SOCH₂CF₃ | |
| 3-308 | Q3c | CH₂O(CH₂)₂SOCH₂CH=CH₂ | |
| 3-309 | Q3c | CH₂O(CH₂)₂SOCH₂C≡CH | |
| 3-310 | Q3c | CH₂O(CH₂)₂SO₂CH₃ | |
| 3-311 | Q3c | CH₂O(CH₂)₂SO₂CH₂-cyclopropyl | |
| 3-312 | Q3c | CH₂O(CH₂)₂SO₂CH₂CF₃ | |
| 3-313 | Q3c | CH₂O(CH₂)₂SO₂CH₂CH=CH₂ | |
| 3-314 | Q3c | CH₂O(CH₂)₂SO₂CH₂C≡CH | |
| 3-315 | Q3c | CH₃-O-CH₂-(oxetan-2-yl) | |
| 3-316 | Q3c | CH₃-O-CH₂-(tetrahydrofuran-2-yl) | |
| 3-317 | Q3c | CH₃-O-CH₂-(tetrahydrofuran-3-yl) | |
| 3-318 | Q3c | CH₃-O-(tetrahydrofuran-3-yl) | |
| 3-319 | Q3c | CH₃-O-CH₂-O-CH₂-(oxetan-2-yl) | |
| 3-320 | Q3c | CH₃-O-CH₂-O-CH₂-(tetrahydrofuran-2-yl) | |

TABLE 53

| compound number | Q | R1 | physical property (melting point-ND) |
|---|---|---|---|
| 3-321 | Q3c | CH₃-O-CH₂-O-CH₂-(tetrahydrofuran-3-yl) | |

TABLE 53-continued

| compound number | Q | R1 | physical property (melting point-ND) |
|---|---|---|---|
| 3-322 | Q3c | $CH_3-O-CH_2-CH_2-O-$(tetrahydrofuran-3-yl) | |
| 3-323 | Q3c | $CH_2O(CH_2)_2NHSO_2CH_3$ | |
| 3-324 | Q3c | $CH_2O(CH_2)_2N(CH_3)(SO_2CH_3)$ | |
| 3-325 | Q3c | $CH_2O(CH_2)_2NH(SO_2CH_2$—cyclopropyl$)$ | |
| 3-326 | Q3c | $CH_2O(CH_2)_2NHSO_2CF_3$ | |
| 3-327 | Q3c | $CH_2O(CH_2)_2NHSO_2CHF_2$ | |
| 3-328 | Q3c | $CH_2O(CH_2)_2NHSO_2CH_2CF_3$ | |
| 3-329 | Q3c | $SCH_3$ | |
| 3-330 | Q3c | $SOCH_3$ | |
| 3-331 | Q3c | $SO_2CH_3$ | |
| 3-332 | Q3c | $OCH_3$ | |
| 3-333 | Q3c | $OCH_2CH_3$ | |
| 3-334 | Q3c | $O(CH_2)_2CH_3$ | |
| 3-335 | Q3c | $OCH_2CF_3$ | |
| 3-336 | Q3c | $OCF_2CF_3$ | |
| 3-337 | Q3c | $O(CH_2)_2OCH_3$ | |
| 3-338 | Q3c | $NHCH_3$ | |
| 3-339 | Q3c | $NHCH_2CH_3$ | |
| 3-340 | Q3c | $N(CH_3)_2$ | |
| 3-341 | Q3c | $N(CH_2CH_3)_2$ | |
| 3-342 | Q3c | $N(CH_3)(CH_2CH_3)$ | |
| 3-343 | Q3d | $CH_3$ | NMR |
| 3-344 | Q3d | $CH_2CH_3$ | |
| 3-345 | Q3d | $(CH_2)_2CH_3$ | |
| 3-346 | Q3d | cyclopropyl | |
| 3-347 | Q3d | cyclobutyl | |
| 3-348 | Q3d | cyclopentyl | |
| 3-349 | Q3d | cyclohexyl | |
| 3-350 | Q3d | 1-methylcyclopropyl | |
| 3-351 | Q3d | 2-methylcyclopropyl | |
| 3-352 | Q3d | 2,2-dimethylcyclopropyl | |
| 3-353 | Q3d | 2,3-dimethylcyclopropyl | |
| 3-354 | Q3d | $CF_3$ | |
| 3-355 | Q3d | $CH_2CF_3$ | |
| 3-356 | Q3d | $CF_2CF_3$ | |
| 3-357 | Q3d | $CH_2CH=CH_2$ | |
| 3-358 | Q3d | $CH_2C\equiv CH$ | |
| 3-359 | Q3d | $C_6H_5$ | |
| 3-360 | Q3d | $CH_2C_6H_5$ | |

TABLE 54

| compound number | Q | R1 | physical property (melting point-ND) |
|---|---|---|---|
| 3-361 | Q3d | $CH_2OCH_3$ | |
| 3-362 | Q3d | $CH_2OCH_2CH_3$ | |
| 3-363 | Q3d | $CH_2O(CH_2)_2CH_3$ | |
| 3-364 | Q3d | $(CH_2)_2OCH_3$ | |
| 3-365 | Q3d | $(CH_2)_3OCH_3$ | |
| 3-366 | Q3d | $CH_3-O-CH_2-$cyclopropyl | |
| 3-367 | Q3d | $CH_3-O-CH_2-$cyclobutyl | |
| 3-368 | Q3d | $CH_3-O-CH_2-$cyclopentyl | |
| 3-369 | Q3d | $CH_3-O-CH_2-$cyclohexyl | |
| 3-370 | Q3d | $CH_2OCH_2CF_3$ | |
| 3-371 | Q3d | $CH_2OCF_2CHF_2$ | |
| 3-372 | Q3d | $CH_2OCH2CF2CF3$ | |
| 3-373 | Q3d | $CH_2OCH_2CH=CH_2$ | |
| 3-374 | Q3d | $CH_2OCH_2CH=CCl_2$ | |
| 3-375 | Q3d | $CH_2OCH_2CF=CF_2$ | |
| 3-376 | Q3d | $CH_2OC_2C\equiv CH$ | |
| 3-377 | Q3d | $CH_2OCH_2C\equiv CCH_3$ | |
| 3-378 | Q3d | $CH_2SCH_3$ | |
| 3-379 | Q3d | $CH_2SCH_2CH_3$ | |
| 3-380 | Q3d | $CH_2S(CH_2)_2CH_3$ | |

TABLE 54-continued

| compound number | Q | R1 | physical property (melting point-ND) |
|---|---|---|---|
| 3-381 | Q3d | CH₃-S-CH₂-cyclopropyl | |
| 3-382 | Q3d | CH₃-S-CH₂-cyclobutyl | |
| 3-383 | Q3d | CH₃-S-CH₂-cyclopentyl | |
| 3-384 | Q3d | CH₃-S-CH₂-cyclohexyl | |
| 3-385 | Q3d | CH$_2$SCH$_2$CF$_3$ | |
| 3-386 | Q3d | CH$_2$SCH$_2$CH=CH$_2$ | |
| 3-387 | Q3d | CH$_2$SCH$_2$C≡CH | |
| 3-388 | Q3d | CH$_2$SOCH$_3$ | |
| 3-389 | Q3d | CH$_2$SOCH$_2$CH$_3$ | |
| 3-390 | Q3d | CH$_2$SO(CH$_2$)$_2$CH$_3$ | |
| 3-391 | Q3d | CH₃-S(O)-CH₂-cyclopropyl | |
| 3-392 | Q3d | CH₃-S(O)-CH₂-cyclobutyl | |
| 3-393 | Q3d | CH₃-S(O)-CH₂-cyclopentyl | |
| 3-394 | Q3d | CH₃-S(O)-CH₂-cyclohexyl | |
| 3-395 | Q3d | CH$_2$SOCH$_2$CF$_3$ | |
| 3-396 | Q3d | CH$_2$SOCH$_2$CH=CH$_2$ | |
| 3-397 | Q3d | CH$_2$SOCH$_2$C≡CH | |
| 3-398 | Q3d | CH$_2$SO$_2$CH$_3$ | |
| 3-399 | Q3d | CH$_2$SO$_2$CH$_2$CH$_3$ | |
| 3-400 | Q3d | CH$_2$SO$_2$(CH$_2$)$_2$CH$_3$ | |

TABLE 55

| compound number | Q | R1 | physical property (melting point-ND) |
|---|---|---|---|
| 3-401 | Q3d | CH₃-S(O)₂-CH₂-cyclopropyl | |
| 3-402 | Q3d | CH₃-S(O)₂-CH₂-cyclobutyl | |
| 3-403 | Q3d | CH₃-S(O)₂-CH₂-cyclopentyl | |
| 3-404 | Q3d | CH₃-S(O)₂-CH₂-cyclohexyl | |
| 3-405 | Q3d | CH$_2$SO$_2$CH$_2$CF$_3$ | |
| 3-406 | Q3d | CH$_2$SO$_2$CH$_2$CH=CH$_2$ | |
| 3-407 | Q3d | CH$_2$SO$_2$CH$_2$C≡CH | |
| 3-408 | Q3d | CH$_2$O(CH$_2$)$_2$OCH$_3$ | |
| 3-409 | Q3d | CH$_2$O(CH$_2$)$_2$OCH$_2$CH$_3$ | |
| 3-410 | Q3d | CH$_2$O(CH$_2$)$_2$OCH$_2$-cyclopropyl | |
| 3-411 | Q3d | CH$_2$O(CH$_2$)$_2$OCH$_2$CF$_3$ | |
| 3-412 | Q3d | CH$_2$O(CH$_2$)$_2$OCH$_2$CH=CH$_2$ | |
| 3-413 | Q3d | CH$_2$O(CH$_2$)$_2$OCH$_2$C≡CH | |
| 3-414 | Q3d | CH$_2$O(CH$_2$)$_2$SCH$_3$ | |
| 3-415 | Q3d | CH$_2$O(CH$_2$)$_2$SCH$_2$-cyclopropyl | |
| 3-416 | Q3d | CH$_2$O(CH$_2$)$_2$SCH$_2$CF$_3$ | |
| 3-417 | Q3d | CH$_2$O(CH$_2$)$_2$SCH$_2$CH=CH$_2$ | |
| 3-418 | Q3d | CH$_2$O(CH$_2$)$_2$SCH$_2$C≡CH | |
| 3-419 | Q3d | CH$_2$O(CH$_2$)$_2$SOCH$_3$ | |
| 3-420 | Q3d | CH$_2$O(CH$_2$)$_2$SOCH$_2$-cyclopropyl | |
| 3-421 | Q3d | CH$_2$O(CH$_2$)$_2$SOCH$_2$CF$_3$ | |
| 3-422 | Q3d | CH$_2$O(CH$_2$)$_2$SOCH$_2$CH=CH$_2$ | |
| 3-423 | Q3d | CH$_2$O(CH$_2$)$_2$SOCH$_2$C≡CH | |
| 3-424 | Q3d | CH$_2$O(CH$_2$)$_2$SO$_2$CH$_3$ | |
| 3-425 | Q3d | CH$_2$O(CH$_2$)$_2$SO$_2$CH$_2$-cyclopropyl | |
| 3-426 | Q3d | CH$_2$O(CH$_2$)$_2$SO$_2$CH$_2$CF$_3$ | |
| 3-427 | Q3d | CH$_2$O(CH$_2$)$_2$SO$_2$CH$_2$CH=CH$_2$ | |
| 3-428 | Q3d | CH$_2$O(CH$_2$)$_2$SO$_2$CH$_2$C≡CH | |
| 3-429 | Q3d | CH₃-O-CH₂-oxetanyl | |
| 3-430 | Q3d | CH₃-O-CH₂-tetrahydrofuranyl | |

TABLE 55-continued

| compound number | Q | R1 | physical property (melting point-ND) |
|---|---|---|---|
| 3-431 | Q3d | 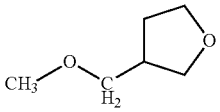 | |
| 3-432 | Q3d | 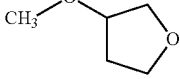 | |
| 3-433 | Q3d | 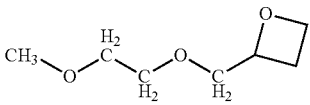 | |
| 3-434 | Q3d | 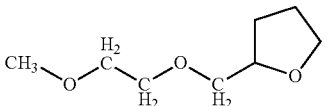 | |
| 3-435 | Q3d | 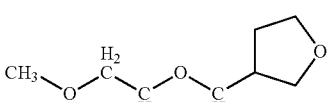 | |
| 3-436 | Q3d | 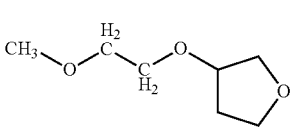 | |
| 3-437 | Q3d | CH$_2$O(CH$_2$)$_2$NHSO$_2$CH$_3$ | |
| 3-438 | Q3d | CH$_2$O(CH$_2$)$_2$N(CH$_3$)(SO$_2$CH$_3$) | |
| 3-439 | Q3d | CH$_2$O(CH$_2$)$_2$NH(SO$_2$CH$_2$—) | |
| 3-440 | Q3d | CH$_2$O(CH$_2$)$_2$NHSO$_2$CF$_3$ | |

TABLE 56

| compound number | Q | R1 | physical property (melting point-ND) |
|---|---|---|---|
| 3-441 | Q3d | CH$_2$O(CH$_2$)$_2$NHSO$_2$CHF$_2$ | |
| 3-442 | Q3d | CH$_2$O(CH$_2$)$_2$NHSO$_2$CH$_2$CF$_3$ | |
| 3-443 | Q3d | SCH$_3$ | |
| 3-444 | Q3d | SOCH$_3$ | |
| 3-445 | Q3d | SO$_2$CH$_3$ | |
| 3-446 | Q3d | OCH$_3$ | |
| 3-447 | Q3d | OCH$_2$CH$_3$ | |
| 3-448 | Q3d | O(CH$_2$)$_2$CH$_3$ | |
| 3-449 | Q3d | OCH$_2$CF$_3$ | |
| 3-450 | Q3d | OCF$_2$CF$_3$ | |
| 3-451 | Q3d | O(CH$_2$)$_2$OCH$_3$ | |
| 3-452 | Q3d | NHCH$_3$ | |
| 3-453 | Q3d | NHCH$_2$CH$_3$ | |
| 3-454 | Q3d | N(CH$_3$)$_2$ | |
| 3-455 | Q3d | N(CH$_2$CH$_3$)$_2$ | |
| 3-456 | Q3d | N(CH$_3$)(CH$_2$CH$_3$) | |
| 3-457 | Q3e | CH$_3$ | |
| 3-458 | Q3e | CH$_2$CH$_3$ | |
| 3-459 | Q3e | (CH$_2$)$_2$CH$_3$ | |

TABLE 56-continued

| compound number | Q | R1 | physical property (melting point-ND) |
|---|---|---|---|
| 3-460 | Q3e | 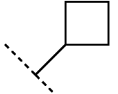 | |
| 3-461 | Q3e |  | |
| 3-462 | Q3e | 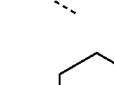 | |
| 3-463 | Q3e |  | |
| 3-464 | Q3e |  | |
| 3-465 | Q3e |  | |
| 3-466 | Q3e |  | |
| 3-467 | Q3e |  | |
| 3-468 | Q3e | CF$_3$ | |
| 3-469 | Q3e | CH$_2$CF$_3$ | |
| 3-470 | Q3e | CF$_2$CF$_3$ | |
| 3-471 | Q3e | CH$_2$CH=CH$_2$ | |
| 3-472 | Q3e | CH2C≡CH | |
| 3-473 | Q3e | C$_6$H$_5$ | |
| 3-474 | Q3e | CH$_2$C$_6$H$_5$ | |
| 3-475 | Q3e | CH$_2$OCH$_3$ | |
| 3-476 | Q3e | CH$_2$OCH$_2$CH$_3$ | |
| 3-477 | Q3e | CH$_2$O(CH2)$_2$CH$_3$ | |
| 3-478 | Q3e | (CH$_2$)$_2$OCH$_3$ | |
| 3-479 | Q3e | (CH$_2$)$_3$OCH$_3$ | |
| 3-480 | Q3e | 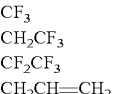 | |

TABLE 57

| compound number | Q | R1 | physical property (melting point-ND) |
|---|---|---|---|
| 3-481 | Q3e | CH₃-O-CH₂-cyclobutyl | |
| 3-482 | Q3e | CH₃-O-CH₂-cyclopentyl | |
| 3-483 | Q3e | CH₃-O-CH₂-cyclohexyl | |
| 3-484 | Q3e | CH₂OCH₂CF₃ | |
| 3-485 | Q3e | | |
| 3-486 | Q3e | CH₂OCH2CF2CF3 | |
| 3-487 | Q3e | CH₂OCH₂CH=CH₂ | |
| 3-488 | Q3e | CH₂OCH₂CH=CCl₂ | |
| 3-489 | Q3e | CH₂OCH₂CF=CF₂ | |
| 3-490 | Q3e | CH₂OC₂C=CH | |
| 3-491 | Q3e | CH₂OCH₂C=CCH₃ | |
| 3-492 | Q3e | CH₂SCH₃ | |
| 3-493 | Q3e | CH₂SCH₂CH₃ | |
| 3-494 | Q3e | CH₂S(CH₂)₂CH₃ | |
| 3-495 | Q3e | CH₃-S-CH₂-cyclopropyl | |
| 3-496 | Q3e | CH₃-S-CH₂-cyclobutyl | |
| 3-497 | Q3e | CH₃-S-CH₂-cyclopentyl | |
| 3-498 | Q3e | CH₃-S-CH₂-cyclohexyl | |
| 3-499 | Q3e | CH₂SCH₂CF₃ | |
| 3-500 | Q3e | CH₂SCH₂CH=CH₂ | |
| 3-501 | Q3e | CH₂SCH₂C=CH | |
| 3-502 | Q3e | CH₂SOCH₃ | |
| 3-503 | Q3e | CH₂SOCH₂CH₃ | |
| 3-504 | Q3e | CH₂SO(CH₂)₂CH₃ | |
| 3-505 | Q3e | CH₃-S(O)-CH₂-cyclopropyl | |
| 3-506 | Q3e | CH₃-S(O)-CH₂-cyclobutyl | |
| 3-507 | Q3e | CH₃-S(O)-CH₂-cyclopentyl | |
| 3-508 | Q3e | CH₃-S(O)-CH₂-cyclohexyl | |
| 3-509 | Q3e | CH₂SOCH₂CF₃ | |
| 3-510 | Q3e | CH₂SOCH₂CH=CH₂ | |
| 3-511 | Q3e | CH₂SOCH₂C=CH | |
| 3-512 | Q3e | CH₂SO₂CH₃ | |
| 3-513 | Q3e | CH₂SO₂CH₂CH₃ | |
| 3-514 | Q3e | CH₂SO₂(CH₂)₂CH₃ | |
| 3-515 | Q3e | CH₃-SO₂-CH₂-cyclopropyl | |
| 3-516 | Q3e | CH₃-SO₂-CH₂-cyclobutyl | |
| 3-517 | Q3e | CH₃-SO₂-CH₂-cyclopentyl | |
| 3-518 | Q3e | CH₃-SO₂-CH₂-cyclohexyl | |
| 3-519 | Q3e | CH₂SO₂CH₂CF₃ | |
| 3-520 | Q3e | CH₂SO₂CH₂CH=CH₂ | |

TABLE 58

| compound number | Q | R1 | physical property (melting point-ND) |
|---|---|---|---|
| 3-521 | Q3e | CH₂SO₂CH₂C=CH | |
| 3-522 | Q3e | CH₂O(CH₂)₂OCH₃ | |
| 3-523 | Q3e | CH₂O(CH₂)₂OCH₂CH₃ | |
| 3-524 | Q3e | CH₂O(CH₂)₂OCH₂-cyclopropyl | |
| 3-525 | Q3e | CH₂O(CH₂)₂OCH₂CF₃ | |
| 3-526 | Q3e | CH₂O(CH₂)₂OCH₂CH=CH₂ | |
| 3-527 | Q3e | CH₂O(CH₂)₂OCH₂C=CH | |
| 3-528 | Q3e | CH₂O(CH₂)₂SCH₃ | |
| 3-529 | Q3e | CH₂O(CH₂)₂SCH₂-cyclopropyl | |
| 3-530 | Q3e | CH₂O(CH₂)₂SCH₂CF₃ | |
| 3-531 | Q3e | CH₂O(CH₂)₂SCH₂CH=CH₂ | |
| 3-532 | Q3e | CH₂O(CH₂)₂SCH₂C=CH | |

TABLE 58-continued

| compound number | Q | R1 | physical property (melting point-ND) |
|---|---|---|---|
| 3-533 | Q3e | CH$_2$O(CH$_2$)$_2$SOCH$_3$ | |
| 3-534 | Q3e | CH$_2$O(CH$_2$)$_2$OCH$_2$– | |
| 3-535 | Q3e | CH$_2$O(CH$_2$)$_2$SOCH$_2$CF$_3$ | |
| 3-536 | Q3e | CH$_2$O(CH$_2$)$_2$SOCH$_2$CH=CH$_2$ | |
| 3-537 | Q3e | CH$_2$O(CH$_2$)$_2$SOCH$_2$C≡CH | |
| 3-538 | Q3e | CH$_2$O(CH$_2$)$_2$SO$_2$CH$_3$ | |
| 3-539 | Q3e | CH$_2$O(CH$_2$)$_2$SO$_2$CH$_2$– | |
| 3-540 | Q3e | CH$_2$O(CH$_2$)$_2$SO$_2$CH$_2$CF$_3$ | |
| 3-541 | Q3e | CH$_2$O(CH$_2$)$_2$SO$_2$CH$_2$CH=CH$_2$ | |
| 3-542 | Q3e | CH$_2$O(CH$_2$)$_2$SO$_2$CH$_2$C≡CH | |
| 3-543 | Q3e | 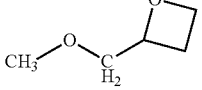 | |
| 3-544 | Q3e | 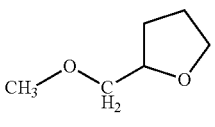 | |
| 3-545 | Q3e | 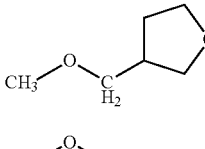 | |
| 3-546 | Q3e | 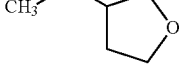 | |
| 3-547 | Q3e | 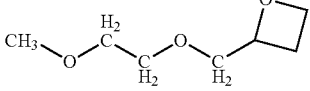 | |
| 3-548 | Q3e | 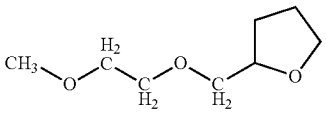 | |
| 3-549 | Q3e | 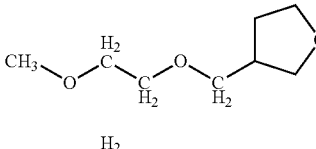 | |
| 3-550 | Q3e | 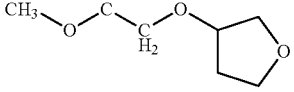 | |
| 3-551 | Q3e | CH$_2$O(CH$_2$)$_2$NHSO$_2$CH$_3$ | |
| 3-552 | Q3e | CH$_2$O(CH$_2$)$_2$N(CH$_3$)(SO$_2$CH$_3$) | |
| 3-553 | Q3e | CH$_2$O(CH$_2$)$_2$NH(SO$_2$CH$_2$–) | |
| 3-554 | Q3e | CH$_2$O(CH$_2$)$_2$NHSO$_2$CF$_3$ | |
| 3-555 | Q3e | CH$_2$O(CH2)$_2$NHSO$_2$CHF$_2$ | |
| 3-556 | Q3e | CH$_2$O(CH$_2$)$_2$NHSO$_2$CH$_2$CF$_3$ | |
| 3-557 | Q3e | SCH$_3$ | |
| 3-558 | Q3e | SOCH$_3$ | |
| 3-559 | Q3e | SO$_2$CH$_3$ | |
| 3-560 | Q3e | OCH$_3$ | |

TABLE 59

| compound number | Q | R1 | physical property (melting point-ND) |
|---|---|---|---|
| 3-561 | Q3e | OCH$_2$CH$_3$ | |
| 3-562 | Q3e | O(CH$_2$)$_2$CH$_3$ | |
| 3-563 | Q3e | OCH$_2$CF$_3$ | |
| 3-564 | Q3e | OCF$_2$CF$_3$ | |
| 3-565 | Q3e | O(CH$_2$)$_2$OCH$_3$ | |
| 3-566 | Q3e | NHCH$_3$ | |
| 3-567 | Q3e | NHCH$_2$CH$_3$ | |
| 3-568 | Q3e | N(CH$_3$)$_2$ | |
| 3-569 | Q3e | N(CH$_2$CH$_3$)$_2$ | |
| 3-570 | Q3e | N(CH$_3$)(CH$_2$CH$_3$) | |
| 3-571 | Q3f | CH$_3$ | |
| 3-572 | Q3f | CH$_2$CH$_3$ | |
| 3-573 | Q3f | (CH$_2$)$_2$CH$_3$ | |
| 3-574 | Q3f |  | |
| 3-575 | Q3f |  | |
| 3-576 | Q3f |  | |
| 3-577 | Q3f |  | |
| 3-578 | Q3f |  | |
| 3-579 | Q3f |  | |
| 3-580 | Q3f |  | |

TABLE 59-continued

| compound number | Q | R1 | physical property (melting point-ND) |
|---|---|---|---|
| 3-581 | Q3f | 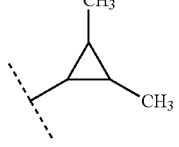 | |
| 3-582 | Q3f | CF$_3$ | |
| 3-583 | Q3f | CH$_2$CF$_3$ | |
| 3-584 | Q3f | CF$_2$CF$_3$ | |
| 3-585 | Q3f | CH$_2$CH=CH$_2$ | |
| 3-586 | Q3f | CH$_2$C≡CH | |
| 3-587 | Q3f | C$_6$H$_5$ | |
| 3-588 | Q3f | CH$_2$C$_6$H$_5$ | |
| 3-589 | Q3f | CH$_2$OCH$_3$ | |
| 3-590 | Q3f | CH$_2$OCH$_2$CH$_3$ | |
| 3-591 | Q3f | CH$_2$O(CH2)$_2$CH$_3$ | |
| 3-592 | Q3f | (CH$_2$)$_2$OCH$_3$ | |
| 3-593 | Q3f | (CH$_2$)$_3$OCH$_3$ | |
| 3-594 | Q3f | 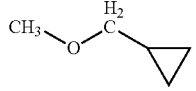 | |
| 3-595 | Q3f | 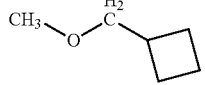 | |
| 3-596 | Q3f | 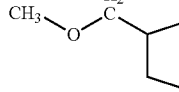 | |
| 3-597 | Q3f | 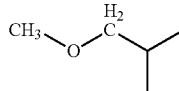 | |
| 3-598 | Q3f | CH$_2$OCH$_2$CF$_3$ | |
| 3-599 | Q3f | CH$_2$OCF$_2$CHF$_2$ | |
| 3-600 | Q3f | CH$_2$OCH2CF2CF3 | |

TABLE 60

| compound number | Q | R1 | physical property (melting point-ND) |
|---|---|---|---|
| 3-601 | Q3f | CH$_2$OCH$_2$CH=CH$_2$ | |
| 3-602 | Q3f | CH$_2$OCH$_2$CH=CCl$_2$ | |
| 3-603 | Q3f | CH$_2$OCH$_2$CF=CF$_2$ | |
| 3-604 | Q3f | CH$_2$OC$_2$C≡CH | |
| 3-605 | Q3f | CH$_2$OCH$_2$C≡CCH$_3$ | |
| 3-606 | Q3f | CH$_2$SCH$_3$ | |
| 3-607 | Q3f | CH$_2$SCH$_2$CH$_3$ | |
| 3-608 | Q3f | CH$_2$S(CH$_2$)$_2$CH$_3$ | |
| 3-609 | Q3f | 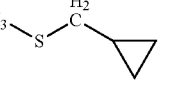 | |
| 3-610 | Q3f | 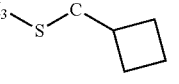 | |
| 3-611 | Q3f | 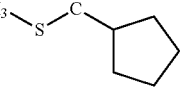 | |
| 3-612 | Q3f | 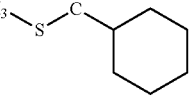 | |
| 3-613 | Q3f | CH$_2$SCH$_2$CF$_3$ | |
| 3-614 | Q3f | CH$_2$SCH$_2$CH=CH$_2$ | |
| 3-615 | Q3f | CH$_2$SCH$_2$C≡CH | |
| 3-616 | Q3f | CH$_2$SOCH$_3$ | |
| 3-617 | Q3f | CH$_2$SOCH$_2$CH$_3$ | |
| 3-618 | Q3f | CH$_2$SO(CH$_2$)$_2$CH$_3$ | |
| 3-619 | Q3f | 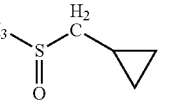 | |
| 3-620 | Q3f | 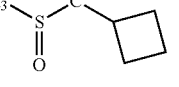 | |
| 3-621 | Q3f | 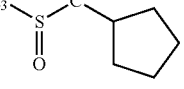 | |
| 3-622 | Q3f | 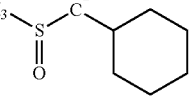 | |
| 3-623 | Q3f | CH$_2$SOCH$_2$CF$_3$ | |
| 3-624 | Q3f | CH$_2$SOCH$_2$CH=CH$_2$ | |
| 3-625 | Q3f | CH$_2$SOCH$_2$C≡CH | |
| 3-626 | Q3f | CH$_2$SO$_2$CH$_3$ | |
| 3-627 | Q3f | CH$_2$SO$_2$CH$_2$CH$_3$ | |
| 3-628 | Q3f | CH$_2$SO$_2$(CH$_2$)$_2$CH$_3$ | |
| 3-629 | Q3f | 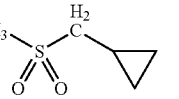 | |
| 3-630 | Q3f | 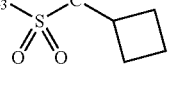 | |
| 3-631 | Q3f | 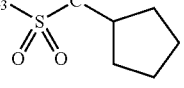 | |

TABLE 60-continued

| compound number | Q | R1 | physical property (melting point-ND) |
|---|---|---|---|
| 3-632 | Q3f | CH₃-S(O)₂-CH₂-cyclohexyl | |
| 3-633 | Q3f | CH₂SO₂CH₂CF₃ | |
| 3-634 | Q3f | CH₂SO₂CH₂CH=CH₂ | |
| 3-635 | Q3f | CH₂SO₂CH₂C≡CH | |
| 3-636 | Q3f | CH₂O(CH₂)₂OCH₃ | |
| 3-637 | Q3f | CH₂O(CH₂)₂OCH₂CH₃ | |
| 3-638 | Q3f | CH₂O(CH₂)₂OCH₂-cyclopropyl | |
| 3-639 | Q3f | CH₂O(CH₂)₂OCH₂CF₃ | |
| 3-640 | Q3f | CH₂O(CH₂)₂OCH₂CH=CH₂ | |

TABLE 61

| compound | Q | R1 | physical property (melting point-ND) |
|---|---|---|---|
| 3-641 | Q3f | CH₂O(CH₂)₂OCH₂C≡CH | |
| 3-642 | Q3f | CH₂O(CH₂)₂SCH₃ | |
| 3-643 | Q3f | CH₂O(CH₂)₂SCH₂-cyclopropyl | |
| 3-644 | Q3f | CH₂O(CH₂)₂SCH₂CF₃ | |
| 3-645 | Q3f | CH₂O(CH₂)₂SCH₂CH=CH₂ | |
| 3-646 | Q3f | CH₂O(CH₂)₂SCH₂C≡CH | |
| 3-647 | Q3f | CH₂O(CH₂)₂SOCH₃ | |
| 3-648 | Q3f | CH₂O(CH₂)₂SOCH₂-cyclopropyl | |
| 3-649 | Q3f | CH₂O(CH₂)₂SOCH₂CF₃ | |
| 3-650 | Q3f | CH₂O(CH₂)₂SOCH₂CH=CH₂ | |
| 3-651 | Q3f | CH₂O(CH₂)₂SOCH₂C≡CH | |
| 3-652 | Q3f | CH₂O(CH₂)₂SO₂CH₃ | |
| 3-653 | Q3f | CH₂O(CH₂)₂SO₂CH₂-cyclopropyl | |
| 3-654 | Q3f | CH₂O(CH₂)₂SO₂CH₂CF₃ | |
| 3-655 | Q3f | CH₂O(CH₂)₂SO₂CH₂CH=CH₂ | |
| 3-656 | Q3f | CH₂O(CH₂)₂SO₂CH₂C≡CH | |
| 3-657 | Q3f | CH₃-O-CH₂-oxetanyl | |
| 3-658 | Q3f | CH₃-O-CH₂-tetrahydrofuranyl (2-yl) | |
| 3-659 | Q3f | CH₃-O-CH₂-tetrahydrofuranyl (3-yl) | |

TABLE 61-continued

| compound | Q | R1 | physical property (melting point-ND) |
|---|---|---|---|
| 3-660 | Q3f | CH₃-O-tetrahydrofuranyl | |
| 3-661 | Q3f | CH₃-O-CH₂-O-CH₂-oxetanyl | |
| 3-662 | Q3f | CH₃-O-CH₂-O-CH₂-tetrahydrofuranyl (2-yl) | |
| 3-663 | Q3f | CH₃-O-CH₂-O-CH₂-tetrahydrofuranyl (3-yl) | |
| 3-664 | Q3f | CH₃-O-CH₂-O-tetrahydrofuranyl | |
| 3-665 | Q3f | CH₂O(CH₂)₂NHSO₂CH₃ | |
| 3-666 | Q3f | CH₂O(CH₂)₂N(CH₃)(SO₂CH₃) | |
| 3-667 | Q3f | CH₂O(CH₂)₂NH(SO₂CH₂-cyclopropyl) | |
| 3-668 | Q3f | CH₂O(CH₂)₂NHSO₂CF₃ | |
| 3-669 | Q3f | CH₂O(CH2)₂NHSO₂CHF₂ | |
| 3-670 | Q3f | CH₂O(CH₂)₂NHSO₂CH₂CF₃ | |
| 3-671 | Q3f | SCH₃ | |
| 3-672 | Q3f | SOCH₃ | |
| 3-673 | Q3f | SO₂CH₃ | |
| 3-674 | Q3f | OCH₃ | |
| 3-675 | Q3f | OCH₂CH₃ | |
| 3-676 | Q3f | O(CH₂)₂CH₃ | |
| 3-677 | Q3f | OCH₂CF₃ | |
| 3-678 | Q3f | OCF₂CF₃ | |
| 3-679 | Q3f | O(CH₂)₂OCH₃ | |
| 3-680 | Q3f | NHCH₃ | |

TABLE 62

| compound number | Q | R1 | physical property (melting point-ND) |
|---|---|---|---|
| 3-681 | Q3f | NHCH₂CH₃ | |
| 3-682 | Q3f | N(CH₃)₂ | |
| 3-683 | Q3f | N(CH₂CH₃)₂ | |
| 3-684 | Q3f | N(CH₃(CH₂CH₃) | |

TABLE 63

Structure: Benzoate with triazole substituent, ester group O-Q, R1 on ortho position, 1,2,4-triazol-1-yl at para position.

Q4a: C(=O)-C(CH3)(...)- pivaloyl-type group with cyano-methyl branch: (CH3)3C-C(=O)-CH(CH3)-CN (attached via the CH)

Q4b: cyclopropyl-C(=O)-CH(CH3)-CN (attached via the CH)

| compound number | Q | R1 | physical property (melting point-ND) |
|---|---|---|---|
| 4-1 | Q4a | CH$_3$ | |
| 4-2 | Q4a | CH$_2$CH$_3$ | |
| 4-3 | Q4a | (CH$_2$)$_2$CH$_3$ | |
| 4-4 | Q4a | -CH$_2$-cyclopropyl | |
| 4-5 | Q4a | -CH$_2$-cyclobutyl | |
| 4-6 | Q4a | -CH$_2$-cyclopentyl | |
| 4-7 | Q4a | -CH$_2$-cyclohexyl | |
| 4-8 | Q4a | -CH$_2$-(1-methylcyclopropyl) | |
| 4-9 | Q4a | -CH$_2$-(2-methylcyclopropyl) | |
| 4-10 | Q4a | -CH$_2$-(2,2-dimethylcyclopropyl) | |
| 4-11 | Q4a | -CH$_2$-(2,3-dimethylcyclopropyl) | |
| 4-12 | Q4a | CF$_3$ | |
| 4-13 | Q4a | CH$_2$CF$_3$ | |
| 4-14 | Q4a | CF$_2$CF$_3$ | |
| 4-15 | Q4a | CH$_2$CH=CH$_2$ | |
| 4-16 | Q4a | CH2C≡CH | |
| 4-17 | Q4a | C$_6$H$_5$ | |
| 4-18 | Q4a | CH$_2$C$_6$H$_5$ | |
| 4-19 | Q4a | CH$_2$OCH$_3$ | |
| 4-20 | Q4a | CH$_2$OCH$_2$CH$_3$ | |
| 4-21 | Q4a | CH$_2$O(CH2)$_2$CH$_3$ | |
| 4-22 | Q4a | (CH$_2$)$_2$OCH$_3$ | |
| 4-23 | Q4a | (CH$_2$)$_3$OCH$_3$ | |
| 4-24 | Q4a | CH$_3$-O-CH$_2$-cyclopropyl | |
| 4-25 | Q4a | CH$_3$-O-CH$_2$-cyclobutyl | |
| 4-26 | Q4a | CH$_3$-O-CH$_2$-cyclopentyl | |

TABLE 63-continued

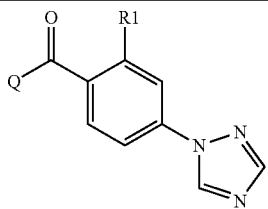

Q4a

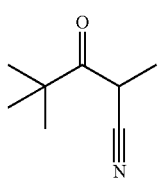

Q4b

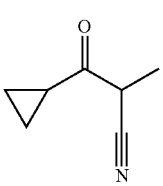

| compound number | Q | R1 | physical property (melting point-ND) |
|---|---|---|---|
| 4-27 | Q4a | CH₃—O—CH₂—cyclohexyl | |
| 4-28 | Q4a | CH₂OCH₂CF₃ | |
| 4-29 | Q4a | CH₂OCF₂CHF₂ | |
| 4-30 | Q4a | CH2OCH2CF2CF3 | |
| 4-31 | Q4a | CH₂OCH₂CH=CH₂ | |
| 4-32 | Q4a | CH₂OCH₂CH=CCl₂ | |
| 4-33 | Q4a | CH₂OCH₂CF=CF₂ | |
| 4-34 | Q4a | CH₂OC₂C≡CH | |
| 4-35 | Q4a | CH₂OCH₂C≡CCH₃ | |
| 4-36 | Q4a | CH₂SCH₃ | |
| 4-37 | Q4a | CH₂SCH₂CH₃ | |
| 4-38 | Q4a | CH₂S(CH₂)₂CH₃ | |
| 4-39 | Q4a | CH₃—S—CH₂—cyclopropyl | |
| 4-40 | Q4a | CH₃—S—CH₂—cyclobutyl | |

TABLE 64

| compound number | Q | R1 | physical property (melting point-ND) |
|---|---|---|---|
| 4-41 | Q4a | CH₃—S—CH₂—cyclopentyl | |
| 4-42 | Q4a | CH₃—S—CH₂—cyclohexyl | |
| 4-43 | Q4a | CH₂SCH₂CF₃ | |
| 4-44 | Q4a | CH₂SCH₂CH=CH₂ | |
| 4-45 | Q4a | CH₂SCH₂C≡CH | |
| 4-46 | Q4a | CH₂SOCH₃ | |
| 4-47 | Q4a | CH₂SOCH₂CH₃ | |
| 4-48 | Q4a | CH₂SO(CH₂)₂CH₃ | |
| 4-49 | Q4a | CH₃—S(O)—CH₂—cyclopropyl | |
| 4-50 | Q4a | CH₃—S(O)—CH₂—cyclobutyl | |
| 4-51 | Q4a | CH₃—S(O)—CH₂—cyclopentyl | |
| 4-52 | Q4a | CH₃—S(O)—CH₂—cyclohexyl | |
| 4-53 | Q4a | CH₂SOCH₂CF₃ | |
| 4-54 | Q4a | CH₂SOCH₂CH=CH₂ | |
| 4-55 | Q4a | CH₂SOCH₂C≡CH | |
| 4-56 | Q4a | CH₂SO₂CH₃ | |
| 4-57 | Q4a | CH₂SO₂CH₂CH₃ | |
| 4-58 | Q4a | CH₂SO₂(CH₂)₂CH₃ | |
| 4-59 | Q4a | CH₃—S(O)₂—CH₂—cyclopropyl | |
| 4-60 | Q4a | CH₃—S(O)₂—CH₂—cyclobutyl | |
| 4-61 | Q4a | CH₃—S(O)₂—CH₂—cyclopentyl | |
| 4-62 | Q4a | CH₃—S(O)₂—CH₂—cyclohexyl | |
| 4-63 | Q4a | CH₂SO₂CH₂CF₃ | |
| 4-64 | Q4a | CH₂SO₂CH₂CH=CH₂ | |
| 4-65 | Q4a | CH₂SO₂CH₂C≡CH | |
| 4-66 | Q4a | CH₂O(CH₂)₂OCH₃ | |
| 4-67 | Q4a | CH₂O(CH₂)₂OCH₂CH₃ | |

TABLE 64-continued

| compound number | Q | R1 | physical property (melting point-ND) |
|---|---|---|---|
| 4-68 | Q4a | CH$_2$O(CH$_2$)$_2$OCH$_2$—[cyclopropyl] | |
| 4-69 | Q4a | CH$_2$O(CH$_2$)$_2$OCH$_2$CF$_3$ | |
| 4-70 | Q4a | CH$_2$O(CH$_2$)$_2$OCH$_2$CH=CH$_2$ | |
| 4-71 | Q4a | CH$_2$O(CH$_2$)$_2$OCH$_2$C≡CH | |
| 4-72 | Q4a | CH$_2$O(CH$_2$)$_2$SCH$_3$ | |
| 4-73 | Q4a | CH$_2$O(CH$_2$)$_2$SCH$_2$—[cyclopropyl] | |
| 4-74 | Q4a | CH$_2$O(CH$_2$)$_2$SCH$_2$CF$_3$ | |
| 4-75 | Q4a | CH$_2$O(CH$_2$)$_2$SCH$_2$CH=CH$_2$ | |
| 4-76 | Q4a | CH$_2$O(CH$_2$)$_2$SCH$_2$C≡CH | |
| 4-77 | Q4a | CH$_2$O(CH$_2$)$_2$SOCH$_3$ | |
| 4-78 | Q4a | CH$_2$O(CH$_2$)$_2$SOCH$_2$—[cyclopropyl] | |
| 4-79 | Q4a | CH$_2$O(CH$_2$)$_2$SOCH$_2$CF$_3$ | |
| 4-80 | Q4a | CH$_2$O(CH$_2$)$_2$SOCH$_2$CH=CH$_2$ | |

TABLE 65

| compound number | Q | R1 | physical property (melting point-ND) |
|---|---|---|---|
| 4-81 | Q4a | CH$_2$O(CH$_2$)$_2$SOCH$_2$C≡CH | |
| 4-82 | Q4a | CH$_2$O(CH$_2$)$_2$SO$_2$CH$_3$ | |
| 4-83 | Q4a | CH$_2$O(CH$_2$)$_2$SO$_2$CH$_2$—[cyclopropyl] | |
| 4-84 | Q4a | CH$_2$O(CH$_2$)$_2$SO$_2$CH$_2$CF$_3$ | |
| 4-85 | Q4a | CH$_2$O(CH$_2$)$_2$SO$_2$CH$_2$CH=CH$_2$ | |
| 4-86 | Q4a | CH$_2$O(CH$_2$)$_2$SO$_2$CH$_2$C≡CH | |
| 4-87 | Q4a | CH$_3$-O-CH$_2$-[oxetan-2-yl] | |
| 4-88 | Q4a | CH$_3$-O-CH$_2$-[tetrahydrofuran-2-yl] | |
| 4-89 | Q4a | CH$_3$-O-CH$_2$-[tetrahydrofuran-3-yl] | |
| 4-90 | Q4a | CH$_3$-O-[tetrahydrofuran-3-yl] | |
| 4-91 | Q4a | CH$_3$-O-CH$_2$-CH$_2$-O-CH$_2$-[oxetan-2-yl] | |
| 4-92 | Q4a | CH$_3$-O-CH$_2$-CH$_2$-O-CH$_2$-[tetrahydrofuran-2-yl] | |
| 4-93 | Q4a | CH$_3$-O-CH$_2$-CH$_2$-O-CH$_2$-[tetrahydrofuran-3-yl] | |
| 4-94 | Q4a | CH$_3$-O-CH$_2$-CH$_2$-O-CH$_2$-[tetrahydrofuran-3-yl] | |
| 4-95 | Q4a | CH$_2$O(CH$_2$)$_2$NHSO$_2$CH$_3$ | |
| 4-96 | Q4a | CH$_2$O(CH$_2$)$_2$N(CH$_3$)(SO$_2$CH$_3$) | |
| 4-97 | Q4a | CH$_2$O(CH$_2$)$_2$NH(SO$_2$CH$_2$—[cyclopropyl]) | |
| 4-98 | Q4a | CH$_2$O(CH$_2$)$_2$NHSO$_2$CF$_3$ | |
| 4-99 | Q4a | CH$_2$O(CH$_2$)$_2$NHSO$_2$CHF$_2$ | |
| 4-100 | Q4a | CH$_2$O(CH$_2$)$_2$NHSO$_2$CH$_2$CF$_3$ | |
| 4-101 | Q4a | SCH$_3$ | |
| 4-102 | Q4a | SOCH$_3$ | |
| 4-103 | Q4a | SO$_2$CH$_3$ | |
| 4-104 | Q4a | OCH$_3$ | |
| 4-105 | Q4a | OCH$_2$CH$_3$ | |
| 4-106 | Q4a | O(CH$_2$)$_2$CH$_3$ | |
| 4-107 | Q4a | OCH$_2$CF$_3$ | |
| 4-108 | Q4a | OCF$_2$CF$_3$ | |
| 4-109 | Q4a | O(CH$_2$)$_2$OCH$_3$ | |
| 4-110 | Q4a | NHCH$_3$ | |
| 4-111 | Q4a | NHCH$_2$CH$_3$ | |
| 4-112 | Q4a | N(CH$_3$)$_2$ | |
| 4-113 | Q4a | N(CH$_2$CH$_3$)$_2$ | |
| 4-114 | Q4a | N(CH$_3$)(CH$_2$CH$_3$) | |
| 4-115 | Q4b | CH$_3$ | NMR |
| 4-116 | Q4b | CH$_2$CH$_3$ | |
| 4-117 | Q4b | (CH$_2$)$_2$CH$_3$ | |
| 4-118 | Q4b | [cyclopropyl] | |
| 4-119 | Q4b | [cyclobutyl] | |
| 4-120 | Q4b | [cyclopentyl] | |

TABLE 66

| compound number | Q | R1 | physical property (melting point-ND) |
|---|---|---|---|
| 4-121 | Q4b | -CH2-cyclohexyl | |
| 4-122 | Q4b | -CH2-(1-methylcyclopropyl) | |
| 4-123 | Q4b | -CH2-(2-methylcyclopropyl) | |
| 4-124 | Q4b | -CH2-(2,2-dimethylcyclopropyl) | |
| 4-125 | Q4b | -CH2-(2,3-dimethylcyclopropyl) | |
| 4-126 | Q4b | CF$_3$ | 122-132° C. |
| 4-127 | Q4b | CH$_2$CF$_3$ | |
| 4-128 | Q4b | CF$_2$CF$_3$ | |
| 4-129 | Q4b | CH$_2$CH=CH$_2$ | |
| 4-130 | Q4b | CH2C≡CH | |
| 4-131 | Q4b | C$_6$H$_5$ | |
| 4-132 | Q4b | CH$_2$C$_6$H$_5$ | |
| 4-133 | Q4b | CH$_2$OCH$_3$ | 1.5723(25) |
| 4-134 | Q4b | CH$_2$OCH$_2$CH$_3$ | |
| 4-135 | Q4b | CH$_2$O(CH$_2$)$_2$CH$_3$ | |
| 4-136 | Q4b | (CH$_2$)$_2$OCH$_3$ | |
| 4-137 | Q4b | (CH$_2$)$_3$OCH$_3$ | |
| 4-138 | Q4b | CH$_3$-O-CH$_2$-cyclopropyl | |
| 4-139 | Q4b | CH$_3$-O-CH$_2$-cyclobutyl | |
| 4-140 | Q4b | CH$_3$-O-CH$_2$-cyclopentyl | |
| 4-141 | Q4b | CH$_2$OCH$_2$CF$_3$ | |
| 4-142 | Q4b | CH$_2$OCF$_2$CHF$_2$ | NMR |
| 4-143 | Q4b | CH$_2$OCH2CF2CF3 | |
| 4-144 | Q4b | CH$_2$OCH$_2$CH=CH$_2$ | |
| 4-145 | Q4b | CH$_2$OCH$_2$CH=CCl$_2$ | |
| 4-146 | Q4b | CH$_2$OCH$_2$CF=CF$_2$ | |
| 4-147 | Q4b | CH$_2$OC$_2$C≡CH | |
| 4-148 | Q4b | CH$_2$OCH$_2$C≡CCH$_3$ | |
| 4-149 | Q4b | CH$_2$SCH$_3$ | |
| 4-150 | Q4b | CH$_2$SCH$_2$CH$_3$ | |
| 4-151 | Q4b | CH$_2$S(CH$_2$)$_2$CH$_3$ | |
| 4-152 | Q4b | | |

TABLE 66-continued

| compound number | Q | R1 | physical property (melting point-ND) |
|---|---|---|---|
| 4-153 | Q4b | CH$_3$-S-CH$_2$-cyclopropyl | |
| 4-154 | Q4b | CH$_3$-S-CH$_2$-cyclobutyl | |
| 4-155 | Q4b | CH$_3$-S-CH$_2$-cyclopentyl | |
| 4-156 | Q4b | CH$_3$-S-CH$_2$-cyclohexyl | |
| 4-157 | Q4b | CH$_2$SCH$_2$CF$_3$ | |
| 4-158 | Q4b | CH$_2$SCH$_2$CH=CH$_2$ | |
| 4-159 | Q4b | CH$_2$SCH$_2$C≡CH | |
| 4-160 | Q4b | CH$_2$SOCH$_3$ | |

TABLE 67

| compound number | Q | R1 | physical property (melting point-ND) |
|---|---|---|---|
| 4-161 | Q4b | CH$_2$SOCH$_2$CH$_3$ | |
| 4-162 | Q4b | CH$_2$SO(CH$_2$)$_2$CH$_3$ | |
| 4-163 | Q4b | CH$_3$-S(O)-CH$_2$-cyclopropyl | |
| 4-164 | Q4b | CH$_3$-S(O)-CH$_2$-cyclobutyl | |
| 4-165 | Q4b | CH$_3$-S(O)-CH$_2$-cyclopentyl | |
| 4-166 | Q4b | CH$_3$-S(O)-CH$_2$-cyclohexyl | |
| 4-167 | Q4b | CH$_2$SOCH$_2$CF$_3$ | |
| 4-168 | Q4b | CH$_2$SOCH$_2$CH=CH$_2$ | |
| 4-169 | Q4b | CH$_2$SOCH$_2$C≡CH | |
| 4-170 | Q4b | CH$_2$SO$_2$CH$_3$ | |
| 4-171 | Q4b | CH$_2$SO$_2$CH$_2$CH$_3$ | |
| 4-172 | Q4b | CH$_2$SO$_2$(CH$_2$)$_2$CH$_3$ | |

TABLE 67-continued

| compound number | Q | R1 | physical property (melting point-ND) |
|---|---|---|---|
| 4-173 | Q4b | CH₃-S(=O)₂-CH₂-cyclopropyl | |
| 4-174 | Q4b | CH₃-S(=O)₂-CH₂-cyclobutyl | |
| 4-175 | Q4b | CH₃-S(=O)₂-CH₂-cyclopentyl | |
| 4-176 | Q4b | CH₃-S(=O)₂-CH₂-cyclohexyl | |
| 4-177 | Q4b | CH$_2$SO$_2$CH$_2$CF$_3$ | |
| 4-178 | Q4b | CH$_2$SO$_2$CH$_2$CH=CH$_2$ | |
| 4-179 | Q4b | CH$_2$SO$_2$CH$_2$C≡CH | |
| 4-180 | Q4b | CH$_2$O(CH$_2$)$_2$OCH$_3$ | |
| 4-181 | Q4b | CH$_2$O(CH$_2$)$_2$OCH$_2$CH$_3$ | |
| 4-182 | Q4b | CH$_2$O(CH$_2$)$_2$OCH$_2$-cyclopropyl | |
| 4-183 | Q4b | CH$_2$O(CH$_2$)$_2$OCH$_2$CF$_3$ | |
| 4-184 | Q4b | CH$_2$O(CH$_2$)$_2$OCH$_2$CH=CH$_2$ | |
| 4-185 | Q4b | CH$_2$O(CH$_2$)$_2$OCH$_2$C≡CH | |
| 4-186 | Q4b | CH$_2$O(CH$_2$)$_2$SCH$_3$ | |
| 4-187 | Q4b | CH$_2$O(CH$_2$)$_2$SCH$_2$-cyclopropyl | |
| 4-188 | Q4b | CH$_2$O(CH$_2$)$_2$SCH$_2$CF$_3$ | |
| 4-189 | Q4b | CH$_2$O(CH$_2$)$_2$SCH$_2$CH=CH$_2$ | |
| 4-190 | Q4b | CH$_2$O(CH$_2$)$_2$SCH$_2$C≡CH | |
| 4-191 | Q4b | CH$_2$O(CH$_2$)$_2$SOCH$_3$ | |
| 4-192 | Q4b | CH$_2$O(CH$_2$)$_2$SOCH$_2$-cyclopropyl | |
| 4-193 | Q4b | CH$_2$O(CH$_2$)$_2$SOCH$_2$CF$_3$ | |
| 4-194 | Q4b | CH$_2$O(CH$_2$)$_2$SOCH$_2$CH=CH$_2$ | |
| 4-195 | Q4b | CH$_2$O(CH$_2$)$_2$SOCH$_2$C≡CH | |
| 4-196 | Q4b | CH$_2$O(CH$_2$)$_2$SO$_2$CH$_3$ | |
| 4-197 | Q4b | CH$_2$O(CH$_2$)$_2$SO$_2$CH$_2$-cyclopropyl | |
| 4-198 | Q4b | CH$_2$O(CH$_2$)$_2$SO$_2$CH$_2$CF$_3$ | |
| 4-199 | Q4b | CH$_2$O(CH$_2$)$_2$SO$_2$CH$_2$CH=CH$_2$ | |
| 4-200 | Q4b | CH$_2$O(CH$_2$)$_2$SO$_2$CH$_2$C≡CH | |

TABLE 68

| compound number | Q | R1 | physical property (melting point-ND) |
|---|---|---|---|
| 4-201 | Q4b | CH₃-O-CH₂-(oxetan-2-yl) | |
| 4-202 | Q4b | CH₃-O-CH₂-(tetrahydrofuran-2-yl) | |
| 4-203 | Q4b | CH₃-O-CH₂-(tetrahydrofuran-3-yl) | |
| 4-204 | Q4b | CH₃-O-(tetrahydrofuran-3-yl) | |
| 4-205 | Q4b | CH₃-O-CH₂-O-CH₂-(oxetan-2-yl) | |
| 4-206 | Q4b | CH₃-O-CH₂-O-CH₂-(tetrahydrofuran-2-yl) | |
| 4-207 | Q4b | CH₃-O-CH₂-O-CH₂-(tetrahydrofuran-3-yl) | |
| 4-208 | Q4b | CH₃-O-CH₂-O-(tetrahydrofuran-3-yl) | |
| 4-209 | Q4b | CH$_2$O(CH$_2$)$_2$NHSO$_2$CH$_3$ | |
| 4-210 | Q4b | CH$_2$O(CH$_2$)$_2$N(CH$_3$)(SO$_2$CH$_3$) | |
| 4-211 | Q4b | CH$_2$O(CH$_2$)$_2$NH(SO$_2$CH$_2$-cyclopropyl) | |
| 4-212 | Q4b | CH$_2$O(CH$_2$)$_2$NHSO$_2$CF$_3$ | |
| 4-213 | Q4b | CH$_2$O(CH$_2$)$_2$NHSO$_2$CHF$_2$ | |
| 4-214 | Q4b | CH$_2$O(CH$_2$)$_2$NHSO$_2$CH$_2$CF$_3$ | |
| 4-215 | Q4b | SCH$_3$ | |
| 4-216 | Q4b | SOCH$_3$ | |
| 4-217 | Q4b | SO$_2$CH$_3$ | |
| 4-218 | Q4b | OCH$_3$ | |
| 4-219 | Q4b | OCH$_2$CH$_3$ | |
| 4-220 | Q4b | O(CH$_2$)$_2$CH$_3$ | |
| 4-221 | Q4b | OCH$_2$CF$_3$ | |
| 4-222 | Q4b | OCF$_2$CF$_3$ | |
| 4-223 | Q4b | O(CH$_2$)$_2$OCH$_3$ | |
| 4-224 | Q4b | NHCH$_3$ | |
| 4-225 | Q4b | NHCH$_2$CH$_3$ | |
| 4-226 | Q4b | N(CH$_3$)$_2$ | |
| 4-227 | Q4b | N(CH$_2$CH$_3$)$_2$ | |
| 4-228 | Q4b | N(CH$_3$)(CH$_2$CH$_3$) | |

TABLE 69

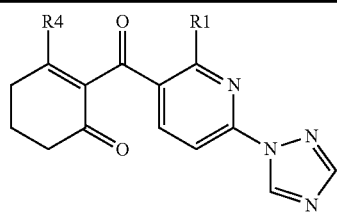

| compound number | R4 | R1 | physical property (melting point-ND) |
|---|---|---|---|
| 5-1 | Cl | CH$_3$ | |
| 5-2 | Cl | CF$_3$ | |
| 5-3 | Cl | CH$_2$OCH$_3$ | |
| 5-4 | Cl | CH$_2$OCH$_2$CH$_3$ | |
| 5-5 | Cl | CH$_3$-O-CH$_2$-cyclopropyl | |
| 5-6 | Cl | CH$_2$OCH$_2$CF$_3$ | |
| 5-7 | Cl | CH$_2$SCH$_3$ | |
| 5-8 | Cl | CH$_2$SCH$_2$CH$_3$ | |
| 5-9 | Cl | CH$_3$-S-CH$_2$-cyclopropyl | |
| 5-10 | Cl | CH$_2$SCH$_2$CF$_3$ | |
| 5-11 | Cl | CH$_2$SOCH$_3$ | |
| 5-12 | Cl | CH$_2$SOCH$_2$CH$_3$ | |
| 5-13 | Cl | CH$_3$-S(O)-CH$_2$-cyclopropyl | |
| 5-14 | Cl | CH$_2$SOCH$_2$CF$_3$ | |
| 5-15 | Cl | CH$_2$SO$_2$CH$_3$ | |
| 5-16 | Cl | CH$_2$SO$_2$CH$_2$CH$_3$ | |
| 5-17 | Cl | CH$_3$-S(O)$_2$-CH$_2$-cyclopropyl | |
| 5-18 | Cl | CH$_2$SO$_2$CH$_2$CF$_3$ | |
| 5-19 | Cl | CH$_2$O(CH$_2$)$_2$OCH$_3$ | |
| 5-20 | Cl | CH$_2$O(CH$_2$)$_2$OCH$_2$CH$_3$ | |
| 5-21 | Cl | CH$_2$O(CH$_2$)$_2$OCH$_2$CF$_3$ | |
| 5-22 | Cl | CH$_2$O(CH$_2$)$_2$SCH$_3$ | |
| 5-23 | Cl | CH$_2$O(CH$_2$)$_2$SCH$_2$CF$_3$ | |
| 5-24 | Cl | CH$_2$O(CH$_2$)$_2$SOCH$_3$ | |
| 5-25 | Cl | CH$_2$O(CH$_2$)$_2$SOCH$_2$CF$_3$ | |
| 5-26 | Cl | CH$_2$O(CH$_2$)$_2$SO$_2$CH$_3$ | |
| 5-27 | Cl | CH$_2$O(CH$_2$)$_2$SO$_2$CH$_2$CF$_3$ | |
| 5-28 | Cl | CH$_3$-O-CH$_2$-(tetrahydrofuran-2-yl) | |
| 5-29 | Cl | CH$_3$-O-(tetrahydrofuran-3-yl) | |
| 5-30 | Cl | CH$_2$O(CH$_2$)$_2$NHSO$_2$CH$_3$ | |
| 5-31 | Cl | CH$_2$O(CH$_2$)$_2$N(CH$_3$)(SO$_2$CH$_3$) | |

TABLE 69-continued

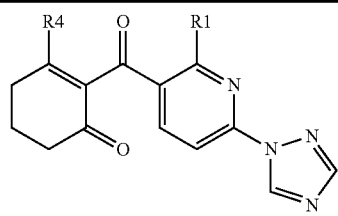

| compound number | R4 | R1 | physical property (melting point-ND) |
|---|---|---|---|
| 5-32 | SCH$_3$ | CH$_3$ | |
| 5-33 | SCH$_3$ | CF$_3$ | |
| 5-34 | SCH$_3$ | CH$_2$OCH$_3$ | |
| 5-35 | SCH$_3$ | CH$_2$OCH$_2$CH$_3$ | |
| 5-36 | SCH$_3$ | CH$_3$-O-CH$_2$-cyclopropyl | |
| 5-37 | SCH$_3$ | CH$_2$OCH$_2$CF$_3$ | |
| 5-38 | SCH$_3$ | CH$_2$SCH$_3$ | |
| 5-39 | SCH$_3$ | CH$_2$SCH$_2$CH$_3$ | |
| 5-40 | SCH$_3$ | CH$_3$-S-CH$_2$-cyclopropyl | |

TABLE 70

| compound number | R4 | R1 | physical property (melting point-ND) |
|---|---|---|---|
| 5-41 | SCH$_3$ | CH$_2$SCH$_2$CF$_3$ | |
| 5-42 | SCH$_3$ | CH$_2$SOCH$_3$ | |
| 5-43 | SCH$_3$ | CH$_2$SOCH$_2$CH$_3$ | |
| 5-44 | SCH$_3$ | CH$_3$-S(O)-CH$_2$-cyclopropyl | |
| 5-45 | SCH$_3$ | CH$_2$SOCH$_2$CF$_3$ | |
| 5-46 | SCH$_3$ | CH$_2$SO$_2$CH$_3$ | |
| 5-47 | SCH$_3$ | CH$_2$SO$_2$CH$_2$CH$_3$ | |
| 5-48 | SCH$_3$ | CH$_3$-S(O)$_2$-CH$_2$-cyclopropyl | |
| 5-49 | SCH$_3$ | CH$_2$SO$_2$CH$_2$CF$_3$ | |
| 5-50 | SCH$_3$ | CH$_2$O(CH$_2$)$_2$OCH$_3$ | |
| 5-51 | SCH$_3$ | CH$_2$O(CH$_2$)$_2$OCH$_2$CH$_3$ | |
| 5-52 | SCH$_3$ | CH$_2$O(CH$_2$)$_2$OCH$_3$CF$_3$ | |
| 5-53 | SCH$_3$ | CH$_2$O(CH$_2$)$_2$SCH$_3$ | |
| 5-54 | SCH$_3$ | CH$_2$O(CH$_2$)$_2$SCH$_2$CF$_3$ | |
| 5-55 | SCH$_3$ | CH$_2$O(CH$_2$)$_2$SOCH$_3$ | |
| 5-56 | SCH$_3$ | CH$_2$O(CH$_2$)$_2$SOCH$_2$CF$_3$ | |
| 5-57 | SCH$_3$ | CH$_2$O(CH$_2$)$_2$SO$_2$CH$_3$ | |
| 5-58 | SCH$_3$ | CH$_2$O(CH$_2$)$_2$SO$_2$CH$_2$CF$_3$ | |
| 5-59 | SCH$_3$ | CH$_3$-O-CH$_2$-(tetrahydrofuran-2-yl) | |

TABLE 70-continued

| compound number | R4 | R1 | physical property (melting point-ND) |
|---|---|---|---|
| 5-60 | SCH$_3$ | 3-methoxytetrahydrofuran (CH$_3$O-tetrahydrofuran-3-yl) | |
| 5-61 | SCH$_3$ | CH$_2$O(CH$_2$)$_2$NHSO$_2$CH$_3$ | |
| 5-62 | SCH$_3$ | CH$_2$O(CH$_2$)$_2$N(CH$_3$)(SO$_2$CH$_3$) | |
| 5-63 | SCH$_2$CH$_3$ | CH$_3$ | |
| 5-64 | SCH$_2$CH$_3$ | CF$_3$ | |
| 5-65 | SCH$_2$CH$_3$ | CH$_2$OCH$_3$ | |
| 5-66 | SCH$_2$CH$_3$ | CH$_2$OCH$_2$CH$_3$ | |
| 5-67 | SCH$_2$CH$_3$ | CH$_3$O-CH$_2$-cyclopropyl | |
| 5-68 | SCH$_2$CH$_3$ | CH$_2$OCH$_2$CF$_3$ | |
| 5-69 | SCH$_2$CH$_3$ | CH$_2$SCH$_3$ | |
| 5-70 | SCH$_2$CH$_3$ | CH$_2$SCH$_2$CH$_3$ | |
| 5-71 | SCH$_2$CH$_3$ | CH$_3$S-CH$_2$-cyclopropyl | |
| 5-72 | SCH$_2$CH$_3$ | CH$_2$SCH$_2$CF$_3$ | |
| 5-73 | SCH$_2$CH$_3$ | CH$_2$SOCH$_3$ | |
| 5-74 | SCH$_2$CH$_3$ | CH$_2$SOCH$_2$CH$_3$ | |
| 5-75 | SCH$_2$CH$_3$ | CH$_3$S(O)-CH$_2$-cyclopropyl | |
| 5-76 | SCH$_2$CH$_3$ | CH$_2$SOCH$_2$CF$_3$ | |
| 5-77 | SCH$_2$CH$_3$ | CH$_2$SO$_2$CH$_3$ | |
| 5-78 | SCH$_2$CH$_3$ | CH$_2$SO$_2$CH$_2$CH$_3$ | |
| 5-79 | SCH$_2$CH$_3$ | CH$_3$SO$_2$-CH$_2$-cyclopropyl | |
| 5-80 | SCH$_2$CH$_3$ | CH$_2$SO$_2$CH$_2$CF$_3$ | |

TABLE 71

| compound number | R4 | R1 | physical property (melting point-ND) |
|---|---|---|---|
| 5-81 | SCH$_2$CH$_3$ | CH$_2$O(CH$_2$)$_2$OCH$_3$ | |
| 5-82 | SCH$_2$CH$_3$ | CH$_2$O(CH$_2$)$_2$OCH$_2$CH$_3$ | |
| 5-83 | SCH$_2$CH$_3$ | CH$_2$O(CH$_2$)$_2$OCH$_2$CF$_3$ | |
| 5-84 | SCH$_2$CH$_3$ | CH$_2$O(CH$_2$)$_2$SCH$_3$ | |
| 5-85 | SCH$_2$CH$_3$ | CH$_2$O(CH$_2$)$_2$SCH$_2$CF$_3$ | |
| 5-86 | SCH$_2$CH$_3$ | CH$_2$O(CH$_2$)$_2$SOCH$_3$ | |
| 5-87 | SCH$_2$CH$_3$ | CH$_2$O(CH$_2$)$_2$SOCH$_2$CF$_3$ | |
| 5-88 | SCH$_2$CH$_3$ | CH$_2$O(CH$_2$)$_2$SO$_2$CH$_3$ | |
| 5-89 | SCH$_2$CH$_3$ | CH$_2$O(CH$_2$)$_2$SO$_2$CH$_2$CF$_3$ | |
| 5-90 | SCH$_2$CH$_3$ | CH$_3$O-CH$_2$-tetrahydrofuran-2-yl | |

TABLE 71-continued

| compound number | R4 | R1 | physical property (melting point-ND) |
|---|---|---|---|
| 5-91 | SCH$_2$CH$_3$ | 3-methoxytetrahydrofuran (CH$_3$O-tetrahydrofuran-3-yl) | |
| 5-92 | SCH$_2$CH$_3$ | CH$_2$O(CH$_2$)$_2$NHSO$_2$CH$_3$ | |
| 5-93 | SCH$_2$CH$_3$ | CH$_2$O(CH$_2$)$_2$N(CH$_3$)(SO$_2$CH$_3$) | |
| 5-94 | S(CH$_2$)$_2$CH$_3$ | CH$_3$ | |
| 5-95 | S(CH$_2$)$_2$CH$_3$ | CF$_3$ | |
| 5-96 | S(CH$_2$)$_2$CH$_3$ | CH$_2$OCH$_3$ | |
| 5-97 | S(CH$_2$)$_2$CH$_3$ | CH$_2$OCH$_2$CH$_3$ | |
| 5-98 | S(CH$_2$)$_2$CH$_3$ | CH$_3$O-CH$_2$-cyclopropyl | |
| 5-99 | S(CH$_2$)$_2$CH$_3$ | CH$_2$OCH$_2$CF$_3$ | |
| 5-100 | S(CH$_2$)$_2$CH$_3$ | CH$_2$SCH$_3$ | |
| 5-101 | S(CH$_2$)$_2$CH$_3$ | CH$_2$SCH$_2$CH$_3$ | |
| 5-102 | S(CH$_2$)$_2$CH$_3$ | CH$_3$S-CH$_2$-cyclopropyl | |
| 5-103 | S(CH$_2$)$_2$CH$_3$ | CH$_2$SCH$_2$CF$_3$ | |
| 5-104 | S(CH$_2$)$_2$CH$_3$ | CH$_2$SOCH$_3$ | |
| 5-105 | S(CH$_2$)$_2$CH$_3$ | CH$_2$SOCH$_2$CH$_3$ | |
| 5-106 | S(CH$_2$)$_2$CH$_3$ | CH$_3$S(O)-CH$_2$-cyclopropyl | |
| 5-107 | S(CH$_2$)$_2$CH$_3$ | CH$_2$SOCH$_2$CF$_3$ | |
| 5-108 | S(CH$_2$)$_2$CH$_3$ | CH$_2$SO$_2$CH$_3$ | |
| 5-109 | S(CH$_2$)$_2$CH$_3$ | CH$_2$SO$_2$CH$_2$CH$_3$ | |
| 5-110 | S(CH$_2$)$_2$CH$_3$ | CH$_3$SO$_2$-CH$_2$-cyclopropyl | |
| 5-111 | S(CH$_2$)$_2$CH$_3$ | CH$_2$SO$_2$CH$_2$CF$_3$ | |
| 5-112 | S(CH$_2$)$_2$CH$_3$ | CH$_2$O(CH$_2$)$_2$OCH$_3$ | |
| 5-113 | S(CH$_2$)$_2$CH$_3$ | CH$_2$O(CH$_2$)$_2$OCH$_2$CH$_3$ | |
| 5-114 | S(CH$_2$)$_2$CH$_3$ | CH$_2$O(CH$_2$)$_2$OCH$_2$CF$_3$ | |
| 5-115 | S(CH$_2$)$_2$CH$_3$ | CH$_2$O(CH$_2$)$_2$SCH$_3$ | |
| 5-116 | S(CH$_2$)$_2$CH$_3$ | CH$_2$O(CH$_2$)$_2$SCH$_2$CF$_3$ | |
| 5-117 | S(CH$_2$)$_2$CH$_3$ | CH$_2$O(CH$_2$)$_2$SOCH$_3$ | |
| 5-118 | S(CH$_2$)$_2$CH$_3$ | CH$_2$O(CH$_2$)$_2$SOCH$_2$CF$_3$ | |
| 5-119 | S(CH$_2$)$_2$CH$_3$ | CH$_2$O(CH$_2$)$_2$SO$_2$CH$_3$ | |
| 5-120 | S(CH$_2$)$_2$CH$_3$ | CH$_2$O(CH$_2$)$_2$SO$_2$CH$_2$CF$_3$ | |

TABLE 72

| compound number | R4 | R1 | physical property (melting point-ND) |
|---|---|---|---|
| 5-121 | S(CH$_2$)$_2$CH$_3$ | CH$_3$O-CH$_2$-tetrahydrofuran-2-yl | |

TABLE 72-continued

| compound number | R4 | R1 | physical property (melting point-ND) |
|---|---|---|---|
| 5-122 | S(CH₂)₂CH₃ | CH₃-O-[tetrahydrofuran-3-yl] | |
| 5-123 | S(CH₂)₂CH₃ | CH₂O(CH₂)₂NHSO₂CH₃ | |
| 5-124 | S(CH₂)₂CH₃ | CH₂O(CH₂)₂N(CH₃)(SO₂CH₃) | |
| 5-125 | SC₆H₅ | CH₃ | |
| 5-126 | SC₆H₅ | CF₃ | |
| 5-127 | SC₆H₅ | CH₂OCH₃ | |
| 5-128 | SC₆H₅ | CH₂OCH₂CH₃ | |
| 5-129 | SC₆H₅ | CH₃-O-CH₂-cyclopropyl | |
| 5-130 | SC₆H₅ | CH₂OCH₂CF₃ | |
| 5-131 | SC₆H₅ | CH₂SCH₃ | |
| 5-132 | SC₆H₅ | CH₂SCH₂CH₃ | |
| 5-133 | SC₆H₅ | CH₃-S-CH₂-cyclopropyl | |
| 5-134 | SC₆H₅ | CH₂SCH₂CF₃ | |
| 5-135 | SC₆H₅ | CH₂SOCH₃ | |
| 5-136 | SC₆H₅ | CH₂SOCH₂CH₃ | |
| 5-137 | SC₆H₅ | CH₃-S(=O)-CH₂-cyclopropyl | |
| 5-138 | SC₆H₅ | CH₂SOCH₂CF₃ | |
| 5-139 | SC₆H₅ | CH₂SO₂CH₃ | |
| 5-140 | SC₆H₅ | CH₂SO₂CH₂CH₃ | |
| 5-141 | SC₆H₅ | CH₃-S(=O)₂-CH₂-cyclopropyl | |
| 5-142 | SC₆H₅ | CH₂SO₂CH₂CF₃ | |
| 5-143 | SC₆H₅ | CH₂O(CH₂)₂OCH₃ | |
| 5-144 | SC₆H₅ | CH₂O(CH₂)₂OCH₂CH₃ | |
| 5-145 | SC₆H₅ | CH₂O(CH₂)₂OCH₂CF₃ | |
| 5-146 | SC₆H₅ | CH₂O(CH₂)₂SCH₃ | |
| 5-147 | SC₆H₅ | CH₂O(CH₂)₂SCH₂CF₃ | |
| 5-148 | SC₆H₅ | CH₂O(CH₂)₂SOCH₃ | |
| 5-149 | SC₆H₅ | CH₂O(CH₂)₂SOCH₂CF₃ | |
| 5-150 | SC₆H₅ | CH₂O(CH₂)₂SO₂CH₃ | |
| 5-151 | SC₆H₅ | CH₂O(CH₂)₂SO₂CH₂CF₃ | |
| 5-152 | SC₆H₅ | CH₃-O-CH₂-[tetrahydrofuran-2-yl] | |
| 5-153 | SC₆H₅ | CH₃-O-[tetrahydrofuran-3-yl] | |
| 5-154 | SC₆H₅ | CH₂O(CH₂)₂NHSO₂CH₃ | |
| 5-155 | SC₆H₅ | CH₂O(CH₂)₂N(CH₃)(SO₂CH₃) | |
| 5-156 | SCH₂C₆H₅ | CH₃ | |
| 5-157 | SCH₂C₆H₅ | CF₃ | |
| 5-158 | SCH₂C₆H₅ | CH₂OCH₃ | |
| 5-159 | SCH₂C₆H₅ | CH₂OCH₂CH₃ | |
| 5-160 | SCH₂C₆H₅ | CH₃-O-CH₂-cyclopropyl | |

TABLE 73

| compound number | R4 | R1 | physical property (melting point-ND) |
|---|---|---|---|
| 5-161 | SCH₂C₆H₅ | CH₂OCH₂CF₃ | |
| 5-162 | SCH₂C₆H₅ | CH₂SCH₃ | |
| 5-163 | SCH₂C₆H₅ | CH₂SCH₂CH₃ | |
| 5-164 | SCH₂C₆H₅ | CH₃-S-CH₂-cyclopropyl | |
| 5-165 | SCH₂C₆H₅ | CH₂SCH₂CF₃ | |
| 5-166 | SCH₂C₆H₅ | CH₂SOCH₃ | |
| 5-167 | SCH₂C₆H₅ | CH₂SOCH₂CH₃ | |
| 5-168 | SCH₂C₆H₅ | CH₃-S(=O)-CH₂-cyclopropyl | |
| 5-169 | SCH₂C₆H₅ | CH₂SOCH₂CF₃ | |
| 5-170 | SCH₂C₆H₅ | CH₂SO₂CH₃ | |
| 5-171 | SCH₂C₆H₅ | CH₂SO₂CH₂CH₃ | |
| 5-172 | SCH₂C₆H₅ | CH₃-S(=O)₂-CH₂-cyclopropyl | |
| 5-173 | SCH₂C₆H₅ | CH₂SO₂CH₂CF₃ | |
| 5-174 | SCH₂C₆H₅ | CH₂O(CH₂)₂OCH₃ | |
| 5-175 | SCH₂C₆H₅ | CH₂O(CH₂)₂OCH₂CH₃ | |
| 5-176 | SCH₂C₆H₅ | CH₂O(CH₂)₂OCH₂CF₃ | |
| 5-177 | SCH₂C₆H₅ | CH₂O(CH₂)₂SCH₃ | |
| 5-178 | SCH₂C₆H₅ | CH₂O(CH₂)₂SCH₂CF₃ | |
| 5-179 | SCH₂C₆H₅ | CH₂O(CH₂)₂SOCH₃ | |
| 5-180 | SCH₂C₆H₅ | CH₂O(CH₂)₂SOCH₂CF₃ | |
| 5-181 | SCH₂C₆H₅ | CH₂O(CH₂)₂SO₂CH₃ | |
| 5-182 | SCH₂C₆H₅ | CH₂O(CH₂)₂SO₂CH₂CF₃ | |
| 5-183 | SCH₂C₆H₅ | CH₃-O-CH₂-[tetrahydrofuran-2-yl] | |
| 5-184 | SCH₂C₆H₅ | CH₃-O-[tetrahydrofuran-3-yl] | |
| 5-185 | SCH₂C₆H₅ | CH₂O(CH₂)₂NHSO₂CH₃ | |
| 5-186 | SCH₂C₆H₅ | CH₂O(CH₂)₂N(CH₃)(SO₂CH₃) | |
| 5-187 | 1H-pyrazole-1-yl | CH₃ | |
| 5-188 | 1H-pyrazole-1-yl | CF₃ | |
| 5-189 | 1H-pyrazole-1-yl | CH₂OCH₃ | |
| 5-190 | 1H-pyrazole-1-yl | CH₂OCH₂CH₃ | |

TABLE 73-continued

| compound number | R4 | R1 | physical property (melting point-ND) |
|---|---|---|---|
| 5-191 | 1H-pyrazole-1-yl | CH₃-O-CH(cyclopropyl) | |
| 5-192 | 1H-pyrazole-1-yl | CH$_2$OCH$_2$CF$_3$ | |
| 5-193 | 1H-pyrazole-1-yl | CH$_2$SCH$_3$ | |
| 5-194 | 1H-pyrazole-1-yl | CH$_2$SCH$_2$CH$_3$ | |
| 5-195 | 1H-pyrazole-1-yl | CH₃-S-CH(cyclopropyl) | |
| 5-196 | 1H-pyrazole-1-yl | CH$_2$SCH$_2$CF$_3$ | |
| 5-197 | 1H-pyrazole-1-yl | CH$_2$SOCH$_3$ | |
| 5-198 | 1H-pyrazole-1-yl | CH$_2$SOCH$_2$CH$_3$ | |
| 5-199 | 1H-pyrazole-1-yl | CH₃-S(=O)-CH(cyclopropyl) | |
| 5-200 | 1H-pyrazole-1-yl | CH$_2$SOCH$_2$CF$_3$ | |

TABLE 74

| compound number | R4 | R1 | physical property (melting point-ND) |
|---|---|---|---|
| 5-201 | 1H-pyrazole-1-yl | CH$_2$SO$_2$CH$_3$ | |
| 5-202 | 1H-pyrazole-1-yl | CH$_2$SO$_2$CH$_2$CH$_3$ | |
| 5-203 | 1H-pyrazole-1-yl | CH₃-S(=O)$_2$-CH(cyclopropyl) | |
| 5-204 | 1H-pyrazole-1-yl | CH$_2$SO$_2$CH$_2$CF$_3$ | |
| 5-205 | 1H-pyrazole-1-yl | CH$_2$O(CH$_2$)$_2$OCH$_3$ | |
| 5-206 | 1H-pyrazole-1-yl | CH$_2$O(CH$_2$)$_2$OCH$_2$CH$_3$ | |
| 5-207 | 1H-pyrazole-1-yl | CH$_2$O(CH$_2$)$_2$OCH$_2$CF$_3$ | |
| 5-208 | 1H-pyrazole-1-yl | CH$_2$O(CH$_2$)$_2$SCH$_3$ | |
| 5-209 | 1H-pyrazole-1-yl | CH$_2$O(CH$_2$)$_2$SCH$_2$CF$_3$ | |
| 5-210 | 1H-pyrazole-1-yl | CH$_2$O(CH$_2$)$_2$SOCH$_3$ | |
| 5-211 | 1H-pyrazole-1-yl | CH$_2$O(CH$_2$)$_2$SOCH$_2$CF$_3$ | |
| 5-212 | 1H-pyrazole-1-yl | CH$_2$O(CH$_2$)$_2$SO$_2$CH$_3$ | |
| 5-213 | 1H-pyrazole-1-yl | CH$_2$O(CH$_2$)$_2$SO$_2$CH$_2$CF$_3$ | |
| 5-214 | 1H-pyrazole-1-yl | CH₃-O-CH(tetrahydrofuran-2-yl)-CH₂ | |
| 5-215 | 1H-pyrazole-1-yl | CH₃-O-(tetrahydrofuran-3-yl) | |
| 5-216 | 1H-pyrazole-1-yl | CH$_2$O(CH$_2$)$_2$NHSO$_2$CH$_3$ | |
| 5-217 | 1H-pyrazole-1-yl | CH$_2$O(CH$_2$)$_2$N(CH$_3$)(SO$_2$CH$_3$) | |
| 5-218 | 1H-imidazole-1-yl | CH$_3$ | |
| 5-219 | 1H-imidazole-1-yl | CF$_3$ | |
| 5-220 | 1H-imidazole-1-yl | CH$_2$OCH$_3$ | |
| 5-221 | 1H-imidazole-1-yl | CH$_2$OCH$_2$CH$_3$ | |

TABLE 74-continued

| compound number | R4 | R1 | physical property (melting point-ND) |
|---|---|---|---|
| 5-222 | 1H-imidazole-1-yl | CH₃-O-CH(cyclopropyl) | |
| 5-223 | 1H-imidazole-1-yl | CH$_2$OCH$_2$CF$_3$ | |
| 5-224 | 1H-imidazole-1-yl | CH$_2$SCH$_3$ | |
| 5-225 | 1H-imidazole-1-yl | CH$_2$SCH$_2$CH$_3$ | |
| 5-226 | 1H-imidazole-1-yl | CH₃-S-CH(cyclopropyl) | |
| 5-227 | 1H-imidazole-1-yl | CH$_2$SCH$_2$CF$_3$ | |
| 5-228 | 1H-imidazole-1-yl | CH$_2$SOCH$_3$ | |
| 5-229 | 1H-imidazole-1-yl | CH$_2$SOCH$_2$CH$_3$ | |
| 5-230 | 1H-imidazole-1-yl | CH₃-S(=O)-CH(cyclopropyl) | |
| 5-231 | 1H-imidazole-1-yl | CH$_2$SOCH$_2$CF$_3$ | |
| 5-232 | 1H-imidazole-1-yl | CH$_2$SO$_2$CH$_3$ | |
| 5-233 | 1H-imidazole-1-yl | CH$_2$SO$_2$CH$_2$CH$_3$ | |
| 5-234 | 1H-imidazole-1-yl | CH₃-S(=O)$_2$-CH(cyclopropyl) | |
| 5-235 | 1H-imidazole-1-yl | CH$_2$SO$_2$CH$_2$CF$_3$ | |
| 5-236 | 1H-imidazole-1-yl | CH$_2$O(CH$_2$)$_2$OCH$_3$ | |
| 5-237 | 1H-imidazole-1-yl | CH$_2$O(CH$_2$)$_2$OCH$_2$CH$_3$ | |
| 5-238 | 1H-imidazole-1-yl | CH$_2$O(CH$_2$)$_2$OCH$_2$CF$_3$ | |
| 5-239 | 1H-imidazole-1-yl | CH$_2$O(CH$_2$)$_2$SCH$_3$ | |
| 5-240 | 1H-imidazole-1-yl | CH$_2$O(CH$_2$)$_2$SCH$_2$CF$_3$ | |

TABLE 75

| compound number | R4 | R1 | physical property (melting point-ND) |
|---|---|---|---|
| 5-241 | 1H-imidazole-1-yl | CH$_2$O(CH$_2$)$_2$SOCH$_3$ | |
| 5-242 | 1H-imidazole-1-yl | CH$_2$O(CH$_2$)$_2$SOCH$_2$CF$_3$ | |
| 5-243 | 1H-imidazole-1-yl | CH$_2$O(CH$_2$)$_2$SO$_2$CH$_3$ | |
| 5-244 | 1H-imidazole-1-yl | CH$_2$O(CH$_2$)$_2$SO$_2$CH$_2$CF$_3$ | |
| 5-245 | 1H-imidazole-1-yl | CH₃-O-CH(tetrahydrofuran-2-yl)-CH₂ | |
| 5-246 | 1H-imidazole-1-yl | CH₃-O-(tetrahydrofuran-3-yl) | |
| 5-247 | 1H-imidazole-1-yl | CH$_2$O(CH$_2$)$_2$NHSO$_2$CH$_3$ | |
| 5-248 | 1H-imidazole-1-yl | CH$_2$O(CH$_2$)$_2$N(CH$_3$)(SO$_2$CH$_3$) | |
| 5-249 | 1H-triazole-1-yl | CH$_3$ | |
| 5-250 | 1H-triazole-1-yl | CF$_3$ | |
| 5-251 | 1H-triazole-1-yl | CH$_2$OCH$_3$ | |
| 5-252 | 1H-triazole-1-yl | CH$_2$OCH$_2$CH$_3$ | |

TABLE 75-continued

| compound number | R4 | R1 | physical property (melting point-ND) |
|---|---|---|---|
| 5-253 | 1H-triazole-1-yl | 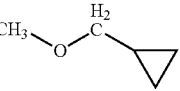 | |
| 5-254 | 1H-triazole-1-yl | CH₂OCH₂CF₃ | |
| 5-255 | 1H-triazole-1-yl | CH₂SCH₃ | |
| 5-256 | 1H-triazole-1-yl | CH₂SCH₂CH₃ | |
| 5-257 | 1H-triazole-1-yl | 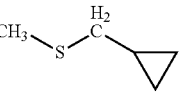 | |
| 5-258 | 1H-triazole-1-yl | CH₂SCH₂CF₃ | |
| 5-259 | 1H-triazole-1-yl | CH₂SOCH₃ | |
| 5-260 | 1H-triazole-1-yl | CH₂SOCH₂CH₃ | |
| 5-261 | 1H-triazole-1-yl | 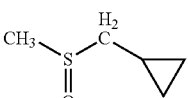 | |
| 5-262 | 1H-triazole-1-yl | CH₂SOCH₂CF₃ | |
| 5-263 | 1H-triazole-1-yl | CH₂SO₂CH₃ | |
| 5-264 | 1H-triazole-1-yl | CH₂SO₂CH₂CH₃ | |
| 5-265 | 1H-triazole-1-yl | 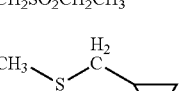 | |
| 5-266 | 1H-triazole-1-yl | CH₂SO₂CH₂CF₃ | |
| 5-267 | 1H-triazole-1-yl | CH₂O(CH₂)₂OCH₃ | |
| 5-268 | 1H-triazole-1-yl | CH₂O(CH₂)₂OCH₂CH₃ | |
| 5-269 | 1H-triazole-1-yl | CH₂O(CH₂)₂OCH₂CF₃ | |
| 5-270 | 1H-triazole-1-yl | CH₂O(CH₂)₂SCH₃ | |
| 5-271 | 1H-triazole-1-yl | CH₂O(CH₂)₂SCH₂CF₃ | |
| 5-272 | 1H-triazole-1-yl | CH₂O(CH₂)₂SOCH₃ | |
| 5-273 | 1H-triazole-1-yl | CH₂O(CH₂)₂SOCH₂CF₃ | |
| 5-274 | 1H-triazole-1-yl | CH₂O(CH₂)₂SO₂CH₃ | |
| 5-275 | 1H-triazole-1-yl | CH₂O(CH₂)₂SO₂CH₂CF₃ | |
| 5-276 | 1H-triazole-1-yl | 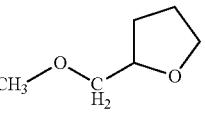 | |
| 5-277 | 1H-triazole-1-yl | 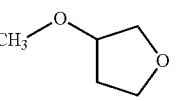 | |
| 5-278 | 1H-triazole-1-yl | CH₂O(CH₂)₂NHSO₂CH₃ | |
| 5-279 | 1H-triazole-1-yl | CH₂O(CH₂)₂N(CH₃)(SO₂CH₃) | |
| 5-280 | 1H-tetrazole-1-yl | CH₃ | |
| 5-281 | 1H-tetrazole-1-yl | CF₃ | |
| 5-282 | 1H-tetrazole-1-yl | CH₂OCH₃ | |
| 5-283 | 1H-tetrazole-1-yl | CH₂OCH₂CH₃ | |
| 5-284 | 1H-tetrazole-1-yl | 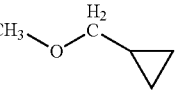 | |
| 5-285 | 1H-tetrazole-1-yl | CH₂OCH₂CF₃ | |
| 5-286 | 1H-tetrazole-1-yl | CH₂SCH₃ | |
| 5-287 | 1H-tetrazole-1-yl | CH₂SCH₂CH₃ | |
| 5-288 | 1H-tetrazole-1-yl | 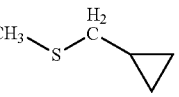 | |
| 5-289 | 1H-tetrazole-1-yl | CH₂SCH₂CF₃ | |
| 5-290 | 1H-tetrazole-1-yl | CH₂SOCH₃ | |
| 5-291 | 1H-tetrazole-1-yl | CH₂SOCH₂CH₃ | |
| 5-292 | 1H-tetrazole-1-yl | 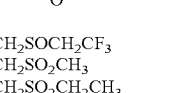 | |
| 5-293 | 1H-tetrazole-1-yl | CH₂SOCH₂CF₃ | |
| 5-294 | 1H-tetrazole-1-yl | CH₂SO₂CH₃ | |
| 5-295 | 1H-tetrazole-1-yl | CH₂SO₂CH₂CH₃ | |
| 5-296 | 1H-tetrazole-1-yl | 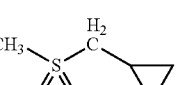 | |
| 5-297 | 1H-tetrazole-1-yl | CH₂SO₂CH₂CF₃ | |
| 5-298 | 1H-tetrazole-1-yl | CH₂O(CH₂)₂OCH₃ | |
| 5-299 | 1H-tetrazole-1-yl | CH₂O(CH₂)₂OCH₂CH₃ | |
| 5-300 | 1H-tetrazole-1-yl | CH₂O(CH₂)₂OCH₂CF₃ | |
| 5-301 | 1H-tetrazole-1-yl | CH₂O(CH₂)₂SCH₃ | |
| 5-302 | 1H-tetrazole-1-yl | CH₂O(CH₂)₂SCH₂CF₃ | |
| 5-303 | 1H-tetrazole-1-yl | CH₂O(CH₂)₂SOCH₃ | |
| 5-304 | 1H-tetrazole-1-yl | CH₂O(CH₂)₂SOCH₂CF₃ | |
| 5-305 | 1H-tetrazole-1-yl | CH₂O(CH₂)₂SO₂CH₃ | |
| 5-306 | 1H-tetrazole-1-yl | CH₂O(CH₂)₂SO₂CH₂CF₃ | |
| 5-307 | 1H-tetrazole-1-yl | 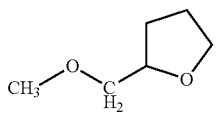 | |
| 5-308 | 1H-tetrazole-1-yl | 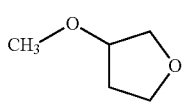 | |
| 5-309 | 1H-tetrazole-1-yl | CH₂O(CH₂)₂NHSO₂CH₃ | |
| 5-310 | 1H-tetrazole-1-yl | CH₂O(CH₂)₂N(CH₃)(SO₂CH₃) | |
| 5-311 | 1H-tetrazole-2-yl | CH₃ | |
| 5-312 | 1H-tetrazole-2-yl | CF₃ | |
| 5-313 | 1H-tetrazole-2-yl | CH₂OCH₃ | |
| 5-314 | 1H-tetrazole-2-yl | CH₂OCH₂CH₃ | |
| 5-315 | 1H-tetrazole-2-yl | 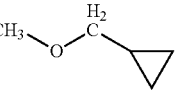 | |
| 5-316 | 1H-tetrazole-2-yl | CH₂OCH₂CF₃ | |
| 5-317 | 1H-tetrazole-2-yl | CH₂SCH₃ | |
| 5-318 | 1H-tetrazole-2-yl | CH₂SCH₂CH₃ | |

-continued

| compound number | R4 | R1 | physical property (melting point-ND) |
|---|---|---|---|
| 5-319 | 1H-tetrazole-2-yl | CH₃-S-CH₂-cyclopropyl | |
| 5-320 | 1H-tetrazole-2-yl | CH₂SCH₂CF₃ | |

TABLE 77

| compound number | R4 | R1 | physical property (melting point-ND) |
|---|---|---|---|
| 5-321 | 1H-tetrazole-2-yl | CH₂SOCH₃ | |
| 5-322 | 1H-tetrazole-2-yl | CH₂SOCH₂CH₃ | |
| 5-323 | 1H-tetrazole-2-yl | CH₃-S(O)-CH₂-cyclopropyl | |
| 5-324 | 1H-tetrazole-2-yl | CH₂SOCH₂CF₃ | |
| 5-325 | 1H-tetrazole-2-yl | CH₂SO₂CH₃ | |
| 5-326 | 1H-tetrazole-2-yl | CH₂SO₂CH₂CH₃ | |
| 5-327 | 1H-tetrazole-2-yl | CH₃-S(O)₂-CH₂-cyclopropyl | |
| 5-328 | 1H-tetrazole-2-yl | CH₂SO₂CH₂CF₃ | |
| 5-329 | 1H-tetrazole-2-yl | CH₂O(CH₂)₂OCH₃ | |
| 5-330 | 1H-tetrazole-2-yl | CH₂O(CH₂)₂OCH₂CH₃ | |
| 5-331 | 1H-tetrazole-2-yl | CH₂O(CH₂)₂OCH₂CF₃ | |
| 5-332 | 1H-tetrazole-2-yl | CH₂O(CH₂)₂SCH₃ | |
| 5-333 | 1H-tetrazole-2-yl | CH₂O(CH₂)₂SCH₂CF₃ | |
| 5-334 | 1H-tetrazole-2-yl | CH₂O(CH₂)₂SOCH₃ | |
| 5-335 | 1H-tetrazole-2-yl | CH₂O(CH₂)₂SOCH₂CF₃ | |
| 5-336 | 1H-tetrazole-2-yl | CH₂O(CH₂)₂SO₂CH₃ | |
| 5-337 | 1H-tetrazole-2-yl | CH₂O(CH₂)₂SO₂CH₂CF₃ | |
| 5-338 | 1H-tetrazole-2-yl | CH₃-O-CH₂-(tetrahydrofuran-2-yl) | |
| 5-339 | 1H-tetrazole-2-yl | CH₃-O-(tetrahydrofuran-3-yl) | |
| 5-340 | 1H-tetrazole-2-yl | CH₂O(CH₂)₂NHSO₂CH₃ | |
| 5-341 | 1H-tetrazole-2-yl | CH₂O(CH₂)₂N(CH₃)(SO₂CH₃) | |

TABLE 78

[Structure: cyclohexanone with R4 substituent and methyl group, linked via C=O to pyridine ring bearing R1 and 1,2,4-triazol-1-yl]

| compound number | R4 | R1 | physical property (melting point-ND) |
|---|---|---|---|
| 6-1 | Cl | CH₃ | |
| 6-2 | Cl | CF₃ | |
| 6-3 | Cl | CH₂OCH₃ | |
| 6-4 | Cl | CH₂OCH₂CH₃ | |
| 6-5 | Cl | CH₃-O-CH₂-cyclopropyl | |
| 6-6 | Cl | CH₂OCH₂CF₃ | |
| 6-7 | Cl | CH₂SCH₃ | |
| 6-8 | Cl | CH₂SCH₂CH₃ | |
| 6-9 | Cl | CH₃-S-CH₂-cyclopropyl | |
| 6-10 | Cl | CH₂SCH₂CF₃ | |
| 6-11 | Cl | CH₂SOCH₃ | |
| 6-12 | Cl | CH₂SOCH₂CH₃ | |
| 6-13 | Cl | CH₃-S(O)-CH₂-cyclopropyl | |
| 6-14 | Cl | CH₂SOCH₂CF₃ | |
| 6-15 | Cl | CH₂SO₂CH₃ | |
| 6-16 | Cl | CH₂SO₂CH₂CH₃ | |
| 6-17 | Cl | CH₃-S(O)₂-CH₂-cyclopropyl | |
| 6-18 | Cl | CH₂SO₂CH₂CF₃ | |
| 6-19 | Cl | CH₂O(CH₂)₂OCH₃ | |
| 6-20 | Cl | CH₂O(CH₂)₂OCH₂CH₃ | |
| 6-21 | Cl | CH₂O(CH₂)₂OCH₂CF₃ | |
| 6-22 | Cl | CH₂O(CH₂)₂SCH₃ | |
| 6-23 | Cl | CH₂O(CH₂)₂SCH₂CF₃ | |
| 6-24 | Cl | CH₂O(CH₂)₂SOCH₃ | |
| 6-25 | Cl | CH₂O(CH₂)₂SOCH₂CF₃ | |
| 6-26 | Cl | CH₂O(CH₂)₂SO₂CH₃ | |
| 6-27 | Cl | CH₂O(CH₂)₂SO₂CH₂CF₃ | |
| 6-28 | Cl | CH₃-O-CH₂-(tetrahydrofuran-2-yl) | |
| 6-29 | Cl | CH₃-O-(tetrahydrofuran-3-yl) | |
| 6-30 | Cl | CH₂O(CH₂)₂NHSO₂CH₃ | |
| 6-31 | Cl | CH₂O(CH₂)₂N(CH₃)(SO₂CH₃) | |
| 6-32 | SCH₃ | CH₃ | |

TABLE 78-continued

Structure: cyclohexanedione with R4 substituent and methyl group, connected via C=O to a pyridine ring bearing R1 and a 1,2,4-triazol-1-yl group.

| compound number | R4 | R1 | physical property (melting point-ND) |
|---|---|---|---|
| 6-33 | SCH$_3$ | CF$_3$ | |
| 6-34 | SCH$_3$ | CH$_2$OCH$_3$ | |
| 6-35 | SCH$_3$ | CH$_2$OCH$_2$CH$_3$ | |
| 6-36 | SCH$_3$ | CH$_3$—O—CH$_2$—cyclopropyl | |
| 6-37 | SCH$_3$ | CH$_2$OCH$_2$CF$_3$ | |
| 6-38 | SCH$_3$ | CH$_2$SCH$_3$ | |
| 6-39 | SCH$_3$ | CH$_2$SCH$_2$CH$_3$ | |
| 6-40 | SCH$_3$ | CH$_3$—S—CH$_2$—cyclopropyl | |

TABLE 79

| compound number | R4 | R1 | physical property (melting point-ND) |
|---|---|---|---|
| 6-41 | SCH$_3$ | CH$_2$SCH$_2$CF$_3$ | |
| 6-42 | SCH$_3$ | CH$_2$SOCH$_3$ | |
| 6-43 | SCH$_3$ | CH$_2$SOCH$_2$CH$_3$ | |
| 6-44 | SCH$_3$ | CH$_3$—S(=O)—CH$_2$—cyclopropyl | |
| 6-45 | SCH$_3$ | CH$_2$SOCH$_2$CF$_3$ | |
| 6-46 | SCH$_3$ | CH$_2$SO$_2$CH$_3$ | |
| 6-47 | SCH$_3$ | CH$_2$SO$_2$CH$_2$CH$_3$ | |
| 6-48 | SCH$_3$ | CH$_3$—S(=O)$_2$—CH$_2$—cyclopropyl | |
| 6-49 | SCH$_3$ | CH$_2$SO$_2$CH$_2$CF$_3$ | |
| 6-50 | SCH$_3$ | CH$_2$O(CH$_2$)$_2$OCH$_3$ | |
| 6-51 | SCH$_3$ | CH$_2$O(CH$_2$)$_2$OCH$_2$CH$_3$ | |
| 6-52 | SCH$_3$ | CH$_2$O(CH$_2$)$_2$OCH$_2$CF$_3$ | |
| 6-53 | SCH$_3$ | CH$_2$O(CH$_2$)$_2$SCH$_3$ | |
| 6-54 | SCH$_3$ | CH$_2$O(CH$_2$)$_2$SCH$_2$CF$_3$ | |
| 6-55 | SCH$_3$ | CH$_2$O(CH$_2$)$_2$SOCH$_3$ | |
| 6-56 | SCH$_3$ | CH$_2$O(CH$_2$)$_2$SOCH$_2$CF$_3$ | |
| 6-57 | SCH$_3$ | CH$_2$O(CH$_2$)$_2$SO$_2$CH$_3$ | |
| 6-58 | SCH$_3$ | CH$_2$O(CH$_2$)$_2$SO$_2$CH$_2$CF$_3$ | |
| 6-59 | SCH$_3$ | CH$_3$—O—CH$_2$—(tetrahydrofuran-2-yl) | |

TABLE 79-continued

| compound number | R4 | R1 | physical property (melting point-ND) |
|---|---|---|---|
| 6-60 | SCH$_3$ | CH$_3$—O—(tetrahydrofuran-3-yl) | |
| 6-61 | SCH$_3$ | CH$_2$O(CH$_2$)$_2$NHSO$_2$CH$_3$ | |
| 6-62 | SCH$_3$ | CH$_2$O(CH$_2$)$_2$N(CH$_3$)(SO$_2$CH$_3$) | |
| 6-63 | SCH$_2$CH$_3$ | CH$_3$ | |
| 6-64 | SCH$_2$CH$_3$ | CF$_3$ | |
| 6-65 | SCH$_2$CH$_3$ | CH$_2$OCH$_3$ | |
| 6-66 | SCH$_2$CH$_3$ | CH$_2$OCH$_2$CH$_3$ | |
| 6-67 | SCH$_2$CH$_3$ | CH$_3$—O—CH$_2$—cyclopropyl | |
| 6-68 | SCH$_2$CH$_3$ | CH$_2$OCH$_2$CF$_3$ | |
| 6-69 | SCH$_2$CH$_3$ | CH$_2$SCH$_3$ | |
| 6-70 | SCH$_2$CH$_3$ | CH$_2$SCH$_2$CH$_3$ | |
| 6-71 | SCH$_2$CH$_3$ | CH$_3$—S—CH$_2$—cyclopropyl | |
| 6-72 | SCH$_2$CH$_3$ | CH$_2$SCH$_2$CF$_3$ | |
| 6-73 | SCH$_2$CH$_3$ | CH$_2$SOCH$_3$ | |
| 6-74 | SCH$_2$CH$_3$ | CH$_2$SOCH$_2$CH$_3$ | |
| 6-75 | SCH$_2$CH$_3$ | CH$_3$—S(=O)—CH$_2$—cyclopropyl | |
| 6-76 | SCH$_2$CH$_3$ | CH$_2$SOCH$_2$CF$_3$ | |
| 6-77 | SCH$_2$CH$_3$ | CH$_2$SO$_2$CH$_3$ | |
| 6-78 | SCH$_2$CH$_3$ | CH$_2$SO$_2$CH$_2$CH$_3$ | |
| 6-79 | SCH$_2$CH$_3$ | CH$_3$—S(=O)$_2$—CH$_2$—cyclopropyl | |
| 6-80 | SCH$_2$CH$_3$ | CH$_2$SO$_2$CH$_2$CF$_3$ | |

TABLE 80

| compound number | R4 | R1 | physical property (melting point-ND) |
|---|---|---|---|
| 6-81 | SCH$_2$CH$_3$ | CH$_2$O(CH$_2$)$_2$OCH$_3$ | |
| 6-82 | SCH$_2$CH$_3$ | CH$_2$O(CH$_2$)$_2$OCH$_2$CH$_3$ | |
| 6-83 | SCH$_2$CH$_3$ | CH$_2$O(CH$_2$)$_2$OCH$_2$CF$_3$ | |
| 6-84 | SCH$_2$CH$_3$ | CH$_2$O(CH$_2$)$_2$SCH$_3$ | |
| 6-85 | SCH$_2$CH$_3$ | CH$_2$O(CH$_2$)$_2$SCH$_2$CF$_3$ | |
| 6-86 | SCH$_2$CH$_3$ | CH$_2$O(CH$_2$)$_2$SOCH$_3$ | |
| 6-87 | SCH$_2$CH$_3$ | CH$_2$O(CH$_2$)$_2$SOCH$_2$CF$_3$ | |
| 6-88 | SCH$_2$CH$_3$ | CH$_2$O(CH$_2$)$_2$SO$_2$CH$_3$ | |
| 6-89 | SCH$_2$CH$_3$ | CH$_2$O(CH$_2$)$_2$SO$_2$CH$_2$CF$_3$ | |
| 6-90 | SCH$_2$CH$_3$ | CH$_3$—O—CH$_2$—(tetrahydrofuran-2-yl) | |

TABLE 80-continued

| compound number | R4 | R1 | physical property (melting point-ND) |
|---|---|---|---|
| 6-91 | SCH$_2$CH$_3$ | 3-methoxytetrahydrofuran | |
| 6-92 | SCH$_2$CH$_3$ | CH$_2$O(CH$_2$)$_2$NHSO$_2$CH$_3$ | |
| 6-93 | SCH$_2$CH$_3$ | CH$_2$O(CH$_2$)$_2$N(CH$_3$)(SO$_2$CH$_3$) | |
| 6-94 | S(CH$_2$)$_2$CH$_3$ | CH$_3$ | |
| 6-95 | S(CH$_2$)$_2$CH$_3$ | CF$_3$ | |
| 6-96 | S(CH$_2$)$_2$CH$_3$ | CH$_2$OCH$_3$ | |
| 6-97 | S(CH$_2$)$_2$CH$_3$ | CH$_2$OCH$_2$CH$_3$ | |
| 6-98 | S(CH$_2$)$_2$CH$_3$ | CH$_3$-O-CH$_2$-cyclopropyl | |
| 6-99 | S(CH$_2$)$_2$CH$_3$ | CH$_2$OCH$_2$CF$_3$ | |
| 6-100 | S(CH$_2$)$_2$CH$_3$ | CH$_2$SCH$_3$ | |
| 6-101 | S(CH$_2$)$_2$CH$_3$ | CH$_2$SCH$_2$CH$_3$ | |
| 6-102 | S(CH$_2$)$_2$CH$_3$ | CH$_3$-S-CH$_2$-cyclopropyl | |
| 6-103 | S(CH$_2$)$_2$CH$_3$ | CH$_2$SCH$_2$CF$_3$ | |
| 6-104 | S(CH$_2$)$_2$CH$_3$ | CH$_2$SOCH$_3$ | |
| 6-105 | S(CH$_2$)$_2$CH$_3$ | CH$_2$SOCH$_2$CH$_3$ | |
| 6-106 | S(CH$_2$)$_2$CH$_3$ | CH$_3$-S(O)-CH$_2$-cyclopropyl | |
| 6-107 | S(CH$_2$)$_2$CH$_3$ | CH$_2$SOCH$_2$CF$_3$ | |
| 6-108 | S(CH$_2$)$_2$CH$_3$ | CH$_2$SO$_2$CH$_3$ | |
| 6-109 | S(CH$_2$)$_2$CH$_3$ | CH$_2$SO$_2$CH$_2$CH$_3$ | |
| 6-110 | S(CH$_2$)$_2$CH$_3$ | CH$_3$-SO$_2$-CH$_2$-cyclopropyl | |
| 6-111 | S(CH$_2$)$_2$CH$_3$ | CH$_2$SO$_2$CH$_2$CF$_3$ | |
| 6-112 | S(CH$_2$)$_2$CH$_3$ | CH$_2$O(CH$_2$)$_2$OCH$_3$ | |
| 6-113 | S(CH$_2$)$_2$CH$_3$ | CH$_2$O(CH$_2$)$_2$OCH$_2$CH$_3$ | |
| 6-114 | S(CH$_2$)$_2$CH$_3$ | CH$_2$O(CH$_2$)$_2$OCH$_2$CF$_3$ | |
| 6-115 | S(CH$_2$)$_2$CH$_3$ | CH$_2$O(CH$_2$)$_2$SCH$_3$ | |
| 6-116 | S(CH$_2$)$_2$CH$_3$ | CH$_2$O(CH$_2$)$_2$SCH$_2$CF$_3$ | |
| 6-117 | S(CH$_2$)$_2$CH$_3$ | CH$_2$O(CH$_2$)$_2$SOCH$_3$ | |
| 6-118 | S(CH$_2$)$_2$CH$_3$ | CH$_2$O(CH$_2$)$_2$SOCH$_2$CF$_3$ | |
| 6-119 | S(CH$_2$)$_2$CH$_3$ | CH$_2$O(CH$_2$)$_2$SO$_2$CH$_3$ | |
| 6-120 | S(CH$_2$)$_2$CH$_3$ | CH$_2$O(CH$_2$)$_2$SO$_2$CH$_2$CF$_3$ | |

TABLE 81

| compound number | R4 | R1 | physical property (melting point-ND) |
|---|---|---|---|
| 6-121 | S(CH$_2$)$_2$CH$_3$ | 2-(methoxymethyl)tetrahydrofuran | |
| 6-122 | S(CH$_2$)$_2$CH$_3$ | 3-methoxytetrahydrofuran | |
| 6-123 | S(CH$_2$)$_2$CH$_3$ | CH$_2$O(CH$_2$)$_2$NHSO$_2$CH$_3$ | |
| 6-124 | S(CH$_2$)$_2$CH$_3$ | CH$_2$O(CH$_2$)$_2$N(CH$_3$)(SO$_2$CH$_3$) | |
| 6-125 | SC$_6$H$_5$ | CH$_3$ | |
| 6-126 | SC$_6$H$_5$ | CF$_3$ | |
| 6-127 | SC$_6$H$_5$ | CH$_2$OCH$_3$ | |
| 6-128 | SC$_6$H$_5$ | CH$_2$OCH$_2$CH$_3$ | |
| 6-129 | SC$_6$H$_5$ | CH$_3$-O-CH$_2$-cyclopropyl | |
| 6-130 | SC$_6$H$_5$ | CH$_2$OCH$_2$CF$_3$ | |
| 6-131 | SC$_6$H$_5$ | CH$_2$SCH$_3$ | |
| 6-132 | SC$_6$H$_5$ | CH$_2$SCH$_2$CH$_3$ | |
| 6-133 | SC$_6$H$_5$ | CH$_3$-S-CH$_2$-cyclopropyl | |
| 6-134 | SC$_6$H$_5$ | CH$_2$SCH$_2$CF$_3$ | |
| 6-135 | SC$_6$H$_5$ | CH$_2$SOCH$_3$ | |
| 6-136 | SC$_6$H$_5$ | CH$_2$SOCH$_2$CH$_3$ | |
| 6-137 | SC$_6$H$_5$ | CH$_3$-S(O)-CH$_2$-cyclopropyl | |
| 6-138 | SC$_6$H$_5$ | CH$_2$SOCH$_2$CF$_3$ | |
| 6-139 | SC$_6$H$_5$ | CH$_2$SO$_2$CH$_3$ | |
| 6-140 | SC$_6$H$_5$ | CH$_2$SO$_2$CH$_2$CH$_3$ | |
| 6-141 | SC$_6$H$_5$ | CH$_3$-SO$_2$-CH$_2$-cyclopropyl | |
| 6-142 | SC$_6$H$_5$ | CH$_2$SO$_2$CH$_2$CF$_3$ | |
| 6-143 | SC$_6$H$_5$ | CH$_2$O(CH$_2$)$_2$OCH$_3$ | |
| 6-144 | SC$_6$H$_5$ | CH$_2$O(CH$_2$)$_2$OCH$_2$CH$_3$ | |
| 6-145 | SC$_6$H$_5$ | CH$_2$O(CH$_2$)$_2$OCH$_2$CF$_3$ | |
| 6-146 | SC$_6$H$_5$ | CH$_2$O(CH$_2$)$_2$SCH$_3$ | |
| 6-147 | SC$_6$H$_5$ | CH$_2$O(CH$_2$)$_2$SCH$_2$CF$_3$ | |
| 6-148 | SC$_6$H$_5$ | CH$_2$O(CH$_2$)$_2$SOCH$_3$ | |
| 6-149 | SC$_6$H$_5$ | CH$_2$O(CH$_2$)$_2$SOCH$_2$CF$_3$ | |
| 6-150 | SC$_6$H$_5$ | CH$_2$O(CH$_2$)$_2$SO$_2$CH$_3$ | |
| 6-151 | SC$_6$H$_5$ | CH$_2$O(CH$_2$)$_2$SO$_2$CH$_2$CF$_3$ | |
| 6-152 | SC$_6$H$_5$ | 2-(methoxymethyl)tetrahydrofuran | |
| 6-153 | SC$_6$H$_5$ | 3-methoxytetrahydrofuran | |
| 6-154 | SC$_6$H$_5$ | CH$_2$O(CH$_2$)$_2$NHSO$_2$CH$_3$ | |
| 6-155 | SC$_6$H$_5$ | CH$_2$O(CH$_2$)$_2$N(CH$_3$)(SO$_2$CH$_3$) | |
| 6-156 | SCH$_2$C$_6$H$_5$ | CH$_3$ | |
| 6-157 | SCH$_2$C$_6$H$_5$ | CF$_3$ | |
| 6-158 | SCH$_2$C$_6$H$_5$ | CH$_2$OCH$_3$ | |
| 6-159 | SCH$_2$C$_6$H$_5$ | CH$_2$OCH$_2$CH$_3$ | |

TABLE 81-continued

| compound number | R4 | R1 | physical property (melting point-ND) |
|---|---|---|---|
| 6-160 | SCH₂C₆H₅ | CH₃-O-CH₂-cyclopropyl | |

TABLE 82

| compound number | R4 | R1 | physical property (melting point-ND) |
|---|---|---|---|
| 6-161 | SCH₂C₆H₅ | CH₂OCH₂CF₃ | |
| 6-162 | SCH₂C₆H₅ | CH₂SCH₃ | |
| 6-163 | SCH₂C₆H₅ | CH₂SCH₂CH₃ | |
| 6-164 | SCH₂C₆H₅ | CH₃-S-CH₂-cyclopropyl | |
| 6-165 | SCH₂C₆H₅ | CH₂SCH₂CF₃ | |
| 6-166 | SCH₂C₆H₅ | CH₂SOCH₃ | |
| 6-167 | SCH₂C₆H₅ | CH₂SOCH₂CH₃ | |
| 6-168 | SCH₂C₆H₅ | CH₃-S(=O)-CH₂-cyclopropyl | |
| 6-169 | SCH₂C₆H₅ | CH₂SOCH₂CF₃ | |
| 6-170 | SCH₂C₆H₅ | CH₂SO₂CH₃ | |
| 6-171 | SCH₂C₆H₅ | CH₂SO₂CH₂CH₃ | |
| 6-172 | SCH₂C₆H₅ | CH₃-S(=O)₂-CH₂-cyclopropyl | |
| 6-173 | SCH₂C₆H₅ | CH₂SO₂CH₂CF₃ | |
| 6-174 | SCH₂C₆H₅ | CH₂O(CH₂)₂OCH₃ | |
| 6-175 | SCH₂C₆H₅ | CH₂O(CH₂)₂OCH₂CH₃ | |
| 6-176 | SCH₂C₆H₅ | CH₂O(CH₂)₂OCH₂CF₃ | |
| 6-177 | SCH₂C₆H₅ | CH₂O(CH₂)₂SCH₃ | |
| 6-178 | SCH₂C₆H₅ | CH₂O(CH₂)₂SCH₂CF₃ | |
| 6-179 | SCH₂C₆H₅ | CH₂O(CH₂)₂SOCH₃ | |
| 6-180 | SCH₂C₆H₅ | CH₂O(CH₂)₂SOCH₂CF₃ | |
| 6-181 | SCH₂C₆H₅ | CH₂O(CH₂)₂SO₂CH₃ | |
| 6-182 | SCH₂C₆H₅ | CH₂O(CH₂)₂SO₂CH₂CF₃ | |
| 6-183 | SCH₂C₆H₅ | 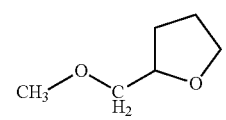 | |
| 6-184 | SCH₂C₆H₅ | CH₃-O-(tetrahydrofuran-3-yl) | |
| 6-185 | SCH₂C₆H₅ | CH₂O(CH₂)₂NHSO₂CH₃ | |
| 6-186 | SCH₂C₆H₅ | CH₂O(CH₂)₂N(CH₃)(SO₂CH₃) | |
| 6-187 | 1H-pyrazole-1-yl | CH₃ | |
| 6-188 | 1H-pyrazole-1-yl | CF₃ | |
| 6-189 | 1H-pyrazole-1-yl | CH₂OCH₃ | |
| 6-190 | 1H-pyrazole-1-yl | CH₂OCH₂CH₃ | |

TABLE 82-continued

| compound number | R4 | R1 | physical property (melting point-ND) |
|---|---|---|---|
| 6-191 | 1H-pyrazole-1-yl | CH₃-O-CH₂-cyclopropyl | |
| 6-192 | 1H-pyrazole-1-yl | CH₂OCH₂CF₃ | |
| 6-193 | 1H-pyrazole-1-yl | CH₂SCH₃ | |
| 6-194 | 1H-pyrazole-1-yl | CH₂SCH₂CH₃ | |
| 6-195 | 1H-pyrazole-1-yl | CH₃-S-CH₂-cyclopropyl | |
| 6-196 | 1H-pyrazole-1-yl | CH₂SCH₂CF₃ | |
| 6-197 | 1H-pyrazole-1-yl | CH₂SOCH₃ | |
| 6-198 | 1H-pyrazole-1-yl | CH₂SOCH₂CH₃ | |
| 6-199 | 1H-pyrazole-1-yl | CH₃-S(=O)-CH₂-cyclopropyl | |
| 6-200 | 1H-pyrazole-1-yl | CH₂SOCH₂CF₃ | |

TABLE 83

| compound number | R4 | R1 | physical property (melting point-ND) |
|---|---|---|---|
| 6-201 | 1H-pyrazole-1-yl | CH₂SO₂CH₃ | |
| 6-202 | 1H-pyrazole-1-yl | CH₂SO₂CH₂CH₃ | |
| 6-203 | 1H-pyrazole-1-yl | CH₃-S(=O)₂-CH₂-cyclopropyl | |
| 6-204 | 1H-pyrazole-1-yl | CH₂SO₂CH₂CF₃ | |
| 6-205 | 1H-pyrazole-1-yl | CH₂O(CH₂)₂OCH₃ | |
| 6-206 | 1H-pyrazole-1-yl | CH₂O(CH₂)₂OCH₂CH₃ | |
| 6-207 | 1H-pyrazole-1-yl | CH₂O(CH₂)₂OCH₂CF₃ | |
| 6-208 | 1H-pyrazole-1-yl | CH₂O(CH₂)₂SCH₃ | |
| 6-209 | 1H-pyrazole-1-yl | CH₂O(CH₂)₂SCH₂CF₃ | |
| 6-210 | 1H-pyrazole-1-yl | CH₂O(CH₂)₂SOCH₃ | |
| 6-211 | 1H-pyrazole-1-yl | CH₂O(CH₂)₂SOCH₂CF₃ | |
| 6-212 | 1H-pyrazole-1-yl | CH₂O(CH₂)₂SO₂CH₃ | |
| 6-213 | 1H-pyrazole-1-yl | CH₂O(CH₂)₂SO₂CH₂CF₃ | |
| 6-214 | 1H-pyrazole-1-yl | CH₃-O-CH₂-(tetrahydrofuran-2-yl) | |
| 6-215 | 1H-pyrazole-1-yl | CH₃-O-(tetrahydrofuran-3-yl) | |
| 6-216 | 1H-pyrazole-1-yl | CH₂O(CH₂)₂NHSO₂CH₃ | |
| 6-217 | 1H-pyrazole-1-yl | CH₂O(CH₂)₂N(CH₃)(SO₂CH₃) | |
| 6-218 | 1H-imidazole-1-yl | CH₃ | |
| 6-219 | 1H-imidazole-1-yl | CF₃ | |
| 6-220 | 1H-imidazole-1-yl | CH₂OCH₃ | |
| 6-221 | 1H-imidazole-1-yl | CH₂OCH₂CH₃ | |

TABLE 83-continued

| compound number | R4 | R1 | physical property (melting point-ND) |
|---|---|---|---|
| 6-222 | 1H-imidazole-1-yl | 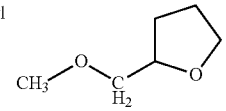 | |
| 6-223 | 1H-imidazole-1-yl | CH$_2$OCH$_2$CF$_3$ | |
| 6-224 | 1H-imidazole-1-yl | CH$_2$SCH$_3$ | |
| 6-225 | 1H-imidazole-1-yl | CH$_2$SCH$_2$CH$_3$ | |
| 6-226 | 1H-imidazole-1-yl | 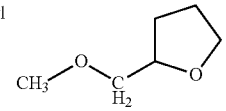 | |
| 6-227 | 1H-imidazole-1-yl | CH$_2$SCH$_2$CF$_3$ | |
| 6-228 | 1H-imidazole-1-yl | CH$_2$SOCH$_3$ | |
| 6-229 | 1H-imidazole-1-yl | CH$_2$SOCH$_2$CH$_3$ | |
| 6-230 | 1H-imidazole-1-yl | (CH$_3$-S(=O)-CH$_2$-cyclopropyl) | |
| 6-231 | 1H-imidazole-1-yl | CH$_2$SOCH$_2$CF$_3$ | |
| 6-232 | 1H-imidazole-1-yl | CH$_2$SO$_2$CH$_3$ | |
| 6-233 | 1H-imidazole-1-yl | CH$_2$SO$_2$CH$_2$CH$_3$ | |
| 6-234 | 1H-imidazole-1-yl | (CH$_3$-SO$_2$-CH$_2$-cyclopropyl) | |
| 6-235 | 1H-imidazole-1-yl | CH$_2$SO$_2$CH$_2$CF$_3$ | |
| 6-236 | 1H-imidazole-1-yl | CH$_2$O(CH$_2$)$_2$OCH$_3$ | |
| 6-237 | 1H-imidazole-1-yl | CH$_2$O(CH$_2$)$_2$OCH$_2$CH$_3$ | |
| 6-238 | 1H-imidazole-1-yl | CH$_2$O(CH$_2$)$_2$OCH$_2$CF$_3$ | |
| 6-239 | 1H-imidazole-1-yl | CH$_2$O(CH$_2$)$_2$SCH$_3$ | |
| 6-240 | 1H-imidazole-1-yl | CH$_2$O(CH$_2$)$_2$SCH$_2$CF$_3$ | |

TABLE 84

| compound number | R4 | R1 | physical property (melting point-ND) |
|---|---|---|---|
| 6-241 | 1H-imidazole-1-yl | CH$_2$O(CH$_2$)$_2$SOCH$_3$ | |
| 6-242 | 1H-imidazole-1-yl | CH$_2$O(CH$_2$)$_2$SOCH$_2$CF$_3$ | |
| 6-243 | 1H-imidazole-1-yl | CH$_2$O(CH$_2$)$_2$SO$_2$CH$_3$ | |
| 6-244 | 1H-imidazole-1-yl | CH$_2$O(CH$_2$)$_2$SO$_2$CH$_2$CF$_3$ | |
| 6-245 | 1H-imidazole-1-yl | 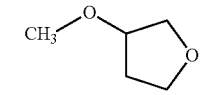 | |
| 6-246 | 1H-imidazole-1-yl | 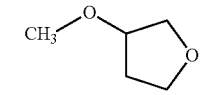 | |
| 6-247 | 1H-imidazole-1-yl | CH$_2$O(CH$_2$)$_2$NHSO$_2$CH$_3$ | |
| 6-248 | 1H-imidazole-1-yl | CH$_2$O(CH$_2$)$_2$N(CH$_3$)(SO$_2$CH$_3$) | |
| 6-249 | 1H-triazole-1-yl | CH$_3$ | |
| 6-250 | 1H-triazole-1-yl | CF$_3$ | |
| 6-251 | 1H-triazole-1-yl | CH$_2$OCH$_3$ | |
| 6-252 | 1H-triazole-1-yl | CH$_2$OCH$_2$CH$_3$ | |

TABLE 84-continued

| compound number | R4 | R1 | physical property (melting point-ND) |
|---|---|---|---|
| 6-253 | 1H-triazole-1-yl | 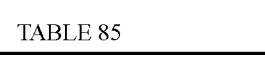 | |
| 6-254 | 1H-triazole-1-yl | CH$_2$OCH$_2$CF$_3$ | |
| 6-255 | 1H-triazole-1-yl | CH$_2$SCH$_3$ | |
| 6-256 | 1H-triazole-1-yl | CH$_2$SCH$_2$CH$_3$ | |
| 6-257 | 1H-triazole-1-yl | 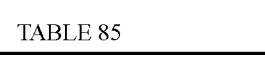 | |
| 6-258 | 1H-triazole-1-yl | CH$_2$SCH$_2$CF$_3$ | |
| 6-259 | 1H-triazole-1-yl | CH$_2$SOCH$_3$ | |
| 6-260 | 1H-triazole-1-yl | CH$_2$SOCH$_2$CH$_3$ | |
| 6-261 | 1H-triazole-1-yl | (CH$_3$-S(=O)-CH$_2$-cyclopropyl) | |
| 6-262 | 1H-triazole-1-yl | CH$_2$SOCH$_2$CF$_3$ | |
| 6-263 | 1H-triazole-1-yl | CH$_2$SO$_2$CH$_3$ | |
| 6-264 | 1H-triazole-1-yl | CH$_2$SO$_2$CH$_2$CH$_3$ | |
| 6-265 | 1H-triazole-1-yl | (CH$_3$-SO$_2$-CH$_2$-cyclopropyl) | |
| 6-266 | 1H-triazole-1-yl | CH$_2$SO$_2$CH$_2$CF$_3$ | |
| 6-267 | 1H-triazole-1-yl | CH$_2$O(CH$_2$)$_2$OCH$_3$ | |
| 6-268 | 1H-triazole-1-yl | CH$_2$O(CH$_2$)$_2$OCH$_2$CH$_3$ | |
| 6-269 | 1H-triazole-1-yl | CH$_2$O(CH$_2$)$_2$OCH$_2$CF$_3$ | |
| 6-270 | 1H-triazole-1-yl | CH$_2$O(CH$_2$)$_2$SCH$_3$ | |
| 6-271 | 1H-triazole-1-yl | CH$_2$O(CH$_2$)$_2$SCH$_2$CF$_3$ | |
| 6-272 | 1H-triazole-1-yl | CH$_2$O(CH$_2$)$_2$SOCH$_3$ | |
| 6-273 | 1H-triazole-1-yl | CH$_2$O(CH$_2$)$_2$SOCH$_2$CF$_3$ | |
| 6-274 | 1H-triazole-1-yl | CH$_2$O(CH$_2$)$_2$SO$_2$CH$_3$ | |
| 6-275 | 1H-triazole-1-yl | CH$_2$O(CH$_2$)$_2$SO$_2$CH$_2$CF$_3$ | |
| 6-276 | 1H-triazole-1-yl | (CH$_3$-O-CH$_2$-tetrahydrofuran) | |
| 6-277 | 1H-triazole-1-yl | (CH$_3$-O-tetrahydrofuran) | |
| 6-278 | 1H-triazole-1-yl | CH$_2$O(CH$_2$)$_2$NHSO$_2$CH$_3$ | |
| 6-279 | 1H-triazole-1-yl | CH$_2$O(CH$_2$)$_2$N(CH$_3$)(SO$_2$CH$_3$) | |
| 6-280 | 1H-tetrazole-1-yl | CH$_3$ | |

TABLE 85

| compound number | R4 | R1 | physical property (melting point-ND) |
|---|---|---|---|
| 6-281 | 1H-tetrazole-1-yl | CF$_3$ | |
| 6-282 | 1H-tetrazole-1-yl | CH$_2$OCH$_3$ | |
| 6-283 | 1H-tetrazole-1-yl | CH$_2$OCH$_2$CH$_3$ | |

TABLE 85-continued

| compound number | R4 | R1 | physical property (melting point-ND) |
|---|---|---|---|
| 6-284 | 1H-tetrazole-1-yl | CH₃-O-CH₂-cyclopropyl | |
| 6-285 | 1H-tetrazole-1-yl | CH₂OCH₂CF₃ | |
| 6-286 | 1H-tetrazole-1-yl | CH₂SCH₃ | |
| 6-287 | 1H-tetrazole-1-yl | CH₂SCH₂CH₃ | |
| 6-288 | 1H-tetrazole-1-yl | CH₃-S-CH₂-cyclopropyl | |
| 6-289 | 1H-tetrazole-1-yl | CH₂SCH₂CF₃ | |
| 6-290 | 1H-tetrazole-1-yl | CH₂SOCH₃ | |
| 6-291 | 1H-tetrazole-1-yl | CH₂SOCH₂CH₃ | |
| 6-292 | 1H-tetrazole-1-yl | CH₃-S(O)-CH₂-cyclopropyl | |
| 6-293 | 1H-tetrazole-1-yl | CH₂SOCH₂CF₃ | |
| 6-294 | 1H-tetrazole-1-yl | CH₂SO₂CH₃ | |
| 6-295 | 1H-tetrazole-1-yl | CH₂SO₂CH₂CH₃ | |
| 6-296 | 1H-tetrazole-1-yl | CH₃-S(O)₂-CH₂-cyclopropyl | |
| 6-297 | 1H-tetrazole-1-yl | CH₂SO₂CH₂CF₃ | |
| 6-298 | 1H-tetrazole-1-yl | CH₂O(CH₂)₂OCH₃ | |
| 6-299 | 1H-tetrazole-1-yl | CH₂O(CH₂)₂OCH₂CH₃ | |
| 6-300 | 1H-tetrazole-1-yl | CH₂O(CH₂)₂OCH₂CF₃ | |
| 6-301 | 1H-tetrazole-1-yl | CH₂O(CH₂)₂SCH₃ | |
| 6-302 | 1H-tetrazole-1-yl | CH₂O(CH₂)₂SCH₂CF₃ | |
| 6-303 | 1H-tetrazole-1-yl | CH₂O(CH₂)₂SOCH₃ | |
| 6-304 | 1H-tetrazole-1-yl | CH₂O(CH₂)₂SOCH₂CF₃ | |
| 6-305 | 1H-tetrazole-1-yl | CH₂O(CH₂)₂SO₂CH₃ | |
| 6-306 | 1H-tetrazole-1-yl | CH₂O(CH₂)₂SO₂CH₂CF₃ | |
| 6-307 | 1H-tetrazole-1-yl | CH₃-O-CH(tetrahydrofuran-2-yl) | |
| 6-308 | 1H-tetrazole-1-yl | CH₃-O-(tetrahydrofuran-3-yl) | |
| 6-309 | 1H-tetrazole-1-yl | CH₂O(CH₂)₂NHSO₂CH₃ | |
| 6-310 | 1H-tetrazole-1-yl | CH₂O(CH₂)₂N(CH₃)(SO₂CH₃) | |
| 6-311 | 1H-tetrazole-2-yl | CH₃ | |
| 6-312 | 1H-tetrazole-2-yl | CF₃ | |
| 6-313 | 1H-tetrazole-2-yl | CH₂OCH₃ | |
| 6-314 | 1H-tetrazole-2-yl | CH₂OCH₂CH₃ | |
| 6-315 | 1H-tetrazole-2-yl | CH₃-O-CH₂-cyclopropyl | |
| 6-316 | 1H-tetrazole-2-yl | CH₂OCH₂CF₃ | |
| 6-317 | 1H-tetrazole-2-yl | CH₂SCH₃ | |
| 6-318 | 1H-tetrazole-2-yl | CH₂SCH₂CH₃ | |
| 6-319 | 1H-tetrazole-2-yl | CH₃-S-CH₂-cyclopropyl | |
| 6-320 | 1H-tetrazole-2-yl | CH₂SCH₂CF₃ | |

TABLE 86

| compound number | R4 | R1 | physical property (melting point-ND) |
|---|---|---|---|
| 6-321 | 1H-tetrazole-2-yl | CH₂SOCH₃ | |
| 6-322 | 1H-tetrazole-2-yl | CH₂SOCH₂CH₃ | |
| 6-323 | 1H-tetrazole-2-yl | CH₃-S(O)-CH₂-cyclopropyl | |
| 6-324 | 1H-tetrazole-2-yl | CH₂SOCH₂CF₃ | |
| 6-325 | 1H-tetrazole-2-yl | CH₂SO₂CH₃ | |
| 6-326 | 1H-tetrazole-2-yl | CH₂SO₂CH₂CH₃ | |
| 6-327 | 1H-tetrazole-2-yl | CH₃-S(O)₂-CH₂-cyclopropyl | |
| 6-328 | 1H-tetrazole-2-yl | CH₂SO₂CH₂CF₃ | |
| 6-329 | 1H-tetrazole-2-yl | CH₂O(CH₂)₂OCH₃ | |
| 6-330 | 1H-tetrazole-2-yl | CH₂O(CH₂)₂OCH₂CH₃ | |
| 6-331 | 1H-tetrazole-2-yl | CH₂O(CH₂)₂OCH₂CF₃ | |
| 6-332 | 1H-tetrazole-2-yl | CH₂O(CH₂)₂SCH₃ | |
| 6-333 | 1H-tetrazole-2-yl | CH₂O(CH₂)₂SCH₂CF₃ | |
| 6-334 | 1H-tetrazole-2-yl | CH₂O(CH₂)₂SOCH₃ | |
| 6-335 | 1H-tetrazole-2-yl | CH₂O(CH₂)₂SOCH₂CF₃ | |
| 6-336 | 1H-tetrazole-2-yl | CH₂O(CH₂)₂SO₂CH₃ | |
| 6-337 | 1H-tetrazole-2-yl | CH₂O(CH₂)₂SO₂CH₂CF₃ | |
| 6-338 | 1H-tetrazole-2-yl | CH₃-O-CH₂(tetrahydrofuran-2-yl) | |
| 6-339 | 1H-tetrazole-2-yl | CH₃-O-(tetrahydrofuran-3-yl) | |
| 6-340 | 1H-tetrazole-2-yl | CH₂O(CH₂)₂NHSO₂CH₃ | |
| 6-341 | 1H-tetrazole-2-yl | CH₂O(CH₂)₂N(CH₃)(SO₂CH₃) | |

TABLE 87

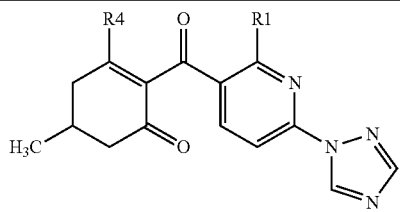

| compound number | R4 | R1 | physical property (melting point-ND) |
|---|---|---|---|
| 7-1 | Cl | CH₃ | |
| 7-2 | Cl | CF₃ | |
| 7-3 | Cl | CH₂OCH₃ | |
| 7-4 | Cl | CH₂OCH₂CH₃ | |
| 7-5 | Cl | CH₃-O-CH₂-cyclopropyl | |
| 7-6 | Cl | CH₂OCH₂CF₃ | |
| 7-7 | Cl | CH₂SCH₃ | |
| 7-8 | Cl | CH₂SCH₂CH₃ | |
| 7-9 | Cl | CH₃-S-CH₂-cyclopropyl | |
| 7-10 | Cl | CH₂SCH₂CF₃ | |
| 7-11 | Cl | CH₂SOCH₃ | |
| 7-12 | Cl | CH₂SOCH₂CH₃ | |
| 7-13 | Cl | CH₃-S(O)-CH₂-cyclopropyl | |
| 7-14 | Cl | CH₂SOCH₂CF₃ | |
| 7-15 | Cl | CH₂SO₂CH₃ | |
| 7-16 | Cl | CH₂SO₂CH₂CH₃ | |
| 7-17 | Cl | CH₃-SO₂-CH₂-cyclopropyl | |
| 7-18 | Cl | CH₂SO₂CH₂CF₃ | |
| 7-19 | Cl | CH₂O(CH₂)₂OCH₃ | |
| 7-20 | Cl | CH₂O(CH₂)₂OCH₂CH₃ | |
| 7-21 | Cl | CH₂O(CH₂)₂OCH₂CF₃ | |
| 7-22 | Cl | CH₂O(CH₂)₂SCH₃ | |
| 7-23 | Cl | CH₂O(CH₂)₂SCH₂CF₃ | |
| 7-24 | Cl | CH₂O(CH₂)₂SOCH₃ | |
| 7-25 | Cl | CH₂O(CH₂)₂SOCH₂CF₃ | |
| 7-26 | Cl | CH₂O(CH₂)₂SO₂CH₃ | |
| 7-27 | Cl | CH₂O(CH₂)₂SO₂CH₂CF₃ | |
| 7-28 | Cl | CH₃-O-CH₂-(tetrahydrofuran-2-yl) | |
| 7-29 | Cl | CH₃-O-(tetrahydrofuran-3-yl) | |
| 7-30 | Cl | CH₂O(CH₂)₂NHSO₂CH₃ | |
| 7-31 | Cl | CH₂O(CH₂)₂N(CH₃)(SO₂CH₃) | |

TABLE 87-continued

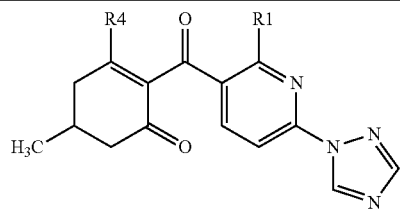

| compound number | R4 | R1 | physical property (melting point-ND) |
|---|---|---|---|
| 7-32 | SCH₃ | CH₃ | |
| 7-33 | SCH₃ | CF₃ | |
| 7-34 | SCH₃ | CH₂OCH₃ | |
| 7-35 | SCH₃ | CH₂OCH₂CH₃ | |
| 7-36 | SCH₃ | CH₃-O-CH₂-cyclopropyl | |
| 7-37 | SCH₃ | CH₂OCH₂CF₃ | |
| 7-38 | SCH₃ | CH₂SCH₃ | |
| 7-39 | SCH₃ | CH₂SCH₂CH₃ | |
| 7-40 | SCH₃ | CH₃-S-CH₂-cyclopropyl | |

TABLE 88

| compound number | R4 | R1 | physical property (melting point-ND) |
|---|---|---|---|
| 7-41 | SCH₃ | CH₂SCH₂CF₃ | |
| 7-42 | SCH₃ | CH₂SOCH₃ | |
| 7-43 | SCH₃ | CH₂SOCH₂CH₃ | |
| 7-44 | SCH₃ | CH₃-S(O)-CH₂-cyclopropyl | |
| 7-45 | SCH₃ | CH₂SOCH₂CF₃ | |
| 7-46 | SCH₃ | CH₂SO₂CH₃ | |
| 7-47 | SCH₃ | CH₂SO₂CH₂CH₃ | |
| 7-48 | SCH₃ | CH₃-SO₂-CH₂-cyclopropyl | |
| 7-49 | SCH₃ | CH₂SO₂CH₂CF₃ | |
| 7-50 | SCH₃ | CH₂O(CH₂)₂OCH₃ | |
| 7-51 | SCH₃ | CH₂O(CH₂)₂OCH₂CH₃ | |
| 7-52 | SCH₃ | CH₂O(CH₂)₂OCH₂CF₃ | |
| 7-53 | SCH₃ | CH₂O(CH₂)₂SCH₃ | |
| 7-54 | SCH₃ | CH₂O(CH₂)₂SCH₂CF₃ | |
| 7-55 | SCH₃ | CH₂O(CH₂)₂SOCH₃ | |
| 7-56 | SCH₃ | CH₂O(CH₂)₂SOCH₂CF₃ | |
| 7-57 | SCH₃ | CH₂O(CH₂)₂SO₂CH₃ | |
| 7-58 | SCH₃ | CH₂O(CH₂)₂SO₂CH₂CF₃ | |
| 7-59 | SCH₃ | CH₃-O-CH₂-(tetrahydrofuran-2-yl) | |

TABLE 88-continued

| compound number | R4 | R1 | physical property (melting point-ND) |
|---|---|---|---|
| 7-60 | SCH$_3$ | 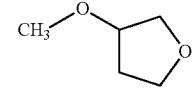 | |
| 7-61 | SCH$_3$ | CH$_2$O(CH$_2$)$_2$NHSO$_2$CH$_3$ | |
| 7-62 | SCH$_3$ | CH$_2$O(CH$_2$)$_2$N(CH$_3$)(SO$_2$CH$_3$) | |
| 7-63 | SCH$_2$CH$_3$ | CH$_3$ | |
| 7-64 | SCH$_2$CH$_3$ | CF$_3$ | |
| 7-65 | SCH$_2$CH$_3$ | CH$_2$OCH$_3$ | |
| 7-66 | SCH$_2$CH$_3$ | CH$_2$OCH$_2$CH$_3$ | |
| 7-67 | SCH$_2$CH$_3$ | 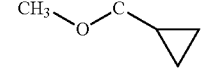 | |
| 7-68 | SCH$_2$CH$_3$ | CH$_2$OCH$_2$CF$_3$ | |
| 7-69 | SCH$_2$CH$_3$ | CH$_2$SCH$_3$ | |
| 7-70 | SCH$_2$CH$_3$ | CH$_2$SCH$_2$CH$_3$ | |
| 7-71 | SCH$_2$CH$_3$ | 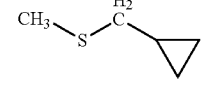 | |
| 7-72 | SCH$_2$CH$_3$ | CH$_2$SCH$_2$CF$_3$ | |
| 7-73 | SCH$_2$CH$_3$ | CH$_2$SOCH$_3$ | |
| 7-74 | SCH$_2$CH$_3$ | CH$_2$SOCH$_2$CH$_3$ | |
| 7-75 | SCH$_2$CH$_3$ | 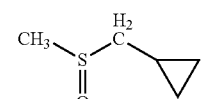 | |
| 7-76 | SCH$_2$CH$_3$ | CH$_2$SOCH$_2$CF$_3$ | |
| 7-77 | SCH$_2$CH$_3$ | CH$_2$SO$_2$CH$_3$ | |
| 7-78 | SCH$_2$CH$_3$ | CH$_2$SO$_2$CH$_2$CH$_3$ | |
| 7-79 | SCH$_2$CH$_3$ | 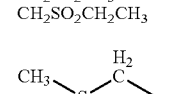 | |
| 7-80 | SCH$_2$CH$_3$ | CH$_2$SO$_2$CH$_2$CF$_3$ | |

TABLE 89

| compound number | R4 | R1 | physical property (melting point-ND) |
|---|---|---|---|
| 7-81 | SCH$_2$CH$_3$ | CH$_2$O(CH$_2$)$_2$OCH$_3$ | |
| 7-82 | SCH$_2$CH$_3$ | CH$_2$O(CH$_2$)$_2$OCH$_2$CH$_3$ | |
| 7-83 | SCH$_2$CH$_3$ | CH$_2$O(CH$_2$)$_2$OCH$_2$CF$_3$ | |
| 7-84 | SCH$_2$CH$_3$ | CH$_2$O(CH$_2$)$_2$SCH$_3$ | |
| 7-85 | SCH$_2$CH$_3$ | CH$_2$O(CH$_2$)$_2$SCH$_2$CF$_3$ | |
| 7-86 | SCH$_2$CH$_3$ | CH$_2$O(CH$_2$)$_2$SOCH$_3$ | |
| 7-87 | SCH$_2$CH$_3$ | CH$_2$O(CH$_2$)$_2$SOCH$_2$CF$_3$ | |
| 7-88 | SCH$_2$CH$_3$ | CH$_2$O(CH$_2$)$_2$SO$_2$CH$_3$ | |
| 7-89 | SCH$_2$CH$_3$ | CH$_2$O(CH$_2$)$_2$SO$_2$CH$_2$CF$_3$ | |
| 7-90 | SCH$_2$CH$_3$ | 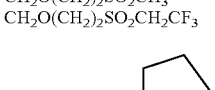 | |
| 7-91 | SCH$_2$CH$_3$ |  | |
| 7-92 | SCH$_2$CH$_3$ | CH$_2$O(CH$_2$)$_2$NHSO$_2$CH$_3$ | |
| 7-93 | SCH$_2$CH$_3$ | CH$_2$O(CH$_2$)$_2$N(CH$_3$)(SO$_2$CH$_3$) | |
| 7-94 | S(CH$_2$)$_2$CH$_3$ | CH$_3$ | |
| 7-95 | S(CH$_2$)$_2$CH$_3$ | CF$_3$ | |
| 7-96 | S(CH$_2$)$_2$CH$_3$ | CH$_2$OCH$_3$ | |
| 7-97 | S(CH$_2$)$_2$CH$_3$ | CH$_2$OCH$_2$CH$_3$ | |
| 7-98 | S(CH$_2$)$_2$CH$_3$ |  | |
| 7-99 | S(CH$_2$)$_2$CH$_3$ | CH$_2$OCH$_2$CF$_3$ | |
| 7-100 | S(CH$_2$)$_2$CH$_3$ | CH$_2$SCH$_3$ | |
| 7-101 | S(CH$_2$)$_2$CH$_3$ | CH$_2$SCH$_2$CH$_3$ | |
| 7-102 | S(CH$_2$)$_2$CH$_3$ |  | |
| 7-103 | S(CH$_2$)$_2$CH$_3$ | CH$_2$SCH$_2$CF$_3$ | |
| 7-104 | S(CH$_2$)$_2$CH$_3$ | CH$_2$SOCH$_3$ | |
| 7-105 | S(CH$_2$)$_2$CH$_3$ | CH$_2$SOCH$_2$CH$_3$ | |
| 7-106 | S(CH$_2$)$_2$CH$_3$ |  | |
| 7-107 | S(CH$_2$)$_2$CH$_3$ | CH$_2$SOCH$_2$CF$_3$ | |
| 7-108 | S(CH$_2$)$_2$CH$_3$ | CH$_2$SO$_2$CH$_3$ | |
| 7-109 | S(CH$_2$)$_2$CH$_3$ | CH$_2$SO$_2$CH$_2$CH$_3$ | |
| 7-110 | S(CH$_2$)$_2$CH$_3$ |  | |
| 7-111 | S(CH$_2$)$_2$CH$_3$ | CH$_2$SO$_2$CH$_2$CF$_3$ | |
| 7-112 | S(CH$_2$)$_2$CH$_3$ | CH$_2$O(CH$_2$)$_2$OCH$_3$ | |
| 7-113 | S(CH$_2$)$_2$CH$_3$ | CH$_2$O(CH$_2$)$_2$OCH$_2$CH$_3$ | |
| 7-114 | S(CH$_2$)$_2$CH$_3$ | CH$_2$O(CH$_2$)$_2$OCH$_2$CF$_3$ | |
| 7-115 | S(CH$_2$)$_2$CH$_3$ | CH$_2$O(CH$_2$)$_2$SCH$_3$ | |
| 7-116 | S(CH$_2$)$_2$CH$_3$ | CH$_2$O(CH$_2$)$_2$SCH$_2$CF$_3$ | |
| 7-117 | S(CH$_2$)$_2$CH$_3$ | CH$_2$O(CH$_2$)$_2$SOCH$_3$ | |
| 7-118 | S(CH$_2$)$_2$CH$_3$ | CH$_2$O(CH$_2$)$_2$SOCH$_2$CF$_3$ | |
| 7-119 | S(CH$_2$)$_2$CH$_3$ | CH$_2$O(CH$_2$)$_2$SO$_2$CH$_3$ | |
| 7-120 | S(CH$_2$)$_2$CH$_3$ | CH$_2$O(CH$_2$)$_2$SO$_2$CH$_2$CF$_3$ | |

TABLE 90

| compound number | R4 | R1 | physical property (melting point-ND) |
|---|---|---|---|
| 7-121 | S(CH$_2$)$_2$CH$_3$ |  | |

TABLE 90-continued

| compound number | R4 | R1 | physical property (melting point-ND) |
|---|---|---|---|
| 7-122 | S(CH$_2$)$_2$CH$_3$ | 3-methoxytetrahydrofuran-yl (CH$_3$O-tetrahydrofuran) | |
| 7-123 | S(CH$_2$)$_2$CH$_3$ | CH$_2$O(CH$_2$)$_2$NHSO$_2$CH$_3$ | |
| 7-124 | S(CH$_2$)$_2$CH$_3$ | CH$_2$O(CH$_2$)$_2$N(CH$_3$)(SO$_2$CH$_3$) | |
| 7-125 | SC$_6$H$_5$ | CH$_3$ | |
| 7-126 | SC$_6$H$_5$ | CF$_3$ | |
| 7-127 | SC$_6$H$_5$ | CH$_2$OCH$_3$ | |
| 7-128 | SC$_6$H$_5$ | CH$_2$OCH$_2$CH$_3$ | |
| 7-129 | SC$_6$H$_5$ | CH$_3$-O-CH$_2$-cyclopropyl | |
| 7-130 | SC$_6$H$_5$ | CH$_2$OCH$_2$CF$_3$ | |
| 7-131 | SC$_6$H$_5$ | CH$_2$SCH$_3$ | |
| 7-132 | SC$_6$H$_5$ | CH$_2$SCH$_2$CH$_3$ | |
| 7-133 | SC$_6$H$_5$ | CH$_3$-S-CH$_2$-cyclopropyl | |
| 7-134 | SC$_6$H$_5$ | CH$_2$SCH$_2$CF$_3$ | |
| 7-135 | SC$_6$H$_5$ | CH$_2$SOCH$_3$ | |
| 7-136 | SC$_6$H$_5$ | CH$_2$SOCH$_2$CH$_3$ | |
| 7-137 | SC$_6$H$_5$ | CH$_3$-S(O)-CH$_2$-cyclopropyl | |
| 7-138 | SC$_6$H$_5$ | CH$_2$SOCH$_2$CF$_3$ | |
| 7-139 | SC$_6$H$_5$ | CH$_2$SO$_2$CH$_3$ | |
| 7-140 | SC$_6$H$_5$ | CH$_2$SO$_2$CH$_2$CH$_3$ | |
| 7-141 | SC$_6$H$_5$ | CH$_3$-S(O)$_2$-CH$_2$-cyclopropyl | |
| 7-142 | SC$_6$H$_5$ | CH$_2$SO$_2$CH$_2$CF$_3$ | |
| 7-143 | SC$_6$H$_5$ | CH$_2$O(CH$_2$)$_2$OCH$_3$ | |
| 7-144 | SC$_6$H$_5$ | CH$_2$O(CH$_2$)$_2$OCH$_2$CH$_3$ | |
| 7-145 | SC$_6$H$_5$ | CH$_2$O(CH$_2$)$_2$OCH$_2$CF$_3$ | |
| 7-146 | SC$_6$H$_5$ | CH$_2$O(CH$_2$)$_2$SCH$_3$ | |
| 7-147 | SC$_6$H$_5$ | CH$_2$O(CH$_2$)$_2$SCH$_2$CF$_3$ | |
| 7-148 | SC$_6$H$_5$ | CH$_2$O(CH$_2$)$_2$SOCH$_3$ | |
| 7-149 | SC$_6$H$_5$ | CH$_2$O(CH$_2$)$_2$SOCH$_2$CF$_3$ | |
| 7-150 | SC$_6$H$_5$ | CH$_2$O(CH$_2$)$_2$SO$_2$CH$_3$ | |
| 7-151 | SC$_6$H$_5$ | CH$_2$O(CH$_2$)$_2$SO$_2$CH$_2$CF$_3$ | |
| 7-152 | SC$_6$H$_5$ | CH$_3$-O-CH$_2$-(tetrahydrofuran-2-yl) | |
| 7-153 | SC$_6$H$_5$ | 3-methoxytetrahydrofuran-yl | |
| 7-154 | SC$_6$H$_5$ | CH$_2$O(CH$_2$)$_2$NHSO$_2$CH$_3$ | |
| 7-155 | SC$_6$H$_5$ | CH$_2$O(CH$_2$)$_2$N(CH$_3$)(SO$_2$CH$_3$) | |
| 7-156 | SCH$_2$C$_6$H$_5$ | CH$_3$ | |
| 7-157 | SCH$_2$C$_6$H$_5$ | CF$_3$ | |
| 7-158 | SCH$_2$C$_6$H$_5$ | CH$_2$OCH$_3$ | |
| 7-159 | SCH$_2$C$_6$H$_5$ | CH$_2$OCH$_2$CH$_3$ | |
| 7-160 | SCH$_2$C$_6$H$_5$ | CH$_3$-O-CH$_2$-cyclopropyl | |

TABLE 91

| compound number | R4 | R1 | physical property (melting point-ND) |
|---|---|---|---|
| 7-161 | SCH$_2$C$_6$H$_5$ | CH$_2$OCH$_2$CF$_3$ | |
| 7-162 | SCH$_2$C$_6$H$_5$ | CH$_2$SCH$_3$ | |
| 7-163 | SCH$_2$C$_6$H$_5$ | CH$_2$SCH$_2$CH$_3$ | |
| 7-164 | SCH$_2$C$_6$H$_5$ | CH$_3$-S-CH$_2$-cyclopropyl | |
| 7-165 | SCH$_2$C$_6$H$_5$ | CH$_2$SCH$_2$CF$_3$ | |
| 7-166 | SCH$_2$C$_6$H$_5$ | CH$_2$SOCH$_3$ | |
| 7-167 | SCH$_2$C$_6$H$_5$ | CH$_2$SOCH$_2$CH$_3$ | |
| 7-168 | SCH$_2$C$_6$H$_5$ | CH$_3$-S(O)-CH$_2$-cyclopropyl | |
| 7-169 | SCH$_2$C$_6$H$_5$ | CH$_2$SOCH$_2$CF$_3$ | |
| 7-170 | SCH$_2$C$_6$H$_5$ | CH$_2$SO$_2$CH$_3$ | |
| 7-171 | SCH$_2$C$_6$H$_5$ | CH$_2$SO$_2$CH$_2$CH$_3$ | |
| 7-172 | SCH$_2$C$_6$H$_5$ | CH$_3$-S(O)$_2$-CH$_2$-cyclopropyl | |
| 7-173 | SCH$_2$C$_6$H$_5$ | CH$_2$SO$_2$CH$_2$CF$_3$ | |
| 7-174 | SCH$_2$C$_6$H$_5$ | CH$_2$O(CH$_2$)$_2$OCH$_3$ | |
| 7-175 | SCH$_2$C$_6$H$_5$ | CH$_2$O(CH$_2$)$_2$OCH$_2$CH$_3$ | |
| 7-176 | SCH$_2$C$_6$H$_5$ | CH$_2$O(CH$_2$)$_2$OCH$_2$CF$_3$ | |
| 7-177 | SCH$_2$C$_6$H$_5$ | CH$_2$O(CH$_2$)$_2$SCH$_3$ | |
| 7-178 | SCH$_2$C$_6$H$_5$ | CH$_2$O(CH$_2$)$_2$SCH$_2$CF$_3$ | |
| 7-179 | SCH$_2$C$_6$H$_5$ | CH$_2$O(CH$_2$)$_2$SOCH$_3$ | |
| 7-180 | SCH$_2$C$_6$H$_5$ | CH$_2$O(CH$_2$)$_2$SOCH$_2$CF$_3$ | |
| 7-181 | SCH$_2$C$_6$H$_5$ | CH$_2$O(CH$_2$)$_2$SO$_2$CH$_3$ | |
| 7-182 | SCH$_2$C$_6$H$_5$ | CH$_2$O(CH$_2$)$_2$SO$_2$CH$_2$CF$_3$ | |
| 7-183 | SCH$_2$C$_6$H$_5$ | CH$_3$-O-CH$_2$-(tetrahydrofuran-2-yl) | |
| 7-184 | SCH$_2$C$_6$H$_5$ | 3-methoxytetrahydrofuran-yl | |
| 7-185 | SCH$_2$C$_6$H$_5$ | CH$_2$O(CH$_2$)$_2$NHSO$_2$CH$_3$ | |
| 7-186 | SCH$_2$C$_6$H$_5$ | CH$_2$O(CH$_2$)$_2$N(CH$_3$)(SO$_2$CH$_3$) | |
| 7-187 | 1H-pyrazole-1-yl | CH$_3$ | |
| 7-188 | 1H-pyrazole-1-yl | CF$_3$ | |
| 7-189 | 1H-pyrazole-1-yl | CH$_2$OCH$_3$ | |
| 7-190 | 1H-pyrazole-1-yl | CH$_2$OCH$_2$CH$_3$ | |

TABLE 91-continued

| compound number | R4 | R1 | physical property (melting point-ND) |
|---|---|---|---|
| 7-191 | 1H-pyrazole-1-yl | CH₃-O-CH₂-cyclopropyl | |
| 7-192 | 1H-pyrazole-1-yl | CH₂OCH₂CF₃ | |
| 7-193 | 1H-pyrazole-1-yl | CH₂SCH₃ | |
| 7-194 | 1H-pyrazole-1-yl | CH₂SCH₂CH₃ | |
| 7-195 | 1H-pyrazole-1-yl | CH₃-S-CH₂-cyclopropyl | |
| 7-196 | 1H-pyrazole-1-yl | CH₂SCH₂CF₃ | |
| 7-197 | 1H-pyrazole-1-yl | CH₂SOCH₃ | |
| 7-198 | 1H-pyrazole-1-yl | CH₂SOCH₂CH₃ | |
| 7-199 | 1H-pyrazole-1-yl | CH₃-S(=O)-CH₂-cyclopropyl | |
| 7-200 | 1H-pyrazole-1-yl | CH₂SOCH₂CF₃ | |

TABLE 92

| compound number | R4 | R1 | physical property (melting point-ND) |
|---|---|---|---|
| 7-201 | 1H-pyrazole-1-yl | CH₂SO₂CH₃ | |
| 7-202 | 1H-pyrazole-1-yl | CH₂SO₂CH₂CH₃ | |
| 7-203 | 1H-pyrazole-1-yl | CH₃-S(=O)₂-CH₂-cyclopropyl | |
| 7-204 | 1H-pyrazole-1-yl | CH₂SO₂CH₂CF₃ | |
| 7-205 | 1H-pyrazole-1-yl | CH₂O(CH₂)₂OCH₃ | |
| 7-206 | 1H-pyrazole-1-yl | CH₂O(CH₂)₂OCH₂CH₃ | |
| 7-207 | 1H-pyrazole-1-yl | CH₂O(CH₂)₂OCH₂CF₃ | |
| 7-208 | 1H-pyrazole-1-yl | CH₂O(CH₂)₂SCH₃ | |
| 7-209 | 1H-pyrazole-1-yl | CH₂O(CH₂)₂SCH₂CF₃ | |
| 7-210 | 1H-pyrazole-1-yl | CH₂O(CH₂)₂SOCH₃ | |
| 7-211 | 1H-pyrazole-1-yl | CH₂O(CH₂)₂SOCH₂CF₃ | |
| 7-212 | 1H-pyrazole-1-yl | CH₂O(CH₂)₂SO₂CH₃ | |
| 7-213 | 1H-pyrazole-1-yl | CH₂O(CH₂)₂SO₂CH₂CF₃ | |
| 7-214 | 1H-pyrazole-1-yl | CH₃-O-CH₂-(tetrahydrofuran-2-yl) | |
| 7-215 | 1H-pyrazole-1-yl | CH₃-O-(tetrahydrofuran-3-yl) | |
| 7-216 | 1H-pyrazole-1-yl | CH₂O(CH₂)₂NHSO₂CH₃ | |
| 7-217 | 1H-pyrazole-1-yl | CH₂O(CH₂)₂N(CH₃)(SO₂CH₃) | |
| 7-218 | 1H-imidazole-1-yl | CH₃ | |
| 7-219 | 1H-imidazole-1-yl | CF₃ | |
| 7-220 | 1H-imidazole-1-yl | CH₂OCH₃ | |
| 7-221 | 1H-imidazole-1-yl | CH₂OCH₂CH₃ | |

TABLE 92-continued

| compound number | R4 | R1 | physical property (melting point-ND) |
|---|---|---|---|
| 7-222 | 1H-imidazole-1-yl | CH₃-O-CH₂-cyclopropyl | |
| 7-223 | 1H-imidazole-1-yl | CH₂OCH₂CF₃ | |
| 7-224 | 1H-imidazole-1-yl | CH₂SCH₃ | |
| 7-225 | 1H-imidazole-1-yl | CH₂SCH₂CH₃ | |
| 7-226 | 1H-imidazole-1-yl | CH₃-S-CH₂-cyclopropyl | |
| 7-227 | 1H-imidazole-1-yl | CH₂SCH₂CF₃ | |
| 7-228 | 1H-imidazole-1-yl | CH₂SOCH₃ | |
| 7-229 | 1H-imidazole-1-yl | CH₂SOCH₂CH₃ | |
| 7-230 | 1H-imidazole-1-yl | CH₃-S(=O)-CH₂-cyclopropyl | |
| 7-231 | 1H-imidazole-1-yl | CH₂SOCH₂CF₃ | |
| 7-232 | 1H-imidazole-1-yl | CH₂SO₂CH₃ | |
| 7-233 | 1H-imidazole-1-yl | CH₂SO₂CH₂CH₃ | |
| 7-234 | 1H-imidazole-1-yl | CH₃-S(=O)₂-CH₂-cyclopropyl | |
| 7-235 | 1H-imidazole-1-yl | CH₂SO₂CH₂CF₃ | |
| 7-236 | 1H-imidazole-1-yl | CH₂O(CH₂)₂OCH₃ | |
| 7-237 | 1H-imidazole-1-yl | CH₂O(CH₂)₂OCH₂CH₃ | |
| 7-238 | 1H-imidazole-1-yl | CH₂O(CH₂)₂OCH₂CF₃ | |
| 7-239 | 1H-imidazole-1-yl | CH₂O(CH₂)₂SCH₃ | |
| 7-240 | 1H-imidazole-1-yl | CH₂O(CH₂)₂SCH₂CF₃ | |

TABLE 93

| compound number | R4 | R1 | physical property (melting point-ND) |
|---|---|---|---|
| 7-241 | 1H-imidazole-1-yl | CH₂O(CH₂)₂SOCH₃ | |
| 7-242 | 1H-imidazole-1-yl | CH₂O(CH₂)₂SOCH₂CF₃ | |
| 7-243 | 1H-imidazole-1-yl | CH₂O(CH₂)₂SO₂CH₃ | |
| 7-244 | 1H-imidazole-1-yl | CH₂O(CH₂)₂SO₂CH₂CF₃ | |
| 7-245 | 1H-imidazole-1-yl | CH₃-O-CH₂-(tetrahydrofuran-2-yl) | |
| 7-246 | 1H-imidazole-1-yl | CH₃-O-(tetrahydrofuran-3-yl) | |
| 7-247 | 1H-imidazole-1-yl | CH₂O(CH₂)₂NHSO₂CH₃ | |
| 7-248 | 1H-imidazole-1-yl | CH₂O(CH₂)₂N(CH₃)(SO₂CH₃) | |
| 7-249 | 1H-triazole-1-yl | CH₃ | |
| 7-250 | 1H-triazole-1-yl | CF₃ | |
| 7-251 | 1H-triazole-1-yl | CH₂OCH₃ | |
| 7-252 | 1H-triazole-1-yl | CH₂OCH₂CH₃ | |

TABLE 93-continued

| compound number | R4 | R1 | physical property (melting point-ND) |
|---|---|---|---|
| 7-253 | 1H-triazole-1-yl | CH₃-O-CH₂-cyclopropyl | |
| 7-254 | 1H-triazole-1-yl | CH₂OCH₂CF₃ | |
| 7-255 | 1H-triazole-1-yl | CH₂SCH₃ | |
| 7-256 | 1H-triazole-1-yl | CH₂SCH₂CH₃ | |
| 7-257 | 1H-triazole-1-yl | CH₃-S-CH₂-cyclopropyl | |
| 7-258 | 1H-triazole-1-yl | CH₂SCH₂CF₃ | |
| 7-259 | 1H-triazole-1-yl | CH₂SOCH₃ | |
| 7-260 | 1H-triazole-1-yl | CH₂SOCH₂CH₃ | |
| 7-261 | 1H-triazole-1-yl | CH₃-S(O)-CH₂-cyclopropyl | |
| 7-262 | 1H-triazole-1-yl | CH₂SOCH₂CF₃ | |
| 7-263 | 1H-triazole-1-yl | CH₂SO₂CH₃ | |
| 7-264 | 1H-triazole-1-yl | CH₂SO₂CH₂CH₃ | |
| 7-265 | 1H-triazole-1-yl | CH₃-SO₂-CH₂-cyclopropyl | |
| 7-266 | 1H-triazole-1-yl | CH₂SO₂CH₂CF₃ | |
| 7-267 | 1H-triazole-1-yl | CH₂O(CH₂)₂OCH₃ | |
| 7-268 | 1H-triazole-1-yl | CH₂O(CH₂)₂OCH₂CH₃ | |
| 7-269 | 1H-triazole-1-yl | CH₂O(CH₂)₂OCH₂CF₃ | |
| 7-270 | 1H-triazole-1-yl | CH₂O(CH₂)₂SCH₃ | |
| 7-271 | 1H-triazole-1-yl | CH₂O(CH₂)₂SCH₂CF₃ | |
| 7-272 | 1H-triazole-1-yl | CH₂O(CH₂)₂SOCH₃ | |
| 7-273 | 1H-triazole-1-yl | CH₂O(CH₂)₂SOCH₂CF₃ | |
| 7-274 | 1H-triazole-1-yl | CH₂O(CH₂)₂SO₂CH₃ | |
| 7-275 | 1H-triazole-1-yl | CH₂O(CH₂)₂SO₂CH₂CF₃ | |
| 7-276 | 1H-triazole-1-yl | CH₃-O-CH₂-tetrahydrofuran-2-yl | |
| 7-277 | 1H-triazole-1-yl | CH₃-O-tetrahydrofuran-3-yl | |
| 7-278 | 1H-triazole-1-yl | CH₂O(CH₂)₂NHSO₂CH₃ | |
| 7-279 | 1H-triazole-1-yl | CH₂O(CH₂)₂N(CH₃)(SO₂CH₃) | |
| 7-280 | 1H-tetrazole-1-yl | CH₃ | |

TABLE 94

| compound number | R4 | R1 | physical property (melting point-ND) |
|---|---|---|---|
| 7-281 | 1H-tetrazole-1-yl | CF₃ | |
| 7-282 | 1H-tetrazole-1-yl | CH₂OCH₃ | |
| 7-283 | 1H-tetrazole-1-yl | CH₂OCH₂CH₃ | |
| 7-284 | 1H-tetrazole-1-yl | CH₃-O-CH₂-cyclopropyl | |
| 7-285 | 1H-tetrazole-1-yl | CH₂OCH₂CF₃ | |
| 7-286 | 1H-tetrazole-1-yl | CH₂SCH₃ | |
| 7-287 | 1H-tetrazole-1-yl | CH₂SCH₂CH₃ | |
| 7-288 | 1H-tetrazole-1-yl | CH₃-S-CH₂-cyclopropyl | |
| 7-289 | 1H-tetrazole-1-yl | CH₂SCH₂CF₃ | |
| 7-290 | 1H-tetrazole-1-yl | CH₂SOCH₃ | |
| 7-291 | 1H-tetrazole-1-yl | CH₂SOCH₂CH₃ | |
| 7-292 | 1H-tetrazole-1-yl | CH₃-S(O)-CH₂-cyclopropyl | |
| 7-293 | 1H-tetrazole-1-yl | CH₂SOCH₂CF₃ | |
| 7-294 | 1H-tetrazole-1-yl | CH₂SO₂CH₃ | |
| 7-295 | 1H-tetrazole-1-yl | CH₂SO₂CH₂CH₃ | |
| 7-296 | 1H-tetrazole-1-yl | CH₃-SO₂-CH₂-cyclopropyl | |
| 7-297 | 1H-tetrazole-1-yl | CH₂SO₂CH₂CF₃ | |
| 7-298 | 1H-tetrazole-1-yl | CH₂O(CH₂)₂OCH₃ | |
| 7-299 | 1H-tetrazole-1-yl | CH₂O(CH₂)₂OCH₂CH₃ | |
| 7-300 | 1H-tetrazole-1-yl | CH₂O(CH₂)₂OCH₂CF₃ | |
| 7-301 | 1H-tetrazole-1-yl | CH₂O(CH₂)₂SCH₃ | |
| 7-302 | 1H-tetrazole-1-yl | CH₂O(CH₂)₂SCH₂CF₃ | |
| 7-303 | 1H-tetrazole-1-yl | CH₂O(CH₂)₂SOCH₃ | |
| 7-304 | 1H-tetrazole-1-yl | CH₂O(CH₂)₂SOCH₂CF₃ | |
| 7-305 | 1H-tetrazole-1-yl | CH₂O(CH₂)₂SO₂CH₃ | |
| 7-306 | 1H-tetrazole-1-yl | CH₂O(CH₂)₂SO₂CH₂CF₃ | |
| 7-307 | 1H-tetrazole-1-yl | CH₃-O-CH₂-tetrahydrofuran-2-yl | |
| 7-308 | 1H-tetrazole-1-yl | CH₃-O-tetrahydrofuran-3-yl | |
| 7-309 | 1H-tetrazole-1-yl | CH₂O(CH₂)₂NHSO₂CH₃ | |
| 7-310 | 1H-tetrazole-1-yl | CH₂O(CH₂)₂N(CH₃)(SO₂CH₃) | |
| 7-311 | 1H-tetrazole-2-yl | CH₃ | |
| 7-312 | 1H-tetrazole-2-yl | CF₃ | |
| 7-313 | 1H-tetrazole-2-yl | CH₂OCH₃ | |
| 7-314 | 1H-tetrazole-2-yl | CH₂OCH₂CH₃ | |
| 7-315 | 1H-tetrazole-2-yl | CH₃-O-CH₂-cyclopropyl | |
| 7-316 | 1H-tetrazole-2-yl | CH₂OCH₂CF₃ | |
| 7-317 | 1H-tetrazole-2-yl | CH₂SCH₃ | |
| 7-318 | 1H-tetrazole-2-yl | CH₂SCH₂CH₃ | |

TABLE 94-continued

| compound number | R4 | R1 | physical property (melting point-ND) |
|---|---|---|---|
| 7-319 | 1H-tetrazole-2-yl | CH₃–S–CH₂–cyclopropyl | |
| 7-320 | 1H-tetrazole-2-yl | CH₂SCH₂CF₃ | |

TABLE 95

| compound number | R4 | R1 | physical property (melting point-ND) |
|---|---|---|---|
| 7-321 | 1H-tetrazole-2-yl | CH₂SOCH₃ | |
| 7-322 | 1Htetrazole-2-yl | CH₂SOCH₂CH₃ | |
| 7-323 | 1H-tetrazole-2-yl | CH₃–S(=O)–CH₂–cyclopropyl | |
| 7-324 | 1H-tetrazole-2-yl | CH₂SOCH₂CF₃ | |
| 7-325 | 1H-tetrazole-2-yl | CH₂SO₂CH₃ | |
| 7-326 | 1H-tetrazole-2-yl | CH₂SO₂CH₂CH₃ | |
| 7-327 | 1H-tetrazole-2-yl | CH₃–S(=O)₂–CH₂–cyclopropyl | |
| 7-328 | 1H-tetrazole-2-yl | CH₂SO₂CH₂CF₃ | |
| 7-329 | 1H-tetrazole-2-yl | CH₂O(CH₂)₂OCH₃ | |
| 7-330 | 1H-tetrazole-2-yl | CH₂O(CH₂)₂OCH₂CH₃ | |
| 7-331 | 1H-tetrazole2-yl | CH₂O(CH₂)₂OCH₂CF₃ | |
| 7-332 | 1H-tetrazole-2-yl | CH₂O(CH₂)₂SCH₃ | |
| 7-333 | 1H-tetrazole-2-yl | CH₂O(CH₂)₂SCH₂CF₃ | |
| 7-334 | 1H-tetrazole-2-yl | CH₂O(CH₂)₂SOCH₃ | |
| 7-335 | 1H-tetrazole-2-yl | CH₂O(CH₂)₂SOCH₂CF₃ | |
| 7-336 | 1H-tetrazole-2-yl | CH₂O(CH₂)₂SO₂CH₃ | |
| 7-337 | 1H-tetrazole-2-yl | CH₂O(CH₂)₂SO₂CH₂CF₃ | |
| 7-338 | 1H-tetrazole-2-yl | CH₃–O–CH₂–(tetrahydrofuran-2-yl) | |
| 7-339 | 1H-tetrazole-2-yl | CH₃–O–(tetrahydrofuran-3-yl) | |
| 7-340 | 1H-tetrazole-2-yl | CH₂O(CH₂)₂NHSO₂CH₃ | |
| 7-341 | 1H-tetrazole-2-yl | CH₂O(CH₂)₂N(CH₃)(SO₂CH₃) | |

TABLE 96

| compound number | R4 | R1 | physical property (melting point-ND) |
|---|---|---|---|
| 8-1 | Cl | CH₃ | |
| 8-2 | Cl | CF₃ | |
| 8-3 | Cl | CH₂OCH₃ | |
| 8-4 | Cl | CH₂OCH₂CH₃ | |
| 8-5 | Cl | CH₃–O–CH₂–cyclopropyl | |
| 8-6 | Cl | CH₂OCH₂CF₃ | |
| 8-7 | Cl | CH₂SCH₃ | |
| 8-8 | Cl | CH₂SCH₂CH₃ | |
| 8-9 | Cl | CH₃–S–CH₂–cyclopropyl | |
| 8-10 | Cl | CH₂SCH₂CF₃ | |
| 8-11 | Cl | CH₂SOCH₃ | |
| 8-12 | Cl | CH₂SOCH₂CH₃ | |
| 8-13 | Cl | CH₃–S(=O)–CH₂–cyclopropyl | |
| 8-14 | Cl | CH₂SOCH₂CF₃ | |
| 8-15 | Cl | CH₂SO₂CH₃ | |
| 8-16 | Cl | CH₂SO₂CH₂CH₃ | |
| 8-17 | Cl | CH₃–S(=O)₂–CH₂–cyclopropyl | |
| 8-18 | Cl | CH₂SO₂CH₂CF₃ | |
| 8-19 | Cl | CH₂O(CH₂)₂OCH₃ | |
| 8-20 | Cl | CH₂O(CH₂)₂OCH₂CH₃ | |
| 8-21 | Cl | CH₂O(CH₂)₂OCH₂CF₃ | |
| 8-22 | Cl | CH₂O(CH₂)₂SCH₃ | |
| 8-23 | Cl | CH₂O(CH₂)₂SCH₂CF₃ | |
| 8-24 | Cl | CH₂O(CH₂)₂SOCH₃ | |
| 8-25 | Cl | CH₂O(CH₂)₂SOCH₂CF₃ | |
| 8-26 | Cl | CH₂O(CH₂)₂SO₂CH₃ | |
| 8-27 | Cl | CH₂O(CH₂)₂SO₂CH₂CF₃ | |
| 8-28 | Cl | CH₃–O–CH₂–(tetrahydrofuran-2-yl) | |
| 8-29 | Cl | CH₃–O–(tetrahydrofuran-3-yl) | |
| 8-30 | Cl | CH₂O(CH₂)₂NHSO₂CH₃ | |
| 8-31 | Cl | CH₂O(CH₂)₂N(CH₃)(SO₂CH₃) | |
| 8-32 | SCH₃ | CH₃ | |
| 8-33 | SCH₃ | CF₃ | |
| 8-34 | SCH₃ | CH₂OCH₃ | |
| 8-35 | SCH₃ | CH₂OCH₂CH₃ | |
| 8-36 | SCH₃ | CH₃–O–CH₂–cyclopropyl | |
| 8-37 | SCH₃ | CH₂OCH₂CF₃ | |
| 8-38 | SCH₃ | CH₂SCH₃ | |
| 8-39 | SCH₃ | CH₂SCH₂CH₃ | |

TABLE 96-continued

| compound number | R4 | R1 | physical property (melting point-ND) |
|---|---|---|---|
| 8-40 | SCH$_3$ | CH$_3$-S-CH$_2$-cyclopropyl | |

TABLE 97

| compound number | R4 | R1 | physical property (melting point-ND) |
|---|---|---|---|
| 8-41 | SCH$_3$ | CH$_2$SCH$_2$CF$_3$ | |
| 8-42 | SCH$_3$ | CH$_2$SOCH$_3$ | |
| 8-43 | SCH$_3$ | CH$_2$SOCH$_2$CH$_3$ | |
| 8-44 | SCH$_3$ | CH$_3$-S(=O)-CH$_2$-cyclopropyl | |
| 8-45 | SCH$_3$ | CH$_2$SOCH$_2$CF$_3$ | |
| 8-46 | SCH$_3$ | CH$_2$SO$_2$CH$_3$ | |
| 8-47 | SCH$_3$ | CH$_2$SO$_2$CH$_2$CH$_3$ | |
| 8-48 | SCH$_3$ | CH$_3$-S(=O)$_2$-CH$_2$-cyclopropyl | |
| 8-49 | SCH$_3$ | CH$_2$SO$_2$CH$_2$CF$_3$ | |
| 8-50 | SCH$_3$ | CH$_2$O(CH$_2$)$_2$OCH$_3$ | |
| 8-51 | SCH$_3$ | CH$_2$O(CH$_2$)$_2$OCH$_2$CH$_3$ | |
| 8-52 | SCH$_3$ | CH$_2$O(CH$_2$)OCH$_2$CF$_3$ | |
| 8-53 | SCH$_3$ | CH$_2$O(CH$_2$)$_2$SCH$_3$ | |
| 8-54 | SCH$_3$ | CH$_2$O(CH$_2$)$_2$SCH$_2$CF$_3$ | |
| 8-55 | SCH$_3$ | CH$_2$O(CH$_2$)$_2$SOCH$_3$ | |
| 8-56 | SCH$_3$ | CH$_2$O(CH$_2$)$_2$SOCH$_2$CF$_3$ | |
| 8-57 | SCH$_3$ | CH$_2$O(CH$_2$)$_2$SO$_2$CH$_3$ | |
| 8-58 | SCH$_3$ | CH$_2$O(CH$_2$)$_2$SO$_2$CH$_2$CF$_3$ | |
| 8-59 | SCH$_3$ | CH$_3$-O-CH$_2$-(tetrahydrofuran-2-yl) | |
| 8-60 | SCH$_3$ | CH$_3$-O-(tetrahydrofuran-3-yl) | |
| 8-61 | SCH$_3$ | CH$_2$O(CH$_2$)$_2$NHSO$_2$CH$_3$ | |
| 8-62 | SCH$_3$ | CH$_2$O(CH$_2$)$_2$N(CH$_3$)(SO$_2$CH$_3$) | |
| 8-63 | SCH$_2$CH$_3$ | CH$_3$ | |
| 8-64 | SCH$_2$CH$_3$ | CF$_3$ | |
| 8-65 | SCH$_2$CH$_3$ | CH$_2$OCH$_3$ | |
| 8-66 | SCH$_2$CH$_3$ | CH$_2$OCH$_2$CH$_3$ | |
| 8-67 | SCH$_2$CH$_3$ | CH$_3$-O-CH$_2$-cyclopropyl | |
| 8-68 | SCH$_2$CH$_3$ | CH$_2$OCH$_2$CF$_3$ | |
| 8-69 | SCH$_2$CH$_3$ | CH$_2$SCH$_3$ | |
| 8-70 | SCH$_2$CH$_3$ | CH$_2$SCH$_2$CH$_3$ | |
| 8-71 | SCH$_2$CH$_3$ | CH$_3$-S-CH$_2$-cyclopropyl | |
| 8-72 | SCH$_2$CH$_3$ | CH$_2$SCH$_2$CF$_3$ | |
| 8-73 | SCH$_2$CH$_3$ | CH$_2$SOCH$_3$ | |
| 8-74 | SCH$_2$CH$_3$ | CH$_2$SOCH$_2$CH$_3$ | |
| 8-75 | SCH$_2$CH$_3$ | CH$_3$-S(=O)-CH$_2$-cyclopropyl | |
| 8-76 | SCH$_2$CH$_3$ | CH$_2$SOCH$_2$CF$_3$ | |
| 8-77 | SCH$_2$CH$_3$ | CH$_2$SO$_2$CH$_3$ | |
| 8-78 | SCH$_2$CH$_3$ | CH$_2$SO$_2$CH$_2$CH$_3$ | |
| 8-79 | SCH$_2$CH$_3$ | CH$_3$-S(=O)$_2$-CH$_2$-cyclopropyl | |
| 8-80 | SCH$_2$CH$_3$ | CH$_2$SO$_2$CH$_2$CF$_3$ | |

TABLE 98

| compound number | R4 | R1 | physical property (melting point-ND) |
|---|---|---|---|
| 8-81 | SCH$_2$CH$_3$ | CH$_2$O(CH$_2$)$_2$OCH$_3$ | |
| 8-82 | SCH$_2$CH$_3$ | CH$_2$O(CH$_2$)$_2$OCH$_2$CH$_3$ | |
| 8-83 | SCH$_2$CH$_3$ | CH$_2$O(CH$_2$)$_2$OCH$_2$CF$_3$ | |
| 8-84 | SCH$_2$CH$_3$ | CH$_2$O(CH$_2$)$_2$SCH$_3$ | |
| 8-85 | SCH$_2$CH$_3$ | CH$_2$O(CH$_2$)$_2$SCH$_2$CF$_3$ | |
| 8-86 | SCH$_2$CH$_3$ | CH$_2$O(CH$_2$)$_2$SOCH$_3$ | |
| 8-87 | SCH$_2$CH$_3$ | CH$_2$O(CH$_2$)$_2$SOCH$_2$CF$_3$ | |
| 8-88 | SCH$_2$CH$_3$ | CH$_2$O(CH$_2$)$_2$SO$_2$CH$_3$ | |
| 8-89 | SCH$_2$CH$_3$ | CH$_2$O(CH$_2$)$_2$SO$_2$CH$_2$CF$_3$ | |
| 8-90 | SCH$_2$CH$_3$ | CH$_3$-O-CH$_2$-(tetrahydrofuran-2-yl) | |
| 8-91 | SCH$_2$CH$_3$ | CH$_3$-O-(tetrahydrofuran-3-yl) | |
| 8-92 | SCH$_2$CH$_3$ | CH$_2$O(CH$_2$)$_2$NHSO$_2$CH$_3$ | |
| 8-93 | SCH$_2$CH$_3$ | CH$_2$O(CH$_2$)$_2$N(CH$_3$)(SO$_2$CH$_3$) | |
| 8-94 | S(CH$_2$)$_2$CH$_3$ | CH$_3$ | |
| 8-95 | S(CH$_2$)$_2$CH$_3$ | CF$_3$ | |
| 8-96 | S(CH$_2$)$_2$CH$_3$ | CH$_2$OCH$_3$ | |
| 8-97 | S(CH$_2$)$_2$CH$_3$ | CH$_2$OCH$_2$CH$_3$ | |
| 8-98 | S(CH$_2$)$_2$CH$_3$ | CH$_3$-O-CH$_2$-cyclopropyl | |
| 8-99 | S(CH$_2$)$_2$CH$_3$ | CH$_2$OCH$_2$CF$_3$ | |
| 8-100 | S(CH$_2$)$_2$CH$_3$ | CH$_2$SCH$_3$ | |
| 8-101 | S(CH$_2$)$_2$CH$_3$ | CH$_2$SCH$_2$CH$_3$ | |

TABLE 98-continued

| compound number | R4 | R1 | physical property (melting point-ND) |
|---|---|---|---|
| 8-102 | S(CH$_2$)$_2$CH$_3$ | CH$_3$-S-CH$_2$-cyclopropyl | |
| 8-103 | S(CH$_2$)$_2$CH$_3$ | CH$_2$SCH$_2$CF$_3$ | |
| 8-104 | S(CH$_2$)$_2$CH$_3$ | CH$_2$SOCH$_3$ | |
| 8-105 | S(CH$_2$)$_2$CH$_3$ | CH$_2$SOCH$_2$CH$_3$ | |
| 8-106 | S(CH$_2$)$_2$CH$_3$ | CH$_3$-S(O)-CH$_2$-cyclopropyl | |
| 8-107 | S(CH$_2$)$_2$CH$_3$ | CH$_2$SOCH$_2$CF$_3$ | |
| 8-108 | S(CH$_2$)$_2$CH$_3$ | CH$_2$SO$_2$CH$_3$ | |
| 8-109 | S(CH$_2$)$_2$CH$_3$ | CH$_2$SO$_2$CH$_2$CH$_3$ | |
| 8-110 | S(CH$_2$)$_2$CH$_3$ | CH$_3$-SO$_2$-CH$_2$-cyclopropyl | |
| 8-111 | S(CH$_2$)$_2$CH$_3$ | CH$_2$SO$_2$CH$_2$CF$_3$ | |
| 8-112 | S(CH$_2$)$_2$CH$_3$ | CH$_2$O(CH$_2$)$_2$OCH$_3$ | |
| 8-113 | S(CH$_2$)$_2$CH$_3$ | CH$_2$O(CH$_2$)$_2$OCH$_2$CH$_3$ | |
| 8-114 | S(CH$_2$)$_2$CH$_3$ | CH$_2$O(CH$_2$)$_2$OCH$_2$CF$_3$ | |
| 8-115 | S(CH$_2$)$_2$CH$_3$ | CH$_2$O(CH$_2$)$_2$SCH$_3$ | |
| 8-116 | S(CH$_2$)$_2$CH$_3$ | CH$_2$O(CH$_2$)$_2$SCH$_2$CF$_3$ | |
| 8-117 | S(CH$_2$)$_2$CH$_3$ | CH$_2$O(CH$_2$)$_2$SOCH$_3$ | |
| 8-118 | S(CH$_2$)$_2$CH$_3$ | CH$_2$O(CH$_2$)$_2$SOCH$_2$CF$_3$ | |
| 8-119 | S(CH$_2$)$_2$CH$_3$ | CH$_2$O(CH$_2$)$_2$SO$_2$CH$_3$ | |
| 8-120 | S(CH$_2$)$_2$CH$_3$ | CH$_2$O(CH$_2$)$_2$SO$_2$CH$_2$CF$_3$ | |

TABLE 99

| compound number | R4 | R1 | physical property (melting point-ND) |
|---|---|---|---|
| 8-121 | S(CH$_2$)$_2$CH$_3$ | CH$_3$-O-CH$_2$-(tetrahydrofuran-2-yl) | |
| 8-122 | S(CH$_2$)$_2$CH$_3$ | CH$_3$-O-(tetrahydrofuran-3-yl) | |
| 8-123 | S(CH$_2$)$_2$CH$_3$ | CH$_2$O(CH$_2$)$_2$NHSO$_2$CH$_3$ | |
| 8-124 | S(CH$_2$)$_2$CH$_3$ | CH$_2$O(CH$_2$)$_2$N(CH$_3$)(SO$_2$CH$_3$) | |
| 8-125 | SC$_6$H$_5$ | CH$_3$ | |
| 8-126 | SC$_6$H$_5$ | CF$_3$ | |
| 8-127 | SC$_6$H$_5$ | CH$_2$OCH$_3$ | |
| 8-128 | SC$_6$H$_5$ | CH$_2$OCH$_2$CH$_3$ | |
| 8-129 | SC$_6$H$_5$ | CH$_3$-O-CH$_2$-cyclopropyl | |
| 8-130 | SC$_6$H$_5$ | CH$_2$OCH$_2$CF$_3$ | |
| 8-131 | SC$_6$H$_5$ | CH$_2$SCH$_3$ | |
| 8-132 | SC$_6$H$_5$ | CH$_2$SCH$_2$CH$_3$ | |

TABLE 99-continued

| compound number | R4 | R1 | physical property (melting point-ND) |
|---|---|---|---|
| 8-133 | SC$_6$H$_5$ | CH$_3$-S-CH$_2$-cyclopropyl | |
| 8-134 | SC$_6$H$_5$ | CH$_2$SCH$_2$CF$_3$ | |
| 8-135 | SC$_6$H$_5$ | CH$_2$SOCH$_3$ | |
| 8-136 | SC$_6$H$_5$ | CH$_2$SOCH$_2$CH$_3$ | |
| 8-137 | SC$_6$H$_5$ | CH$_3$-S(O)-CH$_2$-cyclopropyl | |
| 8-138 | SC$_6$H$_5$ | CH$_2$SOCH$_2$CF$_3$ | |
| 8-139 | SC$_6$H$_5$ | CH$_2$SO$_2$CH$_3$ | |
| 8-140 | SC$_6$H$_5$ | CH$_2$SO$_2$CH$_2$CH$_3$ | |
| 8-141 | SC$_6$H$_5$ | CH$_3$-SO$_2$-CH$_2$-cyclopropyl | |
| 8-142 | SC$_6$H$_5$ | CH$_2$SO$_2$CH$_2$CF$_3$ | |
| 8-143 | SC$_6$H$_5$ | CH$_2$O(CH$_2$)$_2$OCH$_3$ | |
| 8-144 | SC$_6$H$_5$ | CH$_2$O(CH$_2$)$_2$OCH$_2$CH$_3$ | |
| 8-145 | SC$_6$H$_5$ | CH$_2$O(CH$_2$)$_2$OCH$_2$CF$_3$ | |
| 8-146 | SC$_6$H$_5$ | CH$_2$O(CH$_2$)$_2$SCH$_3$ | |
| 8-147 | SC$_6$H$_5$ | CH$_2$O(CH$_2$)$_2$SCH$_2$CF$_3$ | |
| 8-148 | SC$_6$H$_5$ | CH$_2$O(CH$_2$)$_2$SOCH$_3$ | |
| 8-149 | SC$_6$H$_5$ | CH$_2$O(CH$_2$)$_2$SOCH$_2$CF$_3$ | |
| 8-150 | SC$_6$H$_5$ | CH$_2$O(CH$_2$)$_2$SO$_2$CH$_3$ | |
| 8-151 | SC$_6$H$_5$ | CH$_2$O(CH$_2$)$_2$SO$_2$CH$_2$CF$_3$ | |
| 8-152 | SC$_6$H$_5$ | CH$_3$-O-CH$_2$-(tetrahydrofuran-2-yl) | |
| 8-153 | SC$_6$H$_5$ | CH$_3$-O-(tetrahydrofuran-3-yl) | |
| 8-154 | SC$_6$H$_5$ | CH$_2$O(CH$_2$)$_2$NHSO$_2$CH$_3$ | |
| 8-155 | SC$_6$H$_5$ | CH$_2$O(CH$_2$)$_2$N(CH$_3$)(SO$_2$CH$_3$) | |
| 8-156 | SCH$_2$C$_6$H$_5$ | CH$_3$ | |
| 8-157 | SCH$_2$C$_6$H$_5$ | CF$_3$ | |
| 8-158 | SCH$_2$C$_6$H$_5$ | CH$_2$OCH$_3$ | |
| 8-159 | SCH$_2$C$_6$H$_5$ | CH$_2$OCH$_2$CH$_3$ | |
| 8-160 | SCH$_2$C$_6$H$_5$ | CH$_3$-O-CH$_2$-cyclopropyl | |

TABLE 100

| compound number | R4 | R1 | physical property (melting point-ND) |
|---|---|---|---|
| 8-161 | SCH$_2$C$_6$H$_5$ | CH$_2$OCH$_2$CF$_3$ | |
| 8-162 | SCH$_2$C$_6$H$_5$ | CH$_2$SCH$_3$ | |
| 8-163 | SCH$_2$C$_6$H$_5$ | CH$_2$SCH$_2$CH$_3$ | |

TABLE 100-continued

| compound number | R4 | R1 | physical property (melting point-ND) |
|---|---|---|---|
| 8-164 | SCH$_2$C$_6$H$_5$ | 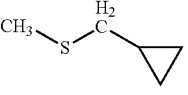 | |
| 8-165 | SCH$_2$C$_6$H$_5$ | CH$_2$SCH$_2$CF$_3$ | |
| 8-166 | SCH$_2$C$_6$H$_5$ | CH$_2$SOCH$_3$ | |
| 8-167 | SCH$_2$C$_6$H$_5$ | CH$_2$SOCH$_2$CH$_3$ | |
| 8-168 | SCH$_2$C$_6$H$_5$ | 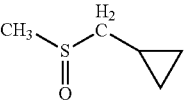 | |
| 8-169 | SCH$_2$C$_6$H$_5$ | CH$_2$SOCH$_2$CF$_3$ | |
| 8-170 | SCH$_2$C$_6$H$_5$ | CH$_2$SO$_2$CH$_3$ | |
| 8-171 | SCH$_2$C$_6$H$_5$ | CH$_2$SO$_2$CH$_2$CH$_3$ | |
| 8-172 | SCH$_2$C$_6$H$_5$ | 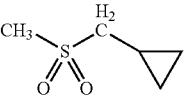 | |
| 8-173 | SCH$_2$C$_6$H$_5$ | CH$_2$SO$_2$CH$_2$CF$_3$ | |
| 8-174 | SCH$_2$C$_6$H$_5$ | CH$_2$O(CH$_2$)$_2$OCH$_3$ | |
| 8-175 | SCH$_2$C$_6$H$_5$ | CH$_2$O(CH$_2$)$_2$OCH$_2$CH$_3$ | |
| 8-176 | SCH$_2$C$_6$H$_5$ | CH$_2$O(CH$_2$)$_2$OCH$_2$CF$_3$ | |
| 8-177 | SCH$_2$C$_6$H$_5$ | CH$_2$O(CH$_2$)$_2$SCH$_3$ | |
| 8-178 | SCH$_2$C$_6$H$_5$ | CH$_2$O(CH$_2$)$_2$SCH$_2$CF$_3$ | |
| 8-179 | SCH$_2$C$_6$H$_5$ | CH$_2$O(CH$_2$)$_2$SOCH$_3$ | |
| 8-180 | SCH$_2$C$_6$H$_5$ | CH$_2$O(CH$_2$)$_2$SOCH$_2$CF$_3$ | |
| 8-181 | SCH$_2$C$_6$H$_5$ | CH$_2$O(CH$_2$)$_2$SO$_2$CH$_3$ | |
| 8-182 | SCH$_2$C$_6$H$_5$ | CH$_2$O(CH$_2$)$_2$SO$_2$CH$_2$CF$_3$ | |
| 8-183 | SCH$_2$C$_6$H$_5$ | 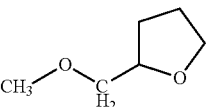 | |
| 8-184 | SCH$_2$C$_6$H$_5$ | 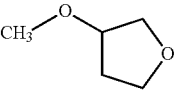 | |
| 8-185 | SCH$_2$C$_6$H$_5$ | CH$_2$O(CH$_2$)$_2$NHSO$_2$CH$_3$ | |
| 8-186 | SCH$_2$C$_6$H$_5$ | CH$_2$O(CH$_2$)$_2$N(CH$_3$)(SO$_2$CH$_3$) | |
| 8-187 | 1H-pyrazole-1-yl | CH$_3$ | |
| 8-188 | 1H-pyrazole-1-yl | CF$_3$ | |
| 8-189 | 1H-pyrazole-1-yl | CH$_2$OCH$_3$ | |
| 8-190 | 1H-pyrazole-1-yl | CH$_2$OCH$_2$CH$_3$ | |
| 8-191 | 1H-pyrazole-1-yl | 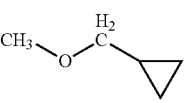 | |
| 8-192 | 1H-pyrazole-1-yl | CH$_2$OCH$_2$CF$_3$ | |
| 8-193 | 1H-pyrazole-1-yl | CH$_2$SCH$_3$ | |
| 8-194 | 1H-pyrazole-1-yl | CH$_2$SCH$_2$CH$_3$ | |
| 8-195 | 1H-pyrazole-1-yl | 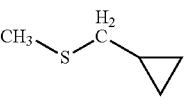 | |
| 8-196 | 1H-pyrazole-1-yl | CH$_2$SCH$_2$CF$_3$ | |
| 8-197 | 1H-pyrazole-1-yl | CH$_2$SOCH$_3$ | |
| 8-198 | 1H-pyrazole-1-yl | CH$_2$SOCH$_2$CH$_3$ | |

TABLE 100-continued

| compound number | R4 | R1 | physical property (melting point-ND) |
|---|---|---|---|
| 8-199 | 1H-pyrazole-1-yl | 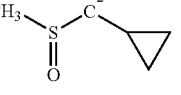 | |
| 8-200 | 1H-pyrazole-1-yl | CH$_2$SOCH$_2$CF$_3$ | |

TABLE 101

| compound number | R4 | R1 | physical property (melting point-ND) |
|---|---|---|---|
| 8-201 | 1H-pyrazole-1-yl | CH$_2$SO$_2$CH$_3$ | |
| 8-202 | 1H-pyrazole-1-yl | CH$_2$SO$_2$CH$_2$CH$_3$ | |
| 8-203 | 1H-pyrazole-1-yl | 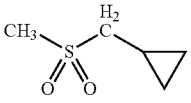 | |
| 8-204 | 1H-pyrazole-1-yl | CH$_2$SO$_2$CH$_2$CF$_3$ | |
| 8-205 | 1H-pyrazole-1-yl | CH$_2$O(CH$_3$)$_2$OCH$_3$ | |
| 8-206 | 1H-pyrazole-1-yl | CH$_2$O(CH$_3$)$_2$OCH$_2$CH$_3$ | |
| 8-207 | 1H-pyrazole-1-yl | CH$_2$O(CH$_3$)$_2$OCH$_2$CF$_3$ | |
| 8-208 | 1H-pyrazole-1-yl | CH$_2$O(CH$_3$)$_2$SCH$_3$ | |
| 8-209 | 1H-pyrazole-1-yl | CH$_2$O(CH$_3$)$_2$SCH$_2$CF$_3$ | |
| 8-210 | 1H-pyrazole-1-yl | CH$_2$O(CH$_3$)$_2$SOCH$_3$ | |
| 8-211 | 1H-pyrazole-1-yl | CH$_2$O(CH$_3$)$_2$SOCH$_2$CF$_3$ | |
| 8-212 | 1H-pyrazole-1-yl | CH$_2$O(CH$_3$)$_2$SO$_2$CH$_3$ | |
| 8-213 | 1H-pyrazole-1-yl | CH$_2$O(CH$_3$)$_2$SO$_2$CH$_2$CF$_3$ | |
| 8-214 | 1H-pyrazole-1-yl | 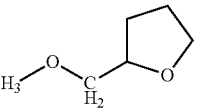 | |
| 8-215 | 1H-pyrazole-1-yl | 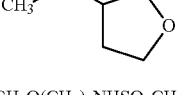 | |
| 8-216 | 1H-pyrazole-1-yl | CH$_2$O(CH$_3$)$_2$NHSO$_2$CH$_3$ | |
| 8-217 | 1H-pyrazole-1-yl | CH$_2$O(CH$_3$)$_2$N(CH$_3$)(SO$_2$CH$_3$) | |
| 8-218 | 1H-imidazole-1-yl | CH$_3$ | |
| 8-219 | 1H-imidazole-1-yl | CF$_3$ | |
| 8-220 | 1H-imidazole-1-yl | CH$_2$OCH$_3$ | |
| 8-221 | 1H-imidazole-1-yl | CH$_2$OCH$_2$CH$_3$ | |
| 8-222 | 1H-imidazole-1-yl | 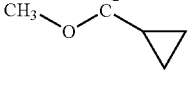 | |
| 8-223 | 1H-imidazole-1-yl | CH$_2$OCH$_2$CF$_3$ | |
| 8-224 | 1H-imidazole-1-yl | CH$_2$SCH$_3$ | |
| 8-225 | 1H-imidazole-1-yl | CH$_2$SCH$_2$CH$_3$ | |
| 8-226 | 1H-imidazole-1-yl | 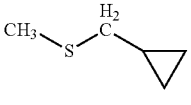 | |
| 8-227 | 1H-imidazole-1-yl | CH$_2$SCH$_2$CF$_3$ | |
| 8-228 | 1H-imidazole-1-yl | CH$_2$SOCH$_3$ | |
| 8-229 | 1H-imidazole-1-yl | CH$_2$SOCH$_2$CH$_3$ | |

TABLE 101-continued

| compound number | R4 | R1 | physical property (melting point-ND) |
|---|---|---|---|
| 8-230 | 1H-imidazole-1-yl | 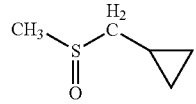 | |
| 8-231 | 1H-imidazole-1-yl | $CH_2SOCH_2CF_3$ | |
| 8-232 | 1H-imidazole-1-yl | $CH_2SO_2CH_3$ | |
| 8-233 | 1H-imidazole-1-yl | $CH_2SO_2CH_2CH_3$ | |
| 8-234 | 1H-imidazole-1-yl | 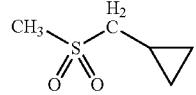 | |
| 8-235 | 1H-imidazole-1-yl | $CH_2SO_2CH_2CF_3$ | |
| 8-236 | 1H-imidazole-1-yl | $CH_2O(CH_3)_2OCH_3$ | |
| 8-237 | 1H-imidazole-1-yl | $CH_2O(CH_3)_2OCH_2CH_3$ | |
| 8-238 | 1H-imidazole-1-yl | $CH_2O(CH_3)_2OCH_2CF_3$ | |
| 8-239 | 1H-imidazole-1-yl | $CH_2O(CH_3)_2SCH_3$ | |
| 8-240 | 1H-imidazole-1-yl | $CH_2O(CH_3)_2SCH_2CF_3$ | |

TABLE 102

| compound number | R4 | R1 | physical property (melting point-ND) |
|---|---|---|---|
| 8-241 | 1H-imidazole-1-yl | $CH_2O(CH_3)_2SOCH_3$ | |
| 8-242 | 1H-imidazole-1-yl | $CH_2O(CH_3)_2SOCH_2CF_3$ | |
| 8-243 | 1H-imidazole-1-yl | $CH_2O(CH_3)_2SO_2CH_3$ | |
| 8-244 | 1H-imidazole-1-yl | $CH_2O(CH_3)_2SO_2CH_2CF_3$ | |
| 8-245 | 1H-imidazole-1-yl | 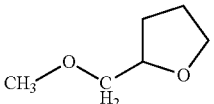 | |
| 8-246 | 1H-imidazole-1-yl | 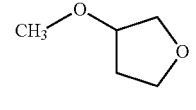 | |
| 8-247 | 1H-imidazole-1-yl | $CH_2O(CH_3)_2NHSO_2CH_3$ | |
| 8-248 | 1H-imidazole-1-yl | $CH_2O(CH_3)_2N(CH_3)(SO_2CH_3)$ | |
| 8-249 | 1H-triazole-1-yl | $CH_3$ | |
| 8-250 | 1H-triazole-1-yl | $CF_3$ | |
| 8-251 | 1H-triazole-1-yl | $CH_2OCH_3$ | |
| 8-252 | 1H-triazole-1-yl | $CH_2OCH_2CH_3$ | |
| 8-253 | 1H-triazole-1-yl | 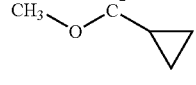 | |
| 8-254 | 1H-triazole-1-yl | $CH_2OCH_2CF_3$ | |
| 8-255 | 1H-triazole-1-yl | $CH_2SCH_3$ | |
| 8-256 | 1H-triazole-1-yl | $CH_2SCH_2CH_3$ | |
| 8-257 | 1H-triazole-1-yl | 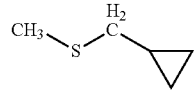 | |
| 8-258 | 1H-triazole-1-yl | $CH_2SCH_2CF_3$ | |
| 8-259 | 1H-triazole-1-yl | $CH_2SOCH_3$ | |
| 8-260 | 1H-triazole-1-yl | $CH_2SOCH_2CH_3$ | |

TABLE 102-continued

| compound number | R4 | R1 | physical property (melting point-ND) |
|---|---|---|---|
| 8-261 | 1H-triazole-1-yl | 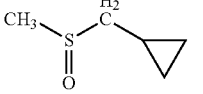 | |
| 8-262 | 1H-triazole-1-yl | $CH_2SOCH_2CF_3$ | |
| 8-263 | 1H-triazole-1-yl | $CH_2SO_2CH_3$ | |
| 8-264 | 1H-triazole-1-yl | $CH_2SO_2CH_2CH_3$ | |
| 8-265 | 1H-triazole-1-yl | 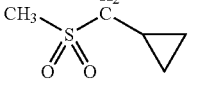 | |
| 8-266 | 1H-triazole-1-yl | $CH_2SO_2CH_2CF_3$ | |
| 8-267 | 1H-triazole-1-yl | $CH_2O(CH_3)_2OCH_3$ | |
| 8-268 | 1H-triazole-1-yl | $CH_2O(CH_3)_2OCH_2CH_3$ | |
| 8-269 | 1H-triazole-1-yl | $CH_2O(CH_3)_2OCH_2CF_3$ | |
| 8-270 | 1H-triazole-1-yl | $CH_2O(CH_3)_2SCH_3$ | |
| 8-271 | 1H-triazole-1-yl | $CH_2O(CH_3)_2SCH_2CF_3$ | |
| 8-272 | 1H-triazole-1-yl | $CH_2O(CH_3)_2SOCH_3$ | |
| 8-273 | 1H-triazole-1-yl | $CH_2O(CH_3)_2SOCH_2CF_3$ | |
| 8-274 | 1H-triazole-1-yl | $CH_2O(CH_3)_2SO_2CH_3$ | |
| 8-275 | 1H-triazole-1-yl | $CH_2O(CH_3)_2SO_2CH_2CF_3$ | |
| 8-276 | 1H-triazole-1-yl | 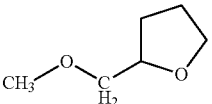 | |
| 8-277 | 1H-triazole-1-yl | 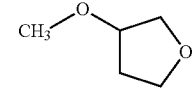 | |
| 8-278 | 1H-triazole-1-yl | $CH_2O(CH_3)_2NHSO_2CH_3$ | |
| 8-279 | 1H-triazole-1-yl | $CH_2O(CH_3)_2N(CH_3)(SO_2CH_3)$ | |
| 8-280 | 1H-tetrazole-1-yl | $CH_3$ | |

TABLE 103

| compound number | R4 | R1 | physical property (melting point-ND) |
|---|---|---|---|
| 8-281 | 1H-tetrazole-1-yl | $CF_3$ | |
| 8-282 | 1H-tetrazole-1-yl | $CH_2OCH_3$ | |
| 8-283 | 1H-tetrazole-1-yl | $CH_2OCH_2CH_3$ | |
| 8-284 | 1H-tetrazole-1-yl | 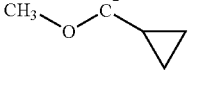 | |
| 8-285 | 1H-tetrazole-1-yl | $CH_2OCH_2CF_3$ | |
| 8-286 | 1H-tetrazole-1-yl | $CH_2SCH_3$ | |
| 8-287 | 1H-tetrazole-1-yl | $CH_2SCH_2CH_3$ | |
| 8-288 | 1H-tetrazole-1-yl | 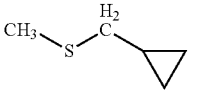 | |
| 8-289 | 1H-tetrazole-1-yl | $CH_2SCH_2CF_3$ | |
| 8-290 | 1H-tetrazole-1-yl | $CH_2SOCH_3$ | |
| 8-291 | 1H-tetrazole-1-yl | $CH_2SOCH_2CH_3$ | |

TABLE 103-continued

| compound number | R4 | R1 | physical property (melting point-ND) |
|---|---|---|---|
| 8-292 | 1H-tetrazole-1-yl | CH₃-S(=O)-CH₂-cyclopropyl | |
| 8-293 | 1H-tetrazole-1-yl | $CH_2SOCH_2CF_3$ | |
| 8-294 | 1H-tetrazole-1-yl | $CH_2SO_2CH_3$ | |
| 8-295 | 1H-tetrazole-1-yl | $CH_2SO_2CH_2CH_3$ | |
| 8-296 | 1H-tetrazole-1-yl | CH₃-S(=O)₂-CH₂-cyclopropyl | |
| 8-297 | 1H-tetrazole-1-yl | $CH_2SO_2CH_2CF_3$ | |
| 8-298 | 1H-tetrazole-1-yl | $CH_2O(CH_3)_2OCH_3$ | |
| 8-299 | 1H-tetrazole-1-yl | $CH_2O(CH_3)_2OCH_2CH_3$ | |
| 8-300 | 1H-tetrazole-1-yl | $CH_2O(CH_3)_2OCH_2CF_3$ | |
| 8-301 | 1H-tetrazole-1-yl | $CH_2O(CH_3)_2SCH_3$ | |
| 8-302 | 1H-tetrazole-1-yl | $CH_2O(CH_3)_2SCH_2CF_3$ | |
| 8-303 | 1H-tetrazole-1-yl | $CH_2O(CH_3)_2SOCH_3$ | |
| 8-304 | 1H-tetrazole-1-yl | $CH_2O(CH_3)_2SOCH_2CF_3$ | |
| 8-305 | 1H-tetrazole-1-yl | $CH_2O(CH_3)_2SO_2CH_3$ | |
| 8-306 | 1H-tetrazole-1-yl | $CH_2O(CH_3)_2SO_2CH_2CF_3$ | |
| 8-307 | 1H-tetrazole-1-yl | CH₃-O-CH₂-(tetrahydrofuran-2-yl) | |
| 8-308 | 1H-tetrazole-1-yl | CH₃-O-(tetrahydrofuran-3-yl) | |
| 8-309 | 1H-tetrazole-1-yl | $CH_2O(CH_3)_2NHSO_2CH_3$ | |
| 8-310 | 1H-tetrazole-1-yl | $CH_2O(CH_3)_2N(CH_3)(SO_2CH_3)$ | |
| 8-311 | 1H-tetrazole-2-yl | $CH_3$ | |
| 8-312 | 1H-tetrazole-2-yl | $CF_3$ | |
| 8-313 | 1H-tetrazole-2-yl | $CH_2OCH_3$ | |
| 8-314 | 1H-tetrazole-2-yl | $CH_2OCH_2CH_3$ | |
| 8-315 | 1H-tetrazole-2-yl | CH₃-O-CH₂-cyclopropyl | |
| 8-316 | 1H-tetrazole-2-yl | $CH_2OCH_2CF_3$ | |
| 8-317 | 1H-tetrazole-2-yl | $CH_2SCH_3$ | |
| 8-318 | 1H-tetrazole-2-yl | $CH_2SCH_2CH_3$ | |
| 8-319 | 1H-tetrazole-2-yl | CH₃-S-CH₂-cyclopropyl | |
| 8-320 | 1H-tetrazole-2-yl | $CH_2SCH_2CF_3$ | |

TABLE 104

| compound number | R4 | R1 | physical property (melting point-ND) |
|---|---|---|---|
| 8-321 | 1H-tetrazole-2-yl | $CH_2SOCH_3$ | |
| 8-322 | 1H-tetrazole-2-yl | $CH_2SOCH_2CH_3$ | |
| 8-323 | 1H-tetrazole-2-yl | CH₃-S(=O)-CH₂-cyclopropyl | |
| 8-324 | 1H-tetrazole-2-yl | $CH_2SOCH_2CF_3$ | |
| 8-325 | 1H-tetrazole-2-yl | $CH_2SO_2CH_3$ | |
| 8-326 | 1H-tetrazole-2-yl | $CH_2SO_2CH_2CH_3$ | |
| 8-327 | 1H-tetrazole-2-yl | CH₃-S(=O)₂-CH₂-cyclopropyl | |
| 8-328 | 1H-tetrazole-2-yl | $CH_2SO_2CH_2CF_3$ | |
| 8-329 | 1H-tetrazole-2-yl | $CH_2O(CH_3)_2OCH_3$ | |
| 8-330 | 1H-tetrazole-2-yl | $CH_2O(CH_3)_2OCH_2CH_3$ | |
| 8-331 | 1H-tetrazole-2-yl | $CH_2O(CH_3)_2OCH_2CF_3$ | |
| 8-332 | 1H-tetrazole-2-yl | $CH_2O(CH_3)_2SCH_3$ | |
| 8-333 | 1H-tetrazole-2-yl | $CH_2O(CH_3)_2SCH_2CF_3$ | |
| 8-334 | 1H-tetrazole-2-yl | $CH_2O(CH_3)_2SOCH_3$ | |
| 8-335 | 1H-tetrazole-2-yl | $CH_2O(CH_3)_2SOCH_2CF_3$ | |
| 8-336 | 1H-tetrazole-2-yl | $CH_2O(CH_3)_2SO_2CH_3$ | |
| 8-337 | 1H-tetrazole-2-yl | $CH_2O(CH_3)_2SO_2CH_2CF_3$ | |
| 8-338 | 1H-tetrazole-2-yl | CH₃-O-CH₂-(tetrahydrofuran-2-yl) | |
| 8-339 | 1H-tetrazole-2-yl | CH₃-O-(tetrahydrofuran-3-yl) | |
| 8-340 | 1H-tetrazole-2-yl | $CH_2O(CH_3)_2NHSO_2CH_3$ | |
| 8-341 | 1H-tetrazole-2-yl | $CH_2O(CH_3)_2N(CH_3)(SO_2CH_3)$ | |

TABLE 105

[Structure: cyclohexenone substituted with R4, carbonyl linked to pyridine bearing R1 and 1,2,4-triazol-1-yl group, with gem-dimethyl on cyclohexenone]

| compound number | R4 | R1 | physical property (melting point-ND) |
|---|---|---|---|
| 9-1 | Cl | $CH_3$ | |
| 9-2 | Cl | $CF_3$ | |
| 9-3 | Cl | $CH_2OCH_3$ | |
| 9-4 | Cl | $CH_2OCH_2CH_3$ | |
| 9-5 | Cl | CH₃-O-CH₂-cyclopropyl | |
| 9-6 | Cl | $CH_2OCH_2CF_3$ | |
| 9-7 | Cl | $CH_2SCH_3$ | |
| 9-8 | Cl | $CH_2SCH_2CH_3$ | |

TABLE 105-continued

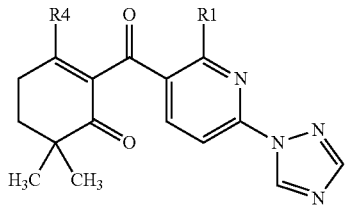

| compound number | R4 | R1 | physical property (melting point-ND) |
|---|---|---|---|
| 9-9 | Cl | 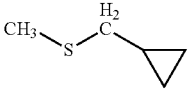 | |
| 9-10 | Cl | CH$_2$SCH$_2$CF$_3$ | |
| 9-11 | Cl | CH$_2$SOCH$_3$ | |
| 9-12 | Cl | CH$_2$SOCH$_2$CH$_3$ | |
| 9-13 | Cl | 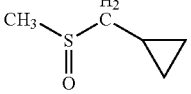 | |
| 9-14 | Cl | CH$_2$SOCH$_2$CF$_3$ | |
| 9-15 | Cl | CH$_2$SO$_2$CH$_3$ | |
| 9-16 | Cl | CH$_2$SO$_2$CH$_2$CH$_3$ | |
| 9-17 | Cl | 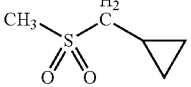 | |
| 9-18 | Cl | CH$_2$SO$_2$CH$_2$CF$_3$ | |
| 9-19 | Cl | CH$_2$O(CH$_3$)$_2$OCH$_3$ | |
| 9-20 | Cl | CH$_2$O(CH$_3$)$_2$OCH$_2$CH$_3$ | |
| 9-21 | Cl | CH$_2$O(CH$_3$)$_2$OCH$_2$CF$_3$ | |
| 9-22 | Cl | CH$_2$O(CH$_3$)$_2$SCH$_3$ | |
| 9-23 | Cl | CH$_2$O(CH$_3$)$_2$SCH$_2$CF$_3$ | |
| 9-24 | Cl | CH$_2$O(CH$_3$)$_2$SOCH$_3$ | |
| 9-25 | Cl | CH$_2$O(CH$_3$)$_2$SOCH$_2$CF$_3$ | |
| 9-26 | Cl | CH$_2$O(CH$_3$)$_2$SO$_2$CH$_3$ | |
| 9-27 | Cl | CH$_2$O(CH$_3$)$_2$SO$_2$CH$_2$CF$_3$ | |
| 9-28 | Cl | 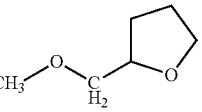 | |
| 9-29 | Cl | 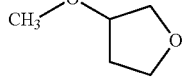 | |
| 9-30 | Cl | CH$_2$O(CH$_3$)$_2$NHSO$_2$CH$_3$ | |
| 9-31 | Cl | CH$_2$O(CH$_3$)$_2$N(CH$_3$)(SO$_2$CH$_3$) | |
| 9-32 | SCH$_3$ | CH$_3$ | |
| 9-33 | SCH$_3$ | CF$_3$ | |
| 9-34 | SCH$_3$ | CH$_2$OCH$_3$ | |
| 9-35 | SCH$_3$ | CH$_2$OCH$_2$CH$_3$ | |
| 9-36 | SCH$_3$ | 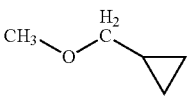 | |
| 9-37 | SCH$_3$ | CH$_2$OCH$_2$CF$_3$ | |
| 9-38 | SCH$_3$ | CH$_2$SCH$_3$ | |
| 9-39 | SCH$_3$ | CH$_2$SCH$_2$CH$_3$ | |

TABLE 105-continued

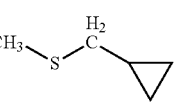

| compound number | R4 | R1 | physical property (melting point-ND) |
|---|---|---|---|
| 9-40 | SCH$_3$ | 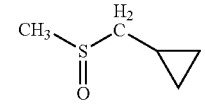 | |

TABLE 106

| compound number | R4 | R1 | physical property (melting point-ND) |
|---|---|---|---|
| 9-41 | SCH$_3$ | CH$_2$SCH$_2$CF$_3$ | |
| 9-42 | SCH$_3$ | CH$_2$SOCH$_3$ | |
| 9-43 | SCH$_3$ | CH$_2$SOCH$_2$CH$_3$ | |
| 9-44 | SCH$_3$ | 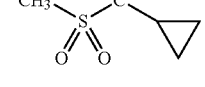 | |
| 9-45 | SCH$_3$ | CH$_2$SOCH$_2$CF$_3$ | |
| 9-46 | SCH$_3$ | CH$_2$SO$_2$CH$_3$ | |
| 9-47 | SCH$_3$ | CH$_2$SO$_2$CH$_2$CH$_3$ | |
| 9-48 | SCH$_3$ | 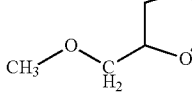 | |
| 9-49 | SCH$_3$ | CH$_2$SO$_2$CH$_2$CF$_3$ | |
| 9-50 | SCH$_3$ | CH$_2$O(CH$_3$)$_2$OCH$_3$ | |
| 9-51 | SCH$_3$ | CH$_2$O(CH$_3$)$_2$OCH$_2$CH$_3$ | |
| 9-52 | SCH$_3$ | CH$_2$O(CH$_3$)$_2$OCH$_2$CF$_3$ | |
| 9-53 | SCH$_3$ | CH$_2$O(CH$_3$)$_2$SCH$_3$ | |
| 9-54 | SCH$_3$ | CH$_2$O(CH$_3$)$_2$SCH$_2$CF$_3$ | |
| 9-55 | SCH$_3$ | CH$_2$O(CH$_3$)$_2$SOCH$_3$ | |
| 9-56 | SCH$_3$ | CH$_2$O(CH$_3$)$_2$SOCH$_2$CF$_3$ | |
| 9-57 | SCH$_3$ | CH$_2$O(CH$_3$)$_2$SO$_2$CH$_3$ | |
| 9-58 | SCH$_3$ | CH$_2$O(CH$_3$)$_2$SO$_2$CH$_2$CF$_3$ | |
| 9-59 | SCH$_3$ | 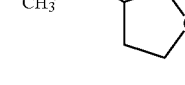 | |
| 9-60 | SCH$_3$ |  | |
| 9-61 | SCH$_3$ | CH$_2$O(CH$_3$)$_2$NHSO$_2$CH$_3$ | |
| 9-62 | SCH$_3$ | CH$_2$O(CH$_3$)$_2$N(CH$_3$)(SO$_2$CH$_3$) | |
| 9-63 | SCH$_2$CH$_3$ | CH$_3$ | |
| 9-64 | SCH$_2$CH$_3$ | CF$_3$ | |
| 9-65 | SCH$_2$CH$_3$ | CH$_2$OCH$_3$ | |
| 9-66 | SCH$_2$CH$_3$ | CH$_2$OCH$_2$CH$_3$ | |

TABLE 106-continued

| compound number | R4 | R1 | physical property (melting point-ND) |
|---|---|---|---|
| 9-67 | SCH$_2$CH$_3$ | CH$_3$-O-CH(H$_2$)-cyclopropyl | |
| 9-68 | SCH$_2$CH$_3$ | CH$_2$OCH$_2$CF$_3$ | |
| 9-69 | SCH$_2$CH$_3$ | CH$_2$SCH$_3$ | |
| 9-70 | SCH$_2$CH$_3$ | CH$_2$SCH$_2$CH$_3$ | |
| 9-71 | SCH$_2$CH$_3$ | CH$_3$-S-CH(H$_2$)-cyclopropyl | |
| 9-72 | SCH$_2$CH$_3$ | CH$_2$SCH$_2$CF$_3$ | |
| 9-73 | SCH$_2$CH$_3$ | CH$_2$SOCH$_3$ | |
| 9-74 | SCH$_2$CH$_3$ | CH$_2$SOCH$_2$CH$_3$ | |
| 9-75 | SCH$_2$CH$_3$ | CH$_3$-S(=O)-CH(H$_2$)-cyclopropyl | |
| 9-76 | SCH$_2$CH$_3$ | CH$_2$SOCH$_2$CF$_3$ | |
| 9-77 | SCH$_2$CH$_3$ | CH$_2$SO$_2$CH$_3$ | |
| 9-78 | SCH$_2$CH$_3$ | CH$_2$SO$_2$CH$_2$CH$_3$ | |
| 9-79 | SCH$_2$CH$_3$ | CH$_3$-S(=O)$_2$-CH(H$_2$)-cyclopropyl | |
| 9-80 | SCH$_2$CH$_3$ | CH$_2$SO$_2$CH$_2$CF$_3$ | |

TABLE 107

| compound number | R4 | R1 | physical property (melting point-ND) |
|---|---|---|---|
| 9-81 | SCH$_2$CH$_3$ | CH$_2$O(CH$_3$)$_2$OCH$_3$ | |
| 9-82 | SCH$_2$CH$_3$ | CH$_2$O(CH$_3$)$_2$OCH$_2$CH$_3$ | |
| 9-83 | SCH$_2$CH$_3$ | CH$_2$O(CH$_3$)$_2$OCH$_2$CF$_3$ | |
| 9-84 | SCH$_2$CH$_3$ | CH$_2$O(CH$_3$)$_2$SCH$_3$ | |
| 9-85 | SCH$_2$CH$_3$ | CH$_2$O(CH$_3$)$_2$SCH$_2$CF$_3$ | |
| 9-86 | SCH$_2$CH$_3$ | CH$_2$O(CH$_3$)$_2$SOCH$_3$ | |
| 9-87 | SCH$_2$CH$_3$ | CH$_2$O(CH$_3$)$_2$SOCH$_2$CF$_3$ | |
| 9-88 | SCH$_2$CH$_3$ | CH$_2$O(CH$_3$)$_2$SO$_2$CH$_3$ | |
| 9-89 | SCH$_2$CH$_3$ | CH$_2$O(CH$_3$)$_2$SO$_2$CH$_2$CF$_3$ | |
| 9-90 | SCH$_2$CH$_3$ | CH$_3$-O-CH(H$_2$)-tetrahydrofuran-2-yl | |
| 9-91 | SCH$_2$CH$_3$ | CH$_3$-O-tetrahydrofuran-3-yl | |
| 9-92 | SCH$_2$CH$_3$ | CH$_2$O(CH$_3$)$_2$NHSO$_2$CH$_3$ | |
| 9-93 | SCH$_2$CH$_3$ | CH$_2$O(CH$_3$)$_2$N(CH$_3$)(SO$_2$CH$_3$) | |
| 9-94 | S(CH$_3$)$_2$CH$_3$ | CH$_3$ | |
| 9-95 | S(CH$_3$)$_2$CH$_3$ | CF$_3$ | |
| 9-96 | S(CH$_3$)$_2$CH$_3$ | CH$_2$OCH$_3$ | |
| 9-97 | S(CH$_3$)$_2$CH$_3$ | CH$_2$OCH$_2$CH$_3$ | |

TABLE 107-continued

| compound number | R4 | R1 | physical property (melting point-ND) |
|---|---|---|---|
| 9-98 | S(CH$_3$)$_2$CH$_3$ | CH$_3$-O-CH(H$_2$)-cyclopropyl | |
| 9-99 | S(CH$_3$)$_2$CH$_3$ | CH$_2$OCH$_2$CF$_3$ | |
| 9-100 | S(CH$_3$)$_2$CH$_3$ | CH$_2$SCH$_3$ | |
| 9-101 | S(CH$_3$)$_2$CH$_3$ | CH$_2$SCH$_2$CH$_3$ | |
| 9-102 | S(CH$_3$)$_2$CH$_3$ | CH$_3$-S-CH(H$_2$)-cyclopropyl | |
| 9-103 | S(CH$_3$)$_2$CH$_3$ | CH$_2$SCH$_2$CF$_3$ | |
| 9-104 | S(CH$_3$)$_2$CH$_3$ | CH$_2$SOCH$_3$ | |
| 9-105 | S(CH$_3$)$_2$CH$_3$ | CH$_2$SOCH$_2$CH$_3$ | |
| 9-106 | S(CH$_3$)$_2$CH$_3$ | CH$_3$-S(=O)-CH(H$_2$)-cyclopropyl | |
| 9-107 | S(CH$_3$)$_2$CH$_3$ | CH$_2$SOCH$_2$CF$_3$ | |
| 9-108 | S(CH$_3$)$_2$CH$_3$ | CH$_2$SO$_2$CH$_3$ | |
| 9-109 | S(CH$_3$)$_2$CH$_3$ | CH$_2$SO$_2$CH$_2$CH$_3$ | |
| 9-110 | S(CH$_3$)$_2$CH$_3$ | CH$_3$-S(=O)$_2$-CH(H$_2$)-cyclopropyl | |
| 9-111 | S(CH$_3$)$_2$CH$_3$ | CH$_2$SO$_2$CH$_2$CF$_3$ | |
| 9-112 | S(CH$_3$)$_2$CH$_3$ | CH$_2$O(CH$_3$)$_2$OCH$_3$ | |
| 9-113 | S(CH$_3$)$_2$CH$_3$ | CH$_2$O(CH$_3$)$_2$OCH$_2$CH$_3$ | |
| 9-114 | S(CH$_3$)$_2$CH$_3$ | CH$_2$O(CH$_3$)$_2$OCH$_2$CF$_3$ | |
| 9-115 | S(CH$_3$)$_2$CH$_3$ | CH$_2$O(CH$_3$)$_2$SCH$_3$ | |
| 9-116 | S(CH$_3$)$_2$CH$_3$ | CH$_2$O(CH$_3$)$_2$SCH$_2$CF$_3$ | |
| 9-117 | S(CH$_3$)$_2$CH$_3$ | CH$_2$O(CH$_3$)$_2$SOCH$_3$ | |
| 9-118 | S(CH$_3$)$_2$CH$_3$ | CH$_2$O(CH$_3$)$_2$SOCH$_2$CF$_3$ | |
| 9-119 | S(CH$_3$)$_2$CH$_3$ | CH$_2$O(CH$_3$)$_2$SO$_2$CH$_3$ | |
| 9-120 | S(CH$_3$)$_2$CH$_3$ | CH$_2$O(CH$_3$)$_2$SO$_2$CH$_2$CF$_3$ | |

TABLE 108

| compound number | R4 | R1 | physical property (melting point-ND) |
|---|---|---|---|
| 9-121 | S(CH$_3$)$_2$CH$_3$ | CH$_3$-O-CH(H$_2$)-tetrahydrofuran-2-yl | |
| 9-122 | S(CH$_3$)$_2$CH$_3$ | CH$_3$-O-tetrahydrofuran-3-yl | |
| 9-123 | S(CH$_3$)$_2$CH$_3$ | CH$_2$O(CH$_3$)$_2$NHSO$_2$CH$_3$ | |
| 9-124 | S(CH$_3$)$_2$CH$_3$ | CH$_2$O(CH$_3$)$_2$N(CH$_3$)(SO$_2$CH$_3$) | |
| 9-125 | SC$_6$H$_5$ | CH$_3$ | |
| 9-126 | SC$_6$H$_5$ | CF$_3$ | |
| 9-127 | SC$_6$H$_5$ | CH$_2$OCH$_3$ | |
| 9-128 | SC$_6$H$_5$ | CH$_2$OCH$_2$CH$_3$ | |

TABLE 108-continued

| compound number | R4 | R1 | physical property (melting point-ND) |
|---|---|---|---|
| 9-129 | SC₆H₅ | 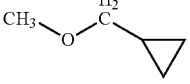 | |
| 9-130 | SC₆H₅ | CH₂OCH₂CF₃ | |
| 9-131 | SC₆H₅ | CH₂SCH₃ | |
| 9-132 | SC₆H₅ | CH₂SCH₂CH₃ | |
| 9-133 | SC₆H₅ | 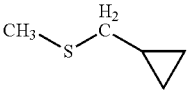 | |
| 9-134 | SC₆H₅ | CH₂SCH₂CF₃ | |
| 9-135 | SC₆H₅ | CH₂SOCH₃ | |
| 9-136 | SC₆H₅ | CH₂SOCH₂CH₃ | |
| 9-137 | SC₆H₅ | 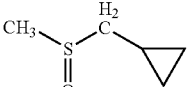 | |
| 9-138 | SC₆H₅ | CH₂SOCH₂CF₃ | |
| 9-139 | SC₆H₅ | CH₂SO₂CH₃ | |
| 9-140 | SC₆H₅ | CH₂SO₂CH₂CH₃ | |
| 9-141 | SC₆H₅ | 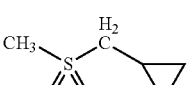 | |
| 9-142 | SC₆H₅ | CH₂SO₂CH₂CF₃ | |
| 9-143 | SC₆H₅ | CH₂O(CH₃)₂OCH₃ | |
| 9-144 | SC₆H₅ | CH₂O(CH₃)₂OCH₂CH₃ | |
| 9-145 | SC₆H₅ | CH₂O(CH₃)₂OCH₂CF₃ | |
| 9-146 | SC₆H₅ | CH₂O(CH₃)₂SCH₃ | |
| 9-147 | SC₆H₅ | CH₂O(CH₃)₂SCH₂CF₃ | |
| 9-148 | SC₆H₅ | CH₂O(CH₃)₂SOCH₃ | |
| 9-149 | SC₆H₅ | CH₂O(CH₃)₂SOCH₂CF₃ | |
| 9-150 | SC₆H₅ | CH₂O(CH₃)₂SO₂CH₃ | |
| 9-151 | SC₆H₅ | CH₂O(CH₃)₂SO₂CH₂CF₃ | |
| 9-152 | SC₆H₅ | 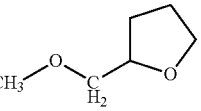 | |
| 9-153 | SC₆H₅ | 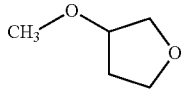 | |
| 9-154 | SC₆H₅ | CH₂O(CH₃)₂NHSO₂CH₃ | |
| 9-155 | SC₆H₅ | CH₂O(CH₃)₂N(CH₃)(SO₂CH₃) | |
| 9-156 | SCH₂C₆H₅ | CH₃ | |
| 9-157 | SCH₂C₆H₅ | CF₃ | |
| 9-158 | SCH₂C₆H₅ | CH₂OCH₃ | |
| 9-159 | SCH₂C₆H₅ | CH₂OCH₂CH₃ | |
| 9-160 | SCH₂C₆H₅ | 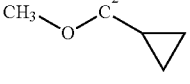 | |

TABLE 109

| compound number | R4 | R1 | physical property (melting point-ND) |
|---|---|---|---|
| 9-161 | SCH₂C₆H₅ | CH₂OCH₂CF₃ | |
| 9-162 | SCH₂C₆H₅ | CH₂SCH₃ | |
| 9-163 | SCH₂C₆H₅ | CH₂SCH₂CH₃ | |
| 9-164 | SCH₂C₆H₅ | 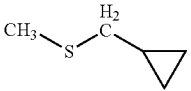 | |
| 9-165 | SCH₂C₆H₅ | CH₂SCH₂CF₃ | |
| 9-166 | SCH₂C₆H₅ | CH₂SOCH₃ | |
| 9-167 | SCH₂C₆H₅ | CH₂SOCH₂CH₃ | |
| 9-168 | SCH₂C₆H₅ | 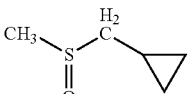 | |
| 9-169 | SCH₂C₆H₅ | CH₂SOCH₂CF₃ | |
| 9-170 | SCH₂C₆H₅ | CH₂SO₂CH₃ | |
| 9-171 | SCH₂C₆H₅ | CH₂SO₂CH₂CH₃ | |
| 9-172 | SCH₂C₆H₅ | 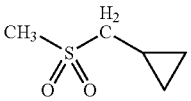 | |
| 9-173 | SCH₂C₆H₅ | CH₂SO₂CH₂CF₃ | |
| 9-174 | SCH₂C₆H₅ | CH₂O(CH₃)₂OCH₃ | |
| 9-175 | SCH₂C₆H₅ | CH₂O(CH₃)₂OCH₂CH₃ | |
| 9-176 | SCH₂C₆H₅ | CH₂O(CH₃)₂OCH₂CF₃ | |
| 9-177 | SCH₂C₆H₅ | CH₂O(CH₃)₂SCH₃ | |
| 9-178 | SCH₂C₆H₅ | CH₂O(CH₃)₂SCH₂CF₃ | |
| 9-179 | SCH₂C₆H₅ | CH₂O(CH₃)₂SOCH₃ | |
| 9-180 | SCH₂C₆H₅ | CH₂O(CH₃)₂SOCH₂CF₃ | |
| 9-181 | SCH₂C₆H₅ | CH₂O(CH₃)₂SO₂CH₃ | |
| 9-182 | SCH₂C₆H₅ | CH₂O(CH₃)₂SO₂CH₂CF₃ | |
| 9-183 | SCH₂C₆H₅ | 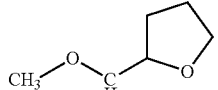 | |
| 9-184 | SCH₂C₆H₅ | 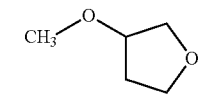 | |
| 9-185 | SCH₂C₆H₅ | CH₂O(CH₃)₂NHSO₂CH₃ | |
| 9-186 | SCH₂C₆H₅ | CH₂O(CH₃)₂N(CH₃)(SO₂CH₃) | |
| 9-187 | 1H-pyrazole-1-yl | CH₃ | |
| 9-188 | 1H-pyrazole-1-yl | CF₃ | |
| 9-189 | 1H-pyrazole-1-yl | CH₂OCH₃ | |
| 9-190 | 1H-pyrazole-1-yl | CH₂OCH₂CH₃ | |
| 9-191 | 1H-pyrazole-1-yl | 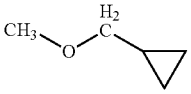 | |
| 9-192 | 1H-pyrazole-1-yl | CH₂OCH₂CF₃ | |
| 9-193 | 1H-pyrazole-1-yl | CH₂SCH₃ | |
| 9-194 | 1H-pyrazole-1-yl | CH₂SCH₂CH₃ | |
| 9-195 | 1H-pyrazole-1-yl | 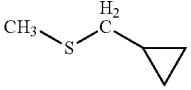 | |
| 9-196 | 1H-pyrazole-1-yl | CH₂SCH₂CF₃ | |

TABLE 109-continued

| compound number | R4 | R1 | physical property (melting point-ND) |
|---|---|---|---|
| 9-197 | 1H-pyrazole-1-yl | CH$_2$SOCH$_3$ | |
| 9-198 | 1H-pyrazole-1-yl | CH$_2$SOCH$_2$CH$_3$ | |
| 9-199 | 1H-pyrazole-1-yl | 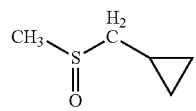 | |
| 9-200 | 1H-pyrazole-1-yl | CH$_2$SOCH$_2$CF$_3$ | |

TABLE 110

| compound number | R4 | R1 | physical property (melting point-ND) |
|---|---|---|---|
| 9-201 | 1H-pyrazole-1-yl | CH$_2$SO$_2$CH$_3$ | |
| 9-202 | 1H-pyrazole-1-yl | CH$_2$SO$_2$CH$_2$CH$_3$ | |
| 9-203 | 1H-pyrazole-1-yl | 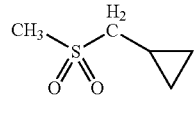 | |
| 9-204 | 1H-pyrazole-1-yl | CH$_2$SO$_2$CH$_2$CF$_3$ | |
| 9-205 | 1H-pyrazole-1-yl | CH$_2$O(CH$_3$)$_2$OCH$_3$ | |
| 9-206 | 1H-pyrazole-1-yl | CH$_2$O(CH$_3$)$_2$OCH$_2$CH$_3$ | |
| 9-207 | 1H-pyrazole-1-yl | CH$_2$O(CH$_3$)$_2$OCH$_2$CF$_3$ | |
| 9-208 | 1H-pyrazole-1-yl | CH$_2$O(CH$_3$)$_2$SCH$_3$ | |
| 9-209 | 1H-pyrazole-1-yl | CH$_2$O(CH$_3$)$_2$SCH$_2$CF$_3$ | |
| 9-210 | 1H-pyrazole-1-yl | CH$_2$O(CH$_3$)$_2$SOCH$_3$ | |
| 9-211 | 1H-pyrazole-1-yl | CH$_2$O(CH$_3$)$_2$SOCH$_2$CF$_3$ | |
| 9-212 | 1H-pyrazole-1-yl | CH$_2$O(CH$_3$)$_2$SO$_2$CH$_3$ | |
| 9-213 | 1H-pyrazole-1-yl | CH$_2$O(CH$_3$)$_2$SO$_2$CH$_2$CF$_3$ | |
| 9-214 | 1H-pyrazole-1-yl | 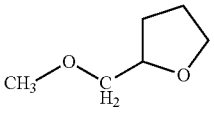 | |
| 9-215 | 1H-pyrazole-1-yl | 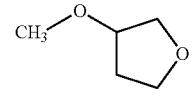 | |
| 9-216 | 1H-pyrazole-1-yl | CH$_2$O(CH$_3$)$_2$NHSO$_2$CH$_3$ | |
| 9-217 | 1H-pyrazole-1-yl | CH$_2$O(CH$_3$)$_2$N(CH$_3$)(SO$_2$CH$_3$) | |
| 9-218 | 1H-imidazole-1-yl | CH$_3$ | |
| 9-219 | 1H-imidazole-1-yl | CF$_3$ | |
| 9-220 | 1H-imidazole-1-yl | CH$_2$OCH$_3$ | |
| 9-221 | 1H-imidazole-1-yl | CH$_2$OCH$_2$CH$_3$ | |
| 9-222 | 1H-imidazole-1-yl | 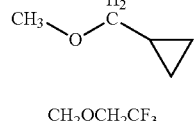 | |
| 9-223 | 1H-imidazole-1-yl | CH$_2$OCH$_2$CF$_3$ | |
| 9-224 | 1H-imidazole-1-yl | CH$_2$SCH$_3$ | |
| 9-225 | 1H-imidazole-1-yl | CH$_2$SCH$_2$CH$_3$ | |
| 9-226 | 1H-imidazole-1-yl | 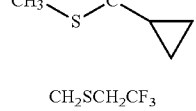 | |
| 9-227 | 1H-imidazole-1-yl | CH$_2$SCH$_2$CF$_3$ | |
| 9-228 | 1H-imidazole-1-yl | CH$_2$SOCH$_3$ | |

TABLE 110-continued

| compound number | R4 | R1 | physical property (melting point-ND) |
|---|---|---|---|
| 9-229 | 1H-imidazole-1-yl | CH$_2$SOCH$_2$CH$_3$ | |
| 9-230 | 1H-imidazole-1-yl | 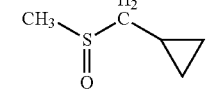 | |
| 9-231 | 1H-imidazole-1-yl | CH$_2$SOCH$_2$CF$_3$ | |
| 9-232 | 1H-imidazole-1-yl | CH$_2$SO$_2$CH$_3$ | |
| 9-233 | 1H-imidazole-1-yl | CH$_2$SO$_2$CH$_2$CH$_3$ | |
| 9-234 | 1H-imidazole-1-yl | 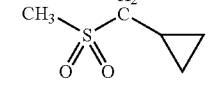 | |
| 9-235 | 1H-imidazole-1-yl | CH$_2$SO$_2$CH$_2$CF$_3$ | |
| 9-236 | 1H-imidazole-1-yl | CH$_2$O(CH$_3$)$_2$OCH$_3$ | |
| 9-237 | 1H-imidazole-1-yl | CH$_2$O(CH$_3$)$_2$OCH$_2$CH$_3$ | |
| 9-238 | 1H-imidazole-1-yl | CH$_2$O(CH$_3$)$_2$OCH$_2$CF$_3$ | |
| 9-239 | 1H-imidazole-1-yl | CH$_2$O(CH$_3$)$_2$SCH$_3$ | |
| 9-240 | 1H-imidazole-1-yl | CH$_2$O(CH$_3$)$_2$SCH$_2$CF$_3$ | |

TABLE 111

| compound number | R4 | R1 | physical property (melting point-ND) |
|---|---|---|---|
| 9-241 | 1H-imidazole-1-yl | CH$_2$O(CH$_3$)$_2$SOCH$_3$ | |
| 9-242 | 1H-imidazole-1-yl | CH$_2$O(CH$_3$)$_2$SOCH$_2$CF$_3$ | |
| 9-243 | 1H-imidazole-1-yl | CH$_2$O(CH$_3$)$_2$SO$_2$CH$_3$ | |
| 9-244 | 1H-imidazole-1-yl | CH$_2$O(CH$_3$)$_2$SO$_2$CH$_2$CF$_3$ | |
| 9-245 | 1H-imidazole-1-yl | 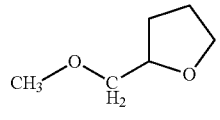 | |
| 9-246 | 1H-imidazole-1-yl | 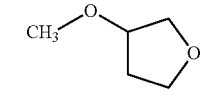 | |
| 9-247 | 1H-imidazole-1-yl | CH$_2$O(CH$_3$)$_2$NHSO$_2$CH$_3$ | |
| 9-248 | 1H-imidazole-1-yl | CH$_2$O(CH$_3$)$_2$N(CH$_3$)(SO$_2$CH$_3$) | |
| 9-249 | 1H-triazole-1-yl | CH$_3$ | |
| 9-250 | 1H-triazole-1-yl | CF$_3$ | |
| 9-251 | 1H-triazole-1-yl | CH$_2$OCH$_3$ | |
| 9-252 | 1H-triazole-1-yl | CH$_2$OCH$_2$CH$_3$ | |
| 9-253 | 1H-triazole-1-yl | 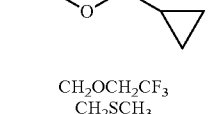 | |
| 9-254 | 1H-triazole-1-yl | CH$_2$OCH$_2$CF$_3$ | |
| 9-255 | 1H-triazole-1-yl | CH$_2$SCH$_3$ | |
| 9-256 | 1H-triazole-1-yl | CH$_2$SCH$_2$CH$_3$ | |
| 9-257 | 1H-triazole-1-yl | 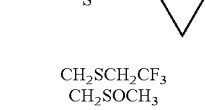 | |
| 9-258 | 1H-triazole-1-yl | CH$_2$SCH$_2$CF$_3$ | |
| 9-259 | 1H-triazole-1-yl | CH$_2$SOCH$_3$ | |
| 9-260 | 1H-triazole-1-yl | CH$_2$SOCH$_2$CH$_3$ | |

TABLE 111-continued

| compound number | R4 | R1 | physical property (melting point-ND) |
|---|---|---|---|
| 9-261 | 1H-triazole-1-yl | CH₃-S(=O)-CH₂-cyclopropyl | |
| 9-262 | 1H-triazole-1-yl | CH₂SOCH₂CF₃ | |
| 9-263 | 1H-triazole-1-yl | CH₂SO₂CH₃ | |
| 9-264 | 1H-triazole-1-yl | CH₂SO₂CH₂CH₃ | |
| 9-265 | 1H-triazole-1-yl | CH₃-S(=O)₂-CH₂-cyclopropyl | |
| 9-266 | 1H-triazole-1-yl | CH₂SO₂CH₂CF₃ | |
| 9-267 | 1H-triazole-1-yl | CH₂O(CH₃)₂OCH₃ | |
| 9-268 | 1H-triazole-1-yl | CH₂O(CH₃)₂OCH₂CH₃ | |
| 9-269 | 1H-triazole-1-yl | CH₂O(CH₃)₂OCH₂CF₃ | |
| 9-270 | 1H-triazole-1-yl | CH₂O(CH₃)₂SCH₃ | |
| 9-271 | 1H-triazole-1-yl | CH₂O(CH₃)₂SCH₂CF₃ | |
| 9-272 | 1H-triazole-1-yl | CH₂O(CH₃)₂SOCH₃ | |
| 9-273 | 1H-triazole-1-yl | CH₂O(CH₃)₂SOCH₂CF₃ | |
| 9-274 | 1H-triazole-1-yl | CH₂O(CH₃)₂SO₂CH₃ | |
| 9-275 | 1H-triazole-1-yl | CH₂O(CH₃)₂SO₂CH₂CF₃ | |
| 9-276 | 1H-triazole-1-yl | CH₃-O-CH₂-(tetrahydrofuran-2-yl) | |
| 9-277 | 1H-triazole-1-yl | CH₃-O-(tetrahydrofuran-3-yl) | |
| 9-278 | 1H-triazole-1-yl | CH₂O(CH₃)₂NHSO₂CH₃ | |
| 9-279 | 1H-triazole-1-yl | CH₂O(CH₃)₂N(CH₃)(SO₂CH₃) | |
| 9-280 | 1H-tetrazole-1-yl | CH₃ | |

TABLE 112

| compound number | R4 | R1 | physical property (melting point-ND) |
|---|---|---|---|
| 9-281 | 1H-tetrazole-1-yl | CF₃ | |
| 9-282 | 1H-tetrazole-1-yl | CH₂OCH₃ | |
| 9-283 | 1H-tetrazole-1-yl | CH₂OCH₂CH₃ | |
| 9-284 | 1H-tetrazole-1-yl | CH₃-O-CH₂-cyclopropyl | |
| 9-285 | 1H-tetrazole-1-yl | CH₂OCH₂CF₃ | |
| 9-286 | 1H-tetrazole-1-yl | CH₂SCH₃ | |
| 9-287 | 1H-tetrazole-1-yl | CH₂SCH₂CH₃ | |
| 9-288 | 1H-tetrazole-1-yl | CH₃-S-CH₂-cyclopropyl | |
| 9-289 | 1H-tetrazole-1-yl | CH₂SCH₂CF₃ | |
| 9-290 | 1H-tetrazole-1-yl | CH₂SOCH₃ | |
| 9-291 | 1H-tetrazole-1-yl | CH₂SOCH₂CH₃ | |
| 9-292 | 1H-tetrazole-1-yl | CH₃-S(=O)-CH₂-cyclopropyl | |
| 9-293 | 1H-tetrazole-1-yl | CH₂SOCH₂CF₃ | |
| 9-294 | 1H-tetrazole-1-yl | CH₂SO₂CH₃ | |
| 9-295 | 1H-tetrazole-1-yl | CH₂SO₂CH₂CH₃ | |
| 9-296 | 1H-tetrazole-1-yl | CH₃-S(=O)₂-CH₂-cyclopropyl | |
| 9-297 | 1H-tetrazole-1-yl | CH₂SO₂CH₂CF₃ | |
| 9-298 | 1H-tetrazole-1-yl | CH₂O(CH₃)₂OCH₃ | |
| 9-299 | 1H-tetrazole-1-yl | CH₂O(CH₃)₂OCH₂CH₃ | |
| 9-300 | 1H-tetrazole-1-yl | CH₂O(CH₃)₂OCH₂CF₃ | |
| 9-301 | 1H-tetrazole-1-yl | CH₂O(CH₃)₂SCH₃ | |
| 9-302 | 1H-tetrazole-1-yl | CH₂O(CH₃)₂SCH₂CF₃ | |
| 9-303 | 1H-tetrazole-1-yl | CH₂O(CH₃)₂SOCH₃ | |
| 9-304 | 1H-tetrazole-1-yl | CH₂O(CH₃)₂SOCH₂CF₃ | |
| 9-305 | 1H-tetrazole-1-yl | CH₂O(CH₃)₂SO₂CH₃ | |
| 9-306 | 1H-tetrazole-1-yl | CH₂O(CH₃)₂SO₂CH₂CF₃ | |
| 9-307 | 1H-tetrazole-1-yl | CH₃-O-CH₂-(tetrahydrofuran-2-yl) | |
| 9-308 | 1H-tetrazole-1-yl | CH₃-O-(tetrahydrofuran-3-yl) | |
| 9-309 | 1H-tetrazole-1-yl | CH₂O(CH₃)₂NHSO₂CH₃ | |
| 9-310 | 1H-tetrazole-1-yl | CH₂O(CH₃)₂N(CH₃)(SO₂CH₃) | |
| 9-311 | 1H-tetrazole-2-yl | CH₃ | |
| 9-312 | 1H-tetrazole-2-yl | CF₃ | |
| 9-313 | 1H-tetrazole-2-yl | CH₂OCH₃ | |
| 9-314 | 1H-tetrazole-2-yl | CH₂OCH₂CH₃ | |
| 9-315 | 1H-tetrazole-2-yl | CH₃-O-CH₂-cyclopropyl | |
| 9-316 | 1H-tetrazole-2-yl | CH₂OCH₂CF₃ | |
| 9-317 | 1H-tetrazole-2-yl | CH₂SCH₃ | |
| 9-318 | 1H-tetrazole-2-yl | CH₂SCH₂CH₃ | |
| 9-319 | 1H-tetrazole-2-yl | CH₃-S-CH₂-cyclopropyl | |
| 9-320 | 1H-tetrazole-2-yl | CH₂SCH₂CF₃ | |

TABLE 113

| compound number | R4 | R1 | physical property (melting point-ND) |
|---|---|---|---|
| 9-321 | 1H-tetrazole-2-yl | CH₂SOCH₃ | |
| 9-322 | 1H-tetrazole-2-yl | CH₂SOCH₂CH₃ | |

TABLE 113-continued

| compound number | R4 | R1 | physical property (melting point-ND) |
|---|---|---|---|
| 9-323 | 1H-tetrazole-2-yl | CH$_3$-S(=O)-CH$_2$-cyclopropyl | |
| 9-324 | 1H-tetrazole-2-yl | CH$_2$SOCH$_2$CF$_3$ | |
| 9-325 | 1H-tetrazole-2-yl | CH$_2$SO$_2$CH$_3$ | |
| 9-326 | 1H-tetrazole-2-yl | CH$_2$SO$_2$CH$_2$CH$_3$ | |
| 9-327 | 1H-tetrazole-2-yl | CH$_3$-S(=O)$_2$-CH$_2$-cyclopropyl | |
| 9-328 | 1H-tetrazole-2-yl | CH$_2$SO$_2$CH$_2$CF$_3$ | |
| 9-329 | 1H-tetrazole-2-yl | CH$_2$O(CH$_3$)$_2$OCH$_3$ | |
| 9-330 | 1H-tetrazole-2-yl | CH$_2$O(CH$_3$)$_2$OCH$_2$CH$_3$ | |
| 9-331 | 1H-tetrazole-2-yl | CH$_2$O(CH$_3$)$_2$OCH$_2$CF$_3$ | |
| 9-332 | 1H-tetrazole-2-yl | CH$_2$O(CH$_3$)$_2$SCH$_3$ | |
| 9-333 | 1H-tetrazole-2-yl | CH$_2$O(CH$_3$)$_2$SCH$_2$CF$_3$ | |
| 9-334 | 1H-tetrazole-2-yl | CH$_2$O(CH$_3$)$_2$SOCH$_3$ | |
| 9-335 | 1H-tetrazole-2-yl | CH$_2$O(CH$_3$)$_2$SOCH$_2$CF$_3$ | |
| 9-336 | 1H-tetrazole-2-yl | CH$_2$O(CH$_3$)$_2$SO$_2$CH$_3$ | |
| 9-337 | 1H-tetrazole-2-yl | CH$_2$O(CH$_3$)$_2$SO$_2$CH$_2$CF$_3$ | |
| 9-338 | 1H-tetrazole-2-yl | CH$_3$-O-CH$_2$-(tetrahydrofuran-2-yl) | |
| 9-339 | 1H-tetrazole-2-yl | CH$_3$-O-(tetrahydrofuran-3-yl) | |
| 9-340 | 1H-tetrazole-2-yl | CH$_2$O(CH$_3$)$_2$NHSO$_2$CH$_3$ | |
| 9-341 | 1H-tetrazole-2-yl | CH$_2$O(CH$_3$)$_2$N(CH$_3$)(SO$_2$CH$_3$) | |

TABLE 114

Structure: cyclohexenone with gem-dimethyl, carbonyl-linked to pyridine bearing R1 and 1,2,4-triazol-1-yl group; R4 on cyclohexenone.

| compound number | R4 | R1 | physical property (melting point-ND) |
|---|---|---|---|
| 10-1 | Cl | CH$_3$ | |
| 10-2 | Cl | CF$_3$ | |
| 10-3 | Cl | CH$_2$OCH$_3$ | |
| 10-4 | Cl | CH$_2$OCH$_2$CH$_3$ | |
| 10-5 | Cl | CH$_3$-O-CH$_2$-cyclopropyl | |
| 10-6 | Cl | CH$_2$OCH$_2$CF$_3$ | |
| 10-7 | Cl | CH$_2$SCH$_3$ | |
| 10-8 | Cl | CH$_2$SCH$_2$CH$_3$ | |
| 10-9 | Cl | CH$_3$-S-CH$_2$-cyclopropyl | |
| 10-10 | Cl | CH$_2$SCH$_2$CF$_3$ | |
| 10-11 | Cl | CH$_2$SOCH$_3$ | |
| 10-12 | Cl | CH$_2$SOCH$_2$CH$_3$ | |
| 10-13 | Cl | CH$_3$-S(=O)-CH$_2$-cyclopropyl | |
| 10-14 | Cl | CH$_2$SOCH$_2$CF$_3$ | |
| 10-15 | Cl | CH$_2$SO$_2$CH$_3$ | |
| 10-16 | Cl | CH$_2$SO$_2$CH$_2$CH$_3$ | |
| 10-17 | Cl | CH$_3$-S(=O)$_2$-CH$_2$-cyclopropyl | |
| 10-18 | Cl | CH$_2$SO$_2$CH$_2$CF$_3$ | |
| 10-19 | Cl | CH$_2$O(CH$_3$)$_2$OCH$_3$ | |
| 10-20 | Cl | CH$_2$O(CH$_3$)$_2$OCH$_2$CH$_3$ | |
| 10-21 | Cl | CH$_2$O(CH$_3$)$_2$OCH$_2$CF$_3$ | |
| 10-22 | Cl | CH$_2$O(CH$_3$)$_2$SCH$_3$ | |
| 10-23 | Cl | CH$_2$O(CH$_3$)$_2$SCH$_2$CF$_3$ | |
| 10-24 | Cl | CH$_2$O(CH$_3$)$_2$SOCH$_3$ | |
| 10-25 | Cl | CH$_2$O(CH$_3$)$_2$SOCH$_2$CF$_3$ | |
| 10-26 | Cl | CH$_2$O(CH$_3$)$_2$SO$_2$CH$_3$ | |
| 10-27 | Cl | CH$_2$O(CH$_3$)$_2$SO$_2$CH$_2$CF$_3$ | |
| 10-28 | Cl | CH$_3$-O-CH$_2$-(tetrahydrofuran-2-yl) | |
| 10-29 | Cl | CH$_3$-O-(tetrahydrofuran-3-yl) | |
| 10-30 | Cl | CH$_2$O(CH$_3$)$_2$NHSO$_2$CH$_3$ | |
| 10-31 | Cl | CH$_2$O(CH$_3$)$_2$N(CH$_3$)(SO$_2$CH$_3$) | |
| 10-32 | SCH$_3$ | CH$_3$ | |
| 10-33 | SCH$_3$ | CF$_3$ | |
| 10-34 | SCH$_3$ | CH$_2$OCH$_3$ | |
| 10-35 | SCH$_3$ | CH$_2$OCH$_2$CH$_3$ | |
| 10-36 | SCH$_3$ | CH$_3$-O-CH$_2$-cyclopropyl | |
| 10-37 | SCH$_3$ | CH$_2$OCH$_2$CF$_3$ | |
| 10-38 | SCH$_3$ | CH$_2$SCH$_3$ | |
| 10-39 | SCH$_3$ | CH$_2$SCH$_2$CH$_3$ | |

TABLE 114-continued

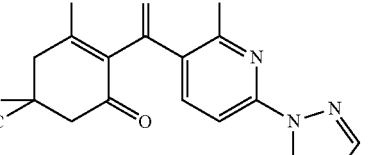

| compound number | R4 | R1 | physical property (melting point- ND) |
|---|---|---|---|
| 10-40 | SCH₃ | 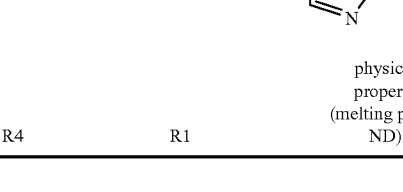 | |

TABLE 115

| compound number | R4 | R1 | physical property (melting point- ND) |
|---|---|---|---|
| 10-41 | SCH₃ | CH₂SCH₂CF₃ | |
| 10-42 | SCH₃ | CH₂SOCH₃ | |
| 10-43 | SCH₃ | CH₂SOCH₂CH₃ | |
| 10-44 | SCH₃ | 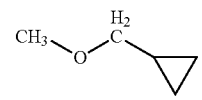 | |
| 10-45 | SCH₃ | CH₂SOCH₂CF₃ | |
| 10-46 | SCH₃ | CH₂SO₂CH₃ | |
| 10-47 | SCH₃ | CH₂SO₂CH₂CH₃ | |
| 10-48 | SCH₃ | 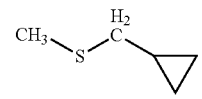 | |
| 10-49 | SCH₃ | CH₂SO₂CH₂CF₃ | |
| 10-50 | SCH₃ | CH₂O(CH₃)₂OCH₃ | |
| 10-51 | SCH₃ | CH₂O(CH₃)₂OCH₂CH₃ | |
| 10-52 | SCH₃ | CH₂O(CH₃)₂OCH₂CF₃ | |
| 10-53 | SCH₃ | CH₂O(CH₃)₂SCH₃ | |
| 10-54 | SCH₃ | CH₂O(CH₃)₂SCH₂CF₃ | |
| 10-55 | SCH₃ | CH₂O(CH₃)₂SOCH₃ | |
| 10-56 | SCH₃ | CH₂O(CH₃)₂SOCH₂CF₃ | |
| 10-57 | SCH₃ | CH₂O(CH₃)₂SO₂CH₃ | |
| 10-58 | SCH₃ | CH₂O(CH₃)₂SO₂CH₂CF₃ | |
| 10-59 | SCH₃ | 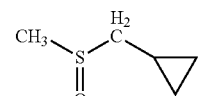 | |
| 10-60 | SCH₃ | 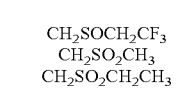 | |
| 10-61 | SCH₃ | CH₂O(CH₃)₂NHSO₂CH₃ | |
| 10-62 | SCH₃ | CH₂O(CH₃)₂N(CH₃)(SO₂CH₃) | |
| 10-63 | SCH₂CH₃ | CH₃ | |
| 10-64 | SCH₂CH₃ | CF₃ | |
| 10-65 | SCH₂CH₃ | CH₂OCH₃ | |
| 10-66 | SCH₂CH₃ | CH₂OCH₂CH₃ | |

TABLE 115-continued

| compound number | R4 | R1 | physical property (melting point- ND) |
|---|---|---|---|
| 10-67 | SCH₂CH₃ | CH₃-O-CH₂-cyclopropyl | |
| 10-68 | SCH₂CH₃ | CH₂OCH₂CF₃ | |
| 10-69 | SCH₂CH₃ | CH₂SCH₃ | |
| 10-70 | SCH₂CH₃ | CH₂SCH₂CH₃ | |
| 10-71 | SCH₂CH₃ | CH₃-S-CH₂-cyclopropyl | |
| 10-72 | SCH₂CH₃ | CH₂SCH₂CF₃ | |
| 10-73 | SCH₂CH₃ | CH₂SOCH₃ | |
| 10-74 | SCH₂CH₃ | CH₂SOCH₂CH₃ | |
| 10-75 | SCH₂CH₃ | CH₃-S(O)-CH₂-cyclopropyl | |
| 10-76 | SCH₂CH₃ | CH₂SOCH₂CF₃ | |
| 10-77 | SCH₂CH₃ | CH₂SO₂CH₃ | |
| 10-78 | SCH₂CH₃ | CH₂SO₂CH₂CH₃ | |
| 10-79 | SCH₂CH₃ | CH₃-SO₂-CH₂-cyclopropyl | |
| 10-80 | SCH₂CH₃ | CH₂SO₂CH₂CF₃ | |

TABLE 116

| compound number | R4 | R1 | physical property (melting point- ND) |
|---|---|---|---|
| 10-81 | SCH₂CH₃ | CH₂O(CH₂)₂OCH₃ | |
| 10-82 | SCH₂CH₃ | CH₂O(CH₂)₂OCH₂CH₃ | |
| 10-83 | SCH₂CH₃ | CH₂O(CH₂)₂OCH₂CF₃ | |
| 10-84 | SCH₂CH₃ | CH₂O(CH₂)₂SCH₃ | |
| 10-85 | SCH₂CH₃ | CH₂O(CH₂)₂SCH₂CF₃ | |
| 10-86 | SCH₂CH₃ | CH₂O(CH₂)₂SOCH₃ | |
| 10-87 | SCH₂CH₃ | CH₂O(CH₂)₂SOCH₂CF₃ | |
| 10-88 | SCH₂CH₃ | CH₂O(CH₂)₂SO₂CH₃ | |
| 10-89 | SCH₂CH₃ | CH₂O(CH₂)₂SO₂CH₂CF₃ | |
| 10-90 | SCH₂CH₃ | CH₃-O-CH₂-tetrahydrofuran | |
| 10-91 | SCH₂CH₃ | CH₃-O-tetrahydrofuran | |
| 10-92 | SCH₂CH₃ | CH₂O(CH₂)₂NHSO₂CH₃ | |
| 10-93 | SCH₂CH₃ | CH₂O(CH₂)₂N(CH₃)(SO₂CH₃) | |
| 10-94 | S(CH₂)₂CH₃ | CH₃ | |
| 10-95 | S(CH₂)₂CH₃ | CF₃ | |
| 10-96 | S(CH₂)₂CH₃ | CH₂OCH₃ | |
| 10-97 | S(CH₂)₂CH₃ | CH₂OCH₂CH₃ | |

TABLE 116-continued

| compound number | R4 | R1 | physical property (melting point-ND) |
|---|---|---|---|
| 10-98 | S(CH₂)₂CH₃ | 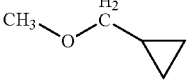 | |
| 10-99 | S(CH₂)₂CH₃ | CH₂OCH₂CF₃ | |
| 10-100 | S(CH₂)₂CH₃ | CH₂SCH₃ | |
| 10-101 | S(CH₂)₂CH₃ | CH₂SCH₂CH₃ | |
| 10-102 | S(CH₂)₂CH₃ | 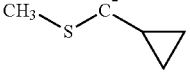 | |
| 10-103 | S(CH₂)₂CH₃ | CH₂SCH₂CF₃ | |
| 10-104 | S(CH₂)₂CH₃ | CH₂SOCH₃ | |
| 10-105 | S(CH₂)₂CH₃ | CH₂SOCH₂CH₃ | |
| 10-106 | S(CH₂)₂CH₃ | 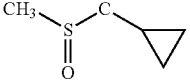 | |
| 10-107 | S(CH₂)₂CH₃ | CH₂SOCH₂CF₃ | |
| 10-108 | S(CH₂)₂CH₃ | CH₂SO₂CH₃ | |
| 10-109 | S(CH₂)₂CH₃ | CH₂SO₂CH₂CH₃ | |
| 10-110 | S(CH₂)₂CH₃ | 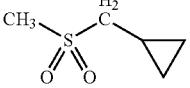 | |
| 10-111 | S(CH₂)₂CH₃ | CH₂SO₂CH₂CF₃ | |
| 10-112 | S(CH₂)₂CH₃ | CH₂O(CH₂)₂OCH₃ | |
| 10-113 | S(CH₂)₂CH₃ | CH₂O(CH₂)₂OCH₂CH₃ | |
| 10-114 | S(CH₂)₂CH₃ | CH₂O(CH₂)₂OCH₂CF₃ | |
| 10-115 | S(CH₂)₂CH₃ | CH₂O(CH₂)₂SCH₃ | |
| 10-116 | S(CH₂)₂CH₃ | CH₂O(CH₂)₂SCH₂CF₃ | |
| 10-117 | S(CH₂)₂CH₃ | CH₂O(CH₂)₂SOCH₃ | |
| 10-118 | S(CH₂)₂CH₃ | CH₂O(CH₂)₂SOCH₂CF₃ | |
| 10-119 | S(CH₂)₂CH₃ | CH₂O(CH₂)₂SO₂CH₃ | |
| 10-120 | S(CH₂)₂CH₃ | CH₂O(CH₂)₂SO₂CH₂CF₃ | |

TABLE 117

| compound number | R4 | R1 | physical property (melting point-ND) |
|---|---|---|---|
| 10-121 | S(CH₂)₂CH₃ | 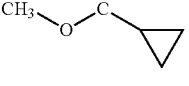 | |
| 10-122 | S(CH₂)₂CH₃ | 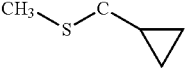 | |
| 10-123 | S(CH₂)₂CH₃ | CH₂O(CH₂)₂NHSO₂CH₃ | |
| 10-124 | S(CH₂)₂CH₃ | CH₂O(CH₂)₂N(CH₃)(SO₂CH₃) | |
| 10-125 | SC₆H₅ | CH₃ | |
| 10-126 | SC₆H₅ | CF₃ | |
| 10-127 | SC₆H₅ | CH₂OCH₃ | |
| 10-128 | SC₆H₅ | CH₂OCH₂CH₃ | |

TABLE 117-continued

| compound number | R4 | R1 | physical property (melting point-ND) |
|---|---|---|---|
| 10-129 | SC₆H₅ | 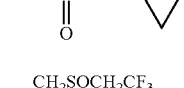 | |
| 10-130 | SC₆H₅ | CH₂OCH₂CF₃ | |
| 10-131 | SC₆H₅ | CH₂SCH₃ | |
| 10-132 | SC₆H₅ | CH₂SCH₂CH₃ | |
| 10-133 | SC₆H₅ | 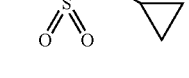 | |
| 10-134 | SC₆H₅ | CH₂SCH₂CF₃ | |
| 10-135 | SC₆H₅ | CH₂SOCH₃ | |
| 10-136 | SC₆H₅ | CH₂SOCH₂CH₃ | |
| 10-137 | SC₆H₅ | 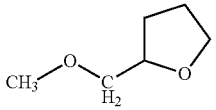 | |
| 10-138 | SC₆H₅ | CH₂SOCH₂CF₃ | |
| 10-139 | SC₆H₅ | CH₂SO₂CH₃ | |
| 10-140 | SC₆H₅ | CH₂SO₂CH₂CH₃ | |
| 10-141 | SC₆H₅ | 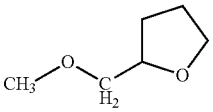 | |
| 10-142 | SC₆H₅ | CH₂SO₂CH₂CF₃ | |
| 10-143 | SC₆H₅ | CH₂O(CH₂)₂OCH₃ | |
| 10-144 | SC₆H₅ | CH₂O(CH₂)₂OCH₂CH₃ | |
| 10-145 | SC₆H₅ | CH₂O(CH₂)₂OCH₂CF₃ | |
| 10-146 | SC₆H₅ | CH₂O(CH₂)₂SCH₃ | |
| 10-147 | SC₆H₅ | CH₂O(CH₂)₂SCH₂CF₃ | |
| 10-148 | SC₆H₅ | CH₂O(CH₂)₂SOCH₃ | |
| 10-149 | SC₆H₅ | CH₂O(CH₂)₂SOCH₂CF₃ | |
| 10-150 | SC₆H₅ | CH₂O(CH₂)₂SO₂CH₃ | |
| 10-151 | SC₆H₅ | CH₂O(CH₂)₂SO₂CH₂CF₃ | |
| 10-152 | SC₆H₅ | 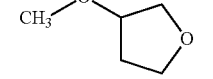 | |
| 10-153 | SC₆H₅ | 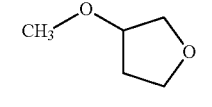 | |
| 10-154 | SC₆H₅ | CH₂O(CH₂)₂NHSO₂CH₃ | |
| 10-155 | SC₆H₅ | CH₂O(CH₂)₂N(CH₃)(SO₂CH₃) | |
| 10-156 | SCH₂C₆H₅ | CH₃ | |
| 10-157 | SCH₂C₆H₅ | CF₃ | |
| 10-158 | SCH₂C₆H₅ | CH₂OCH₃ | |
| 10-159 | SCH₂C₆H₅ | CH₂OCH₂CH₃ | |
| 10-160 | SCH₂C₆H₅ | 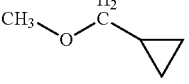 | |

TABLE 118

| compound number | R4 | R1 | physical property (melting point-ND) |
|---|---|---|---|
| 10-161 | SCH$_2$C$_6$H$_5$ | CH$_2$OCH$_2$CF$_3$ | |
| 10-162 | SCH$_2$C$_6$H$_5$ | CH$_2$SCH$_3$ | |
| 10-163 | SCH$_2$C$_6$H$_5$ | CH$_2$SCH$_2$CH$_3$ | |
| 10-164 | SCH$_2$C$_6$H$_5$ | CH$_3$–S–CH$_2$–cyclopropyl | |
| 10-165 | SCH$_2$C$_6$H$_5$ | CH$_2$SCH$_2$CF$_3$ | |
| 10-166 | SCH$_2$C$_6$H$_5$ | CH$_2$SOCH$_3$ | |
| 10-167 | SCH$_2$C$_6$H$_5$ | CH$_2$SOCH$_2$CH$_3$ | |
| 10-168 | SCH$_2$C$_6$H$_5$ | CH$_3$–S(O)–CH$_2$–cyclopropyl | |
| 10-169 | SCH$_2$C$_6$H$_5$ | CH$_2$SOCH$_2$CF$_3$ | |
| 10-170 | SCH$_2$C$_6$H$_5$ | CH$_2$SO$_2$CH$_3$ | |
| 10-171 | SCH$_2$C$_6$H$_5$ | CH$_2$SO$_2$CH$_2$CH$_3$ | |
| 10-172 | SCH$_2$C$_6$H$_5$ | CH$_3$–S(O)$_2$–CH$_2$–cyclopropyl | |
| 10-173 | SCH$_2$C$_6$H$_5$ | CH$_2$SO$_2$CH$_2$CF$_3$ | |
| 10-174 | SCH$_2$C$_6$H$_5$ | CH$_2$O(CH$_3$)$_2$OCH$_3$ | |
| 10-175 | SCH$_2$C$_6$H$_5$ | CH$_2$O(CH$_3$)$_2$OCH$_2$CH$_3$ | |
| 10-176 | SCH$_2$C$_6$H$_5$ | CH$_2$O(CH$_3$)$_2$OCH$_2$CF$_3$ | |
| 10-177 | SCH$_2$C$_6$H$_5$ | CH$_2$O(CH$_3$)$_2$SCH$_3$ | |
| 10-178 | SCH$_2$C$_6$H$_5$ | CH$_2$O(CH$_3$)$_2$SCH$_2$CF$_3$ | |
| 10-179 | SCH$_2$C$_6$H$_5$ | CH$_2$O(CH$_3$)$_2$SOCH$_3$ | |
| 10-180 | SCH$_2$C$_6$H$_5$ | CH$_2$O(CH$_3$)$_2$SOCH$_2$CF$_3$ | |
| 10-181 | SCH$_2$C$_6$H$_5$ | CH$_2$O(CH$_3$)$_2$SO$_2$CH$_3$ | |
| 10-182 | SCH$_2$C$_6$H$_5$ | CH$_2$O(CH$_3$)$_2$SO$_2$CH$_2$CF$_3$ | |
| 10-183 | SCH$_2$C$_6$H$_5$ | CH$_3$–O–CH$_2$–(tetrahydrofuran-2-yl) | |
| 10-184 | SCH$_2$C$_6$H$_5$ | CH$_3$–O–(tetrahydrofuran-3-yl) | |
| 10-185 | SCH$_2$C$_6$H$_5$ | CH$_2$O(CH$_3$)$_2$NHSO$_2$CH$_3$ | |
| 10-186 | SCH$_2$C$_6$H$_5$ | CH$_2$O(CH$_3$)$_2$N(CH$_3$)(SO$_2$CH$_3$) | |
| 10-187 | 1H-pyrazole-1-yl | CH$_3$ | |
| 10-188 | 1H-pyrazole-1-yl | CF$_3$ | |
| 10-189 | 1H-pyrazole-1-yl | CH$_2$OCH$_3$ | |
| 10-190 | 1H-pyrazole-1-yl | CH$_2$OCH$_2$CH$_3$ | |
| 10-191 | 1H-pyrazole-1-yl | CH$_3$–O–CH$_2$–cyclopropyl | |
| 10-192 | 1H-pyrazole-1-yl | CH$_2$OCH$_2$CF$_3$ | |
| 10-193 | 1H-pyrazole-1-yl | CH$_2$SCH$_3$ | |
| 10-194 | 1H-pyrazole-1-yl | CH$_2$SCH$_2$CH$_3$ | |
| 10-195 | 1H-pyrazole-1-yl | CH$_3$–S–CH$_2$–cyclopropyl | |
| 10-196 | 1H-pyrazole-1-yl | CH$_2$SCH$_2$CF$_3$ | |
| 10-197 | 1H-pyrazole-1-yl | CH$_2$SOCH$_3$ | |
| 10-198 | 1H-pyrazole-1-yl | CH$_2$SOCH$_2$CH$_3$ | |
| 10-199 | 1H-pyrazole-1-yl | CH$_3$–S(O)–CH$_2$–cyclopropyl | |
| 10-200 | 1H-pyrazole-1-yl | CH$_2$SOCH$_2$CF$_3$ | |

TABLE 119

| compound number | R4 | R1 | physical property (melting point-ND) |
|---|---|---|---|
| 10-201 | 1H-pyrazole-1-yl | CH$_2$SO$_2$CH$_3$ | |
| 10-202 | 1H-pyrazole-1-yl | CH$_2$SO$_2$CH$_2$CH$_3$ | |
| 10-203 | 1H-pyrazole-1-yl | CH$_3$–S(O)$_2$–CH$_2$–cyclopropyl | |
| 10-204 | 1H-pyrazole-1-yl | CH$_2$SO$_2$CH$_2$CF$_3$ | |
| 10-205 | 1H-pyrazole-1-yl | CH$_2$O(CH$_3$)$_2$OCH$_3$ | |
| 10-206 | 1H-pyrazole-1-yl | CH$_2$O(CH$_3$)$_2$OCH$_2$CH$_3$ | |
| 10-207 | 1H-pyrazole-1-yl | CH$_2$O(CH$_3$)$_2$OCH$_2$CF$_3$ | |
| 10-208 | 1H-pyrazole-1-yl | CH$_2$O(CH$_3$)$_2$SCH$_3$ | |
| 10-209 | 1H-pyrazole-1-yl | CH$_2$O(CH$_3$)$_2$SCH$_2$CF$_3$ | |
| 10-210 | 1H-pyrazole-1-yl | CH$_2$O(CH$_3$)$_2$SOCH$_3$ | |
| 10-211 | 1H-pyrazole-1-yl | CH$_2$O(CH$_3$)$_2$SOCH$_2$CF$_3$ | |
| 10-212 | 1H-pyrazole-1-yl | CH$_2$O(CH$_3$)$_2$SO$_2$CH$_3$ | |
| 10-213 | 1H-pyrazole-1-yl | CH$_2$O(CH$_3$)$_2$SO$_2$CH$_2$CF$_3$ | |
| 10-214 | 1H-pyrazole-1-yl | CH$_3$–O–CH$_2$–(tetrahydrofuran-2-yl) | |
| 10-215 | 1H-pyrazole-1-yl | CH$_3$–O–(tetrahydrofuran-3-yl) | |
| 10-216 | 1H-pyrazole-1-yl | CH$_2$O(CH$_3$)$_2$NHSO$_2$CH$_3$ | |
| 10-217 | 1H-pyrazole-1-yl | CH$_2$O(CH$_3$)$_2$N(CH$_3$)(SO$_2$CH$_3$) | |
| 10-218 | 1H-imidazole-1-yl | CH$_3$ | |
| 10-219 | 1H-imidazole-1-yl | CF$_3$ | |
| 10-220 | 1H-imidazole-1-yl | CH$_2$OCH$_3$ | |
| 10-221 | 1H-imidazole-1-yl | CH$_2$OCH$_2$CH$_3$ | |
| 10-222 | 1H-imidazole-1-yl | CH$_3$–O–CH$_2$–cyclopropyl | |
| 10-223 | 1H-imidazole-1-yl | CH$_2$OCH$_2$CF$_3$ | |
| 10-224 | 1H-imidazole-1-yl | CH$_2$SCH$_3$ | |
| 10-225 | 1H-imidazole-1-yl | CH$_2$SCH$_2$CH$_3$ | |
| 10-226 | 1H-imidazole-1-yl | CH$_3$–S–CH$_2$–cyclopropyl | |
| 10-227 | 1H-imidazole-1-yl | CH$_2$SCH$_2$CF$_3$ | |
| 10-228 | 1H-imidazole-1-yl | CH$_2$SOCH$_3$ | |
| 10-229 | 1H-imidazole-1-yl | CH$_2$SOCH$_2$CH$_3$ | |

TABLE 119-continued

| compound number | R4 | R1 | physical property (melting point-ND) |
|---|---|---|---|
| 10-230 | 1H-imidazole-1-yl | CH$_3$-S(=O)-CH$_2$-cyclopropyl | |
| 10-231 | 1H-imidazole-1-yl | CH$_2$SOCH$_2$CF$_3$ | |
| 10-232 | 1H-imidazole-1-yl | CH$_2$SO$_2$CH$_3$ | |
| 10-233 | 1H-imidazole-1-yl | CH$_2$SO$_2$CH$_2$CH$_3$ | |
| 10-234 | 1H-imidazole-1-yl | CH$_3$-S(=O)$_2$-CH$_2$-cyclopropyl | |
| 10-235 | 1H-imidazole-1-yl | CH$_2$SO$_2$CH$_2$CF$_3$ | |
| 10-236 | 1H-imidazole-1-yl | CH$_2$O(CH$_3$)$_2$OCH$_3$ | |
| 10-237 | 1H-imidazole-1-yl | CH$_2$O(CH$_3$)$_2$OCH$_2$CH$_3$ | |
| 10-238 | 1H-imidazole-1-yl | CH$_2$O(CH$_3$)$_2$OCH$_2$CF$_3$ | |
| 10-239 | 1H-imidazole-1-yl | CH$_2$O(CH$_3$)$_2$SCH$_3$ | |
| 10-240 | 1H-imidazole-1-yl | CH$_2$O(CH$_3$)$_2$SCH$_2$CF$_3$ | |

TABLE 120

| compound number | R4 | R1 | physical property (melting point-ND) |
|---|---|---|---|
| 10-241 | 1H-imidazole-1-yl | CH$_2$O(CH$_3$)$_2$SOCH$_3$ | |
| 10-242 | 1H-imidazole-1-yl | CH$_2$O(CH$_3$)$_2$SOCH$_2$CF$_3$ | |
| 10-243 | 1H-imidazole-1-yl | CH$_2$O(CH$_3$)$_2$SO$_2$CH$_3$ | |
| 10-244 | 1H-imidazole-1-yl | CH$_2$O(CH$_3$)$_2$SO$_2$CH$_2$CF$_3$ | |
| 10-245 | 1H-imidazole-1-yl | CH$_3$-O-CH$_2$-(tetrahydrofuran-2-yl) | |
| 10-246 | 1H-imidazole-1-yl | CH$_3$-O-(tetrahydrofuran-3-yl) | |
| 10-247 | 1H-imidazole-1-yl | CH$_2$O(CH$_3$)$_2$NHSO$_2$CH$_3$ | |
| 10-248 | 1H-imidazole-1-yl | CH$_2$O(CH$_3$)$_2$N(CH$_3$)(SO$_2$CH$_3$) | |
| 10-249 | 1H-triazole-1-yl | CH$_3$ | |
| 10-250 | 1H-triazole-1-yl | CF$_3$ | |
| 10-251 | 1H-triazole-1-yl | CH$_2$OCH$_3$ | |
| 10-252 | 1H-triazole-1-yl | CH$_2$OCH$_2$CH$_3$ | |
| 10-253 | 1H-triazole-1-yl | CH$_3$-O-CH$_2$-cyclopropyl | |
| 10-254 | 1H-triazole-1-yl | CH$_2$OCH$_2$CF$_3$ | |
| 10-255 | 1H-triazole-1-yl | CH$_2$SCH$_3$ | |
| 10-256 | 1H-triazole-1-yl | CH$_2$SCH$_2$CH$_3$ | |
| 10-257 | 1H-triazole-1-yl | CH$_3$-S-CH$_2$-cyclopropyl | |
| 10-258 | 1H-triazole-1-yl | CH$_2$SCH$_2$CF$_3$ | |
| 10-259 | 1H-triazole-1-yl | CH$_2$SOCH$_3$ | |
| 10-260 | 1H-triazole-1-yl | CH$_2$SOCH$_2$CH$_3$ | |

TABLE 120-continued

| compound number | R4 | R1 | physical property (melting point-ND) |
|---|---|---|---|
| 10-261 | 1H-triazole-1-yl | CH$_3$-S(=O)-CH$_2$-cyclopropyl | |
| 10-262 | 1H-triazole-1-yl | CH$_2$SOCH$_2$CF$_3$ | |
| 10-263 | 1H-triazole-1-yl | CH$_2$SO$_2$CH$_3$ | |
| 10-264 | 1H-triazole-1-yl | CH$_2$SO$_2$CH$_2$CH$_3$ | |
| 10-265 | 1H-triazole-1-yl | CH$_3$-S(=O)$_2$-CH$_2$-cyclopropyl | |
| 10-266 | 1H-triazole-1-yl | CH$_2$SO$_2$CH$_2$CF$_3$ | |
| 10-267 | 1H-triazole-1-yl | CH$_2$O(CH$_3$)$_2$OCH$_3$ | |
| 10-268 | 1H-triazole-1-yl | CH$_2$O(CH$_3$)$_2$OCH$_2$CH$_3$ | |
| 10-269 | 1H-triazole-1-yl | CH$_2$O(CH$_3$)$_2$OCH$_2$CF$_3$ | |
| 10-270 | 1H-triazole-1-yl | CH$_2$O(CH$_3$)$_2$SCH$_3$ | |
| 10-271 | 1H-triazole-1-yl | CH$_2$O(CH$_3$)$_2$SCH$_2$CF$_3$ | |
| 10-272 | 1H-triazole-1-yl | CH$_2$O(CH$_3$)$_2$SOCH$_3$ | |
| 10-273 | 1H-triazole-1-yl | CH$_2$O(CH$_3$)$_2$SOCH$_2$CF$_3$ | |
| 10-274 | 1H-triazole-1-yl | CH$_2$O(CH$_3$)$_2$SO$_2$CH$_3$ | |
| 10-275 | 1H-triazole-1-yl | CH$_2$O(CH$_3$)$_2$SO$_2$CH$_2$CF$_3$ | |
| 10-276 | 1H-triazole-1-yl | CH$_3$-O-CH$_2$-(tetrahydrofuran-2-yl) | |
| 10-277 | 1H-triazole-1-yl | CH$_3$-O-(tetrahydrofuran-3-yl) | |
| 10-278 | 1H-triazole-1-yl | CH$_2$O(CH$_3$)$_2$NHSO$_2$CH$_3$ | |
| 10-279 | 1H-triazole-1-yl | CH$_2$O(CH$_3$)$_2$N(CH$_3$)(SO$_2$CH$_3$) | |
| 10-280 | 1H-tetrazole-1-yl | CH$_3$ | |

TABLE 121

| compound number | R4 | R1 | physical property (melting point-ND) |
|---|---|---|---|
| 10-281 | 1H-tetrazole-1-yl | CF$_3$ | |
| 10-282 | 1H-tetrazole-1-yl | CH$_2$OCH$_3$ | |
| 10-283 | 1H-tetrazole-1-yl | CH$_2$OCH$_2$CH$_3$ | |
| 10-284 | 1H-tetrazole-1-yl | CH$_3$-O-CH$_2$-cyclopropyl | |
| 10-285 | 1H-tetrazole-1-yl | CH$_2$OCH$_2$CF$_3$ | |
| 10-286 | 1H-tetrazole-1-yl | CH$_2$SCH$_3$ | |
| 10-287 | 1H-tetrazole-1-yl | CH$_2$SCH$_2$CH$_3$ | |
| 10-288 | 1H-tetrazole-1-yl | CH$_3$-S-CH$_2$-cyclopropyl | |
| 10-289 | 1H-tetrazole-1-yl | CH$_2$SCH$_2$CF$_3$ | |
| 10-290 | 1H-tetrazole-1-yl | CH$_2$SOCH$_3$ | |
| 10-291 | 1H-tetrazole-1-yl | CH$_2$SOCH$_2$CH$_3$ | |

TABLE 121-continued

| compound number | R4 | R1 | physical property (melting point- ND) |
|---|---|---|---|
| 10-292 | 1H-tetrazole-1-yl | CH₃-S(=O)-CH₂-cyclopropyl | |
| 10-293 | 1H-tetrazole-1-yl | CH$_2$SOCH$_2$CF$_3$ | |
| 10-294 | 1H-tetrazole-1-yl | CH$_2$SO$_2$CH$_3$ | |
| 10-295 | 1H-tetrazole-1-yl | CH$_2$SO$_2$CH$_2$CH$_3$ | |
| 10-296 | 1H-tetrazole-1-yl | CH₃-S(=O)₂-CH₂-cyclopropyl | |
| 10-297 | 1H-tetrazole-1-yl | CH$_2$SO$_2$CH$_2$CF$_3$ | |
| 10-298 | 1H-tetrazole-1-yl | CH$_2$O(CH$_3$)$_2$OCH$_3$ | |
| 10-299 | 1H-tetrazole-1-yl | CH$_2$O(CH$_3$)$_2$OCH$_2$CH$_3$ | |
| 10-300 | 1H-tetrazole-1-yl | CH$_2$O(CH$_3$)$_2$OCH$_2$CF$_3$ | |
| 10-301 | 1H-tetrazole-1-yl | CH$_2$O(CH$_3$)$_2$SCH$_3$ | |
| 10-302 | 1H-tetrazole-1-yl | CH$_2$O(CH$_3$)$_2$SCH$_2$CF$_3$ | |
| 10-303 | 1H-tetrazole-1-yl | CH$_2$O(CH$_3$)$_2$SOCH$_3$ | |
| 10-304 | 1H-tetrazole-1-yl | CH$_2$O(CH$_3$)$_2$SOCH$_2$CF$_3$ | |
| 10-305 | 1H-tetrazole-1-yl | CH$_2$O(CH$_3$)$_2$SO$_2$CH$_3$ | |
| 10-306 | 1H-tetrazole-1-yl | CH$_2$O(CH$_3$)$_2$SO$_2$CH$_2$CF$_3$ | |
| 10-307 | 1H-tetrazole-1-yl | CH₃-O-CH₂-(tetrahydrofuran-2-yl) | |
| 10-308 | 1H-tetrazole-1-yl | CH₃-O-(tetrahydrofuran-3-yl) | |
| 10-309 | 1H-tetrazole-1-yl | CH$_2$O(CH$_3$)$_2$NHSO$_2$CH$_3$ | |
| 10-310 | 1H-tetrazole-1-yl | CH$_2$O(CH$_3$)$_2$N(CH$_3$)(SO$_2$CH$_3$) | |
| 10-311 | 1H-tetrazole-2-yl | CH$_3$ | |
| 10-312 | 1H-tetrazole-2-yl | CF$_3$ | |
| 10-313 | 1H-tetrazole-2-yl | CH$_2$OCH$_3$ | |
| 10-314 | 1H-tetrazole-2-yl | CH$_2$OCH$_2$CH$_3$ | |
| 10-315 | 1H-tetrazole-2-yl | CH₃-O-CH₂-cyclopropyl | |
| 10-316 | 1H-tetrazole-2-yl | CH$_2$OCH$_2$CF$_3$ | |
| 10-317 | 1H-tetrazole-2-yl | CH$_2$SCH$_3$ | |
| 10-318 | 1H-tetrazole-2-yl | CH$_2$SCH$_2$CH$_3$ | |
| 10-319 | 1H-tetrazole-2-yl | CH₃-S-CH₂-cyclopropyl | |
| 10-320 | 1H-tetrazole-2-yl | CH$_2$SCH$_2$CF$_3$ | |

TABLE 122

| compound number | R4 | R1 | physical property (melting point- ND) |
|---|---|---|---|
| 10-321 | 1H-tetrazole-2-yl | CH$_2$SOCH$_3$ | |
| 10-322 | 1H-tetrazole-2-yl | CH$_2$SOCH$_2$CH$_3$ | |
| 10-323 | 1H-tetrazole-2-yl | CH₃-S(=O)-CH₂-cyclopropyl | |
| 10-324 | 1H-tetrazole-2-yl | CH$_2$SOCH$_2$CF$_3$ | |
| 10-325 | 1H-tetrazole-2-yl | CH$_2$SO$_2$CH$_3$ | |
| 10-326 | 1H-tetrazole-2-yl | CH$_2$SO$_2$CH$_2$CH$_3$ | |
| 10-327 | 1H-tetrazole-2-yl | CH₃-S(=O)₂-CH₂-cyclopropyl | |
| 10-328 | 1H-tetrazole-2-yl | CH$_2$SO$_2$CH$_2$CF$_3$ | |
| 10-329 | 1H-tetrazole-2-yl | CH$_2$O(CH$_3$)$_2$OCH$_3$ | |
| 10-330 | 1H-tetrazole-2-yl | CH$_2$O(CH$_3$)$_2$OCH$_2$CH$_3$ | |
| 10-331 | 1H-tetrazole-2-yl | CH$_2$O(CH$_3$)$_2$OCH$_2$CF$_3$ | |
| 10-332 | 1H-tetrazole-2-yl | CH$_2$O(CH$_3$)$_2$SCH$_3$ | |
| 10-333 | 1H-tetrazole-2-yl | CH$_2$O(CH$_3$)$_2$SCH$_2$CF$_3$ | |
| 10-334 | 1H-tetrazole-2-yl | CH$_2$O(CH$_3$)$_2$SOCH$_3$ | |
| 10-335 | 1H-tetrazole-2-yl | CH$_2$O(CH$_3$)$_2$SOCH$_2$CF$_3$ | |
| 10-336 | 1H-tetrazole-2-yl | CH$_2$O(CH$_3$)$_2$SO$_2$CH$_3$ | |
| 10-337 | 1H-tetrazole-2-yl | CH$_2$O(CH$_3$)$_2$SO$_2$CH$_2$CF$_3$ | |
| 10-338 | 1H-tetrazole-2-yl | CH₃-O-CH₂-(tetrahydrofuran-2-yl) | |
| 10-339 | 1H-tetrazole-2-yl | CH₃-O-(tetrahydrofuran-3-yl) | |
| 10-340 | 1H-tetrazole-2-yl | CH$_2$O(CH$_3$)$_2$NHSO$_2$CH$_3$ | |
| 10-341 | 1H-tetrazole-2-yl | CH$_2$O(CH$_3$)$_2$N(CH$_3$)(SO$_2$CH$_3$) | |

TABLE 123

[Structure: cyclohexenone-diketone core with R4, C(=O)-pyridine-R1, pyridine linked to 1,2,4-triazol-1-yl; gem-dimethyl groups on ring]

| compound number | R4 | R1 | physical property (melting point- ND) |
|---|---|---|---|
| 11-1 | Cl | CH$_3$ | |
| 11-2 | Cl | CF$_3$ | |
| 11-3 | Cl | CH$_2$OCH$_3$ | |
| 11-4 | Cl | CH$_2$OCH$_2$CH$_3$ | |
| 11-5 | Cl | CH₃-O-CH₂-cyclopropyl | |
| 11-6 | Cl | CH$_2$OCH$_2$CF$_3$ | |
| 11-7 | Cl | CH$_2$SCH$_3$ | |
| 11-8 | Cl | CH$_2$SCH$_2$CH$_3$ | |

TABLE 123-continued

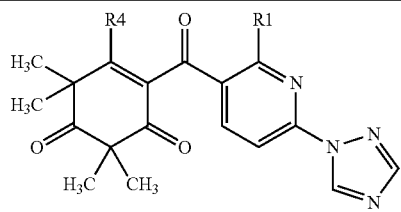

| compound number | R4 | R1 | physical property (melting point-ND) |
|---|---|---|---|
| 11-9 | Cl | 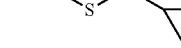 | |
| 11-10 | Cl | CH₂SCH₂CF₃ | |
| 11-11 | Cl | CH₂SOCH₃ | |
| 11-12 | Cl | CH₂SOCH₂CH₃ | |
| 11-13 | Cl |  | |
| 11-14 | Cl | CH₂SOCH₂CF₃ | |
| 11-15 | Cl | CH₂SO₂CH₃ | |
| 11-16 | Cl | CH₂SO₂CH₂CH₃ | |
| 11-17 | Cl | 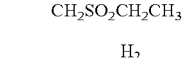 | |
| 11-18 | Cl | CH₂SO₂CH₂CF₃ | |
| 11-19 | Cl | CH₂O(CH₃)₂OCH₃ | |
| 11-20 | Cl | CH₂O(CH₃)₂OCH₂CH₃ | |
| 11-21 | Cl | CH₂O(CH₃)₂OCH₂CF₃ | |
| 11-22 | Cl | CH₂O(CH₃)₂SCH₃ | |
| 11-23 | Cl | CH₂O(CH₃)₂SCH₂CF₃ | |
| 11-24 | Cl | CH₂O(CH₃)₂SOCH₃ | |
| 11-25 | Cl | CH₂O(CH₃)₂SOCH₂CF₃ | |
| 11-26 | Cl | CH₂O(CH₃)₂SO₂CH₃ | |
| 11-27 | Cl | CH₂O(CH₃)₂SO₂CH₂CF₃ | |
| 11-28 | Cl | 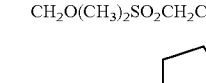 | |
| 11-29 | Cl | 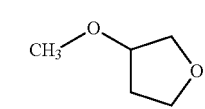 | |
| 11-30 | Cl | CH₂O(CH₃)₂NHSO₂CH₃ | |
| 11-31 | Cl | CH₂O(CH₃)₂N(CH₃)(SO₂CH₃) | |
| 11-32 | SCH₃ | CH₃ | |
| 11-33 | SCH₃ | CF₃ | |
| 11-34 | SCH₃ | CH₂OCH₃ | |
| 11-35 | SCH₃ | CH₂OCH₂CH₃ | |
| 11-36 | SCH₃ | 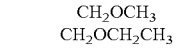 | |
| 11-37 | SCH₃ | CH₂OCH₂CF₃ | |
| 11-38 | SCH₃ | CH₂SCH₃ | |
| 11-39 | SCH₃ | CH₂SCH₂CH₃ | |

TABLE 123-continued

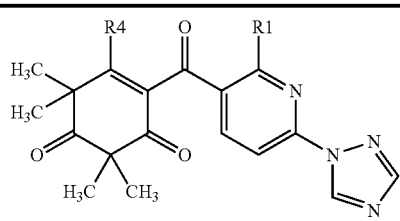

| compound number | R4 | R1 | physical property (melting point-ND) |
|---|---|---|---|
| 11-40 | SCH₃ | 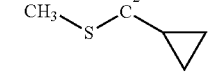 | |

TABLE 124

| compound number | R4 | R1 | physical property (melting point-ND) |
|---|---|---|---|
| 11-41 | SCH₃ | CH₂SCH₂CF₃ | |
| 11-42 | SCH₃ | CH₂SOCH₃ | |
| 11-43 | SCH₃ | CH₂SOCH₂CH₃ | |
| 11-44 | SCH₃ | 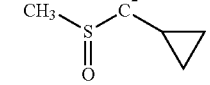 | |
| 11-45 | SCH₃ | CH₂SOCH₂CF₃ | |
| 11-46 | SCH₃ | CH₂SO₂CH₃ | |
| 11-47 | SCH₃ | CH₂SO₂CH₂CH₃ | |
| 11-48 | SCH₃ | 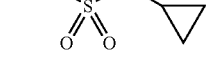 | |
| 11-49 | SCH₃ | CH₂SO₂CH₂CF₃ | |
| 11-50 | SCH₃ | CH₂O(CH₃)₂OCH₃ | |
| 11-51 | SCH₃ | CH₂O(CH₃)₂OCH₂CH₃ | |
| 11-52 | SCH₃ | CH₂O(CH₃)₂OCH₂CF₃ | |
| 11-53 | SCH₃ | CH₂O(CH₃)₂SCH₃ | |
| 11-54 | SCH₃ | CH₂O(CH₃)₂SCH₂CF₃ | |
| 11-55 | SCH₃ | CH₂O(CH₃)₂SOCH₃ | |
| 11-56 | SCH₃ | CH₂O(CH₃)₂SOCH₂CF₃ | |
| 11-57 | SCH₃ | CH₂O(CH₃)₂SO₂CH₃ | |
| 11-58 | SCH₃ | CH₂O(CH₃)₂SO₂CH₂CF₃ | |
| 11-59 | SCH₃ | 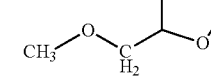 | |
| 11-60 | SCH₃ | 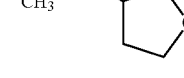 | |
| 11-61 | SCH₃ | CH₂O(CH₃)₂NHSO₂CH₃ | |
| 11-62 | SCH₃ | CH₂O(CH₃)₂N(CH₃)(SO₂CH₃) | |
| 11-63 | SCH₂CH₃ | CH₃ | |
| 11-64 | SCH₂CH₃ | CF₃ | |
| 11-65 | SCH₂CH₃ | CH₂OCH₃ | |
| 11-66 | SCH₂CH₃ | CH₂OCH₂CH₃ | |

TABLE 124-continued

| compound number | R4 | R1 | physical property (melting point-ND) |
|---|---|---|---|
| 11-67 | SCH$_2$CH$_3$ | CH$_3$-O-CH$_2$-cyclopropyl | |
| 11-68 | SCH$_2$CH$_3$ | CH$_2$OCH$_2$CF$_3$ | |
| 11-69 | SCH$_2$CH$_3$ | CH$_2$SCH$_3$ | |
| 11-70 | SCH$_2$CH$_3$ | CH$_2$SCH$_2$CH$_3$ | |
| 11-71 | SCH$_2$CH$_3$ | CH$_3$-S-CH$_2$-cyclopropyl | |
| 11-72 | SCH$_2$CH$_3$ | CH$_2$SCH$_2$CF$_3$ | |
| 11-73 | SCH$_2$CH$_3$ | CH$_2$SOCH$_3$ | |
| 11-74 | SCH$_2$CH$_3$ | CH$_2$SOCH$_2$CH$_3$ | |
| 11-75 | SCH$_2$CH$_3$ | CH$_3$-S(=O)-CH$_2$-cyclopropyl | |
| 11-76 | SCH$_2$CH$_3$ | CH$_2$SOCH$_2$CF$_3$ | |
| 11-77 | SCH$_2$CH$_3$ | CH$_2$SO$_2$CH$_3$ | |
| 11-78 | SCH$_2$CH$_3$ | CH$_2$SO$_2$CH$_2$CH$_3$ | |
| 11-79 | SCH$_2$CH$_3$ | CH$_3$-S(=O)$_2$-CH$_2$-cyclopropyl | |
| 11-80 | SCH$_2$CH$_3$ | CH$_2$SO$_2$CH$_2$CF$_3$ | |

TABLE 125

| compound number | R4 | R1 | physical property (melting point-ND) |
|---|---|---|---|
| 11-81 | SCH$_2$CH$_3$ | CH$_2$O(CH$_3$)$_2$OCH$_3$ | |
| 11-82 | SCH$_2$CH$_3$ | CH$_2$O(CH$_3$)$_2$OCH$_2$CH$_3$ | |
| 11-83 | SCH$_2$CH$_3$ | CH$_2$O(CH$_3$)$_2$OCH$_2$CF$_3$ | |
| 11-84 | SCH$_2$CH$_3$ | CH$_2$O(CH$_3$)$_2$SCH$_3$ | |
| 11-85 | SCH$_2$CH$_3$ | CH$_2$O(CH$_3$)$_2$SCH$_2$CF$_3$ | |
| 11-86 | SCH$_2$CH$_3$ | CH$_2$O(CH$_3$)$_2$SOCH$_3$ | |
| 11-87 | SCH$_2$CH$_3$ | CH$_2$O(CH$_3$)$_2$SOCH$_2$CF$_3$ | |
| 11-88 | SCH$_2$CH$_3$ | CH$_2$O(CH$_3$)$_2$SO$_2$CH$_3$ | |
| 11-89 | SCH$_2$CH$_3$ | CH$_2$O(CH$_3$)$_2$SO$_2$CH$_2$CF$_3$ | |
| 11-90 | SCH$_2$CH$_3$ | CH$_3$-O-CH$_2$-(tetrahydrofuran-2-yl) | |
| 11-91 | SCH$_2$CH$_3$ | CH$_3$-O-(tetrahydrofuran-3-yl) | |
| 11-92 | SCH$_2$CH$_3$ | CH$_2$O(CH$_3$)$_2$NHSO$_2$CH$_3$ | |
| 11-93 | SCH$_2$CH$_3$ | CH$_2$O(CH$_3$)$_2$N(CH$_3$)(SO$_2$CH$_3$) | |
| 11-94 | S(CH$_3$)$_2$CH$_3$ | CH$_3$ | |
| 11-95 | S(CH$_3$)$_2$CH$_3$ | CF$_3$ | |
| 11-96 | S(CH$_3$)$_2$CH$_3$ | CH$_2$OCH$_3$ | |
| 11-97 | S(CH$_3$)$_2$CH$_3$ | CH$_2$OCH$_2$CH$_3$ | |

TABLE 125-continued

| compound number | R4 | R1 | physical property (melting point-ND) |
|---|---|---|---|
| 11-98 | S(CH$_3$)$_2$CH$_3$ | CH$_3$-O-CH$_2$-cyclopropyl | |
| 11-99 | S(CH$_3$)$_2$CH$_3$ | CH$_2$OCH$_2$CF$_3$ | |
| 11-100 | S(CH$_3$)$_2$CH$_3$ | CH$_2$SCH$_3$ | |
| 11-101 | S(CH$_3$)$_2$CH$_3$ | CH$_2$SCH$_2$CH$_3$ | |
| 11-102 | S(CH$_3$)$_2$CH$_3$ | CH$_3$-S-CH$_2$-cyclopropyl | |
| 11-103 | S(CH$_3$)$_2$CH$_3$ | CH$_2$SCH$_2$CF$_3$ | |
| 11-104 | S(CH$_3$)$_2$CH$_3$ | CH$_2$SOCH$_3$ | |
| 11-105 | S(CH$_3$)$_2$CH$_3$ | CH$_2$SOCH$_2$CH$_3$ | |
| 11-106 | S(CH$_3$)$_2$CH$_3$ | CH$_3$-S(=O)-CH$_2$-cyclopropyl | |
| 11-107 | S(CH$_3$)$_2$CH$_3$ | CH$_2$SOCH$_2$CF$_3$ | |
| 11-108 | S(CH$_3$)$_2$CH$_3$ | CH$_2$SO$_2$CH$_3$ | |
| 11-109 | S(CH$_3$)$_2$CH$_3$ | CH$_2$SO$_2$CH$_2$CH$_3$ | |
| 11-110 | S(CH$_3$)$_2$CH$_3$ | CH$_3$-S(=O)$_2$-CH$_2$-cyclopropyl | |
| 11-111 | S(CH$_3$)$_2$CH$_3$ | CH$_2$SO$_2$CH$_2$CF$_3$ | |
| 11-112 | S(CH$_3$)$_2$CH$_3$ | CH$_2$O(CH$_3$)$_2$OCH$_3$ | |
| 11-113 | S(CH$_3$)$_2$CH$_3$ | CH$_2$O(CH$_3$)$_2$OCH$_2$CH$_3$ | |
| 11-114 | S(CH$_3$)$_2$CH$_3$ | CH$_2$O(CH$_3$)$_2$OCH$_2$CF$_3$ | |
| 11-115 | S(CH$_3$)$_2$CH$_3$ | CH$_2$O(CH$_3$)$_2$SCH$_3$ | |
| 11-116 | S(CH$_3$)$_2$CH$_3$ | CH$_2$O(CH$_3$)$_2$SCH$_2$CF$_3$ | |
| 11-117 | S(CH$_3$)$_2$CH$_3$ | CH$_2$O(CH$_3$)$_2$SOCH$_3$ | |
| 11-118 | S(CH$_3$)$_2$CH$_3$ | CH$_2$O(CH$_3$)$_2$SOCH$_2$CF$_3$ | |
| 11-119 | S(CH$_3$)$_2$CH$_3$ | CH$_2$O(CH$_3$)$_2$SO$_2$CH$_3$ | |
| 11-120 | S(CH$_3$)$_2$CH$_3$ | CH$_2$O(CH$_3$)$_2$SO$_2$CH$_2$CF$_3$ | |

TABLE 126

| compound number | R4 | R1 | physical property (melting point-ND) |
|---|---|---|---|
| 11-121 | S(CH$_2$)$_2$CH$_3$ | CH$_3$-O-CH$_2$-(tetrahydrofuran-2-yl) | |
| 11-122 | S(CH$_2$)$_2$CH$_3$ | CH$_3$-O-(tetrahydrofuran-3-yl) | |
| 11-123 | S(CH$_2$)$_2$CH$_3$ | CH$_2$O(CH$_2$)$_2$NHSO$_2$CH$_3$ | |
| 11-124 | S(CH$_2$)$_2$CH$_3$ | CH$_2$O(CH$_2$)$_2$N(CH$_3$)(SO$_2$CH$_3$) | |
| 11-125 | SC$_6$H$_5$ | CH$_3$ | |
| 11-126 | SC$_6$H$_5$ | CF$_3$ | |
| 11-127 | SC$_6$H$_5$ | CH$_2$OCH$_3$ | |
| 11-128 | SC$_6$H$_5$ | CH$_2$OCH$_2$CH$_3$ | |

TABLE 126-continued

| compound number | R4 | R1 | physical property (melting point-ND) |
|---|---|---|---|
| 11-129 | SC$_6$H$_5$ | CH$_3$-O-CH(cyclopropyl) | |
| 11-130 | SC$_6$H$_5$ | CH$_2$OCH$_2$CF$_3$ | |
| 11-131 | SC$_6$H$_5$ | CH$_2$SCH$_3$ | |
| 11-132 | SC$_6$H$_5$ | CH$_2$SCH$_2$CH$_3$ | |
| 11-133 | SC$_6$H$_5$ | CH$_3$-S-CH(cyclopropyl) | |
| 11-134 | SC$_6$H$_5$ | CH$_2$SCH$_2$CF$_3$ | |
| 11-135 | SC$_6$H$_5$ | CH$_2$SOCH$_3$ | |
| 11-136 | SC$_6$H$_5$ | CH$_2$SOCH$_2$CH$_3$ | |
| 11-137 | SC$_6$H$_5$ | CH$_3$-S(=O)-CH(cyclopropyl) | |
| 11-138 | SC$_6$H$_5$ | CH$_2$SOCH$_2$CF$_3$ | |
| 11-139 | SC$_6$H$_5$ | CH$_2$SO$_2$CH$_3$ | |
| 11-140 | SC$_6$H$_5$ | CH$_2$SO$_2$CH$_2$CH$_3$ | |
| 11-141 | SC$_6$H$_5$ | CH$_3$-S(=O)$_2$-CH(cyclopropyl) | |
| 11-142 | SC$_6$H$_5$ | CH$_2$SO$_2$CH$_2$CF$_3$ | |
| 11-143 | SC$_6$H$_5$ | CH$_2$O(CH$_2$)$_2$OCH$_3$ | |
| 11-144 | SC$_6$H$_5$ | CH$_2$O(CH$_2$)$_2$OCH$_2$CH$_3$ | |
| 11-145 | SC$_6$H$_5$ | CH$_2$O(CH$_2$)$_2$OCH$_2$CF$_3$ | |
| 11-146 | SC$_6$H$_5$ | CH$_2$O(CH$_2$)$_2$SCH$_3$ | |
| 11-147 | SC$_6$H$_5$ | CH$_2$O(CH$_2$)$_2$SCH$_2$CF$_3$ | |
| 11-148 | SC$_6$H$_5$ | CH$_2$O(CH$_2$)$_2$SOCH$_3$ | |
| 11-149 | SC$_6$H$_5$ | CH$_2$O(CH$_2$)$_2$SOCH$_2$CF$_3$ | |
| 11-150 | SC$_6$H$_5$ | CH$_2$O(CH$_2$)$_2$SO$_2$CH$_3$ | |
| 11-151 | SC$_6$H$_5$ | CH$_2$O(CH$_2$)$_2$SO$_2$CH$_2$CF$_3$ | |
| 11-152 | SC$_6$H$_5$ | CH$_3$-O-CH$_2$-(tetrahydrofuran-2-yl) | |
| 11-153 | SC$_6$H$_5$ | CH$_3$-O-(tetrahydrofuran-3-yl) | |
| 11-154 | SC$_6$H$_5$ | CH$_2$O(CH$_2$)$_2$NHSO$_2$CH$_3$ | |
| 11-155 | SC$_6$H$_5$ | CH$_2$O(CH$_2$)$_2$N(CH$_3$)(SO$_2$CH$_3$) | |
| 11-156 | SCH$_2$C$_6$H$_5$ | CH$_3$ | |
| 11-157 | SCH$_2$C$_6$H$_5$ | CF$_3$ | |
| 11-158 | SCH$_2$C$_6$H$_5$ | CH$_2$OCH$_3$ | |
| 11-159 | SCH$_2$C$_6$H$_5$ | CH$_2$OCH$_2$CH$_3$ | |
| 11-160 | SCH$_2$C$_6$H$_5$ | CH$_3$-O-CH(cyclopropyl) | |

TABLE 127

| compound number | R4 | R1 | physical property (melting point-ND) |
|---|---|---|---|
| 11-161 | SCH$_2$C$_6$H$_5$ | CH$_2$OCH$_2$CF$_3$ | |
| 11-162 | SCH$_2$C$_6$H$_5$ | CH$_2$SCH$_3$ | |
| 11-163 | SCH$_2$C$_6$H$_5$ | CH$_2$SCH$_2$CH$_3$ | |
| 11-164 | SCH$_2$C$_6$H$_5$ | CH$_3$-S-CH(cyclopropyl) | |
| 11-165 | SCH$_2$C$_6$H$_5$ | CH$_2$SCH$_2$CF$_3$ | |
| 11-166 | SCH$_2$C$_6$H$_5$ | CH$_2$SOCH$_3$ | |
| 11-167 | SCH$_2$C$_6$H$_5$ | CH$_2$SOCH$_2$CH$_3$ | |
| 11-168 | SCH$_2$C$_6$H$_5$ | CH$_3$-S(=O)-CH(cyclopropyl) | |
| 11-169 | SCH$_2$C$_6$H$_5$ | CH$_2$SOCH$_2$CF$_3$ | |
| 11-170 | SCH$_2$C$_6$H$_5$ | CH$_2$SO$_2$CH$_3$ | |
| 11-171 | SCH$_2$C$_6$H$_5$ | CH$_2$SO$_2$CH$_2$CH$_3$ | |
| 11-172 | SCH$_2$C$_6$H$_5$ | CH$_3$-S(=O)$_2$-CH(cyclopropyl) | |
| 11-173 | SCH$_2$C$_6$H$_5$ | CH$_2$SO$_2$CH$_2$CF$_3$ | |
| 11-174 | SCH$_2$C$_6$H$_5$ | CH$_2$O(CH$_2$)$_2$OCH$_3$ | |
| 11-175 | SCH$_2$C$_6$H$_5$ | CH$_2$O(CH$_2$)$_2$OCH$_2$CH$_3$ | |
| 11-176 | SCH$_2$C$_6$H$_5$ | CH$_2$O(CH$_2$)$_2$OCH$_2$CF$_3$ | |
| 11-177 | SCH$_2$C$_6$H$_5$ | CH$_2$O(CH$_2$)$_2$SCH$_3$ | |
| 11-178 | SCH$_2$C$_6$H$_5$ | CH$_2$O(CH$_2$)$_2$SCH$_2$CF$_3$ | |
| 11-179 | SCH$_2$C$_6$H$_5$ | CH$_2$O(CH$_2$)$_2$SOCH$_3$ | |
| 11-180 | SCH$_2$C$_6$H$_5$ | CH$_2$O(CH$_2$)$_2$SOCH$_2$CF$_3$ | |
| 11-181 | SCH$_2$C$_6$H$_5$ | CH$_2$O(CH$_2$)$_2$SO$_2$CH$_3$ | |
| 11-182 | SCH$_2$C$_6$H$_5$ | CH$_2$O(CH$_2$)$_2$SO$_2$CH$_2$CF$_3$ | |
| 11-183 | SCH$_2$C$_6$H$_5$ | CH$_3$-O-CH$_2$-(tetrahydrofuran-2-yl) | |
| 11-184 | SCH$_2$C$_6$H$_5$ | CH$_3$-O-(tetrahydrofuran-3-yl) | |
| 11-185 | SCH$_2$C$_6$H$_5$ | CH$_2$O(CH$_2$)$_2$NHSO$_2$CH$_3$ | |
| 11-186 | SCH$_2$C$_6$H$_5$ | CH$_2$O(CH$_2$)$_2$N(CH$_3$)(SO$_2$CH$_3$) | |
| 11-187 | 1H-pyrazole-1-yl | CH$_3$ | |
| 11-188 | 1H-pyrazole-1-yl | CF$_3$ | |
| 11-189 | 1H-pyrazole-1-yl | CH$_2$OCH$_3$ | |
| 11-190 | 1H-pyrazole-1-yl | CH$_2$OCH$_2$CH$_3$ | |
| 11-191 | 1H-pyrazole-1-yl | CH$_3$-O-CH(cyclopropyl) | |
| 11-192 | 1H-pyrazole-1-yl | CH$_2$OCH$_2$CF$_3$ | |
| 11-193 | 1H-pyrazole-1-yl | CH$_2$SCH$_3$ | |
| 11-194 | 1H-pyrazole-1-yl | CH$_2$SCH$_2$CH$_3$ | |
| 11-195 | 1H-pyrazole-1-yl | CH$_3$-S-CH(cyclopropyl) | |
| 11-196 | 1H-pyrazole-1-yl | CH$_2$SCH$_2$CF$_3$ | |
| 11-197 | 1H-pyrazole-1-yl | CH$_2$SOCH$_3$ | |

TABLE 127-continued

| compound number | R4 | R1 | physical property (melting point-ND) |
|---|---|---|---|
| 11-198 | 1H-pyrazole-1-yl | CH$_2$SOCH$_2$CH$_3$ | |
| 11-199 | 1H-pyrazole-1-yl | CH$_3$-S(=O)-CH$_2$-cyclopropyl | |
| 11-200 | 1H-pyrazole-1-yl | CH$_2$SOCH$_2$CF$_3$ | |

TABLE 128

| compound number | R4 | R1 | physical property (melting point-ND) |
|---|---|---|---|
| 11-201 | 1H-pyrazole-1-yl | CH$_2$SO$_2$CH$_3$ | |
| 11-202 | 1H-pyrazole-1-yl | CH$_2$SO$_2$CH$_2$CH$_3$ | |
| 11-203 | 1H-pyrazole-1-yl | CH$_3$-S(=O)$_2$-CH$_2$-cyclopropyl | |
| 11-204 | 1H-pyrazole-1-yl | CH$_2$SO$_2$CH$_2$CF$_3$ | |
| 11-205 | 1H-pyrazole-1-yl | CH$_2$O(CH$_2$)$_2$OCH$_3$ | |
| 11-206 | 1H-pyrazole-1-yl | CH$_2$O(CH$_2$)$_2$OCH$_2$CH$_3$ | |
| 11-207 | 1H-pyrazole-1-yl | CH$_2$O(CH$_2$)$_2$OCH$_2$CF$_3$ | |
| 11-208 | 1H-pyrazole-1-yl | CH$_2$O(CH$_2$)$_2$SCH$_3$ | |
| 11-209 | 1H-pyrazole-1-yl | CH$_2$O(CH$_2$)$_2$SCH$_2$CF$_3$ | |
| 11-210 | 1H-pyrazole-1-yl | CH$_2$O(CH$_2$)$_2$SOCH$_3$ | |
| 11-211 | 1H-pyrazole-1-yl | CH$_2$O(CH$_2$)$_2$SOCH$_2$CF$_3$ | |
| 11-212 | 1H-pyrazole-1-yl | CH$_2$O(CH$_2$)$_2$SO$_2$CH$_3$ | |
| 11-213 | 1H-pyrazole-1-yl | CH$_2$O(CH$_2$)$_2$SO$_2$CH$_2$CF$_3$ | |
| 11-214 | 1H-pyrazole-1-yl | CH$_3$-O-CH$_2$-(tetrahydrofuran-2-yl) | |
| 11-215 | 1H-pyrazole-1-yl | CH$_3$-O-(tetrahydrofuran-3-yl) | |
| 11-216 | 1H-pyrazole-1-yl | CH$_2$O(CH$_2$)$_2$NHSO$_2$CH$_3$ | |
| 11-217 | 1H-pyrazole-1-yl | CH$_2$O(CH$_2$)$_2$N(CH$_3$)(SO$_2$CH$_3$) | |
| 11-218 | 1H-imidazole-1-yl | CH$_3$ | |
| 11-219 | 1H-imidazole-1-yl | CF$_3$ | |
| 11-220 | 1H-imidazole-1-yl | CH$_2$OCH$_3$ | |
| 11-221 | 1H-imidazole-1-yl | CH$_2$OCH$_2$CH$_3$ | |
| 11-222 | 1H-imidazole-1-yl | CH$_3$-O-CH$_2$-cyclopropyl | |
| 11-223 | 1H-imidazole-1-yl | CH$_2$OCH$_2$CF$_3$ | |
| 11-224 | 1H-imidazole-1-yl | CH$_2$SCH$_3$ | |
| 11-225 | 1H-imidazole-1-yl | CH$_2$SCH$_2$CH$_3$ | |
| 11-226 | 1H-imidazole-1-yl | CH$_3$-S-CH$_2$-cyclopropyl | |
| 11-227 | 1H-imidazole-1-yl | CH$_2$SCH$_2$CF$_3$ | |
| 11-228 | 1H-imidazole-1-yl | CH$_2$SOCH$_3$ | |
| 11-229 | 1H-imidazole-1-yl | CH$_2$SOCH$_2$CH$_3$ | |

TABLE 128-continued

| compound number | R4 | R1 | physical property (melting point-ND) |
|---|---|---|---|
| 11-230 | 1H-imidazole-1-yl | CH$_3$-S(=O)-CH$_2$-cyclopropyl | |
| 11-231 | 1H-imidazole-1-yl | CH$_2$SOCH$_2$CF$_3$ | |
| 11-232 | 1H-imidazole-1-yl | CH$_2$SO$_2$CH$_3$ | |
| 11-233 | 1H-imidazole-1-yl | CH$_2$SO$_2$CH$_2$CH$_3$ | |
| 11-234 | 1H-imidazole-1-yl | CH$_3$-S(=O)$_2$-CH$_2$-cyclopropyl | |
| 11-235 | 1H-imidazole-1-yl | CH$_2$SO$_2$CH$_2$CF$_3$ | |
| 11-236 | 1H-imidazole-1-yl | CH$_2$O(CH$_2$)$_2$OCH$_3$ | |
| 11-237 | 1H-imidazole-1-yl | CH$_2$O(CH$_2$)$_2$OCH$_2$CH$_3$ | |
| 11-238 | 1H-imidazole-1-yl | CH$_2$O(CH$_2$)$_2$OCH$_2$CF$_3$ | |
| 11-239 | 1H-imidazole-1-yl | CH$_2$O(CH$_2$)$_2$SCH$_3$ | |
| 11-240 | 1H-imidazole-1-yl | CH$_2$O(CH$_2$)$_2$SCH$_2$CF$_3$ | |

TABLE 129

| compound number | R4 | R1 | physical property (melting point-ND) |
|---|---|---|---|
| 11-241 | 1H-imidazole-1-yl | CH$_2$O(CH$_2$)$_2$SOCH$_3$ | |
| 11-242 | 1H-imidazole-1-yl | CH$_2$O(CH$_2$)$_2$SOCH$_2$CF$_3$ | |
| 11-243 | 1H-imidazole-1-yl | CH$_2$O(CH$_2$)$_2$SO$_2$CH$_3$ | |
| 11-244 | 1H-imidazole-1-yl | CH$_2$O(CH$_2$)$_2$SO$_2$CH$_2$CF$_3$ | |
| 11-245 | 1H-imidazole-1-yl | CH$_3$-O-CH$_2$-(tetrahydrofuran-2-yl) | |
| 11-246 | 1H-imidazole-1-yl | CH$_3$-O-(tetrahydrofuran-3-yl) | |
| 11-247 | 1H-imidazole-1-yl | CH$_2$O(CH$_2$)$_2$NHSO$_2$CH$_3$ | |
| 11-248 | 1H-imidazole-1-yl | CH$_2$O(CH$_2$)$_2$N(CH$_3$)(SO$_2$CH$_3$) | |
| 11-249 | 1H-triazole-1-yl | CH$_3$ | |
| 11-250 | 1H-triazole-1-yl | CF$_3$ | |
| 11-251 | 1H-triazole-1-yl | CH$_2$OCH$_3$ | |
| 11-252 | 1H-triazole-1-yl | CH$_2$OCH$_2$CH$_3$ | |
| 11-253 | 1H-triazole-1-yl | CH$_3$-O-CH$_2$-cyclopropyl | |
| 11-254 | 1H-triazole-1-yl | CH$_2$OCH$_2$CF$_3$ | |
| 11-255 | 1H-triazole-1-yl | CH$_2$SCH$_3$ | |
| 11-256 | 1H-triazole-1-yl | CH$_2$SCH$_2$CH$_3$ | |
| 11-257 | 1H-triazole-1-yl | CH$_3$-S-CH$_2$-cyclopropyl | |
| 11-258 | 1H-triazole-1-yl | CH$_2$SCH$_2$CF$_3$ | |
| 11-259 | 1H-triazole-1-yl | CH$_2$SOCH$_3$ | |
| 11-260 | 1H-triazole-1-yl | CH$_2$SOCH$_2$CH$_3$ | |

TABLE 129-continued

| compound number | R4 | R1 | physical property (melting point-ND) |
|---|---|---|---|
| 11-261 | 1H-triazole-1-yl | 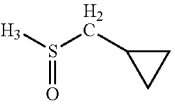 | |
| 11-262 | 1H-triazole-1-yl | CH$_2$SOCH$_2$CF$_3$ | |
| 11-263 | 1H-triazole-1-yl | CH$_2$SO$_2$CH$_3$ | |
| 11-264 | 1H-triazole-1-yl | CH$_2$SO$_2$CH$_2$CH$_3$ | |
| 11-265 | 1H-triazole-1-yl | 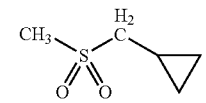 | |
| 11-266 | 1H-triazole-1-yl | CH$_2$SO$_2$CH$_2$CF$_3$ | |
| 11-267 | 1H-triazole-1-yl | CH$_2$O(CH$_2$)$_2$OCH$_3$ | |
| 11-268 | 1H-triazole-1-yl | CH$_2$O(CH$_2$)$_2$OCH$_2$CH$_3$ | |
| 11-269 | 1H-triazole-1-yl | CH$_2$O(CH$_2$)$_2$OCH$_2$CF$_3$ | |
| 11-270 | 1H-triazole-1-yl | CH$_2$O(CH$_2$)$_2$SCH$_3$ | |
| 11-271 | 1H-triazole-1-yl | CH$_2$O(CH$_2$)$_2$SCH$_2$CF$_3$ | |
| 11-272 | 1H-triazole-1-yl | CH$_2$O(CH$_2$)$_2$SOCH$_3$ | |
| 11-273 | 1H-triazole-1-yl | CH$_2$O(CH$_2$)$_2$SOCH$_2$CF$_3$ | |
| 11-274 | 1H-triazole-1-yl | CH$_2$O(CH$_2$)$_2$SO$_2$CH$_3$ | |
| 11-275 | 1H-triazole-1-yl | CH$_2$O(CH$_2$)$_2$SO$_2$CH$_2$CF$_3$ | |
| 11-276 | 1H-triazole-1-yl | 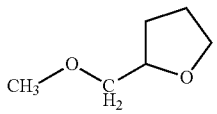 | |
| 11-277 | 1H-triazole-1-yl | 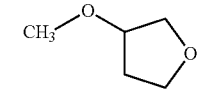 | |
| 11-278 | 1H-triazole-1-yl | CH$_2$O(CH$_2$)$_2$NHSO$_2$CH$_3$ | |
| 11-279 | 1H-triazole-1-yl | CH$_2$O(CH$_2$)$_2$N(CH$_3$)(SO$_2$CH$_3$) | |
| 11-280 | 1H-tetrazole-1-yl | CH$_3$ | |

TABLE 130

| compound number | R4 | R1 | physical property (melting point-ND) |
|---|---|---|---|
| 11-281 | 1H-tetrazole-1-yl | CF$_3$ | |
| 11-282 | 1H-tetrazole-1-yl | CH$_2$OCH$_3$ | |
| 11-283 | 1H-tetrazole-1-yl | CH$_2$OCH$_2$CH$_3$ | |
| 11-284 | 1H-tetrazole-1-yl | 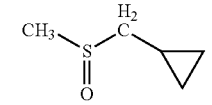 | |
| 11-285 | 1H-tetrazole-1-yl | CH$_2$OCH$_2$CF$_3$ | |
| 11-286 | 1H-tetrazole-1-yl | CH$_2$SCH$_3$ | |
| 11-287 | 1H-tetrazole-1-yl | CH$_2$SCH$_2$CH$_3$ | |
| 11-288 | 1H-tetrazole-1-yl | 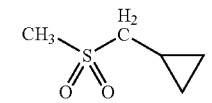 | |
| 11-289 | 1H-tetrazole-1-yl | CH$_2$SCH$_2$CF$_3$ | |
| 11-290 | 1H-tetrazole-1-yl | CH$_2$SOCH$_3$ | |
| 11-291 | 1H-tetrazole-1-yl | CH$_2$SOCH$_2$CH$_3$ | |

TABLE 130-continued

| compound number | R4 | R1 | physical property (melting point-ND) |
|---|---|---|---|
| 11-292 | 1H-tetrazole-1-yl | 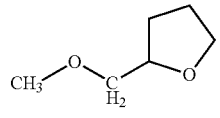 | |
| 11-293 | 1H-tetrazole-1-yl | CH$_2$SOCH$_2$CF$_3$ | |
| 11-294 | 1H-tetrazole-1-yl | CH$_2$SO$_2$CH$_3$ | |
| 11-295 | 1H-tetrazole-1-yl | CH$_2$SO$_2$CH$_2$CH$_3$ | |
| 11-296 | 1H-tetrazole-1-yl | 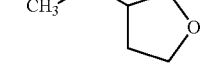 | |
| 11-297 | 1H-tetrazole-1-yl | CH$_2$SO$_2$CH$_2$CF$_3$ | |
| 11-298 | 1H-tetrazole-1-yl | CH$_2$O(CH$_2$)$_2$OCH$_3$ | |
| 11-299 | 1H-tetrazole-1-yl | CH$_2$O(CH$_2$)$_2$OCH$_2$CH$_3$ | |
| 11-300 | 1H-tetrazole-1-yl | CH$_2$O(CH$_2$)$_2$OCH$_2$CF$_3$ | |
| 11-301 | 1H-tetrazole-1-yl | CH$_2$O(CH$_2$)$_2$SCH$_3$ | |
| 11-302 | 1H-tetrazole-1-yl | CH$_2$O(CH$_2$)$_2$SCH$_2$CF$_3$ | |
| 11-303 | 1H-tetrazole-1-yl | CH$_2$O(CH$_2$)$_2$SOCH$_3$ | |
| 11-304 | 1H-tetrazole-1-yl | CH$_2$O(CH$_2$)$_2$SOCH$_2$CF$_3$ | |
| 11-305 | 1H-tetrazole-1-yl | CH$_2$O(CH$_2$)$_2$SO$_2$CH$_3$ | |
| 11-306 | 1H-tetrazole-1-yl | CH$_2$O(CH$_2$)$_2$SO$_2$CH$_2$CF$_3$ | |
| 11-307 | 1H-tetrazole-1-yl | 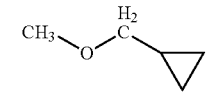 | |
| 11-308 | 1H-tetrazole-1-yl | 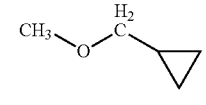 | |
| 11-309 | 1H-tetrazole-1-yl | CH$_2$O(CH$_2$)$_2$NHSO$_2$CH$_3$ | |
| 11-310 | 1H-tetrazole-1-yl | CH$_2$O(CH$_2$)$_2$N(CH$_3$)(SO$_2$CH$_3$) | |
| 11-311 | 1H-tetrazole-2-yl | CH$_3$ | |
| 11-312 | 1H-tetrazole-2-yl | CF$_3$ | |
| 11-313 | 1H-tetrazole-2-yl | CH$_2$OCH$_3$ | |
| 11-314 | 1H-tetrazole-2-yl | CH$_2$OCH$_2$CH$_3$ | |
| 11-315 | 1H-tetrazole-2-yl | 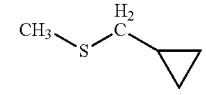 | |
| 11-316 | 1H-tetrazole-2-yl | CH$_2$OCH$_2$CF$_3$ | |
| 11-317 | 1H-tetrazole-2-yl | CH$_2$SCH$_3$ | |
| 11-318 | 1H-tetrazole-2-yl | CH$_2$SCH$_2$CH$_3$ | |
| 11-319 | 1H-tetrazole-2-yl | | |
| 11-320 | 1H-tetrazole-2-yl | CH$_2$SCH$_2$CF$_3$ | |

TABLE 146

| compound number | R4 | R1 | physical property (melting point-ND) |
|---|---|---|---|
| 13-201 | 1H-pyrazole-1-yl | CH$_2$SO$_2$CH$_3$ | |
| 13-202 | 1H-pyrazole-1-yl | CH$_2$SO$_2$CH$_2$CH$_3$ | |

TABLE 146-continued

| compound number | R4 | R1 | physical property (melting point-ND) |
|---|---|---|---|
| 13-203 | 1H-pyrazole-1-yl | 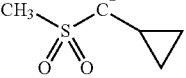 | |
| 13-204 | 1H-pyrazole-1-yl | CH$_2$SO$_2$CH$_2$CF$_3$ | |
| 13-205 | 1H-pyrazole-1-yl | CH$_2$O(CH$_2$)$_2$OCH$_3$ | |
| 13-206 | 1H-pyrazole-1-yl | CH$_2$O(CH$_2$)$_2$OCH$_2$CH$_3$ | |
| 13-207 | 1H-pyrazole-1-yl | CH$_2$O(CH$_2$)$_2$OCH$_2$CF$_3$ | |
| 13-208 | 1H-pyrazole-1-yl | CH$_2$O(CH$_2$)$_2$SCH$_3$ | |
| 13-209 | 1H-pyrazole-1-yl | CH$_2$O(CH$_2$)$_2$SCH$_2$CF$_3$ | |
| 13-210 | 1H-pyrazole-1-yl | CH$_2$O(CH$_2$)$_2$SOCH$_3$ | |
| 13-211 | 1H-pyrazole-1-yl | CH$_2$O(CH$_2$)$_2$SOCH$_2$CF$_3$ | |
| 13-212 | 1H-pyrazole-1-yl | CH$_2$O(CH$_2$)$_2$SO$_2$CH$_3$ | |
| 13-213 | 1H-pyrazole-1-yl | CH$_2$O(CH$_2$)$_2$SO$_2$CH$_2$CF$_3$ | |
| 13-214 | 1H-pyrazole-1-yl | 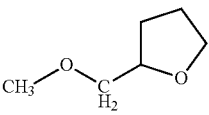 | |
| 13-215 | 1H-pyrazole-1-yl | 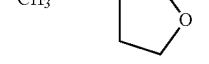 | |
| 13-216 | 1H-pyrazole-1-yl | CH$_2$O(CH$_2$)$_2$NHSO$_2$CH$_3$ | |
| 13-217 | 1H-pyrazole-1-yl | CH$_2$O(CH$_2$)$_2$N(CH$_3$)(SO$_2$CH$_3$) | |
| 13-218 | 1H-imidazole-1-yl | CH$_3$ | |
| 13-219 | 1H-imidazole-1-yl | CF$_3$ | |
| 13-220 | 1H-imidazole-1-yl | CH$_2$OCH$_3$ | |
| 13-221 | 1H-imidazole-1-yl | CH$_2$OCH$_2$CH$_3$ | |
| 13-222 | 1H-imidazole-1-yl | 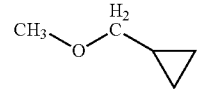 | |
| 13-223 | 1H-imidazole-1-yl | CH$_2$OCH$_2$CF$_3$ | |
| 13-224 | 1H-imidazole-1-yl | CH$_2$SCH$_3$ | |
| 13-225 | 1H-imidazole-1-yl | CH$_2$SCH$_2$CH$_3$ | |
| 13-226 | 1H-imidazole-1-yl | 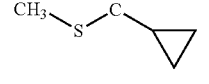 | |
| 13-227 | 1H-imidazole-1-yl | CH$_2$SCH$_2$CF$_3$ | |
| 13-228 | 1H-imidazole-1-yl | CH$_2$SOCH$_3$ | |
| 13-229 | 1H-imidazole-1-yl | CH$_2$SOCH$_2$CH$_3$ | |
| 13-230 | 1H-imidazole-1-yl | 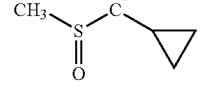 | |
| 13-231 | 1H-imidazole-1-yl | CH$_2$SOCH$_2$CF$_3$ | |
| 13-232 | 1H-imidazole-1-yl | CH$_2$SO$_2$CH$_3$ | |
| 13-233 | 1H-imidazole-1-yl | CH$_2$SO$_2$CH$_2$CH$_3$ | |
| 13-234 | 1H-imidazole-1-yl | 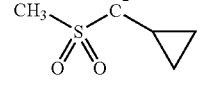 | |
| 13-235 | 1H-imidazole-1-yl | CH$_2$SO$_2$CH$_2$CF$_3$ | |
| 13-236 | 1H-imidazole-1-yl | CH$_2$O(CH$_2$)$_2$OCH$_3$ | |
| 13-237 | 1H-imidazole-1-yl | CH$_2$O(CH$_2$)$_2$OCH$_2$CH$_3$ | |
| 13-238 | 1H-imidazole-1-yl | CH$_2$O(CH$_2$)$_2$OCH$_2$CF$_3$ | |
| 13-239 | 1H-imidazole-1-yl | CH$_2$O(CH$_2$)$_2$SCH$_3$ | |
| 13-240 | 1H-imidazole-1-yl | CH$_2$O(CH$_2$)$_2$SCH$_2$CF$_3$ | |

TABLE 147

| compound number | R4 | R1 | physical property (melting point-ND) |
|---|---|---|---|
| 13-241 | 1H-imidazole-1-yl | CH$_2$O(CH$_2$)$_2$SOCH$_3$ | |
| 13-242 | 1H-imidazole-1-yl | CH$_2$O(CH$_2$)$_2$SOCH$_2$CF$_3$ | |
| 13-243 | 1H-imidazole-1-yl | CH$_2$O(CH$_2$)$_2$SO$_2$CH$_3$ | |
| 13-244 | 1H-imidazole-1-yl | CH$_2$O(CH$_2$)$_2$SO$_2$CH$_2$CF$_3$ | |
| 13-245 | 1H-imidazole-1-yl | 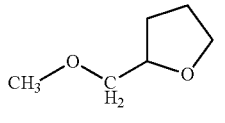 | |
| 13-246 | 1H-imidazole-1-yl | 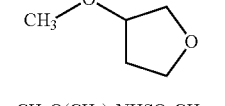 | |
| 13-247 | 1H-imidazole-1-yl | CH$_2$O(CH$_2$)$_2$NHSO$_2$CH$_3$ | |
| 13-248 | 1H-imidazole-1-yl | CH$_2$O(CH$_2$)$_2$N(CH$_3$)(SO$_2$CH$_3$) | |
| 13-249 | 1H-triazole-1-yl | CH$_3$ | |
| 13-250 | 1H-triazole-1-yl | CF$_3$ | |
| 13-251 | 1H-triazole-1-yl | CH$_2$OCH$_3$ | |
| 13-252 | 1H-triazole-1-yl | CH$_2$OCH$_2$CH$_3$ | |
| 13-253 | 1H-triazole-1-yl | 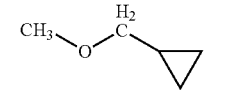 | |
| 13-254 | 1H-triazole-1-yl | CH$_2$OCH$_2$CF$_3$ | |
| 13-255 | 1H-triazole-1-yl | CH$_2$SCH$_3$ | |
| 13-256 | 1H-triazole-1-yl | CH$_2$SCH$_2$CH$_3$ | |
| 13-257 | 1H-triazole-1-yl | 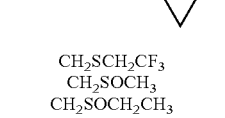 | |
| 13-258 | 1H-triazole-1-yl | CH$_2$SCH$_2$CF$_3$ | |
| 13-259 | 1H-triazole-1-yl | CH$_2$SOCH$_3$ | |
| 13-260 | 1H-triazole-1-yl | CH$_2$SOCH$_2$CH$_3$ | |
| 13-261 | 1H-triazole-1-yl | 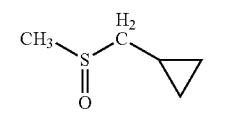 | |
| 13-262 | 1H-triazole-1-yl | CH$_2$SOCH$_2$CF$_3$ | |
| 13-263 | 1H-triazole-1-yl | CH$_2$SO$_2$CH$_3$ | |
| 13-264 | 1H-triazole-1-yl | CH$_2$SO$_2$CH$_2$CH$_3$ | |
| 13-265 | 1H-triazole-1-yl | 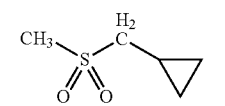 | |
| 13-266 | 1H-triazole-1-yl | CH$_2$SO$_2$CH$_2$CF$_3$ | |
| 13-267 | 1H-triazole-1-yl | CH$_2$O(CH$_2$)$_2$OCH$_3$ | |
| 13-268 | 1H-triazole-1-yl | CH$_2$O(CH$_2$)$_2$OCH$_2$CH$_3$ | |

TABLE 147-continued

| compound number | R4 | R1 | physical property (melting point-ND) |
|---|---|---|---|
| 13-269 | 1H-triazole-1-yl | CH$_2$O(CH$_2$)$_2$OCH$_2$CF$_3$ | |
| 13-270 | 1H-triazole-1-yl | CH$_2$O(CH$_2$)$_2$SCH$_3$ | |
| 13-271 | 1H-triazole-1-yl | CH$_2$O(CH$_2$)$_2$SCH$_2$CF$_3$ | |
| 13-272 | 1H-triazole-1-yl | CH$_2$O(CH$_2$)$_2$SOCH$_3$ | |
| 13-273 | 1H-triazole-1-yl | CH$_2$O(CH$_2$)$_2$SOCH$_2$CF$_3$ | |
| 13-274 | 1H-triazole-1-yl | CH$_2$O(CH$_2$)$_2$SO$_2$CH$_3$ | |
| 13-275 | 1H-triazole-1-yl | CH$_2$O(CH$_2$)$_2$SO$_2$CH$_2$CF$_3$ | |
| 13-276 | 1H-triazole-1-yl | CH$_3$-O-CH$_2$-(tetrahydrofuran-2-yl) | |
| 13-277 | 1H-triazole-1-yl | CH$_3$-O-(tetrahydrofuran-3-yl) | |
| 13-278 | 1H-triazole-1-yl | CH$_2$O(CH$_2$)$_2$NHSO$_2$CH$_3$ | |
| 13-279 | 1H-triazole-1-yl | CH$_2$O(CH$_2$)$_2$N(CH$_3$)(SO$_2$CH$_3$) | |
| 13-280 | 1H-tetrazole-1-yl | CH$_3$ | |

TABLE 148

| compound number | R4 | R1 | physical property (melting point-ND) |
|---|---|---|---|
| 13-281 | 1H-tetrazole-1-yl | CF$_3$ | |
| 13-282 | 1H-tetrazole-1-yl | CH$_2$OCH$_3$ | |
| 13-283 | 1H-tetrazole-1-yl | CH$_2$OCH$_2$CH$_3$ | |
| 13-284 | 1H-tetrazole-1-yl | CH$_3$-O-CH$_2$-cyclopropyl | |
| 13-285 | 1H-tetrazole-1-yl | CH$_2$OCH$_2$CF$_3$ | |
| 13-286 | 1H-tetrazole-1-yl | CH$_2$SCH$_3$ | |
| 13-287 | 1H-tetrazole-1-yl | CH$_2$SCH$_2$CH$_3$ | |
| 13-288 | 1H-tetrazole-1-yl | CH$_3$-S-CH$_2$-cyclopropyl | |
| 13-289 | 1H-tetrazole-1-yl | CH$_2$SCH$_2$CF$_3$ | |
| 13-290 | 1H-tetrazole-1-yl | CH$_2$SOCH$_3$ | |
| 13-291 | 1H-tetrazole-1-yl | CH$_2$SOCH$_2$CH$_3$ | |
| 13-292 | 1H-tetrazole-1-yl | CH$_3$-S(=O)-CH$_2$-cyclopropyl | |
| 13-293 | 1H-tetrazole-1-yl | CH$_2$SOCH$_2$CF$_3$ | |
| 13-294 | 1H-tetrazole-1-yl | CH$_2$SO$_2$CH$_3$ | |
| 13-295 | 1H-tetrazole-1-yl | CH$_2$SO$_2$CH$_2$CH$_3$ | |
| 13-296 | 1H-tetrazole-1-yl | CH$_3$-S(=O)$_2$-CH$_2$-cyclopropyl | |
| 13-297 | 1H-tetrazole-1-yl | CH$_2$SO$_2$CH$_2$CF$_3$ | |
| 13-298 | 1H-tetrazole-1-yl | CH$_2$O(CH$_2$)$_2$OCH$_3$ | |

TABLE 148-continued

| compound number | R4 | R1 | physical property (melting point-ND) |
|---|---|---|---|
| 13-299 | 1H-tetrazole-1-yl | CH$_2$O(CH$_2$)$_2$OCH$_2$CH$_3$ | |
| 13-300 | 1H-tetrazole-1-yl | CH$_2$O(CH$_2$)$_2$OCH$_2$CF$_3$ | |
| 13-301 | 1H-tetrazole-1-yl | CH$_2$O(CH$_2$)$_2$SCH$_3$ | |
| 13-302 | 1H-tetrazole-1-yl | CH$_2$O(CH$_2$)$_2$SCH$_2$CF$_3$ | |
| 13-303 | 1H-tetrazole-1-yl | CH$_2$O(CH$_2$)$_2$SOCH$_3$ | |
| 13-304 | 1H-tetrazole-1-yl | CH$_2$O(CH$_2$)$_2$SOCH$_2$CF$_3$ | |
| 13-305 | 1H-tetrazole-1-yl | CH$_2$O(CH$_2$)$_2$SO$_2$CH$_3$ | |
| 13-306 | 1H-tetrazole-1-yl | CH$_2$O(CH$_2$)$_2$SO$_2$CH$_2$CF$_3$ | |
| 13-307 | 1H-tetrazole-1-yl | CH$_3$-O-CH$_2$-(tetrahydrofuran-2-yl) | |
| 13-308 | 1H-tetrazole-1-yl | CH$_3$-O-(tetrahydrofuran-3-yl) | |
| 13-309 | 1H-tetrazole-1-yl | CH$_2$O(CH$_2$)$_2$NHSO$_2$CH$_3$ | |
| 13-310 | 1H-tetrazole-1-yl | CH$_2$O(CH$_2$)$_2$N(CH$_3$)(SO$_2$CH$_3$) | |
| 13-311 | 1H-tetrazole-2-yl | CH$_3$ | |
| 13-312 | 1H-tetrazole-2-yl | CF$_3$ | |
| 13-313 | 1H-tetrazole-2-yl | CH$_2$OCH$_3$ | |
| 13-314 | 1H-tetrazole-2-yl | CH$_2$OCH$_2$CH$_3$ | |
| 13-315 | 1H-tetrazole-2-yl | CH$_3$-O-CH$_2$-cyclopropyl | |
| 13-316 | 1H-tetrazole-2-yl | CH$_2$OCH$_2$CF$_3$ | |
| 13-317 | 1H-tetrazole-2-yl | CH$_2$SCH$_3$ | |
| 13-318 | 1H-tetrazole-2-yl | CH$_2$SCH$_2$CH$_3$ | |
| 13-319 | 1H-tetrazole-2-yl | CH$_3$-S-CH$_2$-cyclopropyl | |
| 13-320 | 1H-tetrazole-2-yl | CH$_2$SCH$_2$CF$_3$ | |

TABLE 149

| compound number | R4 | R1 | physical property (melting point-ND) |
|---|---|---|---|
| 13-321 | 1H-tetrazole-2-yl | CH$_2$SOCH$_3$ | |
| 13-322 | 1H-tetrazole-2-yl | CH$_2$SOCH$_2$CH$_3$ | |
| 13-323 | 1H-tetrazole-2-yl | CH$_3$-S(=O)-CH$_2$-cyclopropyl | |
| 13-324 | 1H-tetrazole-2-yl | CH$_2$SOCH$_2$CF$_3$ | |
| 13-325 | 1H-tetrazole-2-yl | CH$_2$SO$_2$CH$_3$ | |
| 13-326 | 1H-tetrazole-2-yl | CH$_2$SO$_2$CH$_2$CH$_3$ | |
| 13-327 | 1H-tetrazole-2-yl | CH$_3$-S(=O)$_2$-CH$_2$-cyclopropyl | |

TABLE 149-continued

| compound number | R4 | R1 | physical property (melting point-ND) |
|---|---|---|---|
| 13-328 | 1H-tetrazole-2-yl | CH$_2$SO$_2$CH$_2$CF$_3$ | |
| 13-329 | 1H-tetrazole-2-yl | CH$_2$O(CH$_2$)$_2$OCH$_3$ | |
| 13-330 | 1H-tetrazole-2-yl | CH$_2$O(CH$_2$)$_2$OCH$_2$CH$_3$ | |
| 13-331 | 1H-tetrazole-2-yl | CH$_2$O(CH$_2$)$_2$OCH$_2$CF$_3$ | |
| 13-332 | 1H-tetrazole-2-yl | CH$_2$O(CH$_2$)$_2$SCH$_3$ | |
| 13-333 | 1H-tetrazole-2-yl | CH$_2$O(CH$_2$)$_2$SCH$_2$CF$_3$ | |
| 13-334 | 1H-tetrazole-2-yl | CH$_2$O(CH$_2$)$_2$SOCH$_3$ | |
| 13-335 | 1H-tetrazole-2-yl | CH$_2$O(CH$_2$)$_2$SOCH$_2$CF$_3$ | |
| 13-336 | 1H-tetrazole-2-yl | CH$_2$O(CH$_2$)$_2$SO$_2$CH$_3$ | |
| 13-337 | 1H-tetrazole-2-yl | CH$_2$O(CH$_2$)$_2$SO$_2$CH$_2$CF$_3$ | |
| 13-338 | 1H-tetrazole-2-yl | CH$_3$-O-CH$_2$-(tetrahydrofuran-2-yl) | |
| 13-339 | 1H-tetrazole-2-yl | 3-(OCH$_3$)-tetrahydrofuran | |
| 13-340 | 1H-tetrazole-2-yl | CH$_2$O(CH$_2$)$_2$NHSO$_2$CH$_3$ | |
| 13-341 | 1H-tetrazole-2-yl | CH$_2$O(CH$_2$)$_2$N(CH$_3$)(SO$_2$CH$_3$) | |

TABLE 150

| compound number | R13 | R1 | physical property (melting point-ND) |
|---|---|---|---|
| 14-1 | CH$_3$ | CH$_3$ | |
| 14-2 | CH$_3$ | CF$_3$ | |
| 14-3 | CH$_3$ | CH$_2$OCH$_3$ | |
| 14-4 | CH$_3$ | CH$_2$OCH$_2$CH$_3$ | |
| 14-5 | CH$_3$ | CH$_3$-O-CH$_2$-cyclopropyl | |
| 14-6 | CH$_3$ | CH$_2$OCH$_2$CF$_3$ | |
| 14-7 | CH$_3$ | CH$_2$SCH$_3$ | |
| 14-8 | CH$_3$ | CH$_2$SCH$_2$CH$_3$ | |
| 14-9 | CH$_3$ | CH$_3$-S-CH$_2$-cyclopropyl | |
| 14-10 | CH$_3$ | CH$_2$SCH$_2$CF$_3$ | |
| 14-11 | CH$_3$ | CH$_2$SOCH$_3$ | |
| 14-12 | CH$_3$ | CH$_2$SOCH$_2$CH$_3$ | |
| 14-13 | CH$_3$ | CH$_3$-S(O)-CH$_2$-cyclopropyl | |
| 14-14 | CH$_3$ | CH$_2$SOCH$_2$CF$_3$ | |
| 14-15 | CH$_3$ | CH$_2$SO$_2$CH$_3$ | |
| 14-16 | CH$_3$ | CH$_2$SO$_2$CH$_2$CH$_3$ | |
| 14-17 | CH$_3$ | CH$_3$-S(O)$_2$-CH$_2$-cyclopropyl | |
| 14-18 | CH$_3$ | CH$_2$SO$_2$CH$_2$CF$_3$ | |
| 14-19 | CH$_3$ | CH$_2$O(CH$_2$)$_2$OCH$_3$ | |
| 14-20 | CH$_3$ | CH$_2$O(CH$_2$)$_2$OCH$_2$CH$_3$ | |
| 14-21 | CH$_3$ | CH$_2$O(CH$_2$)$_2$OCH$_2$CF$_3$ | |
| 14-22 | CH$_3$ | CH$_2$O(CH$_2$)$_2$SCH$_3$ | |
| 14-23 | CH$_3$ | CH$_2$O(CH$_2$)$_2$SCH$_2$CF$_3$ | |
| 14-24 | CH$_3$ | CH$_2$O(CH$_2$)$_2$SOCH$_3$ | |
| 14-25 | CH$_3$ | CH$_2$O(CH$_2$)$_2$SOCH$_2$CF$_3$ | |
| 14-26 | CH$_3$ | CH$_2$O(CH$_2$)$_2$SO$_2$CH$_3$ | |
| 14-27 | CH$_3$ | CH$_2$O(CH$_2$)$_2$SO$_2$CH$_2$CF$_3$ | |
| 14-28 | CH$_3$ | CH$_3$-O-CH$_2$-(tetrahydrofuran-2-yl) | |
| 14-29 | CH$_3$ | 3-(OCH$_3$)-tetrahydrofuran | |
| 14-30 | CH$_3$ | CH$_2$O(CH$_2$)$_2$NHSO$_2$CH$_3$ | |
| 14-31 | CH$_3$ | CH$_2$O(CH$_2$)$_2$N(CH$_3$)(SO$_2$CH$_3$) | |
| 14-32 | CH$_2$CH$_3$ | CH$_3$ | |
| 14-33 | CH$_2$CH$_3$ | CF$_3$ | |
| 14-34 | CH$_2$CH$_3$ | CH$_2$OCH$_3$ | |
| 14-35 | CH$_2$CH$_3$ | CH$_2$OCH$_2$CH$_3$ | |
| 14-36 | CH$_2$CH$_3$ | CH$_3$-O-CH$_2$-cyclopropyl | |
| 14-37 | CH$_2$CH$_3$ | CH$_2$OCH$_2$CF$_3$ | |
| 14-38 | CH$_2$CH$_3$ | CH$_2$SCH$_3$ | |
| 14-39 | CH$_2$CH$_3$ | CH$_2$SCH$_2$CH$_3$ | |
| 14-40 | CH$_2$CH$_3$ | CH$_3$-S-CH$_2$-cyclopropyl | |

TABLE 151

| compound number | R13 | R1 | physical property (melting point-ND) |
|---|---|---|---|
| 14-41 | CH$_2$CH$_3$ | CH$_2$SCH$_2$CF$_3$ | |
| 14-42 | CH$_2$CH$_3$ | CH$_2$SOCH$_3$ | |
| 14-43 | CH$_2$CH$_3$ | CH$_2$SOCH$_2$CH$_3$ | |
| 14-44 | CH$_2$CH$_3$ | CH$_3$-S(=O)-CH$_2$-cyclopropyl | |
| 14-45 | CH$_2$CH$_3$ | CH$_2$SOCH$_2$CF$_3$ | |
| 14-46 | CH$_2$CH$_3$ | CH$_2$SO$_2$CH$_3$ | |
| 14-47 | CH$_2$CH$_3$ | CH$_2$SO$_2$CH$_2$CH$_3$ | |
| 14-48 | CH$_2$CH$_3$ | CH$_3$-S(=O)$_2$-CH$_2$-cyclopropyl | |
| 14-49 | CH$_2$CH$_3$ | CH$_2$SO$_2$CH$_2$CF$_3$ | |
| 14-50 | CH$_2$CH$_3$ | CH$_2$O(CH$_2$)$_2$OCH$_3$ | |
| 14-51 | CH$_2$CH$_3$ | CH$_2$O(CH$_2$)$_2$OCH$_2$CH$_3$ | |
| 14-52 | CH$_2$CH$_3$ | CH$_2$O(CH$_2$)$_2$OCH$_2$CF$_3$ | |
| 14-53 | CH$_2$CH$_3$ | CH$_2$O(CH$_2$)$_2$SCH$_3$ | |
| 14-54 | CH$_2$CH$_3$ | CH$_2$O(CH$_2$)$_2$SCH$_2$CF$_3$ | |
| 14-55 | CH$_2$CH$_3$ | CH$_2$O(CH$_2$)$_2$SOCH$_3$ | |
| 14-56 | CH$_2$CH$_3$ | CH$_2$O(CH$_2$)$_2$SOCH$_2$CF$_3$ | |
| 14-57 | CH$_2$CH$_3$ | CH$_2$O(CH$_2$)$_2$SO$_2$CH$_3$ | |
| 14-58 | CH$_2$CH$_3$ | CH$_2$O(CH$_2$)$_2$SO$_2$CH$_2$CF$_3$ | |
| 14-59 | CH$_2$CH$_3$ | CH$_3$-O-CH$_2$-(tetrahydrofuran-2-yl) | |
| 14-60 | CH$_2$CH$_3$ | CH$_3$-O-(tetrahydrofuran-3-yl) | |
| 14-61 | CH$_2$CH$_3$ | CH$_2$O(CH$_2$)$_2$NHSO$_2$CH$_3$ | |
| 14-62 | CH$_2$CH$_3$ | CH$_2$O(CH$_2$)$_2$N(CH$_3$)(SO$_2$CH$_3$) | |
| 14-63 | (CH$_2$)$_2$CH$_3$ | CH$_3$ | |
| 14-64 | (CH$_2$)$_2$CH$_3$ | CF$_3$ | |
| 14-65 | (CH$_2$)$_2$CH$_3$ | CH$_2$OCH$_3$ | |
| 14-66 | (CH$_2$)$_2$CH$_3$ | CH$_2$OCH$_2$CH$_3$ | |
| 14-67 | (CH$_2$)$_2$CH$_3$ | CH$_3$-O-CH$_2$-cyclopropyl | |
| 14-68 | (CH$_2$)$_2$CH$_3$ | CH$_2$OCH$_2$CF$_3$ | |
| 14-69 | (CH$_2$)$_2$CH$_3$ | CH$_2$SCH$_3$ | |
| 14-70 | (CH$_2$)$_2$CH$_3$ | CH$_2$SCH$_2$CH$_3$ | |
| 14-71 | (CH$_2$)$_2$CH$_3$ | CH$_3$-S-CH$_2$-cyclopropyl | |
| 14-72 | (CH$_2$)$_2$CH$_3$ | CH$_2$SCH$_2$CF$_3$ | |
| 14-73 | (CH$_2$)$_2$CH$_3$ | CH$_2$SOCH$_3$ | |
| 14-74 | (CH$_2$)$_2$CH$_3$ | CH$_2$SOCH$_2$CH$_3$ | |
| 14-75 | (CH$_2$)$_2$CH$_3$ | CH$_3$-S(=O)-CH$_2$-cyclopropyl | |
| 14-76 | (CH$_2$)$_2$CH$_3$ | CH$_2$SOCH$_2$CF$_3$ | |
| 14-77 | (CH$_2$)$_2$CH$_3$ | CH$_2$SO$_2$CH$_3$ | |
| 14-78 | (CH$_2$)$_2$CH$_3$ | CH$_2$SO$_2$CH$_2$CH$_3$ | |
| 14-79 | (CH$_2$)$_2$CH$_3$ | CH$_3$-S(=O)$_2$-CH$_2$-cyclopropyl | |
| 14-80 | (CH$_2$)$_2$CH$_3$ | CH$_2$SO$_2$CH$_2$CF$_3$ | |

TABLE 152

| compound number | R13 | R1 | physical property (melting point-ND) |
|---|---|---|---|
| 14-81 | (CH$_2$)$_2$CH$_3$ | CH$_2$O(CH$_2$)$_2$OCH$_3$ | |
| 14-82 | (CH$_2$)$_2$CH$_3$ | CH$_2$O(CH$_2$)$_2$OCH$_2$CH$_3$ | |
| 14-83 | (CH$_2$)$_2$CH$_3$ | CH$_2$O(CH$_2$)$_2$OCH$_2$CF$_3$ | |
| 14-84 | (CH$_2$)$_2$CH$_3$ | CH$_2$O(CH$_2$)$_2$SCH$_3$ | |
| 14-85 | (CH$_2$)$_2$CH$_3$ | CH$_2$O(CH$_2$)$_2$SCH$_2$CF$_3$ | |
| 14-86 | (CH$_2$)$_2$CH$_3$ | CH$_2$O(CH$_2$)$_2$SOCH$_3$ | |
| 14-87 | (CH$_2$)$_2$CH$_3$ | CH$_2$O(CH$_2$)$_2$SOCH$_2$CF$_3$ | |
| 14-88 | (CH$_2$)$_2$CH$_3$ | CH$_2$O(CH$_2$)$_2$SO$_2$CH$_3$ | |
| 14-89 | (CH$_2$)$_2$CH$_3$ | CH$_2$O(CH$_2$)$_2$SO$_2$CH$_2$CF$_3$ | |
| 14-90 | (CH$_2$)$_2$CH$_3$ | CH$_3$-O-CH$_2$-(tetrahydrofuran-2-yl) | |
| 14-91 | (CH$_2$)$_2$CH$_3$ | CH$_3$-O-(tetrahydrofuran-3-yl) | |
| 14-92 | (CH$_2$)$_2$CH$_3$ | CH$_2$O(CH$_2$)$_2$NHSO$_2$CH$_3$ | |
| 14-93 | (CH$_2$)$_2$CH$_3$ | CH$_2$O(CH$_2$)$_2$N(CH$_3$)(SO$_2$CH$_3$) | |
| 14-94 | CH$_2$CH=CH$_2$ | CH$_3$ | |
| 14-95 | CH$_2$CH=CH$_2$ | CF$_3$ | |
| 14-96 | CH$_2$CH=CH$_2$ | CH$_2$OCH$_3$ | |
| 14-97 | CH$_2$CH=CH$_2$ | CH$_2$OCH$_2$CH$_3$ | |
| 14-98 | CH$_2$CH=CH$_2$ | CH$_3$-O-CH$_2$-cyclopropyl | |
| 14-99 | CH$_2$CH=CH$_2$ | CH$_2$OCH$_2$CF$_3$ | |
| 14-100 | CH$_2$CH=CH$_2$ | CH$_2$SCH$_3$ | |
| 14-101 | CH$_2$CH=CH$_2$ | CH$_2$SCH$_2$CH$_3$ | |
| 14-102 | CH$_2$CH=CH$_2$ | CH$_3$-S-CH$_2$-cyclopropyl | |
| 14-103 | CH$_2$CH=CH$_2$ | CH$_2$SCH$_2$CF$_3$ | |
| 14-104 | CH$_2$CH=CH$_2$ | CH$_2$SOCH$_3$ | |
| 14-105 | CH$_2$CH=CH$_2$ | CH$_2$SOCH$_2$CH$_3$ | |
| 14-106 | CH$_2$CH=CH$_2$ | CH$_3$-S(=O)-CH$_2$-cyclopropyl | |
| 14-107 | CH$_2$CH=CH$_2$ | CH$_2$SOCH$_2$CF$_3$ | |
| 14-108 | CH$_2$CH=CH$_2$ | CH$_2$SO$_2$CH$_3$ | |

TABLE 152-continued

| compound number | R13 | R1 | physical property (melting point-ND) |
|---|---|---|---|
| 14-109 | CH$_2$CH=CH$_2$ | CH$_2$SO$_2$CH$_2$CH$_3$ | |
| 14-110 | CH$_2$CH=CH$_2$ | CH$_3$-S(=O)$_2$-CH$_2$-cyclopropyl | |
| 14-111 | CH$_2$CH=CH$_2$ | CH$_2$SO$_2$CH$_2$CF$_3$ | |
| 14-112 | CH$_2$CH=CH$_2$ | CH$_2$O(CH$_2$)$_2$OCH$_3$ | |
| 14-113 | CH$_2$CH=CH$_2$ | CH$_2$O(CH$_2$)$_2$OCH$_2$CH$_3$ | |
| 14-114 | CH$_2$CH=CH$_2$ | CH$_2$O(CH$_2$)$_2$OCH$_2$CF$_3$ | |
| 14-115 | CH$_2$CH=CH$_2$ | CH$_2$O(CH$_2$)$_2$SCH$_3$ | |
| 14-116 | CH$_2$CH=CH$_2$ | CH$_2$O(CH$_2$)$_2$SCH$_2$CF$_3$ | |
| 14-117 | CH$_2$CH=CH$_2$ | CH$_2$O(CH$_2$)$_2$SOCH$_3$ | |
| 14-118 | CH$_2$CH=CH$_2$ | CH$_2$O(CH$_2$)$_2$SOCH$_2$CF$_3$ | |
| 14-119 | CH$_2$CH=CH$_2$ | CH$_2$O(CH$_2$)$_2$SO$_2$CH$_3$ | |
| 14-120 | CH$_2$CH=CH$_2$ | CH$_2$O(CH$_2$)$_2$SO$_2$CH$_2$CF$_3$ | |

TABLE 153

| compound number | R13 | R1 | physical property (melting point-ND) |
|---|---|---|---|
| 14-121 | CH$_2$CH=CH$_2$ | CH$_3$-O-CH$_2$-(tetrahydrofuran-2-yl) | |
| 14-122 | CH$_2$CH=CH$_2$ | CH$_3$-O-(tetrahydrofuran-3-yl) | |
| 14-123 | CH$_2$CH=CH$_2$ | CH$_2$O(CH$_2$)$_2$NHSO$_2$CH$_3$ | |
| 14-124 | CH$_2$CH=CH$_2$ | CH$_2$O(CH$_2$)$_2$N(CH$_3$)(SO$_2$CH$_3$) | |
| 14-125 | CH$_2$CH=CH$_2$ | CH$_3$ | |
| 14-126 | CH$_2$CH=CH$_2$ | CF$_3$ | |
| 14-127 | CH$_2$CH=CH$_2$ | CH$_2$OCH$_3$ | |
| 14-128 | CH$_2$CH=CH$_2$ | CH$_2$OCH$_2$CH$_3$ | |
| 14-129 | CH$_2$CH=CH$_2$ | CH$_3$-O-CH$_2$-cyclopropyl | |
| 14-130 | CH$_2$CH=CH$_2$ | CH$_2$OCH$_2$CF$_3$ | |
| 14-131 | CH$_2$CH=CH$_2$ | CH$_2$SCH$_3$ | |
| 14-132 | CH$_2$CH=CH$_2$ | CH$_2$SCH$_2$CH$_3$ | |
| 14-133 | CH$_2$CH=CH$_2$ | CH$_3$-S-CH$_2$-cyclopropyl | |
| 14-134 | CH$_2$CH=CH$_2$ | CH$_2$SCH$_2$CF$_3$ | |
| 14-135 | CH$_2$CH=CH$_2$ | CH$_2$SOCH$_3$ | |
| 14-136 | CH$_2$CH=CH$_2$ | CH$_2$SOCH$_2$CH$_3$ | |
| 14-137 | CH$_2$CH=CH$_2$ | CH$_3$-S(=O)-CH$_2$-cyclopropyl | |
| 14-138 | CH$_2$CH=CH$_2$ | CH$_2$SOCH$_2$CF$_3$ | |
| 14-139 | CH$_2$CH=CH$_2$ | CH$_2$SO$_2$CH$_3$ | |
| 14-140 | CH$_2$CH=CH$_2$ | CH$_2$SO$_2$CH$_2$CH$_3$ | |

TABLE 153-continued

| compound number | R13 | R1 | physical property (melting point-ND) |
|---|---|---|---|
| 14-141 | CH$_2$CH=CH$_2$ | CH$_3$-S(=O)$_2$-CH$_2$-cyclopropyl | |
| 14-142 | CH$_2$CH=CH$_2$ | CH$_2$SO$_2$CH$_2$CF$_3$ | |
| 14-143 | CH$_2$CH=CH$_2$ | CH$_2$O(CH$_2$)$_2$OCH$_3$ | |
| 14-144 | CH$_2$CH=CH$_2$ | CH$_2$O(CH$_2$)$_2$OCH$_2$CH$_3$ | |
| 14-145 | CH$_2$CH=CH$_2$ | CH$_2$O(CH$_2$)$_2$OCH$_2$CF$_3$ | |
| 14-146 | CH$_2$CH=CH$_2$ | CH$_2$O(CH$_2$)$_2$SCH$_3$ | |
| 14-147 | CH$_2$CH=CH$_2$ | CH$_2$O(CH$_2$)$_2$SCH$_2$CF$_3$ | |
| 14-148 | CH$_2$CH=CH$_2$ | CH$_2$O(CH$_2$)$_2$SOCH$_3$ | |
| 14-149 | CH$_2$CH=CH$_2$ | CH$_2$O(CH$_2$)$_2$SOCH$_2$CF$_3$ | |
| 14-150 | CH$_2$CH=CH$_2$ | CH$_2$O(CH$_2$)$_2$SO$_2$CH$_3$ | |
| 14-151 | CH$_2$CH=CH$_2$ | CH$_2$O(CH$_2$)$_2$SO$_2$CH$_2$CF$_3$ | |
| 14-152 | CH$_2$CH=CH$_2$ | CH$_3$-O-CH$_2$-(tetrahydrofuran-2-yl) | |
| 14-153 | CH$_2$CH=CH$_2$ | CH$_3$-O-(tetrahydrofuran-3-yl) | |
| 14-154 | CH$_2$CH=CH$_2$ | CH$_2$O(CH$_2$)$_2$NHSO$_2$CH$_3$ | |
| 14-155 | CH$_2$CH=CH$_2$ | CH$_2$O(CH$_2$)$_2$N(CH$_3$)(SO$_2$CH$_3$) | |
| 14-156 | CH$_2$C$_6$H$_5$ | CH$_3$ | |
| 14-157 | CH$_2$C$_6$H$_5$ | CF$_3$ | |
| 14-158 | CH$_2$C$_6$H$_5$ | CH$_2$OCH$_3$ | |
| 14-159 | CH$_2$C$_6$H$_5$ | CH$_2$OCH$_2$CH$_3$ | |
| 14-160 | CH$_2$C$_6$H$_5$ | CH$_3$-O-CH$_2$-cyclopropyl | |

TABLE 154

| compound number | R13 | R1 | physical property (melting point-ND) |
|---|---|---|---|
| 14-161 | CH$_2$C$_6$H$_5$ | CH$_2$OCH$_2$CF$_3$ | |
| 14-162 | CH$_2$C$_6$H$_5$ | CH$_2$SCH$_3$ | |
| 14-163 | CH$_2$C$_6$H$_5$ | CH$_2$SCH$_2$CH$_3$ | |
| 14-164 | CH$_2$C$_6$H$_5$ | CH$_3$-S-CH$_2$-cyclopropyl | |
| 14-165 | CH$_2$C$_6$H$_5$ | CH$_2$SCH$_2$CF$_3$ | |
| 14-166 | CH$_2$C$_6$H$_5$ | CH$_2$SOCH$_3$ | |
| 14-167 | CH$_2$C$_6$H$_5$ | CH$_2$SOCH$_2$CH$_3$ | |
| 14-168 | CH$_2$C$_6$H$_5$ | CH$_3$-S(=O)-CH$_2$-cyclopropyl | |
| 14-169 | CH$_2$C$_6$H$_5$ | CH$_2$SOCH$_2$CF$_3$ | |
| 14-170 | CH$_2$C$_6$H$_5$ | CH$_2$SO$_2$CH$_3$ | |
| 14-171 | CH$_2$C$_6$H$_5$ | CH$_2$SO$_2$CH$_2$CH$_3$ | |

TABLE 154-continued

| compound number | R13 | R1 | physical property (melting point-ND) |
|---|---|---|---|
| 14-172 | CH₂C₆H₅ | 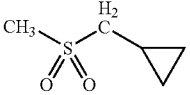 | |
| 14-173 | CH₂C₆H₅ | CH₂SO₂CH₂CF₃ | |
| 14-174 | CH₂C₆H₅ | CH₂O(CH₂)₂OCH₃ | |
| 14-175 | CH₂C₆H₅ | CH₂O(CH₂)₂OCH₂CH₃ | |
| 14-176 | CH₂C₆H₅ | CH₂O(CH₂)₂OCH₂CF₃ | |
| 14-177 | CH₂C₆H₅ | CH₂O(CH₂)₂SCH₃ | |
| 14-178 | CH₂C₆H₅ | CH₂O(CH₂)₂SCH₂CF₃ | |
| 14-179 | CH₂C₆H₅ | CH₂O(CH₂)₂SOCH₃ | |
| 14-180 | CH₂C₆H₅ | CH₂O(CH₂)₂SOCH₂CF₃ | |
| 14-181 | CH₂C₆H₅ | CH₂O(CH₂)₂SO₂CH₃ | |
| 14-182 | CH₂C₆H₅ | CH₂O(CH₂)₂SO₂CH₂CF₃ | |
| 14-183 | CH₂C₆H₅ | 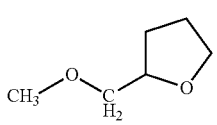 | |
| 14-184 | CH₂C₆H₅ | 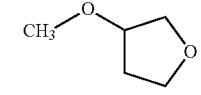 | |
| 14-185 | CH₂C₆H₅ | CH₂O(CH₂)₂NHSO₂CH₃ | |
| 14-186 | CH₂C₆H₅ | CH₂O(CH₂)₂N(CH₃)(SO₂CH₃) | |
| 14-187 | SO₂CH₃ | CH₃ | |
| 14-188 | SO₂CH₃ | CF₃ | |
| 14-189 | SO₂CH₃ | CH₂OCH₃ | |
| 14-190 | SO₂CH₃ | CH₂OCH₂CH₃ | |
| 14-191 | SO₂CH₃ | 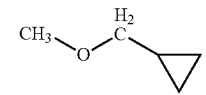 | |
| 14-192 | SO₂CH₃ | CH₂OCH₂CF₃ | |
| 14-193 | SO₂CH₃ | CH₂SCH₃ | |
| 14-194 | SO₂CH₃ | CH₂SCH₂CH₃ | |
| 14-195 | SO₂CH₃ | 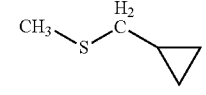 | |
| 14-196 | SO₂CH₃ | CH₂SCH₂CF₃ | |
| 14-197 | SO₂CH₃ | CH₂SOCH₃ | |
| 14-198 | SO₂CH₃ | CH₂SOCH₂CH₃ | |
| 14-199 | SO₂CH₃ | 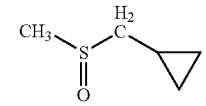 | |
| 14-200 | SO₂CH₃ | CH₂SOCH₂CF₃ | |

TABLE 155

| compound number | R13 | R1 | physical property (melting point-ND) |
|---|---|---|---|
| 14-201 | SO₂CH₃ | CH₂SO₂CH₃ | |
| 14-202 | SO₂CH₃ | CH₂SO₂CH₂CH₃ | |
| 14-203 | SO₂CH₃ | 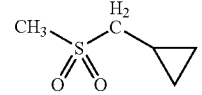 | |
| 14-204 | SO₂CH₃ | CH₂SO₂CH₂CF₃ | |
| 14-205 | SO₂CH₃ | CH₂O(CH₂)₂OCH₃ | |
| 14-206 | SO₂CH₃ | CH₂O(CH₂)₂OCH₂CH₃ | |
| 14-207 | SO₂CH₃ | CH₂O(CH₂)₂OCH₂CF₃ | |
| 14-208 | SO₂CH₃ | CH₂O(CH₂)₂SCH₃ | |
| 14-209 | SO₂CH₃ | CH₂O(CH₂)₂SCH₂CF₃ | |
| 14-210 | SO₂CH₃ | CH₂O(CH₂)₂SOCH₃ | |
| 14-211 | SO₂CH₃ | CH₂O(CH₂)₂SOCH₂CF₃ | |
| 14-212 | SO₂CH₃ | CH₂O(CH₂)₂SO₂CH₃ | |
| 14-213 | SO₂CH₃ | CH₂O(CH₂)₂SO₂CH₂CF₃ | |
| 14-214 | SO₂CH₃ | 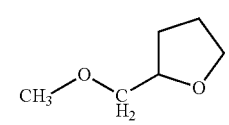 | |
| 14-215 | SO₂CH₃ | 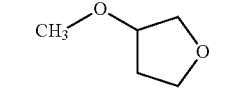 | |
| 14-216 | SO₂CH₃ | CH₂O(CH₂)₂NHSO₂CH₃ | |
| 14-217 | SO₂CH₃ | CH₂O(CH₂)₂N(CH₃)(SO₂CH₃) | |
| 14-218 | SO₂CH₂CH₃ | CH₃ | |
| 14-219 | SO₂CH₂CH₃ | CF₃ | |
| 14-220 | SO₂CH₂CH₃ | CH₂OCH₃ | |
| 14-221 | SO₂CH₂CH₃ | CH₂OCH₂CH₃ | |
| 14-222 | SO₂CH₂CH₃ | 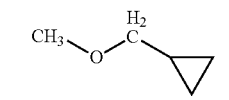 | |
| 14-223 | SO₂CH₂CH₃ | CH₂OCH₂CF₃ | |
| 14-224 | SO₂CH₂CH₃ | CH₂SCH₃ | |
| 14-225 | SO₂CH₂CH₃ | CH₂SCH₂CH₃ | |
| 14-226 | SO₂CH₂CH₃ | 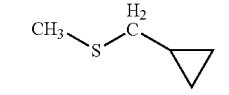 | |
| 14-227 | SO₂CH₂CH₃ | CH₂SCH₂CF₃ | |
| 14-228 | SO₂CH₂CH₃ | CH₂SOCH₃ | |
| 14-229 | SO₂CH₂CH₃ | CH₂SOCH₂CH₃ | |
| 14-230 | SO₂CH₂CH₃ | 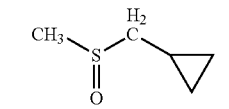 | |
| 14-231 | SO₂CH₂CH₃ | CH₂SOCH₂CF₃ | |
| 14-232 | SO₂CH₂CH₃ | CH₂SO₂CH₃ | |
| 14-233 | SO₂CH₂CH₃ | CH₂SO₂CH₂CH₃ | |
| 14-234 | SO₂CH₂CH₃ | 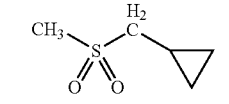 | |
| 14-235 | SO₂CH₂CH₃ | CH₂SO₂CH₂CF₃ | |
| 14-236 | SO₂CH₂CH₃ | CH₂O(CH₂)₂OCH₃ | |
| 14-237 | SO₂CH₂CH₃ | CH₂O(CH₂)₂OCH₂CH₃ | |
| 14-238 | SO₂CH₂CH₃ | CH₂O(CH₂)₂OCH₂CF₃ | |

TABLE 155-continued

| compound number | R13 | R1 | physical property (melting point-ND) |
|---|---|---|---|
| 14-239 | $SO_2CH_2CH_3$ | $CH_2O(CH_2)_2SCH_3$ | |
| 14-240 | $SO_2CH_2CH_3$ | $CH_2O(CH_2)_2SCH_2CF_3$ | |

TABLE 156

| compound number | R13 | R1 | physical property (melting point-ND) |
|---|---|---|---|
| 14-241 | $SO_2CH_2CH_3$ | $CH_2O(CH_2)_2SOCH_3$ | |
| 14-242 | $SO_2CH_2CH_3$ | $CH_2O(CH_2)_2SOCH_2CF_3$ | |
| 14-243 | $SO_2CH_2CH_3$ | $CH_2O(CH_2)_2SO_2CH_3$ | |
| 14-244 | $SO_2CH_2CH_3$ | $CH_2O(CH_2)_2SO_2CH_2CF_3$ | |
| 14-245 | $SO_2CH_2CH_3$ | (CH₃-O-CH₂-tetrahydrofuran-2-yl) | |
| 14-246 | $SO_2CH_2CH_3$ | (CH₃-O-tetrahydrofuran-3-yl) | |
| 14-247 | $SO_2CH_2CH_3$ | $CH_2O(CH_2)_2NHSO_2CH_3$ | |
| 14-248 | $SO_2CH_2CH_3$ | $CH_2O(CH_2)_2N(CH_3)(SO_2CH_3)$ | |
| 14-249 | $SO_2(CH_2)_2CH_3$ | $CH_3$ | |
| 14-250 | $SO_2(CH_2)_2CH_3$ | $CF_3$ | |
| 14-251 | $SO_2(CH_2)_2CH_3$ | $CH_2OCH_3$ | |
| 14-252 | $SO_2(CH_2)_2CH_3$ | $CH_2OCH_2CH_3$ | |
| 14-253 | $SO_2(CH_2)_2CH_3$ | (CH₃-O-CH₂-cyclopropyl) | |
| 14-254 | $SO_2(CH_2)_2CH_3$ | $CH_2OCH_2CF_3$ | |
| 14-255 | $SO_2(CH_2)_2CH_3$ | $CH_2SCH_3$ | |
| 14-256 | $SO_2(CH_2)_2CH_3$ | $CH_2SCH_2CH_3$ | |
| 14-257 | $SO_2(CH_2)_2CH_3$ | (CH₃-S-CH₂-cyclopropyl) | |
| 14-258 | $SO_2(CH_2)_2CH_3$ | $CH_2SCH_2CF_3$ | |
| 14-259 | $SO_2(CH_2)_2CH_3$ | $CH_2SOCH_3$ | |
| 14-260 | $SO_2(CH_2)_2CH_3$ | $CH_2SOCH_2CH_3$ | |
| 14-261 | $SO_2(CH_2)_2CH_3$ | (CH₃-S(=O)-CH₂-cyclopropyl) | |
| 14-262 | $SO_2(CH_2)_2CH_3$ | $CH_2SOCH_2CF_3$ | |
| 14-263 | $SO_2(CH_2)_2CH_3$ | $CH_2SO_2CH_3$ | |
| 14-264 | $SO_2(CH_2)_2CH_3$ | $CH_2SO_2CH_2CH_3$ | |
| 14-265 | $SO_2(CH_2)_2CH_3$ | (CH₃-S(=O)₂-CH₂-cyclopropyl) | |
| 14-266 | $SO_2(CH_2)_2CH_3$ | $CH_2SO_2CH_2CF_3$ | |
| 14-267 | $SO_2(CH_2)_2CH_3$ | $CH_2O(CH_2)_2OCH_3$ | |
| 14-268 | $SO_2(CH_2)_2CH_3$ | $CH_2O(CH_2)_2OCH_2CH_3$ | |
| 14-269 | $SO_2(CH_2)_2CH_3$ | $CH_2O(CH_2)_2OCH_2CF_3$ | |
| 14-270 | $SO_2(CH_2)_2CH_3$ | $CH_2O(CH_2)_2SCH_3$ | |

TABLE 156-continued

| compound number | R13 | R1 | physical property (melting point-ND) |
|---|---|---|---|
| 14-271 | $SO_2(CH_2)_2CH_3$ | $CH_2O(CH_2)_2SCH_2CF_3$ | |
| 14-272 | $SO_2(CH_2)_2CH_3$ | $CH_2O(CH_2)_2SOCH_3$ | |
| 14-273 | $SO_2(CH_2)_2CH_3$ | $CH_2O(CH_2)_2SOCH_2CF_3$ | |
| 14-274 | $SO_2(CH_2)_2CH_3$ | $CH_2O(CH_2)_2SO_2CH_3$ | |
| 14-275 | $SO_2(CH_2)_2CH_3$ | $CH_2O(CH_2)_2SO_2CH_2CF_3$ | |
| 14-276 | $SO_2(CH_2)_2CH_3$ | (CH₃-O-CH₂-tetrahydrofuran-2-yl) | |
| 14-277 | $SO_2(CH_2)_2CH_3$ | (CH₃-O-tetrahydrofuran-3-yl) | |
| 14-278 | $SO_2(CH_2)_2CH_3$ | $CH_2O(CH_2)_2NHSO_2CH_3$ | |
| 14-279 | $SO_2(CH_2)_2CH_3$ | $CH_2O(CH_2)_2N(CH_3)(SO_2CH_3)$ | |
| 14-280 | $SO_2C_6H_5$ | $CH_3$ | |

TABLE 157

| compound number | R13 | R1 | physical property (melting point-ND) |
|---|---|---|---|
| 14-281 | $SO_2C_6H_5$ | $CF_3$ | |
| 14-282 | $SO_2C_6H_5$ | $CH_2OCH_3$ | |
| 14-283 | $SO_2C_6H_5$ | $CH_2OCH_2CH_3$ | |
| 14-284 | $SO_2C_6H_5$ | (CH₃-O-CH₂-cyclopropyl) | |
| 14-285 | $SO_2C_6H_5$ | $CH_2OCH_2CF_3$ | |
| 14-286 | $SO_2C_6H_5$ | $CH_2SCH_3$ | |
| 14-287 | $SO_2C_6H_5$ | $CH_2SCH_2CH_3$ | |
| 14-288 | $SO_2C_6H_5$ | (CH₃-S-CH₂-cyclopropyl) | |
| 14-289 | $SO_2C_6H_5$ | $CH_2SCH_2CF_3$ | |
| 14-290 | $SO_2C_6H_5$ | $CH_2SOCH_3$ | |
| 14-291 | $SO_2C_6H_5$ | $CH_2SOCH_2CH_3$ | |
| 14-292 | $SO_2C_6H_5$ | (CH₃-S(=O)-CH₂-cyclopropyl) | |
| 14-293 | $SO_2C_6H_5$ | $CH_2SOCH_2CF_3$ | |
| 14-294 | $SO_2C_6H_5$ | $CH_2SO_2CH_3$ | |
| 14-295 | $SO_2C_6H_5$ | $CH_2SO_2CH_2CH_3$ | |
| 14-296 | $SO_2C_6H_5$ | (CH₃-S(=O)₂-CH₂-cyclopropyl) | |
| 14-297 | $SO_2C_6H_5$ | $CH_2SO_2CH_2CF_3$ | |
| 14-298 | $SO_2C_6H_5$ | $CH_2O(CH_2)_2OCH_3$ | |
| 14-299 | $SO_2C_6H_5$ | $CH_2O(CH_2)_2OCH_2CH_3$ | |
| 14-300 | $SO_2C_6H_5$ | $CH_2O(CH_2)_2OCH_2CF_3$ | |
| 14-301 | $SO_2C_6H_5$ | $CH_2O(CH_2)_2SCH_3$ | |
| 14-302 | $SO_2C_6H_5$ | $CH_2O(CH_2)_2SCH_2CF_3$ | |

TABLE 157-continued

| compound number | R13 | R1 | physical property (melting point-ND) |
|---|---|---|---|
| 14-303 | SO$_2$C$_6$H$_5$ | CH$_2$O(CH$_2$)$_2$SOCH$_3$ | |
| 14-304 | SO$_2$C$_6$H$_5$ | CH$_2$O(CH$_2$)$_2$SOCH$_2$CF$_3$ | |
| 14-305 | SO$_2$C$_6$H$_5$ | CH$_2$O(CH$_2$)$_2$SO$_2$CH$_3$ | |
| 14-306 | SO$_2$C$_6$H$_5$ | CH$_2$O(CH$_2$)$_2$SO$_2$CH$_2$CF$_3$ | |
| 14-307 | SO$_2$C$_6$H$_5$ | CH$_3$-O-CH$_2$-(tetrahydrofuran-2-yl) | |
| 14-308 | SO$_2$C$_6$H$_5$ | 3-(CH$_3$O)-tetrahydrofuran | |
| 14-309 | SO$_2$C$_6$H$_5$ | CH$_2$O(CH$_2$)$_2$NHSO$_2$CH$_3$ | |
| 14-310 | SO$_2$C$_6$H$_5$ | CH$_2$O(CH$_2$)$_2$N(CH$_3$)(SO$_2$CH$_3$) | |
| 14-311 | SO$_2$(4-CH$_3$)C$_6$H$_4$ | CH$_3$ | |
| 14-312 | SO$_2$(4-CH$_3$)C$_6$H$_4$ | CF$_3$ | |
| 14-313 | SO$_2$(4-CH$_3$)C$_6$H$_4$ | CH$_2$OCH$_3$ | |
| 14-314 | SO$_2$(4-CH$_3$)C$_6$H$_4$ | CH$_2$OCH$_2$CH$_3$ | |
| 14-315 | SO$_2$(4-CH$_3$)C$_6$H$_4$ | CH$_3$-O-CH$_2$-cyclopropyl | |
| 14-316 | SO$_2$(4-CH$_3$)C$_6$H$_4$ | CH$_2$OCH$_2$CF$_3$ | |
| 14-317 | SO$_2$(4-CH$_3$)C$_6$H$_4$ | CH$_2$SCH$_3$ | |
| 14-318 | SO$_2$(4-CH$_3$)C$_6$H$_4$ | CH$_2$SCH$_2$CH$_3$ | |
| 14-319 | SO$_2$(4-CH$_3$)C$_6$H$_4$ | CH$_3$-S-CH$_2$-cyclopropyl | |
| 14-320 | SO$_2$(4-CH$_3$)C$_6$H$_4$ | CH$_2$SCH$_2$CF$_3$ | |

TABLE 158

| compound number | R13 | R1 | physical property (melting point-ND) |
|---|---|---|---|
| 14-321 | SO$_2$(4-CH$_3$)C$_6$H$_4$ | CH$_2$SOCH$_3$ | |
| 14-322 | SO$_2$(4-CH$_3$)C$_6$H$_4$ | CH$_2$SOCH$_2$CH$_3$ | |
| 14-323 | SO$_2$(4-CH$_3$)C$_6$H$_4$ | CH$_3$-S(=O)-CH$_2$-cyclopropyl | |
| 14-324 | SO$_2$(4-CH$_3$)C$_6$H$_4$ | CH$_2$SOCH$_2$CF$_3$ | |
| 14-325 | SO$_2$(4-CH$_3$)C$_6$H$_4$ | CH$_2$SO$_2$CH$_3$ | |
| 14-326 | SO$_2$(4-CH$_3$)C$_6$H$_4$ | CH$_2$SO$_2$CH$_2$CH$_3$ | |
| 14-327 | SO$_2$(4-CH$_3$)C$_6$H$_4$ | CH$_3$-S(=O)$_2$-CH$_2$-cyclopropyl 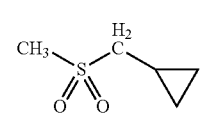 | |
| 14-328 | SO$_2$(4-CH$_3$)C$_6$H$_4$ | CH$_2$SO$_2$CH$_2$CF$_3$ | |
| 14-329 | SO$_2$(4-CH$_3$)C$_6$H$_4$ | CH$_2$O(CH$_2$)$_2$OCH$_3$ | |
| 14-330 | SO$_2$(4-CH$_3$)C$_6$H$_4$ | CH$_2$O(CH$_2$)$_2$OCH$_2$CH$_3$ | |
| 14-331 | SO$_2$(4-CH$_3$)C$_6$H$_4$ | CH$_2$O(CH$_2$)$_2$OCH$_2$CF$_3$ | |
| 14-332 | SO$_2$(4-CH$_3$)C$_6$H$_4$ | CH$_2$O(CH$_2$)$_2$SCH$_3$ | |
| 14-333 | SO$_2$(4-CH$_3$)C$_6$H$_4$ | CH$_2$O(CH$_2$)$_2$SCH$_2$CF$_3$ | |
| 14-334 | SO$_2$(4-CH$_3$)C$_6$H$_4$ | CH$_2$O(CH$_2$)$_2$SOCH$_3$ | |

TABLE 158-continued

| compound number | R13 | R1 | physical property (melting point-ND) |
|---|---|---|---|
| 14-335 | SO$_2$(4-CH$_3$)C$_6$H$_4$ | CH$_2$O(CH$_2$)$_2$SOCH$_2$CF$_3$ | |
| 14-336 | SO$_2$(4-CH$_3$)C$_6$H$_4$ | CH$_2$O(CH$_2$)$_2$SO$_2$CH$_3$ | |
| 14-337 | SO$_2$(4-CH$_3$)C$_6$H$_4$ | CH$_2$O(CH$_2$)$_2$SO$_2$CH$_2$CF$_3$ | |
| 14-338 | SO$_2$(4-CH$_3$)C$_6$H$_4$ | CH$_3$-O-CH$_2$-(tetrahydrofuran-2-yl) | |
| 14-339 | SO$_2$(4-CH$_3$)C$_6$H$_4$ | 3-(CH$_3$O)-tetrahydrofuran | |
| 14-340 | SO$_2$(4-CH$_3$)C$_6$H$_4$ | CH$_2$O(CH$_2$)$_2$NHSO$_2$CH$_3$ | |
| 14-341 | SO$_2$(4-CH$_3$)C$_6$H$_4$ | CH$_2$O(CH$_2$)$_2$N(CH$_3$)(SO$_2$CH$_3$) | |
| 14-342 | COCH$_3$ | CH$_3$ | |
| 14-343 | COCH$_3$ | CF$_3$ | |
| 14-344 | COCH$_3$ | CH$_2$OCH$_3$ | |
| 14-345 | COCH$_3$ | CH$_2$OCH$_2$CH$_3$ | |
| 14-346 | COCH$_3$ | CH$_3$-O-CH$_2$-cyclopropyl | |
| 14-347 | COCH$_3$ | CH$_2$OCH$_2$CF$_3$ | |
| 14-348 | COCH$_3$ | CH$_2$SCH$_3$ | |
| 14-349 | COCH$_3$ | CH$_2$SCH$_2$CH$_3$ | |
| 14-350 | COCH$_3$ | CH$_3$-S-CH$_2$-cyclopropyl | |
| 14-351 | COCH$_3$ | CH$_2$SCH$_2$CF$_3$ | |
| 14-352 | COCH$_3$ | CH$_2$SOCH$_3$ | |
| 14-353 | COCH$_3$ | CH$_2$SOCH$_2$CH$_3$ | |
| 14-354 | COCH$_3$ | CH$_3$-S(=O)-CH$_2$-cyclopropyl | |
| 14-355 | COCH$_3$ | CH$_2$SOCH$_2$CF$_3$ | |
| 14-356 | COCH$_3$ | CH$_2$SO$_2$CH$_3$ | |
| 14-357 | COCH$_3$ | CH$_2$SO$_2$CH$_2$CH$_3$ | |
| 14-358 | COCH$_3$ | CH$_3$-S(=O)$_2$-CH$_2$-cyclopropyl | |
| 14-359 | COCH$_3$ | CH$_2$SO$_2$CH$_2$CF$_3$ | |
| 14-360 | COCH$_3$ | CH$_2$O(CH$_2$)$_2$OCH$_3$ | |

TABLE 159

| compound number | R13 | R1 | physical property (melting point-ND) |
|---|---|---|---|
| 14-361 | COCH$_3$ | CH$_2$O(CH$_2$)$_2$OCH$_2$CH$_3$ | |
| 14-362 | COCH$_3$ | CH$_2$O(CH$_2$)$_2$OCH$_2$CF$_3$ | |
| 14-363 | COCH$_3$ | CH$_2$O(CH$_2$)$_2$SCH$_3$ | |
| 14-364 | COCH$_3$ | CH$_2$O(CH$_2$)$_2$SCH$_2$CF$_3$ | |
| 14-365 | COCH$_3$ | CH$_2$O(CH$_2$)$_2$SOCH$_3$ | |
| 14-366 | COCH$_3$ | CH$_2$O(CH$_2$)$_2$SOCH$_2$CF$_3$ | |

TABLE 159-continued

| compound number | R13 | R1 | physical property (melting point-ND) |
|---|---|---|---|
| 14-367 | $COCH_3$ | $CH_2O(CH_2)_2SO_2CH_3$ | |
| 14-368 | $COCH_3$ | $CH_2O(CH_2)_2SO_2CH_2CF_3$ | |
| 14-369 | $COCH_3$ | $CH_3-O-CH_2-\text{(tetrahydrofuran-2-yl)}$ | |
| 14-370 | $COCH_3$ | $CH_3-O-\text{(tetrahydrofuran-3-yl)}$ | |
| 14-371 | $COCH_3$ | $CH_2O(CH_2)_2NHSO_2CH_3$ | |
| 14-372 | $COCH_3$ | $CH_2O(CH_2)_2N(CH_3)(SO_2CH_3)$ | |
| 14-373 | $COC_6H_5$ | $CH_3$ | |
| 14-374 | $COC_6H_5$ | $CF_3$ | |
| 14-375 | $COC_6H_5$ | $CH_2OCH_3$ | |
| 14-376 | $COC_6H_5$ | $CH_2OCH_2CH_3$ | |
| 14-377 | $COC_6H_5$ | $CH_3-O-CH_2-\text{cyclopropyl}$ | |
| 14-378 | $COC_6H_5$ | $CH_2OCH_2CF_3$ | |
| 14-379 | $COC_6H_5$ | $CH_2SCH_3$ | |
| 14-380 | $COC_6H_5$ | $CH_2SCH_2CH_3$ | |
| 14-381 | $COC_6H_5$ | $CH_3-S-CH_2-\text{cyclopropyl}$ | |
| 14-382 | $COC_6H_5$ | $CH_2SCH_2CF_3$ | |
| 14-383 | $COC_6H_5$ | $CH_2SOCH_3$ | |
| 14-384 | $COC_6H_5$ | $CH_2SOCH_2CH_3$ | |
| 14-385 | $COC_6H_5$ | $CH_3-S(O)-CH_2-\text{cyclopropyl}$ | |
| 14-386 | $COC_6H_5$ | $CH_2SOCH_2CF_3$ | |
| 14-387 | $COC_6H_5$ | $CH_2SO_2CH_3$ | |
| 14-388 | $COC_6H_5$ | $CH_2SO_2CH_2CH_3$ | |
| 14-389 | $COC_6H_5$ | $CH_3-SO_2-CH_2-\text{cyclopropyl}$ | |
| 14-390 | $COC_6H_5$ | $CH_2SO_2CH_2CF_3$ | |
| 14-391 | $COC_6H_5$ | $CH_2O(CH_2)_2OCH_3$ | |
| 14-392 | $COC_6H_5$ | $CH_2O(CH_2)_2OCH_2CH_3$ | |
| 14-393 | $COC_6H_5$ | $CH_2O(CH_2)_2OCH_2CF_3$ | |
| 14-394 | $COC_6H_5$ | $CH_2O(CH_2)_2SCH_3$ | |
| 14-395 | $COC_6H_5$ | $CH_2O(CH_2)_2SCH_2CF_3$ | |
| 14-396 | $COC_6H_5$ | $CH_2O(CH_2)_2SOCH_3$ | |
| 14-397 | $COC_6H_5$ | $CH_2O(CH_2)_2SOCH_2CF_3$ | |
| 14-398 | $COC_6H_5$ | $CH_2O(CH_2)_2SO_2CH_3$ | |
| 14-399 | $COC_6H_5$ | $CH_2O(CH_2)_2SO_2CH_2CF_3$ | |
| 14-400 | $COC_6H_5$ | $CH_3-O-CH_2-\text{(tetrahydrofuran-2-yl)}$ | |

TABLE 160

| compound number | R13 | R1 | physical property (melting point-ND) |
|---|---|---|---|
| 14-401 | $COC_6H_5$ | $CH_3-O-\text{(tetrahydrofuran-3-yl)}$ | |
| 14-402 | $COC_6H_5$ | $CH_2O(CH_2)_2NHSO_2CH_3$ | |
| 14-403 | $COC_6H_5$ | $CH_2O(CH_2)_2N(CH_3)(SO_2CH_3)$ | |
| 14-404 | $COCH_2C_6H_5$ | $CH_3$ | |
| 14-405 | $COCH_2C_6H_5$ | $CF_3$ | |
| 14-406 | $COCH_2C_6H_5$ | $CH_2OCH_3$ | |
| 14-407 | $COCH_2C_6H_5$ | $CH_2OCH_2CH_3$ | |
| 14-408 | $COCH_2C_6H_5$ | $CH_3-O-CH_2-\text{cyclopropyl}$ | |
| 14-409 | $COCH_2C_6H_5$ | $CH_2OCH_2CF_3$ | |
| 14-410 | $COCH_2C_6H_5$ | $CH_2SCH_3$ | |
| 14-411 | $COCH_2C_6H_5$ | $CH_2SCH_2CH_3$ | |
| 14-412 | $COCH_2C_6H_5$ | $CH_3-S-CH_2-\text{cyclopropyl}$ | |
| 14-413 | $COCH_2C_6H_5$ | $CH_2SCH_2CF_3$ | |
| 14-414 | $COCH_2C_6H_5$ | $CH_2SOCH_3$ | |
| 14-415 | $COCH_2C_6H_5$ | $CH_2SOCH_2CH_3$ | |
| 14-416 | $COCH_2C_6H_5$ | $CH_3-S(O)-CH_2-\text{cyclopropyl}$ | |
| 14-417 | $COCH_2C_6H_5$ | $CH_2SOCH_2CF_3$ | |
| 14-418 | $COCH_2C_6H_5$ | $CH_2SO_2CH_3$ | |
| 14-419 | $COCH_2C_6H_5$ | $CH_2SO_2CH_2CH_3$ | |
| 14-420 | $COCH_2C_6H_5$ | $CH_3-SO_2-CH_2-\text{cyclopropyl}$ | |
| 14-421 | $COCH_2C_6H_5$ | $CH_2SO_2CH_2CF_3$ | |
| 14-422 | $COCH_2C_6H_5$ | $CH_2O(CH_2)_2OCH_3$ | |
| 14-423 | $COCH_2C_6H_5$ | $CH_2O(CH_2)_2OCH_2CH_3$ | |
| 14-424 | $COCH_2C_6H_5$ | $CH_2O(CH_2)_2OCH_2CF_3$ | |
| 14-425 | $COCH_2C_6H_5$ | $CH_2O(CH_2)_2SCH_3$ | |
| 14-426 | $COCH_2C_6H_5$ | $CH_2O(CH_2)_2SCH_2CF_3$ | |
| 14-427 | $COCH_2C_6H_5$ | $CH_2O(CH_2)_2SOCH_3$ | |
| 14-428 | $COCH_2C_6H_5$ | $CH_2O(CH_2)_2SOCH_2CF_3$ | |
| 14-429 | $COCH_2C_6H_5$ | $CH_2O(CH_2)_2SO_2CH_3$ | |
| 14-430 | $COCH_2C_6H_5$ | $CH_2O(CH_2)_2SO_2CH_2CF_3$ | |
| 14-431 | $COCH_2C_6H_5$ | $CH_3-O-CH_2-\text{(tetrahydrofuran-2-yl)}$ | |
| 14-432 | $COCH_2C_6H_5$ | $CH_3-O-\text{(tetrahydrofuran-3-yl)}$ | |
| 14-433 | $COCH_2C_6H_5$ | $CH_2O(CH_2)_2NHSO_2CH_3$ | |
| 14-434 | $COCH_2C_6H_5$ | $CH_2O(CH_2)_2N(CH_3)(SO_2CH_3)$ | |
| 14-435 | $CH_2COCH_3$ | $CH_3$ | |
| 14-436 | $CH_2COCH_3$ | $CF_3$ | |
| 14-437 | $CH_2COCH_3$ | $CH_2OCH_3$ | |
| 14-438 | $CH_2COCH_3$ | $CH_2OCH_2CH_3$ | |

TABLE 160-continued

| compound number | R13 | R1 | physical property (melting point-ND) |
|---|---|---|---|
| 14-439 | CH₂COCH₃ | 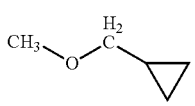 | |
| 14-440 | CH₂COCH₃ | CH₂OCH₂CF₃ | |

TABLE 131

| compound number | R4 | R1 | physical property (melting point-ND) |
|---|---|---|---|
| 11-321 | 1H-tetrazole-2-yl | CH₂SOCH₃ | |
| 11-322 | 1H-tetrazole-2-yl | CH₂SOCH₂CH₃ | |
| 11-323 | 1H-tetrazole-2-yl | 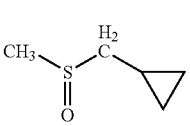 | |
| 11-324 | 1H-tetrazole-2-yl | CH₂SOCH₂CF₃ | |
| 11-325 | 1H-tetrazole-2-yl | CH₂SO₂CH₃ | |
| 11-326 | 1H-tetrazole-2-yl | CH₂SO₂CH₂CH₃ | |
| 11-327 | 1H-tetrazole-2-yl | 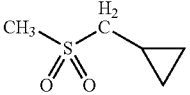 | |
| 11-328 | 1H-tetrazole-2-yl | CH₂SO₂CH₂CH₃ | |
| 11-329 | 1H-tetrazole-2-yl | CH₂O(CH₂)₂OCH₃ | |
| 11-330 | 1H-tetrazole-2-yl | CH₂O(CH₂)₂OCH₂CH₃ | |
| 11-331 | 1H-tetrazole-2-yl | CH₂O(CH₂)₂OCH₂CF₃ | |
| 11-332 | 1H-tetrazole-2-yl | CH₂O(CH₂)₂SCH₃ | |
| 11-333 | 1H-tetrazole-2-yl | CH₂O(CH₂)₂SCH₂CF₃ | |
| 11-334 | 1H-tetrazole-2-yl | CH₂O(CH₂)₂SOCH₃ | |
| 11-335 | 1H-tetrazole-2-yl | CH₂O(CH₂)₂SOCH₂CF₃ | |
| 11-336 | 1H-tetrazole-2-yl | CH₂O(CH₂)₂SO₂CH₃ | |
| 11-337 | 1H-tetrazole-2-yl | CH₂O(CH₂)₂SO₂CH₂CF₃ | |
| 11-338 | 1H-tetrazole-2-yl | 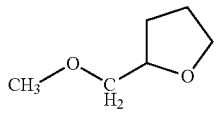 | |
| 11-339 | 1H-tetrazole-2-yl | 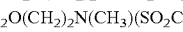 | |
| 11-340 | 1H-tetrazole-2-yl | CH₂O(CH₂)₂NHSO₂CH₃ | |
| 11-341 | 1H-tetrazole-2-yl | CH₂O(CH₂)₂N(CH₃)(SO₂CH₃) | |

TABLE 132

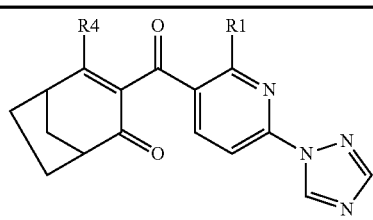

| compound number | R4 | R1 | physical property (melting point-ND) |
|---|---|---|---|
| 12-1 | Cl | CH₃ | |
| 12-2 | Cl | CF₃ | |
| 12-3 | Cl | CH₂OCH₃ | |
| 12-4 | Cl | CH₂OCH₂CH₃ | |
| 12-5 | Cl | 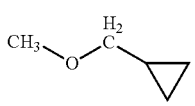 | |
| 12-6 | Cl | CH₂OCH₂CF₃ | |
| 12-7 | Cl | CH₂SCH₃ | |
| 12-8 | Cl | CH₂SCH₂CH₃ | |
| 12-9 | Cl | 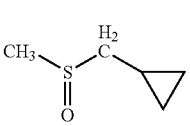 | |
| 12-10 | Cl | CH₂SCH₂CF₃ | |
| 12-11 | Cl | CH₂SOCH₃ | |
| 12-12 | Cl | CH₂SOCH₂CH₃ | |
| 12-13 | Cl | 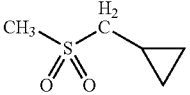 | |
| 12-14 | Cl | CH₂SOCH₂CF₃ | |
| 12-15 | Cl | CH₂SO₂CH₃ | |
| 12-16 | Cl | CH₂SO₂CH₂CH₃ | |
| 12-17 | Cl | 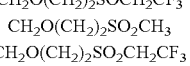 | |
| 12-18 | Cl | CH₂SO₂CH₂CF₃ | |
| 12-19 | Cl | CH₂O(CH₂)₂OCH₃ | |
| 12-20 | Cl | CH₂O(CH₂)₂OCH₂CH₃ | |
| 12-21 | Cl | CH₂O(CH₂)₂OCH₂CF₃ | |
| 12-22 | Cl | CH₂O(CH₂)₂SCH₃ | |
| 12-23 | Cl | CH₂O(CH₂)₂SCH₂CF₃ | |
| 12-24 | Cl | CH₂O(CH₂)₂SOCH₃ | |
| 12-25 | Cl | CH₂O(CH₂)₂SOCH₂CF₃ | |
| 12-26 | Cl | CH₂O(CH₂)₂SO₂CH₃ | |
| 12-27 | Cl | CH₂O(CH₂)₂SO₂CH₂CF₃ | |
| 12-28 | Cl | 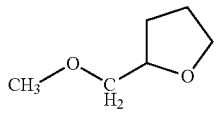 | |
| 12-29 | Cl | 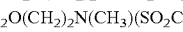 | |
| 12-30 | Cl | CH₂O(CH₂)₂NHSO₂CH₃ | |
| 12-31 | Cl | CH₂O(CH₂)₂N(CH₃)(SO₂CH₃) | |

TABLE 132-continued

[Structure: R4 and R1 substituted bicyclic diketone with pyridine-triazole]

| compound number | R4 | R1 | physical property (melting point-ND) |
|---|---|---|---|
| 12-32 | SCH$_3$ | CH$_3$ | |
| 12-33 | SCH$_3$ | CF$_3$ | |
| 12-34 | SCH$_3$ | CH$_2$OCH$_3$ | |
| 12-35 | SCH$_3$ | CH$_2$OCH$_2$CH$_3$ | |
| 12-36 | SCH$_3$ | 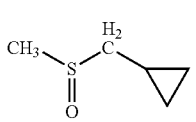 | |
| 12-37 | SCH$_3$ | CH$_2$OCH$_2$CF$_3$ | |
| 12-38 | SCH$_3$ | CH$_2$SCH$_3$ | |
| 12-39 | SCH$_3$ | CH$_2$SCH$_2$CH$_3$ | |
| 12-40 | SCH$_3$ | 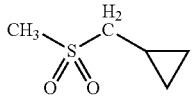 | |

TABLE 133

| compound number | R4 | R1 | physical property (melting point-ND) |
|---|---|---|---|
| 12-41 | SCH$_3$ | CH$_2$SCH$_2$CF$_3$ | |
| 12-42 | SCH$_3$ | CH$_2$SOCH$_3$ | |
| 12-43 | SCH$_3$ | CH$_2$SOCH$_2$CH$_3$ | |
| 12-44 | SCH$_3$ | 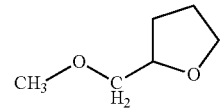 | |
| 12-45 | SCH$_3$ | CH$_2$SOCH$_2$CF$_3$ | |
| 12-46 | SCH$_3$ | CH$_2$SO$_2$CH$_3$ | |
| 12-47 | SCH$_3$ | CH$_2$SO$_2$CH$_2$CH$_3$ | |
| 12-48 | SCH$_3$ | 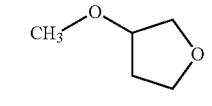 | |
| 12-49 | SCH$_3$ | CH$_2$SO$_2$CH$_2$CF$_3$ | |
| 12-50 | SCH$_3$ | CH$_2$O(CH$_2$)$_2$OCH$_3$ | |
| 12-51 | SCH$_3$ | CH$_2$O(CH$_2$)$_2$OCH$_2$CH$_3$ | |
| 12-52 | SCH$_3$ | CH$_2$O(CH$_2$)$_2$OCH$_2$CF$_3$ | |
| 12-53 | SCH$_3$ | CH$_2$O(CH$_2$)$_2$SCH$_3$ | |
| 12-54 | SCH$_3$ | CH$_2$O(CH$_2$)$_2$SCH$_2$CF$_3$ | |
| 12-55 | SCH$_3$ | CH$_2$O(CH$_2$)$_2$SOCH$_3$ | |
| 12-56 | SCH$_3$ | CH$_2$O(CH$_2$)$_2$SOCH$_2$CF$_3$ | |
| 12-57 | SCH$_3$ | CH$_2$O(CH$_2$)$_2$SO$_2$CH$_3$ | |
| 12-58 | SCH$_3$ | CH$_2$O(CH$_2$)$_2$SO$_2$CH$_2$CF$_3$ | |

TABLE 133-continued

| compound number | R4 | R1 | physical property (melting point-ND) |
|---|---|---|---|
| 12-59 | SCH$_3$ | 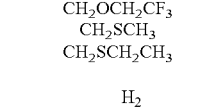 | |
| 12-60 | SCH$_3$ | 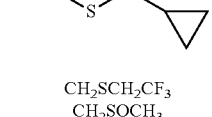 | |
| 12-61 | SCH$_3$ | CH$_2$O(CH$_2$)$_2$NHSO$_2$CH$_3$ | |
| 12-62 | SCH$_3$ | CH$_2$O(CH$_2$)$_2$N(CH$_3$)(SO$_2$CH$_3$) | |
| 12-63 | SCH$_2$CH$_3$ | CH$_3$ | |
| 12-64 | SCH$_2$CH$_3$ | CF$_3$ | |
| 12-65 | SCH$_2$CH$_3$ | CH$_2$OCH$_3$ | |
| 12-66 | SCH$_2$CH$_3$ | CH$_2$OCH$_2$CH$_3$ | |
| 12-67 | SCH$_2$CH$_3$ | 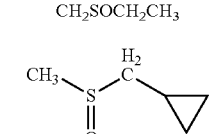 | |
| 12-68 | SCH$_2$CH$_3$ | CH$_2$OCH$_2$CF$_3$ | |
| 12-69 | SCH$_2$CH$_3$ | CH$_2$SCH$_3$ | |
| 12-70 | SCH$_2$CH$_3$ | CH$_2$SCH$_2$CH$_3$ | |
| 12-71 | SCH$_2$CH$_3$ | 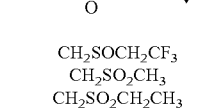 | |
| 12-72 | SCH$_2$CH$_3$ | CH$_2$SCH$_2$CF$_3$ | |
| 12-73 | SCH$_2$CH$_3$ | CH$_2$SOCH$_3$ | |
| 12-74 | SCH$_2$CH$_3$ | CH$_2$SOCH$_2$CH$_3$ | |
| 12-75 | SCH$_2$CH$_3$ | 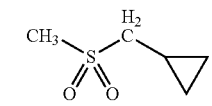 | |
| 12-76 | SCH$_2$CH$_3$ | CH$_2$SOCH$_2$CF$_3$ | |
| 12-77 | SCH$_2$CH$_3$ | CH$_2$SO$_2$CH$_3$ | |
| 12-78 | SCH$_2$CH$_3$ | CH$_2$SO$_2$CH$_2$CH$_3$ | |
| 12-79 | SCH$_2$CH$_3$ | 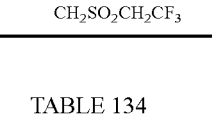 | |
| 12-80 | SCH$_2$CH$_3$ | CH$_2$SO$_2$CH$_2$CF$_3$ | |

TABLE 134

| compound number | R4 | R1 | physical property (melting point-ND) |
|---|---|---|---|
| 12-81 | SCH$_2$CH$_3$ | CH$_2$O(CH$_2$)$_2$OCH$_3$ | |
| 12-82 | SCH$_2$CH$_3$ | CH$_2$O(CH$_2$)$_2$OCH$_2$CH$_3$ | |
| 12-83 | SCH$_2$CH$_3$ | CH$_2$O(CH$_2$)$_2$OCH$_2$CF$_3$ | |
| 12-84 | SCH$_2$CH$_3$ | CH$_2$O(CH$_2$)$_2$SCH$_3$ | |
| 12-85 | SCH$_2$CH$_3$ | CH$_2$O(CH$_2$)$_2$SCH$_2$CH$_3$ | |
| 12-86 | SCH$_2$CH$_3$ | CH$_2$O(CH$_2$)$_2$SOCH$_3$ | |
| 12-87 | SCH$_2$CH$_3$ | CH$_2$O(CH$_2$)$_2$SOCH$_2$CF$_3$ | |
| 12-88 | SCH$_2$CH$_3$ | CH$_2$O(CH$_2$)$_2$SO$_2$CH$_3$ | |
| 12-89 | SCH$_2$CH$_3$ | CH$_2$O(CH$_2$)$_2$SO$_2$CH$_2$CF$_3$ | |

TABLE 134-continued

| compound number | R4 | R1 | physical property (melting point-ND) |
|---|---|---|---|
| 12-90 | SCH₂CH₃ | CH₃-O-CH₂-(tetrahydrofuran-2-yl) | |
| 12-91 | SCH₂CH₃ | CH₃-O-(tetrahydrofuran-3-yl) | |
| 12-92 | SCH₂CH₃ | CH₂O(CH₂)₂NHSO₂CH₃ | |
| 12-93 | SCH₂CH₃ | CH₂O(CH₂)₂N(CH₃)(SO₂CH₃) | |
| 12-94 | S(CH₂)₂CH₃ | CH₃ | |
| 12-95 | S(CH₂)₂CH₃ | CF₃ | |
| 12-96 | S(CH₂)₂CH₃ | CH₂OCH₃ | |
| 12-97 | S(CH₂)₂CH₃ | CH₂OCH₂CH₃ | |
| 12-98 | S(CH₂)₂CH₃ | CH₃-O-CH₂-cyclopropyl | |
| 12-99 | S(CH₂)₂CH₃ | CH₂OCH₂CF₃ | |
| 12-100 | S(CH₂)₂CH₃ | CH₂SCH₃ | |
| 12-101 | S(CH₂)₂CH₃ | CH₂SCH₂CH₃ | |
| 12-102 | S(CH₂)₂CH₃ | CH₃-S-CH₂-cyclopropyl | |
| 12-103 | S(CH₂)₂CH₃ | CH₂SCH₂CF₃ | |
| 12-104 | S(CH₂)₂CH₃ | CH₂SOCH₃ | |
| 12-105 | S(CH₂)₂CH₃ | CH₂SOCH₂CH₃ | |
| 12-106 | S(CH₂)₂CH₃ | CH₃-S(O)-CH₂-cyclopropyl | |
| 12-107 | S(CH₂)₂CH₃ | CH₂SOCH₂CF₃ | |
| 12-108 | S(CH₂)₂CH₃ | CH₂SO₂CH₃ | |
| 12-109 | S(CH₂)₂CH₃ | CH₂SO₂CH₂CH₃ | |
| 12-110 | S(CH₂)₂CH₃ | CH₃-S(O)₂-CH₂-cyclopropyl | |
| 12-111 | S(CH₂)₂CH₃ | CH₂SO₂CH₂CF₃ | |
| 12-112 | S(CH₂)₂CH₃ | CH₂O(CH₂)₂OCH₃ | |
| 12-113 | S(CH₂)₂CH₃ | CH₂O(CH₂)₂OCH₂CH₃ | |
| 12-114 | S(CH₂)₂CH₃ | CH₂O(CH₂)₂OCH₂CF₃ | |
| 12-115 | S(CH₂)₂CH₃ | CH₂O(CH₂)₂SCH₃ | |
| 12-116 | S(CH₂)₂CH₃ | CH₂O(CH₂)₂SCH₂CF₃ | |
| 12-117 | S(CH₂)₂CH₃ | CH₂O(CH₂)₂SOCH₃ | |
| 12-118 | S(CH₂)₂CH₃ | CH₂O(CH₂)₂SOCH₂CF₃ | |
| 12-119 | S(CH₂)₂CH₃ | CH₂O(CH₂)₂SO₂CH₃ | |
| 12-120 | S(CH₂)₂CH₃ | CH₂O(CH₂)₂SO₂CH₂CF₃ | |

TABLE 135

| compound number | R4 | R1 | physical property (melting point-ND) |
|---|---|---|---|
| 12-121 | S(CH₂)₂CH₃ | CH₃-O-CH₂-(tetrahydrofuran-2-yl) | |
| 12-122 | S(CH₂)₂CH₃ | CH₃-O-(tetrahydrofuran-3-yl) | |
| 12-123 | S(CH₂)₂CH₃ | CH₂O(CH₂)₂NHSO₂CH₃ | |
| 12-124 | S(CH₂)₂CH₃ | CH₂O(CH₂)₂N(CH₃)(SO₂CH₃) | |
| 12-125 | SC₆H₅ | CH₃ | |
| 12-126 | SC₆H₅ | CF₃ | |
| 12-127 | SC₆H₅ | CH₂OCH₃ | |
| 12-128 | SC₆H₅ | CH₂OCH₂CH₃ | |
| 12-129 | SC₆H₅ | CH₃-O-CH₂-cyclopropyl | |
| 12-130 | SC₆H₅ | CH₂OCH₂CF₃ | |
| 12-131 | SC₆H₅ | CH₂SCH₃ | |
| 12-132 | SC₆H₅ | CH₂SCH₂CH₃ | |
| 12-133 | SC₆H₅ | CH₃-S-CH₂-cyclopropyl | |
| 12-134 | SC₆H₅ | CH₂SCH₂CF₃ | |
| 12-135 | SC₆H₅ | CH₂SOCH₃ | |
| 12-136 | SC₆H₅ | CH₂SOCH₂CH₃ | |
| 12-137 | SC₆H₅ | CH₃-S(O)-CH₂-cyclopropyl | |
| 12-138 | SC₆H₅ | CH₂SOCH₂CF₃ | |
| 12-139 | SC₆H₅ | CH₂SO₂CH₃ | |
| 12-140 | SC₆H₅ | CH₂SO₂CH₂CH₃ | |
| 12-141 | SC₆H₅ | CH₃-S(O)₂-CH₂-cyclopropyl | |
| 12-142 | SC₆H₅ | CH₂SO₂CH₂CF₃ | |
| 12-143 | SC₆H₅ | CH₂O(CH₂)₂OCH₃ | |
| 12-144 | SC₆H₅ | CH₂O(CH₂)₂OCH₂CH₃ | |
| 12-145 | SC₆H₅ | CH₂O(CH₂)₂OCH₂CF₃ | |
| 12-146 | SC₆H₅ | CH₂O(CH₂)₂SCH₃ | |
| 12-147 | SC₆H₅ | CH₂O(CH₂)₂SCH₂CF₃ | |
| 12-148 | SC₆H₅ | CH₂O(CH₂)₂SOCH₃ | |
| 12-149 | SC₆H₅ | CH₂O(CH₂)₂SOCH₂CF₃ | |
| 12-150 | SC₆H₅ | CH₂O(CH₂)₂SO₂CH₃ | |
| 12-151 | SC₆H₅ | CH₂O(CH₂)₂SO₂CH₂CF₃ | |
| 12-152 | SC₆H₅ | CH₃-O-CH₂-(tetrahydrofuran-2-yl) | |
| 12-153 | SC₆H₅ | CH₃-O-(tetrahydrofuran-3-yl) | |

TABLE 135-continued

| compound number | R4 | R1 | physical property (melting point-ND) |
|---|---|---|---|
| 12-154 | SC$_6$H$_5$ | CH$_2$O(CH$_2$)$_2$NHSO$_2$CH$_3$ | |
| 12-155 | SC$_6$H$_5$ | CH$_2$O(CH$_2$)$_2$N(CH$_3$)(SO$_2$CH$_3$) | |
| 12-156 | SCH$_2$C$_6$H$_5$ | CH$_3$ | |
| 12-157 | SCH$_2$C$_6$H$_5$ | CF$_3$ | |
| 12-158 | SCH$_2$C$_6$H$_5$ | CH$_2$OCH$_3$ | |
| 12-159 | SCH$_2$C$_6$H$_5$ | CH$_2$OCH$_2$CH$_3$ | |
| 12-160 | SCH$_2$C$_6$H$_5$ | CH$_3$–O–CH$_2$–cyclopropyl | |

TABLE 136

| compound number | R4 | R1 | physical property (melting point-ND) |
|---|---|---|---|
| 12-161 | SCH$_2$C$_6$H$_5$ | CH$_2$OCH$_2$CF$_3$ | |
| 12-162 | SCH$_2$C$_6$H$_5$ | CH$_2$SCH$_3$ | |
| 12-163 | SCH$_2$C$_6$H$_5$ | CH$_2$SCH$_2$CH$_3$ | |
| 12-164 | SCH$_2$C$_6$H$_5$ | CH$_3$–S–CH$_2$–cyclopropyl | |
| 12-165 | SCH$_2$C$_6$H$_5$ | CH$_2$SCH$_2$CF$_3$ | |
| 12-166 | SCH$_2$C$_6$H$_5$ | CH$_2$SOCH$_3$ | |
| 12-167 | SCH$_2$C$_6$H$_5$ | CH$_2$SOCH$_2$CH$_3$ | |
| 12-168 | SCH$_2$C$_6$H$_5$ | CH$_3$–S(O)–CH$_2$–cyclopropyl | |
| 12-169 | SCH$_2$C$_6$H$_5$ | CH$_2$SOCH$_2$CF$_3$ | |
| 12-170 | SCH$_2$C$_6$H$_5$ | CH$_2$SO$_2$CH$_3$ | |
| 12-171 | SCH$_2$C$_6$H$_5$ | CH$_2$SO$_2$CH$_2$CH$_3$ | |
| 12-172 | SCH$_2$C$_6$H$_5$ | CH$_3$–SO$_2$–CH$_2$–cyclopropyl | |
| 12-173 | SCH$_2$C$_6$H$_5$ | CH$_2$SO$_2$CH$_2$CF$_3$ | |
| 12-174 | SCH$_2$C$_6$H$_5$ | CH$_2$O(CH$_2$)$_2$OCH$_3$ | |
| 12-175 | SCH$_2$C$_6$H$_5$ | CH$_2$O(CH$_2$)$_2$OCH$_2$CH$_3$ | |
| 12-176 | SCH$_2$C$_6$H$_5$ | CH$_2$O(CH$_2$)$_2$OCH$_2$CF$_3$ | |
| 12-177 | SCH$_2$C$_6$H$_5$ | CH$_2$O(CH$_2$)$_2$SCH$_3$ | |
| 12-178 | SCH$_2$C$_6$H$_5$ | CH$_2$O(CH$_2$)$_2$SCH$_2$CF$_3$ | |
| 12-179 | SCH$_2$C$_6$H$_5$ | CH$_2$O(CH$_2$)$_2$SOCH$_3$ | |
| 12-180 | SCH$_2$C$_6$H$_5$ | CH$_2$O(CH$_2$)$_2$SOCH$_2$CF$_3$ | |
| 12-181 | SCH$_2$C$_6$H$_5$ | CH$_2$O(CH$_2$)$_2$SO$_2$CH$_3$ | |
| 12-182 | SCH$_2$C$_6$H$_5$ | CH$_2$O(CH$_2$)$_2$SO$_2$CH$_2$CF$_3$ | |
| 12-183 | SCH$_2$C$_6$H$_5$ | CH$_3$–O–CH$_2$–(tetrahydrofuran-2-yl) | |
| 12-184 | SCH$_2$C$_6$H$_5$ | CH$_3$–O–(tetrahydrofuran-3-yl) | |
| 12-185 | SCH$_2$C$_6$H$_5$ | CH$_2$O(CH$_2$)$_2$NHSO$_2$CH$_3$ | |

TABLE 136-continued

| compound number | R4 | R1 | physical property (melting point-ND) |
|---|---|---|---|
| 12-186 | SCH$_2$C$_6$H$_5$ | CH$_2$O(CH$_2$)$_2$N(CH$_3$)(SO$_2$CH$_3$) | |
| 12-187 | 1H-pyrazole-1-yl | CH$_3$ | |
| 12-188 | 1H-pyrazole-1-yl | CF$_3$ | |
| 12-189 | 1H-pyrazole-1-yl | CH$_2$OCH$_3$ | |
| 12-190 | 1H-pyrazole-1-yl | CH$_2$OCH$_2$CH$_3$ | |
| 12-191 | 1H-pyrazole-1-yl | CH$_3$–O–CH$_2$–cyclopropyl | |
| 12-192 | 1H-pyrazole-1-yl | CH$_2$OCH$_2$CF$_3$ | |
| 12-193 | 1H-pyrazole-1-yl | CH$_2$SCH$_3$ | |
| 12-194 | 1H-pyrazole-1-yl | CH$_2$SCH$_2$CH$_3$ | |
| 12-195 | 1H-pyrazole-1-yl | CH$_3$–S–CH$_2$–cyclopropyl | |
| 12-196 | 1H-pyrazole-1-yl | CH$_2$SCH$_2$CF$_3$ | |
| 12-197 | 1H-pyrazole-1-yl | CH$_2$SOCH$_3$ | |
| 12-198 | 1H-pyrazole-1-yl | CH$_2$SOCH$_2$CH$_3$ | |
| 12-199 | 1H-pyrazole-1-yl | CH$_3$–S(O)–CH$_2$–cyclopropyl | |
| 12-200 | 1H-pyrazole-1-yl | CH$_2$SOCH$_2$CF$_3$ | |

TABLE 137

| compound number | R4 | R1 | physical property (melting point-ND) |
|---|---|---|---|
| 12-201 | 1H-pyrazole-1-yl | CH$_2$SO$_2$CH$_3$ | |
| 12-202 | 1H-pyrazole-1-yl | CH$_2$SO$_2$CH$_2$CH$_3$ | |
| 12-203 | 1H-pyrazole-1-yl | CH$_3$–SO$_2$–CH$_2$–cyclopropyl | |
| 12-204 | 1H-pyrazole-1-yl | CH$_2$SO$_2$CH$_2$CF$_3$ | |
| 12-205 | 1H-pyrazole-1-yl | CH$_2$O(CH$_2$)$_2$OCH$_3$ | |
| 12-206 | 1H-pyrazole-1-yl | CH$_2$O(CH$_2$)$_2$OCH$_2$CH$_3$ | |
| 12-207 | 1H-pyrazole-1-yl | CH$_2$O(CH$_2$)$_2$OCH$_2$CF$_3$ | |
| 12-208 | 1H-pyrazole-1-yl | CH$_2$O(CH$_2$)$_2$SCH$_3$ | |
| 12-209 | 1H-pyrazole-1-yl | CH$_2$O(CH$_2$)$_2$SCH$_2$CF$_3$ | |
| 12-210 | 1H-pyrazole-1-yl | CH$_2$O(CH$_2$)$_2$SOCH$_3$ | |
| 12-211 | 1H-pyrazole-1-yl | CH$_2$O(CH$_2$)$_2$SOCH$_2$CF$_3$ | |
| 12-212 | 1H-pyrazole-1-yl | CH$_2$O(CH$_2$)$_2$SO$_2$CH$_3$ | |
| 12-213 | 1H-pyrazole-1-yl | CH$_2$O(CH$_2$)$_2$SO$_2$CH$_2$CF$_3$ | |
| 12-214 | 1H-pyrazole-1-yl | CH$_3$–O–CH$_2$–(tetrahydrofuran-2-yl) | |
| 12-215 | 1H-pyrazole-1-yl | CH$_3$–O–(tetrahydrofuran-3-yl) | |
| 12-216 | 1H-pyrazole-1-yl | CH$_2$O(CH$_2$)$_2$NHSO$_2$CH$_3$ | |
| 12-217 | 1H-pyrazole-1-yl | CH$_2$O(CH$_2$)$_2$N(CH$_3$)(SO$_2$CH$_3$) | |

TABLE 137-continued

| compound number | R4 | R1 | physical property (melting point-ND) |
|---|---|---|---|
| 12-218 | 1H-imidazole-1-yl | CH$_3$ | |
| 12-219 | 1H-imidazole-1-yl | CF$_3$ | |
| 12-220 | 1H-imidazole-1-yl | CH$_2$OCH$_3$ | |
| 12-221 | 1H-imidazole-1-yl | CH$_2$OCH$_2$CH$_3$ | |
| 12-222 | 1H-imidazole-1-yl | CH$_3$-O-CH$_2$-cyclopropyl | |
| 12-223 | 1H-imidazole-1-yl | CH$_2$OCH$_2$CF$_3$ | |
| 12-224 | 1H-imidazole-1-yl | CH$_2$SCH$_3$ | |
| 12-225 | 1H-imidazole-1-yl | CH$_2$SCH$_2$CH$_3$ | |
| 12-226 | 1H-imidazole-1-yl | CH$_3$-S-CH$_2$-cyclopropyl | |
| 12-227 | 1H-imidazole-1-yl | CH$_2$SCH$_2$CF$_3$ | |
| 12-228 | 1H-imidazole-1-yl | CH$_2$SOCH$_3$ | |
| 12-229 | 1H-imidazole-1-yl | CH$_2$SOCH$_2$CH$_3$ | |
| 12-230 | 1H-imidazole-1-yl | CH$_3$-S(O)-CH$_2$-cyclopropyl | |
| 12-231 | 1H-imidazole-1-yl | CH$_2$SOCH$_2$CF$_3$ | |
| 12-232 | 1H-imidazole-1-yl | CH$_2$SO$_2$CH$_3$ | |
| 12-233 | 1H-imidazole-1-yl | CH$_2$SO$_2$CH$_2$CH$_3$ | |
| 12-234 | 1H-imidazole-1-yl | CH$_3$-S(O)$_2$-CH$_2$-cyclopropyl | |
| 12-235 | 1H-imidazole-1-yl | CH$_2$SO$_2$CH$_2$CF$_3$ | |
| 12-236 | 1H-imidazole-1-yl | CH$_2$O(CH$_2$)$_2$OCH$_3$ | |
| 12-237 | 1H-imidazole-1-yl | CH$_2$O(CH$_2$)$_2$OCH$_2$CH$_3$ | |
| 12-238 | 1H-imidazole-1-yl | CH$_2$O(CH$_2$)$_2$OCH$_2$CF$_3$ | |
| 12-239 | 1H-imidazole-1-yl | CH$_2$O(CH$_2$)$_2$SCH$_3$ | |
| 12-240 | 1H-imidazole-1-yl | CH$_2$O(CH$_2$)$_2$SCH$_2$CF$_3$ | |

TABLE 138

| compound number | R4 | R1 | physical property (melting point-ND) |
|---|---|---|---|
| 12-241 | 1H-imidazole-1-yl | CH$_2$O(CH$_2$)$_2$SOCH$_3$ | |
| 12-242 | 1H-imidazole-1-yl | CH$_2$O(CH$_2$)$_2$SOCH$_2$CF$_3$ | |
| 12-243 | 1H-imidazole-1-yl | CH$_2$O(CH$_2$)$_2$SO$_2$CH$_3$ | |
| 12-244 | 1H-imidazole-1-yl | CH$_2$O(CH$_2$)$_2$SO$_2$CH$_2$CF$_3$ | |
| 12-245 | 1H-imidazole-1-yl | CH$_3$-O-CH$_2$-tetrahydrofuran-2-yl | |
| 12-246 | 1H-imidazole-1-yl | CH$_3$-O-tetrahydrofuran-3-yl | |
| 12-247 | 1H-imidazole-1-yl | CH$_2$O(CH$_2$)$_2$NHSO$_2$CH$_3$ | |
| 12-248 | 1H-imidazole-1-yl | CH$_2$O(CH$_2$)$_2$N(CH$_3$)(SO$_2$CH$_3$) | |

TABLE 138-continued

| compound number | R4 | R1 | physical property (melting point-ND) |
|---|---|---|---|
| 12-249 | 1H-triazole-1-yl | CH$_3$ | |
| 12-250 | 1H-triazole-1-yl | CF$_3$ | |
| 12-251 | 1H-triazole-1-yl | CH$_2$OCH$_3$ | |
| 12-252 | 1H-triazole-1-yl | CH$_2$OCH$_2$CH$_3$ | |
| 12-253 | 1H-triazole-1-yl | CH$_3$-O-CH$_2$-cyclopropyl | |
| 12-254 | 1H-triazole-1-yl | CH$_2$OCH$_2$CF$_3$ | |
| 12-255 | 1H-triazole-1-yl | CH$_2$SCH$_3$ | |
| 12-256 | 1H-triazole-1-yl | CH$_2$SCH$_2$CH$_3$ | |
| 12-257 | 1H-triazole-1-yl | CH$_3$-S-CH$_2$-cyclopropyl | |
| 12-258 | 1H-triazole-1-yl | CH$_2$SCH$_2$CF$_3$ | |
| 12-259 | 1H-triazole-1-yl | CH$_2$SOCH$_3$ | |
| 12-260 | 1H-triazole-1-yl | CH$_2$SOCH$_2$CH$_3$ | |
| 12-261 | 1H-triazole-1-yl | CH$_3$-S(O)-CH$_2$-cyclopropyl | |
| 12-262 | 1H-triazole-1-yl | CH$_2$SOCH$_2$CF$_3$ | |
| 12-263 | 1H-triazole-1-yl | CH$_2$SO$_2$CH$_3$ | |
| 12-264 | 1H-triazole-1-yl | CH$_2$SO$_2$CH$_2$CH$_3$ | |
| 12-265 | 1H-triazole-1-yl | CH$_3$-S(O)$_2$-CH$_2$-cyclopropyl | |
| 12-266 | 1H-triazole-1-yl | CH$_2$SO$_2$CH$_2$CF$_3$ | |
| 12-267 | 1H-triazole-1-yl | CH$_2$O(CH$_2$)$_2$OCH$_3$ | |
| 12-268 | 1H-triazole-1-yl | CH$_2$O(CH$_2$)$_2$OCH$_2$CH$_3$ | |
| 12-269 | 1H-triazole-1-yl | CH$_2$O(CH$_2$)$_2$OCH$_2$CF$_3$ | |
| 12-270 | 1H-triazole-1-yl | CH$_2$O(CH$_2$)$_2$SCH$_3$ | |
| 12-271 | 1H-triazole-1-yl | CH$_2$O(CH$_2$)$_2$SCH$_2$CF$_3$ | |
| 12-272 | 1H-triazole-1-yl | CH$_2$O(CH$_2$)$_2$SOCH$_3$ | |
| 12-273 | 1H-triazole-1-yl | CH$_2$O(CH$_2$)$_2$SOCH$_2$CF$_3$ | |
| 12-274 | 1H-triazole-1-yl | CH$_2$O(CH$_2$)$_2$SO$_2$CH$_3$ | |
| 12-275 | 1H-triazole-1-yl | CH$_2$O(CH$_2$)$_2$SO$_2$CH$_2$CF$_3$ | |
| 12-276 | 1H-triazole-1-yl | CH$_3$-O-CH$_2$-tetrahydrofuran-2-yl | |
| 12-277 | 1H-triazole-1-yl | CH$_3$-O-tetrahydrofuran-3-yl | |
| 12-278 | 1H-triazole-1-yl | CH$_2$O(CH$_2$)$_2$NHSO$_2$CH$_3$ | |
| 12-279 | 1H-triazole-1-yl | CH$_2$O(CH$_2$)$_2$N(CH$_3$)(SO$_2$CH$_3$) | |
| 12-280 | 1H-tetrazole-1-yl | CH$_3$ | |

TABLE 139

| compound number | R4 | R1 | physical property (melting point-ND) |
|---|---|---|---|
| 12-281 | 1H-tetrazole-1-yl | CF$_3$ | |
| 12-282 | 1H-tetrazole-1-yl | CH$_2$OCH$_3$ | |
| 12-283 | 1H-tetrazole-1-yl | CH$_2$OCH$_2$CH$_3$ | |
| 12-284 | 1H-tetrazole-1-yl | CH$_3$-O-CH$_2$-cyclopropyl | |
| 12-285 | 1H-tetrazole-1-yl | CH$_2$OCH$_2$CF$_3$ | |
| 12-286 | 1H-tetrazole-1-yl | CH$_2$SCH$_3$ | |
| 12-287 | 1H-tetrazole-1-yl | CH$_2$SCH$_2$CH$_3$ | |
| 12-288 | 1H-tetrazole-1-yl | CH$_3$-S-CH$_2$-cyclopropyl | |
| 12-289 | 1H-tetrazole-1-yl | CH$_2$SCH$_2$CF$_3$ | |
| 12-290 | 1H-tetrazole-1-yl | CH$_2$SOCH$_3$ | |
| 12-291 | 1H-tetrazole-1-yl | CH$_2$SOCH$_2$CH$_3$ | |
| 12-292 | 1H-tetrazole-1-yl | CH$_3$-S(O)-CH$_2$-cyclopropyl | |
| 12-293 | 1H-tetrazole-1-yl | CH$_2$SOCH$_2$CF$_3$ | |
| 12-294 | 1H-tetrazole-1-yl | CH$_2$SO$_2$CH$_3$ | |
| 12-295 | 1H-tetrazole-1-yl | CH$_2$SO$_2$CH$_2$CH$_3$ | |
| 12-296 | 1H-tetrazole-1-yl | CH$_3$-S(O)$_2$-CH$_2$-cyclopropyl | |
| 12-297 | 1H-tetrazole-1-yl | CH$_2$SO$_2$CH$_2$CF$_3$ | |
| 12-298 | 1H-tetrazole-1-yl | CH$_2$O(CH$_2$)$_2$OCH$_3$ | |
| 12-299 | 1H-tetrazole-1-yl | CH$_2$O(CH$_2$)$_2$OCH$_2$CH$_3$ | |
| 12-300 | 1H-tetrazole-1-yl | CH$_2$O(CH$_2$)$_2$OCH$_2$CF$_3$ | |
| 12-301 | 1H-tetrazole-1-yl | CH$_2$O(CH$_2$)$_2$SCH$_3$ | |
| 12-302 | 1H-tetrazole-1-yl | CH$_2$O(CH$_2$)$_2$SCH$_2$CF$_3$ | |
| 12-303 | 1H-tetrazole-1-yl | CH$_2$O(CH$_2$)$_2$SOCH$_3$ | |
| 12-304 | 1H-tetrazole-1-yl | CH$_2$O(CH$_2$)$_2$SOCH$_2$CF$_3$ | |
| 12-305 | 1H-tetrazole-1-yl | CH$_2$O(CH$_2$)$_2$SO$_2$CH$_3$ | |
| 12-306 | 1H-tetrazole-1-yl | CH$_2$O(CH$_2$)$_2$SO$_2$CH$_2$CF$_3$ | |
| 12-307 | 1H-tetrazole-1-yl | CH$_3$-O-CH$_2$-(tetrahydrofuran-2-yl) | |
| 12-308 | 1H-tetrazole-1-yl | CH$_3$-O-(tetrahydrofuran-3-yl) | |
| 12-309 | 1H-tetrazole-1-yl | CH$_2$O(CH$_2$)$_2$NHSO$_2$CH$_3$ | |
| 12-310 | 1H-tetrazole-1-yl | CH$_2$O(CH$_2$)$_2$N(CH$_3$)(SO$_2$CH$_3$) | |
| 12-311 | 1H-tetrazole-2-yl | CH$_3$ | |
| 12-312 | 1H-tetrazole-2-yl | CF$_3$ | |
| 12-313 | 1H-tetrazole-2-yl | CH$_2$OCH$_3$ | |
| 12-314 | 1H-tetrazole-2-yl | CH$_2$OCH$_2$CH$_3$ | |
| 12-315 | 1H-tetrazole-2-yl | CH$_3$-O-CH$_2$-cyclopropyl | |
| 12-316 | 1H-tetrazole-2-yl | CH$_2$OCH$_2$CF$_3$ | |
| 12-317 | 1H-tetrazole-2-yl | CH$_2$SCH$_3$ | |
| 12-318 | 1H-tetrazole-2-yl | CH$_2$SCH$_2$CH$_3$ | |
| 12-319 | 1H-tetrazole-2-yl | CH$_3$-S-CH$_2$-cyclopropyl | |
| 12-320 | 1H-tetrazole-2-yl | CH$_2$SCH$_2$CF$_3$ | |

TABLE 140

| compound number | R4 | R1 | physical property (melting point-ND) |
|---|---|---|---|
| 12-321 | 1H-tetrazole-2-yl | CH$_2$SOCH$_3$ | |
| 12-322 | 1H-tetrazole-2-yl | CH$_2$SOCH$_2$CH$_3$ | |
| 12-323 | 1H-tetrazole-2-yl | CH$_3$-S(O)-CH$_2$-cyclopropyl | |
| 12-324 | 1H-tetrazole-2-yl | CH$_2$SOCH$_2$CF$_3$ | |
| 12-325 | 1H-tetrazole-2-yl | CH$_2$SO$_2$CH$_3$ | |
| 12-326 | 1H-tetrazole-2-yl | CH$_3$SO$_2$CH$_2$CH$_3$ | |
| 11-327 | 1H-tetrazole-2-yl | CH$_3$-S(O)$_2$-CH$_2$-cyclopropyl | |
| 12-328 | 1H-tetrazole-2-yl | CH$_2$SO$_2$CH$_2$CH$_3$ | |
| 12-329 | 1H-tetrazole-2-yl | CH$_2$O(CH$_2$)$_2$OCH$_3$ | |
| 12-330 | 1H-tetrazole-2-yl | CH$_2$O(CH$_2$)$_2$OCH$_2$CH$_3$ | |
| 12-331 | 1H-tetrazole-2-yl | CH$_2$O(CH$_2$)$_2$OCH$_2$CF$_3$ | |
| 12-332 | 1H-tetrazole-2-yl | CH$_2$O(CH$_2$)$_2$SCH$_3$ | |
| 12-333 | 1H-tetrazole-2-yl | CH$_2$O(CH$_2$)$_2$SCH$_2$CF$_3$ | |
| 12-334 | 1H-tetrazole-2-yl | CH$_2$O(CH$_2$)$_2$SOCH$_3$ | |
| 12-335 | 1H-tetrazole-2-yl | CH$_2$O(CH$_2$)$_2$SOCH$_2$CF$_3$ | |
| 12-336 | 1H-tetrazole-2-yl | CH$_2$O(CH$_2$)$_2$SO$_2$CH$_3$ | |
| 12-337 | 1H-tetrazole-2-yl | CH$_2$O(CH$_2$)$_2$SO$_2$CH$_2$CF$_3$ | |
| 12-338 | 1H-tetrazole-2-yl | CH$_3$-O-CH$_2$-(tetrahydrofuran-2-yl) | |
| 11-339 | 1H-tetrazole-2-yl | CH$_3$-O-(tetrahydrofuran-3-yl) | |
| 12-340 | 1H-tetrazole-2-yl | CH$_2$O(CH$_2$)$_2$NHSO$_2$CH$_3$ | |
| 12-341 | 1H-tetrazole-2-yl | CH$_2$O(CH$_2$)$_2$N(CH$_3$)(SO$_2$CH$_3$) | |

TABLE 141

| compound number | R4 | R1 | physical property (melting point-ND) |
|---|---|---|---|
| 13-1 | Cl | CH₃ | |
| 13-2 | Cl | CF₃ | |
| 13-3 | Cl | CH₂OCH₃ | |
| 13-4 | Cl | CH₂OCH₂CH₃ | |
| 13-5 | Cl | CH₃-O-CH₂-cyclopropyl | |
| 13-6 | Cl | CH₂OCH₂CF₃ | |
| 13-7 | Cl | CH₂SCH₃ | |
| 13-8 | Cl | CH₂SCH₂CH₃ | |
| 13-9 | Cl | | |
| 13-10 | Cl | CH₂SCH₂CF₃ | |
| 13-11 | Cl | CH₂SOCH₃ | |
| 13-12 | Cl | CH₂SOCH₂CH₃ | |
| 13-13 | Cl | CH₃-S(O)-CH₂-cyclopropyl | |
| 13-14 | Cl | CH₂SOCH₂CF₃ | |
| 13-15 | Cl | CH₂SO₂CH₃ | |
| 13-16 | Cl | CH₂SO₂CH₂CH₃ | |
| 13-17 | Cl | CH₃-SO₂-CH₂-cyclopropyl | |
| 13-18 | Cl | CH₂SO₂CH₂CF₃ | |
| 13-19 | Cl | CH₂O(CH₂)₂OCH₃ | |
| 13-20 | Cl | CH₂O(CH₂)₂OCH₂CH₃ | |
| 13-21 | Cl | CH₂O(CH₂)₂OCH₂CF₃ | |
| 13-22 | Cl | CH₂O(CH₂)₂SCH₃ | |
| 13-23 | Cl | CH₂O(CH₂)₂SCH₂CF₃ | |
| 13-24 | Cl | CH₂O(CH₂)₂SOCH₃ | |
| 13-25 | Cl | CH₂O(CH₂)₂SOCH₂CF₃ | |
| 13-26 | Cl | CH₂O(CH₂)₂SO₂CH₃ | |
| 13-27 | Cl | CH₂O(CH₂)₂SO₂CH₂CF₃ | |
| 13-28 | Cl | CH₃-O-CH₂-(tetrahydrofuran-2-yl) | |
| 13-29 | Cl | CH₃-O-(tetrahydrofuran-3-yl) | |
| 13-30 | Cl | CH₂O(CH₂)₂NHSO₂CH₃ | |
| 13-31 | Cl | CH₂O(CH₂)₂N(CH₃)(SO₂CH₃) | |
| 13-32 | SCH₃ | CH₃ | |
| 13-33 | SCH₃ | CF₃ | |
| 13-34 | SCH₃ | CH₂OCH₃ | |
| 13-35 | SCH₃ | CH₂OCH₂CH₃ | |
| 13-36 | SCH₃ | CH₃-O-CH₂-cyclopropyl | |
| 13-37 | SCH₃ | CH₂OCH₂CF₃ | |
| 13-38 | SCH₃ | CH₂SCH₃ | |
| 13-39 | SCH₃ | CH₂SCH₂CH₃ | |
| 13-40 | SCH₃ | CH₃-S-CH₂-cyclopropyl | |

TABLE 142

| compound number | R4 | R1 | physical property (melting point-ND) |
|---|---|---|---|
| 13-41 | SCH₃ | CH₂SCH₂CF₃ | |
| 13-42 | SCH₃ | CH₂SOCH₃ | |
| 13-43 | SCH₃ | CH₂SOCH₂CH₃ | |
| 13-44 | SCH₃ | CH₃-S(O)-CH₂-cyclopropyl | |
| 13-45 | SCH₃ | CH₂SOCH₂CF₃ | |
| 13-46 | SCH₃ | CH₂SO₂CH₃ | |
| 13-47 | SCH₃ | CH₂SO₂CH₂CH₃ | |
| 13-48 | SCH₃ | CH₃-SO₂-CH₂-cyclopropyl | |
| 13-49 | SCH₃ | CH₂SO₂CH₂CF₃ | |
| 13-50 | SCH₃ | CH₂O(CH₂)₂OCH₃ | |
| 13-51 | SCH₃ | CH₂O(CH₂)₂OCH₂CH₃ | |
| 13-52 | SCH₃ | CH₂O(CH₂)₂OCH₂CF₃ | |
| 13-53 | SCH₃ | CH₂O(CH₂)₂SCH₃ | |
| 13-54 | SCH₃ | CH₂O(CH₂)₂SCH₂CF₃ | |
| 13-55 | SCH₃ | CH₂O(CH₂)₂SOCH₃ | |
| 13-56 | SCH₃ | CH₂O(CH₂)₂SOCH₂CF₃ | |
| 13-57 | SCH₃ | CH₂O(CH₂)₂SO₂CH₃ | |
| 13-58 | SCH₃ | CH₂O(CH₂)₂SO₂CH₂CF₃ | |
| 13-59 | SCH₃ | CH₃-O-CH₂-(tetrahydrofuran-2-yl) | |

TABLE 142-continued

| compound number | R4 | R1 | physical property (melting point-ND) |
|---|---|---|---|
| 13-60 | SCH$_3$ | 3-methoxytetrahydrofuran (CH$_3$O-tetrahydrofuran-3-yl) | |
| 13-61 | SCH$_3$ | CH$_2$O(CH$_2$)$_2$NHSO$_2$CH$_3$ | |
| 13-62 | SCH$_3$ | CH$_2$O(CH$_2$)$_2$N(CH$_3$)(SO$_2$CH$_3$) | |
| 13-63 | SCH$_2$CH$_3$ | CH$_3$ | |
| 13-64 | SCH$_2$CH$_3$ | CF$_3$ | |
| 13-65 | SCH$_2$CH$_3$ | CH$_2$OCH$_3$ | |
| 13-66 | SCH$_2$CH$_3$ | CH$_2$OCH$_2$CH$_3$ | |
| 13-67 | SCH$_2$CH$_3$ | CH$_3$O-CH$_2$-cyclopropyl | |
| 13-68 | SCH$_2$CH$_3$ | CH$_2$OCH$_2$CF$_3$ | |
| 13-69 | SCH$_2$CH$_3$ | CH$_2$SCH$_3$ | |
| 13-70 | SCH$_2$CH$_3$ | CH$_2$SCH$_2$CH$_3$ | |
| 13-71 | SCH$_2$CH$_3$ | CH$_3$S-CH$_2$-cyclopropyl | |
| 13-72 | SCH$_2$CH$_3$ | CH$_2$SCH$_2$CF$_3$ | |
| 13-73 | SCH$_2$CH$_3$ | CH$_2$SOCH$_3$ | |
| 13-74 | SCH$_2$CH$_3$ | CH$_2$SOCH$_2$CH$_3$ | |
| 13-75 | SCH$_2$CH$_3$ | CH$_3$S(O)-CH$_2$-cyclopropyl | |
| 13-76 | SCH$_2$CH$_3$ | CH$_2$SOCH$_2$CF$_3$ | |
| 13-77 | SCH$_2$CH$_3$ | CH$_2$SO$_2$CH$_3$ | |
| 13-78 | SCH$_2$CH$_3$ | CH$_2$SO$_2$CH$_2$CH$_3$ | |
| 13-79 | SCH$_2$CH$_3$ | CH$_3$S(O)$_2$-CH$_2$-cyclopropyl | |
| 13-80 | SCH$_2$CH$_3$ | CH$_2$SO$_2$CH$_2$CF$_3$ | |

TABLE 143

| compound number | R4 | R1 | physical property (melting point-ND) |
|---|---|---|---|
| 13-81 | SCH$_2$CH$_3$ | CH$_2$O(CH$_2$)$_2$OCH$_3$ | |
| 13-82 | SCH$_2$CH$_3$ | CH$_2$O(CH$_2$)$_2$OCH$_2$CH$_3$ | |
| 13-83 | SCH$_2$CH$_3$ | CH$_2$O(CH$_2$)$_2$OCH$_2$CF$_3$ | |
| 13-84 | SCH$_2$CH$_3$ | CH$_2$O(CH$_2$)$_2$SCH$_3$ | |
| 13-85 | SCH$_2$CH$_3$ | CH$_2$O(CH$_2$)$_2$SCH$_2$CF$_3$ | |
| 13-86 | SCH$_2$CH$_3$ | CH$_2$O(CH$_2$)$_2$SOCH$_3$ | |
| 13-87 | SCH$_2$CH$_3$ | CH$_2$O(CH$_2$)$_2$SOCH$_2$CF$_3$ | |
| 13-88 | SCH$_2$CH$_3$ | CH$_2$O(CH$_2$)$_2$SO$_2$CH$_3$ | |
| 13-89 | SCH$_2$CH$_3$ | CH$_2$O(CH$_2$)$_2$SO$_2$CH$_2$CF$_3$ | |
| 13-90 | SCH$_2$CH$_3$ | CH$_3$O-CH$_2$-tetrahydrofuran-2-yl | |
| 13-91 | SCH$_2$CH$_3$ | 3-methoxytetrahydrofuran (CH$_3$O-tetrahydrofuran-3-yl) | |
| 13-92 | SCH$_2$CH$_3$ | CH$_2$O(CH$_2$)$_2$NHSO$_2$CH$_3$ | |
| 13-93 | SCH$_2$CH$_3$ | CH$_2$O(CH$_2$)$_2$N(CH$_3$)(SO$_2$CH$_3$) | |
| 13-94 | S(CH$_2$)$_2$CH$_3$ | CH$_3$ | |
| 13-95 | S(CH$_2$)$_2$CH$_3$ | CF$_3$ | |
| 13-96 | S(CH$_2$)$_2$CH$_3$ | CH$_2$OCH$_3$ | |
| 13-97 | S(CH$_2$)$_2$CH$_3$ | CH$_2$OCH$_2$CH$_3$ | |
| 13-98 | S(CH$_2$)$_2$CH$_3$ | CH$_3$O-CH$_2$-cyclopropyl | |
| 13-99 | S(CH$_2$)$_2$CH$_3$ | CH$_2$OCH$_2$CF$_3$ | |
| 13-100 | S(CH$_2$)$_2$CH$_3$ | CH$_2$SCH$_3$ | |
| 13-101 | S(CH$_2$)$_2$CH$_3$ | CH$_2$SCH$_2$CH$_3$ | |
| 13-102 | S(CH$_2$)$_2$CH$_3$ | CH$_3$S-CH$_2$-cyclopropyl | |
| 13-103 | S(CH$_2$)$_2$CH$_3$ | CH$_2$SCH$_2$CF$_3$ | |
| 13-104 | S(CH$_2$)$_2$CH$_3$ | CH$_2$SOCH$_3$ | |
| 13-105 | S(CH$_2$)$_2$CH$_3$ | CH$_2$SOCH$_2$CH$_3$ | |
| 13-106 | S(CH$_2$)$_2$CH$_3$ | CH$_3$S(O)-CH$_2$-cyclopropyl | |
| 13-107 | S(CH$_2$)$_2$CH$_3$ | CH$_2$SOCH$_2$CF$_3$ | |
| 13-108 | S(CH$_2$)$_2$CH$_3$ | CH$_2$SO$_2$CH$_3$ | |
| 13-109 | S(CH$_2$)$_2$CH$_3$ | CH$_2$SO$_2$CH$_2$CH$_3$ | |
| 13-110 | S(CH$_2$)$_2$CH$_3$ | CH$_3$S(O)$_2$-CH$_2$-cyclopropyl | |
| 13-111 | S(CH$_2$)$_2$CH$_3$ | CH$_2$SO$_2$CH$_2$CF$_3$ | |
| 13-112 | S(CH$_2$)$_2$CH$_3$ | CH$_2$O(CH$_2$)$_2$OCH$_3$ | |
| 13-113 | S(CH$_2$)$_2$CH$_3$ | CH$_2$O(CH$_2$)$_2$OCH$_2$CH$_3$ | |
| 13-114 | S(CH$_2$)$_2$CH$_3$ | CH$_2$O(CH$_2$)$_2$OCH$_2$CF$_3$ | |
| 13-115 | S(CH$_2$)$_2$CH$_3$ | CH$_2$O(CH$_2$)$_2$SCH$_3$ | |
| 13-116 | S(CH$_2$)$_2$CH$_3$ | CH$_2$O(CH$_2$)$_2$SCH$_2$CF$_3$ | |
| 13-117 | S(CH$_2$)$_2$CH$_3$ | CH$_2$O(CH$_2$)$_2$SOCH$_3$ | |
| 13-118 | S(CH$_2$)$_2$CH$_3$ | CH$_2$O(CH$_2$)$_2$SOCH$_2$CF$_3$ | |
| 13-119 | S(CH$_2$)$_2$CH$_3$ | CH$_2$O(CH$_2$)$_2$SO$_2$CH$_3$ | |
| 13-120 | S(CH$_2$)$_2$CH$_3$ | CH$_2$O(CH$_2$)$_2$SO$_2$CH$_2$CF$_3$ | |

TABLE 144

| compound number | R4 | R1 | physical property (melting point-ND) |
|---|---|---|---|
| 13-121 | S(CH$_2$)$_2$CH$_3$ | CH$_3$O-CH$_2$-tetrahydrofuran-2-yl | |

TABLE 144-continued

| compound number | R4 | R1 | physical property (melting point-ND) |
|---|---|---|---|
| 13-122 | S(CH₂)₂CH₃ | 3-methoxytetrahydrofuran | |
| 13-123 | S(CH₂)₂CH₃ | CH₂O(CH₂)₂NHSO₂CH₃ | |
| 13-124 | S(CH₂)₂CH₃ | CH₂O(CH₂)₂N(CH₃)(SO₂CH₃) | |
| 13-125 | SC₆H₅ | CH₃ | |
| 13-126 | SC₆H₅ | CF₃ | |
| 13-127 | SC₆H₅ | CH₂OCH₃ | |
| 13-128 | SC₆H₅ | CH₂OCH₂CH₃ | |
| 13-129 | SC₆H₅ | CH₃-O-CH₂-cyclopropyl | |
| 13-130 | SC₆H₅ | CH₂OCH₂CF₃ | |
| 13-131 | SC₆H₅ | CH₂SCH₃ | |
| 13-132 | SC₆H₅ | CH₂SCH₂CH₃ | |
| 13-133 | SC₆H₅ | CH₃-S-CH₂-cyclopropyl | |
| 13-134 | SC₆H₅ | CH₂SCH₂CF₃ | |
| 13-135 | SC₆H₅ | CH₂SOCH₃ | |
| 13-136 | SC₆H₅ | CH₂SOCH₂CH₃ | |
| 13-137 | SC₆H₅ | CH₃-S(O)-CH₂-cyclopropyl | |
| 13-138 | SC₆H₅ | CH₂SOCH₂CF₃ | |
| 13-139 | SC₆H₅ | CH₂SO₂CH₃ | |
| 13-140 | SC₆H₅ | CH₂SO₂CH₂CH₃ | |
| 13-141 | SC₆H₅ | CH₃-S(O)₂-CH₂-cyclopropyl | |
| 13-142 | SC₆H₅ | CH₂SO₂CH₂CF₃ | |
| 13-143 | SC₆H₅ | CH₂O(CH₂)₂OCH₃ | |
| 13-144 | SC₆H₅ | CH₂O(CH₂)₂OCH₂CH₃ | |
| 13-145 | SC₆H₅ | CH₂O(CH₂)₂OCH₂CF₃ | |
| 13-146 | SC₆H₅ | CH₂O(CH₂)₂SCH₃ | |
| 13-147 | SC₆H₅ | CH₂O(CH₂)₂SCH₂CF₃ | |
| 13-148 | SC₆H₅ | CH₂O(CH₂)₂SOCH₃ | |
| 13-149 | SC₆H₅ | CH₂O(CH₂)₂SO₂CH₂CF₃ | |
| 13-150 | SC₆H₅ | CH₂O(CH₂)₂SO₂CH₃ | |
| 13-151 | SC₆H₅ | CH₂O(CH₂)₂SO₂CH₂CF₃ | |
| 13-152 | SC₆H₅ | CH₃-O-CH₂-tetrahydrofuran-2-yl | |
| 13-153 | SC₆H₅ | 3-methoxytetrahydrofuran | |
| 13-154 | SC₆H₅ | CH₂O(CH₂)₂NHSO₂CH₃ | |
| 13-155 | SC₆H₅ | CH₂O(CH₂)₂N(CH₃)(SO₂CH₃) | |
| 13-156 | SCH₂C₆H₅ | CH₃ | |
| 13-157 | SCH₂C₆H₅ | CF₃ | |
| 13-158 | SCH₂C₆H₅ | CH₂OCH₃ | |
| 13-159 | SCH₂C₆H₅ | CH₂OCH₂CH₃ | |
| 13-160 | SCH₂C₆H₅ | CH₃-O-CH₂-cyclopropyl | |

TABLE 145

| compound number | R4 | R1 | physical property (melting point-ND) |
|---|---|---|---|
| 13-161 | SCH₂C₆H₅ | CH₂OCH₂CF₃ | |
| 13-162 | SCH₂C₆H₅ | CH₂SCH₃ | |
| 13-163 | SCH₂C₆H₅ | CH₂SCH₂CH₃ | |
| 13-164 | SCH₂C₆H₅ | CH₃-S-CH₂-cyclopropyl | |
| 13-165 | SCH₂C₆H₅ | CH₂SCH₂CF₃ | |
| 13-166 | SCH₂C₆H₅ | CH₂SOCH₃ | |
| 13-167 | SCH₂C₆H₅ | CH₂SOCH₂CH₃ | |
| 13-168 | SCH₂C₆H₅ | CH₃-S(O)-CH₂-cyclopropyl | |
| 13-169 | SCH₂C₆H₅ | CH₂SOCH₂CF₃ | |
| 13-170 | SCH₂C₆H₅ | CH₂SO₂CH₃ | |
| 13-171 | SCH₂C₆H₅ | CH₂SO₂CH₂CH₃ | |
| 13-172 | SCH₂C₆H₅ | CH₃-S(O)₂-CH₂-cyclopropyl | |
| 13-173 | SCH₂C₆H₅ | CH₂SO₂CH₂CF₃ | |
| 13-174 | SCH₂C₆H₅ | CH₂O(CH₂)₂OCH₃ | |
| 13-175 | SCH₂C₆H₅ | CH₂O(CH₂)₂OCH₂CH₃ | |
| 13-176 | SCH₂C₆H₅ | CH₂O(CH₂)₂OCH₂CF₃ | |
| 13-177 | SCH₂C₆H₅ | CH₂O(CH₂)₂SCH₃ | |
| 13-178 | SCH₂C₆H₅ | CH₂O(CH₂)₂SCH₂CF₃ | |
| 13-179 | SCH₂C₆H₅ | CH₂O(CH₂)₂SOCH₃ | |
| 13-180 | SCH₂C₆H₅ | CH₂O(CH₂)₂SO₂CH₂CF₃ | |
| 13-181 | SCH₂C₆H₅ | CH₂O(CH₂)₂SO₂CH₃ | |
| 13-182 | SCH₂C₆H₅ | CH₂O(CH₂)₂SO₂CH₂CF₃ | |
| 13-183 | SCH₂C₆H₅ | CH₃-O-CH₂-tetrahydrofuran-2-yl | |
| 13-184 | SCH₂C₆H₅ | 3-methoxytetrahydrofuran | |
| 13-185 | SCH₂C₆H₅ | CH₂O(CH₂)₂NHSO₂CH₃ | |
| 13-186 | SCH₂C₆H₅ | CH₂O(CH₂)₂N(CH₃)(SO₂CH₃) | |
| 13-187 | 1H-pyrazole-1-yl | CH₃ | |
| 13-188 | 1H-pyrazole-1-yl | CF₃ | |
| 13-189 | 1H-pyrazole-1-yl | CH₂OCH₃ | |
| 13-190 | 1H-pyrazole-1-yl | CH₂OCH₂CH₃ | |

TABLE 145-continued

| compound number | R4 | R1 | physical property (melting point-ND) |
|---|---|---|---|
| 13-191 | 1H-pyrazole-1-yl | 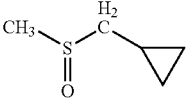 | |
| 13-192 | 1H-pyrazole-1-yl | $CH_2OCH_2CF_3$ | |
| 13-193 | 1H-pyrazole-1-yl | $CH_2SCH_3$ | |
| 13-194 | 1H-pyrazole-1-yl | $CH_2SCH_2CH_3$ | |
| 13-195 | 1H-pyrazole-1-yl | 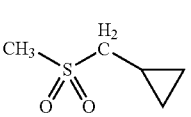 | |
| 13-196 | 1H-pyrazole-1-yl | $CH_2SCH_2CF_3$ | |
| 13-197 | 1H-pyrazole-1-yl | $CH_2SOCH_3$ | |
| 13-198 | 1H-pyrazole-1-yl | $CH_2SOCH_2CH_3$ | |
| 13-199 | 1H-pyrazole-1-yl | 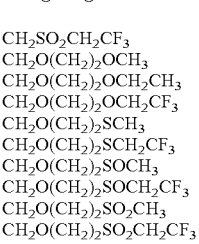 | |
| 13-200 | 1H-pyrazole-1-yl | $CH_2SOCH_2CF_3$ | |

TABLE 161

| compound number | R13 | R1 | physical property (melting point-ND) |
|---|---|---|---|
| 4-441 | $CH_2OCH_3$ | $CH_2SCH_3$ | |
| 4-442 | $CH_2OCH_3$ | $CH_2SCH_2CH_3$ | |
| 4-443 | $CH_2OCH_3$ | (CH₃-S-CH₂-cyclopropyl) | |
| 4-444 | $CH_2OCH_3$ | $CH_2SCH_2CF_3$ | |
| 4-445 | $CH_2OCH_3$ | $CH_2SOCH_3$ | |
| 4-446 | $CH_2OCH_3$ | $CH_2SOCH_2CH_3$ | |
| 4-447 | $CH_2OCH_3$ | (CH₃-S(O)-CH₂-cyclopropyl) | |
| 4-448 | $CH_2OCH_3$ | $CH_2SOCH_2CF_3$ | |
| 4-449 | $CH_2OCH_3$ | $CH_2SO_2CH_3$ | |
| 4-450 | $CH_2OCH_3$ | $CH_2SO_2CH_2CH_3$ | |
| 4-451 | $CH_2OCH_3$ | (CH₃-S(O)₂-CH₂-cyclopropyl) | |
| 4-452 | $CH_2OCH_3$ | $CH_2SO_2CH_2CF_3$ | |
| 4-453 | $CH_2OCH_3$ | $CH_2O(CH_2)_2OCH_3$ | |
| 4-454 | $CH_2OCH_3$ | $CH_2O(CH_2)_2OCH_2CH_3$ | |
| 4-455 | $CH_2OCH_3$ | $CH_2O(CH_2)_2OCH_2CF_3$ | |
| 4-456 | $CH_2OCH_3$ | $CH_2O(CH_2)_2SCH_3$ | |
| 4-457 | $CH_2OCH_3$ | $CH_2O(CH_2)_2SCH_2CF_3$ | |
| 4-458 | $CH_2OCH_3$ | $CH_2O(CH_2)_2SOCH_3$ | |
| 4-459 | $CH_2OCH_3$ | $CH_2O(CH_2)_2SOCH_2CF_3$ | |
| 4-460 | $CH_2OCH_3$ | $CH_2O(CH_2)_2SO_2CH_3$ | |
| 4-461 | $CH_2OCH_3$ | $CH_2O(CH_2)_2SO_2CH_2CF_3$ | |

TABLE 161-continued

| compound number | R13 | R1 | physical property (melting point-ND) |
|---|---|---|---|
| 4-462 | $CH_2OCH_3$ | (CH₃-O-CH₂-tetrahydrofuran-2-yl) | |
| 4-463 | $CH_2OCH_3$ | (CH₃-O-tetrahydrofuran-3-yl) | |
| 4-464 | $CH_2OCH_3$ | $CH_2O(CH_2)_2NHSO_2CH_3$ | |
| 4-465 | $CH_2OCH_3$ | $CH_2O(CH_2)_2N(CH_3)(SO_2CH_3)$ | |
| 4-466 | $CH_2COC_6H_5$ | $CH_3$ | |
| 4-467 | $CH_2COC_6H_5$ | $CF_3$ | |
| 4-468 | $CH_2COC_6H_5$ | $CH_2OCH_3$ | |
| 4-469 | $CH_2COC_6H_5$ | $CH_2OCH_2CH_3$ | |
| 4-470 | $CH_2COC_6H_5$ | (CH₃-O-CH₂-cyclopropyl) | |
| 4-471 | $CH_2COC_6H_5$ | $CH_2OCH_2CF_3$ | |
| 4-472 | $CH_2COC_6H_5$ | $CH_2SCH_3$ | |
| 4-473 | $CH_2COC_6H_5$ | $CH_2SCH_2CH_3$ | |
| 4-474 | $CH_2COC_6H_5$ | (CH₃-S-CH₂-cyclopropyl) | |
| 4-475 | $CH_2COC_6H_5$ | $CH_2SCH_2CF_3$ | |
| 4-476 | $CH_2COC_6H_5$ | $CH_2SOCH_3$ | |
| 4-477 | $CH_2COC_6H_5$ | $CH_2SOCH_2CH_3$ | |
| 4-478 | $CH_2COC_6H_5$ | (H₃C-S(O)-CH₂-cyclopropyl) | |
| 4-479 | $CH_2COC_6H_5$ | $CH_2SOCH_2CF_3$ | |
| 4-480 | $CH_2COC_6H_5$ | $CH_2SO_2CH_3$ | |

TABLE 162

| compound number | R13 | R1 | physical property (melting point-ND) |
|---|---|---|---|
| 14-481 | $CH_2COC_6H_5$ | $CH_2SO_2CH_2CH_3$ | |
| 14-482 | $CH_2COC_6H_5$ | (CH₃-S(O)₂-CH₂-cyclopropyl) | |
| 14-483 | $CH_2COC_6H_5$ | $CH_2SO_2CH_2CF_3$ | |
| 14-484 | $CH_2COC_6H_5$ | $CH_2O(CH_2)_2OCH_3$ | |
| 14-485 | $CH_2COC_6H_5$ | $CH_2O(CH_2)_2OCH_2CH_3$ | |
| 14-486 | $CH_2COC_6H_5$ | $CH_2O(CH_2)_2OCH_2CF_3$ | |
| 14-487 | $CH_2COC_6H_5$ | $CH_2O(CH_2)_2SCH_3$ | |
| 14-488 | $CH_2COC_6H_5$ | $CH_2O(CH_2)_2SCH_2CF_3$ | |
| 14-489 | $CH_2COC_6H_5$ | $CH_2O(CH_2)_2SOCH_3$ | |
| 14-490 | $CH_2COC_6H_5$ | $CH_2O(CH_2)_2SOCH_2CF_3$ | |
| 14-491 | $CH_2COC_6H_5$ | $CH_2O(CH_2)_2SO_2CH_3$ | |
| 14-492 | $CH_2COC_6H_5$ | $CH_2O(CH_2)_2SO_2CH_2CF_3$ | |

TABLE 162-continued

| compound number | R13 | R1 | physical property (melting point-ND) |
|---|---|---|---|
| 14-493 | CH₂COC₆H₅ | (tetrahydrofuran-2-yl-CH₂-O-CH₃) | |
| 14-494 | CH₂COC₆H₅ | (tetrahydrofuran-3-yl-O-CH₃) | |
| 14-495 | CH₂COC₆H₅ | CH₂O(CH₂)₂NHSO₂CH₃ | |
| 14-496 | CH₂COC₆H₅ | CH₂O(CH₂)₂N(CH₃)(SO₂CH₃) | |

TABLE 163

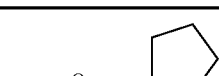

| compound number | R13 | R1 | physical property (melting point-ND) |
|---|---|---|---|
| 15-1 | CH₃ | CH₃ | |
| 15-2 | CH₃ | CF₃ | |
| 15-3 | CH₃ | CH₂OCH₃ | |
| 15-4 | CH₃ | CH₂OCH₂CH₃ | |
| 15-5 | CH₃ | CH₃-O-CH₂-cyclopropyl | |
| 15-6 | CH₃ | CH₂OCH₂CF₃ | |
| 15-7 | CH₃ | CH₂SCH₃ | |
| 15-8 | CH₃ | CH₂SCH₂CH₃ | |
| 15-9 | CH₃ | CH₃-S-CH₂-cyclopropyl | |
| 15-10 | CH₃ | CH₂SCH₂CF₃ | |
| 15-11 | CH₃ | CH₂SOCH₃ | |
| 15-12 | CH₃ | CH₂SOCH₂CH₃ | |
| 15-13 | CH₃ | CH₃-S(O)-CH₂-cyclopropyl | |
| 15-14 | CH₃ | CH₂SOCH₂CF₃ | |
| 15-15 | CH₃ | CH₂SO₂CH₃ | |
| 15-16 | CH₃ | CH₂SO₂CH₂CH₃ | |
| 15-17 | CH₃ | CH₃-S(O)₂-CH₂-cyclopropyl | |
| 15-18 | CH₃ | CH₂SO₂CH₂CF₃ | |

TABLE 163-continued

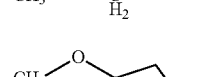

| compound number | R13 | R1 | physical property (melting point-ND) |
|---|---|---|---|
| 15-19 | CH₃ | CH₂O(CH₂)₂OCH₃ | |
| 15-20 | CH₃ | CH₂O(CH₂)₂OCH₂CH₃ | |
| 15-21 | CH₃ | CH₂O(CH₂)₂OCH₂CF₃ | |
| 15-22 | CH₃ | CH₂O(CH₂)₂SCH₃ | |
| 15-23 | CH₃ | CH₂O(CH₂)₂SCH₂CF₃ | |
| 15-24 | CH₃ | CH₂O(CH₂)₂SOCH₃ | |
| 15-25 | CH₃ | CH₂O(CH₂)₂SOCH₂CF₃ | |
| 15-26 | CH₃ | CH₂O(CH₂)₂SO₂CH₃ | |
| 15-27 | CH₃ | CH₂O(CH₂)₂SO₂CH₂CF₃ | |
| 15-28 | CH₃ | (tetrahydrofuran-2-yl-CH₂-O-CH₃) | |
| 15-29 | CH₃ | (tetrahydrofuran-3-yl-O-CH₃) | |
| 15-30 | CH₃ | CH₂O(CH₂)₂NHSO₂CH₃ | |
| 15-31 | CH₃ | CH₂O(CH₂)₂N(CH₃)(SO₂CH₃) | |
| 15-32 | CH₂CH₃ | CH₃ | |
| 15-33 | CH₂CH₃ | CF₃ | |
| 15-34 | CH₂CH₃ | CH₂OCH₃ | |
| 15-35 | CH₂CH₃ | CH₂OCH₂CH₃ | |
| 15-36 | CH₂CH₃ | CH₃-O-CH₂-cyclopropyl | |
| 15-37 | CH₂CH₃ | CH₂OCH₂CF₃ | |
| 15-38 | CH₂CH₃ | CH₂SCH₃ | |
| 15-39 | CH₂CH₃ | CH₂SCH₂CH₃ | |
| 15-40 | CH₂CH₃ | CH₃-S-CH₂-cyclopropyl | |

TABLE 164

| compound number | R13 | R1 | physical property (melting point-ND) |
|---|---|---|---|
| 15-41 | CH₂CH₃ | CH₂SCH₂CF₃ | |
| 15-42 | CH₂CH₃ | CH₂SOCH₃ | |
| 15-43 | CH₂CH₃ | CH₂SOCH₂CH₃ | |
| 15-44 | CH₂CH₃ | CH₃-S(O)-CH₂-cyclopropyl | |
| 15-45 | CH₂CH₃ | CH₂SOCH₂CF₃ | |
| 15-46 | CH₂CH₃ | CH₂SO₂CH₃ | |

TABLE 164-continued

| compound number | R13 | R1 | physical property (melting point-ND) |
|---|---|---|---|
| 15-47 | $CH_2CH_3$ | $CH_2SO_2CH_2CH_3$ | |
| 15-48 | $CH_2CH_3$ | $CH_3SO_2CH_2$-cyclopropyl | |
| 15-49 | $CH_2CH_3$ | $CH_2SO_2CH_2CF_3$ | |
| 15-50 | $CH_2CH_3$ | $CH_2O(CH_2)_2OCH_3$ | |
| 15-51 | $CH_2CH_3$ | $CH_2O(CH_2)_2OCH_2CH_3$ | |
| 15-52 | $CH_2CH_3$ | $CH_2O(CH_2)_2OCH_2CF_3$ | |
| 15-53 | $CH_2CH_3$ | $CH_2O(CH_2)_2SCH_3$ | |
| 15-54 | $CH_2CH_3$ | $CH_2O(CH_2)_2SCH_2CF_3$ | |
| 15-55 | $CH_2CH_3$ | $CH_2O(CH_2)_2SOCH_3$ | |
| 15-56 | $CH_2CH_3$ | $CH_2O(CH_2)_2SOCH_2CF_3$ | |
| 15-57 | $CH_2CH_3$ | $CH_2O(CH_2)_2SO_2CH_3$ | |
| 15-58 | $CH_2CH_3$ | $CH_2O(CH_2)_2SO_2CH_2CF_3$ | |
| 15-59 | $CH_2CH_3$ | $CH_3OCH_2$-(tetrahydrofuran-2-yl) | |
| 15-60 | $CH_2CH_3$ | 3-methoxy-tetrahydrofuran | |
| 15-61 | $CH_2CH_3$ | $CH_2O(CH_2)_2NHSO_2CH_3$ | |
| 15-62 | $CH_2CH_3$ | $CH_2O(CH_2)_2N(CH_3)(SO_2CH_3)$ | |
| 15-63 | $(CH_2)_2CH_3$ | $CH_3$ | |
| 15-64 | $(CH_2)_2CH_3$ | $CF_3$ | |
| 15-65 | $(CH_2)_2CH_3$ | $CH_2OCH_3$ | |
| 15-66 | $(CH_2)_2CH_3$ | $CH_2OCH_2CH_3$ | |
| 15-67 | $(CH_2)_2CH_3$ | $CH_3OCH_2$-cyclopropyl | |
| 15-68 | $(CH_2)_2CH_3$ | $CH_2OCH_2CF_3$ | |
| 15-69 | $(CH_2)_2CH_3$ | $CH_2SCH_3$ | |
| 15-70 | $(CH_2)_2CH_3$ | $CH_2SCH_2CH_3$ | |
| 15-71 | $(CH_2)_2CH_3$ | $CH_3SCH_2$-cyclopropyl | |
| 15-72 | $(CH_2)_2CH_3$ | $CH_2SCH_2CF_3$ | |
| 15-73 | $(CH_2)_2CH_3$ | $CH_2SOCH_3$ | |
| 15-74 | $(CH_2)_2CH_3$ | $CH_2SOCH_2CH_3$ | |
| 15-75 | $(CH_2)_2CH_3$ | $CH_3S(O)CH_2$-cyclopropyl | |
| 15-76 | $(CH_2)_2CH_3$ | $CH_2SOCH_2CF_3$ | |
| 15-77 | $(CH_2)_2CH_3$ | $CH_2SO_2CH_3$ | |
| 15-78 | $(CH_2)_2CH_3$ | $CH_2SO_2CH_2CH_3$ | |
| 15-79 | $(CH_2)_2CH_3$ | $CH_3SO_2CH_2$-cyclopropyl | |
| 15-80 | $(CH_2)_2CH_3$ | $CH_2SO_2CH_2CF_3$ | |

TABLE 165

| compound number | R13 | R1 | physical property (melting point-ND) |
|---|---|---|---|
| 15-81 | $(CH_2)_2CH_3$ | $CH_2O(CH_2)_2OCH_3$ | |
| 15-82 | $(CH_2)_2CH_3$ | $CH_2O(CH_2)_2OCH_2CH_3$ | |
| 15-83 | $(CH_2)_2CH_3$ | $CH_2O(CH_2)_2OCH_2CF_3$ | |
| 15-84 | $(CH_2)_2CH_3$ | $CH_2O(CH_2)_2SCH_3$ | |
| 15-85 | $(CH_2)_2CH_3$ | $CH_2O(CH_2)_2SCH_2CF_3$ | |
| 15-86 | $(CH_2)_2CH_3$ | $CH_2O(CH_2)_2SOCH_3$ | |
| 15-87 | $(CH_2)_2CH_3$ | $CH_2O(CH_2)_2SOCH_2CF_3$ | |
| 15-88 | $(CH_2)_2CH_3$ | $CH_2O(CH_2)_2SO_2CH_3$ | |
| 15-89 | $(CH_2)_2CH_3$ | $CH_2O(CH_2)_2SO_2CH_2CF_3$ | |
| 15-90 | $(CH_2)_2CH_3$ | $CH_3OCH_2$-(tetrahydrofuran-2-yl) | |
| 15-91 | $(CH_2)_2CH_3$ | 3-methoxy-tetrahydrofuran | |
| 15-92 | $(CH_2)_2CH_3$ | $CH_2O(CH_2)_2NHSO_2CH_3$ | |
| 15-93 | $(CH_2)_2CH_3$ | $CH_2O(CH_2)_2N(CH_3)(SO_2CH_3)$ | |
| 15-94 | $CH_2CH=CH_2$ | $CH_3$ | |
| 15-95 | $CH_2CH=CH_2$ | $CF_3$ | |
| 15-96 | $CH_2CH=CH_2$ | $CH_2OCH_3$ | |
| 15-97 | $CH_2CH=CH_2$ | $CH_2OCH_2CH_3$ | |
| 15-98 | $CH_2CH=CH_2$ | $CH_3OCH_2$-cyclopropyl | |
| 15-99 | $CH_2CH=CH_2$ | $CH_2OCH_2CF_3$ | |
| 15-100 | $CH_2CH=CH_2$ | $CH_2SCH_3$ | |
| 15-101 | $CH_2CH=CH_2$ | $CH_2SCH_2CH_3$ | |
| 15-102 | $CH_2CH=CH_2$ | $CH_3SCH_2$-cyclopropyl | |
| 15-103 | $CH_2CH=CH_2$ | $CH_2SCH_2CF_3$ | |
| 15-104 | $CH_2CH=CH_2$ | $CH_2SOCH_3$ | |
| 15-105 | $CH_2CH=CH_2$ | $CH_2SOCH_2CH_3$ | |
| 15-106 | $CH_2CH=CH_2$ | $CH_3S(O)CH_2$-cyclopropyl | |
| 15-107 | $CH_2CH=CH_2$ | $CH_2SOCH_2CF_3$ | |
| 15-108 | $CH_2CH=CH_2$ | $CH_2SO_2CH_3$ | |
| 15-109 | $CH_2CH=CH_2$ | $CH_2SO_2CH_2CH_3$ | |
| 15-110 | $CH_2CH=CH_2$ | $CH_3SO_2CH_2$-cyclopropyl | |
| 15-111 | $CH_2CH=CH_2$ | $CH_2SO_2CH_2CF_3$ | |
| 15-112 | $CH_2CH=CH_2$ | $CH_2O(CH_2)_2OCH_3$ | |
| 15-113 | $CH_2CH=CH_2$ | $CH_2O(CH_2)_2OCH_2CH_3$ | |
| 15-114 | $CH_2CH=CH_2$ | $CH_2O(CH_2)_2OCH_2CF_3$ | |
| 15-115 | $CH_2CH=CH_2$ | $CH_2O(CH_2)_2SCH_3$ | |
| 15-116 | $CH_2CH=CH_2$ | $CH_2O(CH_2)_2SCH_2CF_3$ | |
| 15-117 | $CH_2CH=CH_2$ | $CH_2O(CH_2)_2SOCH_3$ | |
| 15-118 | $CH_2CH=CH_2$ | $CH_2O(CH_2)_2SOCH_2CF_3$ | |
| 15-119 | $CH_2CH=CH_2$ | $CH_2O(CH_2)_2SO_2CH_3$ | |
| 15-120 | $CH_2CH=CH_2$ | $CH_2O(CH_2)_2SO_2CH_2CF_3$ | |

TABLE 166

| compound number | R13 | R1 | physical property (melting point-ND) |
|---|---|---|---|
| 15-121 | CH$_2$CH=CH$_2$ | ![structure: CH$_3$-O-CH$_2$-tetrahydrofuran-2-yl] | |
| 15-122 | CH$_2$CH=CH$_2$ | ![structure: CH$_3$-O-tetrahydrofuran-3-yl] | |
| 15-123 | CH$_2$CH=CH$_2$ | CH$_2$O(CH$_2$)$_2$NHSO$_2$CH$_3$ | |
| 15-124 | CH$_2$CH=CH$_2$ | CH$_2$O(CH$_2$)$_2$N(CH$_3$)(SO$_2$CH$_3$) | |
| 15-125 | CH$_2$CH=CH$_2$ | CH$_3$ | |
| 15-126 | CH$_2$CH=CH$_2$ | CF$_3$ | |
| 15-127 | CH$_2$CH=CH$_2$ | CH$_2$OCH$_3$ | |
| 15-128 | CH$_2$CH=CH$_2$ | CH$_2$OCH$_2$CH$_3$ | |
| 15-129 | CH$_2$CH=CH$_2$ | ![structure: CH$_3$-O-CH$_2$-cyclopropyl] | |
| 15-130 | CH$_2$CH=CH$_2$ | CH$_2$OCH$_2$CF$_3$ | |
| 15-131 | CH$_2$CH=CH$_2$ | CH$_2$SCH$_3$ | |
| 15-132 | CH$_2$CH=CH$_2$ | CH$_2$SCH$_2$CH$_3$ | |
| 15-133 | CH$_2$CH=CH$_2$ | ![structure: CH$_3$-S-CH$_2$-cyclopropyl] | |
| 15-134 | CH$_2$CH=CH$_2$ | CH$_2$SCH$_2$CF$_3$ | |
| 15-135 | CH$_2$CH=CH$_2$ | CH$_2$SOCH$_3$ | |
| 15-136 | CH$_2$CH=CH$_2$ | CH$_2$SOCH$_2$CH$_3$ | |
| 15-137 | CH$_2$CH=CH$_2$ | ![structure: CH$_3$-S(O)-CH$_2$-cyclopropyl] | |
| 15-138 | CH$_2$CH=CH$_2$ | CH$_2$SOCH$_2$CF$_3$ | |
| 15-139 | CH$_2$CH=CH$_2$ | CH$_2$SO$_2$CH$_3$ | |
| 15-140 | CH$_2$CH=CH$_2$ | CH$_2$SO$_2$CH$_2$CH$_3$ | |
| 15-141 | CH$_2$CH=CH$_2$ | ![structure: CH$_3$-SO$_2$-CH$_2$-cyclopropyl] | |
| 15-142 | CH$_2$CH=CH$_2$ | CH$_2$SO$_2$CH$_2$CF$_3$ | |
| 15-143 | CH$_2$CH=CH$_2$ | CH$_2$O(CH$_2$)$_2$OCH$_3$ | |
| 15-144 | CH$_2$CH=CH$_2$ | CH$_2$O(CH$_2$)$_2$OCH$_2$CH$_3$ | |
| 15-145 | CH$_2$CH=CH$_2$ | CH$_2$O(CH$_2$)$_2$OCH$_2$CF$_3$ | |
| 15-146 | CH$_2$CH=CH$_2$ | CH$_2$O(CH$_2$)$_2$SCH$_3$ | |
| 15-147 | CH$_2$CH=CH$_2$ | CH$_2$O(CH$_2$)$_2$SCH$_2$CF$_3$ | |
| 15-148 | CH$_2$CH=CH$_2$ | CH$_2$O(CH$_2$)$_2$SOCH$_3$ | |
| 15-149 | CH$_2$CH=CH$_2$ | CH$_2$O(CH$_2$)$_2$SOCH$_2$CF$_3$ | |
| 15-150 | CH$_2$CH=CH$_2$ | CH$_2$O(CH$_2$)$_2$SO$_2$CH$_3$ | |
| 15-151 | CH$_2$CH=CH$_2$ | CH$_2$O(CH$_2$)$_2$SO$_2$CH$_2$CF$_3$ | |
| 15-152 | CH$_2$CH=CH$_2$ | ![structure: CH$_3$-O-CH$_2$-tetrahydrofuran-2-yl] | |
| 15-153 | CH$_2$CH=CH$_2$ | ![structure: CH$_3$-O-tetrahydrofuran-3-yl] | |
| 15-154 | CH$_2$CH=CH$_2$ | CH$_2$O(CH$_2$)$_2$NHSO$_2$CH$_3$ | |
| 15-155 | CH$_2$CH=CH$_2$ | CH$_2$O(CH$_2$)$_2$N(CH$_3$)(SO$_2$CH$_3$) | |
| 15-156 | CH$_2$C$_6$H$_5$ | CH$_3$ | |
| 15-157 | CH$_2$C$_6$H$_5$ | CF$_3$ | |
| 15-158 | CH$_2$C$_6$H$_5$ | CH$_2$OCH$_3$ | |
| 15-159 | CH$_2$C$_6$H$_5$ | CH$_2$OCH$_2$CH$_3$ | |
| 15-160 | CH$_2$C$_6$H$_5$ | ![structure: CH$_3$-O-CH$_2$-cyclopropyl] | |

TABLE 167

| compound number | R13 | R1 | physical property (melting point-ND) |
|---|---|---|---|
| 15-161 | CH$_2$C$_6$H$_5$ | CH$_2$OCH$_2$CF$_3$ | |
| 15-162 | CH$_2$C$_6$H$_5$ | CH$_2$SCH$_3$ | |
| 15-163 | CH$_2$C$_6$H$_5$ | CH$_2$SCH$_2$CH$_3$ | |
| 15-164 | CH$_2$C$_6$H$_5$ | ![structure: CH$_3$-S-CH$_2$-cyclopropyl] | |
| 15-165 | CH$_2$C$_6$H$_5$ | CH$_2$SCH$_2$CF$_3$ | |
| 15-166 | CH$_2$C$_6$H$_5$ | CH$_2$SOCH$_3$ | |
| 15-167 | CH$_2$C$_6$H$_5$ | CH$_2$SOCH$_2$CH$_3$ | |
| 15-168 | CH$_2$C$_6$H$_5$ | ![structure: CH$_3$-S(O)-CH$_2$-cyclopropyl] | |
| 15-169 | CH$_2$C$_6$H$_5$ | CH$_2$SOCH$_2$CF$_3$ | |
| 15-170 | CH$_2$C$_6$H$_5$ | CH$_2$SO$_2$CH$_3$ | |
| 15-171 | CH$_2$C$_6$H$_5$ | CH$_2$SO$_2$CH$_2$CH$_3$ | |
| 15-172 | CH$_2$C$_6$H$_5$ | ![structure: CH$_3$-SO$_2$-CH$_2$-cyclopropyl] | |
| 15-173 | CH$_2$C$_6$H$_5$ | CH$_2$SO$_2$CH$_2$CF$_3$ | |
| 15-174 | CH$_2$C$_6$H$_5$ | CH$_2$O(CH$_2$)$_2$OCH$_3$ | |
| 15-175 | CH$_2$C$_6$H$_5$ | CH$_2$O(CH$_2$)$_2$OCH$_2$CH$_3$ | |
| 15-176 | CH$_2$C$_6$H$_5$ | CH$_2$O(CH$_2$)$_2$OCH$_2$CF$_3$ | |
| 15-177 | CH$_2$C$_6$H$_5$ | CH$_2$O(CH$_2$)$_2$SCH$_3$ | |
| 15-178 | CH$_2$C$_6$H$_5$ | CH$_2$O(CH$_2$)$_2$SCH$_2$CF$_3$ | |
| 15-179 | CH$_2$C$_6$H$_5$ | CH$_2$O(CH$_2$)$_2$SOCH$_3$ | |
| 15-180 | CH$_2$C$_6$H$_5$ | CH$_2$O(CH$_2$)$_2$SOCH$_2$CF$_3$ | |
| 15-181 | CH$_2$C$_6$H$_5$ | CH$_2$O(CH$_2$)$_2$SO$_2$CH$_3$ | |
| 15-182 | CH$_2$C$_6$H$_5$ | CH$_2$O(CH$_2$)$_2$SO$_2$CH$_2$CF$_3$ | |
| 15-183 | CH$_2$C$_6$H$_5$ | ![structure: CH$_3$-O-CH$_2$-tetrahydrofuran-2-yl] | |
| 15-184 | CH$_2$C$_6$H$_5$ | ![structure: CH$_3$-O-tetrahydrofuran-3-yl] | |
| 15-185 | CH$_2$C$_6$H$_5$ | CH$_2$O(CH$_2$)$_2$NHSO$_2$CH$_3$ | |

TABLE 167-continued

| compound number | R13 | R1 | physical property (melting point-ND) |
|---|---|---|---|
| 15-186 | $CH_2C_6H_5$ | $CH_2O(CH_2)_2N(CH_3)(SO_2CH_3)$ | |
| 15-187 | $SO_2CH_3$ | $CH_3$ | |
| 15-188 | $SO_2CH_3$ | $CF_3$ | |
| 15-189 | $SO_2CH_3$ | $CH_2OCH_3$ | |
| 15-190 | $SO_2CH_3$ | $CH_2OCH_2CH_3$ | |
| 15-191 | $SO_2CH_3$ | $CH_3-O-CH_2-\text{cyclopropyl}$ | |
| 15-192 | $SO_2CH_3$ | $CH_2OCH_2CF_3$ | |
| 15-193 | $SO_2CH_3$ | $CH_2SCH_3$ | |
| 15-194 | $SO_2CH_3$ | $CH_2SCH_2CH_3$ | |
| 15-195 | $SO_2CH_3$ | $CH_3-S-CH_2-\text{cyclopropyl}$ | |
| 15-196 | $SO_2CH_3$ | $CH_2SCH_2CF_3$ | |
| 15-197 | $SO_2CH_3$ | $CH_2SOCH_3$ | |
| 15-198 | $SO_2CH_3$ | $CH_2SOCH_2CH_3$ | |
| 15-199 | $SO_2CH_3$ | $CH_3-S(=O)-CH_2-\text{cyclopropyl}$ | |
| 15-200 | $SO_2CH_3$ | $CH_2SOCH_2CF_3$ | |

TABLE 168

| compound number | R13 | R1 | physical property (melting point-ND) |
|---|---|---|---|
| 15-201 | $SO_2CH_3$ | $CH_2SO_2CH_3$ | |
| 15-202 | $SO_2CH_3$ | $CH_2SO_2CH_2CH_3$ | |
| 15-203 | $SO_2CH_3$ | $CH_3-S(=O)_2-CH_2-\text{cyclopropyl}$ | |
| 15-204 | $SO_2CH_3$ | $CH_2SO_2CH_2CF_3$ | |
| 15-205 | $SO_2CH_3$ | $CH_2O(CH_2)_2OCH_3$ | |
| 15-206 | $SO_2CH_3$ | $CH_2O(CH_2)_2OCH_2CH_3$ | |
| 15-207 | $SO_2CH_3$ | $CH_2O(CH_2)_2OCH_2CF_3$ | |
| 15-208 | $SO_2CH_3$ | $CH_2O(CH_2)_2SCH_3$ | |
| 15-209 | $SO_2CH_3$ | $CH_2O(CH_2)_2SCH_2CF_3$ | |
| 15-210 | $SO_2CH_3$ | $CH_2O(CH_2)_2SOCH_3$ | |
| 15-211 | $SO_2CH_3$ | $CH_2O(CH_2)_2SOCH_2CF_3$ | |
| 15-212 | $SO_2CH_3$ | $CH_2O(CH_2)_2SO_2CH_3$ | |
| 15-213 | $SO_2CH_3$ | $CH_2O(CH_2)_2SO_2CH_2CF_3$ | |
| 15-214 | $SO_2CH_3$ | $CH_3-O-CH_2-\text{tetrahydrofuranyl}$ | |
| 15-215 | $SO_2CH_3$ | $CH_3-O-\text{tetrahydrofuranyl}$ | |
| 15-216 | $SO_2CH_3$ | $CH_2O(CH_2)_2NHSO_2CH_3$ | |
| 15-217 | $SO_2CH_3$ | $CH_2O(CH_2)_2N(CH_3)(SO_2CH_3)$ | |

TABLE 168-continued

| compound number | R13 | R1 | physical property (melting point-ND) |
|---|---|---|---|
| 15-218 | $SO_2CH_2CH_3$ | $CH_3$ | |
| 15-219 | $SO_2CH_2CH_3$ | $CF_3$ | |
| 15-220 | $SO_2CH_2CH_3$ | $CH_2OCH_3$ | |
| 15-221 | $SO_2CH_2CH_3$ | $CH_2OCH_2CH_3$ | |
| 15-222 | $SO_2CH_2CH_3$ | $CH_3-O-CH_2-\text{cyclopropyl}$ | |
| 15-223 | $SO_2CH_2CH_3$ | $CH_2OCH_2CF_3$ | |
| 15-224 | $SO_2CH_2CH_3$ | $CH_2SCH_3$ | |
| 15-225 | $SO_2CH_2CH_3$ | $CH_2SCH_2CH_3$ | |
| 15-226 | $SO_2CH_2CH_3$ | $CH_3-S-CH_2-\text{cyclopropyl}$ | |
| 15-227 | $SO_2CH_2CH_3$ | $CH_2SCH_2CF_3$ | |
| 15-228 | $SO_2CH_2CH_3$ | $CH_2SOCH_3$ | |
| 15-229 | $SO_2CH_2CH_3$ | $CH_2SOCH_2CH_3$ | |
| 15-230 | $SO_2CH_2CH_3$ | $CH_3-S(=O)-CH_2-\text{cyclopropyl}$ | |
| 15-231 | $SO_2CH_2CH_3$ | $CH_2SOCH_2CF_3$ | |
| 15-232 | $SO_2CH_2CH_3$ | $CH_2SO_2CH_3$ | |
| 15-233 | $SO_2CH_2CH_3$ | $CH_2SO_2CH_2CH_3$ | |
| 15-234 | $SO_2CH_2CH_3$ | $CH_3-S(=O)_2-CH_2-\text{cyclopropyl}$ | |
| 15-235 | $SO_2CH_2CH_3$ | $CH_2SO_2CH_2CF_3$ | |
| 15-236 | $SO_2CH_2CH_3$ | $CH_2O(CH_2)_2OCH_3$ | |
| 15-237 | $SO_2CH_2CH_3$ | $CH_2O(CH_2)_2OCH_2CH_3$ | |
| 15-238 | $SO_2CH_2CH_3$ | $CH_2O(CH_2)_2OCH_2CF_3$ | |
| 15-239 | $SO_2CH_2CH_3$ | $CH_2O(CH_2)_2SCH_3$ | |
| 15-240 | $SO_2CH_2CH_3$ | $CH_2O(CH_2)_2SCH_2CF_3$ | |

TABLE 169

| compound number | R13 | R1 | physical property (melting point-ND) |
|---|---|---|---|
| 15-241 | $SO_2CH_2CH_3$ | $CH_2O(CH_2)_2SOCH_3$ | |
| 15-242 | $SO_2CH_2CH_3$ | $CH_2O(CH_2)_2SOCH_2CF_3$ | |
| 15-243 | $SO_2CH_2CH_3$ | $CH_2O(CH_2)_2SO_2CH_3$ | |
| 15-244 | $SO_2CH_2CH_3$ | $CH_2O(CH_2)_2SO_2CH_2CF_3$ | |
| 15-245 | $SO_2CH_2CH_3$ | $CH_3-O-CH_2-\text{tetrahydrofuranyl}$ | |
| 15-246 | $SO_2CH_2CH_3$ | $CH_3-O-\text{tetrahydrofuranyl}$ | |
| 15-247 | $SO_2CH_2CH_3$ | $CH_2O(CH_2)_2NHSO_2CH_3$ | |
| 15-248 | $SO_2CH_2CH_3$ | $CH_2O(CH_2)_2N(CH_3)(SO_2CH_3)$ | |
| 15-249 | $SO_2(CH_2)_2CH_3$ | $CH_3$ | |

TABLE 169-continued

| compound number | R13 | R1 | physical property (melting point-ND) |
|---|---|---|---|
| 15-250 | SO$_2$(CH$_2$)$_2$CH$_3$ | CF$_3$ | |
| 15-251 | SO$_2$(CH$_2$)$_2$CH$_3$ | CH$_2$OCH$_3$ | |
| 15-252 | SO$_2$(CH$_2$)$_2$CH$_3$ | CH$_2$OCH$_2$CH$_3$ | |
| 15-253 | SO$_2$(CH$_2$)$_2$CH$_3$ | CH$_3$-O-CH$_2$-cyclopropyl | |
| 15-254 | SO$_2$(CH$_2$)$_2$CH$_3$ | CH$_2$OCH$_2$CF$_3$ | |
| 15-255 | SO$_2$(CH$_2$)$_2$CH$_3$ | CH$_2$SCH$_3$ | |
| 15-256 | SO$_2$(CH$_2$)$_2$CH$_3$ | CH$_2$SCH$_2$CH$_3$ | |
| 15-257 | SO$_2$(CH$_2$)$_2$CH$_3$ | CH$_3$-S-CH$_2$-cyclopropyl | |
| 15-258 | SO$_2$(CH$_2$)$_2$CH$_3$ | CH$_2$SCH$_2$CF$_3$ | |
| 15-259 | SO$_2$(CH$_2$)$_2$CH$_3$ | CH$_2$SOCH$_3$ | |
| 15-260 | SO$_2$(CH$_2$)$_2$CH$_3$ | CH$_2$SOCH$_2$CH$_3$ | |
| 15-261 | SO$_2$(CH$_2$)$_2$CH$_3$ | CH$_3$-S(=O)-CH$_2$-cyclopropyl | |
| 15-262 | SO$_2$(CH$_2$)$_2$CH$_3$ | CH$_2$SOCH$_2$CF$_3$ | |
| 15-263 | SO$_2$(CH$_2$)$_2$CH$_3$ | CH$_2$SO$_2$CH$_3$ | |
| 15-264 | SO$_2$(CH$_2$)$_2$CH$_3$ | CH$_2$SO$_2$CH$_2$CH$_3$ | |
| 15-265 | SO$_2$(CH$_2$)$_2$CH$_3$ | CH$_3$-S(=O)$_2$-CH$_2$-cyclopropyl | |
| 15-266 | SO$_2$(CH$_2$)$_2$CH$_3$ | CH$_2$SO$_2$CH$_2$CF$_3$ | |
| 15-267 | SO$_2$(CH$_2$)$_2$CH$_3$ | CH$_2$O(CH$_2$)$_2$OCH$_3$ | |
| 15-268 | SO$_2$(CH$_2$)$_2$CH$_3$ | CH$_2$O(CH$_2$)$_2$OCH$_2$CH$_3$ | |
| 15-269 | SO$_2$(CH$_2$)$_2$CH$_3$ | CH$_2$O(CH$_2$)$_2$OCH$_2$CF$_3$ | |
| 15-270 | SO$_2$(CH$_2$)$_2$CH$_3$ | CH$_2$O(CH$_2$)$_2$SCH$_3$ | |
| 15-271 | SO$_2$(CH$_2$)$_2$CH$_3$ | CH$_2$O(CH$_2$)$_2$SCH$_2$CF$_3$ | |
| 15-272 | SO$_2$(CH$_2$)$_2$CH$_3$ | CH$_2$O(CH$_2$)$_2$SOCH$_3$ | |
| 15-273 | SO$_2$(CH$_2$)$_2$CH$_3$ | CH$_2$O(CH$_2$)$_2$SOCH$_2$CF$_3$ | |
| 15-274 | SO$_2$(CH$_2$)$_2$CH$_3$ | CH$_2$O(CH$_2$)$_2$SO$_2$CH$_3$ | |
| 15-275 | SO$_2$(CH$_2$)$_2$CH$_3$ | CH$_2$O(CH$_2$)$_2$SO$_2$CH$_2$CF$_3$ | |
| 15-276 | SO$_2$(CH$_2$)$_2$CH$_3$ | CH$_3$-O-CH$_2$-(tetrahydrofuran-2-yl) | |
| 15-277 | SO$_2$(CH$_2$)$_2$CH$_3$ | CH$_3$-O-(tetrahydrofuran-3-yl) | |
| 15-278 | SO$_2$(CH$_2$)$_2$CH$_3$ | CH$_2$O(CH$_2$)$_2$NHSO$_2$CH$_3$ | |
| 15-279 | SO$_2$(CH$_2$)$_2$CH$_3$ | CH$_2$O(CH$_2$)$_2$N(CH$_3$)(SO$_2$CH$_3$) | |
| 15-280 | SO$_2$C$_6$H$_5$ | CH$_3$ | |

TABLE 170

| compound number | R13 | R1 | physical property (melting point-ND) |
|---|---|---|---|
| 15-281 | SO$_2$C$_6$H$_5$ | CF$_3$ | |
| 15-282 | SO$_2$C$_6$H$_5$ | CH$_2$OCH$_3$ | |
| 15-283 | SO$_2$C$_6$H$_5$ | CH$_2$OCH$_2$CH$_3$ | |
| 15-284 | SO$_2$C$_6$H$_5$ | CH$_3$-O-CH$_2$-cyclopropyl | |
| 15-285 | SO$_2$C$_6$H$_5$ | CH$_2$OCH$_2$CF$_3$ | |
| 15-286 | SO$_2$C$_6$H$_5$ | CH$_2$SCH$_3$ | |
| 15-287 | SO$_2$C$_6$H$_5$ | CH$_2$SCH$_2$CH$_3$ | |
| 15-288 | SO$_2$C$_6$H$_5$ | CH$_3$-S-CH$_2$-cyclopropyl | |
| 15-289 | SO$_2$C$_6$H$_5$ | CH$_2$SCH$_2$CF$_3$ | |
| 15-290 | SO$_2$C$_6$H$_5$ | CH$_2$SOCH$_3$ | |
| 15-291 | SO$_2$C$_6$H$_5$ | CH$_2$SOCH$_2$CH$_3$ | |
| 15-292 | SO$_2$C$_6$H$_5$ | CH$_3$-S(=O)-CH$_2$-cyclopropyl | |
| 15-293 | SO$_2$C$_6$H$_5$ | CH$_2$SOCH$_2$CF$_3$ | |
| 15-294 | SO$_2$C$_6$H$_5$ | CH$_2$SO$_2$CH$_3$ | |
| 15-295 | SO$_2$C$_6$H$_5$ | CH$_2$SO$_2$CH$_2$CH$_3$ | |
| 15-296 | SO$_2$C$_6$H$_5$ | CH$_3$-S(=O)$_2$-CH$_2$-cyclopropyl | |
| 15-297 | SO$_2$C$_6$H$_5$ | CH$_2$SO$_2$CH$_2$CF$_3$ | |
| 15-298 | SO$_2$C$_6$H$_5$ | CH$_2$O(CH$_2$)$_2$OCH$_3$ | |
| 15-299 | SO$_2$C$_6$H$_5$ | CH$_2$O(CH$_2$)$_2$OCH$_2$CH$_3$ | |
| 15-300 | SO$_2$C$_6$H$_5$ | CH$_2$O(CH$_2$)$_2$OCH$_2$CF$_3$ | |
| 15-301 | SO$_2$C$_6$H$_5$ | CH$_2$O(CH$_2$)$_2$SCH$_3$ | |
| 15-302 | SO$_2$C$_6$H$_5$ | CH$_2$O(CH$_2$)$_2$SCH$_2$CF$_3$ | |
| 15-303 | SO$_2$C$_6$H$_5$ | CH$_2$O(CH$_2$)$_2$SOCH$_3$ | |
| 15-304 | SO$_2$C$_6$H$_5$ | CH$_2$O(CH$_2$)$_2$SOCH$_2$CF$_3$ | |
| 15-305 | SO$_2$C$_6$H$_5$ | CH$_2$O(CH$_2$)$_2$SO$_2$CH$_3$ | |
| 15-306 | SO$_2$C$_6$H$_5$ | CH$_2$O(CH$_2$)$_2$SO$_2$CH$_2$CF$_3$ | |
| 15-307 | SO$_2$C$_6$H$_5$ | CH$_3$-O-CH$_2$-(tetrahydrofuran-2-yl) | |
| 15-308 | SO$_2$C$_6$H$_5$ | CH$_3$-O-(tetrahydrofuran-3-yl) | |
| 15-309 | SO$_2$C$_6$H$_5$ | CH$_2$O(CH$_2$)$_2$NHSO$_2$CH$_3$ | |
| 15-310 | SO$_2$C$_6$H$_5$ | CH$_2$O(CH$_2$)$_2$N(CH$_3$)(SO$_2$CH$_3$) | |
| 15-311 | SO$_2$(4-CH$_3$)C$_6$H$_4$ | CH$_3$ | |
| 15-312 | SO$_2$(4-CH$_3$)C$_6$H$_4$ | CF$_3$ | |
| 15-313 | SO$_2$(4-CH$_3$)C$_6$H$_4$ | CH$_2$OCH$_3$ | |
| 15-314 | SO$_2$(4-CH$_3$)C$_6$H$_4$ | CH$_2$OCH$_2$CH$_3$ | |
| 15-315 | SO$_2$(4-CH$_3$)C$_6$H$_4$ | CH$_3$-O-CH$_2$-cyclopropyl | |
| 15-316 | SO$_2$(4-CH$_3$)C$_6$H$_4$ | CH$_2$OCH$_2$CF$_3$ | |

TABLE 170-continued

| compound number | R13 | R1 | physical property (melting point-ND) |
|---|---|---|---|
| 15-317 | SO$_2$(4-CH$_3$)C$_6$H$_4$ | CH$_2$SCH$_3$ | |
| 15-318 | SO$_2$(4-CH$_3$)C$_6$H$_4$ | CH$_2$SCH$_2$CH$_3$ | |
| 15-319 | SO$_2$(4-CH$_3$)C$_6$H$_4$ | CH$_3$–S–CH$_2$–(cyclopropyl) | |
| 15-320 | SO$_2$(4-CH$_3$)C$_6$H$_4$ | CH$_2$SCH$_2$CF$_3$ | |

TABLE 171

| compound number | R13 | R1 | physical property (melting point-ND) |
|---|---|---|---|
| 15-321 | SO$_2$(4-CH$_3$)C$_6$H$_4$ | CH$_2$SOCH$_3$ | |
| 15-322 | SO$_2$(4-CH$_3$)C$_6$H$_4$ | CH$_2$SOCH$_2$CH$_3$ | |
| 15-323 | SO$_2$(4-CH$_3$)C$_6$H$_4$ | CH$_3$–S(=O)–CH$_2$–(cyclopropyl) | |
| 15-324 | SO$_2$(4-CH$_3$)C$_6$H$_4$ | CH$_2$SOCH$_2$CF$_3$ | |
| 15-325 | SO$_2$(4-CH$_3$)C$_6$H$_4$ | CH$_2$SO$_2$CH$_3$ | |
| 15-326 | SO$_2$(4-CH$_3$)C$_6$H$_4$ | CH$_2$SO$_2$CH$_2$CH$_3$ | |
| 15-327 | SO$_2$(4-CH$_3$)C$_6$H$_4$ | CH$_3$–S(=O)$_2$–CH$_2$–(cyclopropyl) | |
| 15-328 | SO$_2$(4-CH$_3$)C$_6$H$_4$ | CH$_2$SO$_2$CH$_2$CF$_3$ | |
| 15-329 | SO$_2$(4-CH$_3$)C$_6$H$_4$ | CH$_2$O(CH$_2$)$_2$OCH$_3$ | |
| 15-330 | SO$_2$(4-CH$_3$)C$_6$H$_4$ | CH$_2$O(CH$_2$)$_2$OCH$_2$CH$_3$ | |
| 15-331 | SO$_2$(4-CH$_3$)C$_6$H$_4$ | CH$_2$O(CH$_2$)$_2$OCH$_2$CF$_3$ | |
| 15-332 | SO$_2$(4-CH$_3$)C$_6$H$_4$ | CH$_2$O(CH$_2$)$_2$SCH$_3$ | |
| 15-333 | SO$_2$(4-CH$_3$)C$_6$H$_4$ | CH$_2$O(CH$_2$)$_2$SCH$_2$CF$_3$ | |
| 15-334 | SO$_2$(4-CH$_3$)C$_6$H$_4$ | CH$_2$O(CH$_2$)$_2$SOCH$_3$ | |
| 15-335 | SO$_2$(4-CH$_3$)C$_6$H$_4$ | CH$_2$O(CH$_2$)$_2$SOCH$_2$CF$_3$ | |
| 15-336 | SO$_2$(4-CH$_3$)C$_6$H$_4$ | CH$_2$O(CH$_2$)$_2$SO$_2$CH$_3$ | |
| 15-337 | SO$_2$(4-CH$_3$)C$_6$H$_4$ | CH$_2$O(CH$_2$)$_2$SO$_2$CH$_2$CF$_3$ | |
| 15-338 | SO$_2$(4-CH$_3$)C$_6$H$_4$ | CH$_3$–O–CH(tetrahydrofuran-2-yl) | |
| 15-339 | SO$_2$(4-CH$_3$)C$_6$H$_4$ | CH$_3$–O–(tetrahydrofuran-3-yl) | |
| 15-340 | SO$_2$(4-CH$_3$)C$_6$H$_4$ | CH$_2$O(CH$_2$)$_2$NHSO$_2$CH$_3$ | |
| 15-341 | SO$_2$(4-CH$_3$)C$_6$H$_4$ | CH$_2$O(CH$_2$)$_2$N(CH$_3$)(SO$_2$CH$_3$) | |
| 15-342 | COCH$_3$ | CH$_3$ | |
| 15-343 | COCH$_3$ | CF$_3$ | |
| 15-344 | COCH$_3$ | CH$_2$OCH$_3$ | |
| 15-345 | COCH$_3$ | CH$_2$OCH$_2$CH$_3$ | |
| 15-346 | COCH$_3$ | CH$_3$–O–CH$_2$–(cyclopropyl) | |
| 15-347 | COCH$_3$ | CH$_2$OCH$_2$CF$_3$ | |
| 15-348 | COCH$_3$ | CH$_2$SCH$_3$ | |
| 15-349 | COCH$_3$ | CH$_2$SCH$_2$CH$_3$ | |
| 15-350 | COCH$_3$ | CH$_3$–S–CH$_2$–(cyclopropyl) | |
| 15-351 | COCH$_3$ | CH$_2$SCH$_2$CF$_3$ | |
| 15-352 | COCH$_3$ | CH$_2$SOCH$_3$ | |
| 15-353 | COCH$_3$ | CH$_2$SOCH$_2$CH$_3$ | |
| 15-354 | COCH$_3$ | CH$_3$–S(=O)–CH$_2$–(cyclopropyl) | |
| 15-355 | COCH$_3$ | CH$_2$SOCH$_2$CF$_3$ | |
| 15-356 | COCH$_3$ | CH$_2$SO$_2$CH$_3$ | |
| 15-357 | COCH$_3$ | CH$_2$SO$_2$CH$_2$CH$_3$ | |
| 15-358 | COCH$_3$ | CH$_3$–S(=O)$_2$–CH$_2$–(cyclopropyl) | |
| 15-359 | COCH$_3$ | CH$_2$SO$_2$CH$_2$CF$_3$ | |
| 15-360 | COCH$_3$ | CH$_2$O(CH$_2$)$_2$OCH$_3$ | |

TABLE 172

| compound number | R13 | R1 | physical property (melting point-ND) |
|---|---|---|---|
| 15-361 | COCH$_3$ | CH$_2$O(CH$_2$)$_2$OCH$_2$CH$_3$ | |
| 15-362 | COCH$_3$ | CH$_2$O(CH$_2$)$_2$OCH$_2$CF$_3$ | |
| 15-363 | COCH$_3$ | CH$_2$O(CH$_2$)$_2$SCH$_3$ | |
| 15-364 | COCH$_3$ | CH$_2$O(CH$_2$)$_2$SCH$_2$CF$_3$ | |
| 15-365 | COCH$_3$ | CH$_2$O(CH$_2$)$_2$SOCH$_3$ | |
| 15-366 | COCH$_3$ | CH$_2$O(CH$_2$)$_2$SOCH$_2$CF$_3$ | |
| 15-367 | COCH$_3$ | CH$_2$O(CH$_2$)$_2$SO$_2$CH$_3$ | |
| 15-368 | COCH$_3$ | CH$_2$O(CH$_2$)$_2$SO$_2$CH$_2$CF$_3$ | |
| 15-369 | COCH$_3$ | CH$_3$–O–CH(tetrahydrofuran-2-yl) | |
| 15-370 | COCH$_3$ | CH$_3$–O–(tetrahydrofuran-3-yl) | |
| 15-371 | COCH$_3$ | CH$_2$O(CH$_2$)$_2$NHSO$_2$CH$_3$ | |
| 15-372 | COCH$_3$ | CH$_2$O(CH$_2$)$_2$N(CH$_3$)(SO$_2$CH$_3$) | |
| 15-373 | COC$_6$H$_5$ | CH$_3$ | |
| 15-374 | COC$_6$H$_5$ | CF$_3$ | |
| 15-375 | COC$_6$H$_5$ | CH$_2$OCH$_3$ | |
| 15-376 | COC$_6$H$_5$ | CH$_2$OCH$_2$CH$_3$ | |
| 15-377 | COC$_6$H$_5$ | CH$_3$–O–CH$_2$–(cyclopropyl) | |

TABLE 172-continued

| compound number | R13 | R1 | physical property (melting point-ND) |
|---|---|---|---|
| 15-378 | COC$_6$H$_5$ | CH$_2$OCH$_2$CF$_3$ | |
| 15-379 | COC$_6$H$_5$ | CH$_2$SCH$_3$ | |
| 15-380 | COC$_6$H$_5$ | CH$_2$SCH$_2$CH$_3$ | |
| 15-381 | COC$_6$H$_5$ | CH$_3$-S-CH$_2$-cyclopropyl | |
| 15-382 | COC$_6$H$_5$ | CH$_2$SCH$_2$CF$_3$ | |
| 15-383 | COC$_6$H$_5$ | CH$_2$SOCH$_3$ | |
| 15-384 | COC$_6$H$_5$ | CH$_2$SOCH$_2$CH$_3$ | |
| 15-385 | COC$_6$H$_5$ | CH$_3$-S(O)-CH$_2$-cyclopropyl | |
| 15-386 | COC$_6$H$_5$ | CH$_2$SOCH$_2$CF$_3$ | |
| 15-387 | COC$_6$H$_5$ | CH$_2$SO$_2$CH$_3$ | |
| 15-388 | COC$_6$H$_5$ | CH$_2$SO$_2$CH$_2$CH$_3$ | |
| 15-389 | COC$_6$H$_5$ | CH$_3$-S(O)$_2$-CH$_2$-cyclopropyl | |
| 15-390 | COC$_6$H$_5$ | CH$_2$SO$_2$CH$_2$CF$_3$ | |
| 15-391 | COC$_6$H$_5$ | CH$_2$O(CH$_2$)$_2$OCH$_3$ | |
| 15-392 | COC$_6$H$_5$ | CH$_2$O(CH$_2$)$_2$OCH$_2$CH$_3$ | |
| 15-393 | COC$_6$H$_5$ | CH$_2$O(CH$_2$)$_2$OCH$_2$CF$_3$ | |
| 15-394 | COC$_6$H$_5$ | CH$_2$O(CH$_2$)$_2$SCH$_3$ | |
| 15-395 | COC$_6$H$_5$ | CH$_2$O(CH$_2$)$_2$SCH$_2$CF$_3$ | |
| 15-396 | COC$_6$H$_5$ | CH$_2$O(CH$_2$)$_2$SOCH$_3$ | |
| 15-397 | COC$_6$H$_5$ | CH$_2$O(CH$_2$)$_2$SOCH$_2$CF$_3$ | |
| 15-398 | COC$_6$H$_5$ | CH$_2$O(CH$_2$)$_2$SO$_2$CH$_3$ | |
| 15-399 | COC$_6$H$_5$ | CH$_2$O(CH$_2$)$_2$SO$_2$CH$_2$CF$_3$ | |
| 15-400 | COC$_6$H$_5$ | CH$_3$-O-CH$_2$-(tetrahydrofuran-2-yl) | |

TABLE 173

| compound number | R13 | R1 | physical property (melting point-ND) |
|---|---|---|---|
| 15-401 | COC$_6$H$_5$ | CH$_3$-O-(tetrahydrofuran-3-yl) | |
| 15-402 | COC$_6$H$_5$ | CH$_2$O(CH$_2$)$_2$NHSO$_2$CH$_3$ | |
| 15-403 | COC$_6$H$_5$ | CH$_2$O(CH$_2$)$_2$N(CH$_3$)(SO$_2$CH$_3$) | |
| 15-404 | COCH$_2$C$_6$H$_5$ | CH$_3$ | |
| 15-405 | COCH$_2$C$_6$H$_5$ | CF$_3$ | |
| 15-406 | COCH$_2$C$_6$H$_5$ | CH$_2$OCH$_3$ | |
| 15-407 | COCH$_2$C$_6$H$_5$ | CH$_2$OCH$_2$CH$_3$ | |
| 15-408 | COCH$_2$C$_6$H$_5$ | CH$_3$-O-CH$_2$-cyclopropyl | |
| 15-409 | COCH$_2$C$_6$H$_5$ | CH$_2$OCH$_2$CF$_3$ | |
| 15-410 | COCH$_2$C$_6$H$_5$ | CH$_2$SCH$_3$ | |

TABLE 173-continued

| compound number | R13 | R1 | physical property (melting point-ND) |
|---|---|---|---|
| 15-411 | COCH$_2$C$_6$H$_5$ | CH$_2$SCH$_2$CH$_3$ | |
| 15-412 | COCH$_2$C$_6$H$_5$ | CH$_3$-S-CH$_2$-cyclopropyl | |
| 15-413 | COCH$_2$C$_6$H$_5$ | CH$_2$SCH$_2$CF$_3$ | |
| 15-414 | COCH$_2$C$_6$H$_5$ | CH$_2$SOCH$_3$ | |
| 15-415 | COCH$_2$C$_6$H$_5$ | CH$_2$SOCH$_2$CH$_3$ | |
| 15-416 | COCH$_2$C$_6$H$_5$ | CH$_3$-S(O)-CH$_2$-cyclopropyl | |
| 15-417 | COCH$_2$C$_6$H$_5$ | CH$_2$SOCH$_2$CF$_3$ | |
| 15-418 | COCH$_2$C$_6$H$_5$ | CH$_2$SO$_2$CH$_3$ | |
| 15-419 | COCH$_2$C$_6$H$_5$ | CH$_2$SO$_2$CH$_2$CH$_3$ | |
| 15-420 | COCH$_2$C$_6$H$_5$ | CH$_3$-S(O)$_2$-CH$_2$-cyclopropyl | |
| 15-421 | COCH$_2$C$_6$H$_5$ | CH$_2$SO$_2$CH$_2$CF$_3$ | |
| 15-422 | COCH$_2$C$_6$H$_5$ | CH$_2$O(CH$_2$)$_2$OCH$_3$ | |
| 15-423 | COCH$_2$C$_6$H$_5$ | CH$_2$O(CH$_2$)$_2$OCH$_2$CH$_3$ | |
| 15-424 | COCH$_2$C$_6$H$_5$ | CH$_2$O(CH$_2$)$_2$OCH$_2$CF$_3$ | |
| 15-425 | COCH$_2$C$_6$H$_5$ | CH$_2$O(CH$_2$)$_2$SCH$_3$ | |
| 15-426 | COCH$_2$C$_6$H$_5$ | CH$_2$O(CH$_2$)$_2$SCH$_2$CF$_3$ | |
| 15-427 | COCH$_2$C$_6$H$_5$ | CH$_2$O(CH$_2$)$_2$SOCH$_3$ | |
| 15-428 | COCH$_2$C$_6$H$_5$ | CH$_2$O(CH$_2$)$_2$SOCH$_2$CF$_3$ | |
| 15-429 | COCH$_2$C$_6$H$_5$ | CH$_2$O(CH$_2$)$_2$SO$_2$CH$_3$ | |
| 15-430 | COCH$_2$C$_6$H$_5$ | CH$_2$O(CH$_2$)$_2$SO$_2$CH$_2$CF$_3$ | |
| 15-431 | COCH$_2$C$_6$H$_5$ | CH$_3$-O-CH$_2$-(tetrahydrofuran-2-yl) | |
| 15-432 | COCH$_2$C$_6$H$_5$ | CH$_3$-O-(tetrahydrofuran-3-yl) | |
| 15-433 | COCH$_2$C$_6$H$_5$ | CH$_2$O(CH$_2$)$_2$NHSO$_2$CH$_3$ | |
| 15-434 | COCH$_2$C$_6$H$_5$ | CH$_2$O(CH$_2$)$_2$N(CH$_3$)(SO$_2$CH$_3$) | |
| 15-435 | CH$_2$COCH$_3$ | CH$_3$ | |
| 15-436 | CH$_2$COCH$_3$ | CF$_3$ | |
| 15-437 | CH$_2$COCH$_3$ | CH$_2$OCH$_3$ | |
| 15-438 | CH$_2$COCH$_3$ | CH$_2$OCH$_2$CH$_3$ | |
| 15-439 | CH$_2$COCH$_3$ | CH$_3$-O-CH$_2$-cyclopropyl | |
| 15-440 | CH$_2$COCH$_3$ | CH$_2$OCH$_2$CF$_3$ | |

TABLE 174

| compound number | R13 | R1 | physical property (melting point-ND) |
|---|---|---|---|
| 4-441 | CH$_2$COCH$_3$ | CH$_2$SCH$_3$ | |
| 4-442 | CH$_2$COCH$_3$ | CH$_2$SCH$_2$CH$_3$ | |

TABLE 174-continued

| compound number | R13 | R1 | physical property (melting point-ND) |
|---|---|---|---|
| 4-443 | CH₂COCH₃ | CH₃-S-CH₂-cyclopropyl | |
| 4-444 | CH₂COCH₃ | CH₂SCH₂CF₃ | |
| 4-445 | CH₂COCH₃ | CH₂SOCH₃ | |
| 4-446 | CH₂COCH₃ | CH₂SOCH₂CH₃ | |
| 4-447 | CH₂COCH₃ | CH₃-S(=O)-CH₂-cyclopropyl | |
| 4-448 | CH₂COCH₃ | CH₂SOCH₂CF₃ | |
| 4-449 | CH₂COCH₃ | CH₂SO₂CH₃ | |
| 4-450 | CH₂COCH₃ | CH₂SO₂CH₂CH₃ | |
| 4-451 | CH₂COCH₃ | CH₃-SO₂-CH₂-cyclopropyl | |
| 4-452 | CH₂COCH₃ | CH₂SO₂CH₂CF₃ | |
| 4-453 | CH₂COCH₃ | CH₂O(CH₂)₂OCH₃ | |
| 4-454 | CH₂COCH₃ | CH₂O(CH₂)₂OCH₂CH₃ | |
| 4-455 | CH₂COCH₃ | CH₂O(CH₂)₂OCH₂CF₃ | |
| 4-456 | CH₂COCH₃ | CH₂O(CH₂)₂SCH₃ | |
| 4-457 | CH₂COCH₃ | CH₂O(CH₂)₂SCH₂CF₃ | |
| 4-458 | CH₂COCH₃ | CH₂O(CH₂)₂SOCH₃ | |
| 4-459 | CH₂COCH₃ | CH₂O(CH₂)₂SOCH₂CF₃ | |
| 4-460 | CH₂COCH₃ | CH₂O(CH₂)₂SO₂CH₃ | |
| 4-461 | CH₂COCH₃ | CH₂O(CH₂)₂SO₂CH₂CF₃ | |
| 4-462 | CH₂COCH₃ | CH₃-O-CH₂-(tetrahydrofuran-2-yl) | |
| 4-463 | CH₂COCH₃ | CH₃-O-(tetrahydrofuran-3-yl) | |
| 4-464 | CH₂COCH₃ | CH₂O(CH₂)₂NHSO₂CH₃ | |
| 4-465 | CH₂COCH₃ | CH₂O(CH₂)₂N(CH₃)(SO₂CH₃) | |
| 15-466 | CH₂COC₆H₅ | CH₃ | |
| 15-467 | CH₂COC₆H₅ | CF₃ | |
| 15-468 | CH₂COC₆H₅ | CH₂OCH₃ | |
| 15-469 | CH₂COC₆H₅ | CH₂OCH₂CH₃ | |
| 15-470 | CH₂COC₆H₅ | CH₃-O-CH₂-cyclopropyl | |
| 15-471 | CH₂COC₆H₅ | CH₂OCH₂CF₃ | |
| 15-472 | CH₂COC₆H₅ | CH₂SCH₃ | |
| 15-473 | CH₂COC₆H₅ | CH₂SCH₂CH₃ | |
| 15-474 | CH₂COC₆H₅ | CH₃-S-CH₂-cyclopropyl | |
| 15-475 | CH₂COC₆H₅ | CH₂SCH₂CF₃ | |
| 15-476 | CH₂COC₆H₅ | CH₂SOCH₃ | |
| 15-477 | CH₂COC₆H₅ | CH₂SOCH₂CH₃ | |
| 15-478 | CH₂COC₆H₅ | CH₃-S(=O)-CH₂-cyclopropyl | |
| 15-479 | CH₂COC₆H₅ | CH₂SOCH₂CF₃ | |
| 15-480 | CH₂COC₆H₅ | CH₂SO₂CH₃ | |

TABLE 175

| compound number | R13 | R1 | physical property (melting point-ND) |
|---|---|---|---|
| 15-481 | CH₂COC₆H₅ | CH₂SO₂CH₂CH₃ | |
| 15-482 | CH₂COC₆H₅ | CH₃-SO₂-CH₂-cyclopropyl | |
| 15-483 | CH₂COC₆H₅ | CH₂SO₂CH₂CF₃ | |
| 15-484 | CH₂COC₆H₅ | CH₂O(CH₂)₂OCH₃ | |
| 15-485 | CH₂COC₆H₅ | CH₂O(CH₂)₂OCH₂CH₃ | |
| 15-486 | CH₂COC₆H₅ | CH₂O(CH₂)₂OCH₂CF₃ | |
| 15-487 | CH₂COC₆H₅ | CH₂O(CH₂)₂SCH₃ | |
| 15-488 | CH₂COC₆H₅ | CH₂O(CH₂)₂SCH₂CF₃ | |
| 15-489 | CH₂COC₆H₅ | CH₂O(CH₂)₂SOCH₃ | |
| 15-490 | CH₂COC₆H₅ | CH₂O(CH₂)₂SOCH₂CF₃ | |
| 15-491 | CH₂COC₆H₅ | CH₂O(CH₂)₂SO₂CH₃ | |
| 15-492 | CH₂COC₆H₅ | CH₂O(CH₂)₂SO₂CH₂CF₃ | |
| 15-493 | CH₂COC₆H₅ | CH₃-O-CH₂-(tetrahydrofuran-2-yl) | |
| 15-494 | CH₂COC₆H₅ | CH₃-O-(tetrahydrofuran-3-yl) | |
| 15-495 | CH₂COC₆H₅ | CH₂O(CH₂)₂NHSO₂CH₃ | |
| 15-496 | CH₂COC₆H₅ | CH₂O(CH₂)₂N(CH₃)(SO₂CH₃) | |

TABLE 176

| | $^1$H NMR (CDCl$_3$, 300 MHz) |
|---|---|
| 1-1 | δ 2.02-2.16(2H, m), 2.49(3H, s), 2.45-2.59(2H, m), 2.70-2.91(2H, m), 7.59(1H, d), 7.74(1H, d), 8.09(1H, s), 9.21(1H, s) |
| 1-19 | δ 2.01-2.11(2H, m), 2.45(2H, t), 2.80(2H, t), 3.27(3H, s), 4.63(2H, s), 7.65(1H, d), 7.85(1H, d), 8.11(1H, s), 9.21(1H, s) |
| 1-28 | δ 1.77-1.94(2H, m), 2.01-2.36(2H, m), 2.62-2.75(2H, m), 3.87(2H, q), 4.64(2H, s), 7.54(1H, d), 7.61(1H, d), 7.99(1H, s), 9.09(1H, s) |
| 1-66 | δ 2.02-2.10(2H, m), 2.44(2H, t), 2.79(2H, t), 3.34(3H, s), 3.42-3.45(2H, m), 3.52-3.55(2H, m), 4.73(2H, s), 7.65(1H, d), 7.79(1H, d), 8.11(1H, s), 9.21(1H, s) |
| 1-115 | δ 1.13(3H, d), 1.72-1.86(1H, m), 2.10-2.16(1H, m), 2.39-2.60(2H, m), 2.48(3H, s), 2.79-2.92(2H, m), 7.60(1H, d), 7.75(1H, d), 8.10(1H, s), 9.21(1H, s) |
| 1-142 | δ 1.14(3H, d), 1.73-2.68(5H, m), 3.80(2H, q), 4.84(2H, s), 7.67(1H, d), 7.88(1H, d), 8.12(1H, s), 9.19(1H, s) |
| 1-457 | δ 1.12(3H, s), 1.19(1H, s), 1.76-1.89(2H, m), 2.38-2.87(2H, m), 2.44(3H, s), 7.54(1H, d), 7.71(1H, d), 8.07(1H, s), 9.19(1H, s) |
| 1-685 | δ 1.26(6H, s), 1.36(6H, s), 2.55(3H, s), 7.60(1H, d), 7.78(1H, d), 8.10(1H, s), 9.22(1H, s) |
| 1-712 | δ 1.34(12H, s), 3.84(2H, q), 4.91(2H, s), 7.69(1H, d), 7.91(1H, d), 8.14(1H, s), 9.221(1H, s) |
| 1-799 | δ 1.72-2.25(6H, m), 2.47(3H, s), 2.99-3.18(2H, m), 7.61(1H, d), 7.73(1H, d), 8.09(1H, s), 9.21(1H, s) |
| 1-826 | δ 1.71-2.07(6H, m), 2.90-3.19(2H, m), 4.84(2H, q), 4.84 (2H, s), 7.39(1H, d), 7.88(1H, d), 8.11(1H, s), 9.17(1H, s) |
| 1-913 | δ 2.40-2.68(2H, m), 2.44(3H, s), 3.33-3.55(2H, m), 6.21-6.22(1H, m), 6.36-6.93(2H, m), 6.44-6.47(1H, m), 7.61(1H, d), 7.75(1H, d), 8.10(1H, s), 9.21(1H, s) |
| 2-1 | δ 2.71(3H, s), 3.73(3H, s), 7.43(1H, s), 7.84(1H, d), 8.00(1H, d), 8.13(1H, s), 9.25(1H, s) |
| 2-28 | δ 3.73(3H, s), 3.93(2H, q), 5.01(1H, s), 7.45(1H, s), 7.99(1H, d), 8.10(1H, d), 8.15(1H, s), 9.24(1H, s) |
| 2-229 | δ 1.81(3H, s), 2.59(3H, s), 3.66(3H, s), 7.76(1H, d), 7.84(1H, d), 8.14(1H, s), 9.26(1H, s) |
| 3-115 | δ 1.21-1.40(4H, m), 2.60-2.73(1H, m), 2.66(3H, s), 7.82(1H, d), 7.90(1H, d), 8.11(1H, s), 8.22(1H, s), 9.22(1H, s) |
| 3-343 | δ 1.16-1.38(7H, m), 2.30-2.39(1H, m), 2.77(3H, s), 4.10-4.17(2H, q), 7.75(1H, d), 7.85(1H, d), 8.11(1H, s), 9.24(1H, s) |
| 4.115 | δ 1.26-1.49(4H, m), 2.38-2.46(1H, m), 2.70(3H, s), 7.85(1H, d), 8.05(1H, d), 8.12(1H, s), 9.23(1H, s) |
| 4-142 | δ 1.29-1.36(2H, m), 1.43-1.49(2H, m), 2.33-2.41(1H, m), 3.91(2H, q), 5.00(2H, s), 7.99(1H, d), 8.12(1H, d), 8.14(1H, s), 9.19(1H, s) |

Biological Test Example

Test example 1

Herbicide Effect Test Against Field Weed (Soil Spray Treatment before Germination)

Preparing preparation of active compound
Carrier: DMF 5 parts by weight
Emulsifier: benzyloxy polyglycol ether 1 part by weight A preparation of active compound is obtained as an emulsion by mixing 1 part by weight of active compound with the above amounts of carrier and emulsifier. A prescribed amount of preparation is diluted with water.

In a greenhouse, seeds of field weeds [livid amaranth (*Amaranthus*), green bristle grass (*Setaria*)] were sown on the surface layer of 16 cm$^2$ pots filled with field soil (sandy loam), and covered with soil. Here, one kind of grass was sown for one pot. Immediately after sowing, the prescribed diluted solutions which were prepared according to the above preparation method of the preparation of respective active compounds were sprayed to soil. After 2 weeks from the treatment, the herbicide effect of each of the compounds was examined. In the evaluation of herbicide effect, complete death was evaluated as 100%, and the case of no herbicide effect was evaluated as 0%. When the herbicide effect is 80% or more, such active compounds are evaluated to have practical utility as a herbicide. Results are shown in Table 177.

TABLE 177

| Soil spray treatment before germination | | | |
|---|---|---|---|
| Compound number | Dosage (g ai/ha) | Green bristle grass | Livid amaranth |
| 1-1 | 500 | 100 | 100 |
| 2-1 | 500 | 100 | 100 |
| 2-229 | 500 | 100 | 100 |
| 3-343 | 500 | 95 | 100 |
| 4-115 | 500 | 100 | 100 |

Test example 2

Herbicide Effect Test Against Field Weed (Foliage Spray Treatment after Germination)

In a greenhouse, to 16 cm$^2$ pots filled with field soil (sandy loam), seedling plants (2nd-3rd leaf stage) of a field weed (Green bristle grass) were transplanted. After 1 day, the prescribed diluted solutions of preparations of respective active compounds, which were prepared according to the above Test example 1, were sprayed from the upside of the plant body. After 2 weeks from the treatment, the herbicide effect of each of the compounds was examined. Evaluation of herbicidal effect was carried out similarly to Test example 1. Results are shown in Table 178.

TABLE 178

| Foliage spray treatment after germination | | |
|---|---|---|
| Compound number | Dosage (g ai/ha) | Green bristle grass |
| 1-36 | 500 | 100 |
| 1-66 | 500 | 90 |
| 1-115 | 500 | 100 |
| 1-457 | 500 | 100 |
| 3-115 | 500 | 100 |

Test example 3

Selective Herbicide Effect Test to Field Crop (Soil Spray Treatment before Germination)

In a greenhouse, seeds of field crops [wheat (*Triticum*), corn (*Zea*), soy bean (*Glycine*)] and weeds [barnyardgrass (*Echinochloa*), southern crabgrass (*Digitaria*), livid amaranth (*Amaranthus*), fat hen (*Chenopodium*)] were sown on the surface layer of 16 cm$^2$ pots filled with field soil (sandy loam), and covered with soil. After 1 day, the prescribed diluted solutions of preparations of respective active compounds, which were prepared according to Test example 1, were sprayed to the soil. After 2 weeks from the treatment, phytotoxicity to crops and herbicide effect of respective compounds were examined. In the evaluation of herbicide effect and phytotoxicity, complete death was evaluated as 100%, and the case of no herbicide effect or no phytotoxicity was evaluated as 0%. When the herbicide effect is 80% or more, such active compounds are evaluated to have practical utility as a herbicide. When phytotoxicity is 20% or less, such active compounds are evaluated to have excellent safety as a herbicide. Results are shown in Table 179.

TABLE 179

| Compound number | Dosage (g/ha) | Wheat | Corn | Soy bean | Barnyardgrass | Southern crabgrass | Livid amaranth | Fat hen |
|---|---|---|---|---|---|---|---|---|
| 1-1 | 320 | 10 | 0 | 20 | 100 | 100 | 80 | 100 |
| 1-28 | 320 | 0 | 5 | 10 | 100 | 100 | 90 | 100 |
| 1-115 | 320 | 0 | 0 | 10 | 100 | 100 | 90 | 100 |
| 1-685 | 80 | 40 | 30 | 10 | 100 | 100 | 90 | 90 |
| 1-799 | 320 | 0 | 5 | 30 | 90 | 100 | 100 | 90 |
| 1-913 | 320 | 0 | 0 | 0 | 100 | 100 | 100 | 90 |
| 3-115 | 320 | 5 | 10 | 20 | 100 | 100 | 90 | 100 |
| 3-343 | 320 | 0 | 0 | 0 | 90 | 100 | 100 | 100 |
| 4-115 | 320 | 20 | 30 | 0 | 100 | 100 | 100 | 100 |

Test example 4

Selective Herbicide Effect Test to Field Crop (Foliage Spray Treatment after Germination)

In a greenhouse, respective seeds of weeds (barnyardgrass, southern crabgrass, fat hen, and livid amaranth) and crops (wheat, corn, and soy bean) were sown on the surface layer of pots filled with field soil, and covered with soil. After one day and 10 days (average 2nd leaf stage for weeds) from the sowing and covering the seeds with soil, the prescribed diluted solutions of preparations of respective active compounds, which were prepared according to Test example 1, were uniformly sprayed onto the soil surfaces of respective test pots and the foliage parts of the plant bodies.

After 14 days from the spraying, the degree of herbicide effect was examined. Evaluation of herbicide effect and phytotoxicity were carried out similarly to Test example 3. Results are shown in Table 180.

TABLE 180

| Compound number | Dosage (g/ha) | Wheat | Corn | Soy bean | Barnyardgrass | Southern crabgrass | Livid amaranth | Fat hen |
|---|---|---|---|---|---|---|---|---|
| 1-36 | 320 | 0 | 10 | 50 | 100 | 100 | 80 | 90 |
| 1-56 | 320 | 0 | 50 | 50 | 100 | 100 | 80 | 90 |
| 1-66 | 320 | 10 | 50 | 50 | 100 | 100 | 100 | 100 |
| 1-457 | 320 | 20 | 50 | 40 | 100 | 100 | 100 | 100 |
| 2-1 | 80 | 0 | 5 | 50 | 100 | 95 | 100 | 90 |
| 2-229 | 320 | 10 | 50 | 60 | 100 | 100 | 100 | 90 |

Formulation Example

Formulation Example 1 (Granule)

Water (25 parts) is added to a mixture of compound No. 1-1 (10 parts) of the present invention, bentonite (montmorillonite) (30 parts), talc (58 parts), and lignin sulfonate (2 parts), and the mixture is kneaded well, made into granules of 10-40 mesh with an extrusion granulator, and dried at 40-50° C. to prepare granules.

Formulation Example 2 (Granule)

Clay mineral grains (95 parts) having particle size distribution of 0.2-2 mm are put into a rotary mixer, and compound No. 1-1 (5 parts) of the present invention is sprayed together with a liquid diluent under revolution, and the grains are uniformly humidified and then dried at 40-50° C. to prepare granules.

Formulation Example 3 (Emulsion)

Compound No. 1-1 (30 parts) of the present invention, xylene (55 parts), polyoxyethylene alkyl phenyl ether (8 parts), and calcium alkylbenzene sulfonate (7 parts) are mixed and stirred to prepare an emulsion.

Formulation Example 4 (Wettable Powder)

Compound No. 1-1 (15 parts) of the present invention, a mixture of white carbon (water-containing amorphous silica fine powders) and powder clay (1:5) (80 parts), sodium alkylbenzene sulfonate (2 parts), and sodium alkylnaphthalene sulfonate-formalin polymer (3 parts) are powder-blended to prepare a wettable powder.

Formulation Example 5 (Water-dispersible Granule)

Compound No. 1-1 (20 parts) of the present invention, sodium lignin sulfonate (30 parts), bentonite (15 parts), and calcinated diatomaceous earth powder (35 parts) are sufficiently blended, and water is added thereto, and the mixture is extruded and dried through a screen of 0.3 mm to prepare water-dispersible granules.

The invention claimed is:

1. A triazolylpyridine ketone derivative represented by the formula (I)

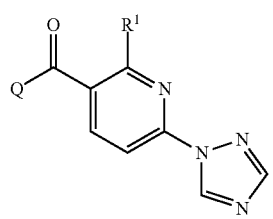

Formula (I)

wherein
$R^1$ represents $C_{1-6}$ alkyl, and
Q represents

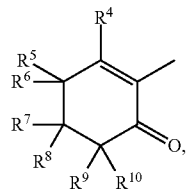

Q1 wherein
$R^4$ represents hydroxy,
$R^5$, $R^6$, $R^7$, $R^8$, $R^9$, and $R^{10}$ independently represent hydrogen or $C_{1-6}$ alkyl,
$R^5$ and $R^{10}$ together represent ethylene or —CH=CH—,
$R^7$ and $R^8$ together represent carbonyl.

2. A compound according to claim 1, wherein
$R^1$ represents $C_{1-4}$ alkyl, and
Q represents

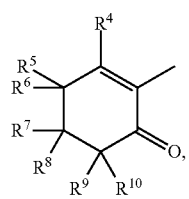

Q1 wherein
$R^4$ represents hydroxy,
$R^5$, $R^6$, $R^7$, $R^8$, $R^9$, and $R^{10}$ independently represent hydrogen or $C_{1-4}$ alkyl,
$R^5$ and $R^{10}$ together represent ethylene or —CH=CH—,
$R^7$ and $R^8$ together represent carbonyl.

3. A composition for controlling a weed comprising at least one compound of the formula (I) according to claim 1 and an extender.

4. A composition according to claim 3 further comprising a surfactant.

5. A composition according to claim 3 further comprising an additional herbicide and/or a phytotoxicity-reducing agent.

6. A method of controlling a weed comprising applying at least one compound of formula (I) according to claim 1 to the weed and/or soil around the weed.

7. A compound of formula (I) according to claim 1, wherein
$R^1$ represents methyl, and
Q represents

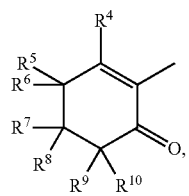

Q1 wherein
R⁴ represents hydroxyl, and
R⁵, R⁶, R⁷, R⁸, R⁹, and R¹⁰ independently represent hydrogen or alkyl.
8. A compound according to claim 1, wherein the compound is
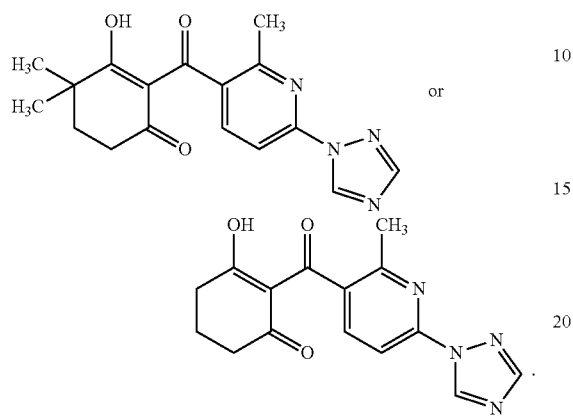
.